(12) United States Patent
Pratt et al.

(10) Patent No.: US 7,902,203 B2
(45) Date of Patent: Mar. 8, 2011

(54) ANTI-INFECTIVE AGENTS

(75) Inventors: John K. Pratt, Kenosha, WI (US);
David A. Betebenner, Libertyville, IL (US); Pamela L. Donner, Mundelein, IL (US); Brian E. Green, Wonder Lake, IL (US); Dale J. Kempf, Libertyville, IL (US); Keith F. McDaniel, Wauconda, IL (US); Clarence J. Maring, Palatine, IL (US); Vincent S. Stoll, Libertyville, IL (US); Rong Zhang, Skokie, IL (US); Hui-Ju Chen, Grayslake, IL (US); William J. Flosi, Evanston, IL (US); Larry L. Klein, Lake Forest, IL (US); Allan C. Krueger, Gurnee, IL (US); Dachun Liu, Waukegan, IL (US); Darold L. Madigan, Elk Grove Village, IL (US); Laura M. Maymon, Chicago, IL (US); Todd W. Rockway, Grayslake, IL (US); Kent D. Stewart, Gurnee, IL (US); Ming C. Yeung, Grayslake, IL (US); Qinghua Xie, Libertyville, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 717 days.

(21) Appl. No.: 10/699,513

(22) Filed: Oct. 31, 2003

(65) Prior Publication Data
US 2004/0167123 A1    Aug. 26, 2004

Related U.S. Application Data

(60) Provisional application No. 60/509,107, filed on Oct. 6, 2003, provisional application No. 60/489,448, filed on Jul. 23, 2003, provisional application No. 60/461,784, filed on Apr. 10, 2003, provisional application No. 60/423,209, filed on Nov. 1, 2002.

(51) Int. Cl.
*A01N 43/54* (2006.01)
*A01N 43/90* (2006.01)
*C07D 285/00* (2006.01)
*C07D 285/22* (2006.01)

(52) U.S. Cl. .................. 514/258.1; 514/260.1; 514/267; 544/3; 544/9; 544/10; 544/11; 544/12

(58) Field of Classification Search .................. 424/623; 514/258.1, 260.1; 544/3, 9, 10, 11, 12
See application file for complete search history.

(56) References Cited

U.S. PATENT DOCUMENTS

| | | | |
|---|---|---|---|
| 3,133,918 A | 5/1964 | MacPhillamy et al. | |
| 3,291,794 A | 12/1966 | Huebner | |
| 3,499,082 A | 3/1970 | De Stevens et al. | |
| 5,378,704 A | 1/1995 | Weller | |
| 6,348,587 B1 | 2/2002 | Schinazi et al. | 536/25.3 |
| 7,378,414 B2 | 5/2008 | Hutchinson et al. | 514/223.2 |
| 2004/0087577 A1 | 5/2004 | Pratt et al. | 514/222.8 |
| 2004/0097492 A1 | 5/2004 | Pratt et al. | 514/222.8 |
| 2004/0162285 A1 | 8/2004 | Pratt et al. | 514/222.3 |
| 2005/0075331 A1 | 4/2005 | Pratt et al. | 514/223.2 |
| 2008/0193413 A1 | 8/2008 | Hutchinson et al. | 424/85.5 |
| 2008/0214528 A1 | 9/2008 | Wagner et al. | 514/222.8 |

FOREIGN PATENT DOCUMENTS

| | | |
|---|---|---|
| CH | 386435 | 4/1965 |
| EP | 0 618 209 | 12/1998 |
| GB | 885950 | 2/1962 |
| WO | WO0132153 A2 | 5/2001 |
| WO | WO0132153 A3 | 5/2001 |
| WO | WO0160315 A2 | 8/2001 |
| WO | WO0160315 A3 | 8/2001 |
| WO | 01/85172 | 11/2001 |
| WO | WO0190121 A2 | 11/2001 |
| WO | WO0190121 A3 | 11/2001 |
| WO | WO0204425 A2 | 1/2002 |
| WO | WO0204425 A3 | 1/2002 |
| WO | 02/098424 | 12/2002 |

(Continued)

OTHER PUBLICATIONS

Dhanak et al, Identification and Biological Characterization of Heterocyclic Inhibitors of the Hepatitis C Virus RNA-dependent RNA Polymerase, J. Biol. Chem., vol. 277, Issue 41, 38322-7, 2002.*

(Continued)

*Primary Examiner* — Alton N Pryor
(74) *Attorney, Agent, or Firm* — Bradley E. Davis

(57) ABSTRACT

The present invention provides an HCV polymerase inhibiting compound having the formula (I)

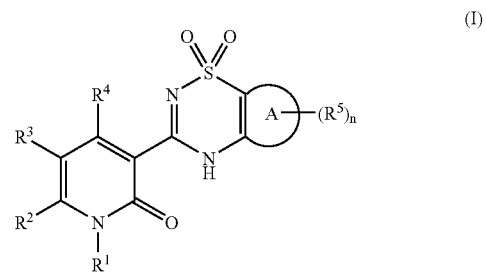

and a composition comprising a therapeutically effective amount of said compound. The present invention also provides a method for inhibiting hepatitis C virus (HCV) polymerase, a method for inhibiting HCV viral replication, and a method for treating or preventing HCV infection. Processes for making said compounds, and synthetic intermediates employed in said processes, are also provided.

23 Claims, No Drawings

FOREIGN PATENT DOCUMENTS

| WO | WO-0185172 | * | 12/2002 |
|---|---|---|---|
| WO | WO-02098424 | * | 12/2002 |
| WO | 03/037262 | | 5/2003 |
| WO | 03/059356 | | 7/2003 |
| WO | WO 03/059356 A2 | * | 7/2003 |
| WO | WO-03059356 | * | 7/2003 |
| WO | WO2004041818 A1 | | 5/2004 |
| WO | WO-2004/058150 | * | 7/2004 |
| WO | WO2005019191 A2 | | 3/2005 |
| WO | WO2005019191 A3 | | 3/2005 |
| WO | WO2008011337 A1 | | 1/2008 |

OTHER PUBLICATIONS

Dhanak et al., "Identification and Biological Characterization of Heterocyclic Inhibitors of the Hepatitis C Virus RNA-dependent RNA Polymerase," Journal of Biological Chemistry 277(41); 38322-38327 (2002).

Dhanak et al., "Identification and Biological Characterization of Heterocyclic Inhibitors of the Heptitis C Virus RNA-Dependent RNA Polymerase," 9th International Meeting on HCV and Related Viruses, Jul. 7-11, 2002; San Diego, CA; Abstract #0-3, p. 21.

McHutchison, The American Association for the Study of Liver Diseases, Hepatitis Single Topic Conference: Hepatitis C New Drug and Clinical Trials Development: Promises and Pitfalls. Abstract #5; Feb. 27-Mar. 1, 2003, Chicago, IL.

Ukrainets et al., "4-Hydroxy-2-Quinolones. 42*. Synthesis and biological Activity of 1-R-2-Oxo-3-(2H-1,2,4-Benzothiadiazine-1,1-Dioxid-3-Yl)-4-Hydroxyquinolines," Chemistry of Heterocyclic Compounds 36(3):346-350 (2000).

M. Barbero et al., *Synthetic Application of Tris(methylthio)methyl Salts. An Efficient Route to Trithioorthocarboxylic Esters from Strongly Activated Aromatic and Heteroaromatic Systems*, Synthesis pp. 22-25 (Jan. 1988).

K.J. Blight et al., *Efficient Initiation of HCV RNA Replication in Cell Culture*, Science 290:1972-4 (2000).

D.R. Buckle et al., *4-Hydroxy-3-nitro-2-quinolones and Related Compounds as Inhibitors of Allergic Reactions*, J. Med. Chem. 18(7):726-32 (1975).

I.D. Entwistle et al., *Rapid Catalytic Transfer Reduction of Aromatic Nitro Compounds to Hydroxylamines*, Tetrahedron 34(2):213-5 (1978).

H. Eschenhof et al, *A New Synthesis of 3-Deazathymidine and of a Related Phosphoramidite Synthon*, Tetrahedron 48(30):6225-30 (1992).

F. Fabis et al., *Thiaisatoic Anhydrides: Efficient Synthesis under Microwave Heating Conditions and Study of their Reactivity*, Tetrahedron 54(36):10789-800 (1998).

E. Fischer et al, *Ueber Einige Neue Indazolderivate*, Chem. Ber. 35: 2315-9 (1902).

Y. Girard et al., *A New Synthesis of 1,2,4-Benzothiadiazines and a Selective Preparation of o-Aminobenzenesulphonamides*, J. Chem. Soc. Perkin I:1043-7 (1979).

A. Goldfarb, *New Compounds. Derivatives of 2,5-Diaminobenzenesulfonamide*, J. Amer. Chem. Soc. 65(4):738-9 (1943).

M. Ikeda et al., *Selectable Subgenomic and Genome-Length Dicistronic RNAs Derived from an Infectious Molecular Clone of the HCV-N Strain of Hepatitis C Virus Replicate Efficiently in cultured Huh7 Cells*, J. Virol. 76(6):2997-3006 (2002).

S.N. Kovalenko et al., *Recyclization of 2-Imino-2H-1-Benzopyrans Under the Influence of Nucleophilic Reagents. 2. Reaction of 2-Iminocoumarin-3-carboxamindes with oAminobenzenesulfonamide*, Chem. Het. Com. 34(7):791-5 (1998).

D.J. LeCount et al., *Synthesis of 3-Diethylamino-1-ethylisothiazolo[3,4-b]pyridinium Perchlorate and an Improved Route to 3-Azaisatoic Anhydride*, Synthesis pp. 972-3 (1982).

D.C. Leysen et al., *Thiazolopyridine Analogs of Naldixic Acid 1. Thiazolo[5,4-b]pyridines*, J. Het. Chem. 21:401-6 (1984).

J.F. Morrison et al., *Approaches to the Study and Analysis of the Inhibition of Enzymes by Slow- and Tight-Binding Inhibitors*, Comm. Mol. Cell. Biophys. 2:347-68 (1985).

F.E. Nielsen et al., *6-Chloro-3-alkylamino-4h-thieno[3,2-e]-1,2,4-thiadiazine 1,1-Dioxide Derivatives Potently and Selectively Activate ATP Sensitive Potassium Channels of Pancreatic β-Cells*, J. Med. Chem. 45(19):4171-87 (2002).

M. Rowley et al., *3-Acyl-4-hydroxyquinolin-2(1H)-ones. Systemically active anticonvulsants acting by antagonism at the glycine site of the N-methyl-D-aspartate receptor complex*, J. Med. Chem. 36(22):3386-96 (1993).

W. Stadlbauer et al., *Ring Closure and Rearrangement Reactions of 4-Azido-2-oxoquinoline-3-carboxylates and 4-Azidocoumarin-3-carboxylates [1]*, J. Het. Chem. 35:627-36 (1998).

P. Stanetty et al., *An Improved Synthetic Approach to Thieno[2,3-d]-1,2,3-thiadiazole-carboxylates via Diazotization of Aminothiophene Derivatives*, J. Het. Chem 36:761-5 (1999).

J.G. Topliss et al., *Antihypertensive Agents. I Non-diuretic 2H-1 ,2,4-Benzothiadiazine 1,1-Dioxides*, J. Med. Chem. 6(2):122-7 (1963).

B. Unterhalt et al., *2,3-Dihydro-3-oxo-thienoisothiazol-1,1-dioxide and ihre 3-Thioxo-Verbindungen*, Pharmazie 6:115-7 (1994).

J.D. Warren et al., *Synthesis of substituted 2H-1,3-oxazine-2,6-diones by Reaction of Trimethylsilyl Azide with Maleic Anhydrides*, J. Org. Chem. 40(6):743-6 (1975).

S.S. Washburne et al., *Ethyl Oxaorotate—A New Synthetic Route to 1,3-Oxazine-2,6-Diones*, Tetrahedron Let. 4: 243-6 (1976).

M. Winn et al., *2-(Alkylamino)nicotinic acid and analogs. Potent angiotensin II antagonists*, J. Med. Chem. 36(18):2676-88 (1993).

* cited by examiner

SEQUENCE LISTING

<160> NUMBER OF SEQ ID NOS: 1

<210> SEQ ID NO 1
<211> LENGTH: 171
<212> TYPE: RNA
<213> ORGANISM: Hepatitis C Virus

<400> SEQUENCE: 1
gggcgaauug ggcccucuag augcaugcuc gagcggccgc cagugugaug gauaucugca 60
gaauucgccc uugguggcuc caucuuagcc cuagucacgg cuagcuguga aagguccgug 120
agccgcuuga cugcagagag ugcugauacu ggccucucug cagaucaagu c 171

ANTI-INFECTIVE AGENTS

This application claims priority to U.S. Provisional Application Ser. No. 60/509,107, filed Oct. 6, 2003, U.S. Provisional Application Ser. No. 60/489,448, filed Jul. 23, 2003, U.S. Provisional Application Ser. No. 60/461,784, filed Apr. 10, 2003, and U.S. Provisional Application Ser. No. 60/423,209, filed Nov. 1, 2002.

TECHNICAL FIELD

The present invention provides novel anti-infective agents. Specifically, the present invention provides an HCV polymerase inhibiting compound, and a composition comprising a therapeutically effective amount of said compound. The present invention also provides a method for inhibiting hepatitis C virus (HCV) polymerase, a method for inhibiting HCV viral replication, and a method for treating or preventing HCV infection. Processes for making said compounds, and synthetic intermediates employed in said processes, are also provided.

BACKGROUND OF THE INVENTION

Infection with hepatitis C virus (HCV) is a major cause of human liver disease throughout the world. More than 85% of all infected individuals become chronically infected. Chronic HCV infection accounts for 30% of all cirrhosis, end-stage liver disease, and liver cancer in the United States. The CDC estimates that the number of deaths due to HCV will increase to 38,000/year by the year 2010.

While initially therapy consisted of interferon alone, the combination of interferon alpha-2b with ribavirin for either 24 or 48 weeks is currently the most efficacious approved therapy for the treatment of chronic HCV infection. However, there are many adverse side effects associated with this therapy (flu-like symptoms, leukopenia, thrombocytopenia, and depression from interferon, as well as anemia induced by ribavirin). Furthermore, this therapy is less effective against infections caused by HCV genotype 1 which constitutes about 75% of all HCV infections.

Based on the foregoing, there exists a significant need to identify compounds with the ability to inhibit HCV. The present invention provides novel anti-infective agents which are HCV polymerase inhibitors.

SUMMARY OF THE INVENTION

The present invention provides a compound of formula (I)

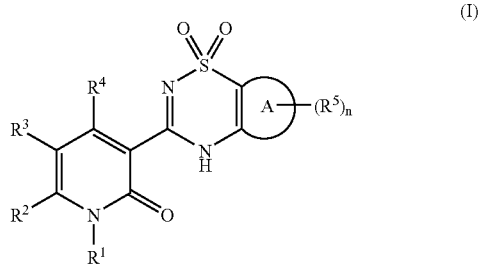

(I)

or a pharmaceutically acceptable salt form, stereoisomer or tautomer thereof, wherein:

A is a monocyclic or bicyclic ring selected from the group consisting of aryl, cycloalkyl, cycloalkenyl, heteroaryl and heterocycle;

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN—$, $R_aR_bNalkyl-$, $R_aR_bNC(O)alkyl-$, $R_aR_bNC(O)Oalkyl-$, $R_aR_bNC(O)NR_calkyl-$, $R_fR_gC=N—$ and $R_kO—$, wherein $R^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_e$), $—SR_c$, $—S(O)R_c$, $—S(O)_2R_c$, $—OR_c$, $—N(R_c)(R_e)$, $—C(O)R_c$, $—C(O)OR_c$ and $—C(O)NR_cR_e$;

$R^2$ and $R^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, $—N(R_a)(R_b)$, $R_aR_bNC(O)—$, $—SR_a$, $—S(O)R_a$, $—S(O)_2R_a$ and $R_aC(O)—$; wherein $R^2$ and $R^3$ are independently substituted with 0, 1, 2 or 3 substituents independently selected from the group consisting of $R_a$, alkyl, alkenyl, alkynyl, oxo, halo, cyano, nitro, haloalkyl, -(alkyl)($OR_k$), -(alkyl)($NR_aR_b$), $—SR_a$, $—S(O)R_a$, $—S(O)_2R_a$, $—OR_k$, $—N(R_a)(R_b)$, $—C(O)R_a$, $—C(O)OR_a$ and $—C(O)NR_aR_b$;

alternatively, $R^2$ and $R^3$, together with the carbon atoms to which they are attached form a five- or six-membered ring selected from the group consisting of aryl, cycloalkyl, heteroaryl and heterocycle, wherein said aryl, cycloalkyl, heteroaryl and heterocycle is optionally substituted with $(R^6)_m$;

$R^4$ is selected from the group consisting of alkoxy, arylalkoxy, aryloxy, halo, hydroxy, $R_aR_bN—$, $N_3—$, $—R_eS—$, wherein $R^4$ is independently substituted with 0, 1 or 2 substituents independently selected from the group consisting of halo, nitro, cyano, $—OH$, $—NH_2$, and $—COOH$;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydroxyalkyl, cycloalkyl, cyano, cyanoalkyl, nitro, $R_aR_bN—$, $R_aC(O)—$, $R_aS—$, $R_a(O)S—$, $R_a(O)_2S—$, $R_aR_bNalkyl-$, $R_a(O)SN(R_f)—$, $R_aSO_2N(R_f)—$, $R_a(O)SN(R_f)alkyl-$, $R_aSO_2N(R_f)alkyl-$, $R_aR_bNSO_2N(R_f)—$, $R_aR_bNSO_2N(R_f)alkyl-$, $R_aR_bNC(O)—$, $R_kOC(O)—$, $R_kOC(O)alkyl-$, $R_kOalkyl-$, $R_aR_bNSO_2—$, $R_aR_bNSO_2alkyl-$, $(R_bO)(R_a)P(O)O—$ and $—OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $—SR_c$, $—S(O)R_c$, $—S(O)_2R_c$, $—OR_c$, $—N(R_c)(R_d)$, $—C(O)R_c$, $—C(O)OR_c$ and $—C(O)NR_cR_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), $—SR_a$, $—S(O)R_a$, $—S(O)_2R_a$, $—OR_k$, $—N(R_a)(R_b)$, $—C(O)R_a$, $—C(O)OR_a$ and $—C(O)NR_aR_b$; wherein each $R^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, R$_c$R$_d$N—, R$_k$O—, R$_k$Oalkyl-, R$_c$R$_d$Nalkyl-, R$_c$R$_d$NC(O)alkyl-, R$_c$SO$_2$—, R$_c$SO$_2$alkyl-, R$_c$C(O)—, R$_c$C(O)alkyl-, R$_c$OC(O)—, R$_c$OC(O)alkyl-, R$_c$R$_d$NalkylC(O)—, R$_c$R$_d$NC(O)—, R$_c$R$_d$NC(O)Oalkyl-, R$_c$R$_d$NC(O)N(R$_e$)alkyl-, wherein R$_a$ and R$_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, R$_a$ and R$_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR), -(alkyl)(NR$_c$R$_d$), -(alkyl)SO$_2$NR$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$_c$ and R$_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each R$_c$ and R$_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, R$_c$ and R$_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

R$_e$ is selected from the group consisting of hydrogen, alkenyl, alkyl and cycloalkyl;

R$_f$, R$_g$ and R$_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each R$_f$, R$_g$ and R$_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, R$_f$ and R$_g$ together with the carbon atom to which they are attached form a three- to seven-membered ring selected from the group consisting of cycloalkyl, cycloalkenyl and heterocycle;

alternatively, R$_f$ and R$_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

R$_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, R$_a$R$_b$Nalkyl-, R$_a$Oalkyl-, R$_a$R$_b$NC(O)—, R$_a$R$_b$NC(O)alkyl, R$_a$S—, R$_a$S(O)—, R$_a$SO$_2$—, R$_a$S-alkyl-, R$_a$(O)Salkyl-, R$_a$SO$_2$alkyl-, R$_a$OC(O)—, R$_a$OC(O)alkyl-, R$_a$C(O)—, R$_a$C(O)alkyl-, wherein each R$_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(N$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

m is 0, 1, 2, 3, or 4; and n is 0, 1, 2, 3, or 4;

with the proviso that when A is a monocyclic ring other than

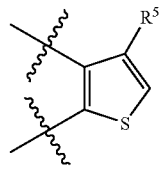

and R$^4$ is alkoxy, aryloxy, hydroxy or R$_e$S—, and R$^5$ is hydrogen, alkenyl, alkoxy, alkyl, alkynyl, aryl, halo, heteroaryl, heterocyclealkyl, cycloalkyl, cyano, nitro, R$_a$R$_b$N—, R$_a$C(O)—, R$_a$S—, R$_a$(O)S—, R$_a$(O)$_2$S—, R$_a$SO$_2$N(R$_f$)—, R$_a$R$_b$NC(O)—, R$_k$OC(O)—, R$_a$R$_b$NSO$_2$— or —OR$_k$, and R$^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)

$NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl;

and with the further proviso that when A is

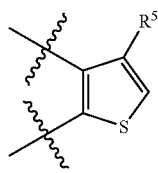

and $R^4$ is hydroxy or $R_eS$—, and $R^5$ is hydrogen, unsubstituted alkyl, halo or —$OR_k$, and $R^6$ is hydrogen, alkyl, alkenyl, alkynyl, halo, cyano, nitro, aryl, heteroaryl, heterocyclealkyl, —$SR_a$, —$S(O)R_a$, —$S(O)_2R_a$, —$OR_k$, —$N(R_a)(R_b)$, —$C(O)R_a$, —$C(O)OR_a$ and —$C(O)NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

The present invention also provides the processes of making a compound of the present invention and intermediates employed in the processes.

The present invention further provides a pharmaceutical composition comprising a therapeutically effective amount of the compound or combination of compounds of the present invention or a pharmaceutically acceptable salt form thereof, and a pharmaceutically acceptable carrier.

The present invention also provides a method of treating or preventing infection caused by an RNA-containing virus comprising administering to a patient in need of such treatment the pharmaceutical composition of the present invention.

The present invention still further provides a method of inhibiting the replication of an RNA-containing virus comprising contacting said virus with a therapeutically effective amount of a compound or combination of compounds of the present invention or a pharmaceutically acceptable salt thereof.

The present invention yet further provides a method of treating or preventing infection caused by an RNA-containing virus comprising administering to a patient in need of such treatment the pharmaceutical composition of the present invention.

DETAILED DESCRIPTION OF THE INVENTION

As used in the present specification the following terms have the meanings indicated:

As used herein, the singular forms "a", "an", and "the" may include plural reference unless the context clearly dictates otherwise.

The term "alkyl," as used herein, refers to a group derived from a straight or branched chain saturated hydrocarbon containing 1, 2, 3, 4, 5, 6, 7, 8, 9 or 10 carbon atoms. Examples of alkyl groups include butyl, methyl, 2-methylbutyl, and the like.

The term "alkenyl," as used herein, refers to a straight or branched chain group of 2, 3, 4, 5, 6, 7, 8, 9 or 10 carbon atoms containing at least one carbon-carbon double bond. Examples of alkenyl groups include allyl, propenyl, 3-methyl-2-butenyl, and the like.

The term "alkynyl," as used herein, refers to a straight or branched chain hydrocarbon of 2, 3, 4, 5, 6, 7, 8, 9 or 10 carbon atoms containing at least one carbon-carbon triple bond. Examples of alkynyl groups include ethynyl, 2-methyl-3-butynyl, 3-pentynyl, and the like.

The term "alkoxy," as used herein, refers to an alkyl group attached to the parent molecular moiety through an oxygen atom. Examples of alkoxy groups include tert-butoxy, methoxy, isopropoxy, and the like.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl," as used herein, refers to an alkyl group substituted by at least one alkoxy group.

The term "alkoxycarbonyl," as used herein, refers to an alkoxy group attached to the parent molecular moiety through a carbonyl group. Examples of alkoxycarbonyl groups include tert-butoxycarbonyl, ethoxycarbonyl, methoxycarbonyl, and the like.

The term "alkoxycarbonylalkyl," as used herein, refers to an alkoxycarbonyl group attached to the parent molecular moiety through an alkyl group.

The term "alkylcarbonyl," as used herein, refers to an alkyl group attached to the parent molecular moiety through a carbonyl group. Examples of alkylcarbonyl groups include acyl, butanoyl, 2,2-dimethylpropanoyl, and the like.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylsulfanyl," as used herein, refers to an alkyl group attached to the parent molecular moiety through a sulfur atom. Examples of alkylsulfanyl groups include methylsulfanyl, (1-methylethyl)sulfanyl, (2-methylpropyl)sulfanyl, and the like.

The term "alkylsulfanylalkyl," as used herein, refers to an alkylsulfanyl group attached to the parent molecular moiety through an alkyl group.

The term "alkylsulfinyl," as used herein, refers to an alkyl group attached to the parent molecular moiety through a —S(O)— group.

The term "alkylsulfinylalkyl," as used herein, refers to an alkylsulfinyl group attached to the parent molecular moiety through an alkyl group.

The term "alkylsulfonyl," as used herein, refers to an alkyl group attached to the parent molecular moiety through a —$S(O)_2$— group.

The term "alkylsulfonylalkyl," as used herein, refers to an alkylsulfonyl group attached to the parent molecular moiety through an alkyl group.

The term "aryl" as used herein, refers to a phenyl group, or a bicyclic or tricyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Examples of aryl groups include anthracenyl, azulenyl, fluorenyl, indanyl, indenyl, naphthyl, phenyl, tetrahydronaphthyl, and the like. The aryl groups of the present invention can be connected to the parent molecular moiety through any substitutable carbon atom of the group. The aryl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_e$, —$N(R_e)SO_2NR_aR_b$, —$N(R_e)SO_2N(R_e)C(O)OR_a$, —$C(O)R_e$, —$C(O)OR_a$, —$C(O)NR_aR_b$, cycloalkyl, cycloalkenyl, heterocycle, a second aryl group and heteroaryl; wherein each of the alkyl, alkenyl and alkynyl is independently substituted with 0, 1, 2 or 3 substituents independently selected from the group consisting of cyano, formyl, halo, nitro, oxo, —$OR_a$, —$OC(O)R_e$, —$OC(O)OR_a$, —$OC(O)NR_aR_b$, —$OSO_2R_e$, —$OSO_2NR_aR_b$, —$SR_a$, —$SOR_e$, —$SO_2R_e$, —$SO_2OR_e$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_e$, —$C(O)R_a$, —$C(O)OR_a$, —$C(O)NR_aR_b$, cycloalkyl, cycloalkenyl, heterocycle, a second aryl group and heteroaryl; wherein $R_a$, $R_b$ and $R_e$ are defined herein, and wherein the second aryl group, the heteroaryl, the cycloalkyl, the cycloalkenyl and the heterocycle can be substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, —$NH_2$, —N(H)(alkyl), —N(alkyl)$_2$, —C(O)OH, —C(O)O(alkyl), —C(O)NH$_2$, —C(O)N(H)(alkyl), —C(O)N(alkyl)$_2$ and oxo.

The term "arylalkenyl," as used herein, refers to an aryl group attached to the parent molecular moiety through an alkenyl group.

The term "arylalkoxy," as used herein, refers to an arylalkyl group attached to the parent molecular moiety through an oxygen atom.

The term "arylalkyl," as used herein, refers to an aryl group attached to the parent molecular moiety through an alkyl group.

The term "arylcarbonyl," as used herein, refers to an aryl group attached to the parent molecular moiety through a carbonyl group.

The term "arylcarbonylalkyl" as used herein, means an arylcarbonyl group, as defined herein, appended to the parent molecular moiety through an alkyl group, as defined herein.

The term "aryloxy," as used herein, refers to an aryl group attached to the parent molecular moiety through an oxygen atom.

The term "aryloxyalkyl," as used herein, refers to an aryloxy group attached to the parent molecular moiety through an alkyl atom.

The term "arylsulfanyl," as used herein, refers to an aryl group attached to the parent molecular moiety through a sulfur atom.

The term "arylsulfanylalkyl," as used herein, refers to an arylsulfanyl group attached to the parent molecular moiety through an alkyl group.

The term "arylsulfonyl," as used herein, refers to an aryl group attached to the parent molecular moiety through a sulfonyl group.

The term "arylsulfonylalkyl," as used herein, refers to an arylsulfonyl group attached to the parent molecular moiety through an alkyl group.

The term "carboxy," as used herein, refers to —$CO_2H$.

The term "carboxyalkyl," as used herein, refers to a carboxy group attached to the parent molecular moiety through an alkyl group.

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic, partially unsaturated, monocyclic, bicyclic or tricyclic ring system, having three to fourteen carbon atoms and zero heteroatom. Examples of cycloalkenyl groups include cyclohexenyl, octahydronaphthalenyl, norbornylenyl, and the like. The cycloalkenyl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$ cycloalkyl, a second cycloalkenyl, heterocycle, aryl, heteroaryl and ethylenedioxy; wherein each of the alkyl, alkenyl and alkynyl is independently substituted with 0, 1, 2 or 3 substituents independently selected from the group consisting of cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, cycloalkyl, a second cycloalkenyl, heterocycle, aryl and heteroaryl; wherein $R_a$, $R_b$ and $R_e$ are defined herein, and wherein the cycloalkyl, the second cycloalkenyl, the heterocycle, the aryl and the heteroaryl can be substituted with 0, 1, 2 or 3 substituents independently selected from the group consisting of —OH, —O(alkyl), alkyl, alkenyl, alkynyl, cyano, formyl, halo, oxo, haloalkoxy, haloalkyl, nitro, oxo, —$NH_2$, —N(H)(alkyl), —N(alkyl)$_2$, —C(O)OH, —C(O)O(alkyl), —C(O)NH$_2$, —C(O)N(H)(alkyl), and —C(O)N(alkyl)$_2$.

The term "cycloalkenylalkyl," as used herein, refers to a cycloalkenyl group attached to the parent molecular moiety through an alkyl group.

The term "cycloalkyl," as used herein, refers to a saturated monocyclic, bicyclic, or tricyclic hydrocarbon ring system having three to fourteen carbon atoms and zero heteroatom. Examples of cycloalkyl groups include cyclopropyl, cyclobutyl, cyclopentyl, cyclohexyl, cycloheptyl, bicyclo[3.1.1]heptyl, 6,6-dimethylbcyclo[3.1.1]heptyl, adamantyl, and the like. The cycloalkyl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, a second cycloalkyl, cycloalkenyl, heterocycle, aryl, heteroaryl and ethylenedioxy; wherein each of the alkyl, alkenyl and alkynyl is independently substituted with 0, 1, 2 or 3 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —SOR$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_b$, —C(O)NR$_a$R$_b$, a second cycloalkyl, cycloalkenyl, heterocycle, aryl and heteroaryl; wherein R$_a$, R$_b$ and R$_e$ are defined herein, and wherein the second cycloalkyl, the cycloalkenyl, the heterocycle, the aryl and the heteroaryl can be substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, oxo, —NH$_2$, —N(H)(alkyl), —N(alkyl)$_2$, —C(O)OH, —C(O)O(alkyl), —C(O)NH$_2$, —C(O)N(H)(alkyl), and —C(O)N(alkyl)$_2$.

The term "cycloalkylalkenyl," as used herein, refers to a cycloalkyl group attached to the parent molecular moiety through an alkenyl group.

The term "cycloalkylalkyl," as used herein, refers to a cycloalkyl group attached to the parent molecular moiety through an alkyl group.

The term "formyl," as used herein, refers to —CHO.

The term "formylalkyl," as used herein, refers to a formyl group attached to the parent molecular moiety through an alkyl group.

The terms "halo," and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to a haloalkoxy group attached to the parent molecular moiety through an alkyl group.

The term "haloalkyl," as used herein, refers to an alkyl group substituted by one, two, three, or four halogen atoms.

The term "heteroaryl," as used herein, refers to an aromatic five- or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkyl group, as defined herein, a heterocycle group, as defined herein, or an additional heteroaryl group. The term "heteroaryl" also includes tricyclic systems where a bicyclic system is fused to a phenyl group, a monocyclic cycloalkyl group, as defined herein, a heterocycle group, as defined herein, or an additional heteroaryl group. The heteroaryl groups are connected to the parent molecular moiety through any substitutable carbon or nitrogen atom in the groups. Examples of heteroaryl groups include benzothienyl, benzoxazolyl, benzimidazolyl, benzoxadiazolyl, dibenzofuranyl, dihydrobenzothiazolyl, furanyl, imidazolyl, indazolyl, indolyl, isoindolyl, isoxazolyl, isoquinolinyl, isothiazolyl, oxadiazolyl, oxazolyl, thiazolyl, thienopyridinyl, thienyl, triazolyl, thiadiazolyl, tetrazolyl, pyridyl, pyridazinyl, pyrimidinyl, pyrazinyl, pyrazolyl, pyrrolyl, quinolinyl, tetrahydroquinolinyl, tetrahydropyranyl, triazinyl, and the like. The heteroaryl groups of the present invention can be substituted with 0, 1, 2, 3, 4 or 5 substituents independently selected from the group consisting of alkyl, alkenyl, alkynyl, cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —SOR$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, cycloalkyl, cycloalkenyl, heterocycle, aryl and a second heteroaryl group; wherein each of the alkyl, alkenyl and alkynyl is independently substituted with 0, 1, 2 or 3 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —SOR$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, cycloalkyl, cycloalkenyl, heterocycle, aryl and a second heteroaryl group; wherein R$_a$, R$_b$ and R$_e$ are defined herein, and wherein the second heteroaryl group, the aryl, the cycloalkyl, the cycloalkenyl and the heterocycle can be independently substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, —NH$_2$, —N(H)(alkyl), —N(alkyl)$_2$, —C(O)OH, —C(O)O(alkyl), —C(O)NH$_2$, —C(O)N(H)(alkyl), —C(O)N(alkyl)$_2$ and oxo. In addition, The nitrogen heteroatoms can be optionally quaternized or oxidized to the N-oxide. Also, the nitrogen containing rings can be optionally N-protected.

The term "heteroarylalkenyl," as used herein, refers to a heteroaryl group attached to the parent molecular moiety through an alkenyl group.

The term "heteroarylalkyl," as used herein, refers to a heteroaryl group attached to the parent molecular moiety through an alkyl group.

The term "heteroarylsulfonyl," as used herein, refers to a heteroaryl group attached to the parent molecular moiety through a sulfonyl group.

The term "heteroarylsulfonylalkyl," as used herein, refers to a heteroarylsulfonyl group attached to the parent molecular moiety through a alkyl group.

The term "heterocycle," as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic systems where a heterocycle ring is fused to a phenyl group, a monocyclic cycloalkenyl group, as defined herein, a monocyclic cycloalkyl group, as defined herein, or an additional monocyclic heterocycle group. The term "heterocycle" also includes tricyclic systems where a bicyclic system is fused to a phenyl group, a monocyclic cycloalkenyl group, as defined herein, a monocyclic cycloalkyl group, as defined herein, or an additional monocyclic heterocycle group. The heterocycle groups of the invention are connected to the parent molecular moiety through any substitutable carbon or nitrogen atom in the group. Examples of heterocycle groups include benzoxazinyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, tetrahydropyranyl, and the like. The heterocycle groups of the present invention can be substituted with 0, 1, 2, 3, 4 or 5 substituents independently selected from the group consisting of alkyl, alkenyl, alkynyl, cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —SOR$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, cycloalkyl, cycloalkenyl, a second heterocycle, aryl, heteroaryl and ethylenedioxy; wherein each of the alkyl, alkenyl and alkynyl is independently substituted with 0, 1, 2 or 3 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —SOR$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$R$_b$, —N(R$_e$)C(O) NR$_a$R$_b$, —N(R$_c$)SO$_2$R$_a$, —N(R$_e$)SO$_2$NR$_a$R$_b$, —N(R$_e$)SO$_2$N (R$_e$)C(O)OR$_a$, —C(O)R$_a$, —C(O)OR$_a$, —C(O)NR$_a$R$_b$, cycloalkyl, cycloalkenyl, a second heterocycle, aryl and heteroaryl; wherein R$_a$, R$_b$ and R$_e$ are defined herein, and wherein the cycloalkyl, cycloalkenyl, the second heterocycle, the aryl and the heteroaryl can be independently substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, oxo, —NH$_2$, —N(H)(alkyl), —N(alkyl)$_2$, —C(O)OH, —C(O)O (alkyl), —C(O)NH$_2$, —C(O)N(H)(alkyl), and —C(O)N (alkyl)$_2$. In addition, The nitrogen heteroatoms can be optionally quaternized or oxidized to the N-oxide. Also, the nitrogen containing heterocyclic rings can be optionally N-protected.

The term "heterocyclealkenyl," as used herein, refers to a heterocycle group attached to the parent molecular moiety through an alkenyl group.

The term "heterocyclealkyl," as used herein, refers to a heterocycle group attached to the parent molecular moiety through an alkyl group.

The term "heterocyclecarbonyl" as used herein, means a heterocycle, as defined herein, appended to the parent molecular moiety through a carbonyl group, as defined herein. Representative examples of heterocyclecarbonyl include, but are not limited to, pyrrolidinylcarbonyl and piperazin-1-ylcarbonyl.

The term "hydroxy," as used herein, refers to —OH.

The term "hydroxyalkyl," as used herein, refers to an alkyl group substituted by at least one hydroxy group.

The term "nitro," as used herein, refers to —NO$_2$.

The term "nitroalkyl," as used herein, refers to an alkyl group substituted by at least one nitro group.

The term "oxo," as used herein, refers to =O.

The term "sulfanyl," as used herein, refers to —S—.

The term "sulfinyl," as used herein, refers to —SO—.

The term "sulfonyl," as used herein, refers to —SO$_2$—.

It is understood that alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkynyl, alkylsulfanyl, alkylsulfanylalkyl, alkylsulfinyl, alkylsulfinylalkyl, alkylsulfonyl, alkylsulfonylalkyl, arylalkenyl, arylalkoxy, arylalkyl, aryloxyalkyl, arylsulfanylalkyl, arylsulfonylalkyl, carboxyalkyl, cyanoalkyl, cycloalkenylalkyl, cycloalkenylalkenyl, cycloalkylalkyl, formylalkyl, haloalkoxy, haloalkoxyalkyl, haloalkyl, heteroarylalkenyl, heteroarylalkyl, heterosulfonylalkyl, heterocyclealkenyl, heterocyclealkyl, hydroxyalkyl and nitroalkyl may optionally be substituted.

In a first embodiment the present invention provides a compound of formula (I)

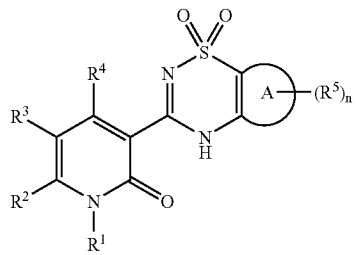

(I)

or a pharmaceutically acceptable salt form, stereoisomer or tautomer thereof, wherein:

A is a monocyclic or bicyclic ring selected from the group consisting of aryl, cycloalkyl, cycloalkenyl, heteroaryl and heterocycle;

R$^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, R$_a$R$_b$N—, R$_a$R$_b$Nalkyl-, R$_a$R$_b$NC(O)alkyl-, R$_a$R$_b$NC(O)Oalkyl-, R$_a$R$_b$NC(O)NR$_c$alkyl-, R$_f$R$_g$C=N— and R$_k$O—, wherein R$^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_e$), —SR$_c$, —S(O)R$_c$, —S(O)$_2$R$_c$, —OR$_c$, —N(R$_c$)(R$_e$), —C(O)R$_c$, —C(O)OR$_a$ and —C(O)NR$_a$R$_b$;

R$^2$ and R$^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$ and R$_a$C(O)—; wherein R$^2$ and R$^3$ are independently substituted with 0, 1, 2 or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$;

alternatively, R$^2$ and R$^3$, together with the carbon atoms to which they are attached form a five- or six-membered ring selected from the group consisting of aryl, cycloalkyl, heteroaryl and heterocycle, wherein said aryl, cycloalkyl, heteroaryl and heterocycle is optionally substituted with (R$^6$)$_m$;

R$^4$ is selected from the group consisting of alkoxy, arylalkoxy, aryloxy, halo, hydroxy, R$_a$R$_b$N—, N$_3$—, R$_e$S—, wherein R$^4$ is independently substituted with 0, 1 or 2 substituents independently selected from the group consisting of halo, nitro, cyano, —OH, —NH$_2$, and —COOH;

R$^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, R$_a$R$_b$N—, R$_a$C(O)—, R$_a$S—, R$_a$(O)S—, R$_a$(O)$_2$S—, R$_a$R$_b$Nalkyl-, R$_a$(O)SN(R$_f$)—, R$_a$SO$_2$N(R$_f$)—, R$_a$(O)SN(R$_f$)alkyl-, R$_a$SO$_2$N(R$_f$)alkyl-, R$_a$R$_b$NSO$_2$N(R$_f$)—, R$_a$R$_b$NSO$_2$N(R$_f$)alkyl-, R$_a$R$_b$NC(O)—, R$_k$OC(O)—, R$_k$OC (O)alkyl-, R$_k$Oalkyl-, R$_a$R$_b$NSO$_2$—, R$_a$R$_b$NSO$_2$alkyl-, (R$_b$O)(R$_a$)P(O)O— and —OR$_k$, wherein each R$^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O) R$_c$, —S(O)$_2$R$_c$, —OR$_c$, —N(R$_c$)(R$_d$), —C(O)R$_c$, —C(O) OR$_c$ and —C(O)NR$_c$R$_d$;

R$^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$;

wherein each $R^6$ is independently substituted with 0, 1, 2 or 3 substituents independently selected from the group consisting of alkyl, alkenyl, alkynyl, oxo, halo, haloalkyl, cyano, nitro, —$OR_a$, —$NR_aR_b$, —$SR_a$, —$SOR_a$, —$SO_2R_a$, —C(O) $OR_a$, —C(O)$NR_aR_b$ and —NC(O)$R_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN$—, $R_kO$—, $R_kO$alkyl-, $R_cR_dN$alkyl-, $R_cR_dNC(O)$alkyl-, $R_cSO_2$—, $R_cSO_2$alkyl-, $R_cC(O)$—, $R_cC(O)$alkyl-, $R_cOC(O)$—, $R_cOC(O)$alkyl-, $R_cR_dN$alkylC(O)—, $R_cR_dNC(O)$—, $R_cR_dNC(O)O$alkyl-, $R_cR_dNC(O)N(R_e)$alkyl-, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(O$R_c$), -(alkyl)(N$R_cR_d$), —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(O$R_c$), -(alkyl)(N$R_cR_d$), -(alkyl)SO$_2$N$R_cR_d$, -alkylC(O)N$R_cR_d$, —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

$R_c$ and $R_d$, at each occurrence, are independently selected from the group consisting of hydrogen, —$NR_fR_h$, —$OR_f$, —CO($R_f$), —$SR_f$, —$SOR_f$, —$SO_2R_f$, —C(O)$NR_fR_h$, —$SO_2NR_fR_h$, —C(O)$OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(O$R_f$), -(alkyl)(N$R_fR_h$), —$SR_f$, —S(O)$R_f$, —S(O)$_2R_f$, —$OR_f$, —N($R_f$)($R_h$), —C(O)$R_f$, —C(O)$OR_f$, —C(O)$NR_fR_h$, —C(O)N(H)$NR_fR_h$, —N($R_e$)C(O)$OR_f$, —N($R_e$)SO$_2NR_fR_h$, —N($R_e$)C(O)$NR_fR_h$, -(alkyl)N($R_e$)C(O)$OR_f$, -(alkyl)N($R_e$)SO$_2NR_fR_h$, and -alkylN($R_e$)C(O)$NR_fR_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(O$R_f$), -(alkyl)(N$R_fR_h$), —$SR_f$, —S(O)$R_f$, —S(O)$_2R_f$, —$OR_f$, —N($R_f$)($R_h$), —C(O)$R_f$, —C(O)$OR_f$ and —C(O)$NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_aS$—, $R_aS(O)$—, $R_aSO_2$—, $R_a$S-alkyl-, $R_a(O)S$alkyl-, $R_aSO_2$alkyl-, $R_aOC(O)$—, $R_aOC(O)$alkyl-, $R_aC(O)$—, $R_aC(O)$alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(O$R_c$), -(alkyl)(N$R_cR_d$), —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

m is 0, 1, 2, 3, or 4; and
n is 0, 1, 2, 3, or 4;
with the proviso that when A is a monocyclic ring other than

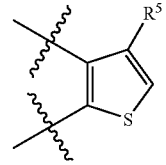

and $R^4$ is alkoxy, aryloxy, hydroxy or $R_eS$—, and $R^5$ is hydrogen, alkenyl, alkoxy, alkyl, alkynyl, aryl, halo, heteroaryl, heterocyclealkyl, cycloalkyl, cyano, nitro, $R_aR_bN$—, $R_aC(O)$—, $R_aS$—, $R_a(O)S$—, $R_a(O)_2S$—, $R_aSO_2N(R_f)$—, $R_aR_bNC(O)$—, $R_kOC(O)$—, $R_aR_bNSO_2$— or —$OR_k$, and $R^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$, then R$^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl;

and with the further proviso that when A is

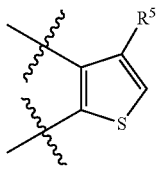

and R$^4$ is hydroxy or R$_e$S—, and R$^5$ is hydrogen, unsubstituted alkyl, halo or —OR$_k$, and R$^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$, then R$^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (I) wherein A is a monocyclic ring selected from the group consisting of aryl and heteroaryl.

For example, the present invention provides a compound of formula (I) wherein A is a bicyclic ring selected from the group consisting of heterocycle and heteroaryl.

For example, the present invention provides a compound of formula (I) wherein A is selected from the group consisting of naphthyl, indolizinyl, indolyl, isoindolyl, benzofuranyl, benzothienyl, indazolyl, benzimidazolyl, benzthiazolyl, benzoxazolyl, benzoisothiazolyl, benzoisoxazolyl, benzoxazinyl, benzothiadiazolyl, quinolinyl, isoquinolinyl, quinazolinyl, quinoxalinyl and naphthyridinyl, cinnolinyl and pteridinyl.

For example, the present invention provides a compound of formula (I) wherein R$^2$ and R$^3$, together with the carbon atoms to which they are attached, form a five- or six-membered ring selected from the group consisting of thienyl, furanyl, pyrrolyl, imidazolyl, oxazolyl, thiazolyl, isoxazolyl, isothiazolyl, pyrazolyl, oxadiazolyl, triazolyl, thiadiazolyl, tetrazolyl, phenyl, pyridyl, pyridazinyl and pyrimidinyl.

For example, the present invention provides a compound of formula (I) wherein R$^2$ and R$^3$ together with the carbon atoms to which they are attached form a cycloalkyl ring.

For example, the present invention provides a compound of formula (I) wherein R$^2$ and R$^3$ together with the carbon atoms to which they are attached form a cyclopentyl or cyclohexyl ring.

For example, the present invention provides a compound of formula (I) wherein R$^2$ and R$^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, S(O)$_2$R$_a$ and R$_a$C(O)—; wherein R$^2$ and R$^3$ are independently substituted with 0, 1, 2 or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$.

For example, the present invention provides a compound of formula (I) wherein R$^4$ is hydroxy, halo, —NH$_2$, —NH(alkyl), —N(alkyl)$_2$, —N(H)NH$_2$, —N$_3$, —N(H)(hydroxyalkyl), or R$_e$S—.

For example, the present invention provides a compound of formula (I) wherein A is aryl and R$^2$ and R$^3$, together with the carbon atoms to which they are attached form a five- or six-membered ring selected from the group consisting of phenyl, pyridyl, pyrimidinyl, pyridazinyl, thienyl, furanyl, pyrazolyl, oxazolyl, thiazolyl, imidazolyl, isoxazolyl, isothiazolyl, triazolyl, thiadiazolyl, tetrazolyl, cyclopentyl and cyclohexyl.

For example, the present invention provides a compound of formula (I) wherein A is phenyl and R$^2$ and R$^3$, together with the carbon atoms to which they are attached form a five- or six-membered ring selected from the group consisting of phenyl, pyridyl, pyrimidinyl, pyridazinyl, thienyl, furanyl, pyrazolyl, oxazolyl, thiazolyl, imidazolyl, isoxazolyl, isothiazolyl, triazolyl, thiadiazolyl, tetrazolyl, cyclopentyl and cyclohexyl.

For example, the present invention provides a compound of formula (I) wherein A is phenyl and R$^2$ and R$^3$, together with the carbon atoms to which they are attached is pyridyl.

For example, the present invention provides a compound of formula (I) wherein A is phenyl and R$^2$ and R$^3$, together with the carbon atoms to which they are attached is thienyl.

For example, the present invention provides a compound of formula (I) wherein A is heteroaryl and R$^2$ and R$^3$, together with the carbon atoms to which they are attached form a five- or six-membered ring selected from the group consisting of phenyl, pyridyl, pyrimidinyl, pyridazinyl, thienyl, furanyl, pyrrolyl, pyrazolyl, oxazolyl, thiazolyl, imidazolyl, isoxazolyl, isothiazolyl, triazolyl, thiadiazolyl, tetrazolyl, cyclopentyl and cyclohexyl.

For example, the present invention provides a compound of formula (I) wherein A is thienyl and R$^2$ and R$^3$, together with the carbon atoms to which they are attached form a five- or six-membered ring selected from the group consisting of phenyl, pyridyl, pyrimidinyl, pyridazinyl, thienyl, furanyl, pyrrolyl, pyrazolyl, oxazolyl, thiazolyl, imidazolyl, isoxazolyl, isothiazolyl, triazolyl, thiadiazolyl, tetrazolyl, cyclopentyl and cyclohexyl.

For example, the present invention provides a compound of formula (I) wherein A is thienyl, and R$^2$ and R$^3$ together with the carbon atoms to which they are attached form a phenyl ring.

For example, the present invention provides a compound of formula (I) wherein A is thienyl, and R$^2$ and R$^3$ together with the carbon atoms to which they are attached is pyridyl.

For example, the present invention provides a compound of formula (I) wherein A is pyridyl, and R$^2$ and R$^3$, together with the carbon atoms to which they are attached form a five- or six-membered ring selected from the group consisting of phenyl, pyridyl, pyrimidinyl, pyridazinyl, thienyl, furanyl, pyrrolyl, pyrazolyl, oxazolyl, thiazolyl, imidazolyl, isoxazolyl, isothiazolyl, triazolyl, thiadiazolyl, tetrazolyl, cyclopentyl and cyclohexyl.

For example, the present invention provides a compound of formula (I) wherein A is pyridyl, and R$^2$ and R$^3$ together with the carbon atoms to which they are attached form a pyridyl ring.

For example, the present invention provides a compound of formula (I) wherein A is phenyl, thienyl, pyridyl, imidazolyl, benzoxazolyl, benzoxazinyl, or benzimidazolyl, and R$^2$ and R$^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$ and R$_a$C(O)—; wherein R$^2$ and R$^3$ are independently substituted with 0, 1, 2 or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$.

For example, the present invention provides a compound of formula (I) wherein R$^2$ and R$^3$ together with the carbon atoms to which they are attached form a five- or six-membered ring selected from the group consisting of thienyl, furanyl, pyrrolyl, imidazolyl, oxazolyl, thiazolyl, isoxazolyl, isothiazolyl, pyrazolyl, oxadiazolyl, triazolyl, thiadiazolyl, tetrazolyl, phenyl, pyridyl, pyridazinyl and pyrimidinyl, and R$^4$ is hydroxy. In an even more preferred embodiment, the present invention provides a compound of formula (I) wherein A is pyridyl, phenyl, thienyl, imidazolyl, benzoxazolyl, benzimidazolyl or benzoxazinyl, R$^2$ and R$^3$ together with the carbon atoms to which they are attached form a five- or six-membered ring selected from phenyl, thienyl, pyrazolyl, pyridyl, pyrimidinyl or pyridazinyl, and R$^4$ is hydroxy.

For example, the present invention provides a compound of formula (I) wherein A is pyridyl; R$^2$ and R$^3$, together with the carbon atoms to which they are attached, form a pyridyl ring; and R$^4$ is hydroxyl.

For example, the present invention provides a compound of formula (I) wherein A is pyridyl, phenyl, thienyl, imidazolyl, benzoxazolyl, benzimidazolyl or benzoxazinyl, R$^2$ and R$^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$ and R$_a$C(O)—; wherein R$^2$ and R$^3$ are independently substituted with 0, 1, 2 or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, N(R$_a$)(R$_b$), —C(O)R$_a$, —C(O)OR$_a$ and —C(O)NR$_a$R$_b$; and R$^4$ is hydroxy.

For example, the present invention provides a compound of formula (I) wherein A is pyridyl, phenyl, thienyl, imidazolyl, benzimidazolyl, benzoxazolyl or benzoxazinyl, R$^2$ and R$^3$ together with the carbon atoms to which they are attached form five- or six-membered ring selected from the group consisting of phenyl, pyridyl, thienyl, pyrimidinyl, pyrazolyl, pyridazinyl, cyclohexyl or cyclopentyl, R$^4$ is hydroxy and R$^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, R$_a$R$_b$N—, R$_a$R$_b$Nalkyl-, R$_a$R$_b$NC(O)alkyl-, R$_f$R$_g$C=N— and R$_k$O—.

Exemplary compounds of the first embodiment of the present invention of formula (I) include, but not limited to, the following:

1-[2-(1-cyclohexen-1-yl)ethyl]-3-(1,1-dioxido-4H-1,2,4-benzothiadiazin-3-yl)-4-hydroxy-1,8-naphthyridin-2(1H)-one;
ethyl [3-(1,1-dioxido-4H-1,2,4-benzothiadiazin-3-yl)-4-hydroxy-2-oxo-1,8-naphthyridin-1(2H)-yl]acetate;
1-(3-anilinopropyl)-3-(1,1-dioxido-4H-1,2,4-benzothiadiazin-3-yl)-4-hydroxy-1,8-naphthyridin-2(1H)-one;
3-[3-(1,1-dioxido-4H-1,2,4-benzothiadiazin-3-yl)-4-hydroxy-2-oxo-1,8-naphthyridin-1(2H)-yl]propanal;
1-[3-(dimethylamino)propyl]-3-(1,1-dioxido-4H-1,2,4-benzothiadiazin-3-yl)-4-hydroxy-1,8-naphthyridin-2(1H)-one;
1-{3-[[2-(dimethylamino)ethyl](methyl)amino]propyl}-3-(1,1-dioxido-4H-1,2,4-benzothiadiazin-3-yl)-4-hydroxy-1,8-naphthyridin-2(1H)-one;
1-(2-aminoethyl)-3-(1,1-dioxido-4H-1,2,4-benzothiadiazin-3-yl)-4-hydroxy-1,8-naphthyridin-2(1H)-one;
1-[3-(diethylamino)propyl]-3-(1,1-dioxido-4H-1,2,4-benzothiadiazin-3-yl)-4-hydroxy-1,8-naphthyridin-2(1H)-one;
1-(benzyloxy)-3-(1,1-dioxido-4H-1,2,4-benzothiadiazin-3-yl)-4-hydroxy-1,8-naphthyridin-2(1H)-one;
1-(benzyloxy)-3-(1,1-dioxido-4H-1,2,4-benzothiadiazin-3-yl)-4-hydroxy-1,8-naphthyridin-2(1H)-one
3-(1,1-dioxido-4H-1,2,4-benzothiadiazin-3-yl)-4-hydroxy-1-isobutoxy-1,8-naphthyridin-2(1H)-one;
1-benzyl-4-chloro-3-(1,1-dioxido-4H-1,2,4-benzothiadiazin-3-yl)-1,8-naphthyridin-2(1H)-one;
1-butyl-4-chloro-3-(1,1-dioxido-4H-1,2,4-benzothiadiazin-3-yl)-1,8-naphthyridin-2(1H)-one;
4-amino-1-butyl-3-(1,1-dioxido-4H-1,2,4-benzothiadiazin-3-yl)-1,8-naphthyridin-2(1H)-one;
1-butyl-3-(1,1-dioxido-4H-1,2,4-benzothiadiazin-3-yl)-4-(methylamino)-1,8-naphthyridin-2(1H)-one;
1-butyl-4-(dimethylamino)-3-(1,1-dioxido-4H-1,2,4-benzothiadiazin-3-yl)-1,8-naphthyridin-2(1H)-one;
1-butyl-3-(1,1-dioxido-4H-1,2,4-benzothiadiazin-3-yl)-4-hydrazino-1,8-naphthyridin-2(1H)-one;
4-azido-1-butyl-3-(1,1-dioxido-4H-1,2,4-benzothiadiazin-3-yl)-1,8-naphthyridin-2(1H)-one;
1-butyl-3-(1,1-dioxido-4H-1,2,4-benzothiadiazin-3-yl)-4-[(2-hydroxyethyl)amino]-1,8-naphthyridin-2(1H)-one;
N-[3-(4-hydroxy-1-isopentyl-2-oxo-1,2-dihydro-1,8-naphthyridin-3-yl)-1,1-dioxido-4H-1,2,4-benzothiadiazin-7-yl]-N'-(2-phenylethyl)sulfamide;
benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;
N-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide;
benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]-1-propyldiazathiane-1-carboxylate 2,2-dioxide;
N-[3-(4-hydroxy-1-isopentyl-2-oxo-1,2-dihydro[1,8]naphthyridin-3-yl)-1,1-dioxido-4H-1,2,4-benzothiadiazin-7-yl]-N'-propylsulfamide;
methyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;
allyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;
2-propynyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;
2-cyanoethyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;
2-(trimethylsilyl)ethyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;

benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;

methyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;

benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]-1-methyldiazathiane-1-carboxylate 2,2-dioxide;

N-[3-(4-hydroxy-1-isopentyl-2-oxo-1,2-dihydro[1,8]naphthyridin-3-yl)-1,1-dioxido-4H-1,2,4-benzothiadiazin-7-yl]-N'-methylsulfamide;

2-aminoethyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide;

N-cyclopentyl-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide;

N-cyclobutyl-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide;

N-[3-(4-hydroxy-1-isopentyl-2-oxo-1,2-dihydro[1,8]naphthyridin-3-yl)-1,1-dioxido-4H-1,2,4-benzothiadiazin-7-yl]-N-(4-piperidinyl)sulfamide;

N-(2-hydroxyethyl)-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide;

3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]propanamide;

N-[3-(4-hydroxy-1-isopentyl-2-oxo-1,2-dihydro[1,8]naphthyridin-3-yl)-1,1-dioxido-4H-1,2,4-benzothiadiazin-7-yl]-1-azetidinesulfonamide;

3-hydroxy-N-[3-(4-hydroxy-1-isopentyl-2-oxo-1,2-dihydro[1,8]naphthyridin-3-yl)-1,1-dioxido-4H-1,2,4-benzothiadiazin-7-yl]-1-azetidinesulfonamide;

3-amino-N-[3-(4-hydroxy-1-isopentyl-2-oxo-1,2-dihydro[1,8]naphthyridin-3-yl)-1,1-dioxido-4H-1,2,4-benzothiadiazin-7-yl]-1-pyrrolidinesulfonamide;

N-[3-(4-hydroxy-1-isopentyl-2-oxo-1,2-dihydro[1,8]naphthyridin-3-yl)-1,1-dioxido-4H-1,2,4-benzothiadiazin-7-yl]-1-piperidinesulfonamide;

N-benzyl-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide;

ethyl 3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]benzoate;

3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]benzoic acid;

3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]benzamide;

N-(2-aminoethyl)-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide;

ethyl 1-({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)-3-piperidinecarboxylate;

methyl(2S)-1-({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)-2-pyrrolidinecarboxylate;

N-[3-(4-hydroxy-1-isopentyl-2-oxo-1,2-dihydro[1,8]naphthyridin-3-yl)-1,1-dioxido-4H-1,2,4-benzothiadiazin-7-yl]-1-pyrrolidinesulfonamide;

3-hydroxy-N-[3-(4-hydroxy-1-isopentyl-2-oxo-1,2-dihydro[1,8]naphthyridin-3-yl)-1,1-dioxido-4H-1,2,4-benzothiadiazin-7-yl]-1-piperidinesulfonamide;

N-(2-furylmethyl)-3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxamide 2,2-dioxide;

4-amino-6-(1,1-dioxido-4H-1,2,4-benzothiadiazin-3-yl)-7-hydroxythieno[3,2-b]pyridin-5(4H)-one;

6-(1,1-Dioxido-4H-1,2,4-benzothiadiazin-3-yl)-7-hydroxy-4-(isobutylamino)thieno[3,2-b]pyridin-5(4H)-one;

6-(1,1-dioxido-4H-1,2,4-benzothiadiazin-3-yl)-7-hydroxy-4-{[(3S)-3-methylcyclopentyl]amino}thieno[3,2-b]pyridin-5(4H)-one;

4-{[1-cyclopropylethyl]amino}-6-(1,1-dioxido-4H-1,2,4-benzothiadiazin-3-yl)-7-hydroxythieno[3,2-b]pyridin-5(4H)-one;

4-(butylamino)-6-(1,1-dioxido-4H-1,2,4-benzothiadiazin-3-yl)-7-hydroxythieno[3,2-b]pyridin-5(4H)-one;

6-(1,1-dioxido-4H-1,2,4-benzothiadiazin-3-yl)-4-[(2-ethylbutyl)amino]-7-hydroxythieno[3,2-b]pyridin-5(4H)-one;

6-(1,1-dioxido-4H-1,2,4-benzothiadiazin-3-yl)-7-hydroxy-4-(pentylamino)thieno[3,2-b]pyridin-5(4H)-one;

6-(1,1-dioxido-4H-1,2,4-benzothiadiazin-3-yl)-7-hydroxy-4-[(3-methylbutyl)amino]thieno[3,2-b]pyridin-5(4H)-one;

4-[(3,3-dimethylbutyl)amino]-6-(1,1-dioxido-4H-1,2,4-benzothiadiazin-3-yl)-7-hydroxythieno[3,2-b]pyridin-5(4H)-one;

6-(1,1-dioxido-4H-1,2,4-benzothiadiazin-3-yl)-7-hydroxy-4-[(3-methylbenzyl)amino]thieno[3,2-b]pyridin-5(4H)-one;

6-(1,1-dioxido-4H-1,2,4-benzothiadiazin-3-yl)-7-hydroxy-4-[(2-methylbenzyl)amino]thieno[3,2-b]pyridin-5(4H)-one;

6-(1,1-dioxido-4H-1,2,4-benzothiadiazin-3-yl)-7-hydroxy-4-[(4-methylbenzyl)amino]thieno[3,2-b]pyridin-5(4H)-one;

6-(1,1-dioxido-4H-1,2,4-benzothiadiazin-3-yl)-7-hydroxy-4-[(3-methylbut-2-enyl)amino]thieno[3,2-b]pyridin-5(4H)-one;

6-(1,1-dioxido-4H-1,2,4-benzothiadiazin-3-yl)-7-hydroxy-4-(propylamino)thieno[3,2-b]pyridin-5(4H)-one;

6-(1,1-dioxido-4H-1,2,4-benzothiadiazin-3-yl)-7-hydroxy-4-[(pyridin-4-ylmethyl)amino]thieno[3,2-b]pyridin-5(4H)-one;

6-(1,1-dioxido-4H-1,2,4-benzothiadiazin-3-yl)-7-hydroxy-4-[(pyridin-3-ylmethyl)amino]thieno[3,2-b]pyridin-5(4H)-one;

6-(1,1-dioxido-4H-1,2,4-benzothiadiazin-3-yl)-7-hydroxy-4-[(pyridin-2-ylmethyl)amino]thieno[3,2-b]pyridin-5(4H)-one;

6-(1,1-dioxido-4H-1,2,4-benzothiadiazin-3-yl)-7-hydroxy-4-[(3-methoxybenzyl)amino]thieno[3,2-b]pyridin-5(4H)-one;

6-(1,1-dioxido-4H-1,2,4-benzothiadiazin-3-yl)-4-[(3-furylmethyl)amino]-7-hydroxythieno[3,2-b]pyridin-5(4H)-one;

3-({[6-(1,1-dioxido-4H-1,2,4-benzothiadiazin-3-yl)-7-hydroxy-5-oxothieno[3,2-b]pyridin-4(5H)-yl]amino}methyl)benzonitrile;

6-(1,1-dioxido-4H-1,2,4-benzothiadiazin-3-yl)-7-hydroxy-4-[(thien-3-ylmethyl)amino]thieno[3,2-b]pyridin-5(4H)-one;

4-(cyclobutylamino)-6-(1,1-dioxido-4H-1,2,4-benzothiadiazin-3-yl)-7-hydroxythieno[3,2-b]pyridin-5(4H)-one;

4-(benzylamino)-6-(1,1-dioxido-4H-1,2,4-benzothiadiazin-3-yl)-7-hydroxythieno[3,2-b]pyridin-5(4H)-one;

4-[(cyclohexylmethyl)amino]-6-(1,1-dioxido-4H-1,2,4-benzothiadiazin-3-yl)-7-hydroxythieno[3,2-b]pyridin-5(4H)-one;

6-(1,1-dioxido-4H-1,2,4-benzothiadiazin-3-yl)-7-hydroxy-4-[(1,3-thiazol-5-ylmethyl)amino]thieno[3,2-b]pyridin-5(4H)-one;

4-[(3-bromobenzyl)amino]-6-(1,1-dioxido-4H-1,2,4-benzothiadiazin-3-yl)-7-hydroxythieno[3,2-b]pyridin-5(4H)-one;

4-(cyclohexylamino)-6-(1,1-dioxido-4H-1,2,4-benzothiadiazin-3-yl)-7-hydroxythieno[3,2-b]pyridin-5(4H)-one;

4-(cyclopentylamino)-6-(1,1-dioxido-4H-1,2,4-benzothiadiazin-3-yl)-7-hydroxythieno[3,2-b]pyridin-5(4H)-one;

4-(cycloheptylamino)-6-(1,1-dioxido-4H-1,2,4-benzothiadiazin-3-yl)-7-hydroxythieno[3,2-b]pyridin-5(4H)-one;

6-(1,1-dioxido-4H-1,2,4-benzothiadiazin-3-yl)-7-hydroxy-4-{[(1R,3S)-3-methylcyclohexyl]amino}thieno[3,2-b]pyridin-5(4H)-one;

6-(1,1-dioxido-4H-1,2,4-benzothiadiazin-3-yl)-7-hydroxy-4-{[(1R,3R)-3-methylcyclohexyl]amino}thieno[3,2-b]pyridin-5(4H)-one;

6-(1,1-dioxido-4H-1,2,4-benzothiadiazin-3-yl)-4-[(1-ethylpropyl)amino]-7-hydroxythieno[3,2-b]pyridin-5(4H)-one;

6-(1,1-dioxido-4H-1,2,4-benzothiadiazin-3-yl)-7-hydroxy-4-{[1-phenylethyl]amino}thieno[3,2-b]pyridin-5(4H)-one;

6-(1,1-dioxido-4H-1,2,4-benzothiadiazin-3-yl)-7-hydroxy-4-{[(1R)-1-methylbutyl]amino}thieno[3,2-b]pyridin-5(4H)-one;

4-(cyclobutylamino)-6-(1,1-dioxido-4H-1,2,4-benzothiadiazin-3-yl)-7-hydroxythieno[3,2-b]pyridin-5(4H)-one;

4-[(cyclopropylmethyl)amino]-6-(1,1-dioxido-4H-1,2,4-benzothiadiazin-3-yl)-7-hydroxythieno[3,2-b]pyridin-5(4H)-one;

2-({3-[4-(cyclohexylamino)-7-hydroxy-5-oxo-4,5-dihydrothieno[3,2-b]pyridin-6-yl]-1,1-dioxido-4H-1,2,4-benzothiadiazin-7-yl}oxy)acetamide;

N-({3-[1-(cyclobutylamino)-4-hydroxy-2-oxo-1,2-dihydro-3-quinolinyl]-1,1-dioxido-4H-thieno[2,3-e][1,2,4]thiadiazin-7-yl}methyl)urea;

1-benzyl-4-hydroxy-3-{7-[(methoxymethoxy)methyl]-1,1-dioxido-4H-thieno[2,3-e][1,2,4]thiadiazin-3-yl}quinolin-2(1H)-one;

1-Benzyl-4-hydroxy-3-[7-(hydroxymethyl)-1,1-dioxido-4H-thieno[2,3-e][1,2,4]thiadiazin-3-yl]quinolin-2(1H)-one;

3-(1-benzyl-4-hydroxy-2-oxo-1,2-dihydroquinolin-3-yl)-4H-thieno[2,3-e][1,2,4]thiadiazine-7-carboxylic acid 1,1-dioxide;

3-(1-benzyl-4-hydroxy-2-oxo-1,2-dihydroquinolin-3-yl)-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-(2-hydroxyethyl)-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[(1S)-2-hydroxy-1-(aminocarbonyl)ethyl]-4H-thieno[2,3-e][1,2,4]thiadiazine-7-carboxamide 1,1-dioxide;

N-(2-amino-2-oxoethyl)-3-(1-benzyl-4-hydroxy-2-oxo-1,2-dihydroquinolin-3-yl)-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[(1S)-2-hydroxy-1-methylethyl]-4H-thieno[2,3-e][1,2,4]thiadiazine-7-carboxamide 1,1-dioxide;

3-(1-benzyl-4-hydroxy-2-oxo-1,2-dihydroquinolin-3-yl)-N,N-bis(2-hydroxyethyl)-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[2-hydroxy-1-(hydroxymethyl)ethyl]-4H-thieno[2,3-e][1,2,4]thiadiazine-7-carboxamide 1,1-dioxide;

1-benzyl-4-hydroxy-3-(7-{[(3R)-3-hydroxypyrrolidin-1-yl]carbonyl}-1,1-dioxido-4H-thieno[2,3-e][1,2,4]thiadiazin-3-yl)quinolin-2(1H)-one;

3-(1-benzyl-4-hydroxy-2-oxo-1,2-dihydroquinolin-3-yl)-N-(3-hydroxypropyl)-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[(2S)-2,3-dihydroxypropyl]-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[(1S)-1-(hydroxymethyl)propyl]-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[(1S)-1-(hydroxymethyl)-2-methylpropyl]-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[2-hydroxybutyl]-4H-thieno[2,3-e][1,2,4]thiadiazine-7-carboxamide 1,1-dioxide;

3-(1-benzyl-4-hydroxy-2-oxo-1,2-dihydroquinolin-3-yl)-N-[2-hydroxy-2-(4-hydroxyphenyl)ethyl]-4H-thieno[2,3-e][1,2,4]thiadiazine-7-carboxamide 1,1-dioxide;

1-benzyl-3-[1,1-dioxido-7-(piperazin-1-ylcarbonyl)-4H-thieno[2,3-e][1,2,4]thiadiazin-3-yl]-4-hydroxyquinolin-2(1H)-one;

N-[5-(aminocarbonyl)pyridin-2-yl]-3-(1-benzyl-4-hydroxy-2-oxo-1,2-dihydroquinolin-3-yl)-4H-thieno[2,3-e][1,2,4]thiadiazine-7-carboxamide 1,1-dioxide;

[3-(1-benzyl-4-hydroxy-2-oxo-1,2-dihydroquinolin-3-yl)-1,1-dioxido-4H-thieno[2,3-e][1,2,4]thiadiazin-7-yl]methyl carbamate;

[3-(1-benzyl-4-hydroxy-2-oxo-1,2-dihydroquinolin-3-yl)-1,1-dioxido-4H-thieno[2,3-e][1,2,4]thiadiazin-7-yl]methyl aminocarbonylcarbamate;

3-[7-(azidomethyl)-1,1-dioxido-4H-thieno[2,3-e][1,2,4]thiadiazin-3-yl]-1-benzyl-4-hydroxyquinolin-2(1H)-one;

3-[7-(aminomethyl)-1,1-dioxido-4H-thieno[2,3-e][1,2,4]thiadiazin-3-yl]-1-benzyl-4-hydroxyquinolin-2(1H)-one;

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}methanesulfonamide;

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}nicotinamide;

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}morpholine-4-carboxamide;

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}-2-hydroxyacetamide;

1-[(cyclopropylmethyl)amino]-4-hydroxy-3-{7-[(methoxymethoxy)methyl]-1,1-dioxido-4H-thieno[2,3-e][1,2,4]thiadiazin-3-yl}quinolin-2(1H)-one;

1-[(cyclopropylmethyl)amino]-4-hydroxy-3-[7-(hydroxymethyl)-1,1-dioxido-4H-thieno[2,3-e][1,2,4]thiadiazin-3-yl]quinolin-2(1H)-one;

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]methanesulfonamide;

N-[(3-{1-[(cyclopropylmethyl)amino]-4-hydroxy-2-oxo-1,
2-dihydroquinolin-3-yl}-1,1-dioxido-4H-thieno[2,3-e][1,
2,4]thiadiazin-7-yl)methyl]ethanesulfonamide;
N-[(3-{1-[(cyclopropylmethyl)amino]-4-hydroxy-2-oxo-1,
2-dihydroquinolin-3-yl}-1,1-dioxido-4H-thieno[2,3-e][1,
2,4]thiadiazin-7-yl)methyl]propane-1-sulfonamide;
N-[(3-{1-[(cyclopropylmethyl)amino]-4-hydroxy-2-oxo-1,
2-dihydroquinolin-3-yl}-1,1-dioxido-4H-thieno[2,3-e][1,
2,4]thiadiazin-7-yl)methyl]propane-2-sulfonamide;
N-[(3-{1-[(cyclopropylmethyl)amino]-4-hydroxy-2-oxo-1,
2-dihydroquinolin-3-yl}-1,1-dioxido-4H-thieno[2,3-e][1,
2,4]thiadiazin-7-yl)methyl]benzenesulfonamide;
N-[(3-{1-[(cyclopropylmethyl)amino]-4-hydroxy-2-oxo-1,
2-dihydroquinolin-3-yl}-1,1-dioxido-4H-thieno[2,3-e][1,
2,4]thiadiazin-7-yl)methyl]-1-phenylmethanesulfonamide;
1-butyl-4-hydroxy-3-{7-[(methoxymethoxy)methyl]-1,1-dioxido-4H-thieno[2,3-e][1,2,4]thiadiazin-3-yl}-1,8-naphthyridin-2(1H)-one;
1-butyl-4-hydroxy-3-[7-(hydroxymethyl)-1,1-dioxido-4H-thieno[2,3-e][1,2,4]thiadiazin-3-yl]-1,8-naphthyridin-2(1H)-one;
methyl 3-(1-benzyl-4-hydroxy-2-oxo-1,2-dihydro-1,8-naphthyridin-3-yl)-4H-thieno[2,3-e][1,2,4]thiadiazine-7-carboxylate 1,1-dioxide;
4-hydroxy-3-{7-[(methoxymethoxy)methyl]-1,1-dioxido-4H-thieno[2,3-e][1,2,4]thiadiazin-3-yl}-1-(3-methylbutyl)-1,8-naphthyridin-2(1H)-one;
4-hydroxy-3-[7-(hydroxymethyl)-1,1-dioxido-4H-thieno[2,3-e][1,2,4]thiadiazin-3-yl]-1-(3-methylbutyl)-1,8-naphthyridin-2(1H)-one;
1-benzyl-3-(1,1-dioxido-4H-1,2,4-benzothiadiazin-3-yl)-4-hydroxy-2(1H)-pyridinone;
1-benzyl-3-(1,1-dioxido-4H-1,2,4-benzothiadiazin-3-yl)-4-hydroxy-5,6-dimethyl-2(1H)-pyridinone;
1-benzyl-3-(1,1-dioxido-4H-1,2,4-benzothiadiazin-3-yl)-4-hydroxy-6-methyl-5-phenyl-2(1H)-pyridinone;
3-(1,1-dioxido-4H-1,2,4-benzothiadiazin-3-yl)-4-hydroxy-5,6-dimethyl-1-(3-methylbutyl)-2(1H)-pyridinone;
3-(1,1-dioxido-4H-1,2,4-benzothiadiazin-3-yl)-1-(2-ethylbutyl)-4-hydroxy-5,6-dimethyl-2(1H)-pyridinone;
1-benzyl-3-(1,1-dioxido-4H-1,2,4-benzothiadiazin-3-yl)-4-hydroxy-6-phenyl-2(1H)-pyridinone;
1,5-dibenzyl-3-(1,1-dioxido-4H-1,2,4-benzothiadiazin-3-yl)-4-hydroxy-6-methyl-2(1H)-pyridinone;
3-(1,1-dioxido-4H-1,2,4-benzothiadiazin-3-yl)-1-(2-ethylbutyl)-4-hydroxy-6-methyl-5-phenyl-2(1H)-pyridinone;
1-butyl-3-(1,1-dioxido-4H-1,2,4-benzothiadiazin-3-yl)-2(1H)-pyridinone;
N-{3-[4-hydroxy-1-(3-methylbutyl)-2-oxo-1,2-dihydropyridin-3-yl]-1,1-dioxido-4H-1,2,4-benzothiadiazin-7-yl}methanesulfonamide;
N-[3-(1-benzyl-4-hydroxy-2-oxo-1,2-dihydropyridin-3-yl)-1,1-dioxido-4H-1,2,4-benzothiadiazin-7-yl]methanesulfonamide;
N-[3-(4-hydroxy-2-oxo-1,2-dihydro-3-pyridinyl)-1,1-dioxido-4H-1,2,4-benzothiadiazin-7-yl]methanesulfonamide;
N-[3-(4-hydroxy-1-isopentyl-5,6-dimethyl-2-oxo-1,2-dihydro-3-pyridinyl)-1,1-dioxido-4H-1,2,4-benzothiadiazin-7-yl]methanesulfonamide;
benzyl 3-[3-(4-hydroxy-1-isopentyl-2-oxo-1,2-dihydro-3-pyridinyl)-1,1-dioxido-4H-1,2,4-benzothiadiazin-7-yl]diazathiane-1-carboxylate 2,2-dioxide;
N-[3-(4-hydroxy-1-isopentyl-2-oxo-1,2-dihydro-3-pyridinyl)-1,1-dioxido-4H-1,2,4-benzothiadiazin-7-yl]sulfamide;
N-{3-[1-(cyclobutylmethyl)-4-hydroxy-2-oxo-1,2-dihydro-3-pyridinyl]-1,1-dioxido-4H-1,2,4-benzothiadiazin-7-yl}methanesulfonamide;
N-{3-[5-bromo-1-(cyclobutylmethyl)-4-hydroxy-2-oxo-1,2-dihydro-3-pyridinyl]-1,1-dioxido-4H-1,2,4-benzothiadiazin-7-yl}methanesulfonamide;
N-[3-(4-hydroxy-1-isopentyl-2-oxo-5-vinyl-1,2-dihydro-3-pyridinyl)-1,1-dioxido-4H-1,2,4-benzothiadiazin-7-yl]methanesulfonamide; and
3-(1,1-dioxido-4H-1,2,4-benzothiadiazin-3-yl)-4-hydroxy-1-propoxyquinolin-2(1H)-one; or a pharmaceutically acceptable salt form, stereoisomer or tautomer thereof.

In a second embodiment the present invention provides a compound of formula (II)

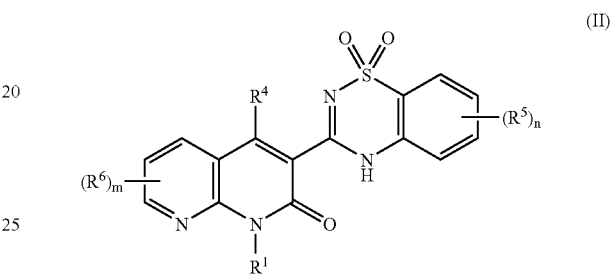

(II)

or a pharmaceutically acceptable salt form, stereoisomer or tautomer thereof, wherein:

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN$—, $R_aR_b$Nalkyl-, $R_aR_b$NC(O)alkyl-, $R_aR_b$NC(O)Oalkyl-, $R_aR_b$NC(O)NR$_c$alkyl-, $R_fR_g$C=N— and $R_kO$—, wherein $R^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_e$), —SR$_c$, —S(O)R$_c$, —S(O)$_2$R$_c$, —OR$_c$, —N(R$_c$)(R), —C(O)R$_c$, —C(O)OR$_c$ and —C(O)NR$_c$R$_e$;

$R^4$ is selected from the group consisting of alkoxy, arylalkoxy, aryloxy, halo, hydroxy, $R_aR_bN$—, $N_3$—, $R_eS$—, wherein $R^4$ is independently substituted with 0, 1 or 2 substituents independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_aC(O)$—, $R_aS$—, $R_a(O)S$—, $R_a(O)_2S$—, $R_aR_b$Nalkyl-, $R_a(O)SN(R_f)$—, $R_aSO_2N(R_f)$—, $R_a(O)SN(R_f)$alkyl-, $R_aSO_2N(R_f)$alkyl-, $R_aR_bNSO_2N(R_f)$—, $R_aR_bNSO_2N(R_f)$alkyl-, $R_aR_bNC(O)$—, $R_kOC(O)$—, $R_kOC(O)$alkyl-, $R_kO$alkyl-, $R_aR_bNSO_2$—, $R_aR_bNSO_2$alkyl-, $(R_bO)(R_a)P(O)O$— and —OR$_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(N$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each R$^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, R$_c$R$_d$N—, R$_k$O—. R$_k$Oalkyl-, R$_c$R$_d$Nalkyl-, R$_c$R$_d$NC(O)alkyl-, R$_c$SO$_2$—, R$_c$SO$_2$alkyl-, R$_c$(O)—, R$_c$C(O)alkyl-, R$_c$OC(O)—, R$_c$OC(O)alkyl-, R$_c$R$_d$NalkylC(O)—, R$_c$R$_d$NC(O)—, R$_c$R$_d$NC(O)Oalkyl-, R$_c$ R$_d$NC(O)N(R$_e$)alkyl-, wherein R$_a$ and R$_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(d), —C(O)R$_c$, —C(O)OR$_c$ and —C(O)NR$_c$R$_d$;

alternatively, R$_a$ and R$_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), -(alkyl)SO$_2$NR$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$_c$ and R$_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each R$_c$ and R$_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, -OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, R$_e$ and R$_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

R$_e$ is selected from the group consisting of hydrogen, alkenyl, alkyl and cycloalkyl;

R$_f$, R$_g$ and R$_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each R$_f$, R$_g$ and R$_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, R$_f$ and R$_g$ together with the carbon atom to which they are attached form a three- to seven-membered ring selected from the group consisting of cycloalkyl, cycloalkenyl and heterocycle;

alternatively, R$_f$ and R$_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

R$_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, R$_a$R$_b$Nalkyl-, R$_a$Oalkyl-, R$_a$R$_b$NC(O)—, R$_a$R$_b$NC(O)alkyl, R$_a$S—, R$_a$S(O)—, R$_a$SO$_2$—, R$_a$Salkyl-, R$_a$(O)Salkyl-, R$_a$SO$_2$alkyl-, R$_a$OC(O)—, R$_a$OC(O)alkyl-, R$_a$C(O)—, R$_a$C(O)alkyl-, wherein each R$_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

m is 0, 1, 2, 3, or 4; and n is 0, 1, 2, 3, or 4;

with the proviso that when R$^4$ is alkoxy, aryloxy, hydroxy or R$_e$—, and R$^5$ is hydrogen, alkenyl, alkoxy, alkyl, alkynyl, aryl, halo, heteroaryl, heterocyclealkyl, cycloalkyl, cyano, nitro, R$_a$R$_b$N—, R$_a$C(O)—, R$_a$S—, R$_a$(O)S—, R$_a$(O)$_2$S—, R$_a$SO$_2$N(R$_f$)—, R$_a$R$_b$NC(O)—, R$_k$OC(O)—, R$_a$R$_b$NSO$_2$— or —OR$_k$, and R$^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$, then R$^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (II) wherein R$^4$ is hydroxy.

For example, the present invention provides a compound of formula (II) wherein R$^4$ is hydroxy and R$^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, R$_a$R$_b$N—, R$_a$R$_b$Nalkyl-, R$_a$R$_b$NC(O)alkyl-, R$_f$R$_g$C=N— and R$_k$O—.

For example, the present invention provides a compound of formula (II) wherein R$^4$ is hydroxy and R$^1$ is selected from the group consisting of, C3 alkyl, C4 alkyl, C5 alkyl, C3 alkenyl, C4 alkenyl, C5 alkenyl, C3 alkynyl, C4 alkynyl, C5 alkynyl, furyl(C1-C2 alkyl)-, thienyl(C1-C2 alkyl)-, phenyl(C1-C2 alkyl)-, pyridinyl(C1-C2 alkyl)-, thiazolyl(C1-C2 alkyl)-, isoxazolyl(C1-C2alkyl)-, naphthyl(C1-C2 alkyl), benzothienyl(C1-C2 alkyl)-, indolyl(C1-C2 alkyl)-, (C3-C7 cycloalkyl)(C1-C2 alkyl)-, (C5-C6 cycloalkenyl)(C1-C2 alkyl)-, C3-C7 cycloalkyl, (phenylalkyl)O—, (C1-C6 alkyl)O—, ((C3-C6 cycloalkyl)alkyl)O—, phenylCH=N—, NH$_2$, (C1-C7 alkyl)N(H)—, (C1-C7 alkenyl)N(H)—, (C3-C7 cycloalkyl)N(H)—, ((C3-C7 cycloalkyl)alkyl)N(H)—, (phenylalkyl)N(H)—, (thienylmethyl)N(H)—, (thiazolylmethyl)N(H)—, (furylmethyl)N(H)—, (pyridinylmethyl)N(H)—, (tetrahydropyran)N(H)—, (benzyl)N(H)—, (tetrahydronaphthalenyl)N(H)—, wherein each R$^1$ is substituted with 0, 1, 2, or 3 substituents selected from the group consisting of alkyl, hydroxy, oxo, halo, cyano, nitro, haloalkyl, haloalkoxy, phenyl, piperazinyl, morphilinyl, carboxy, —C(O)O(alkyl), —NH$_2$, —NH(alkyl), —N(alkyl)$_2$, —Oalkyl, —O-phenyl.

For example, the present invention provides a compound of formula (II) wherein R$^4$ is hydroxy and R$^1$ is selected from the group consisting of (((1-isopropyl)butyl)N(H)—, ((2-chloro-1,3-thiazol-5-yl)methyl)N(H)—, ((2-methyl-1,3-thiazol-4-yl)methyl)N(H)—, ((3-methylthien-2-yl)methyl)N(H)—, ((3-trifluoromethyl)cyclohexyl)N(H)—, ((5-chlorothien-2-yl)methyl)N(H)—, ((pyridin-3-yl)methyl)N(H)—, (1,2,3,4-tetrahydronaphthalen-2-yl)N(H)—, (1,3-thiazol-2-ylmethyl)N(H)—, (1,3-thiazol-5-ylmethyl)N(H)—, (1-cyclohezen-1-yl)ethyl, (1-cyclopropylethyl)N(H)—, (1-ethylbutyl)N(H)—, (1-ethylpropyl)N(H)—, (1-methylbutyl)N(H)—, (1-phenylethyl)N(H)—, (1-propylbutyl)N(H)—, (1-thien-3-ylethyl)N(H)—, (2-(1H-indol-3-yl)ethyl, (2-(dimethylamino)ethyl)(methyl)aminopropyl, (2-bromobenzyl)N(H)—, (2-chloro-1,3-thiazol-5-yl)methyl, (2-chloro-4-pyridinyl)methyl, (2-ethyl-3-methylbutyl)N(H)—, (2-ethylbutyl)N(H)—, (2-furylmethyl)N(H)—, (2-methyl-1,2-thiazol-4-yl)methyl, (2-methyl-1,3-thiazol-4-yl)methyl, (2-methyl-1,3-thiazol-5-yl)methyl, ((2-methylphenyl)methyl)N(H)—, (3,3-dimethylbutyl)N(H)—, (3,5-dimethyl-4-isoxazolyl)methyl, (3,5-dimethylcyclohexyl)N(H)—, (3-bromobenzyl)N(H)—, (3-cyanobenzyl)N(H)—, (3-ethylcyclopentyl)N(H)—, (3-furylmethyl)N(H)—, ((3-methoxyphenyl)methyl)N(H)—, (3-methylbenzyl)N(H)—, (3-methylbut-2-enyl)N(H)—, (3-methylbutyl)N(H)—, (3-methylcyclohexyl)N(H)—, (3-methylcyclopentyl)N(H)—, (3-trifluoromethyl)benzyl, ((4-bromophenyl)methyl)N(H)—, (4-isopropylcyclohexyl)N(H)—, ((4-methoxyphenyl)methyl)N(H)—, ((4-methylphenyl)methyl)N(H)—, (5-bromo-2-thienyl)methyl, (5-bromo-3-pyridinyl)methyl, (5-carboxy-2-furyl)methyl, (5-chloro-2-thienyl)methyl, (5-ethoxycarbonyl-2-furyl)methyl, (5-methyl-2-thienyl)methyl, (5-methyl-3-isoxazolyl)methyl, (5-methyl-3-pyridinyl)methyl, (5-nitro-2-furyl)methyl, (5-phenyl-2-thienyl)methyl, (5-tert-butyl-2-thienyl)methyl, (6,6-dimethylbicyclo[3.1.1]hept-2-yl)methyl, (6-ethoxy-2-pyridinyl)methyl, (6-methyl-2-pyridinyl)methyl, (cyclopropylmethyl)N(H)—, (pyridin-2-ylmethyl)N(H)—, (pyridin-3-ylmethyl)N(H)—, (pyridin-4-ylmethyl)N(H)—, (tetrahydro-2H-pyran-4-yl)N(H)—, (thien-2-ylmethyl)N(H)—, (thien-3-ylmethyl)N(H)—, 1,1'-biphenyl-4-ylmethyl, 1,3-thiazol-4-ylmethyl, 1-adamantylmethyl, 1-benzothien-2-ylmethyl, 1-ethylpropyl, 1-naphthylmethyl, 1-neopentyl, 1-phenylethyl, 2-(1,3-dioxolan-2-yl)ethyl, 2-(3-thienyl)ethyl, 2,3-dihydroxypropyl, 2-aminoethyl, 2-cyanobenzyl, 2-cyclohexylethyl, (2-methylphenyl)methyl), 2-methylbutyl, 2-naphthylmethyl, 2-phenylethyl, 2-phenylpropyl, 2-pyridinylmethyl, 3-(4-methyl-1-piperazinyl)propyl, 3-(4-morpholinyl)propyl, 3-(diethylamino)propyl, 3-(dimethylamino)propyl, 3-anilinopropyl, 3-bromobenzyl, 3-butenyl, 3-chlorobenzyl, 3-cyanobenzyl, 3-ethylbutyl, 3-fluorobenzyl, 3-hydroxybutyl, 3-hydroxypropyl, 3-iodobenzyl, 3-methoxybenzyl, 3-methoxycarbonylbenzyl, 3-methyl-2-butenyl, 3-methylbenzyl, 3-methylbutyl, 3-nitrobenzyl, 3-phenoxybenzyl, 3-pyridinylmethyl, 3-thienylmethyl, 4-bromobenzyl, 4-cyanobenzyl, 4-methoxybenzyl, 4-methyl-3-pentenyl, 4-methylbenzyl, 4-methylpentyl, 4-pyridinylmethyl, 4-tert-butylbenzyl, —NH$_2$, phenylmethyl, (phenylmethyl)N(H)—, benzyloxy, (butyl)N(H)—, (cyclobutyl)N(H)—, cyclobutylmethyl, cycloheptyl, (cycloheptyl)N(H)—, cyclohexyl, (cyclohexyl)N(H)—, cyclohexylmethyl, cyclopentyl, (cyclopentyl)N(H)—, cyclopropylmethyl, cyclopropylethyl, hydrogen, isobutoxy, (isobutyl)N(H)—, (isopropyl)N(H)—, n-butyl, pentyl, (pentyl)N(H)—, (phenylmethylene)N(H)—, prop-2-enyl, propan-3-al, propoxy and (propyl)N(H)—.

In a third embodiment the present invention provides a compound of formula I):

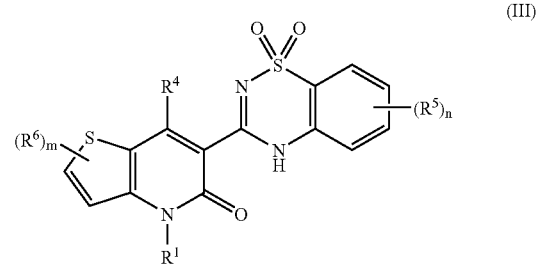

(III)

or a pharmaceutically acceptable salt form, stereoisomer or tautomer thereof, wherein:

R$^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, R$_a$R$_b$N—, R$_a$R$_b$Nalkyl-, R$_a$R$_b$NC(O)alkyl-, R$_a$R$_b$NC(O)Oalkyl-, R$_a$R$_b$NC(O)NR$_c$alkyl-, $R_fR_gC=N-$ and $R_kO-$, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_e$), —SR$_c$, —S(O)R$_c$, —S(O)$_2$R$_c$, —OR$_c$, —N(R$_c$)(R$_e$), —C(O)R$_c$, —C(O)OR$_c$ and —C(O)NR$_c$R$_e$;

$R^4$ is selected from the group consisting of alkoxy, arylalkoxy, aryloxy, halo, hydroxy, $R_aR_bN-$, $N_3-$, $R_e-$, wherein $R^4$ is substituted with 0, 1 or 2 substituents independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN-$, $R_aC(O)-$, $R_aS-$, $R_a(O)S-$, $R_a(O)_2S-$, $R_aR_bNalkyl$-, $R_a(O)SN(R_f)-$, $R_aSO_2N(R_f)-$, $R_a(O)SN(R_f)alkyl$-, $R_aSO_2N(R_f)alkyl$-, $R_aR_bNSO_2N(R_f)-$, $R_aR_bNSO_2N(R_f)alkyl$-, $R_aR_bNC(O)-$, $R_kOC(O)-$, $R_kOC(O)alkyl$-, $R_kOalkyl$-, $R_aR_bNSO_2-$, $R_aR_bNSO_2alkyl$-, $(R_bO)(R_a)P(O)O-$ and $-OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each $R^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN-$, $R_kO-$. $R_kOalkyl$-, $R_cR_dNalkyl$-, $R_cR_dNC(O)alkyl$-, $R_cSO_2-$, $R_cSO_2alkyl$-, $R_cC(O)-$, $R_cC(O)alkyl$-, $R_cOC(O)-$, $R_cOC(O)alkyl$-, $R_cR_dNalkylC(O)-$, $R_cR_dNC(O)-$, $R_cR_dNC(O)Oalkyl$-, $R_cR_dNC(O)N(R_c)alkyl$-, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_k$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)$_2$R$_c$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R_c$ and $R_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)

N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_a$S—, $R_a$S(O)—, $R_a$SO$_2$—, $R_a$S-alkyl-, $R_a$(O)Salkyl-, $R_a$SO$_2$alkyl-, $R_a$OC(O)—, $R_a$OC(O)alkyl-, $R_a$C(O)—, $R_a$C(O)alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

m is 0, 1, or 2; and n is 0, 1, 2, 3, or 4;

with the proviso that when $R^4$ is alkoxy, aryloxy, hydroxy or $R_e$S—, and $R^5$ is hydrogen, alkenyl, alkoxy, alkyl, alkynyl, aryl, halo, heteroaryl, heterocyclealkyl, cycloalkyl, cyano, nitro, $R_aR_b$N—, $R_a$C(O)—, $R_a$S—, $R_a$(O)S—, $R_a$(O)$_2$S—, $R_a$SO$_2$N(R$_f$)—, $R_a$R$_b$NC(O)—, $R_k$OC(O)—, $R_a$R$_b$NSO$_2$— or —OR$_k$, and $R^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (III) wherein $R^4$ is hydroxy.

For example, the present invention provides a compound of formula (III) wherein $R^4$ is hydroxy and $R^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, $R_aR_b$N—, $R_aR_b$Nalkyl-, $R_aR_b$NC(O)alkyl-, $R_jR_g$C=N— and $R_k$O—.

For example, the present invention provides a compound of formula (III) wherein $R^4$ is hydroxy and $R^1$ is selected from the group consisting of ((1-isopropyl)butyl)N(H)—, ((2-chloro-1,3-thiazol-5-yl)methyl)N(H)—, ((2-methyl-1,3-thiazol-4-yl)methyl)N(H)—, ((3-methylthien-2-yl)methyl)N(H)—, ((3-trifluoromethyl)cyclohexyl)N(H)—, ((5-chlorothien-2-yl)methyl)N(H)—, ((pyridin-3-yl)methyl)N(H)—, (1,2,3,4-tetrahydronaphthalen-2-yl)N(H)—, (1,3-thiazol-2-ylmethyl)N(H)—, (1,3-thiazol-5-ylmethyl)N(H)—, (1-cyclohezen-1-yl)ethyl, (1-cyclopropylethyl)N(H)—, (1-ethylbutyl)N(H)—, (1-ethylpropyl)N(H)—, (1-methylbutyl)N(H)—, (1-phenylethyl)N(H)—, (1-propylbutyl)N(H)—, (1-thien-3-ylethyl)N(H)—, (2-(1H-indol-3-yl)ethyl, (2-(dimethylamino)ethyl)(methyl)aminopropyl, ((2-bromophenyl)methyl)N(H)—, (2-chloro-1,3-thiazol-5-yl)methyl, (2-chloro-4-pyridinyl)methyl, (2-ethyl-3-methylbutyl)N(H)—, (2-ethylbutyl)N(H)—, (2-furylmethyl)N(H)—, (2-methyl-1,2-thiazol-4-yl)methyl, (2-methyl-1,3-thiazol-4-yl)methyl, (2-methyl-1,3-thiazol-5-yl)methyl, (2_methylbenzyl)N(H)—, (3,3-dimethylbutyl)N(H)—, (3,5-dimethyl-4-isoxazolyl)methyl, (3,5-dimethylcyclohexyl)N(H)—, (3-bromobenzyl)N(H)—, (3-cyanobenzyl)N(H)—, (3-ethylcyclopentyl)N(H)—, (3-furylmethyl)N(H)—, (3-methoxybenzyl)N(H)—, (3-methylbenzyl)N(H)—, (3-methylbut-2-enyl)N(H)—, (3-methylbutyl)N(H)—, (3-methylcyclohexyl)N(H)—, (3-methylcyclopentyl)N(H)—, (3-trifluoromethyl)benzyl, ((4-bromophenyl)methyl)N(H)—, (4-isopropylcyclohexyl)N(H)—, ((4-methoxyphenyl)methyl)N(H)—, ((4-methylphenyl)methyl)N(H)—, (5-bromo-2-thienyl)methyl, (5-bromo-3-pyridinyl)methyl, (5-carboxy-2-furyl)methyl, (5-chloro-2-thienyl)methyl, (5-ethoxycarbonyl-2-furyl)methyl, (5-methyl-2-thienyl)methyl, (5-methyl-3-isoxazolyl)methyl, (5-methyl-3-pyridinyl)methyl, (5-nitro-2-furyl)methyl, (5-phenyl-2-thienyl)methyl, (5-tert-butyl-2-thienyl)methyl, (6,6-dimethylbicyclo[31.1]hept-2-yl)methyl, (6-ethoxy-2-pyridinyl)methyl, (6-methyl-2-pyridinyl)methyl, (cyclopropylmethyl)N(H)—, (pyridin-2-ylmethyl)N(H)—, (pyridin-3-ylmethyl)N(H)—, (pyridin-4-ylmethyl)N(H)—, (tetrahydro-2H-pyran-4-yl)N(H)—, (thien-2-ylmethyl)N(H)—, (thien-3-ylmethyl)N(H)—, 1,1'-biphenyl-4-ylmethyl, 1,3-thiazol-4-ylmethyl, 1-adamantylmethyl, 1-benzothien-2-ylmethyl, 1-ethylpropyl, 1-naphthylmethyl, 1-neopentyl, 1-phenylethyl, 2-(1,3-dioxolan-2-yl)ethyl, 2-(3-thienyl)ethyl, 2,3-dihydroxypropyl, 2-aminoethyl, (2-cyanophenyl)methyl, 2-cyclohexylethyl, (2-methylphenyl)methyl, 2-methylbutyl, 2-naphthylmethyl, 2-phenylethyl, 2-phenylpropyl, 2-pyridinylmethyl, 3-(4-methyl-1-piperazinyl)propyl, 3-(4-morpholinyl)propyl, 3-(diethylamino)propyl, 3-(dimethylamino)propyl, 3-anilinopropyl, (3-bromophenyl)methyl, 3-butenyl, (3-chlorophenyl)methyl, (3-cyanophenyl)methyl, 3-ethylbutyl, (3-fluorophenyl)methyl, 3-hydroxybutyl, 3-hydroxypropyl, (3-iodophenyl)methyl, (3-methoxyphenyl)methyl, (3-methoxycarbonylphenyl)methyl, 3-methyl-2-butenyl, (3-methylphenyl)methyl, 3-methylbutyl, (3-nitrophenyl)methyl, 3-phenoxybenzyl, 3-pyridinylmethyl, 3-thienylmethyl, (4-bromophenyl)methyl, (4-cyanophenyl)methyl, (4-methoxyphenyl)methyl, 4-methyl-3-pentenyl, (4-methylphenyl)methyl, 4-methylpentyl, 4-pyridinylmethyl, (4-tert-butylphenyl)methyl, —NH$_2$, phenylmethyl, (phenylmethyl)N(H)—, (phenylethyl)N(H)—, benzyloxy, (butyl)N(H)—, (cyclobutyl)N(H)—, cyclobutylmethyl, cycloheptyl, (cycloheptyl)N(H)—, cyclohexyl, (cyclohexyl)N(H)—, cyclohexylmethyl, cyclopentyl, (cyclopentyl)N(H)—, cyclopropylethyl, cyclopropylmethyl, isobutoxy, (isobutyl)N(H)—, (isopropyl)N(H)—, n-butyl, pentyl, (pentyl)N(H)—, (phenylmethylene)N(H)—, prop-2-enyl, propan-3-al, propoxy and (propyl)N(H)—.

In a fourth embodiment the present invention provides a compound of formula (IV)

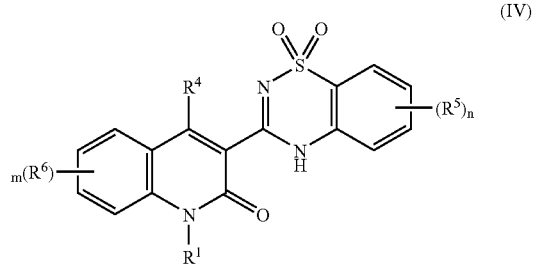

or a pharmaceutically acceptable salt form, stereoisomer or tautomer thereof, wherein:

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN-$, $R_aR_b$Nalkyl-, $R_aR_b$NC(O)alkyl-, $R_aR_b$NC(O)Oalkyl-, $R_aR_b$NC(O)$NR_c$alkyl-, $R_fR_gC=N-$ and $R_kO-$, wherein $R^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_e$), $-SR_c$, $-S(O)R_c$, $-S(O)_2R_c$, $-OR_c$, $-N(R_c)(R_e)$, $-C(O)R_c$, $-C(O)OR_c$ and $-C(O)N_cR_e$;

$R^4$ is selected from the group consisting of alkoxy, arylalkoxy, aryloxy, halo, hydroxy, $R_aR_bN-$, $N_3-$, $R_eS-$, wherein $R^4$ is substituted with 0, 1 or 2 substituents independently selected from the group consisting of halo, nitro, cyano, $-OH$, $-NH_2$, and $-COOH$;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN-$, $R_aC(O)-$, $R_aS-$, $R_a(O)S-$, $R_a(O)_2S-$, $R_aR_b$Nalkyl-, $R_a(O)SN(R_f)-$, $R_aSO_2N(R_f)-$, $R_a(O)SN(R_f)$alkyl-, $R_aSO_2N(R_f)$alkyl-, $R_aR_bNSO_2N(R_f)-$, $R_aR_bNSO_2N(R_f)$alkyl-, $R_aR_bNC(O)-$, $R_kOC(O)-$, $R_kOC(O)$alkyl-, $R_kO$alkyl-, $R_aR_bNSO_2-$, $R_aR_bNSO_2$alkyl-, $(R_bO)(R_a)P(O)O-$ and $-OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkyl, -(alkyl)($OR_c$), -(alkyl)($N_cR_d$), $-SR_c$, $-S(O)R_c$, $-S(O)_2R_c$, $-OR_c$, $-N(R_c)(R_d)$, $-C(O)R_c$, $-C(O)OR_c$ and $-C(O)N_cR_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), $-SR_a$, $-S(O)R_a$, $-S(O)_2R_a$, $-OR_k$, $-N(R_a)(R_b)$, $-C(O)R_a$, $-C(O)OR_a$ and $-C(O)NR_aR_b$; wherein each $R^6$ is independently substituted with 0, 1, 2 or 3 substituents independently selected from the group consisting of alkyl, alkenyl, alkynyl, oxo, halo, haloalkyl, cyano, nitro, $-OR_a$, $-NR_aR_b$, $-SR_a$, $-SOR_a$, $-SO_2R_a$, $-C(O)OR_a$, $-C(O)NR_aR_b$ and $-NC(O)R_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN-$, $R_kO-$. $R_k$Oalkyl-, $R_cR_d$Nalkyl-, $R_cR_d$NC(O)alkyl-, $R_cSO_2-$, $R_cSO_2$alkyl-, $R_cC(O)-$, $R_cC(O)$alkyl-, $R_cOC(O)-$, $R_cOC(O)$alkyl-, $R_cR_d$NalkylC(O)-, $R_cR_d$NC(O)-, $R_cR_d$NC(O)Oalkyl-, $R_cR_d$NC(O)N($R_e$)alkyl-, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $-SR_c$, $-S(O)R_c$, $-S(O)_2R_c$, $-OR_c$, $-N(R_c)(R_d)$, $-C(O)R_c$, $-C(O)OR_c$ and $-C(O)NR_cR_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -(alkyl)$SO_2NR_cR_d$, -alkylC(O)$NR_cR_d$, $-SR_c$, $-S(O)R_c$, $-S(O)_2R_c$, $-OR_c$, $-N(R_c)(R_d)$, $-C(O)R_c$, $-C(O)OR_c$ and $-C(O)NR_cR_d$;

$R_c$ and $R_d$, at each occurrence, are independently selected from the group consisting of hydrogen, $-NR_fR_h$, $-OR_f$, $-CO(R_f)$, $-SR_f$, $-SOR_f$, $-SO_2R_f$, $-C(O)NR_fR_h$, $-SO_2NR_fR_h$, $-C(O)OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), $-SR_f$, $-S(O)R_f$, $-S(O)_2R_f$, $-OR_f$, $-N(R_f)(R_h)$, $-C(O)R_f$, $-C(O)OR_f$, $-C(O)NR_fR_h$, $-C(O)N(H)NR_fR_h$, $-N(R_e)C(O)OR_f$, $-N(R_e)SO_2NR_fR_h$, $-N(R_e)C(O)NR_fR_h$, -(alkyl)N($R_e$)C(O)$OR_f$, -(alkyl)N($R_e$)SO$_2$NR$_f$R$_h$, and -alkylN($R_e$)C(O)NR$_f$R$_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), $-SR_f$, $-S(O)R_f$, $-S(O)_2R_f$, $-OR_f$, $-N(R_f)(R_h)$, $-C(O)R_f$, $-C(O)OR_f$ and $-C(O)NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, $-OH$, $-O$(alkyl), $-NH_2$, $-N(H)$(alkyl), $-N$(alkyl)$_2$, $-S$(alkyl), $-S(O)$(alkyl), $-SO_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, $-N(H)C(O)NH_2$, $-C(O)OH$, $-C(O)O$(alkyl), $-C(O)$alkyl, $-C(O)NH_2$, $-C(O)NH_2$, $-C(O)N(H)$(alkyl), and $-C(O)N$(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_a$S—, $R_a$S(O)—, $R_a$SO$_2$—, $R_a$S-alkyl-, $R_a$(O)Salkyl-, $R_a$SO$_2$alkyl, $R_a$OC(O)—, $R_a$OC(O)alkyl-, $R_a$C(O)—, $R_a$C(O)alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

m is 0, 1, 2, 3, or 4; and n is 0, 1, 2, 3, or 4;

with the proviso that when $R^4$ is alkoxy, aryloxy, hydroxy or $R_e$—, and $R^5$ is hydrogen, alkenyl, alkoxy, alkyl, alkynyl, aryl, halo, heteroaryl, heterocyclealkyl, cycloalkyl, cyano, nitro, $R_aR_b$N—, $R_a$C(O)—, $R_a$S—, $R_a$(O)S—, $R_a$(O)$_2$S—, $R_a$SO$_2$N(R$_f$)—, $R_aR_b$NC(O)—, $R_k$OC(O)—, $R_aR_b$NSO$_2$— or —OR$_k$, and $R^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)N$_a$R$_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (IV) wherein $R^4$ is hydroxy.

For example, the present invention provides a compound of formula (IV) wherein $R^4$ is hydroxy and $R^1$ is selected from the group consisting of $R_aR_b$N—, $R_fR_g$C=N— and $R_k$O—.

For example, the present invention provides a compound of formula (IV) wherein $R^4$ is hydroxy and $R^1$ is selected from the group consisting of alkylO—, (cycloalkyl)O—, (arylalkyl)O—, arylCH=N—, —NH$_2$, alkylN(H)—, alkenylN(H)—, cycloalkylN(H)—, (cycloalkylalkyl)N(H)—, (heteroarylalkyl)N(H)—, (arylalkyl)N(H)— and (heterocycle)N(H)—.

For example, the present invention provides a compound of formula (IV) wherein $R^4$ is hydroxy and $R^1$ is selected from the group consisting of (C3-C7 alkyl)O—, (C3-C6 cycloalkyl)O—, (phenylalkyl)O—, phenylCH=N—, (C3-C7 alkyl)N(H)—, (C3-C7 alkenyl)N(H)—, (C3-C7 cycloalkyl)N(H)—, ((C3-C7 cycloalkyl)C1-C2 alkyl)N(H)—, (thienylmethyl)N(H)—, (thiazolylmethyl)N(H)—, (furylmethyl)N(H)—, (pyridinylmethyl)N(H)—, (tetranaphthalenyl)N(H)—, (tetrahydropyranyl)N(H)— and (phenylalkyl)N(H)—, wherein the phenyl, thienyl, thiazolyl, furyl and pyridinyl of (phenylalkyl)O—, phenylCH=N—, (thienylmethyl)N(H)—, (thiazolylmethyl)N(H)—, (furylmethyl)N(H)—, (pyridinylmethyl)N(H)—, and (phenylalkyl)N(H)— are each independently substituted with 0, 1 or 2 susbstituents selected from the group consisting of nitro, cyano, hydroxyl, alkoxy, —NH$_2$, —N(H)(alkyl), —N(alkyl)$_2$, alkyl, halo, haloalkyl, carboxy, acetyl, and alkyoxycarbonyl.

For example, the present invention provides a compound of formula (IV) wherein $R^4$ is hydroxy and $R^1$ is selected from the group consisting of (phenylmethyl)N(H)—, (1-phenylethyl)N(H)—, (cycloproylmethyl)N(H)—, (cyclohexylmethyl)N(H)—, (1-cyclopropylethyl)N(H)—, phenylCH=N—, propylO—, (1-propylbutyl)N(H)—, (isobutyl)N(H)—, (isopropyl)N(H)—, (1-ethylpropyl)N(H)—, (1-ethylbutyl)N(H)—, (2-ethylbutyl)N(H)—, (1-isopropylbutyl)N(H)—, (1-methylbutyl)N(H)—, (3-methylbutyl)N(H)—, (3,3-dimethylbutyl)N(H)—, (propyl)N(H)—, (butyl)N(H)—, (pentyl)N(H)—, (2-ethyl-3-methylbutyl)N(H)—, (3-methylbut-2-enyl)N(H)—, (cyclobutyl)N(H)—, (cyclopentyl)N(H)—, (cyclohexyl)N(H)—, (cycloheptyl)N(H)—, (thienylmethyl)N(H)—, (furylmethyl)N(H)—, (thiazolylmethyl)N(H)—, (pyridinylmethyl)N(H)—, (tetrahydronaphthalenyl)N(H)—, and (tetrahydropyranyl)N(H)—, wherein the phenyl, thienyl, thiazolyl, furyl and pyridinyl of (phenylmethyl)O—, phenylCH=N—, (thienylmethyl)N(H)—, (thiazolylmethyl)N(H)—, (furylmethyl)N(H)—, (pyridinylmethyl)N(H)—, (phenylmethyl)N(H)— and (1-phenylethyl)N(H)— are each independently substituted with 0, 1 or 2 susbstituents selected from the group consisting of nitro, cyano, hydroxyl, methoxy, —NH$_2$, —N(H)(alkyl), —N(alkyl)$_2$, methyl, halo, halomethyl, carboxy, acetyl, and alkyoxycarbonyl.

Exemplary compounds of the fourth embodiment of the present invention of formula (IV) include, but not limited to, the following:

3-(1,1-dioxido-4H-1,2,4-benzothiadiazin-3-yl)-4-hydroxy-1-{[(1E)-phenylmethylene] amino}-2(1H)-quinolinone;

1-amino-3-(1,1-dioxido-4H-1,2,4-benzothiadiazin-3-yl)-4-hydroxy-2(1H)-quinolinone;

3-(1,1-dioxido-4H-1,2,4-benzothiadiazin-3-yl)-4-hydroxy-1-propoxyquinolin-2(1H)-one;

1-(benzylamino)-3-(1,1-dioxido-4H-1,2,4-benzothiadiazin-3-yl)-4-hydroxyquinolin-2(1H)-one;

1-amino-3-(1,1-dioxido-4H-1,2,4-benzothiadiazin-3-yl)-4-hydroxyquinolin-2(1H)-one;

3-(1,1-dioxido-4H-1,2,4-benzothiadiazin-3-yl)-4-hydroxy-1-[(1-propylbutyl)amino]quinolin-2(1H)-one;

3-(1,1-dioxido-4H-1,2,4-benzothiadiazin-3-yl)-4-hydroxy-1-(isobutylamino)quinolin-2(1H)-one;

3-(1,1-dioxido-4H-1,2,4-benzothiadiazin-3-yl)-1-[(1-ethylpropyl)amino]-4-hydroxyquinolin-2(1H)-one;

3-(1,1-dioxido-4H-1,2,4-benzothiadiazin-3-yl)-4-hydroxy-1-(pentylamino)quinolin-2(1H)-one;

1-(cyclohexylamino)-3-(1,1-dioxido-4H-1,2,4-benzothiadiazin-3-yl)-4-hydroxyquinolin-2(1H)-one;

3-(1,1-dioxido-4H-1,2,4-benzothiadiazin-3-yl)-4-hydroxy-1-{[(2-methyl-1,3-thiazol-4-yl)methyl]amino}quinolin-2(1H)-one;

3-(1,1-dioxido-4H-1,2,4-benzothiadiazin-3-yl)-4-hydroxy-1-(isopropylamino)quinolin-2(1H)-one;

1-(cyclobutylamino)-3-(1,1-dioxido-4H-1,2,4-benzothiadiazin-3-yl)-4-hydroxyquinolin-2(1H)-one;

1-(cyclopentylamino)-3-(1,1-dioxido-4H-1,2,4-benzothiadiazin-3-yl)-4-hydroxyquinolin-2(1H)-one;

3-(1,1-dioxido-4H-1,2,4-benzothiadiazin-3-yl)-4-hydroxy-1-{[3-methylcyclopentyl]amino}quinolin-2(1H)-one;

3-(1,1-dioxido-4H-1,2,4-benzothiadiazin-3-yl)-4-hydroxy-1-(tetrahydro-2H-pyran-4-ylamino)quinolin-2(1H)-one;

3-(1,1-dioxido-4H-1,2,4-benzothiadiazin-3-yl)-1-{[1-ethyl-butyl]amino}-4-hydroxyquinolin-2(1H)-one;
3-(1,1-dioxido-4H-1,2,4-benzothiadiazin-3-yl)-4-hydroxy-1-{[(3R)-3-methylcyclohexyl]amino}quinolin-2(1H)-one;
1-(cycloheptylamino)-3-(1,1-dioxido-4H-1,2,4-benzothiadiazin-3-yl)-4-hydroxyquinolin-2(1H)-one;
3-(1,1-dioxido-4H-1,2,4-benzothiadiazin-3-yl)-1-{[3-ethylcyclopentyl]amino}-4-hydroxyquinolin-2(1H)-one;
3-(1,1-dioxido-4H-1,2,4-benzothiadiazin-3-yl)-4-hydroxy-1-{[1-isopropylbutyl]amino}quinolin-2(1H)-one;
3-(1,1-dioxido-4H-1,2,4-benzothiadiazin-3-yl)-4-hydroxy-1-{[-phenylethyl]amino}quinolin-2(1H)-one;
3-(1,1-dioxido-4H-1,2,4-benzothiadiazin-3-yl)-4-hydroxy-1-{[1-thien-3-ylethyl]amino}quinolin-2(1H)-one;
1-{[3,5-dimethylcyclohexyl]amino}-3-(1,1-dioxido-4H-1,2,4-benzothiadiazin-3-yl)-4-hydroxyquinolin-2(1H)-one;
3-(1,1-dioxido-4H-1,2,4-benzothiadiazin-3-yl)-4-hydroxy-1-[(4-isopropylcyclohexyl)amino]quinolin-2(1H)-one;
3-(1,1-dioxido-4H-1,2,4-benzothiadiazin-3-yl)-4-hydroxy-1-[1,2,3,4-tetrahydronaphthalen-2-ylamino]quinolin-2(1H)-one;
3-(1,1-dioxido-4H-1,2,4-benzothiadiazin-3-yl)-4-hydroxy-1-{[3-(trifluoromethyl)cyclohexyl]amino}quinolin-2(1H)-one;
1-(butylamino)-3-(1,1-dioxido-4H-1,2,4-benzothiadiazin-3-yl)-4-hydroxyquinolin-2(1H)-one;
3-(1,1-dioxido-4H-1,2,4-benzothiadiazin-3-yl)-4-hydroxy-1-[(3-methylbutyl)amino]quinolin-2(1H)-one;
3-(1,1-dioxido-4H-1,2,4-benzothiadiazin-3-yl)-1-[(3-furylmethyl)amino]-4-hydroxyquinolin-2(1H)-one;
3-(1,1-dioxido-4H-1,2,4-benzothiadiazin-3-yl)-1-[(2-furylmethyl)amino]-4-hydroxyquinolin-2(1H)-one;
3-(1,1-dioxido-4H-1,2,4-benzothiadiazin-3-yl)-4-hydroxy-1-[(thien-2-ylmethyl)amino]quinolin-2(1H)-one;
3-(1,1-dioxido-4H-1,2,4-benzothiadiazin-3-yl)-4-hydroxy-1-[(1,3-thiazol-2-ylmethyl)amino]quinolin-2(1H)-one;
3-(1,1-dioxido-4H-1,2,4-benzothiadiazin-3-yl)-1-{[(2R)-2-ethyl-3-methylbutyl]amino}-4-hydroxyquinolin-2(1H)-one;
3-(1,1-dioxido-4H-1,2,4-benzothiadiazin-3-yl)-4-hydroxy-1-[(4-methylbenzyl)amino]quinolin-2(1H)-one;
3-(1,1-dioxido-4H-1,2,4-benzothiadiazin-3-yl)-4-hydroxy-1-[(3-methylbenzyl)amino]quinolin-2(1H)-one;
3-(1,1-dioxido-4H-1,2,4-benzothiadiazin-3-yl)-4-hydroxy-1-[(2-methylbenzyl)amino]quinolin-2(1H)-one;
3-(1,1-dioxido-4H-1,2,4-benzothiadiazin-3-yl)-4-hydroxy-1-{[(3-methylthien-2-yl)methyl]amino}quinolin-2(1H)-one;
3-(1,1-dioxido-4H-1,2,4-benzothiadiazin-3-yl)-4-hydroxy-1-[(4-methoxybenzyl)amino]quinolin-2(1H)-one;
1-{[(5-chlorothien-2-yl)methyl]amino}-3-(1,1-dioxido-4H-1,2,4-benzothiadiazin-3-yl)-4-hydroxyquinolin-2(1H)-one;
1-{[(2-chloro-1,3-thiazol-5-yl)methyl]amino}-3-(1,1-dioxido-4H-1,2,4-benzothiadiazin-3-yl)-4-hydroxyquinolin-2(1H)-one;
1-[(3-bromobenzyl)amino]-3-(1,1-dioxido-4H-1,2,4-benzothiadiazin-3-yl)-4-hydroxyquinolin-2(1H)-one;
1-[(4-bromobenzyl)amino]-3-(1,1-dioxido-4H-1,2,4-benzothiadiazin-3-yl)-4-hydroxyquinolin-2(1H)-one;
1-[(2-bromobenzyl)amino]-3-(1,1-dioxido-4H-1,2,4-benzothiadiazin-3-yl)-4-hydroxyquinolin-2(1H)-one;
3-(1,1-dioxido-4H-1,2,4-benzothiadiazin-3-yl)-4-hydroxy-1-[(pyridin-3-ylmethyl)amino]quinolin-2(1H)-one;
3-({[3-(1,1-dioxido-4H-1,2,4-benzothiadiazin-3-yl)-4-hydroxy-2-oxoquinolin-1(2H)-yl]amino}methyl)benzonitrile;
2-({3-[1-(cyclobutylamino)-4-hydroxy-2-oxo-1,2-dihydroquinolin-3-yl]-1,1-dioxido-4H-1,2,4-benzothiadiazin-7-yl}oxy)acetamide;
2-({3-[1-(cyclopentylamino)-4-hydroxy-2-oxo-1,2-dihydroquinolin-3-yl]-1,1-dioxido-4H-1,2,4-benzothiadiazin-7-yl}oxy)acetamide;
2-({3-[1-(cyclohexylamino)-4-hydroxy-2-oxo-1,2-dihydroquinolin-3-yl]-1,1-dioxido-4H-1,2,4-benzothiadiazin-7-yl}oxy)acetamide;
2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetamide;
2-({3-[4-hydroxy-1-(isobutylamino)-2-oxo-1,2-dihydroquinolin-3-yl]-1,1-dioxido-4H-1,2,4-benzothiazin-7-yl}oxy)acetamide;
2-({3-[1-(butylamino)-4-hydroxy-2-oxo-1,2-dihydroquinolin-3-yl]-1,1-dioxido-4H-1,2,4-benzothiadiazin-7-yl}oxy)acetamide;
2-[(3-{4-hydroxy-1-[(3-methylbutyl)amino]-2-oxo-1,2-dihydroquinolin-3-yl}-1,1-dioxido-4H-1,2,4-benzothiadiazin-7-yl)oxy]acetamide;
3-(8-amino-7-hydroxy-1,1-dioxido-4H-1,2,4-benzothiadiazin-3-yl)-4-hydroxy-1-(isobutylamino)quinolin-2(1H)-one;
2-({8-amino-3-[4-hydroxy-1-(isobutylamino)-2-oxo-1,2-dihydroquinolin-3-yl]-1,1-dioxido-4H-1,2,4-benzothiadiazin-7-yl}oxy)acetamide;
2-({3-[4-hydroxy-2-oxo-1-(propylamino)-1,2-dihydroquinolin-3-yl]-1,1-dioxido-4H-1,2,4-benzothiadiazin-7-yl}oxy)acetamide;
2-({3-[4-hydroxy-1-(isobutylamino)-2-oxo-1,2-dihydroquinolin-3-yl]-1,1-dioxido-4H-1,2,4-benzothiadiazin-7-yl}oxy)propanamide;
2-({3-[4-hydroxy-1-(isobutylamino)-2-oxo-1,2-dihydroquinolin-3-yl]-1,1-dioxido-4H-1,2,4-benzothiadiazin-7-yl}oxy)butanamide;
8-amino-3-[4-hydroxy-1-(isobutylamino)-2-oxo-1,2-dihydroquinolin-3-yl]-1,1-dioxido-4H-1,2,4-benzothiadiazin-7-yl methanesulfonate;
1-[(cyclopropylmethyl)amino]-4-hydroxy-3-(7-hydroxy-8-nitro-1,1-dioxido-4H-1,2,4-benzothiadiazin-3-yl)quinolin-2(1H)-one;
3-(7-{2-[(3S)-3-aminopyrrolidin-1-yl]-2-oxoethoxy}-1,1-dioxido-4H-1,2,4-benzothiadiazin-3-yl)-1-[(cyclopropylmethyl)amino]-4-hydroxyquinolin-2(1H)-one;
2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]-N-ethylacetamide;
[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetic acid;
3-{7-[2-(3-aminopyrrolidin-1-yl)-2-oxoethoxy]-1,1-dioxido-4H-1,2,4-benzothiadiazin-3-yl}-1-[(cyclopropylmethyl)amino]-4-hydroxyquinolin-2(1H)-one;
3-(8-amino-7-hydroxy-1,1-dioxido-4H-1,2,4-benzothiadiazin-3-yl)-1-[(cyclopropylmethyl)amino]-4-hydroxyquinolin-2(1H)-one;
2-[(8-amino-3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetamide;
[(8-amino-3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetonitrile;

1-[(cyclopropylmethyl)amino]-4-hydroxy-3-[7-(2-hydroxy-ethoxy)-1,1-dioxido-4H-1,2,4-benzothiadiazin-3-yl]quinolin-2(1H)-one;

1-[(cyclopropylmethyl)amino]-4-hydroxy-3-[7-(1H-imidazol-2-ylmethoxy)-1,1-dioxido-4H-1,2,4-benzothiadiazin-3-yl]quinolin-2(1H)-one;

1-[(cyclopropylmethyl)amino]-3-[1,1-dioxido-7-(1,3-thiazol-2-ylmethoxy)-4H-1,2,4-benzothiadiazin-3-yl]-4-hydroxyquinolin-2(1H)-one;

1-[(cyclopropylmethyl)amino]-3-[7-(4,5-dihydro-1H-imidazol-2-ylmethoxy)-1,1-dioxido-4H-1,2,4-benzothiadiazin-3-yl]-4-hydroxyquinolin-2(1H)-one;

2-{[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]methyl}-1,3-thiazole-4-carbonitrile;

3-[7-(2-aminoethoxy)-1,1-dioxido-4H-1,2,4-benzothiadiazin-3-yl]-1-[(cyclopropylmethyl)amino]-4-hydroxyquinolin-2(1H)-one;

N-{2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]ethyl}methanesulfonamide;

3-{7-[(5-bromopyridin-2-yl)oxy]-1,1-dioxido-4H-1,2,4-benzothiadiazin-3-yl}-4-hydroxy-1-(isobutylamino)quinolin-2(1H)-one;

4-hydroxy-1-(isobutylamino)-3-{7-[(3-nitropyridin-2-yl)oxy]-1,1-dioxido-4H-1,2,4-benzothiadiazin-3-yl}quinolin-2(1H)-one;

tert-butyl 3-{1-[(cyclopropylmethyl)amino]-4-hydroxy-2-oxo-1,2-dihydroquinolin-3-yl}-1,1-dioxido-4H-1,2,4-benzothiadiazin-7-ylcarbamate;

3-(7-amino-1,1-dioxido-4H-1,2,4-benzothiadiazin-3-yl)-1-[(cyclopropylmethyl)amino]-4-hydroxyquinolin-2(1H)-one;

methyl 2-chloro-6-({3-[4-hydroxy-1-(isobutylamino)-2-oxo-1,2-dihydroquinolin-3-yl]-1,1-dioxido-4H-1,2,4-benzothiadiazin-7-yl}oxy)isonicotinate;

N-{3-[1-(cyclobutylamino)-4-hydroxy-2-oxo-1,2-dihydroquinolin-3-yl]-1,1-dioxido-4H-1,2,4-benzothiadiazin-7-yl}methanesulfonamide;

N-(3-{1-[(cyclopropylmethyl)amino]-4-hydroxy-2-oxo-1,2-dihydroquinolin-3-yl}-1,1-dioxido-4H-1,2,4-benzothiadiazin-7-yl)methanesulfonamide;

N-(3-{1-[(cyclopropylmethyl)amino]-4-hydroxy-2-oxo-1,2-dihydro-3-quinolinyl}-1,1-dioxido-4H-1,2,4-benzothiadiazin-7-yl)methanesulfonamide;

2-{[3-(1-amino-4-hydroxy-2-oxo-1,2-dihydro-3-quinolinyl)-1,1-dioxido-4H-1,2,4-benzothiadiazin-7-yl]oxy}acetamide;

N-{3-[1-(cyclobutylamino)-4-hydroxy-2-oxo-1,2-dihydro-3-quinolinyl]-1,1-dioxido-4H-1,2,4-benzothiadiazin-7-yl}ethanesulfonamide;

benzyl 3-{3-[1-(cyclobutylamino)-4-hydroxy-2-oxo-1,2-dihydro-3-quinolinyl]-1,1-dioxido-4H-1,2,4-benzothiadiazin-7-yl}diazathiane-1-carboxylate 2,2-dioxide;

N-{3-[1-(cyclobutylamino)-4-hydroxy-2-oxo-1,2-dihydro-3-quinolinyl]-1,1-dioxido-4H-1,2,4-benzothiadiazin-7-yl}-N'-methylsulfamide; and N-{3-[1-(cyclobutylamino)-4-hydroxy-2-oxo-1,2-dihydro-3-quinolinyl]-1,1-dioxido-4H-1,2,4-benzothiadiazin-7-yl}sulfamide; or a pharmaceutically acceptable salt form, stereoisomer or tautomer thereof.

In a fifth embodiment the present invention provides a compound of formula (Va)

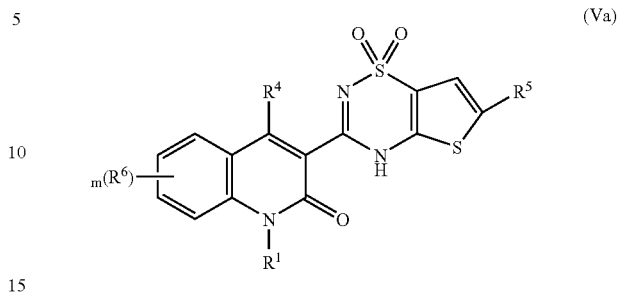

or a pharmaceutically acceptable salt form, stereoisomer or tautomer thereof, wherein:

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN-$, $R_aR_bNalkyl-$, $R_aR_bNC(O)alkyl-$, $R_aR_bNC(O)Oalkyl-$, $R_aR_bNC(O)NR_calkyl-$, $R_fR_gC=N-$ and $R_kO-$, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_e$), —SR$_c$, —S(O)R$_c$, —S(O)$_2$R$_c$, —OR$_c$, —N(R$_c$)(R$_e$), —C(O)R$_c$, —C(O)OR$_c$ and —C(O)NR$_c$R$_e$;

$R^4$ is selected from the group consisting of alkoxy, arylalkoxy, aryloxy, halo, hydroxy, $R_aR_bN-$, $N_3-$, $R_eS-$, wherein $R^4$ is substituted with 0, 1 or 2 substituents independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkoxy, halocarbonyl, heteroaryl, heteroarylalkyl, heterocycle, heterocyclealkyl, hydoxyalkyl, cycloalkyl, cyano, cyanoalkyl, nitro, $R_aR_bN-$, $R_aC(O)-$, $R_aS-$, $R_a(O)S-$, $R_a(O)_2S-$, $R_aR_bNalkyl-$, $R_a(O)SN(R_f)-$, $R_aSO_2N(R_f)-$, $R_a(O)SN(R_f)alkyl-$, $R_aSO_2N(R_f)alkyl-$, $R_aR_bNSO_2N(R_f)-$, $R_aR_bNSO_2N(R_f)alkyl-$, $R_aR_bNC(O)-$, $R_kOC(O)-$, $R_kOC(O)alkyl-$, $R_kOalkyl-$, $R_aR_bNSO_2-$, $R_aR_bNSO_2alkyl-$, $(R_bO)(R_a)P(O)O-$ and $-OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(N$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each $R^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, R$_c$R$_d$N—, R$_k$O—. R$_k$Oalkyl-, R$_c$R$_d$Nalkyl-, R$_c$R$_d$NC(O)alkyl-, —SO$_2$—, R$_c$SO$_2$alkyl-, R$_c$C(O)—, R$_c$(O)alkyl-, R$_c$OC(O)—, —OC(O)alkyl-, R$_c$R$_d$NalkylC(O)—, R$_c$R$_d$NC(O)—, R$_c$R$_d$NC(O)Oalkyl-, —R$_d$NC(O)N(R$_e$)alkyl-, wherein R$_a$ and R$_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, R$_a$ and R$_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), -(alkyl)SO$_2$NR$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$_c$ and R$_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each R$_c$ and R$_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, R$_c$ and R$_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

R$_e$ is selected from the group consisting of hydrogen, alkenyl, alkyl and cycloalkyl;

R$_f$, R$_g$ and R$_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each R$_f$, R$_g$ and R$_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, R$_f$ and R$_g$ together with the carbon atom to which they are attached form a three- to seven-membered ring selected from the group consisting of cycloalkyl, cycloalkenyl and heterocycle;

alternatively, R$_f$ and R$_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

R$_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, R$_a$R$_b$Nalkyl-, R$_a$Oalkyl-, R$_a$R$_b$NC(O)—, R$_a$R$_b$NC(O)alkyl, R$_a$S—, R$_a$S(O)—, R$_a$SO$_2$—, R$_a$S-alkyl-, R$_a$(O)Salkyl-, R$_a$SO$_2$alkyl-, R$_a$OC(O)—, R$_a$OC(O)alkyl-, R$_a$C(O)—, R$_a$C(O)alkyl-, wherein each R$_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$; and m is 0, 1, 2, 3, or 4;

with the proviso that when R$^4$ is alkoxy, aryloxy, hydroxy or R$_c$S—, and R$^5$ is hydrogen, alkenyl, alkoxy, alkyl, alkynyl, aryl, halo, heteroaryl, heterocyclealkyl, cycloalkyl, cyano, nitro, R$_a$R$_b$N—, R$_a$C(O)—, R$_a$S—, R$_a$(O)S—, R$_a$(O)$_2$S—, R$_a$SO$_2$N(R$_f$)—, R$_a$R$_b$NC(O)—, R$_k$OC(O)—, R$_a$R$_b$NSO$_2$— or —OR$_k$, and R$^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$, then R$^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (Va) wherein R$^4$ is hydroxy.

For example, the present invention provides a compound of formula (Va) wherein R$^4$ is hydroxy and wherein R$^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, $R_aR_bN-$, $R_aR_bNalkyl-$, $R_aR_bNC(O)alkyl-$, $R_fR_gC=N-$ and $R_kO-$.

For example, the present invention provides a compound of formula (Va) wherein $R^4$ is hydroxy and wherein $R^1$ is selected from the group consisting of C1-C7 alkyl, phenyl-C1-C2 alkyl-, heteroaryl-C1-C2 alkyl-, ((C3-C6 cycloalkyl)C1-C2 alkyl)-,(C1-C7 alkyl)O—, (C3-C7 cycloalkyl)O—, phenyl-C1-C2 alkyl-O—, —$NH_2$, (C1-C7 alkyl)N(H)—, (C3-C7 cycloalkyl)N(H)—, ((C3-C7 cycloalkyl)C1-C2 alkyl)N(H)—, (heterocycle)N(H)—, (heteroarylalkyl)N(H)—,(arylalkyl)N(H)—.

For example, the present invention provides a compound of formula (Va) wherein $R^4$ is hydroxy and wherein $R^1$ is selected from the group consisting of isopropyl, 3-methylbutyl, butyl, isobutyl, phenylmethyl, thienylmethyl, cyclobutylmethyl, cyclopropylethyl, —$NH_2$, (isopropyl)N(H)—, (isobutyl)N(H)—, (3-methylbutyl)N(H)—, (cyclobutyl)N(H)— and (cyclopropylmethyl)N(H)—; wherein the phenylmethyl and the thienylmethyl are independently unsubstituted or substituted with 1, 2 or 3 substituents selected from the group consisting of alkyl, alkenyl, alkynyl, haloalkyl, halo, cyano, nitro, —$NH_2$, —N(H)alkyl, —$N(alkyl)_2$, hydroxy and alkoxy.

In a sixth embodiment the present invention provides a compound of formula (Vb)

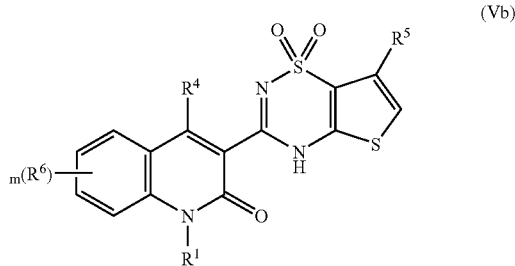

(Vb)

or a pharmaceutically acceptable salt form, stereoisomer or tautomer thereof, wherein:

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN-$, $R_aR_bNalkyl-$, $R_aR_bNC(O)alkyl-$, $R_aR_bNC(O)Oalkyl-$, $R_aR_bNC(O)NR_calkyl-$, $R_fR_gC=N-$ and $R_kO-$, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_e$), —$SR_c$, —$S(O)R_c$, —$S(O)_2R_c$, —$OR_c$, —$N(R_c)(R_e)$, —$C(O)R_c$, —$C(O)OR_c$ and —$C(O)NR_cR_e$;

$R^4$ is selected from the group consisting of alkoxy, arylalkoxy, aryloxy, halo, hydroxy, $R_aR_bN-$, $N_3-$, $R_eS-$, wherein $R^4$ is substituted with 0, 1 or 2 substituents independently selected from the group consisting of halo, nitro, cyano, —OH, —$NH_2$, and —COOH;

$R_5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN-$, $R_aC(O)-$, $R_aS-$, $R_a(O)S-$, $R_a(O)_2S-$, $R_aR_bNalkyl-$, $R_a(O)SN(R_f)-$, $R_aSO_2N(R_f)-$, $R_a(O)SN(R_f)alkyl-$, $R_aSO_2N(R_f)alkyl-$, $R_aR_bNSO_2N(R_f)-$, $R_aR_bNSO_2N(R_f)alkyl-$, $R_aR_bNC(O)-$, $R_kOC(O)-$, $R_kOC(O)alkyl-$, $R_kOalkyl-$, $R_aR_bNSO_2-$, $R_aR_bNSO_2alkyl-$, $(R_bO)(R_a)P(O)O-$ and —$OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), —$SR_a$, $S(O)R_a$, —$S(O)_2R_a$, —$OR_k$, —$N(R_a)(R_b)$, —$C(O)R_a$, —$C(O)OR_a$ and —$C(O)NR_aR_b$; wherein each $R^6$ is independently substituted with 0, 1, 2 or 3 substituents independently selected from the group consisting of alkyl, alkenyl, alkynyl, oxo, halo, haloalkyl, cyano, nitro, —$OR_a$, —$NR_aR_b$, —$SR_a$, —$SOR_a$, —$SO_2R_a$, —$C(O)OR_a$, —$C(O)NR_aR_b$ and —$NC(O)R_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN-$, $R_kO-$. $R_kOalkyl-$, $R_eR_dNalkyl-$, $R_cR_dNC(O)alkyl-$, $R_cSO_2-$, $R_cSO_2alkyl-$, $R_cC(O)-$, $R_cC(O)alkyl-$, $R_cOC(O)-$, $R_cOC(O)alkyl-$, $R_cR_dNalkylC(O)-$, $R_cR_dNC(O)-$, $R_cR_dNC(O)Oalkyl-$, $R_cR_dNC(O)N(R_e)alkyl-$, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_eR_d$), -(alkyl)$SO_2NR_eR_d$, -alkylC(O)$NR_eR_d$, —$SR_c$, —$S(O)R_e$, —$S(O)_2R_c$, —$OR_c$, —$N(R_c)(R_d)$, —$C(O)R_c$, —$C(O)OR_c$ and —$C(O)NR_cR_d$;

$R_c$ and $R_d$, at each occurrence, are independently selected from the group consisting of hydrogen, —$NR_fR_h$, —$OR_f$, —$CO(R_f)$, —$SR_f$, —$SOR_f$, —$SO_2R_f$, —$C(O)NR_fR_h$, —$SO_2NR_fR_h$, —$C(O)OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, R$_c$ and R$_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

R$_e$ is selected from the group consisting of hydrogen, alkenyl, alkyl and cycloalkyl;

R$_f$, R$_g$ and R$_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each R$_f$, R$_g$ and R$_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, R$_f$ and R$_g$ together with the carbon atom to which they are attached form a three- to seven-membered ring selected from the group consisting of cycloalkyl, cycloalkenyl and heterocycle;

alternatively, R$_f$ and R$_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

R$_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, R$_a$R$_b$Nalkyl-, R$_a$Oalkyl-, R$_a$R$_b$NC(O)—, R$_a$R$_b$NC(O)alkyl, R$_a$S—, R$_a$S(O)—, R$_a$SO$_2$—, R$_a$S-alkyl-, R$_a$(O)Salkyl-, R$_a$SO$_2$alkyl-, R$_a$OC(O)—, R$_a$OC(O)alkyl-, R$_a$C(O)—, R$_a$C(O)alkyl-, wherein each R$_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$; and m is 0, 1, 2, 3, or 4;

with the proviso that when R$^4$ is hydroxy or R$_e$S—, and R$^5$ is hydrogen, unsubstituted alkyl, halo or —OR$_k$, and R$^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$, then R$^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (Vb) wherein R$^4$ is hydroxy.

For example, the present invention provides a compound of formula (Vb) wherein R$^4$ is hydroxyl and R$^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, R$_a$R$_b$N—, R$_a$R$_b$Nalkyl-, R$_a$R$_b$NC(O)alkyl-, R$_f$R$_g$C=N— and R$_k$O—.

For example, the present invention provides a compound of formula (Vb) wherein R$^4$ is hydroxy and wherein R$^1$ is selected from the group consisting of C1-C7 alkyl, phenyl-C1-C2 alkyl-, heteroaryl-C1-C2 alkyl-, ((C3-C6 cycloalkyl)C1-C2 alkyl)-,(C1-C7 alkyl)O—, (C3-C7 cycloalkyl)O—, phenyl-C1-C2 alkyl-O—, —NH$_2$, (C1-C7 alkyl)N(H)—, (C3-C7 cycloalkyl)N(H)—, ((C3-C7 cycloalkyl)C1-C2 alkyl)N(H)—, (heterocycle)N(H)—, (heteroarylalkyl)N(H)—,(arylalkyl)N(H)—.

For example, the present invention provides a compound of formula (Vb) wherein R$^4$ is hydroxy and wherein R$^1$ is selected from the group consisting of isopropyl, 3-methylbutyl, butyl, isobutyl, phenylmethyl, thienylmethyl, cyclobutylmethyl, cyclopropylethyl, —NH$_2$, (isopropyl)N(H)—, (isobutyl)N(H)—, (3-methylbutyl)N(H)—, (cyclobutyl)N(H)— and (cyclopropylmethyl)N(H)—; wherein the phenylmethyl and the thienylmethyl are independently unsubstituted or substituted with 1, 2 or 3 substituents selected from the group consisting of alkyl, alkenyl, alkynyl, haloalkyl, halo, cyano, nitro, —NH$_2$, —N(H)alkyl, —N(alkyl)$_2$, hydroxy and alkoxy.

In a seventh embodiment the present invention provides a compound of formula (VIa)

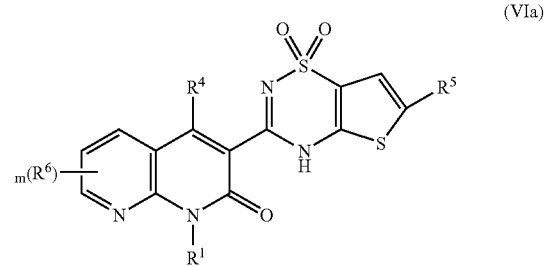

(VIa)

or a pharmaceutically acceptable salt form, stereoisomer or tautomer thereof, wherein:

R$^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN—$, $R_aR_bNalkyl-$, $R_aR_bNC(O)alkyl-$, $R_aR_bNC(O)Oalkyl-$, $R_aR_bNC(O)NR_calkyl-$, $R_fR_gC=N—$ and $R_kO—$, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_e$), $—SR_c$, $—S(O)R_c$, $—S(O)_2R_c$, $—OR_c$, $—N(R_c)(R_c)$, $—C(O)R_c$, $—C(O)OR_c$ and $—C(O)NR_cR_e$;

$R^4$ is selected from the group consisting of alkoxy, arylalkoxy, aryloxy, halo, hydroxy, $R_aR_bN—$, $N_3—$, $R_eS—$, wherein $R^4$ is substituted with 0, 1 or 2 substituents independently selected from the group consisting of halo, nitro, cyano, $—OH$, $—NH_2$, and $—COOH$;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN—$, $R_aC(O)—$, $R_aS—$, $R_a(O)S—$, $R_a(O)_2S—$, $R_aR_bNalkyl-$, $R_a(O)SN(R_f)—$, $R_aSO_2N(R_f)—$, $R_a(O)SN(R_f)alkyl-$, $R_aSO_2N(R_f)alkyl-$, $R_aR_bNSO_2N(R_f)—$, $R_aR_bNSO_2N(R_f)alkyl-$, $R_aR_bNC(O)—$, $R_kOC(O)—$, $R_kOC(O)alkyl-$, $R_kOalkyl-$, $R_aR_bNSO_2—$, $R_aR_bNSO_2alkyl-$, $(R_bO)(R_a)P(O)O—$ and $—OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($R_d$), $—SR_c$, $—S(O)R_c$, $—S(O)_2R_c$, $—OR_c$, $—N(R_c)(R_d)$, $—C(O)R_c$, $—C(O)OR_c$ and $—C(O)NR_cR_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), $—SR_a$, $—S(O)R_a$, $—S(O)_2R_a$, $—OR_k$, $—N(R_a)(R_b)$, $—C(O)R_a$, $—C(O)OR_a$ and $—C(O)NR_aR_b$; wherein each $R^6$ is independently substituted with 0, 1, 2 or 3 substituents independently selected from the group consisting of alkyl, alkenyl, alkynyl, oxo, halo, haloalkyl, cyano, nitro, $—OR_a$, $—NR_aR_b$, $—SR_a$, $—SOR_a$, $—SO_2R_a$, $—C(O)OR_a$, $—C(O)NR_aR_b$ and $—NC(O)R_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN—$, $R_kO—$. $R_tOalkyl-$, $R_cR_dNalkyl-$, $R_cR_dNC(O)alkyl-$, $R_cSO_2—$, $R_cSO_2alkyl-$, $R_cC(O)—$, $R_cC(O)alkyl-$, $R_cOC(O)—$, $R_cOC(O)alkyl-$, $R_cR_dNalkylC(O)—$, $R_cR_dNC(O)—$, $R_cR_dNC(O)Oalkyl-$, $R_cR_dNC(O)N(R_c)alkyl-$, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $—SR_c$, $—S(O)R_c$, $—S(O)_2R_c$, $—OR_c$, $—N(R_c)(R_d)$, $—C(O)R_c$, $—C(O)OR_c$ and $—C(O)NR_cR_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -(alkyl)$SO_2NR_cR_d$, -alkylC(O)$NR_cR_d$, $—SR_c$, $—S(O)R_c$, $—S(O)_2R_c$, $—OR_c$, $—N(R_c)(R_d)$, $—C(O)R_c$, $—C(O)OR_c$ and $—C(O)NR_cR_d$;

$R_c$ and $R_d$, at each occurrence, are independently selected from the group consisting of hydrogen, $—NR_fR_h$, $—OR_f$, $—CO(R_f)$, $—SR_f$, $—SOR_f$, $—SO_2R_f$, $—C(O)NR_fR_h$, $—SO_2NR_fR_h$, $—C(O)OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), $—SR_f$, $—S(O)R_f$, $—S(O)_2R_f$, $—OR_f$, $—N(R_f)(R_h)$, $—C(O)R_f$, $—C(O)OR_f$, $—C(O)NR_fR_h$, $—C(O)N(H)NR_fR_h$, $—N(R_e)C(O)OR_f$, $—N(R_e)SO_2NR_fR_h$, $—N(R_e)C(O)NR_fR_h$, -(alkyl)$N(R_e)C(O)OR_f$, -(alkyl)$N(R_e)SO_2NR_fR_h$, and -alkyl$N(R_e)C(O)NR_fR_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), $—SR_f$, $—S(O)R_f$, $—S(O)_2R_f$, $—OR_f$, $—N(R_f)(R_h)$, $—C(O)R_f$, $—C(O)OR_f$ and $—C(O)NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1 or 2 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, $—OH$, $—O(alkyl)$, $—NH_2$, $—N(H)(alkyl)$, $—N(alkyl)_2$, $—S(alkyl)$, $—S(O)(alkyl)$, $—SO_2alkyl$, -(alkyl)-OH, -(alkyl)-O-alkyl, -(alkyl)$NH_2$, -(alkyl)N(H)(alkyl), -(alkyl)N(alkyl)$_2$, -alkylS(alkyl), -(alkyl)S(O)(alkyl), -(alkyl)$SO_2alkyl$, $—N(H)C(O)NH_2$, $—C(O)OH$, $—C(O)O(alkyl)$, $—C(O)alkyl$, $—C(O)NH_2$, $—C(O)NH_2$, $—C(O)N(H)(alkyl)$, and $—C(O)N(alkyl)_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH₂, —N(H)(alkyl), —N(alkyl)₂, —S(alkyl), —S(alkyl), —S(O)(alkyl), -(alkyl)-OH, -(alkyl)-O-alkyl, -(alkyl)NH₂, -(alkyl)N(H)(alkyl), -alkylS(alkyl), -(alkyl)S(O)(alkyl), -(alkyl)SO₂alkyl, -(alkyl)N(alkyl)₂, —N(H)C(O)NH₂, —C(O)OH, —C(O)O(alkyl), —C(O)alkyl, —C(O)NH₂, —C(O)NH₂, —C(O)N(H)(alkyl), and —C(O)N(alkyl)₂;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_a$S—, $R_a$S(O)—, $R_a$SO₂—, $R_a$S-alkyl-, $R_a$(O)Salkyl-, $R_a$SO₂alkyl-, $R_a$OC(O)—, $R_a$OC(O)alkyl-, $R_a$C(O)—, $R_a$C(O)alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)₂R$_c$, —OR$_c$, —N(R$_c$)(R$_d$), —C(O)R$_c$, —C(O)OR$_c$ and —C(O)NR$_c$R$_d$; and m is 0, 1, 2, 3, or 4;

with the proviso that $R^4$ is alkoxy, aryloxy, hydroxy or $R_c$S—, and $R^5$ is hydrogen, alkenyl, alkoxy, alkyl, alkynyl, aryl, halo, heteroaryl, heterocyclealkyl, cycloalkyl, cyano, nitro, $R_aR_b$N—, $R_a$C(O)—, $R_a$S—, $R_a$(O)S—, $R_a$(O)₂S—, $R_a$SO₂N(R$_f$)—, $R_aR_b$NC(O)—, $R_k$OC(O)—, $R_aR_b$NSO₂— or —OR$_k$, and $R^6$ is hydrogen, alkyl, alkenyl, alkynyl, halo, cyano, nitro, aryl, heteroaryl, heterocyclealkyl, —SR$_a$, —S(O)R$_a$, —S(O)₂R$_a$, —OR$_k$, —N(R$_a$)(R$_b$), —C(O)R$_a$, C(O)OR$_a$ and —C(O)NR$_a$R$_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a comound of formula (VIa) wherein $R^4$ is hydroxy.

For example, the present invention provides a comound of formula (VIa) wherein $R^4$ is hydroxy and $R^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, $R_aR_b$N—, $R_aR_b$Nalkyl-, $R_aR_b$NC(O)alkyl-, $R_fR_g$C=N— and $R_k$O—.

For example, the present invention provides a compound of formula (VIa) wherein $R^4$ is hydroxy and $R^1$ is selected from the group consisting of hydrogen, C1-C7 alkyl, C1-C6 alkenyl, (C3-C7 cycloalkyl)(C1-C2 alkyl)-, (C5-C6 cycloalkenyl)(C1-C2 alkyl)-, C3-C7 cycloalkyl, phenyl-C1-C2 alkyl-, furyl(C1-C2 alkyl)-, thienyl(C1-C2 alkyl)-, phenyl(C1-C2 alkyl)-, pyridinyl(C1-C2 alkyl)-, thiazolyl(C1-C2 alkyl)-, isoxazolyl(C1-C2alkyl)-, naphthyl(C1-C2 alkyl), benzothienyl(C1-C2 alkyl)-, indolyl(C1-C2 alkyl)-, phenylN(H)(C1-C6 alkyl)-, (C1-C7 alkyl)O—, (C3-C6 cycloalkyl)O—, ((phenyl)C1-C2 alkyl)O—, phenylCH=N—, NH₂, (C1-C7 alkyl)N(H)—, (C1-C7 alkenyl)N(H)—, (C3-C7 cycloalkyl)N(H)—, ((C3-C7 cycloalkyl)C1-C2 alkyl)N(H)—, ((phenyl)C1-C2 alkyl)N(H)—, (thienylmethyl)N(H)—, (thiazolylmethyl)N(H)—, (furylmethyl)N(H)—, (pyridinylmethyl)N(H)—, (tetrahydropyran)N(H)—, (benzyl)N(H)—, (tetrahydronaphthalenyl)N(H)—, wherein each $R^1$ is substituted with 0, 1, 2, or 3 substituents selected from the group consisting of alkyl, hydroxy, oxo, halo, cyano, nitro, haloalkyl, hydroxyl, alkoxy, haloalkoxy, phenyl, piperazinyl, morphilinyl, carboxy, —C(O)O(alkyl), —NH₂, —NH(alkyl), —N(alkyl)₂, -Oalkyl, —O-phenyl.

For example, the present invention provides a compound of formula (VIa) wherein $R^4$ is hydroxy and $R^1$ is selected from the group consisting of phenylmethyl, phenylethyl, C3 alkyl, C4 alkyl, C5 alkyl, cyclopropylmethyl, cyclopropylethyl, cyclobutylmethyl, (5-chloro-thien-2-yl)methyl- (C3 alkyl)N(H)—, (C4 alkyl)N(H)—, (C5 alkyl)N(H)—, (cyclobutyl)N(H)— and (cyclopropylmethyl)N(H)—.

In an eighth embodiment the present invention provides a compound of formula

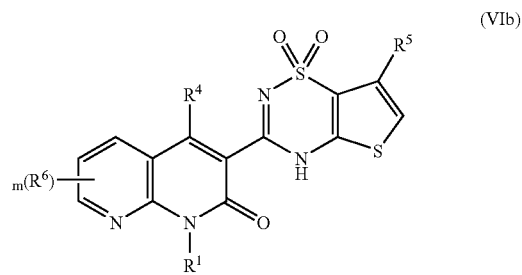

(VIb)

or a pharmaceutically acceptable salt form, stereoisomer or tautomer thereof, wherein:

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_b$N—, $R_aR_b$Nalkyl-, $R_aR_b$NC(O)alkyl-, $R_aR_b$NC(O)Oalkyl-, $R_aR_b$NC(O)NR$_c$alkyl-, $R_fR_g$C=N— and $R_k$O—, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R), —SR$_c$, —S(O)R$_c$, —S(O)₂R$_c$, —OR$_c$, —N(R$_c$)(R$_e$), —C(O)R$_c$, —C(O)OR$_c$ and —C(O)NR$_c$R$_e$;

$R^4$ is selected from the group consisting of alkoxy, arylalkoxy, aryloxy, halo, hydroxy, $R_aR_b$N—, $N_3$—, $R_e$S—, wherein $R^4$ is substituted with 0, 1 or 2 substituents independently selected from the group consisting of halo, nitro, cyano, —OH, —NH₂, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_b$N—, $R_a$C(O)—, $R_a$S—, $R_a$(O)S—, $R_a$(O)₂S—, $R_aR_b$Nalkyl-, $R_a$(O)SN(R$_f$)—, $R_a$SO₂N(R$_f$)—, $R_a$(O)SN(R$_f$)alkyl-, $R_a$SO₂N(R$_f$)alkyl-, $R_aR_b$NSO₂N(R$_f$)—, $R_aR_b$NSO₂N(R$_f$)alkyl-, $R_aR_b$NC(O)—, $R_k$OC(O)—, $R_k$OC(O)alkyl-, $R_k$Oalkyl-, $R_aR_b$NSO₂—, $R_aR_b$NSO₂alkyl-, (R$_b$O)(R$_a$)P(O)O— and —OR$_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(N$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each R$^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, C(O)NR$_a$R$_b$ and —NC(O)R$_a$;

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, R$_c$R$_d$N—, R$_k$O—. R$_k$Oalkyl-, R$_c$R$_d$Nalkyl-, R$_c$R$_d$NC(O)alkyl-, R$_c$SO$_2$—, R$_c$SO$_2$alkyl-, R$_c$C(O)—, R$_c$C(O)alkyl-, R$_c$OC(O)—, R$_c$OC(O)alkyl-, R$_c$R$_d$NalkylC(O)—, R$_c$R$_d$NC(O)—, R$_c$R$_d$NC(O)Oalkyl-, R$_c$R$_d$NC(O)N(R$_c$)alkyl-, wherein R$_a$ and R$_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, R$_a$ and R$_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), -(alkyl)SO$_2$NR$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$_c$ and R$_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each R$_c$ and R$_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, R$_c$ and R$_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

R$_e$ is selected from the group consisting of hydrogen, alkenyl, alkyl and cycloalkyl;

R$_f$, R$_g$ and R$_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each R$_f$, R$_g$ and R$_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, R$_f$ and R$_g$ together with the carbon atom to which they are attached form a three- to seven-membered ring selected from the group consisting of cycloalkyl, cycloalkenyl and heterocycle;

alternatively, R$_f$ and R$_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

R$_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, R$_a$R$_b$Nalkyl-, R$_a$Oalkyl-, R$_a$R$_b$NC(O)—, R$_a$R$_b$NC(O)alkyl, R$_a$S—, R$_a$S(O)—, R$_a$SO$_2$—, R$_a$Salkyl-, R$_a$(O)Salkyl-, R$_a$SO$_2$alkyl-, R$_a$OC(O)—, R$_a$OC(O)alkyl-, R$_a$C(O)—, R$_a$C(O)alkyl-, wherein each R$_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$; and m is 0, 1, 2, 3, or 4;

with the proviso that when R$^4$ is hydroxy or R$_e$S—, and R$^5$ is hydrogen, unsubstituted alkyl, halo or —OR$_k$, and R$^6$ is hydrogen, alkyl, alkenyl, alkynyl, halo, cyano, nitro, aryl, heteroaryl, heterocyclealkyl, —SR$_a$, —S(O)R$_a$, —S(O)$_2$R$_a$, —OR$_k$, —N(R$_a$)(R$_b$), C(O)R$_a$, C(O)OR$_a$ and —C(O)NR$_a$R$_b$, then R$^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (VIb) wherein R$^4$ is hydroxy and R$^1$ is selected from the group consisting of hydrogen, C1-C7 alkyl, C1-C6 alkenyl, (C3-C7 cycloalkyl)(C1-C2 alkyl)-, (C5-C6 cycloalkenyl)(C1-C2 alkyl)-, C3-C7 cycloalkyl, phenyl-C1-C2 alkyl-, furyl(C1-C2 alkyl)-, thienyl(C1-C2 alkyl)-, phenyl (C1-C2 alkyl)-, pyridinyl(C1-C2 alkyl)-, thiazolyl(C1-C2 alkyl)-, isoxazolyl(C1-C2alkyl)-, naphthyl(C1-C2 alkyl), berizothienyl(C1-C2 alkyl)-, indolyl(C1-C2 alkyl)-, phenylN(H)(C1-C6 alkyl)-, (C1-C7 alkyl)O—, (C3-C6 cycloalkyl)O—, ((phenyl)C1-C2 alkyl)O—, phenylCH=N—, NH$_2$, (C1-C7 alkyl)N(H)—, (C1-C7 alkenyl)N(H)—, (C3-C7 cycloalkyl)N(H)—, ((C3-C7 cycloalkyl)C1-C2 alkyl)N(H)—, ((phenyl)C1-C2 alkyl)N(H)—, (thienylmethyl)N(H)—, (thiazolylmethyl)N(H)—, (furylmethyl)N(H)—, (pyridinylmethyl)N(H)—, (tetrahydropyran)N(H)—, (benzyl)N(H)—, (tetrahydronaphthalenyl)N(H)—, wherein each R$^1$ is substituted with 0, 1, 2, or 3 substituents selected from the group consisting of alkyl, hydroxy, oxo, halo, cyano, nitro, haloalkyl, hydroxyl, alkoxy, haloalkoxy, phenyl, piperazinyl, morphilinyl, carboxy, —C(O)O(alkyl), —NH$_2$, —NH(alkyl), —N(alkyl)$_2$, -Oalkyl, —O-phenyl.

For example, the present invention provides a compound of formula (VIb) wherein R$^4$ is hydroxy and R$^1$ is selected from the group consisting of phenylmethyl, phenylethyl, C3 alkyl, C4 alkyl, C5 alkyl, cyclopropylmethyl, cyclopropylethyl, cyclobutylmethyl, (5-chloro-thien-2-yl)methyl- (C3 alkyl)N(H)—, (C4 alkyl)N(H)—, (C5 alkyl)N(H)—, (cyclobutyl)N(H)— and (cyclopropylmethyl)N(H)—.

In a ninth embodiment the present invention provides a compound of formula (VII)

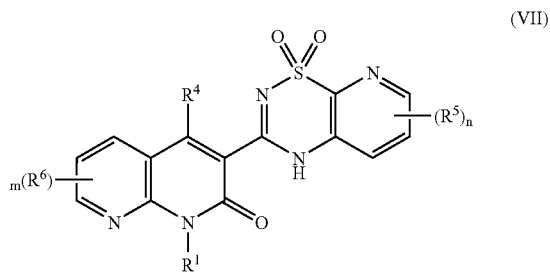

(VII)

or a pharmaceutically acceptable salt form, stereoisomer or tautomer thereof, wherein:

R$^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, R$_a$R$_b$N—, R$_a$R$_b$Nalkyl-, R$_a$R$_b$NC(O)alkyl-, R$_a$R$_b$NC(O)Oalkyl-, R$_a$R$_b$NC(O)NR$_c$alkyl-, R$_f$R$_g$C=N— and R$_k$O—, wherein R$^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(O$_c$), -(alkyl)(NR$_c$R$_e$), —SR$_c$, —S(O)R$_c$, —S(O)$_2$R$_c$, —OR$_c$, —N(R$_c$)(R$_e$), —C(O)R$_c$, —C(O)OR$_c$ and —C(O)NR$_c$R$_e$;

R$^4$ is selected from the group consisting of alkoxy, arylalkoxy, aryloxy, halo, hydroxy, R$_a$R$_b$N—, N$_3$—, R$_e$S—, wherein R$^4$ is substituted with 0, 1 or 2 substituents independently selected from the group consisting of halo, nitro, cyano, —OH, —NH$_2$, and —COOH;

R$^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, R$_a$R$_b$N—, R$_a$C(O)—, R$_a$S—, R$_a$(O)S—, R$_a$(O)$_2$S—, R$_a$R$_b$Nalkyl-, R$_a$(O)SN(R$_f$)—, R$_a$SO$_2$N(R$_f$)—, R$_a$(O)SN(R$_f$)alkyl-, R$_a$SO$_2$N(R$_f$)alkyl-, R$_a$R$_b$NSO$_2$N(R$_f$)—, R$_a$R$_b$NSO$_2$N(R$_f$)alkyl-, R$_a$R$_b$NC(O)—, R$_k$OC(O)—, R$_k$OC(O)alkyl-, R$_k$Oalkyl-, R$_a$R$_b$NSO$_2$—, R$_a$R$_b$NSO$_2$alkyl-, (R$_b$O)(R$_a$)P(O)O— and —OR$_k$, wherein each R$^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)N$_c$R$_e$;

R is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each R$^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, R$_c$R$_d$N—, R$_k$O—. R$_k$Oalkyl-, R$_c$R$_d$Nalkyl-, R$_c$R$_d$NC(O)alkyl-, R$_c$SO$_2$—, R$_c$SO$_2$alkyl-, R$_c$C(O)—, R$_c$C(O)alkyl-, R$_c$OC(O)—, R$_c$OC(O)alkyl-, R$_c$R$_d$NalkylC(O)—, R$_c$R$_d$NC(O)—, R$_c$R$_d$NC(O)Oalkyl-, R$_c$R$_d$NC(O)N(R$_e$)alkyl-, wherein R$_a$ and R$_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, R$_a$ and R$_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), -(alkyl)SO$_2$NR$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

R$_c$ and R$_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —S(O)$R_f$, —S(O)$_2R_f$, —$OR_f$, —N($R_f$)($R_h$), —C(O)$R_f$, —C(O)$OR_f$, —C(O)$NR_fR_h$, —C(O)N(H)$NR_fR_h$, —N($R_e$)C(O)$OR_f$, —N($R_e$)SO$_2NR_fR_h$, —N($R_e$)C(O)$NR_fR_h$, -(alkyl)N($R_e$)C(O)$OR_f$, -(alkyl)N($R_e$)SO$_2NR_fR_h$, and -alkylN($R_e$)C(O)$NR_fR_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —S(O)$R_f$, —S(O)$_2R_f$, —$OR_f$, —N($R_f$)($R_h$), —C(O)$R_f$, —C(O)$OR_f$ and —C(O)$NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_a$S—, $R_a$S(O)—, $R_a$SO$_2$—, $R_a$S-alkyl-, $R_a$(O)Salkyl-, $R_a$SO$_2$alkyl-, $R_a$OC(O)—, $R_a$OC(O)alkyl-, $R_a$C(O)—, $R_a$C(O)alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

m is 0, 1, 2, 3, or 4; and n is 0, 1, 2, 3 or 4;

with the proviso that when $R^4$ is alkoxy, aryloxy, hydroxy or $R_e$S—, and $R^5$ is hydrogen, alkenyl, alkoxy, alkyl, alkynyl, aryl, halo, heteroaryl, heterocyclealkyl, cycloalkyl, cyano, nitro, $R_aR_b$N—, $R_a$C(O)—, $R_a$S—, $R_a$(O)S—, $R_a$(O)$_2$S—, $R_a$SO$_2$N($R_f$)—, $R_aR_b$NC(O)—, $R_k$OC(O)—, $R_aR_b$NSO$_2$— or —$OR_k$, and $R^6$ is hydrogen, alkyl, alkenyl, alkynyl, halo, cyano, nitro, aryl, heteroaryl, heterocyclealkyl, —$SR_a$, —S(O)$R_a$, —S(O)$_2R_a$, —$OR_a$, —N($R_a$)($R_b$), —C(O)$R_a$, —C(O)$OR_a$ and —C(O)$NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl.

For example, the present invention provides a compound of formula (VII) wherein $R^4$ is hydroxy.

For example, the present invention provides a compound of formula (VII) wherein $R^4$ is hydroxy and $R^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, $R_aR_b$N—, $R_aR_b$Nalkyl-, $R_aR_b$NC(O)alkyl-, $R_fR_g$C=N— and $R_k$O—.

For example, the present invention provides a compound of formula (VII) wherein $R^4$ is hydroxy and $R^1$ is selected from the group consisting of hydrogen, C1-C7 alkyl, C1-C6 alkenyl, furyl(C1-C2 alkyl)-, thienyl(C1-C2 alkyl)-, phenyl(C1-C2 alkyl)-, pyridinyl(C1-C2 alkyl)-, thiazolyl(C1-C2 alkyl)-, isoxazolyl(C1-C2alkyl)-, naphthyl(C1-C2 alkyl), benzothienyl(C1-C2 alkyl)-, indolyl(C1-C2 alkyl)-, (C3-C7 cycloalkyl)(C1-C2 alkyl)-, (C5-C6 cycloalkenyl)(C1-C2 alkyl)-, C3-C7 cycloalkyl, phenylN(H)(C1-C6 alkyl)-, (phenylalkyl)O—, (C1-C7 alkyl)O—, (C3-C6 cycloalkyl)O—, phenylCH=N—, NH$_2$, (C1-C7 alkyl)N(H)—, (C1-C7 alkenyl)N(H)—, (C3-C7 cycloalkyl)N(H)—, ((C3-C7 cycloalkyl)C1-C2 alkyl)N(H)—, (thienylmethyl)N(H)—, (thiazolylmethyl)N(H)—, (furylmethyl)N(H)—, (pyridinylmethyl)N(H)—, (tetrahydropyran)N(H)—, (phenylalkyl)N(H)—, (tetrahydronaphthalenyl)N(H)—, wherein each $R^1$ is substituted with 0, 1, 2, or 3 substituents selected from the group consisting of alkyl, hydroxy, oxo, halo, cyano, nitro, haloalkyl, haloalkoxy, phenyl, piperazinyl, morphilinyl, carboxy, —C(O)O(alkyl), —NH$_2$, —NH(alkyl), —N(alkyl)$_2$, -Oalkyl, —O-phenyl.

For example, the present invention provides a compound of formula (VII) wherein $R^4$ is hydroxy and $R^1$ is selected from the group consisting of C3 alkyl, C4 alkyl, C5 alkyl, phenylmethyl, (5-chloro-thien-2-yl)methyl-, —NH$_2$, (C3 alkyl)N(H)—, (C4 alkyl)N(H)—, (C5 alkyl)N(H)—, (cyclobutyl)N(H)— and (cyclopropylmethyl)N(H)—.

In a tenth embodiment the present invention provides a compound of formula (VIII)

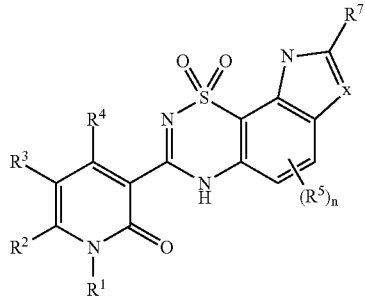

(VIII)

or a pharmaceutically acceptable salt form, stereoisomer or tautomer thereof, wherein:

X is NH, N(alkyl), O or S;

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN$—, $R_aR_b$Nalkyl-, $R_aR_b$NC(O)alkyl-, $R_aR_b$NC(O)Oalkyl-, $R_aR_b$NC(O)NR$_c$alkyl-, $R_fR_gC$=N— and $R_kO$—, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R), —SR$_c$, —S(O)R$_c$, —S(O)$_2$R$_c$, —OR$_c$, —N(R$_c$)(R$_e$), —C(O)R$_c$, —C(O)OR$_c$ and —C(O)NR$_c$R$_e$;

$R^2$ and $R^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$ and R$_a$C(O)—; wherein $R^2$ and $R^3$ are independently substituted with 0, 1, 2 or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$;

alternatively, $R^2$ and $R^3$, together with the carbon atoms to which they are attached form a five- or six-membered ring selected from the group consisting of aryl, cycloalkyl, heteroaryl and heterocycle, wherein said aryl, cycloalkyl, heteroaryl and heterocycle is optionally substituted with $(R^6)_m$;

$R^4$ is selected from the group consisting of alkoxy, arylalkoxy, aryloxy, halo, hydroxy, $R_aR_bN$—, $N_3$—, $R_eS$—, wherein $R^4$ is independently substituted with 0, 1 or 2 substituents independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_aC(O)$—, $R_aS$—, $R_a(O)S$—, $R_a(O)_2S$—, $R_aR_b$Nalkyl-, $R_a(O)SN(R_f)$—, $R_aSO_2N(R_f)$—, $R_a(O)SN(R_f)$alkyl-, $R_aSO_2N(R_f)$alkyl-, $R_aR_bNSO_2N(R_f)$—, $R_aR_bNSO_2N(R_f)$alkyl-, $R_aR_bNC(O)$—, $R_kOC(O)$—, $R_kOC(O)$alkyl-, $R_kO$alkyl-, $R_aR_bNSO_2$—, $R_aR_bNSO_2$alkyl-, $(R_bO)(R_a)P(O)O$— and —OR$_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each $R^6$ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

$R^7$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_aC(O)$—, $R_aS$—, $R_a(O)S$—, $R_a(O)_2S$—, $R_aR_b$Nalkyl-, $R_a(O)SN(R_f)$—, $R_aSO_2N(R_f)$—, $R_a(O)SN(R_f)$alkyl-, $R_aSO_2N(R_f)$alkyl-, $R_aR_bNSO_2N(R_f)$—, $R_aR_bNSO_2N(R_f)$alkyl-, $R_aR_bNC(O)$—, $R_kOC(O)$—, $R_kOC(O)$alkyl-, $R_kO$alkyl-, $R_aR_bNSO_2$—, $R_aR_bNSO_2$alkyl-, $(R_bO)(R_a)P(O)O$— and —OR$_k$, wherein each $R^7$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN$—, $R_kO$—. $R_kO$alkyl-, $R_cR_d$Nalkyl-, $R_cR_d$NC(O)alkyl-, $R_cSO_2$—, —SO$_2$alkyl-, $R_cC(O)$—, $R_cC(O)$alkyl-, ROC(O)—, $R_cOC(O)$alkyl-, $R_cR_d$NalkylC(O)—, $R_cR_d$NC(O)—, $R_cR_d$NC(O)Oalkyl-, $R_cR_d$NC(O)N(R$_c$)alkyl-, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), -(alkyl)

$SO_2NR_eR_d$, -alkylC(O)$NR_eR_d$, —$SR_c$, —S(O)$R_c$, —S(O)$_2$$R_e$, —$OR_c$, —N($R_e$)($R_d$), —C(O)$R_e$, —C(O)$OR_c$ and —C(O)$NR_cR_d$;

$R_c$ and $R_d$, at each occurrence, are independently selected from the group consisting of hydrogen, —$NR_fR_h$, —$OR_f$, —CO($R_f$), —$SR_f$, —$SOR_f$, —$SO_2R_f$, —C(O)$NR_fR_h$, —$SO_2NR_fR_h$, —C(O)$OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —S(O)$R_f$, —S(O)$_2R_f$, —$OR_f$, —N($R_f$)($R_h$), —C(O)$R_f$, —C(O)$OR_f$, —C(O)$NR_fR_h$, —C(O)N(H)$NR_fR_h$, —N($R_e$)C(O)$OR_f$, —N($R_e$)$SO_2NR_fR_h$, —N($R_e$)C(O)$NR_fR_h$, -(alkyl)N($R_e$)C(O)$OR_f$, -(alkyl)N($R_e$)$SO_2NR_fR_h$, and -alkylN($R_e$)C(O)$NR_f$$R_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —S(O)$R_f$, —S(O)$_2R_f$, —$OR_f$, —N($R_f$)($R_h$), —C(O)$R_f$, —C(O)$OR_f$ and —C(O)$NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$ $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(O)(alkyl), —$SO_2$alkyl, -(alkyl)-OH, -(alkyl)-O-alkyl, -(alkyl)$NH_2$, -(alkyl)N(H)(alkyl), -(alkyl)N(alkyl)$_2$, -alkylS(alkyl), -(alkyl)S(O)(alkyl), -(alkyl)$SO_2$alkyl, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(alkyl), —S(O)(alkyl), -(alkyl)-OH, -(alkyl)-O-alkyl, -(alkyl)$NH_2$, -(alkyl)N(H)(alkyl), -alkylS(alkyl), -(alkyl)S(O)(alkyl), -(alkyl)$SO_2$alkyl, -(alkyl) N(alkyl)$_2$, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_a$S—, $R_a$S(O)—, $R_a$$SO_2$—, $R_a$S-alkyl-, $R_a$(O)Salkyl-, $R_a$$SO_2$alkyl-, $R_a$OC(O)—, $R_a$OC(O)alkyl-, $R_a$C(O)—, $R_a$C(O)alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

m is 0, 1, 2, 3, or 4; and n is 0, 1 or 2.

For example, the present invention provides a compound of formula (VIII) wherein $R^2$ and $R^3$, together with the carbon atoms to which they are attached, form a five- or six-membered ring selected from the group consisting of aryl, cycloalkyl, heteroaryl and heterocycle, wherein said aryl, cycloalkyl, heteroaryl and heterocycle is optionally substituted with ($R^6$)$_m$.

For example, the present invention provides a compound of formula (VIII) wherein $R^2$ and $R^3$, together with the carbon atoms to which they are attached, form a five- or six-membered ring selected from the group consisting of phenyl, pyridyl, pyrimidinyl, pyridazinyl, pyrazolyl, cyclopentyl, cyclohexyl and thienyl.

For example, the present invention provides a compound of formula (VIII) wherein $R^2$ and $R^3$, together with the carbon atoms to which they are attached, form a five- or six-membered ring selected from the group consisting of phenyl, pyridyl, pyrimidinyl, pyridazinyl, pyrazolyl, cyclopentyl, cyclohexyl and thienyl and $R^4$ is hydroxy.

For example, the present invention provides a compound of formula (VIII) wherein $R^2$ and $R^3$, together with the carbon atoms to which they are attached, form a five- or six-membered ring selected from the group consisting of phenyl, pyridyl, pyrimidinyl, pyridazinyl, pyrazolyl, cyclopentyl, cyclohexyl and thienyl, $R^4$ is hydroxy, and $R^1$ is selected from the group consisting of hydrogen, alkenyl, alkoxyalkyl, alkoxycarbonylalkyl, alkyl, alkynyl, arylalkenyl, arylalkyl, carboxyalkyl, cyanoalkyl, cycloalkenyl, cycloalkenylalkyl, cycloalkyl, cycloalkylalkenyl, cycloalkylalkyl, formylalkyl, haloalkyl, heteroarylalkenyl, heteroarylalkyl, heterocycle, heterocyclealkenyl, heterocyclealkyl, hydroxyalkyl, $R_aR_b$N—, $R_aR_b$Nalkyl-, $R_aR_b$NC(O)alkyl-, $R_fR_g$C=N— and $R_k$O—.

For example, the present invention provides a compound of formula (VIII) wherein $R^2$ and $R^3$, together with the carbon atoms to which they are attached, form a five- or six-membered ring selected from the group consisting of phenyl, pyridyl, pyrimidinyl, pyridazinyl, pyrazolyl, cyclopentyl, cyclohexyl and thienyl, $R^4$ is hydroxy, and $R^1$ is selected from the group consisting of C1-C7 alkyl, (C3-C6 cycloalkyl)C1-C2 alkyl-, phenyl-C1-C2 alkyl-, heteroaryl-C1-C2 alkyl-, ((phenyl)C1-C2 alkyl)O—, (C3-C7 alkyl)O—, (C3-C6 cycloalkyl)O—, ((phenyl)C1-C2 alkyl)N(H)—, (C3-C6 cycloalkyl)N(H)—, ((C3-C6 cycloalkyl)C1-C2 alkyl)N(H)— and (C1-C7 alkyl)N(H)—.

For example, the present invention provides a compound of formula (VIII) wherein $R^2$ and $R^3$, together with the carbon atoms to which they are attached, form a five- or six-membered ring selected from the group consisting of phenyl, pyridyl, pyrimidinyl, pyridazinyl, pyrazolyl, cyclopentyl, cyclohexyl and thienyl, $R^4$ is hydroxy, and $R^1$ is selected from the group consisting of C3 alkyl, C4 alkyl, C5 alkyl, phenylmethyl, phenylethyl, (5-chloro-thien-2-yl)methyl, cyclobutylmethyl, cyclopropylmethyl, cyclopropylethyl, (cyclopropylmethyl)N(H)—, (cyclobutyl)N(H)—, (cyclopentyl)N(H)—, (cyclohexyl)N(H)—, (phenylmethyl)N(H)—, (C3 alkyl)N(H)—, (C4 alkyl)N(H)— and (C5 alkyl)N(H)—.

Exemplary compounds of the tenth embodiment of the present invention of formula (VIII) include, but not limited to, the following:

3-(1,1-dioxido-4H-[1,3]oxazolo[5,4-h][1,2,4]benzothiadiazin-3-yl)-4-hydroxy-1-(isobutylamino)quinolin-2(1H)-one;

3-[8-(chloromethyl)-1,1-dioxido-4H-[1,3]oxazolo[5,4-h][1,2,4]benzothiadiazin-3-yl]-4-hydroxy-1-(isobutylamino)quinolin-2(1H)-one;

3-{3-[4-hydroxy-1-(isobutylamino)-2-oxo-1,2-dihydroquinolin-3-yl]-1,1-dioxido-4H-[1,3]oxazolo[5,4-h][1,2,4]benzothiadiazin-8-yl}propanoic acid;

3-(8-{[(2-aminoethyl)amino]methyl}-1,1-dioxido-4H-[1,3]oxazolo[5,4-h][1,2,4]benzothiadiazin-3-yl)-4-hydroxy-1-(isobutylamino)quinolin-2(1H)-one;

methyl {3-[4-hydroxy-1-(isobutylamino)-2-oxo-1,2-dihydroquinolin-3-yl]-1,1-dioxido-4H-[1,3]oxazolo[5,4-h][1,2,4]benzothiadiazin-8-yl}acetate;

4-hydroxy-3-(8-{[(3R)-3-hydroxypyrrolidin-1-yl]methyl}-1,1-dioxido-4H-[1,3]oxazolo[5,4-h][1,2,4]benzothiadiazin-3-yl)-1-(isobutylamino)quinolin-2(1H)-one;

3-[1,1-dioxido-8-(pyridinium-1-ylmethyl)-4H-[1,3]oxazolo[5,4-h][1,2,4]benzothiadiazin-3-yl]-1-(isobutylamino)-2-oxo-1,2-dihydroquinolin-4-olate;

3-[1,1-dioxido-8-(pyrrolidin-1-ylmethyl)-4H-[1,3]oxazolo[5,4-h][1,2,4]benzothiadiazin-3-yl]-4-hydroxy-1-(isobutylamino)quinolin-2(1H)-one;

3-[8-(3-aminophenyl)-1,1-dioxido-4H-[1,3]oxazolo[5,4-h][1,2,4]benzothiadiazin-3-yl]-4-hydroxy-1-(isobutylamino)quinolin-2(1H)-one;

3-[8-(aminomethyl)-1,1-dioxido-4H-[1,3]oxazolo[5,4-h][1,2,4]benzothiadiazin-3-yl]-4-hydroxy-1-(isobutylamino)quinolin-2(1H)-one;

4-hydroxy-3-[8-(hydroxymethyl)-1,1-dioxido-4H-[1,3]oxazolo[5,4-h][1,2,4]benzothiadiazin-3-yl]-1-(isobutylamino)quinolin-2(1H)-one;

3-{8-[(butylamino)methyl]-1,1-dioxido-4H-[1,3]oxazolo[5,4-h][1,2,4]benzothiadiazin-3-yl}-4-hydroxy-1-(isobutylamino)quinolin-2(1H)-one;

3-[9-(butylamino)-1,1-dioxido-4H,8H-[1,4]oxazino[2,3-h][1,2,4]benzothiadiazin-3-yl]-4-hydroxy-1-(isobutylamino)quinolin-2(1H)-one;

4-hydroxy-1-(3-methylbutyl)-3-(8-methyl-1,1-dioxido-4H-[1,3]oxazolo[5,4-h][1,2,4]benzothiadiazin-3-yl)-1,8-naphthyridin-2(1H)-one;

3-[1,1-dioxido-8-(trifluoromethyl)-4,7-dihydroimidazo[4,5-h][1,2,4]benzothiadiazin-3-yl]-4-hydroxy-1-(3-methylbutyl)-1,8-naphthyridin-2(1H)-one;

4-hydroxy-3-(8-hydroxy-1,1-dioxido-4,7-dihydroimidazo[4,5-h][1,2,4]benzothiadiazin-3-yl)-1-(3-methylbutyl)-1,8-naphthyridin-2(1H)-one;

4-hydroxy-1-(3-methylbutyl)-3-(8-methyl-1,1-dioxido-4,7-dihydroimidazo[4,5-h][1,2,4]benzothiadiazin-3-yl)-1,8-naphthyridin-2(1H)-one;

3-[1,1-dioxido-8-(pentafluoroethyl)-4,7-dihydroimidazo[4,5-h][1,2,4]benzothiadiazin-3-yl]-4-hydroxy-1-(3-methylbutyl)-1,8-naphthyridin-2(1H)-one;

3-[8-(chloromethyl)-1,1-dioxido-4,7-dihydroimidazo[4,5-h][1,2,4]benzothiadiazin-3-yl]-4-hydroxy-1-(3-methylbutyl)-1,8-naphthyridin-2(1H)-one;

{3-[4-hydroxy-1-(3-methylbutyl)-2-oxo-1,2-dihydro-1,8-naphthyridin-3-yl]-1,1-dioxido-4,7-dihydroimidazo[4,5-h][1,2,4]benzothiadiazin-8-yl}acetonitrile;

methyl{3-[4-hydroxy-1-(3-methylbutyl)-2-oxo-1,2-dihydro-1,8-naphthyridin-3-yl]-1,1-dioxido-4,7-dihydroimidazo[4,5-h][1,2,4]benzothiadiazin-8-yl}acetate;

3-(9,9-dioxido-6H-[1,2,5]thiadiazolo[3,4-h][1,2,4]benzothiadiazin-7-yl)-4-hydroxy-1-(3-methylbutyl)-1,8-naphthyridin-2(1H)-one;

3-(8-amino-1,1-dioxido-4,7-dihydroimidazo[4,5-h][1,2,4]benzothiadiazin-3-yl)-4-hydroxy-1-(3-methylbutyl)-1,8-naphthyridin-2(1H)-one; and 4-hydroxy-3-[8-(hydroxymethyl)-1,1-dioxido-4,9-dihydroimidazo[4,5-h][1,2,4]benzothiadiazin-3-yl]-1-(3-methylbutyl)-1,8-naphthyridin-2(1H)-one, or a pharmaceutically acceptable salt form, stereoisomer or tautomer thereof.

In an eleventh embodiment the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, and a pharmaceutically acceptable carrier.

In a twelfth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, with one or more host immune modulators, and a pharmaceutically acceptable carrier.

For example, the present invention provides a pharmaceutical composition comprising a therapeutically effective amount of a compound or combination of compounds of formula (I), (II), (III), (IV), (V), (VI), (VII) or (VIII), or a pharmaceutically acceptable salt form thereof, with one or more host immune modulators selected from the group consisting of interferon-alpha, pegylated-interferon-alpha, interferon-beta, interferon-gamma, a cytokine, a vaccine and a vaccine comprising an antigen and an adjuvant, and a pharmaceutically acceptable carrier.

In a thirteenth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, with one or more second antiviral agents, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, with one or more second antiviral agents which inhibit the replication of HCV by inhibiting host cellular functions associated with viral replication, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, with one or more second antiviral agents which inhibit the replication of HCV by targeting proteins of the viral genome, and a pharmaceutically acceptable carrier.

In a fourteenth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, and a pharmaceutically acceptable carrier.

For example, the present invention provides a pharmaceutical composition comprising, a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, and a pharmaceutically acceptable carrier.

In a fifteenth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more agents that treat or alleviate symptoms of HCV infection including cirrhosis and inflammation of liver, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more agents that treat or alleviate symptoms of HCV infection including cirrhosis and inflammation of liver, and a pharmaceutically acceptable carrier.

In a sixteenth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents, one or more agents that treat or alleviate symptoms of HCV infection including cirrhosis and inflammation of liver, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, one or more agents that treat or alleviate symptoms of HCV infection including cirrhosis and inflammation of liver, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, one or more agents that treat or alleviate symptoms of HCV infection including cirrhosis and inflammation of liver, and a pharmaceutically acceptable carrier.

In a seventeenth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, one or more agents that treat or alleviate symptoms of HCV infection including cirrhosis and inflammation of liver, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, one or more agents that treat or alleviate symptoms of HCV infection including cirrhosis and inflammation of liver, and a pharmaceutically acceptable carrier.

In an eighteenth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, one or more agents that treat or alleviate symptoms of HCV infection including cirrhosis and inflammation of liver, and a pharmaceutically acceptable carrier.

For example, the present invention provides a pharmaceutical composition comprising a therapeutically effective amount of a compound or combination of compounds of formula (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, one or more agents that treat or alleviate symptoms of HCV infection including cirrhosis and inflammation of liver, and a pharmaceutically acceptable carrier.

In a nineteenth embodiment, the present invention provides a pharmaceutical composition comprising a therapeutically effective amount of a compound or combination of compounds of formula (Va), (Vb), (VIa), (VIb), (VII) or (VIII), or a pharmaceutically acceptable salt form thereof, one or more host immune modulators, one or more agents that treat patients for disease caused by hepatitis B (HBV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more agents that treat patients for disease caused by hepatitis B (HBV) infection, and a pharmaceutically acceptable carrier.

In a twentieth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents, one or more agents that treat patients for disease caused by hepatitis B (HBV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, one or more agents that treat patients for disease caused by hepatitis B (HBV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, one or more agents that treat patients for disease caused by hepatitis B (HBV) infection, and a pharmaceutically acceptable carrier.

In a twenty-first embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, one or more agents that treat patients for disease caused by hepatitis B (HBV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, one or more agents that treat patients for disease caused by hepatitis B (HBV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, one or more agents that treat patients for disease caused by hepatitis B (HBV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, one or more agents that treat patients for disease caused by hepatitis B (HBV) infection, and a pharmaceutically acceptable carrier.

Preferably, the agent that treat patients for disease caused by hepatitis B(HBV) infection in the above mentioned pharmaceutical compositions can be selected from the group consisting of L-deoxythymidine, adefovir, lamivudine and tenfovir.

In a twenty-second embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, and one or more agents that treat patients for disease caused by human immunodeficiency virus (HIV) infection, and a pharmaceutically acceptable carrier.

In a twenty-third embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more agents that treat patients for disease caused by human immunodeficiency virus (HIV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more agents that treat patients for disease caused by human immunodeficiency virus (HIV) infection, and a pharmaceutically acceptable carrier.

In a twenty-fourth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents, one or more agents that treat patients for disease caused by human immunodeficiency virus (HIV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, one or more agents that treat patients for disease caused by human immunodeficiency virus (HIV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, one or more agents that treat patients for disease caused by human immunodeficiency virus (HIV) infection, and a pharmaceutically acceptable carrier.

In a twenty-fifth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, one or more agents that treat patients for disease caused by human immunodeficiency virus (HIV) infection, and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, one or more agents that treat patients for disease caused by human immunodeficiency virus (HIV) infection, and a pharmaceutically acceptable carrier.

In a twenty-sixth embodiment, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, one or more agents that treat patients for disease caused by human immunodeficiency virus (HIV), and a pharmaceutically acceptable carrier.

For example, the present invention provides a pharmaceutical composition comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, one or more agents that treat patients for disease caused by human immunodeficiency virus (HIV) infection, and a pharmaceutically acceptable carrier.

The agent that treats patients for disease caused by human immunodeficiency virus (HIV) infection in the above-mentioned pharmaceutical compositions may be, for example but not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof.

In a twenty-seventh embodiment, the present invention provides a method of treating or preventing infection caused by an RNA-containing virus comprising administering to a patient in need of such treatment any one of the pharmaceutical compositions disclosed hereinabove.

In a twenty-eighth embodiment, the present invention provides a method of inhibiting the replication of an RNA-containing virus comprising contacting said virus with a therapeutically effective amount of a compound or combination of compounds of formula (I), (II), (III), (IV), (Va), (Vb), (VIa), (VIb), (VII) or (VIII) or a pharmaceutically acceptable salt thereof.

In a twenty-ninth embodiment, the present invention provides a method of treating or preventing infection caused by an RNA-containing virus comprising administering to a patient in need of such treatment a therapeutically effective amount of a compound or combination of compounds of formula (I), (II), (III), (IV), (Va), (Vb), (VIa), (VIb), (VII) or (VIII) or a pharmaceutically acceptable salt thereof.

For example, the present invention provides a method of treating or preventing infection caused by an RNA-containing virus comprising administering to a patient in need of such treatment a therapeutically effective amount of a compound or combination of compounds of formula (I), (II), (III), (IV), (Va), (Vb), (VIa), (VIb), (VII) or (VIII) or a pharmaceutically acceptable salt thereof wherein the RNA-containing virus is hepatitis C virus.

In a thirtieth embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) and one or more host immune modulators.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) and one or more host immune modulators selected from the group consisting of interferon-alpha, pegylated-interferon-alpha, interferon-beta, interferon-gamma, a cytokine, a vaccine and a vaccine comprising an antigen and an adjuvant.

In a thirty-first embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) and one or more second antiviral agents.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) and one or more second antiviral agents which inhibit replication of HCV by inhibiting host cellular functions associated with viral replication.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) and one or more second antiviral agents which inhibit replication of HCV by targeting proteins of the viral genome.

In a thirty-second embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) one or more host immune modulators, and one or more second antiviral agents.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more second antiviral agents.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more second antiviral agents which inhibit replication of HCV by inhibiting host cellular functions associated with viral replication.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more second antiviral agents which inhibit replication of HCV by targeting proteins of the viral genome.

In a thirty-third embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) or a pharmaceutically acceptable salt form thereof, one or more host immune modulators, one or more agents that treat or alleviate symptoms of HCV infection including cirrhosis and inflammation of liver, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more agents that treat or alleviate symptoms of HCV infection including cirrhosis and inflammation of liver, and a pharmaceutically acceptable carrier.

In a thirty-fourth embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) or a pharmaceutically acceptable salt form thereof, one or more second antiviral agents, one or more agents that treat or alleviate symptoms of HCV infection including cirrhosis and inflammation of liver, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII) or a pharmaceutically acceptable salt form thereof, one or more second antiviral agents which inhibit the replication of HCV by inhibiting host cellular functions associated with viral replication, one or more agents that treat or alleviate symptoms of HCV infection including cirrhosis and inflammation of liver, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, one or more agents that treat or alleviate symptoms of HCV infection including cirrhosis and inflammation of liver, and a pharmaceutically acceptable carrier.

In a thirty-fifth embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, one or more agents that treat or alleviate symptoms of HCV infection including cirrhosis and inflammation of liver, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, one or more agents that treat or alleviate symptoms of HCV infection including cirrhosis and inflammation of liver, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, one or more agents that treat or alleviate symptoms of HCV infection including cirrhosis and inflammation of liver, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, one or more agents that treat or alleviate symptoms of HCV infection including cirrhosis and inflammation of liver, and a pharmaceutically acceptable carrier.

In a thirty-sixth embodiment, the present invention a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, and one or more agents that treat patients for disease caused by hepatitis B (HBV) infection, and a pharmaceutically acceptable carrier.

In a thirty-seventh embodiment, the present invention a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more agents that treat patients for disease caused by hepatitis B (HBV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more agents that treat patients for disease caused by hepatitis B (HBV) infection, and a pharmaceutically acceptable carrier.

In a thirty-eighth embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents, one or more agents that treat patients for disease caused by hepatitis B (HBV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, one or more agents that treat patients for disease caused by hepatitis B (HBV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, one or more agents that treat patients for disease caused by hepatitis B (HBV) infection, and a pharmaceutically acceptable carrier.

In a thirty-ninth embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, one or more agents that treat patients for disease caused by hepatitis B (HBV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, one or more agents that treat patients for disease caused by hepatitis B (HBV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, one or more agents that treat patients for disease caused by hepatitis B (HBV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, one or more agents that treat patients for disease caused by hepatitis B (HBV) infection, and a pharmaceutically acceptable carrier.

An agent that treats patients for disease caused by hepatitis B (HBV) infection may be, for example but not limited thereto, L-deoxythymidine, adefovir, lamivudine or tenfovir, or any combination thereof.

In a fortieth embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more agents that treat patients for disease caused by human immunodeficiency virus (HIV) infection, and a pharmaceutically acceptable carrier.

In a forty-first embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more agents that treat patients for disease caused by human immunodeficiency virus (HIV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more agents that treat patients for disease caused by human immunodeficiency virus (HIV) infection, and a pharmaceutically acceptable carrier.

In a forty-second embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents, one or more agents that treat patients for disease caused by human immunodeficiency virus (HIV) infection, and a pharmaceutically acceptable carrier.

For example, the present invention provides a method of treating or preventing infection caused by an hepatitis C virus comprising administering to a patient in need of such treatment comprising a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, one or more agents that treat patients for disease caused by human immunodeficiency virus (HIV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, one or more agents that treat patients for disease caused by human immunodeficiency virus (HIV) infection, and a pharmaceutically acceptable carrier.

In a forty-third embodiment, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, one or more agents that treat patients for disease caused by human immunodeficiency virus (HIV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, one or more agents that treat patients for disease caused by human immunodeficiency virus (HIV) infection, and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, one or more agents that treat patients for disease caused by human immunodeficiency virus (HIV), and a pharmaceutically acceptable carrier.

For example, the present invention provides a method of treating or preventing infection caused by an hepatitis C virus comprising administering to a patient in need of such treatment a therapeutically effective amount of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, one or more agents that treat patients for disease caused by human immunodeficiency virus (HIV) infection, and a pharmaceutically acceptable carrier.

An agent that treats patients for disease caused by human immunodeficiency virus (HIV) infection may be, for example but not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof.

In a forty-fourth embodiment the present invention provides a use of a compound or combination of compounds of formula (I), (II), (III), (IV), (Va), (Vb), (VIa), (VIb), (VII) or (VIII), or a therapeutically acceptable salt thereof, to prepare a medicament for treating or preventing infection caused by an RNA-containing virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, to prepare a medicament for treating or preventing infection caused by an RNA-containing virus in a patient, wherein the RNA-containing virus is hepatitis C virus.

In a forty-fifth embodiment, the present invention provides a use of a compound or combination of compounds of formula (I), (II), (III), (IV), (Va), (Vb), (VIa), (VIb), (VII) or (VIII), or a therapeutically acceptable salt thereof, and one or more host immune modulators, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, and one or more host immune modulators selected from the group consisting of interferon-alpha, pegylated-interferon-alpha, interferon-beta, interferon-gamma, a cytokine, a vaccine and a vaccine comprising an antigen and an adjuvant, to prepare a medicament for treating or preventing infection caused by an hepatitis C virus in a patient.

In a forty-sixth embodiment, the present invention provides a use of a compound or combination of compounds of formula (I), (II), (III), (IV), (Va), (Vb), (VIa), (VIb), (VII) or (VIII), or a therapeutically acceptable salt thereof, and one or more second antiviral agents, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, and one or more second antiviral agents which inhibit the replication of HCV by inhibiting host cellular functions associated with viral replication, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, and one or more second antiviral agents which inhibit the replication of HCV by targeting proteins of the viral genome, to prepare a medicament for treating or preventing infection caused by an hepatitis C virus in a patient.

In a forty-seventh embodiment, the present invention provides a use of a compound or combination of compounds of formula (I), (II), (III), (IV), (Va), (Vb), (VIa), (VIb), (VII) or (VIII), or a therapeutically acceptable salt thereof, one or more host immune modulators, and one or more second antiviral agents, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more second antiviral agents, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more second antiviral agents which inhibit replication of HCV by inhibiting host cellular functions associated with viral replication, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a therapeutically acceptable salt thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more second antiviral agents which inhibit replication of HCV by targeting proteins of the viral genome, to prepare a medicament for treating or preventing infection caused by an hepatitis C virus in a patient.

In a forty-eighth embodiment, the present invention provides a use of a compound or combination of compounds of formula (I), (II), (III), (IV), (Va), (Vb), (VIa), (VIb), (VII) or (VIII), or a therapeutically acceptable salt thereof, one or more host immune modulators, and one or more agents that treat or alleviate symptoms of HCV infection including cirrhosis and inflammation of liver, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more agents that treat or alleviate symptoms of HCV infection including cirrhosis and inflammation of liver, to prepare a medicament for treating or preventing infection caused by an hepatitis C virus in a patient.

In a forty-ninth embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents, and one or more agents that treat or alleviate symptoms of HCV infection including cirrhosis, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, and one or more agents that treat or alleviate symptoms of HCV infection including cirrhosis and inflammation of liver, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, and one or more agents that treat or alleviate symptoms of HCV infection including cirrhosis and inflammation of liver, to prepare a medicament for treating or preventing infection caused by an hepatitis C virus in a patient.

In a fiftieth embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, and one or more agents that treat or alleviate symptoms of HCV infection including cirrhosis and inflammation of liver, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, and one or more agents that treat or alleviate symptoms of HCV infection including cirrhosis and inflammation of liver, to prepare a medicament for treating or preventing infection caused by an hepatitis C virus in a patient.

In another preferred embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, and one or more agents that treat or alleviate symptoms of HCV infection including cirrhosis and inflammation of liver, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, and one or more agents that treat or alleviate symptoms of HCV infection including cirrhosis and inflammation of liver, to prepare a medicament for treating or preventing infection caused by an hepatitis C virus in a patient.

In a fifty-first embodiment, the present invention a use of a compound or combination of compounds of formula (I), (II), (III), (IV), (Va), (Vb), (VIa), (VIb), (VII) or (VIII), or a pharmaceutically acceptable salt form thereof, and one or more agents that treat patients for disease caused by hepatitis B (HBV) infection, to prepare a medicament for treating or preventing infection caused by an hepatitis C virus in a patient.

In a fifty-second embodiment, the present invention a use of a compound or combination of compounds of formula (I), (II), (III), (IV), (Va), (Vb), (VIa), (VIb), (VII) or (VIII), or a pharmaceutically acceptable salt form thereof, one or more host immune modulators, and one or more agents that treat patients for disease caused by hepatitis B (HBV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more agents that treat patients for disease caused by hepatitis B (HBV) infection, to prepare a medicament for treating or preventing infection caused by an hepatitis C virus in a patient.

In a fifty-third embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents, and one or more agents that treat patients for disease caused by hepatitis B (HBV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, and one or more agents that treat patients for disease caused by hepatitis B (HBV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, and one or more agents that treat patients for disease caused by hepatitis B (HBV) infection, to prepare a medicament for treating or preventing infection caused by an hepatitis C virus in a patient.

In a fifty-fourth embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, and one or more agents that treat patients for disease caused by hepatitis B (HBV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, and one or more agents that treat patients for disease caused by hepatitis B (HBV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, and one or more agents that treat patients for disease caused by hepatitis B (HBV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, and one or more agents that treat patients for disease caused by hepatitis B (HBV) infection, to prepare a medicament for treating or preventing infection caused by an hepatitis C virus in a patient.

An agent that treats patients for disease caused by hepatitis B (HBV) infection may be, for example but not limited thereto, L-deoxythymidine, adefovir, lamivudine or tenfovir, or any combination thereof.

In a fifty-fifth embodiment, the present invention provides a use of a compound or combination of compounds of formula (I), (II), (III), (IV), (Va), (Vb), (VIa), (VIb), (VII) or (VIII), or a pharmaceutically acceptable salt form thereof, and one or more agents that treat patients for disease caused by human immunodeficiency virus (HIV) infection, to prepare a medicament for treating or preventing infection caused by an hepatitis C virus in a patient.

In a fifty-sixth embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators, and one or more agents that treat patients for disease caused by human immunodeficiency virus (HIV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, and one or more agents that treat patients for disease caused by human immunodeficiency virus (HIV) infection, to prepare a medicament for treating or preventing infection caused by an hepatitis C virus in a patient.

In a fifty-seventh embodiment, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents, and one or more agents that treat patients for disease caused by human immunodeficiency virus (HIV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by inhibiting host cellular functions associated with viral replication, and one or more agents that treat patients for disease caused by human immunodeficiency virus (HIV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more second antiviral agents which inhibit the replication of HCV by targeting proteins of the viral genome, and one or more agents that treat patients for disease caused by human immunodeficiency virus (HIV) infection, to prepare a medicament for treating or preventing infection caused by an hepatitis C virus in a patient.

In a fifty-eighth embodiment, the present invention provides a use of compound or combination of compounds of formula (I), (II), (III), (IV), (Va), (Vb), (VIa), (VIb), (VII) or (VIII), or a pharmaceutically acceptable salt form thereof, one or more host immune modulators, one or more second antiviral agents, and one or more agents that treat patients for disease caused by human immunodeficiency virus (HIV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents, and one or more agents that treat patients for disease caused by human immunodeficiency virus (HIV) infection, to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by inhibiting host cellular functions associated with viral replication, and one or more agents that treat patients for disease caused by human immunodeficiency virus (HIV), to prepare a medicament for treating or preventing infection caused by an hepatitis C virus in a patient.

For example, the present invention provides a use of a compound or combination of compounds of formula (I), (II), (III), (IV), (Va), (Vb), (VIa), (VIb), (VII) or (VIII), or a pharmaceutically acceptable salt form thereof, one or more host immune modulators selected from the group consisting of interferon-alpha, pegylated-interferon-alpha, interferon-beta, interferon-gamma, a cytokine, a vaccine and a vaccine comprising an antigen and an adjuvant, one or more second antiviral agents which inhibit the replication of HCV by targeting proteins of the viral genome, and one or more agents that treat patients for disease caused by human immunodeficiency virus (HIV) infection, to prepare a medicament for treating or preventing infection caused by an hepatitis C virus in a patient.

An agent that treats patients for disease caused by human immunodeficiency virus (HIV) infection may be, for example but not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof.

In a fifty-ninth embodiment, the present invention provides a process for the preparation of a compound having formula (I),

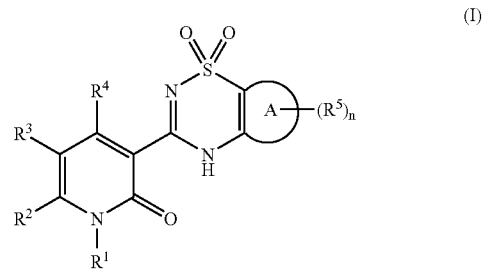

or a pharmaceutically acceptable salt form, stereoisomer or tautomer thereof, wherein:

A is a monocyclic or bicyclic ring selected from the group consisting of aryl, cycloalkyl, cycloalkenyl, heteroaryl and heterocycle;

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN$—, $R_aR_b$Nalkyl-, $R_aR_b$NC(O)alkyl-, $R_aR_b$NC(O)Oalkyl-, $R_aR_b$NC(O)NR$_c$alkyl-, $R_fR_gC$=N— and $R_kO$—, wherein $R^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_e$), —SR$_c$, —S(O)R$_c$, —S(O)$_2$R$_c$, —OR$_c$, —N(R$_c$)(R$_e$), —C(O)R$_c$, —C(O)OR$_c$ and —C(O)NR$_c$R$_e$;

$R^2$ and $R^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$ and R$_a$C(O)—; wherein $R^2$ and $R^3$ are independently substituted with 0, 1, 2 or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$;

alternatively, $R^2$ and $R^3$, together with the carbon atoms to which they are attached form a five- or six-membered ring selected from the group consisting of aryl, cycloalkyl, heteroaryl and heterocycle, wherein said aryl, cycloalkyl, heteroaryl and heterocycle is optionally substituted with $(R^6)_m$;

$R^4$ is selected from the group consisting of alkoxy, arylalkoxy, aryloxy, halo, hydroxy, $R_aR_bN$—, $N_3$—, $R_cS$—, wherein $R^4$ is independently substituted with 0, 1 or 2 substituents independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_aC(O)$—, $R_aS$—, $R_a(O)S$—, $R_a(O)_2S$—, $R_aR_bNalkyl$-, $R_a(O)SN(R_f)$—, $R_aSO_2N(R_f)$—, $R_a(O)SN(R_f)alkyl$-, $R_aSO_2N(R_f)alkyl$-, $R_aR_bNSO_2N(R_f)$—, $R_aR_bNSO_2N(R_f)alkyl$-, $R_aR_bNC(O)$—, $R_kOC(O)$—, $R_kOC(O)alkyl$-, $R_kOalkyl$-, $R_aR_bNSO_2$—, $R_aR_bNSO_2alkyl$-, $(R_kO)(R_a)P(O)O$— and —$OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), —$SR_a$, —$S(O)R_a$, —$S(O)_2R_a$, —$OR_k$, —$N(R_a)(R_b)$, —$C(O)R_a$, —$C(O)OR_a$ and —$C(O)NR_aR_b$; wherein each $R^6$ is independently substituted with 0, 1, 2 or 3 substituents independently selected from the group consisting of alkyl, alkenyl, alkynyl, oxo, halo, haloalkyl, cyano, nitro, —$OR_a$, —$NR_aR_b$, —$SR_a$, $SOR_a$, —$SO_2R_a$, —$C(O)OR_a$, —$C(O)NR_aR_b$ and —$NC(O)R_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN$—, $R_kO$—. $R_kOalkyl$-, $R_cR_dNalkyl$-, $R_cR_dNC(O)alkyl$-, $R_cSO_2$—, $R_cSO_2alkyl$-, $R_cC(O)$—, $R_cC(O)alkyl$-, $R_cOC(O)$—, $R_cOC(O)alkyl$-, $R_cR_dNalkylC(O)$—, $R_cR_dNC(O)$—, $R_cR_dNC(O)Oalkyl$-, $R_cR_dNC(O)N(R_c)alkyl$-, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -(alkyl)$SO_2NR_cR_d$, -alkylC(O)$NR_cR_d$, —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

$R_c$ and $R_d$, at each occurrence, are independently selected from the group consisting of hydrogen, —$NR_fR_h$, —$OR_f$, —$CO(R_f)$, —$SR_f$, —$SOR_f$, —$SO_2R_f$, —$C(O)NR_fR_h$, —$SO_2NR_fR_h$, —$C(O)OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —$S(O)R_f$, —$S(O)_2R_f$, —$OR_f$, —$N(R_f)(R_h)$, —$C(O)R_f$, —$C(O)OR_f$, —$C(O)NR_fR_h$, —$C(O)N(H)NR_fR_h$, —$N(R_e)C(O)OR_f$, —$N(R_e)SO_2NR_fR_h$, —$N(R_e)C(O)NR_fR_h$, -(alkyl)$N(R_e)C(O)OR_f$, -(alkyl)$N(R_e)SO_2NR_fR_h$, and -alkyl$N(R_e)C(O)NR_fR_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —$S(O)R_f$, —$S(O)_2R_f$, —$OR_f$, —$N(R_f)(R_h)$, —$C(O)R_f$, —$C(O)OR_f$ and —$C(O)NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(O)(alkyl), —$SO_2$alkyl, -(alkyl)-OH, -(alkyl)-O-alkyl, -(alkyl)$NH_2$, -(alkyl)N(H)(alkyl), -(alkyl)N(alkyl)$_2$, -alkylS(alkyl), -(alkyl)S(O)(alkyl), -(alkyl)$SO_2$alkyl, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1 or 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(alkyl), —S(O)(alkyl), -(alkyl)-OH, -(alkyl)-O-alkyl, -(alkyl)$NH_2$, -(alkyl)N(H)(alkyl), -alkylS(alkyl), -(alkyl)S(O)(alkyl), -(alkyl)$SO_2$alkyl, -(alkyl)N(alkyl)$_2$, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_bNalkyl$-, $R_aOalkyl$-, $R_aR_bNC(O)$—, $R_aR_bNC(O)alkyl$, $R_aS$—, $R_aS(O)$—, $R_aSO_2$—, $R_aS$-alkyl-, $R_a(O)Salkyl$-, $R_aSO_2alkyl$-, $R_aOC(O)$—, $R_aOC(O)alkyl$-, $R_aC(O)$—, $R_aC(O)alkyl$-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

m is 0, 1, 2, 3, or 4; and n is 0, 1, 2, 3, or 4;

with the proviso that when A is a monocyclic ring other than

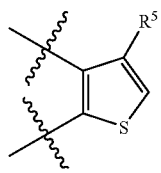

and $R^4$ is alkoxy, aryloxy, hydroxy or $R_eS—$, and $R^5$ is hydrogen, alkenyl, alkoxy, alkyl, alkynyl, aryl, halo, heteroaryl, heterocyclealkyl, cycloalkyl, cyano, nitro, $R_aR_bN—$, $R_aC(O)—$, $R_aS—$, $R_a(O)S—$, $R_a(O)_2S—$, $R_aSO_2N(R_f)—$, $R_aR_bNC(O)—$, $R_kOC(O)—$, $R_aR_bNSO_2—$ or $—OR_k$, and $R^6$ is hydrogen, alkyl, alkenyl, alkynyl, halo, cyano, nitro, aryl, heteroaryl, heterocyclealkyl, $—SR_a$, $—S(O)R_a$, $—S(O)_2R_a$, $—OR_k$, $—N(R_a)(R_b)$, $—C(O)R_a$, $—C(O)OR_a$ and $—C(O)NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl;

and with the further proviso that when A is

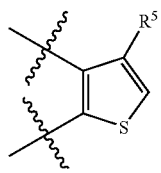

and $R^4$ is hydroxy or $R_eS—$, and R is hydrogen, unsubstituted alkyl, halo or $—OR_k$, and $R_6$ is hydrogen, alkyl, alkenyl, alkynyl, halo, cyano, nitro, aryl, heteroaryl, heterocyclealkyl, $—SR_a$, $—S(O)R_a$, $—S(O)_2R_a$, $—OR_k$, $—N(R_a)(R_b)$, $—C(O)R_a$, $—C(O)OR_a$ and $—C(O)NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl;

comprising:

(a) contacting a compound of formula (26)

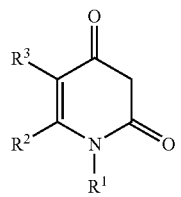

(26)

with carbon disulfide and a methylating agent in the presence of a base to provide a compound of formula (27)

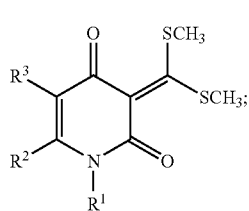

(27)

and (b) contacting the compound of formula (27) with a compound of formula (13)

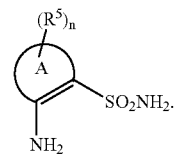

(13)

In a sixtieth embodiment the present invention provides a process for the preparation of a compound having formula (I),

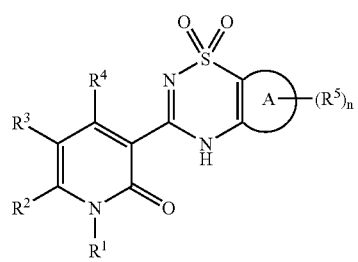

(I)

or a pharmaceutically acceptable salt form, stereoisomer or tautomer thereof, wherein:

A is a monocyclic or bicyclic ring selected from the group consisting of aryl, cycloalkyl, cycloalkenyl, heteroaryl and heterocycle;

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN—$, $R_aR_bNalkyl-$, $R_aR_bNC(O)alkyl-$, $R_aR_bNC(O)Oalkyl-$, $R_aR_bNC(O)NR_calkyl-$, $R_fR_gC=N—$ and $R_kO—$, wherein $R^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, $-(alkyl)(OR_c)$, $-(alkyl)(NR_cR_e)$, $—SR_c$, $—S(O)R_c$, $—S(O)_2R_c$, $—OR_c$, $—N(R_c)(R_e)$, $—C(O)R_c$, $—C(O)OR_c$ and $—C(O)NR_cR_e$;

$R^2$ and $R^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, $—N(R_a)(R_b)$, $R_aR_bNC(O)—$, $—SR_a$, $—S(O)R_a$, $—S(O)_2R_a$ and $R_aC(O)—$; wherein $R^2$ and $R^3$ are independently substituted with 0, 1, 2 or 3 substituents independently selected from the group consisting of $R_a$, alkyl, alkenyl, alkynyl, oxo, halo, cyano, nitro, haloalkyl, $-(alkyl)(OR_k)$, $-(alkyl)(NR_aR_b)$, $—SR_a$, $—S(O)R_a$, $—S(O)_2R_a$, $—OR_k$, $—N(R_a)(R_b)$, $—C(O)R_a$, $—C(O)OR_a$ and $—C(O)NR_aR_b$;

alternatively, $R^2$ and $R^3$, together with the carbon atoms to which they are attached form a five- or six-membered ring selected from the group consisting of aryl, cycloalkyl, heteroaryl and heterocycle, wherein said aryl, cycloalkyl, heteroaryl and heterocycle is optionally substituted with $(R^6)_m$;

$R^4$ is selected from the group consisting of alkoxy, arylalkoxy, aryloxy, halo, hydroxy, $R_aR_bN—$, $N_3—$, $R_eS—$, wherein R⁴ is independently substituted with 0, 1 or 2 substituents independently selected from the group consisting of halo, nitro, cyano, —OH, —NH₂, and —COOH;

R⁵ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_aC(O)$—, $R_aS$—, $R_a(O)S$—, $R_a(O)_2S$—, $R_aR_bN$alkyl-, $R_a(O)SN(R_f)$—, $R_aSO_2N(R_f)$—, $R_a(O)SN(R_f)$alkyl-, $R_aSO_2N(R_f)$alkyl-, $R_aR_bNSO_2N(R_f)$—, $R_aR_bNSO_2N(R_f)$alkyl-, $R_aR_bNC(O)$—, $R_kOC(O)$—, $R_kOC(O)$alkyl-, $R_kO$alkyl-, $R_aR_bNSO_2$—, $R_aR_bNSO_2$alkyl-, $(R_bO)(R_a)P(O)O$— and —$OR_k$, wherein each R⁵ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$, and —C(O)NR$_c$R$_d$;

R⁶ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each R⁶ is independently substituted with 0, 1, 2 or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN$—, $R_kO$—, $R_kO$alkyl-, $R_cR_d$Nalkyl-, $R_cR_dNC(O)$alkyl-, $R_cSO_2$—, $R_cSO_2$alkyl-, $R_c(O)$—, $R_cC(O)$alkyl-, $R_cOC(O)$—, $R_cOC(O)$alkyl-, $R_cR_d$NalkylC(O)—, $R_cR_dNC(O)$—, $R_cR_dNC(O)O$alkyl-, $R_cR_dNC(O)N(R_c)$alkyl-, wherein R$_a$ and R$_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, R$_a$ and R$_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), -(alkyl)SO$_2$N$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$, and —C(O)NR$_c$R$_d$;

R$_c$ and R$_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each R$_c$ and R$_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -(alkyl)N(R$_e$)C(O)OR$_f$, -(alkyl)N(R$_e$)SO$_2$NR$_f$R$_h$, and -alkylN(R$_e$)C(O)NR$_f$R$_h$;

alternatively, R$_c$ and R$_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

R$_e$ is selected from the group consisting of hydrogen, alkenyl, alkyl and cycloalkyl;

R$_f$, R$_g$ and R$_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each R$_f$, R$_g$ and R$_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, R$_f$ and R$_g$ together with the carbon atom to which they are attached form a three- to seven-membered ring selected from the group consisting of cycloalkyl, cycloalkenyl and heterocycle;

alternatively, R$_f$ and R$_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

R$_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_aO$alkyl-, $R_aR_bNC(O)$—, $R_aR_bNC(O)$alkyl, $R_aS$—, $R_aS(O)$—, $R_aSO_2$—, $R_aS$alkyl-, $R_a(O)S$alkyl-, $R_aSO_2$alkyl-, $R_aOC(O)$—, $R_aOC(O)$ alkyl-, $R_aC(O)$—, $R_aC(O)$alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

m is 0, 1, 2, 3, or 4; and n is 0, 1, 2, 3, or 4;

with the proviso that when A is a monocyclic ring other than

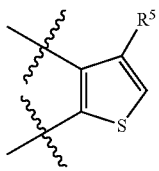

and $R^4$ is alkoxy, aryloxy, hydroxy or $R_cS$—, and $R^5$ is hydrogen, alkenyl, alkoxy, alkyl, alkynyl, aryl, halo, heteroaryl, heterocyclealkyl, cycloalkyl, cyano, nitro, $R_aR_bN$—, $R_aC(O)$—, $R_aS$—, $R_a(O)S$—, $R_a(O)_2S$—, $R_aSO_2N(R_f)$—, $R_aR_bNC(O)$—, $R_kOC(O)$—, $R_aR_bNSO_2$— or —$OR_k$, and $R^6$ is hydrogen, alkyl, alkenyl, alkynyl, halo, cyano, nitro, aryl, heteroaryl, heterocyclealkyl, —$SR_a$, —S(O)$R_a$, —S(O)$_2R_a$, —$OR_k$, —N($R_a$)($R_b$), —C(O)$R_a$, —C(O)$OR_a$ and —C(O)$NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl;

and with the further proviso that when A is

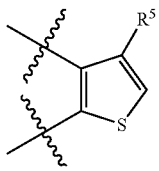

and $R^4$ is hydroxy or $R_cS$—, and $R^5$ is hydrogen, unsubstituted alkyl, halo or —$OR_k$, and $R^6$ is hydrogen, alkyl, alkenyl, alkynyl, halo, cyano, nitro, aryl, heteroaryl, heterocyclealkyl, —$SR_a$, —S(O)$R_a$, —S(O)$_2R_a$, —$OR_k$, —N($R_a$)($R_b$), —C(O)$R_a$, —C(O)$OR_a$ and —C(O)$NR_aR_b$, then $R^1$ is not hydrogen, alkenyl, alkyl, alkynyl, aryl, arylalkenyl, arylalkyl, cycloalkyl, (cycloalkyl)alkenyl, (cycloalkyl)alkyl, heteroaryl, heteroarylalkenyl, heteroarylalkyl, heterocyclealkenyl or heterocyclealkyl; comprising:

(a) contacting a compound of formula (26)

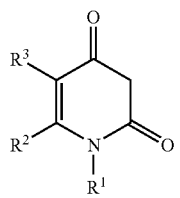

(26)

with tris(methylthio)methyl methyl sulfate in the presence of a base to provide a compound of formula (27)

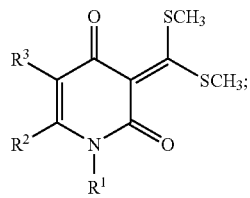

(27)

and (b) contacting the compound of formula (27) with a compound of formula (13)

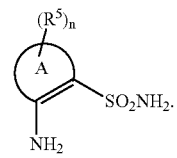

(13)

In a sixty-first embodiment, the present invention provides a compound having formula (IX)

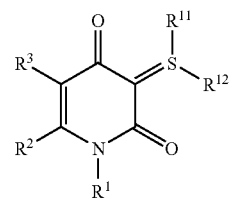

(IX)

or a pharmaceutically acceptable salt form, tautomer or stereoisomer thereof, wherein $R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN$—, $R_aR_bNalkyl$-, $R_aR_bNC(O)alkyl$-, $R_aR_bNC(O)Oalkyl$-, $R_aR_bNC(O)NR_calkyl$-, $R_fR_gC$=N— and $R_kO$—, wherein $R^1$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_e$), —$SR_c$, —S(O)$R_c$, —S(O)$_2R_c$, —$OR_c$, —N($R_c$)($R_e$), —C(O)$R_c$, —C(O)$OR_c$ and —C(O)$NR_c$;

$R^2$ and $R^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N($R_a$)($R_b$), $R_aR_bNC(O)$—, —$SR_a$, —S(O)$R_a$, —S(O)$_2R_a$ and $R_aC(O)$—; wherein $R^2$ and $R^3$ are independently substituted with 0, 1, 2 or 3 substituents independently selected from the group consisting of $R_a$, alkyl, alkenyl, alkynyl, oxo, halo, cyano, nitro, haloalkyl, -(alkyl)($OR_k$), -(alkyl)($NR_aR_b$), —$SR_a$, —S(O)$R_a$, —S(O)$_2$ $R_a$, —$OR_k$, —N($R_a$)($R_b$), —C(O)$R_a$, —C(O)O$R_a$ and —C(O)N$R_aR_b$;

alternatively, $R^2$ and $R^3$, together with the carbon atoms to which they are attached form a five- or six-membered ring selected from the group consisting of aryl, cycloalkyl, heteroaryl and heterocycle, wherein said aryl, cycloalkyl, heteroaryl and heterocycle is optionally substituted with $(R^6)_m$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), —$SR_a$, —S(O)$R_a$, —S(O)$_2R_a$, —$OR_k$, —N($R_a$)($R_b$), —C(O)$R_a$, —C(O)O$R_a$ and —C(O)N$R^aR^b$; wherein each $R^6$ is independently substituted with 0, 1, 2 or 3 substituents independently selected from the group consisting of alkyl, alkenyl, alkynyl, oxo, halo, haloalkyl, cyano, nitro, —$OR_a$, —$NR_aR_b$, —$SR_a$, —SO$R_a$, —SO$_2R_a$, —C(O)O$R_a$, —C(O)N$R_aR_b$ and —NC(O)$R_a$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, —$R_dN$—, $R_kO$—. $R_kOalkyl$-, $R_cR_dNalkyl$-, $R_cR_dNC(O)$alkyl-, $R_cSO_2$—, —SO$_2$alkyl-, $R_cC(O)$—, $R_cC(O)$alkyl-, $R_cOC(O)$—, $R_cOC(O)$alkyl-, $R_cR_dNalkylC(O)$—, $R_cR_dNC(O)$—, $R_cR_dNC(O)Oalkyl$-, $R_cR_dNC(O)N(R_e)alkyl$-, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —S(O)$R_c$, —S(O)$_2R_c$, —$OR_c$, —N($R_c$)($R_d$), —C(O)$R_c$, —C(O)O$R_c$ and —C(O)N$R_cR_d$;

alternatively, $R_a$ and $R_b$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -(alkyl)SO$_2$N$_cR_d$, -alkylC(O)N$R_eR_d$, —$SR_c$, —S(O)$R_e$, —S(O)$_2R_e$, —$OR_e$, —N($R_e$)($R_d$), —C(O)$R_e$, —C(O)O$R_e$ and —C(O)N$R_eR_d$;

$R_e$ and $R_d$, at each occurrence, are independently selected from the group consisting of hydrogen, —$NR_fR_h$, —$OR_f$, —CO($R_f$), —$SR_f$, —SO$R_f$, —SO$_2R_f$, —C(O)N$R_fR_h$, —SO$_2$N$R_fR_h$, —C(O)O$R_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —S(O)$R_f$, —S(O)$_2R_f$, —$OR_f$, —N($R_f$)($R_h$), —C(O)$R_f$, —C(O)O$R_f$, —C(O)N$R_fR_h$, —C(O)N(H)N$R_fR_h$, —N($R_e$)C(O)O$R_f$, —N($R_e$)SO$_2$N$R_fR_h$, —N($R_e$)C(O)N$R_fR_h$, -(alkyl)N($R_e$)C(O)O$R_f$, -(alkyl)N($R_e$)SO$_2$N$R_fR_h$, and -alkylN($R_e$)C(O)N$R_fR_h$;

alternatively, $R_e$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —S(O)$R_f$, —S(O)$_2R_f$, —$OR_f$, —N($R_f$)($R_h$), —C(O)$R_f$, —C(O)O$R_f$ and —C(O)N$R_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$ and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -(alkyl)-OH, -(alkyl)-O-alkyl, -(alkyl)NH$_2$, -(alkyl)N(H)(alkyl), -(alkyl)N(alkyl)$_2$, -alkylS(alkyl), -(alkyl)S(O)(alkyl), -(alkyl)SO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, $R_f$ and $R_g$ together with the carbon atom to which they are attached form a three- to seven-membered ring selected from the group consisting of cycloalkyl, cycloalkenyl and heterocycle;

alternatively, $R_f$ and $R_h$ together with the nitrogen atom to which they are attached form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -(alkyl)-OH, -(alkyl)-O-alkyl, -(alkyl)NH$_2$, -(alkyl)N(H)(alkyl), -alkylS(alkyl), -(alkyl)S(O)(alkyl), -(alkyl)SO$_2$alkyl, -(alkyl)N(alkyl)$_2$, —N(H)C(O)NH$_2$, —C(O)OH, -C(O)O(alkyl), —C(O)alkyl, —C(O)NH$_2$, —C(O)NH$_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_bNalkyl$-, $R_aOalkyl$-, $R_aR_bNC(O)$—, $R_aR_bNC(O)alkyl$, $R_aS$—, $R_aS(O)$—, $R_aSO_2$—, $R_aS$-alkyl-, $R_a(O)Salkyl$-, $R_aSO_2alkyl$-, $R_aOC(O)$—, $R_aOC(O)alkyl$-, $R_aC(O)$—, $R_aC(O)alkyl$-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —S(O)$R_c$, —S(O)$_2R_c$, —$OR_c$, —N($R_c$)($R_d$), —C(O)$R_c$, —C(O)O$R_c$ and —C(O)N$R_cR_d$;

m is 0, 1, 2, 3, or 4; and $R^{11}$ and $R^{12}$ are independently selected from the group consisting of alkyl, alkenyl and alkynyl.

Exemplary compounds of the sixty-first embodiment of the present invention of formula (IX), or a pharmaceutically acceptable salt form, tautomer or stereoisomer thereof, include, but not limited to, the following:

1-benzyl-3-(bis(methylthio)methylene)-1H-quinoline-2,4 (1H,3H)-dione;

3-[bis(methylthio)methylene]-1-butyl-1,8-naphthyridine-2, 4(1H,3H)-dione;

3-[bis(methylthio)methylene]-1-(1,3-dioxo-1,3-dihydro-2H-isoindol-2-yl)quinoline-2,4(1H,3H)-dione;

3-[bis(methylthio)methylene]-1-[(cyclopropylmethyl) amino]quinoline-2,4(1H,3H)-dione;

3-[bis(methylthio)methylene]-1-(3-methylbutyl)pyridine-2, 4(1H,3H)-dione;

1-benzyl-3-[bis(methylthio)methylene]pyridine-2,4(1H, 3H)-dione;

3-[bis(methylthio)methylene]-1-(cyclobutylamino)quinoline-2,4(1H,3H)-dione; and

3-[bis(methylthio)methylene]-1-(cyclobutylmethyl)pyridine-2,4(1H,3H)— dione.

The compounds of the invention can comprise asymmetrically substituted carbon atoms. As a result, all stereoisomers of the compounds of the invention are meant to be included in the invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

The present compounds may exhibit the phenomena of tautomerism or structural isomerism. As the drawings within this specification can only represent one possible tautomeric or structural isomeric form, it should be understood that the invention encompasses any tautomeric or structural isomeric form, or mixtures thereof, which possess the ability to inhibit hepatitis C, and is not limited to any one tautomeric or structural isomeric form utilized within the drawings.

In addition, solvates and hydrates of the compounds of the invention are meant to be included in this invention.

When any variable (for example $R^1$, $R^2$, $R^3$, m, n, etc.) occurs more than one time in any substituent or in the compound of the invention or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

The compounds of the present invention can exist as pharmaceutically acceptable salts. The term "pharmaceutically acceptable salt," as used herein, represents acid or base salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting a basic group (for example, a nitrogen containing group) with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group (for example, a carboxy group or an enol) with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of basic addition salts include ethylenediamine, ethanolamine, diethanolamine, piperidine, and piperazine.

Preferred salts of the compounds of the present invention include monosodium, disodium, triethylamine salt, trifluoroacetate and hydrochloride.

The present compounds can also exist as pharmaceutically acceptable prodrugs. The term "pharmaceutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. "Prodrugs" are considered to be any covalently bonded carriers which release the active parent drug of formula (I), (II), (III), (IV), (V), (Va), (Vb), (VIa), (VIb), (VII) or (VIII) in vivo when such prodrugs is administered to a mammalian subject. Prodrugs of the compounds of formula (I), (II), (III), (IV), (V), (Va), (Vb), (VIa), (VIb), (VII) or (VIII) are prepared by modifying functional groups present in the compounds in such a way that the modifications are cleaved, either in routine manipulation or in vivo, to the parent compounds respectively. Prodrugs include compounds wherein hydroxy, amine, carboxy, or sulfhydryl groups are bonded to any group that, when administered to a mammalian subject, cleaves to form a free hydroxyl, amino, carboxy, or sulfhydryl group, respectively. Examples of prodrugs include, but are not limited to, acetate, formate, and benzoate derivatives of the hydroxy, carboxy and amine functional groups in the compounds of formula (I), (II), (III), (IV), (V), (Va), (Vb), (VIa), (VIb), (VII) and (VIII); and the like.

In accordance with methods of treatment and pharmaceutical compositions of the invention, the compounds can be administered alone or in combination with other antiviral agents. When using the compounds, the specific pharmaceutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrastemal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The antiviral effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The compounds of the invention inhibit HCV RNA dependent RNA polymerase an enzyme essential for HCV viral replication. They can be administered as the sole active pharmaceutical agent, or they can also be used in combination with one or more agents to treat hepatitis C infections or the symptoms associated with HCV infection. Other agents to be administered in combination with a compound of the present invention include therapies for disease caused by HCV infection that suppresses HCV viral replication by direct or indirect mechanisms. These include agents such as host immune modulators, for example, interferon-alpha, pegylated interferon-alpha, CpG oligonucleotides and the like, or antiviral compounds that inhibit host cellular functions such as inosine monophosphate dehydrogenase, for example, ribavirin and the like. Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO0190121(A2), or U.S. Pat. No. 6,348,587B1 or WO0160315 or WO0132153 or non-nucleoside inhibitors such as, for example, benzimidazole polymerase inhibitors described in EP1162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agent include but are not limited to therapies for disease caused by hepatitis B (HBV) infection such as, for example, adefovir, lamivudine, LdT (L-deoxythymidine) and tenofovir or therapies for disease caused by human immunodeficiency virus (HIV) infection such as, for example, protease inhibitors: ritonavir, lopinavir, indinavir, nelfinavir, saquinavir, amprenavir, atazanavir, tipranavir, TMC-114, fosamprenavir; reverse transcriptase inhibitors: zidovudine, lamivudine, didanosine, stavudine, tenofovir, zalcitabine, abacavir, efavirenz, nevirapine, delavirdine, TMC-125; integrase inhibitors: L-870812, S-1360, or entry inhibitors: enfuvirtide (T-20), T-1249.

Other agents to be administered in combination with a compound of the present invention include any agent or combination of agents that treat or alleviate symptoms of HCV infection including cirrhosis and inflammation of the liver.

When administered as a combination, the therapeutic agents can be formulated as separate compositions which are given at the same time or within a predetermined period of time, or the therapeutic agents can be given as a single unit dosage form.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

HCV Polymerase Inhibition Assay: Biochemical $IC_{50}$

Either two-fold serial dilutions (fractional inhibition assay) or a narrower range of dilutions spanning the IC50 of the inhibitor (tight binding assay) of the inhibitors were incubated with 20 mM Tris-Cl pH 7.5, 5 mM MgCl$_2$, 50 mM NaCl, 1 mM dithiothreitol, 1 mM ethylene diamine tetraacetic acid (EDTA), 300 μM GTP and 150 to 300 nM NS5B (HCV Strain 1 B (J4, Genbank accession number AF054247, or H77, Genbank accession number AFO 11751)) for 15 minutes at room temperature. The reaction was initiated by the addition of 20 μM CTP, 20 μM ATP, 1 μM 3H-UTP (10 mCi/umol), 150 mM template RNA and 0.4 U/μl RNase inhibitor (RNasin, Promega), and allowed to proceed for 2 to 4 hours at room temperature. Reaction volume was 50 μl. The reaction was terminated by the addition of 1 volume of 4 mM spermine in 10 mM Tris-Cl pH 8.0, 1 mM EDTA. After incubation for at least 15 minutes at room temperature, the precipitated RNA was captured by filtering through a GF/B filter (Millipore) in a 96 well format. The filter plate was washed three times with 200 μl each of 2 mM spermine, 10 mM Tris-Cl pH 8.0, 1 mM EDTA, and 2 times with ethanol. After air drying, 30 μl of Microscint 20 scintillation cocktail (Packard) was added to each well, and the retained cpm were determined by scintillation counting. IC50 values were calculated by a two-variable nonlinear regression equation using an uninhibited control and a fully inhibited control sample to determine the minimum and maximum for the curve. Tight-binding assays were performed on those compounds exhibiting IC50 values less than 0.15 μM in the fractional inhibition assay in order to more precisely measure the IC50 values. Retained cpm were plotted vs. inhibitor concentration and fit to equation 1 using non-linear regression (ref. 1) to obtain the IC50 values.

$$\text{Retained cpm} = A[\text{sqrt}\{(IC_{50}+I_t-E_t)^2+4IC_{50}E_t\}-(IC_{50}+I_t-E_t)] \quad \text{eqn 1.}$$

where $A=V_{max}[S]/2(K_m+[S])$; $I_t$=total inhibitor concentration and $E_t$=total active concentration of enzyme.

Ref. 1: Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was:

5' GGGCGAAUUGGGCCCUCUAGAUGCAUGCUCGAGCGGCCGCCAGUGUG
AUGGAUAUCUGCAGAAUUCGCCCUUGGUGGCUCCAUCUUAGCCCUAGUCA
CGGCUAGCUGUGAAAGGUCCGUGAGCCGCUUGACUGCAGAGAGUGCUGAU
ACUGGCCUCUCUGCAGAUCAAGUC-3'

When tested by the above method, the compounds of the present invention inhibit HCV polymerase 1B with IC50's in the range of 0.002 μM to 500 μM.

Evaluation of the HCV Inhibitors in HCV Replicon: Cell Culture $EC_{50}$

The cell lines and assays were conducted according to the methods described by Ikeda M, Yi M, Li K, Lemon S M., J Virol 2002 March; 76(6):2997-3006, and Blight K. J, Kolykhalov A., Rice C. M., Science 2000 December, 290: 1972-1974) with the following modifications:

RNA Assay

Replicon cells were plated at $3\times10^3$ cells per well in 96-well plate in DMEM medium containing 5% fetal calf serum. At day 1, culture medium was removed and replaced with fresh medium containing eight serial 2-fold dilutions of compound. The final concentration of DMSO in medium was 0.5%. The untreated control culture was treated in an identical manner except no inhibitor was added to the medium. Plates were incubated in a $CO_2$ incubator at 37° C. On Day 4, 100 μl lysis buffer (RTL) (Qiagen) was added to each well after removal of culture medium. RNA was purified according to manufacturer's recommendations (Qiagen RNAeasy) and eluted in 200 μl of water. The HCV RNA level was quantified from a portion (5 μl out of 200 μl) of the purified RNA by real-time RT-PCR method. The primers and probe are derived from specific sequence in the 5'UTR region. RT-PCR reaction was performed at 48° C. for 30 min, followed by 40 cycles set to 95° C., 15 s; 54° C., 30 s; and 72° C., 40 s. The percentage reduction of HCV RNA in the presence of compound was calculated and the 50% inhibitory concentration ($IC_{50}$) was calculated by non-linear regression analysis using the Prism program.

When tested by the above method, the compounds of the present invention inhibit replicon production with EC50's in the range of 0.002 μM to >100 μM.

Cytotoxity Assays

Cytotoxicity assays were performed in replicon cells. Briefly, HCV replicon cells were plated at $3\times10^3$ cells per well in 96-well plate in DMEM medium containing 5% FCS. At day 1, culture medium was removed and replaced with fresh medium containing eight serial 2-fold dilutions of compound. The final concentration of DMSO in medium was 0.5%. All experiments were performed in duplicate. The untreated control culture was treated in an identical manner except no inhibitor was added to the medium. Plates were incubated in a $CO_2$ incubator at 37° C. On day 4, stock solution of the tetrazolium salt, MTT (4 mg/ml in PBS, Sigma cat.# M 2128) was added to each well at 25 μl per well. Plates were further incubated for 4 hours, treated with 20% SDS plus 0.02 N HCl at 50 μl per well to lyse the cells. After an overnight incubation, optical density was measured by reading the plates at 570/650 nm wavelengths. The percent reduction of formazan blue color formed relative to control was calculated and the cytopathic effect was described as a 50% toxicity concentration ($TC_{50}$) was calculated by non-linear regression analysis using the Prism program.

When tested by the above method, the compounds of the present invention exhibited CPE reduction with TC50's in the range of 6.6 μM to >100 μM.

Cell culture assays for agents targeted toward hepatitis C are not yet available because of the inability to produce infectious virus in a sustained cell line. The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in the references above. The mechanism of RNA replication in these cell lines is considered to be identical to the replication of full length HCV RNA in infected hepatocytes. The compounds and methods of this invention are inhibitors of HCV RNA replication in the replicon assay systems described above. This forms the basis of the claim for their potential as therapies in treating disease resulting from hepatitis C viral infection.

Synthetic Methods

Abbreviations which have been used in the descriptions of the scheme and the examples that follow are: DMF is N,N-dimethylformamide, DMSO is dimethylsulfoxide, and THF is tetrahydrofuran.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, $R^1$, $R^2$, $R^3$, $R^4$, $R^5$, and n are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

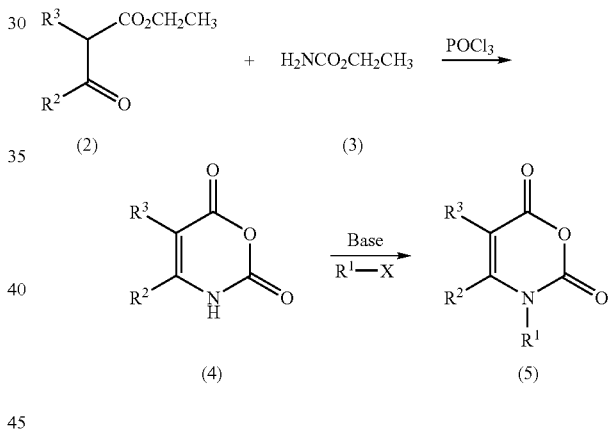

As shown in Scheme 1, compounds of formula (2) can be reacted with compounds of formula (3) in the presence of phosphorous oxychloride under heating conditions to provide compounds of formula (4). Compounds of formula (4) can be reacted with a base such as sodium hydride, potassium hydride, lithium hexamethyldisilazide, and the like in solvent such as but not limited to dimethylacetamide, dimethylformamide, THF, and the like, followed by the addition of $R^1$—X, (wherein $R^1$ is alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, arylalkenyl, arylalkyl, arylsulfanylalkyl, arylsulfonylalkyl, carboxyalkyl, cyanoalkyl, cycloalkenyl, cycloalkenylalkyl, cycloalkyl, cycloalkylalkenyl, cycloalkylalkyl, haloalkoxyalkyl, haloalkyl, heteroarylalkenyl, heteroarylalkyl, heteroarylsulfonylalkyl, heterocyclealkenyl, heterocyclealkyl, hydroxyalkyl, nitroalkyl, $R_aR_b$Nalkyl-, $R_aR_b$NC(O)alkyl-, $R_aR_b$NC(O)Oalkyl- or $R_aR_b$NC(O)NR$_c$alkyl-, and wherein X is Br, Cl, I, $CF_3S(O)_2$—, $CH_3S(O)_2$—, or tosyl) to provide compounds of formula (5).

Scheme 2

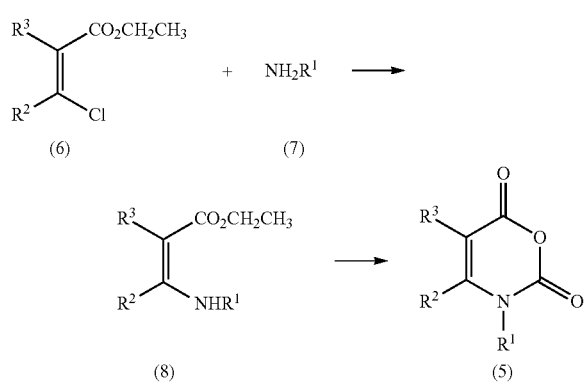

Alternatively, compounds of formula (6) can be treated with compounds of formula (7) (wherein $R^1$ is alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, cycloalkylalkenyl, cycloalkylalkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN-$, $R_aR_bNalkyl$-, $R_aR_bNC(O)alkyl$-, $R_aR_bNC(O)Oalkyl$-, $R_aR_bNC(O)NR_calkyl$-, $R_fR_gC=N-$ or $R_kO-$), under heating conditions optionally in the presence of a base such as potassium carbonate and a catalyst such as copper bromide, to provide compounds of formula (8). Compounds of formula (8) can be treated with reagents including but not limited to phosgene, diphosgene, triphosgene in solvents such as but not limited to 1,2-dichloroethane, carbon tetrachloride, 1,4-dioxane or mixtures thereof, under heating conditions to provide compounds of formula (5).

Scheme 3

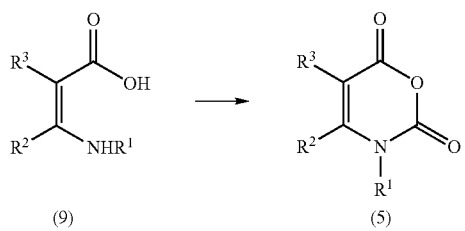

In addition, compounds of formula (9) can also be reacted with reagents including but not limited to phosgene, diphosgene, triphosgene, carbonyldiimidazole, ethyl chloroformate and the like in the presence of a base such as potassium hydroxide, pyridine, lithium hydroxide, and the like in solvents such as but not limited to water, toluene, benzene, and the like under heating conditions to provide compounds of formula (5).

Scheme 4

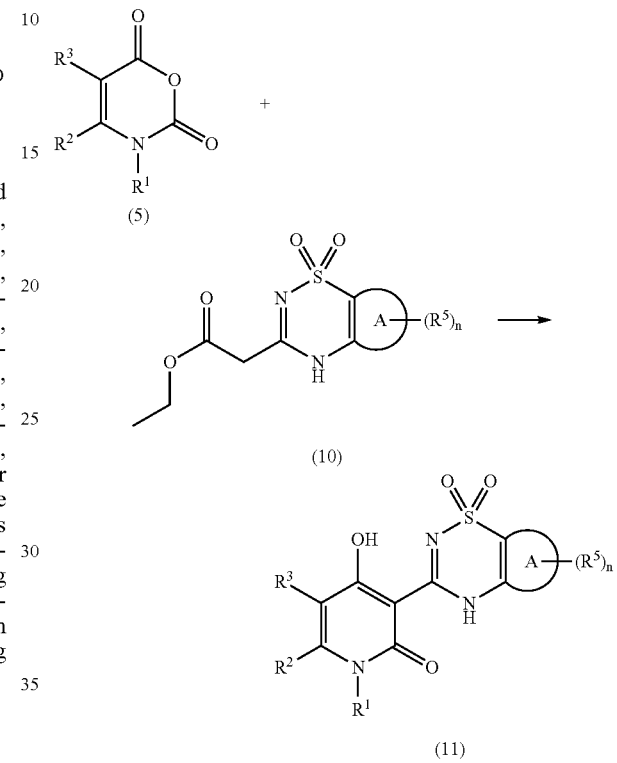

Compounds of formula (5) can be treated with compounds of formula (10) in the presence of a base such as sodium hydride, potassium hydride, lithium hexamethyldisilazide, and the like in a solvent such as but not limited to THF, diethyl ether, methyl tert-butyl ether followed by the treatment with an acid such as acetic acid, dichloroacetic acid or sulfuric acid to provide compounds of formula (11) which are representative of a compound of formula (I), where $R^4$ is hydroxy.

Scheme 5

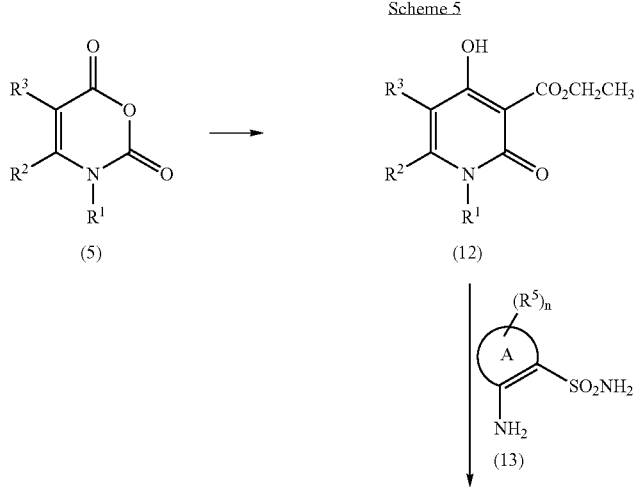

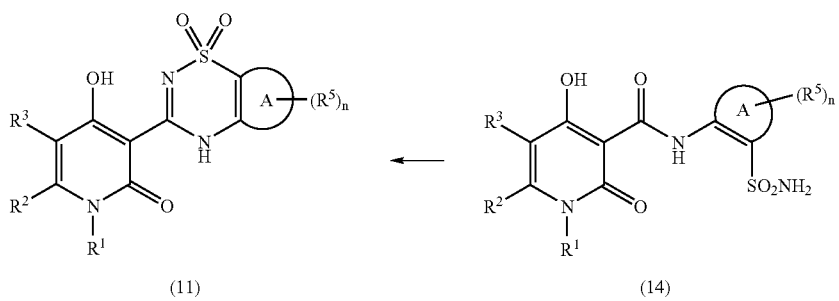

Compounds of formula (5) can be reacted with diethyl malonate that has been pretreated with a base such as sodium hydride, potassium hydride, and the like in solvents such as dimethylacetamide, dimethylformamide, THF, and the like under heated conditions to provide compounds of formula (12). Compounds of formula (12) can be treated with compounds of formula (13) in solvents such as toluene, mesitylene, benzene, and the like under heated conditions to provides compounds of formula (14). Compounds of formula (14) can be treated with a base such as sodium hydroxide, potassium hydroxide, lithium hydroxide, and the like in water under heated conditions to provide compounds of formula (11).

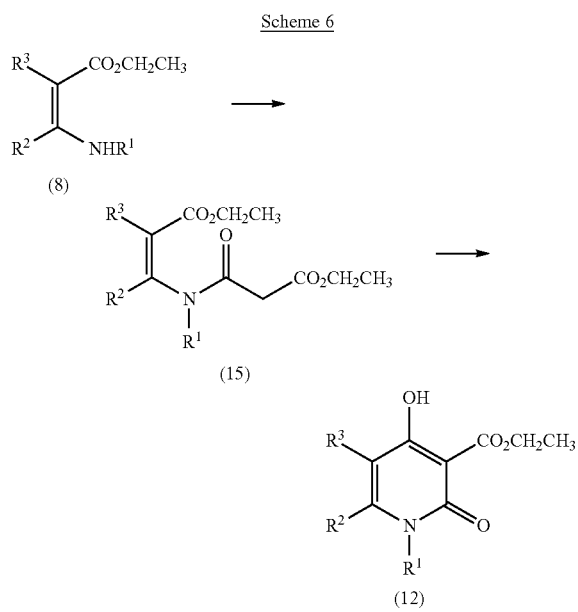

Alternatively, compounds of formula (8) can be treated with ethyl chloromalonate in the presence of a base such as triethylamine, diisopropylethylamine, pyridine, and the like in solvents such as dichloromethane, chloroform, carbon tetrachloride to provide compounds of formula (15). Alternatively, compounds of the formula (8) can be treated with ethyl chloromalonate in solvents such as benzene, toluene under heating conditions to provide compounds of formula (15).

Compounds of formula (15) can be treated with sodium ethoxide in ethanol to provide compounds of formula (12).

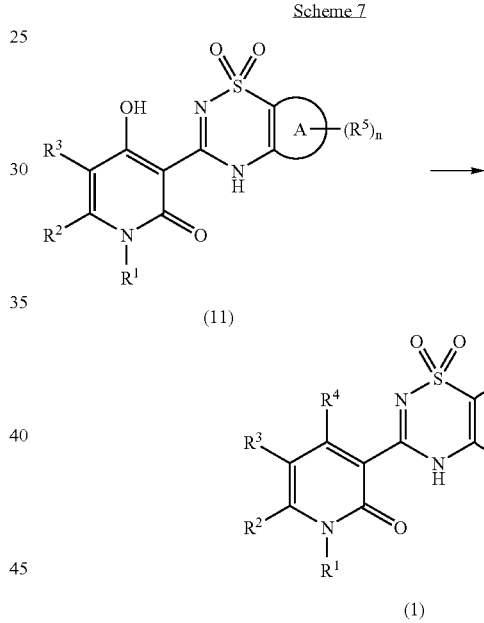

Scheme 7 shows the preparation of compounds of formula (I)) where $R^4$ is halo. Compounds of formula (11) can be treated with reagents known to those skilled in the art which are commonly used to convert alcohols to chlorides. For example, compounds of formula (11) can be treated with reagents including but not limited to $PCl_5$, $PCl_3$, $POCl_3$, or thionyl chloride, with or without solvents such as but not limited to dichloromethane, chloroform and benzene, to provide compounds of formula (I) which are representative of compounds where $R^4$ is chlorine. Similar transformations are possible using $PBr_3$ or DAST to convert the said alcohol to the corresponding compound of formula (I) where $R^4$ is bromide and fluoride, respectively. Alternatively, compound of formula (I) wherein $R^4$ is iodo can be prepared by (a). reacting compound of formula (11) with a mesylating reagent such as methanesulfonyl chloride or methanesulfonyl anhydride in the presence of an amine base such as triethylamine, pyridine or diisopropylethylamine in solvents such as but not limited to dichloromethane, acetonitrile, carbon tetrachloride, chloroform, and (b) treatment of the mesylate thus formed with N-iodosuccinimide.

Scheme 8

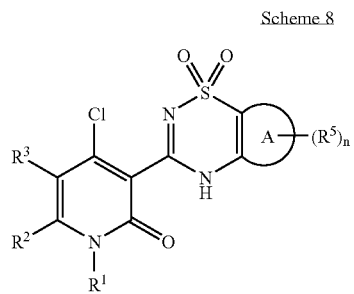

(16)

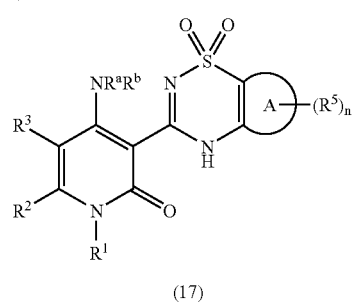

(17)

As shown in Scheme 8, compounds of formula (16) can be converted to compounds of formula (17) which are representative of compounds of formula (I) where $R^4$ is $R_aR_bN$—, by treatment with an amine having the formula $R_aR_bNH$, (where $R_a$ and $R_b$ are as defined herein) in a polar solvent such as methanol, ethanol, and the like, under heating conditions to provide compounds of formula (17).

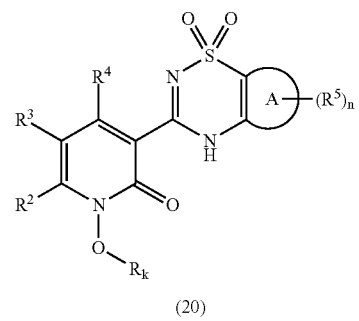

(20)

Compounds of formula (18) (which are representative of compounds of formula (I) where $R^1$ is O-Si(isopropyl)$_3$ or some other easily removed ether protecting group) can be treated with a fluoride containing reagent to provide compounds of formula (19). The hydroxylamine portion of compounds of formula (19) can be treated with a base such as sodium hydride in solvents such as dimethylformamide, or lithium hexamethyldisilazide in solvents such as but not limited to THF, dioxane and the like, followed by the addition of $R_k$—X (wherein $R_k$ is alkoxyalkyl, alkoxycarbonyl, alkoxycarbonylalkyl, alkyl, alkylcarbonylalkyl, alkylsulfanylalkyl, alkylsulfonylalkyl, aryl, arylalkyl, arylsulfanylalkyl, carboxyalkyl, cyanoalkyl, cycloalkenyl, cycloalkenylalkyl, cycloalkyl, cycloalkylalkyl, formylalkyl, haloalkoxyalkyl, haloalkyl, heteroaryl, heteroarylalkyl, heterocycle, heterocyclealkyl, hydroxyalkyl, nitroalkyl, $R_cR_dNalkyl$- or $R_cR_dNC(O)alkyl$, and wherein X is Br, Cl, I, CF$_3$S(O)$_2$—, CH$_3$S(O)$_2$—, or tosyl) to provide compounds of formula (20) which are representative of compounds of formula (I) where $R^1$ is defined as $R_kO$—.

Scheme 9

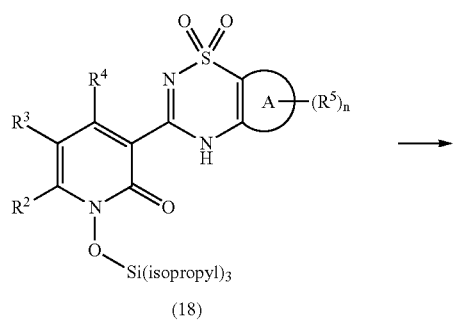

(18)

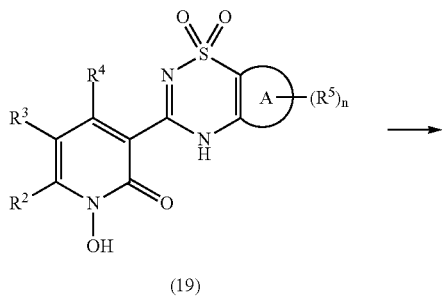

(19)

Scheme 10

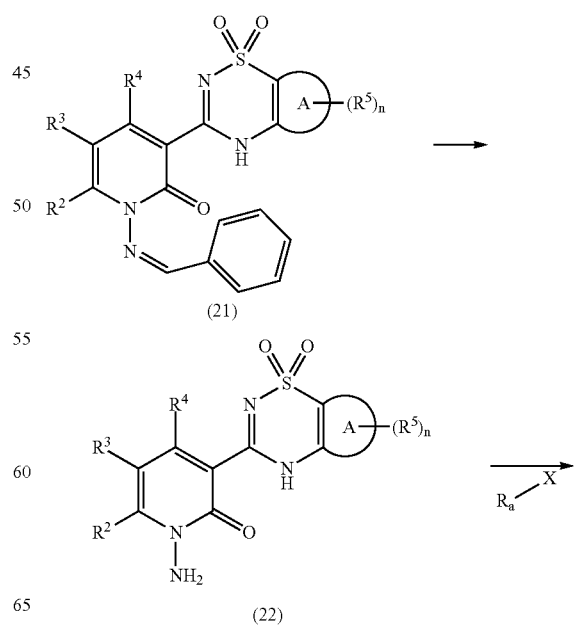

(21)

(22)

-continued

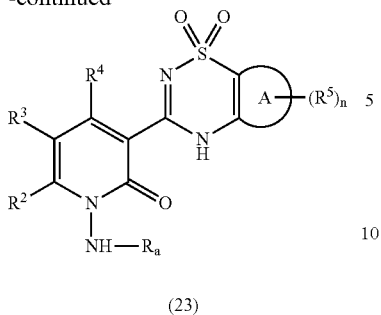

(23)

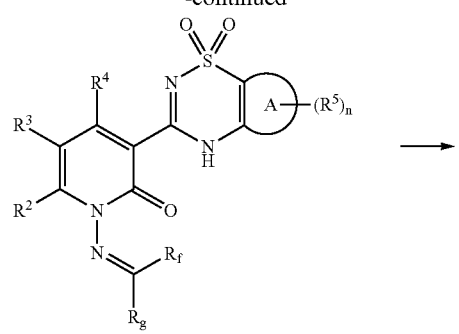

(24)

Compounds of formula (21) can be treated with aqueous base such as but not limited to potassium hydroxide, sodium hydroxide and the like, to provide compounds of formula (22). Compounds of formula (22) can be treated with a metal hydride base such as sodium hydride, an organolithium reagent (e.g. t-BuLi, n-BuLi, or s-BuLi), or lithium hexamethyldisilazide in an appropriate solvent or a mixture of solvents selected from THF, DMSO, DMF, dioxane, ether, dichloromethane, and the like, followed by the addition of $R_aX$ wherein X is Br, Cl, I, $CF_3S(O)_2-$, $CH_3S(O)_2-$, or tosyl to provide compounds of formula (23) which are representative of compounds of formula (I) wherein $R^1$ is $-NHR_a$.

Scheme 11

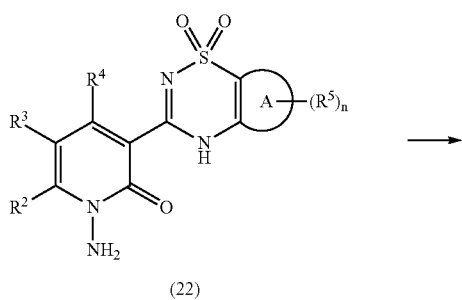

(22)

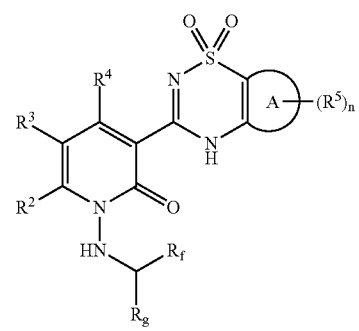

(25)

Alternatively, compounds of formula (22) can be treated with aldehydes or ketones of structure $R_fR_gC(O)$ without solvents or with solvents such as but not limited to dimethylacetamide, tetrahydrofuran, dioxane and the like under heated conditions to provide compounds of formula (24). Reduction of compounds of formula (24) with hydrogen and a catalyst such as palladium and the like or a metal hydrides such as lithium borohydride, sodium cyanoborohydride and the like provide compounds of the formula (25).

Scheme 12

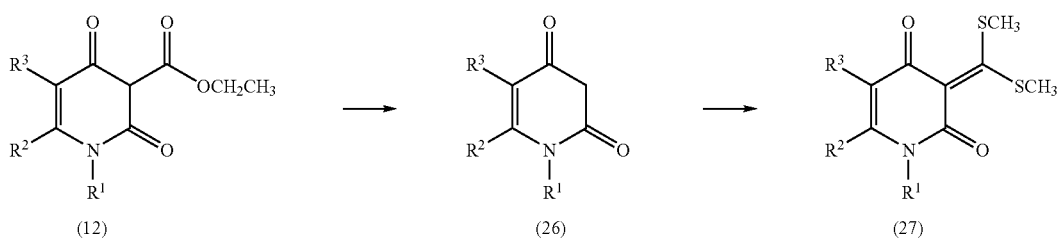

(12)　　　　　　(26)　　　　　　(27)

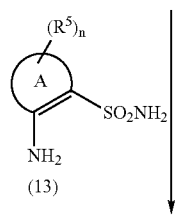

(13)

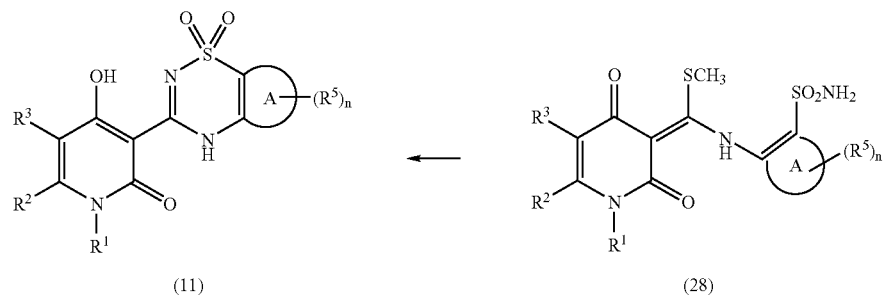

Compounds of formula (12) can be reacted with aqueous base solutions such as potassium hydroxide and the like under heated conditions to provide compounds of formula (26). Compounds of formula (26) can be reacted with a base in a solvent, or mixtures of solvents such as, but not limited to, N,N-dimethylformamide, tetrahydrofuran, diethyl ether, or methyl tert-butyl ether, and the like, followed by treatment with carbon disulfide at a temperature of about room temperature to about 70° C. Examples of the base include, but not limited to, sodium hydride, potassium hydride, lithium diisopropylamide, sodium hexamethyldisilazide and lithium hexamethyldisilazide. Subsequent treatment with a methylating reagent at a temperature of about 25° C. provides compounds of formula (27).

Examples of the methylating agent include, but not limited to, methyl iodide, methyl triflate, dimethylsulfate, and the like.

Alternatively, compounds of the formula (26) can be reacted with tris(methylthio)methyl methyl sulfate in the presence of a base in a solvent such as 1,4-dioxane or dimethylacetamide, and the like, at a temperature of about 25° C. to about 150° C. to give compounds of formula (27). Examples of the base include, but are not limited to, organic amine bases such as imidazole, 1-methylimidazole, 2-methylimidazole, 2-isopropylimidazole, 4-methylimidazole, 4-nitroimidazole, pyridine, N,N-dimethylaminopyridine, 1,2,4-triazole, pyrrole, 3-methylpyrrole, triethylamine, diisopropylethylamine or N-methylmorpholine and the like.

Compounds of formula (27) can be treated with compounds such as (13) in a solvent or a mixture of solvents, such as but not limited to, toluene, benzene, dioxane or tetrahydrofuran, and the like, at a temperature of about 50° C. to about 150° C. to provide compounds of formula (11).

Scheme 13

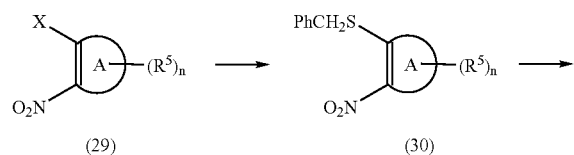

Compounds of the formula (29) wherein X is I, Br, Cl or F can be treated with alkyl thiols such as benzene methylthiol in the presence of a base such as sodium carbonate in solvents such as ethanol and the like under heated conditions to give compounds of the formula (30). Treatment of (30) with chlorine gas in hydrochloric acid or acetic acid provides compounds of the formula (31). Compounds of the formula (31) in solvents such as but not limited to dichloromethane, tetrahydrofuran or dioxane can be treated with ammonia or ammonium hydroxide to give compounds of the formula (32). Reduction of compounds of the formula (32) with iron powder and ammonium chloride in aqueous alcoholic solvents such as methanol or ethanol under heated conditions optionally with iron powder in acetic acid under heated conditions to provide compounds of the formula (13).

Scheme 14

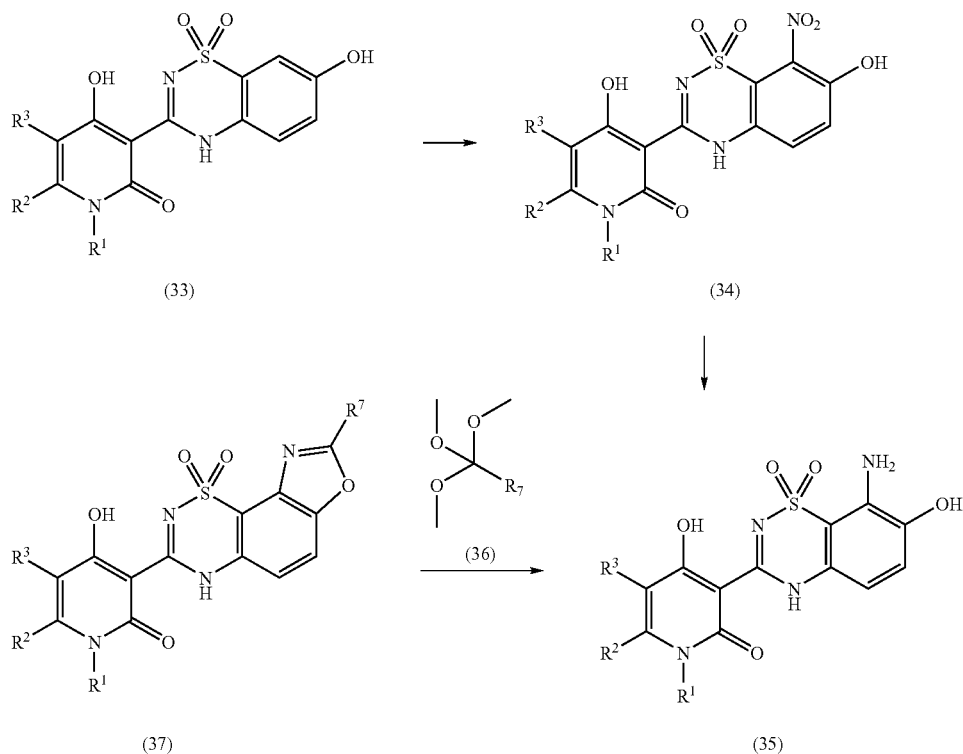

Compounds of the formula (33) can be treated with ammonium nitrate in the presence of a sulfuric acid as solvent under cooling conditions to give compounds of the formula (34). Reduction of compounds of the formula (34) with iron powder and ammonium chloride in aqueous alcoholic solvents such as methanol or ethanol under heated conditions provides compounds of the formula (35). Alternatively, the reduction can also be achieved by treating compounds of formula (35) with iron powder in acids such as but not limited to acetic acid or dilute hydrochloric acid under heated conditions. Treatment of compounds of the formula (35) with an orthoester of the formula (36) under heating conditions to provide compounds of the formula (37).

Scheme 15

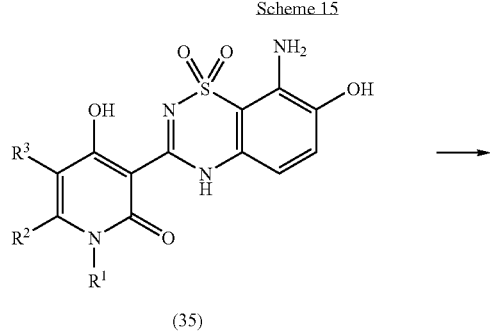

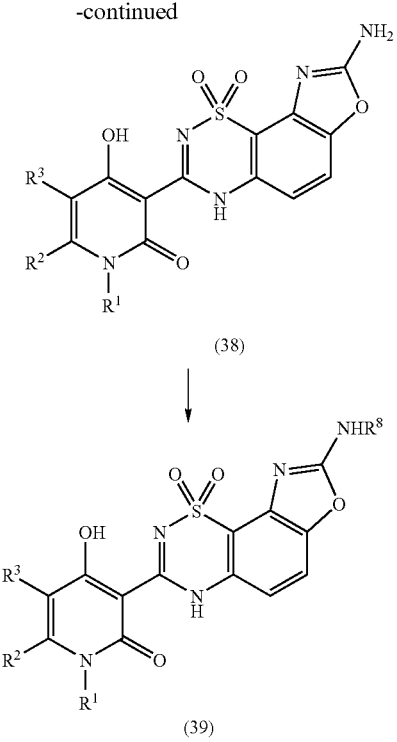

Compounds of the formula (35) can be treated with cyanogen bromide under heating conditions to give compounds of the formula (38). Treatment of compounds of the formula (38) with $R^8X$ wherein X is Br, Cl, or I, $R^8CO_2Cl$, or $R^8SO_2Cl$ in the presence of an amine base such as triethylamine, pyridine, or an inorganic base such as cesium carbonate or potassium carbonate in an appropriate solvent or a mixture of solvents selected from dimethylacetamide, N,N-dimethylformamide, methanol, dichloromethane, tetrahydrofuran, or acetonitrile and the like to provide compounds of the formula (39).

Scheme 16

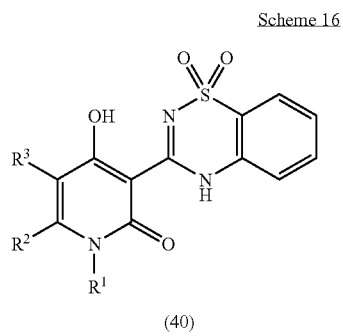

(40)

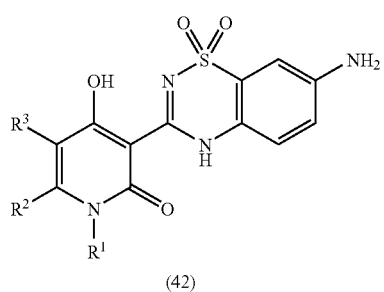

(41)

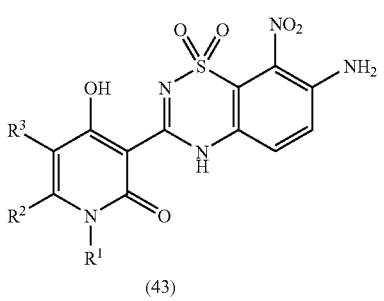

(42)

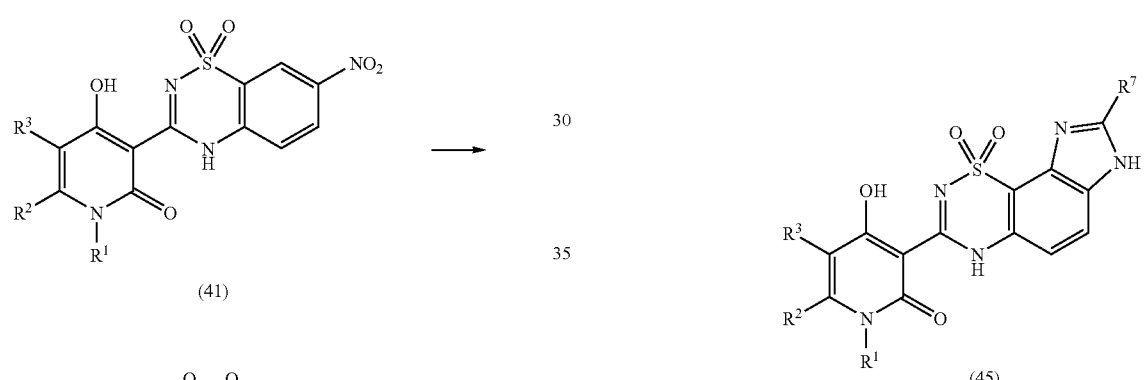

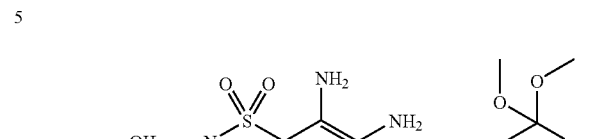

Compounds of formula (40) can be nitrated with ammonium nitrate or potassium nitrate in the presence of an acid such as sulfuric acid, or trifluoroacetic acid in trifluoroacetic anhydride, with or without additional solvent, under cooling conditions to give compounds of the formula (41). Reduction of compounds of the formula (41) with iron powder and ammonium chloride in aqueous alcoholic solvents such as methanol or ethanol under heated conditions provides compounds of the formula (42). Alternatively, the reduction of compounds of formula (42) can also be accomplished using iron powder in acids such as but not limited to acetic acid or dilute hydrochloric acid under heated conditions. Compounds of the formula (42) can be converted to compounds of the formula (44) by (a) nitration and (b) reduction of the product of step (b), using the respective conditions as mentioned above. Compounds of the formula (44) can be treated with an orthoester of the formula (36) under heating conditions to provide compounds of the formula (45).

Scheme 17

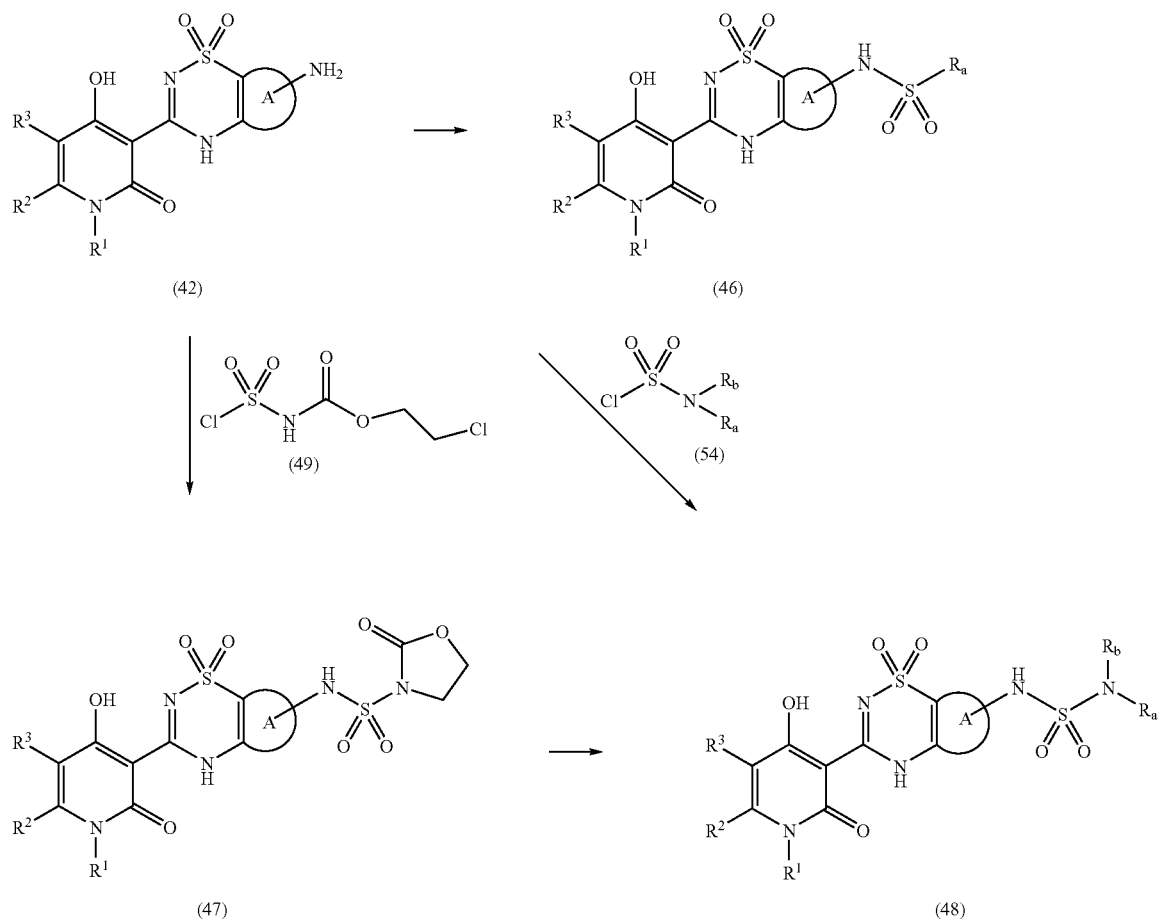

Compounds of formula (42) can be sulfonylated with a sulfonyl chloride of formula $R_aSO_2Cl$ in the presence of a base such as pyridine alone or an amine base such as triethylamine, diisopropylethylamine, and the like in a solvent or combination of solvents such as dichloromethane, tetrahydrofuran, or dioxane, to provide compounds of formula (46).

Alternatively, compounds of formula (42) can be sulfamoylated in the presence of an amine base such as but not limited to triethylamine, or diisopropylethylamine, and the like, in a solvent or combination of solvents such as dichloromethane, tetrahydrofuran or dioxane, and the like, with compounds of formula (49) to give compounds of formula (47). Compounds of formula (49) can be obtained by treating chlorosulfonyl isocyanate and 2-chloroethanol in conditions that are well known in the art. Compounds of formula (47) can be treated further with an amine having the formula $R_aR_bNH$, (where $R_a$ and $R_b$ are as defined herein) in a solvent or combination of solvents such as dichloromethane, THF, or acetonitrile, and the like, under heating conditions to provide compounds of formula (48). Compounds of formula (42) can be sulfamoylated in the presence of an amine base such as triethylamine, or diisopropylethylamine, and the like, in a solvent or combination of solvents such as dichloromethane, tetrahydrofuran or dioxane, and the like, with compounds of formula (54) to give compounds of formula (48). Compounds of formula (54) can be obtained by treating an amine of the formula $R_aR_bNH$ with sulfuryl chloride or by (a) treating an amine of the formula $R_aR_bNH$ with chlorosulfonic acid, and (b) contacting the product of step (a) with a chlorinating agent such as phosphorous pentachloride and the like in conditions that are well known in the art.

Similarly, compounds of formula (11) wherein $R^5$ is -(alkyl)$NH_2$ can be converted to compounds of formula (11) wherein $R^5$ is -(alkyl)$NHSO_2NR_aR_b$ using the conditions for the transformation of compounds of formula (42) to compounds of formula (48). Compounds of formula (11) wherein $R^5$ is -(alkyl)$NH_2$ can be converted to compounds of formula (11) wherein $R^5$ is -(alkyl)$NHSO_2R_a$ can be achieved by employing the conditions for the transformation of compounds of formula (42) to compounds of formula (46).

Scheme 18

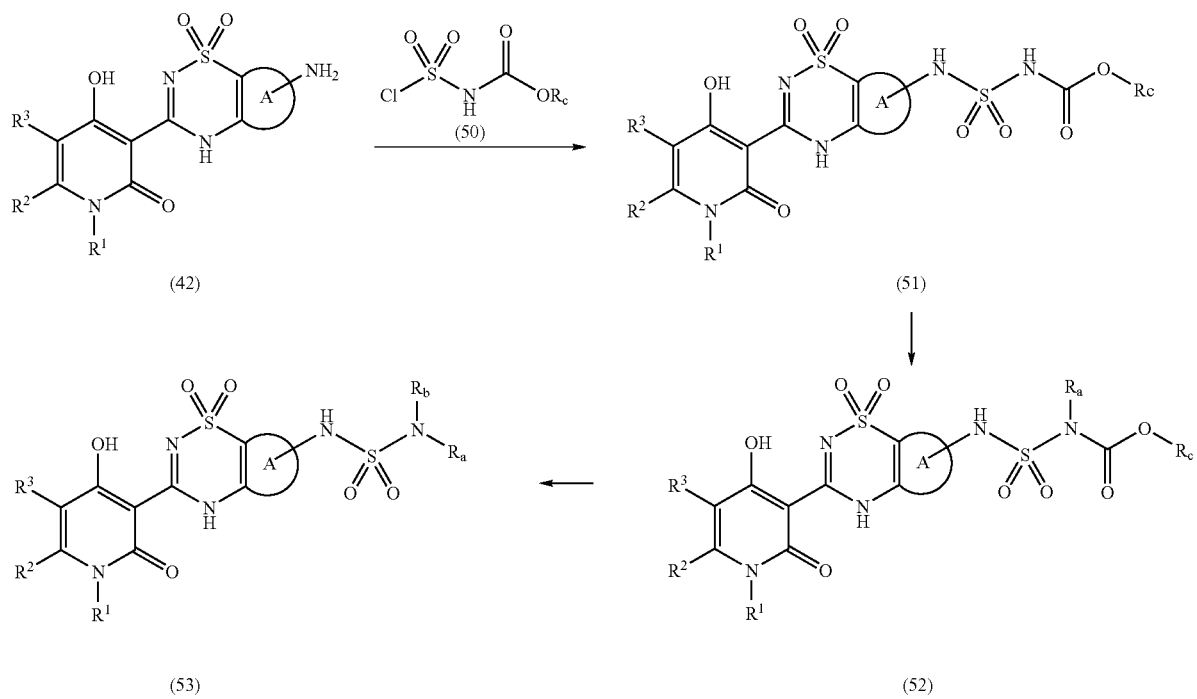

Compounds of formula (42) can be sulfamoylated with a sulfamoyl chloride of formula $R_cOC(O)NHSO_2Cl$ (50), in the presence of an amine base such as pyridine, triethylamine or diisopropylethylamine, and the like, in a solvent or combination of solvents such as dichloromethane, tetrahydrofuran, diethyl ether, benzene, or acetonitrile, and the like, to provide compounds of formula (51). Compounds of formula (50) can be prepared by treating an alcohol of formula $R_cOH$ with chlorosulfonyl isocyanate in a solvent or combination of solvents such as dichloromethane, carbon tetrachloride, diethyl ether, benzene, or toluene, and the like. Compounds of formula (51) can be treated further with an alcohol having the formula $R_aOH$ in the presence of tri-n-butylphosphine or triphenylphosphine, and the like, and diisopropylazodicarboxylate, 1,1'-(azadicarbonyl)piperidine, or diethylazodicarboxylate, and the like, in a solvent or combination of solvents such as dichloromethane or tetrahydrofuran to provide compounds of formula (52). Alternatively, compounds of formula (52) wherein $R_a$ is methyl can be obtained by methylating compounds of formula (51) with a methylating agent such as, but not limited to, methyl iodide, dimethyl sulfate, trimethysilyldiazomethane in conditions that are well known in the art. Transformation of compounds of formula (52) to compounds of formula (53) can be achieved by reaction with an acid such as trifluoroacetic acid or hydrochloric acid, or by hydrogenolysis conditions such as palladium on carbon under hydrogen gas.

Similarly, compounds of formula (11) wherein $R^5$ is -(alkyl)$NH_2$ can be converted to compounds of formula (11) wherein $R^5$ is -(alkyl)$NHSO_2NHCOOR_c$ by the conditions for the transformation of compounds of formula (42) to compounds of formula (51).

Compounds of formula (11) wherein $R^5$ is -(alkyl)$NH_2$ can be converted to compounds of formula (11) wherein $R^5$ is -(alkyl)$NHSO_2N(R_a)COOR_c$ by the conditions employed for the conversion of (51) to (52).

Compounds of formula (11) wherein $R^5$ is -(alkyl)$NH_2$ can be converted to compounds of formula (11) wherein $R^5$ is -(alkyl)$NHSO_2NR_aR_b$ by the conditions employed for the conversion of (52) to (53).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names consistent with ACD nomenclature.

EXAMPLE 1

1-butyl-3-(1,1-dioxido-4H-1,2,4-benzothiadiazin-3-yl)-4-hydroxy-1,8-naphthyridin-2(1H)-one

EXAMPLE 1A 2H-pyrido[2,3-d][1,3]oxazine-2,4(1H)-dione

The title compound was prepared from 2,3-pyridinecarboxylic anhydride (11.4 g, 76 mmol) and trimethylsilyl azide (11.0 mL, 80 mmol) according to the procedure described in Synthesis, 1982, 972-973 as a white solid (7.27 g, 58%). $^1$H NMR (300 MHz, DMSO-$d_6$) δ 7.31 (dd, J=7.72, 4.78 Hz, 1H), 8.31 (dd, J=7.72, 1.84 Hz, 1H), 8.66 (dd, J=4.78, 1.84 Hz, 1H), 12.27 (s, 1H).

EXAMPLE 1B

1-butyl-2H-pyrido[2,3-d][1,3]oxazine-2,4(1H)-dione

A suspension of sodium hydride (95%, 0.96 g, 40 mmol) in dimethylacetamide (60 mL) at 10° C. under nitrogen was reacted with the product of Example 1A (5.7 g, 34.7 mmol) with stirring for 1 hour then treated with n-butylbromide (5.2 g, 38 mmol) and stirred for an additional 16 hours. The reaction was partitioned between ethyl acetate and water. The organic layer was washed with water and brine, dried over sodium sulfate, filtered and concentrated under vacuum. The crude product was purified by flash column chromatography with silica gel eluting with hexane and ethyl acetate (3:1) to give the title compound as a white solid, (2.5 g, 33% yield). $^1$H NMR (300 MHz, DMSO-$d_6$) δ 0.92 (t, J=7.35 Hz, 3H), 1.36 (m, 2H), 1.65 (m, 2H), 4.13 (m, 2H), 7.38 (dd, J=7.72, 4.78 Hz, 1H), 8.39 (dd, J=7.72, 1.84 Hz, 1H), 8.77 (dd, J=5.15, 1.84 Hz, 1H).

EXAMPLE 1C ethyl (1,1-dioxido-4H-1,2,4-benzothiadiazin-3-yl)acetate

The title compound was prepared as a white solid in two steps (46% yield) from 2-aminobenzenesulfonamide according to the procedure described in *Chemistry of Heterocyclic Compounds* (English Translation), 1998, 34(7), 791-795. $^1$H NMR (300 MHz, DMSO-$d_6$) δ 1.21 (t, J=7.17 Hz, 3H), 4.16 (q, J=7.23 Hz, 2H), 7.32 (d, J=7.35 Hz, 1H), 7.47 (m, 1H), 7.69 (m, 1H), 7.82 (dd, J=7.91, 1.29 Hz, 1H), 12.27 (s, 1H).

EXAMPLE 1D

1-butyl-3-(1,1-dioxido-4H-1,2,4-benzothiadiazin-3-yl)-4-hydroxy-1,8-naphthyridin-2(1H)-one To a solution of the product of Example 1B (0.220 g, 1.0 mmol) and the product of EXAMPLE 1C (0.268 g, 1.0 mmol) in anhydrous THF (10 mL) under nitrogen at 0° C. was added sodium hydride (95%, 0.10 g, 4.0 mmol). The reaction was heated to reflux for 3 hours, cooled to 0° C., and to it was added dropwise glacial acetic acid (2 mL). The resulting mixture was heated to reflux for 2 hours, cooled to ambient temperature, and diluted with aqueous hydrochloric acid (0.1 M, 10 mL). The resulting precipitate was collected by filtration, washed with water and diethyl ether and dried to give the title compound (0.130 g, 33%). MS (ESI−) m/z 397 (M−H)−.

A stirred suspension of the title compound (0.130 g, 0.326 mmol) in acetonitrile and water (1:1, 4 mL) was reacted with aqueous sodium hydroxide (1 M, 0.326 mL, 0.326 mmol), for approximately 30 minutes when a clear solution was observed. The solution was lyophilized to give the sodium salt. $^1$H NMR (300 MHz, DMSO-$d_6$) δ 0.92 (t, J=7.35 Hz, 3H), 1.35 (m, 2H), 1.58 (m, 2H), 4.28 (t, J=7.35 Hz, 2H), 7.13 (dd, J=7.72, 4.78 Hz, 1H), 7.28 (m, 2H), 7.55 (m, 1H), 7.66 (dd, J=7.72, 1.47 Hz, 1H), 8.37 (dd, J=7.72, 1.84 Hz, 1H), 8.53 (dd, J=4.60, 2.02 Hz, 1H), 15.92 (s, 1H).

EXAMPLE 2

1-[(5-chloro-2-thienyl)methyl]-3-(1,1-dioxido-4H-1,2,4-benzothiadiazin-3-yl)-4-hydroxy-1,8-naphthyridin-2(1H)-one

EXMAPLE 2A

1-[(5-chloro-2-thienyl)methyl]-2H-pyrido[2,3-d][1,3]oxazine-2,4(1H)-dione

The title compound was prepared according to the procedure of Example 1B substituting 2-chloro-5-chloromethylthiophene for n-butyl bromide (0.195 g, 52%). $^1$H NMR (300 MHz, DMSO-$d_6$) δ 5.38 (s, 2H), 6.98 (d, J=4.04 Hz, 1H), 7.08 (d, J=3.68 Hz, 1H), 7.43 (dd, J=7.72, 4.78 Hz, 1H), 8.41 (dd, J=7.72, 1.84 Hz, 1H), 8.83 (dd, J=4.78, 1.84 Hz, 1H).

EXMAPLE 2B

1-[(5-chloro-2-thienyl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 2A for the product of Example 1B (0.167 g, 58%). MS (ESI−) m/z 471/473 (M−H)−.

The sodium salt of the title compound was prepared according to the procedure of EXAMPLE 1D. $^1$H NMR (300 MHz, DMSO-$d_6$) δ 5.53 (s, 2H), 6.89 (d, J=3.68 Hz, 1H), 7.00 (d, J=3.68 Hz, 1H), 7.20 (dd, J=7.72, 4.78 Hz, 1H), 7.29 (m, 2H), 7.56 (t, J=7.72 Hz, 1H), 7.67 (d, J=7.72 Hz, 1H), 8.40 (dd, J=7.72, 1.84 Hz, 1H), 8.58 (dd, J=4.78, 1.84 Hz, 1H), 15.73 (s, 1H).

EXAMPLE 3

3-(1,1-dioxido-4H-1,2,4-benzothiadiazin-3-yl)-1-(2-ethylbutyl)-4-hydroxy-1,8-naphthyridin-2(1H)-one

EXAMPLE 3A ethyl 2-[(2-ethylbutyl)amino]nicotinate

Ethyl 2-chloronicotinate (0.646 g, 3.48 mmol) and 2-ethylbutylamine (0.74 g, 7.31 mmol) were reacted in a sealed tube at 130° C. for 2 hours. The reaction mixture was partitioned between dichloromethane and water. The aqueous layer was extracted with dichloromethane (2×50 mL). The organic layers were combined and dried over magnesium sulfate, filtered, and concentrated. The residue was purified by column chromatography on silica gel eluting with hexane/ethyl acetate (19:1) to provide the title compound (0.665 g, 76%). MS (ESI+) m/z 251.1 (M+H)+; $^1$H NMR (300 MHz, CDCl$_3$) δ 0.93 (t, J=7.54 Hz, 6H), 1.41 (m, 7H), 1.55 (m, 1H), 3.46 (m, 2H), 4.32 (q, J=6.99 Hz, 2H), 6.48 (dd, J=7.72, 4.78 Hz, 1H), 7.99 (s, 1H), 8.11 (dd, J=7.72, 2.21 Hz, 1H), 8.27 (dd, J=4.78, 1.84 Hz, 1H).

EXAMPLE 3B

1-(2-ethylbutyl)-2H-pyrido[2,3-d][1,3]oxazine-2,4(1H)-dione

The product of Example 3A (0.664 g, 2.65 mmol) and diphosgene (1.57 g, 7.96 mmol) in 13 mL of 1,2-dichloroethane and 1.3 mL of 1,4 dioxane were reacted at 80° C. for 16 hours. The reaction was concentrated under vacuum and the residue was purified by flash column chromatography on silica gel eluting with hexane/ethyl acetate (9:1) to provide the title compound (0.235 g, 36%). $^1$H NMR (300 MHz, CDCl$_3$) δ 0.95 (m, 6H), 1.40 (m, 4H), 1.52 (m, 2H), 4.21 (m, 1H), 7.25 (m, 1H), 8.41 (dd, J=7.72, 1.84 Hz, 1H), 8.70 (dd, J=4.78, 1.84 Hz, 1H).

EXAMPLE 3C 3-(1,1-dioxido-4H-1,2,4-benzothiadiazin-3-yl)-1-(2-ethylbutyl)-4-hydroxy-1,8-naphthyridin-2(1H)-one The title compound was prepared according to the procedure of Example 1D substituting the product of Example 3B for the product of Example 1B (0.041 g, 38%). MS (ESI+) m/z 427.1 (M+H)$^+$, (ESI−) m/z 425.1 (M−H)$^-$; $^1$H NMR (300 MHz, DMSO-d$_6$) δ 0.87 (t, J=7.54 Hz, 6H), 1.30 (m, 4H), 1.99 (m, 1H), 4.44 (d, J=7.35 Hz, 2H), 7.49 (dd, J=7.72, 4.78 Hz, 1H), 7.55 (t, J=7.35 Hz, 1H), 7.68 (d, J=8.09 Hz, 1H), 7.77 (t, J=7.17 Hz, 1H), 7.92 (d, J=8.09 Hz, 1H), 8.57 (dd, J=7.72, 1.84 Hz, 1H), 8.86 (d, J=4.78 Hz, 1H). The sodium salt of the title compound was prepared according to the procedure of Example 1D. MS (ESI+) m/z 427.1 (M+H)$^+$, (ESI−) m/z 425.1 (M−H)$^-$; $^1$H NMR (300 MHz, DMSO-d$_6$) δ 0.86 (t, J=7.35 Hz, 6H), 1.28 (m, 4H), 1.91 (m, 1H), 4.25 (d, J=7.35 Hz, 2H), 7.12 (dd, J=7.72, 4.78 Hz, 1H), 7.28 (m, 2H), 7.55 (m, 1H), 7.67 (dd, J=8.09, 1.47 Hz, 1H), 8.37 (dd, J=7.72, 1.84 Hz, 1H), 8.50 (dd, J=4.60, 2.02 Hz, 1H), 15.97 (s, 1H).

EXAMPLE 4

1-[(5-bromo-2-thienyl)methyl]-3-(1,1-dioxido-4H-1,2,4-benzothiadiazin-3-yl)-4-hydroxy-1,8-naphthyridin-2(1H)-one

EXAMPLE 4A

1-[(5-bromo-2-thienyl)methyl]-2H-pyrido[2,3-d][1,3]oxazine-2,4(1H)-dione

The title compound was prepared according to the procedure of Example 1B substituting 2-bromo-5-chloromethylthiophene for n-butyl bromide (0.229 g, 55%). $^1$H NMR (300 MHz, DMSO-d$_6$) δ 5.40 (s, 2H), 7.06 (m, 2H), 7.43 (dd, J=7.72, 4.78 Hz, 1H), 8.41 (dd, J=7.72, 1.84 Hz, 1H), 8.83 (dd, J=4.78, 1.84 Hz, 1H).

EXAMPLE 4B

1-[(5-bromo-2-thienyl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 4A for the product of Example 1B (0.208 g, 60%). MS (ESI−) m/z 515/517 (M−H)$^-$. The sodium salt of the title compound was prepared according to the procedure of Example 1D. $^1$H NMR (300 MHz, DMSO-d$_6$) δ 5.55 (s, 2H), 6.97 (d, J=3.68 Hz, 1H), 7.00 (d, J=3.68 Hz, 1H), 7.20 (dd, J=7.73, 4.78 Hz, 1H), 7.29 (m, 2H), 7.56 (m, 1H), 7.68 (d, J=7.72 Hz, 1H), 8.40 (dd, J=7.72, 2.21 Hz, 1H), 8.58 (dd, J=4.78, 2.20 Hz, 1H), 15.73 (s, 1H).

EXAMPLE 5

3-(1,1-dioxido-4H-1,2,4-benzothiadiazin-3-yl)-4-hydroxy-1-(3-methylbenzyl)-1,8-naphthyridin-2(1H)-one

EXAMPLE 5A 1-(3-methylbenzyl)-2H-pyrido[2,3-d][1,3]oxazine-2,4(1H)-dione

The title compound was prepared according to the procedure of Example 1B substituting 3-methylbenzyl bromide for n-butyl bromide (0.305 g, 62%). MS (DCI) m/z 269 (M+H)$^+$.

EXAMPLE 5B 3-(1,1-dioxido-4H-1,2,4-benzothiadiazin-3-yl)-4-hydroxy-1-(3-methylbenzyl)-1,8-naphthyridin-2(1H)-one The title compound was prepared according to the procedure of Example 1D substituting the product of Example 5A for the product of Example 1B (0.112 g, 72%). MS (ESI−) m/z 445 (M−H)$^-$. The sodium salt of the title compound was prepared according to the procedure of Example 1D. $^1$H NMR (300 MHz, DMSO-d$_6$) δ 2.23 (s, 3H), 5.48 (s, 2H), 7.01 (m, 3H), 7.14 (t, J=7.35 Hz, 2H), 7.28 (m, 2H), 7.56 (td, J=7.72, 1.47 Hz, 1H), 7.67 (dd, J=7.72, 1.47 Hz, 1H), 8.41 (dd, J=7.72, 1.84 Hz, 1H), 8.48 (dd, J=4.78, 1.84 Hz, 1H), 15.86 (s, 1H).

EXAMPLE 6

3-(1,1-dioxido-4H-1,2,4-benzothiadiazin-3-yl)-4-hydroxy-1-(3-nitrobenzyl)-1,8-naphthyridin-2(1H)-one

EXAMPLE 6A 1-(3-nitrobenzyl)-2H-pyrido[2,3-d][1,3]oxazine-2,4(1H)-dione

The title compound was prepared according to the procedure of Example 1B substituting 3-nitrobenzyl bromide for n-butyl bromide (0.147 g, 28%). MS (DCI) m/z 300 (M+H)$^+$.

EXAMPLE 6B 3-(1,1-dioxido-4H-1,2,4-benzothiadiazin-3-yl)-4-hydroxy-1-(3-nitrobenzyl)-1,8-naphthyridin-2(1H)-one The title compound was prepared according to the procedure of Example 1D substituting the product of Example 6A for the product of Example 1B (0.032 g, 42%). MS (ESI−) m/z 476 (M−H)$^-$. The sodium salt of the title compound was prepared according to the procedure of Example 1D. $^1$H NMR (300 MHz, DMSO-d$_6$) δ 5.62 (s, 2H), 7.19 (dd, J=7.72, 4.78 Hz, 1H), 7.29 (td, J=8.36, 1.29 Hz, 2H), 7.56 (t, J=8.46 Hz, 1H), 7.58 (t, J=7.72 Hz, 1H), 7.67 (d, J=8.09 Hz, 1H), 7.74 (d, J=8.09 Hz, 1H), 8.08 (m, 2H), 8.43 (dd, J=7.54, 2.02 Hz, 1H), 8.50 (dd, J=4.60, 2.02 Hz, 1H), 15.76 (s, 1H).

EXAMPLE 7

3-(1,1-dioxido-4H-1,2,4-benzothiadiazin-3-yl)-4-hydroxy-1-(3-thienylmethyl)-1,8-naphthyridin-2(1H)-one

EXAMPLE 7A 1-(3-thienylmethyl)-2H-pyrido[2,3-d][1,3]oxazine-2,4(1H)-dione

The title compound was prepared according to the procedure of Example 1B substituting 3-(bromomethyl)thiophene for n-butyl bromide (0.170 g, 52%). $^1$H NMR (300 MHz, DMSO-$d_6$) δ 5.32 (s, 2H), 7.15 (m, 1H), 7.40 (dd, J=7.72, 4.78 Hz, 1H), 7.48 (m, 2H), 8.41 (dd, J=7.72, 1.84 Hz, 1H), 8.76 (dd, J=4.78, 1.84 Hz, 1H).

EXAMPLE 7B 3-(1,1-dioxido-4H-1,2,4-benzothiadiazin-3-yl)-4-hydroxy-1-(3-thienylmethyl)-1,8-naphthyridin-2(1H)-one The title compound was prepared according to the procedure of Example 1D substituting the product of Example 7A for the product of Example 1B (0.135 g, 48%). MS (ESI−) m/z 437 (M−H)$^-$. The sodium salt of the title compound was prepared according to the procedure of Example 1D. $^1$H NMR (300 MHz, DMSO-$d_6$) δ 5.48 (s, 2H), 7.09 (d, J=4.04 Hz, 1H), 7.16 (dd, J=7.72, 4.78 Hz, 1H), 7.27 (m, 3H), 7.38 (dd, J=4.96, 3.13 Hz, 1H), 7.56 (t, J=7.72 Hz, 1H), 7.67 (d, J=8.09 Hz, 1H), 8.39 (dd, J=7.72, 1.66 Hz, 1H), 8.53 (dd, J=4.78, 1.66 Hz, 1H), 15.85 (s, 1H).

EXAMPLE 8

1-(3-chlorobenzyl)-3-(1,1-dioxido-4H-1,2,4-benzothiadiazin-3-yl)-4-hydroxy-1,8-naphthyridin-2(1H)-one

EXAMPLE 8A 1-(3-chlorobenzyl)-2H-pyrido[2,3-d][1,3]oxazine-2,4(1H)-dione

The title compound was prepared according to the procedure of Example 1B substituting 3-chlorobenzyl bromide for n-butyl bromide (0.405 g, 77%). MS (DCI) m/z 289 (M+H)$^+$.

EXAMPLE 8B 1-(3-chlorobenzyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 8A for the product of Example 1B (0.050 g, 45%). MS (ESI−) m/z 465 (M−H)$^-$. The sodium salt of the title compound was prepared according to the procedure of Example 1D. $^1$H NMR (300 MHz, DMSO-$d_6$) δ 5.50 (s, 2H), 7.18 (dd, J=7.72, 4.78 Hz, 1H), 7.27 (m, 6H), 7.56 (td, J=7.91, 1.47 Hz, 1H), 7.67 (d, J=7.72 Hz, 1H), 8.42 (dd, J=7.72, 1.84 Hz, 1H), 8.49 (dd, J=4.78, 2.21 Hz, 1H), 15.78 (s, 1H).

EXAMPLE 9

1-(3-bromobenzyl)-3-(1,1-dioxido-4H-1,2,4-benzothiadiazin-3-yl)-4-hydroxy-1,8-naphthyridin-2(1H)-one

EXAMPLE 9A 1-(3-bromobenzyl)-2H-pyrido[2,3-d][1,3]oxazine-2,4(1H)-dione

The title compound was prepared according to the procedure of Example 1B substituting 3-bromobenzyl bromide for n-butyl bromide (0.500 g, 82%). MS (DCI) m/z 333 (M+H)$^+$.

EXAMPLE 9B 1-(3-bromobenzyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 9A for the product of Example 1B (0.050 g, 45%). MS (ESI−) m/z 465 (M−H)$^-$. The sodium salt of the title compound was prepared according to the procedure of Example 1D. $^1$H NMR (300 MHz, DMSO-$d_6$) δ 5.50 (s, 2H), 7.18 (dd, J=7.72, 4.78 Hz, 1H), 7.27 (m, 6H), 7.56 (td, J=7.91, 1.47 Hz, 1H), 7.67 (d, J=7.72 Hz, 1H), 8.42 (dd, J=7.72, 1.84 Hz, 1H), 8.49 (dd, J=4.78, 2.21 Hz, 1H), 15.78 (s, 1H).

EXAMPLE 10

1-[(2-chloro-1,3-thiazol-5-yl)methyl]-3-(1,1-dioxido-4H-1,2,4-benzothiadiazin-3-yl)-4-hydroxy-1,8-naphthyridin-2(1H)-one

EXAMPLE 10A

1-[(2-chloro-1,3-thiazol-5-yl)methyl]-2H-pyrido[2,3-d][1,3]oxazine-2,4(1H)-dione The title compound was prepared according to the procedure of Example 1B substituting 2-chloro-5-bromomethylthiazole for n-butyl bromide (0.360 g, 60%). MS (APCI) m/z 296 (M+H)$^+$; $^1$H NMR (300 MHz, DMSO-$d_6$) δ 5.45 (s, 2H), 7.44 (dd, J=7.72, 4.78 Hz, 1H), 7.76 (s, 1H), 8.42 (dd, J=7.91, 1.65 Hz, 1H), 8.82 (dd, J=4.78, 1.84 Hz, 1H).

EXAMPLE 10B

1-[(2-chloro-1,3-thiazol-5-yl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 10A for the product of Example 1B (0.136 g, 60%). MS (ESI−) m/z 477 (M−H)$^-$; $^1$H NMR (300 MHz, DMSO-$d_6$) δ 5.76 (s, 2H), 7.56 (m, 2H), 7.65 (d, J=7.35 Hz, 1H), 7.77 (s, 1H), 7.78 (m, 1H), 7.92 (d, J=8.09 Hz, 1H), 8.59 (dd, J=8.09, 1.84 Hz, 1H), 8.92 (dd, J=4.78, 1.84 Hz, 1H), 13.72 (s, 1H).

EXAMPLE 11

3-(1,1-dioxido-4H-1,2,4-benzothiadiazin-3-yl)-1-(3-fluorobenzyl)-4-hydroxy-1,8-naphthyridin-2(1H)-one

EXAMPLE 11A 1-(3-fluorobenzyl)-2H-pyrido[2,3-d][1,3]oxazine-2,4(1H)-dione

The title compound was prepared according to the procedure of Example 1B substituting 3-fluorobenzyl bromide for n-butyl bromide (0.382 g, 76%). MS (DCI) m/z 273 (M+H)$^+$.

EXAMPLE 11B 3-(1,1-dioxido-4H-1,2,4-benzothiadiazin-3-yl)-1-(3-fluorobenzyl)-4-hydroxy-1,8-naphthyridin-2(1H)-one The title compound was prepared according to the procedure of Example 1D substituting the product of Example 11A for the product of Example 1B (0.040 g, 37%). MS (ESI−) m/z 449 (M−H)$^-$. The sodium salt of the title compound was prepared according to the procedure of Example 1D. $^1$H NMR (300 MHz, DMSO-d$_6$) δ 5.52 (s, 2H), 7.02 (m, 2H), 7.08 (d, J=7.72 Hz, 1H), 7.17 (dd, J=7.72, 4.41 Hz, 1H), 7.29 (m, 3H), 7.56 (td, J=7.91, 1.47 Hz, 1H), 7.67 (d, J=8.09 Hz, 1H), 8.41 (dd, J=7.72, 1.84 Hz, 1H), 8.49 (dd, J=4.78, 1.84 Hz, 1H), 15.79 (s, 1H).

EXAMPLE 12

3-(1,1-dioxido-4H-1,2,4-benzothiadiazin-3-yl)-4-hydroxy-1-(3-methylbutyl)-1,8-naphthyridin-2(1H)-one

EXAMPLE 12A 1-(3-methylbutyl)-2H-pyrido[2,3-d][1,3]oxazine-2,4(1H)-dione

A suspension of sodium hydride (95%, 0.048 g, 2.0 mmol) in dimethylacetamide (2 mL) at 20° C. under nitrogen was reacted with the product of Example 1A (0.3 g, 1.83 mmol). The reaction mixture was stirred for ½ hour then treated with 1-bromo-3-methylbutane (0.3 g, 2.0 mmol) and stirred for an additional 16 hours. The reaction was partitioned between ethyl acetate and water. The organic layer was washed with water and brine, dried over sodium sulfate, filtered and concentrated under vacuum. The crude product was purified by flash column chromatography on silica gel eluting with hexanes and ethyl acetate (3:1) to give the title compound as a white solid (0.218 g, 51%). MS (ESI−) m/z 233 (M−H)$^-$. $^1$H NMR (300 MHz, DMSO-d$_6$) δ 0.93 (s, 3H), 0.96 (s, 3H), 1.55 (m, 2H), 1.66 (m, 1H), 4.14 (t, J=7.72 Hz, 2H), 7.37 (dd, J=7.91, 4.96 Hz, 1H), 8.38 (dd, J=7.72, 1.84 Hz, 1H), 8.78 (dd, J=4.78, 1.84 Hz, 1H).

EXAMPLE 12B 3-(1,1-dioxido-4H-1,2,4-benzothiadiazin-3-yl)-4-hydroxy-1-(3-methylbutyl)-1,8-naphthyridin-2(1H)-one To a solution of the product of Example 12A (0.216 g, 0.92 mmol) and the product of Example 1C (0.247 g, 0.922 mmol) in anhydrous THF (7.5 mL) under nitrogen at 20° C. was added sodium hydride (95%, 0.089 g, 3.7 mmol). The reaction was heated at reflux for 3 hours, cooled to 20° C., and added dropwise glacial acetic acid (2.4 mL). The resulting mixture was heated at reflux for 1 hour, cooled to 25° C., and diluted with aqueous hydrochloric acid (0.5 M, 35 mL). The resulting precipitate was collected by filtration, washed with water and dried. The crude product was purified by flash column chromatography on silica gel eluting with hexanes and ethyl acetate (3:1) to give the title compound as a white solid (0.031 g, 20%). MS (ESI−) m/z 411 (M−H)$^-$. The sodium salt of the title compound was prepared according to the procedure of Example 1D. MS (ESI−) m/z 411 (M−H)$^-$. $^1$H NMR (300 MHz, DMSO-d$_6$) δ 0.95 (s, 3H), 0.98 (s, 3H), 1.47 (m, 2H), 1.64 (m, 1H), 4.30 (t, J=7.72 Hz, 2H), 7.13 (dd, J=7.72, 4.78 Hz, 1H), 7.26 (d, J=8.09 Hz, 1H), 7.30 (d, J=7.72 Hz, 1H), 7.55 (t, J=7.72 Hz, 1H), 7.66 (d, J=8.09 Hz, 1H), 8.37 (dd, J=7.72, 1.84 Hz, 1H), 8.53 (dd, J=4.78, 2.21 Hz, 1H), 15.94 (s, 1H).

EXAMPLE 13

1-(cyclobutylmethyl)-3-(1,1-dioxido-4H-1,2,4-benzothiadiazin-3-yl)-4-hydroxy-1,8-naphthyridin-2(1H)-one

EXAMPLE 13A 1-(cyclobutylmethyl)-2H-pyrido[2,3-d][1,3]oxazine-2,4(1H)-dione

The title compound was prepared according to the procedure of Example 1B substituting bromomethyl-cyclobutane for n-butyl bromide (0.255 g, 60%). MS (DCI) m/z 233 (M+H)$^+$.

EXAMPLE 13B 1-(cyclobutylmethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 13A for the product of Example 1B (0.120 g, 52%). MS (ESI−) m/z 409 (M−H)$^-$. The sodium salt of the title compound was prepared according to the procedure of Example 1D. $^1$H NMR (300 MHz, DMSO-d$_6$) δ 1.83 (m, 6H), 2.79 (m, 1H), 4.38 (d, J=6.99 Hz, 2H), 7.13 (dd, J=7.72, 4.78 Hz, 1H), 7.29 (t, J=7.54 Hz, 2H), 7.55 (t, J=7.72 Hz, 1H), 7.67 (d, J=7.72 Hz, 1H), 8.36 (dd, J=7.72, 2.21 Hz, 1H), 8.51 (dd, J=4.78, 1.84 Hz, 1H), 15.92 (s, 1H).

EXAMPLE 14

3-(1,1-dioxido-4H-1,2,4-benzothiadiazin-3-yl)-4-hydroxy-1-[(5-methyl-2-thienyl)methyl]-1,8-naphthyridin-2(1H)-one

EXAMPLE 14A

1-[(5-methyl-2-thienyl)methyl]-2H-pyrido[2,3-d][1,3]oxazine-2,4(1H)-dione

The title compound was prepared according to the procedure of Example 1B substituting 2-bromomethyl-5-methylthiophene for n-butyl bromide (0.181 g, 54%). $^1$H NMR (300 MHz, DMSO-$d_6$) δ 2.36 (s, 3H), 5.38 (s, 2H), 6.63 (m, 1H), 6.98 (d, J=3.68 Hz, 1H), 7.42 (dd, J=7.72, 4.78 Hz, 1H), 8.41 (dd, J=7.72, 1.84 Hz, 1H), 8.82 (dd, J=4.78, 1.84 Hz, 1H).

EXAMPLE 14B 3-(1,1-dioxido-4H-1,2,4-benzothiadiazin-3-yl)-4-hydroxy-1-[(5-methyl-2-thienyl)methyl]-1,8-naphthyridin-2(1H)-one The title compound was prepared according to the procedure of Example 1D substituting the product of Example 14A for the product of Example 1B (0.172 g, 58%). MS (ESI−) m/z 451 (M−H)⁻. The sodium salt of the title compound was prepared according to the procedure of Example 1D. ¹H NMR (300 MHz, DMSO-$d_6$) δ 2.32 (s, 3H), 5.54 (s, 2H), 6.56 (d, 1H), 6.88 (d, J=3.31 Hz, 1H), 7.17 (dd, J=7.72, 4.78 Hz, 1H), 7.28 (m, 2H), 7.56 (t, J=7.72 Hz, 1H), 7.67 (d, J=7.72 Hz, 1H), 8.38 (dd, J=7.72, 1.84 Hz, 1H), 8.56 (dd, J=4.78, 1.84 Hz, 1H), 15.81 (s, 1H).

EXAMPLE 15

1-benzyl-3-(1,1-dioxido-4H-1,2,4-benzothiadiazin-3-yl)-4-hydroxy-1,8-naphthyridin-2(1H)-one

EXAMPLE 15A 1-benzyl-2H-pyrido[2,3-d][1,3]oxazine-2,4(1H)-dione

The title compound was prepared according to the procedure of Example 1B substituting benzyl bromide for n-butyl bromide (0.393 g, 51%). MS (DCI) m/z 255 (M+H)⁺.

EXAMPLE 15B 1-benzyl-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 15A for the product of Example 1B (0.217 g, 62%). MS (ESI−) m/z 431 (M−H)⁻. The sodium salt of the title compound was prepared according to the procedure of Example 1D. ¹H NMR (300 MHz, DMSO-$d_6$) δ 5.52 (s, 2H), 7.16 (m, 2H), 7.25 (d, J=4.41 Hz, 4H), 7.29 (m, 2H), 7.56 (td, J=7.91, 1.47 Hz, 1H), 7.67 (dd, J=7.91, 1.65 Hz, 1H), 8.41 (dd, J=7.54, 2.02 Hz, 1H), 8.48 (dd, J=4.78, 2.21 Hz, 1H), 15.84 (s, 1H).

EXAMPLE 16

3-(1,1-dioxido-4H-1,2,4-benzothiadiazin-3-yl)-4-hydroxy-1-[(5-methyl-3-pyridinyl)methyl]-1,8-naphthyridin-2(1H)-one

EXAMPLE 16A

1-[(5-methyl-3-pyridinyl)methyl]-2H-pyrido[2,3-d][1,3]oxazine-2,4(1H)-dione

The title compound was prepared according to the procedure of Example 1B substituting 3-chloromethyl-5-methylpyridine for n-butyl bromide (0.080 g, 24%). ¹H NMR (300 MHz, DMSO-$d_6$) δ 2.25 (s, 3H), 5.34 (s, 2H), 7.40 (dd, J=7.72, 4.78 Hz, 1H), 7.63 (br s, 1H), 8.30 (br s, 1H), 8.43 (dd, J=7.72, 1.84 Hz, 1H), 8.46 (br s, 1H), 8.73 (dd, J=4.78, 1.84 Hz, 1H).

EXAMPLE 16B 3-(1,1-dioxido-4H-1,2,4-benzothiadiazin-3-yl)-4-hydroxy-1-[(5-methyl-3-pyridinyl)methyl]-1,8-naphthyridin-2(1H)-one The title compound was prepared according to the procedure of Example 1D substituting the product of Example 16A for the product of Example 1B (0.013 g, 13%). MS (ESI−) m/z 446 (M−H)⁻. The sodium salt of the title compound was prepared according to the procedure of Example 1D. ¹H NMR (300 MHz, DMSO-$d_6$) δ 2.22 (s, 3H), 5.49 (s, 2H), 7.18 (dd, J=7.72, 4.78 Hz, 1H), 7.29 (m, 2H), 7.44 (s, 1H), 7.56 (m, 1H), 7.67 (d, J=8.09 Hz, 1H), 8.23 (d, J=1.47 Hz, 1H), 8.36 (d, J=1.47 Hz, 1H), 8.41 (dd, J=7.72, 1.84 Hz, 1H), 8.51 (dd, J=4.78, 1.84 Hz, 1H), 15.80 (s, 1H).

EXAMPLE 17

1-[(2-chloro-4-pyridinyl)methyl]-3-(1,1-dioxido-4H-1,2,4-benzothiadiazin-3-yl)-4-hydroxy-1,8-naphthyridin-2(1H)-one

EXAMPLE 17A

1-[(2-chloro-4-pyridinyl)methyl]-2H-pyrido[2,3-d][1,3]oxazine-2,4(1H)-dione

The title compound was prepared according to the procedure of Example 1B substituting 4-bromomethyl-2-chloropyridine for n-butyl bromide (0.219 g, 62%). ¹H NMR (300 MHz, DMSO-$d_6$) δ 5.37 (s, 2H), 7.40 (m, 1H), 7.48 (s, 1H), 7.60 (s, 1H), 8.34 (dd, J=4.60, 2.39 Hz, 1H), 8.45 (m, 1H), 8.68 (m, 1H).

EXAMPLE 17B

1-[(2-chloro-4-pyridinyl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 17A for the product of Example 1B (0.255 g, 73%). MS (ESI−) m/z 466/468 (M−H)⁻. The sodium salt of the title compound was prepared according to the procedure of Example 1D. ¹H NMR (300 MHz, DMSO-$d_6$) δ 5.52 (s, 2H), 7.19 (m, 2H), 7.30 (m, 3H), 7.56 (t, J=7.54 Hz, 1H), 7.67 (d, J=7.72 Hz, 1H), 8.27 (d, J=5.15 Hz, 1H), 8.46 (m, 2H), 15.72 (s, 1H).

EXAMPLE 18

1-[(5-bromo-3-pyridinyl)methyl]-3-(1,1-dioxido-4H-1,2,4-benzothiadiazin-3-yl)-4-hydroxy-1,8-naphthyridin-2(1H)-one

EXAMPLE 18A di-tert-butyl (5-bromo-3-pyridinyl)methylimidodicarbonate

A solution of 5-bromo-3-chloromethylpyridinium hydrochloride (716 mg, 4.189 mmol) in anhydrous DMF (15 mL)

under nitrogen at 0° C. was treated with triethylamine (0.65 mL, 4.61 mmol), tetrabutylammonium bromide (273 mg, 0.838 mmol), and potassium di-tert-butyl imidodicarbonate (1.284 g, 5.027 mmol). The reaction was heated to 50° C.-55° C. for 3.5 hours, then cooled to room temperature, diluted with ethyl acetate (150 mL), and washed with water (2×50 mL) and saturated aqueous sodium chloride. The combined extracts were dried over anhydrous $Na_2SO_4$, filtered, and concentrated by rotary evaporation. The residue was purified by flash column chromatography on silica gel with 6% ethyl acetate/dichloromethane to give the title compound as a colorless oil (0.980 g, 60%). MS (ESI+) m/z 387/389 (M+H)$^+$; $^1$H NMR (300 MHz, CDCl$_3$) δ 1.49 (s, 18H), 4.75 (s, 2H), 7.83 (t, J=2.02 Hz, 1H), 8.50 (d, J=1.84 Hz, 1H), 8.58 (d, J=2.21 Hz, 1H).

EXAMPLE 18B (5-bromo-3-pyridinyl)methylamine

The product of Example 18A (0.98 g, 2.53 mmol) was treated with trifluoroacetic acid and dichloromethane (1:1 v/v, 20 mL) for 2 hours at room temperature. The solvent was removed by rotary evaporation and the resulting oil was chased with benzene/dichloromethane (3 times) to give a waxy solid. The salt was dissolved in anhydrous methanol (20 mL) and stirred with Amberlite IRA-400(OH), resin (10 g) for 2 hrs. The resin was removed by vacuum filtration and thoroughly washed with dry methanol. The filtrate was concentrated by rotary evaporation to give the title compound (0.415 g, 88%). MS (DCI/NH$_3$) M/z 187/189 (M+H)$^+$; $^1$H NMR (300 MHz, DMSO-d$_6$) δ 3.73 (s, 2H), 8.02 (t, J=2.02 Hz, 1H), 8.50 (d, J=1.47 Hz, 1H), 8.53 (d, J=2.21 Hz, 1H).

EXAMPLE 18C ethyl 2-{[(5-bromo-3-pyridinyl)methyl]amino}nicotinate

The title compound was prepared according to the procedure of Example 3A substituting the product of Example 18B for 2-ethylbutylamine (0.116 g, 68%). MS (DCI/NH$_3$) m/z 336/338 (M+H)$^+$; $^1$H NMR (300 MHz, DMSO-d$_6$) δ 1.32 (t, J=6.99 Hz, 3H), 4.31 (q, J=7.23 Hz, 2H), 4.71 (d, J=5.88 Hz, 2H), 6.67 (dd, J=7.72, 4.78 Hz, 1H), 7.97 (t, J=2.02 Hz, 1H), 8.12 (dd, J=7.72, 2.21 Hz, 1H), 8.26 (dd, J=4.78, 1.84 Hz, 1H), 8.45 (t, J=6.07 Hz, 1H), 8.55 (m, 2H).

EXAMPLE 18D

1-[(5-bromo-3-pyridinyl)methyl]-2H-pyrido[2,3-d][1,3]oxazine-2,4(1H)-dione

The title compound was prepared according to the procedure of Example 3B substituting the product of Example 18C for the product of Example 3A and purifying by flash column chromatography on silica gel eluting with 10% ethyl acetate/dichloromethane (0.057 g, 51%). $^1$H NMR (300 MHz, DMSO-d$_6$) δ 5.38 (s, 2H), 7.41 (dd, J=7.72, 5.15 Hz, 1H), 8.10 (t, J=2.02 Hz, 1H), 8.43 (dd, J=7.72, 1.84 Hz, 1H), 8.60 (d, J=2.21 Hz, 1H), 8.66 (d, J=1.84 Hz, 1H), 8.72 (dd, J=5.15, 1.84 Hz, 1H).

EXAMPLE 18E

1-[(5-bromo-3-pyridinyl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 18D for the product of Example 1B (0.037 g, 43%). MS (ESI−) m/z 510/512 (M−H)$^-$. The sodium salt of the title compound was prepared according to the procedure of Example 1D. $^1$H NMR (300 MHz, DMSO-d$_6$) δ 5.52 (s, 2H), 7.20 (dd, J=7.72, 4.78 Hz, 1H), 7.29 (m, 2H), 7.56 (t, J=7.54 Hz, 1H), 7.68 (d, J=7.35 Hz, 1H), 7.89 (br s, 1H), 8.42 (dd, J=7.72, 1.84 Hz, 1H), 8.52 (dd, J=4.78, 1.84 Hz, 1H), 8.55 (br s, 2H), 15.73 (s, 1H).

EXAMPLE 19

1-(cyclohexylmethyl)-3-(1,1-dioxido-4H-1,2,4-benzothiadiazin-3-yl)-4-hydroxy-1,8-naphthyridin-2(1H)-one

EXAMPLE 19A 1-(cyclohexylmethyl)-2H-pyrido[2,3-d][1,3]oxazine-2,4(1H)-dione

The title compound was prepared according to the procedure of Example 1B substituting (bromomethyl)cyclohexane for n-butyl bromide (0.05 g, 11%).

EXAMPLE 19B 1-(cyclohexylmethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 19A for the product of Example 1B (0.025 g, 30%). MS (ESI−) m/z 437 (M−H)$^-$. The sodium salt of the title compound was prepared according to the procedure of Example 1D. MS (ESI−) m/z 437 (M−H)$^-$; $^1$H NMR (300 MHz, DMSO-d$_6$/TFA) δ 0.99 (m, 5H), 1.50 (m, 5H), 1.87 (m, 1H), 4.32 (d, J=7.35 Hz, 2H), 7.23 (dd, J=8.09, 4.78 Hz, 1H), 7.38 (m, 2H), 7.57 (m, 1H), 7.78 (d, J=8.09 Hz, 1H), 8.40 (dd, J=8.09, 1.84 Hz, 1H), 8.66 (dd, J=4.78, 1.84 Hz, 1H).

EXAMPLE 20

3-(1,1-dioxido-4H-1,2,4-benzothiadiazin-3-yl)-4-hydroxy-1-[(2S)-2-methylbutyl]-1,8-naphthyridin-2(1H)-one

EXAMPLE 20A ethyl 2-{[(2S)-2-methylbutyl]amino}nicotinate

The title compound was prepared according to the procedure of Example 3A substituting (S)-(−)-2-methylbutylamine for 2-ethylbutylamine (1.6 g, 77%). $^1$H NMR (300 MHz, DMSO-d$_6$) δ 0.89 (t, J=7.23, 3H), 0.91 (d, J=6.62 Hz, 3H), 1.18 (m, 1H), 1.31 (t, J=6.99 Hz, 3H), 1.42 (m, 1H), 1.66 (m, 1H), 3.35 (m, 2H), 4.29 (q, J=7.23 Hz, 2H), 6.59 (dd, J=7.72, 4.78 Hz, 1H), 8.01 (t, J=5.52 Hz, 1H), 8.08 (dd, J=7.72, 1.84 Hz, 1H), 8.27 (dd, J=4.60, 2.02 Hz, 1H).

EXAMPLE 20B

1-[(2S)-2-methylbutyl]-2H-pyrido[2,3-d][1,3]oxazine-2,4(1H)-dione

The title compound was prepared according to the procedure of Example 3B substituting the product of Example 20A for the product of Example 3A (0.400 g, 68%). MS (DCI) m/z 252 (M+NH$_4$)$^+$.

EXAMPLE 20C

3-(1,1-dioxido-4H-1,2,4-benzothiadiazin-3-yl)-4-hydroxy-1-[(2S)-2-methylbutyl]-1,8-naphthyridin-2(1H)-one The title compound was prepared according to the procedure of Example 1D substituting the product of Example 20B for the product of Example 1B (0.116 g, 43%). MS (ESI−) m/z 411 (M−H)$^-$. The sodium salt of the title compound was prepared according to the procedure of Example 1D. $^1$H NMR (300 MHz, DMSO-d$_6$) δ 0.80 (d, J=6.99 Hz, 3H), 0.87 (t, J=7.54 Hz, 3H), 1.15 (m, 1H), 1.37 (m, 1H), 2.02 (m, 1H), 4.20 (d, J=7.35 Hz, 2H), 7.12 (dd, J=7.72, 4.78 Hz, 1H), 7.27 (m, 2H), 7.55 (m, 1H), 7.66 (d, J=7.72 Hz, 1H), 8.37 (dd, J=7.72, 2.21 Hz, 1H), 8.51 (dd, J=4.60, 2.02 Hz, 1H), 15.95 (s, 1H).

EXAMPLE 21

3-(1,1-dioxido-4H-1,2,4-benzothiadiazin-3-yl)-4-hydroxy-1-(4-methylbenzyl)-1,8-naphthyridin-2(1H)-one

EXAMPLE 21A

1-(4-methylbenzyl)-2H-pyrido[2,3-d][1,3]oxazine-2,4(1H)-dione

The title compound was prepared according to the procedure of Example 1B substituting 4-methylbenzyl bromide for n-butyl bromide (0.402 g, 82%). MS (DCI) m/z 269 (M+H)$^+$.

EXAMPLE 21B

3-(1,1-dioxido-4H-1,2,4-benzothiadiazin-3-yl)-4-hydroxy-1-(4-methylbenzyl)-1,8-naphthyridin-2(1H)-one The title compound was prepared according to the procedure of Example 1D substituting the product of Example 21A for the product of Example 1B (0.099 g, 60%). MS (ESI−) m/z 445 (M−H)$^-$. The sodium salt of the title compound was prepared according to the procedure of Example 1D. $^1$H NMR (300 MHz, DMSO-d$_6$) δ 2.22 (s, 3H), 5.47 (s, 2H), 7.04 (d, J=7.72 Hz, 2H), 7.14 (m, 3H), 7.29 (t, J=7.35 Hz, 2H), 7.55 (t, J=7.72 Hz, 1H), 7.67 (d, J=7.72 Hz, 1H), 8.39 (dd, J=7.72, 1.84 Hz, 1H), 8.48 (dd, J=4.78, 1.84 Hz, 1H), 15.85 (s, 1H).

EXAMPLE 22

3-(1,1-dioxido-4H-1,2,4-benzothiadiazin-3-yl)-4-hydroxy-1-[(5-nitro-2-furyl)methyl]-1,8-naphthyridin-2(1H)-one

EXAMPLE 22A

1-[(5-nitro-2-furyl)methyl]-2H-pyrido[2,3-d][1,3]oxazine-2,4(1H)-dione

The title compound was prepared according to the procedure of Example 1B substituting 2-bromomethyl-5-nitrofuran for n-butyl bromide (0.120 g, 34%). $^1$H NMR (300 MHz, DMSO-d$_6$) δ 5.45 (s, 2H), 6.90 (d, J=3.68 Hz, 1H), 7.44 (dd, J=7.72, 5.15 Hz, 1H), 7.65 (d, J=3.68 Hz, 1H), 8.45 (m, 1H), 8.77 (m, 1H).

EXAMPLE 22B

3-(1,1-dioxido-4H-1,2,4-benzothiadiazin-3-yl)-4-hydroxy-1-[(5-nitro-2-furyl)methyl]-1,8-naphthyridin-2(1H)-one The title compound was prepared according to the procedure of Example 1D substituting the product of Example 21A for the product of Example 1B (0.040 g, 21%). MS (DCI/NH$_3$) m/z 468 (M+H)$^+$. The sodium salt of the title compound was prepared according to the procedure of Example 1D. $^1$H NMR (300 MHz, DMSO-d$_6$) δ 5.60 (s, 2H), 6.54 (d, J=3.68 Hz, 1H), 7.22 (dd, J=7.72, 4.78 Hz, 1H), 7.29 (m, 2H), 7.56 (m, 1H), 7.58 (d, J=3.68 Hz, 1H), 7.67 (d, J=8.09 Hz, 1H), 8.43 (dd, J=7.72, 1.84 Hz, 1H), 8.53 (dd, J=4.78, 1.84 Hz, 1H), 15.68 (s, 1H).

EXAMPLE 23

1-(1-benzothien-2-ylmethyl)-3-(1,1-dioxido-4H-1,2,4-benzothiadiazin-3-yl)-4-hydroxy-1,8-naphthyridin-2(1H)-one

EXAMPLE 23A

1-(1-benzothien-2-ylmethyl)-2H-pyrido[2,3-d][1,3]oxazine-2,4(1H)-dione

The title compound was prepared according to the procedure of Example 1B substituting 2-chloromethyl-benzo[b]thiophene for n-butyl bromide (0.160 g, 42%). $^1$H NMR (300 MHz, DMSO-d$_6$) δ 5.58 (s, 2H), 7.33 (m, 2H), 7.44 (dd, J=7.72, 4.78 Hz, 1H), 7.51 (s, 1H), 7.77 (m, 1H), 7.90 (m, 1H), 8.44 (dd, J=7.72, 1.84 Hz, 1H), 8.83 (dd, J=4.78, 1.84 Hz, 1H).

EXAMPLE 23B

1-(1-benzothien-2-ylmethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 23A for the product of Example 1B (0.148 g, 60%). MS (ESI−) m/z 487 (M−H)$^-$. The sodium salt of the title compound was prepared according to the procedure of Example 1D. $^1$H NMR (300 MHz, DMSO-d$_6$) δ 5.74 (s, 2H), 7.20 (dd, J=7.72, 4.78 Hz, 1H), 7.28 (m, 4H), 7.36 (s, 1H), 7.56 (m, 1H), 7.68 (dd, J=7.72, 1.47 Hz, 1H), 7.75 (m, 1H), 7.82 (dd, J=7.72, 1.47 Hz, 1H), 8.41 (dd, J=7.72, 1.84 Hz, 1H), 8.58 (dd, J=4.78, 1.84 Hz, 1H), 15.77 (s, 1H).

EXAMPLE 24

3-(1,1-dioxido-4H-1,2,4-benzothiadiazin-3-yl)-4-hydroxy-1-(3-methoxybenzyl)-1,8-naphthyridin-2(1H)-one

EXAMPLE 24A

1-(3-methoxybenzyl)-2H-pyrido[2,3-d][1,3]oxazine-2,4(1H)-dione

The title compound was prepared according to the procedure of Example 1B substituting 3-methoxybenzyl bromide for n-butyl bromide (0.446 g, 86%). MS (DCI) m/z 285 (M+H)$^+$.

EXAMPLE 24B

3-(1,1-dioxido-4H-1,2,4-benzothiadiazin-3-yl)-4-hydroxy-1-(3-methoxybenzyl)-1,8-naphthyridin-2(1H)-one The title compound was prepared according to the procedure of Example 1D substituting the product of Example 24A for the product of Example 1B (0.086 g, 53%). MS (ESI−) m/z 461 (M−H)−. The sodium salt of the title compound was prepared according to the procedure of Example 1D. $^1$H NMR (300 MHz, DMSO-$d_6$) δ 3.69 (s, 3H), 5.49 (s, 2H), 6.75 (m, 3H), 7.15 (m, 2H), 7.29 (td, J=8.46, 1.84 Hz, 2H), 7.56 (td, J=7.72, 1.47 Hz, 1H), 7.66 (d, J=7.72 Hz, 1H), 8.41 (dd, J=7.72, 1.84 Hz, 1H), 8.48 (dd, J=4.78, 1.84 Hz, 1H), 15.82 (s, 1H).

EXAMPLE 25

3-(1,1-dioxido-4H-1,2,4-benzothiadiazin-3-yl)-4-hydroxy-1-(3-iodobenzyl)-1,8-naphthyridin-2(1H)-one

EXAMPLE 25A

1-(3-iodobenzyl)-2H-pyrido[2,3-d][1,3]oxazine-2,4(1H)-dione

The title compound was prepared according to the procedure of Example 1B substituting 3-iodobenzyl bromide for n-butyl bromide (0.614 g, 88%). MS (DCI) m/z 381 (M+H)+.

EXAMPLE 25B

3-(1,1-dioxido-4H-1,2,4-benzothiadiazin-3-yl)-4-hydroxy-1-(3-iodobenzyl)-1,8-naphthyridin-2(1H)-one The title compound was prepared according to the procedure of Example 1D substituting the product of Example 25A for the product of Example 1B (0.176 g, 60%). MS (ESI−) m/z 557 (M−H)−. The sodium salt of the title compound was prepared according to the procedure of Example 1D. $^1$H NMR (300 MHz, DMSO-$d_6$) δ 5.47 (s, 2H), 7.07 (t, J=7.72 Hz, 1H), 7.17 (dd, J=7.72, 4.78 Hz, 1H), 7.28 (m, 3H), 7.55 (m, 2H), 7.66 (m, 2H), 8.41 (dd, J=7.72, 1.84 Hz, 1H), 8.49 (dd, J=4.78, 1.84 Hz, 1H), 15.79 (s, 1H).

EXAMPLE 26

1-[(3,5-dimethyl-4-isoxazolyl)methyl]-3-(1,1-dioxido-4H-1,2,4-benzothiadiazin-3-yl)-4-hydroxy-1,8-naphthyridin-2(1H)-one

EXAMPLE 26A

1-[(3,5-dimethyl-4-isoxazolyl)methyl]-2H-pyrido[2,3-d][1,3]oxazine-2,4(1H)-dione The title compound was prepared according to the procedure of Example 1B substituting 4-chloromethyl-3,5-dimethylisoxazole for n-butyl bromide (0.199 g, 60%). $^1$H NMR (300 MHz, DMSO-$d_6$) δ 2.20 (s, 3H), 2.45 (s, 3H), 5.10 (s, 2H), 7.40 (dd, J=7.72, 4.78 Hz, 1H), 8.40 (dd, J=7.72, 1.84 Hz, 1H), 8.80 (dd, J=4.78, 1.84 Hz, 1H).

EXAMPLE 26B

1-[(3,5-dimethyl-4-isoxazolyl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 26A for the product of Example 1B (0.187 g, 63%). MS (DCI/NH$_3$) m/z 452 (M+H)+; $^1$H NMR (300 MHz, DMSO-$d_6$) δ 2.20 (s, 3H), 2.38 (s, 3H), 5.44 (s, 2H), 7.51 (dd, J=7.90, 4.60 Hz, 1H), 7.55 (t, J=7.17 Hz, 1H), 7.64 (d, J=7.72 Hz, 1H), 7.77 (t, J=7.17 Hz, 1H), 7.92 (d, J=7.72 Hz, 1H), 8.58 (dd, J=7.90, 1.66 Hz, 1H), 8.88 (dd, J=4.60, 1.66 Hz, 1H), 13.95 (s, 1H). The sodium salt of the title compound was prepared according to the procedure of Example 1D. $^1$H NMR (300 MHz, DMSO-$d_6$) δ 2.17 (s, 3H), 2.29 (s, 3H), 5.26 (s, 2H), 7.17 (dd, J=7.73, 4.78 Hz, 1H), 7.29 (m, 2H), 7.56 (t, J=7.72 Hz, 1H), 7.67 (d, J=7.72 Hz, 1H), 8.39 (dd, J=7.72, 1.84 Hz, 1H), 8.53 (dd, J=4.78, 1.84 Hz, 1H), 15.78 (s, 1H).

EXAMPLE 27

3-(1,1-dioxido-4H-1,2,4-benzothiadiazin-3-yl)-4-hydroxy-1-[2-(3-thienyl)ethyl]-1,8-naphthyridin-2(1H)-one

EXAMPLE 27A

1-[2-(3-thienyl)ethyl]-2H-pyrido[2,3-d][1,3]oxazine-2,4(1H)-dione

The title compound was prepared according to the procedure of Example 1B substituting 3-(2-bromoethyl)thiophene for n-butyl bromide (0.156 g, 46%). $^1$H NMR (300 MHz, DMSO-$d_6$) δ 2.98 (t, 2H), 4.36 (t, 2H), 7.07 (d, J=5.15 Hz, 1H), 7.31 (m, 1H), 7.39 (dd, J=7.72, 5.15 Hz, 1H), 7.49 (m, 1H), 8.41 (dd, J=7.72, 1.84 Hz, 1H), 8.78 (dd, J=4.78, 1.84 Hz, 1H).

EXAMPLE 27B

3-(1,1-dioxido-4H-1,2,4-benzothiadiazin-3-yl)-4-hydroxy-1-[2-(3-thienyl)ethyl]-1,8-naphthyridin-2(1H)-one The title compound was prepared according to the procedure of Example 1D substituting the product of Example 27A for the product of Example 1B (0.123 g, 48%). MS (ESI−) m/z 451 (M−H)−. The sodium salt of the title compound was prepared according to the procedure of Example 1D. $^1$H NMR (300 MHz, DMSO-$d_6$) δ 2.90 (t, J=7.90 Hz, 2H), 4.51 (t, J=7.90 Hz, 2H), 7.10 (d, J=4.78 Hz, 1H), 7.16 (dd, J=7.72, 4.78 Hz, 1H), 7.29 (m, 3H), 7.49 (dd, J=4.78, 2.94 Hz, 1H), 7.56 (m, 1H), 7.68 (d, J=7.72 Hz, 1H), 8.39 (dd, J=7.72, 1.84 Hz, 1H), 8.55 (dd, J=4.78, 1.84 Hz, 1H), 15.89 (s, 1H).

EXAMPLE 28

3-(1,1-dioxido-4H-1,2,4-benzothiadiazin-3-yl)-4-hydroxy-1-(4-pyridinylmethyl)-1,8-naphthyridin-2(1H)-one

EXAMPLE 28A

1-(4-pyridinylmethyl)-2H-pyrido[2,3-d][1,3]oxazine-2,4(1H)-dione

The title compound was prepared according to the procedure of Example 1B substituting 4-(chloromethyl)pyridine for n-butyl bromide (0.089 g, 29%). $^1$H NMR (300 MHz, DMSO-d$_6$) δ 5.37 (s, 2H), 7.41 (m, 3H), 8.45 (dd, J=7.72, 1.84 Hz, 1H), 8.49 (m, 2H), 8.69 (dd, J=4.78, 1.84 Hz, 1H).

EXAMPLE 28B 3-(1,1-dioxido-4H-1,2,4-benzothiadiazin-3-yl)-4-hydroxy-1-(4-pyridinylmethyl)-1,8-naphthyridin-2(1H)-one The title compound was prepared according to the procedure of Example 1D substituting the product of Example 28A for the product of Example 1B (0.034 g, 19%). MS (DCI/NH$_3$) m/z 434 (M+H)$^+$; $^1$H NMR (300 MHz, DMSO-d$_6$) δ 5.83 (s, 2H), 7.52 (m, 2H), 7.60 (d, J=7.72 Hz, 1H), 7.69 (d, J=6.25 Hz, 2H), 7.73 (m, 1H), 7.91 (d, J=6.99 Hz, 1H), 8.62 (dd, J=7.72, 1.84 Hz, 1H), 8.68 (d, J=6.25 Hz, 2H), 8.75 (dd, J=4.78, 1.84 Hz, 1H), 13.98 (s, 1H). The sodium salt of the title compound was prepared according to the procedure of Example 1D. $^1$H NMR (300 MHz, DMSO-d$_6$) δ 5.56 (s, 2H), 7.22 (m, 3H), 7.33 (m, 2H), 7.59 (m, 1H), 7.71 (m, 1H), 8.45 (m, 3H), 8.50 (dd, J=4.78, 1.83 Hz, 1H), 15.54 (s, 1H).

EXAMPLE 29

1-(4-bromobenzyl)-3-(1,1-dioxido-4H-1,2,4-benzothiadiazin-3-yl)-4-hydroxy-1,8-naphthyridin-2(1H)-one

EXAMPLE 29A 1-(4-bromobenzyl)-2H-pyrido[2,3-d][1,3]oxazine-2,4(1H)-dione

The title compound was prepared according to the procedure of Example 1B substituting 4-bromobenzyl bromide for n-butyl bromide (1.460 g, 72%). MS (DCI) m/z 333 (M+H)$^+$.

EXAMPLE 29B 1-(4-bromobenzyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 29A for the product of Example 1B (0.060 g, 59%). MS (ESI–) m/z 509 (M–H)$^-$. The sodium salt of the title compound was prepared according to the procedure of Example 1D. $^1$H NMR (300 MHz, DMSO-d$_6$) δ 5.47 (s, 2H), 7.16 (dd, J=7.72, 4.78 Hz, 1H), 7.22 (d, J=8.46 Hz, 2H), 7.27 (t, J=7.72 Hz, 2H), 7.44 (d, J=8.46 Hz, 2H), 7.56 (td, J=7.72, 1.47 Hz, 1H), 7.67 (d, J=7.72 Hz, 1H), 8.41 (dd, J=7.72, 1.84 Hz, 1H), 8.48 (dd, J=4.78, 1.84 Hz, 1H), 15.80(s, 1H).

EXAMPLE 30

3-(1,1-dioxido-4H-1,2,4-benzothiadiazin-3-yl)-4-hydroxy-1-neopentyl-1,8-naphthyridin-2(1H)-one

EXAMPLE 30A ethyl 2-(neopentylamino)nicotinate

The title compound was prepared according to the procedure of Example 3A substituting 2,2-dimethylpropylamine for 2-ethylbutylamine (0.407 g, 57%). MS (ESI+) 237 (M+H)$^+$; $^1$H NMR (300 MHz, CDCl$_3$) δ 1.02 (s, 9H), 1.38 (t, J=7.17 Hz, 3H), 3.36 (d, J=5.52 Hz, 2H), 4.33 (q, J=7.35 Hz, 2H), 6.48 (dd, J=7.91, 4.60 Hz, 1H), 8.12 (dd, J=7.72, 2.21 Hz, 1H), 8.16 (s, 1H), 8.26 (dd, J=4.78, 2.21 Hz, 1H).

EXAMPLE 30B 1-neopentyl-2H-pyrido[2,3-d][1,3]oxazine-2,4(1H)-dione

The title compound was prepared according to the procedure of Example 3B substituting the product of Example 30A for the product of Example 3A (0.182 g, 89%). $^1$H NMR (300 MHz, CDCl$_3$) δ 1.12 (s, 9H), 4.28 (s, 2H), 7.25 (dd, J=6.99, 4.04 Hz, 1H), 8.41 (dd, J=7.91, 2.02 Hz, 1H), 8.69 (dd, J=4.78, 1.84 Hz, 1H).

EXAMPLE 30C 3-(1,1-dioxido-4H-1,2,4-benzothiadiazin-3-yl)-4-hydroxy-1-neopentyl-1,8-naphthyridin-2(1H)-one The title compound was prepared according to the procedure of Example 1D substituting the product of Example 30B for the product of Example 1B (0.070 g, 22%). MS (ESI+) m/z 413 (M+H)$^+$; $^1$H NMR (300 MHz, DMSO-d$_6$) δ 0.96 (s, 9H), 4.52 (s, 2H), 7.49 (dd, J=8.09, 4.41 Hz, 1H), 7.56 (t, J=7.54 Hz, 1H), 7.68 (d, J=8.09 Hz, 1H), 7.78 (m, 1H), 7.94 (d, J=6.99 Hz, 1H), 8.57 (dd, J=8.09, 1.84 Hz, 1H), 8.85 (dd, J=4.41, 1.84 Hz, 1H), 14.11 (s, 1H). The sodium salt of the title compound was prepared according to the procedure of Example 1D. MS (ESI+) m/z 413 (M+H)$^+$; $^1$H NMR (300 MHz, DMSO-d$_6$) δ 0.91 (s, 9H), 4.34 (s, 2H), 7.11 (dd, J=7.72, 4.78 Hz, 1H), 7.27 (m, 2H), 7.55 (m, 1H), 7.66 (m, 1H), 8.36 (dd, J=7.54, 2.02 Hz, 1H), 8.48 (dd, J=4.60, 2.02 Hz, 1H), 15.95 (s, 1H).

EXAMPLE 31

1-{[(1S,2R,5S)-6,6-dimethylbicyclo[3.1.1]hept-2-yl]methyl}-3-(1,1-dioxido-4H-1,2,4-benzothiadiazin-3-yl)-4-hydroxy-1,8-naphthyridin-2(1H)-one

EXAMPLE 31A ethyl 2-({[(1S,2R,5S)-6,6-dimethylbicyclo[3.1.1]hept-2-yl]methyl}amino)nicotinate The title compound was prepared according to the procedure of Example 3A substituting (–)-cis-myrtanylamine for 2-ethylbutylamine (0.604 g, 40%). MS (ESI+) m/z 303 (M+H)$^+$.

EXAMPLE 31B

1-{[(1S,2R,5S)-6,6-dimethylbicyclo[3.1.1]hept-2-yl]methyl]-2H-pyrido[2,3-d][1,3]oxazine-2,4(1H)-dione The title compound was prepared according to the procedure of Example 3B substituting the product of Example 31A for the product of Example 3A (0.570 g, 95%). $^1$H NMR (300 MHz, DMSO-d$_6$) δ 0.79 (d, J=9.56 Hz, 1H), 1.14 (s, 3H), 1.22 (s, 3H), 1.62 (m, 1H), 1.87 (m, 5H), 2.26 (m, 1H), 2.53 (m, 1H), 4.04 (dd, J=13.05, 6.07 Hz, 1H), 4.28 (dd, J=13.24, 9.19

Hz, 1H), 7.37 (dd, J=7.72, 4.78 Hz, 1H), 8.38 (dd, J=7.72, 1.84 Hz, 1H), 8.76 (dd, J=4.78, 1.84 Hz, 1H).

EXAMPLE 31C

1-{[(1S,2R,5S)-6,6-dimethylbicyclo[3.1.1]hept-2-yl]methyl}-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 31B for the product of Example 1B (0.050 g, 21%). MS (ESI−) m/z 477 (M−H)⁻. The sodium salt of the title compound was prepared according to the procedure of Example 1D. $^1$H NMR (300 MHz, DMSO-d$_6$) δ 0.78 (d, J=9.56 Hz, 1H), 1.15 (m, 3H), 1.30 (s, 3H), 1.80 (m, 6H), 2.24 (m, 1H), 2.54 (m, 1H), 4.37 (m, 2H), 7.12 (dd, J=7.54, 4.60 Hz, 1H), 7.27 (m, 2H), 7.55 (m, 1H), 7.67 (dd, J=7.72, 1.47 Hz, 1H), 8.36 (dd, J=7.54, 2.02 Hz, 1H), 8.50 (dd, J=4.60, 2.02 Hz, 1H), 15.95 (s, 1H).

EXAMPLE 32

3-{[3-(1,1-dioxido-4H-1,2,4-benzothiadiazin-3-yl)-4-hydroxy-2-oxo-1,8-naphthyridin-1(2H)-yl]methyl}benzonitrile

EXAMPLE 32A

3-[(2,4-dioxo-2H-pyrido[2,3-d][1,3]oxazin-1(4H)-yl)methyl]benzonitrile

The title compound was prepared according to the procedure of Example 1B substituting 3-cyanobenzyl bromide for n-butyl bromide (0.363 g, 71%). MS (DCI) m/z 280 (M+H)⁺.

EXAMPLE 32B

3-{[3-(1,1-dioxido-4H-1,2,4-benzothiadiazin-3-yl)-4-hydroxy-2-oxo-1,8-naphthyridin-1(2H)-yl]methyl}benzonitrile The title compound was prepared according to the procedure of Example 1D substituting the product of Example 32A for the product of Example 1B (0.024 g, 22%). MS (ESI−) m/z 456 (M−H)⁻. The sodium salt of the title compound was prepared according to the procedure of Example 1D. $^1$H NMR (300 MHz, DMSO-d$_6$) δ 5.54 (s, 2H), 7.18 (dd, J=7.72, 4.78 Hz, 1H), 7.29 (m, 2H), 7.48 (t, J=7.72 Hz, 1H), 7.56 (td, J=7.91, 1.47 Hz, 2H), 7.68 (m, 3H), 8.42 (dd, J=7.72, 1.84 Hz, 1H), 8.49 (dd, J=4.60, 2.02 Hz, 1H), 15.77 (s, 1H).

EXAMPLE 33

3-(1,1-dioxido-4H-1,2,4-benzothiadiazin-3-yl)-4-hydroxy-1-(3-pyridinylmethyl)-1,8-naphthyridin-2(1H)-one

EXAMPLE 33A 1-(3-pyridinylmethyl)-2H-pyrido[2,3-d][1,3]oxazine-2,4(1H)-dione The title compound was prepared according to the procedure of Example 1B substituting 3-(bromomethyl)pyridine for n-butyl bromide (0.153 g, 49%). $^1$H NMR (300 MHz, DMSO-d$_6$) δ 5.38 (s, 2H), 7.34 (dd, J=7.72, 4.78 Hz, 1H), 7.40 (dd, J=7.72, 4.78 Hz, 1H), 7.82 (m, 1H), 8.42 (dd, J=7.72, 1.84 Hz, 1H), 8.47 (dd, J=4.78, 1.10 Hz, 1H), 8.66 (d, J=1.84 Hz, 1H), 8.74 (dd, J=5.15, 1.84 Hz, 1H).

EXAMPLE 33B 3-(1,1-dioxido-4H-1,2,4-benzothiadiazin-3-yl)-4-hydroxy-1-(3-pyridinylmethyl)-1,8-naphthyridin-2(1H)-one The title compound was prepared according to the procedure of Example 1D substituting the product of Example 33A for the product of Example 1B (0.098 g, 41%). MS (DCI/NH$_3$) m/z 434 (M+H)⁺; $^1$H NMR (300 MHz, DMSO-d$_6$) δ 5.72 (s, 2H), 7.41 (dd, J=7.72, 4.78 Hz, 1H), 7.50 (m, 2H), 7.61 (d, J=8.09 Hz, 1H), 7.74 (m, 1H), 7.84 (d, J=7.72 Hz, 1H), 7.89 (d, J=8.09 Hz, 1H), 8.50 (d, J=4.04 Hz, 1H), 8.58 (dd, J=7.73, 1.84 Hz, 1H), 8.67 (s, 1H), 8.80 (dd, J=4.78, 1.84 Hz, 1H), 14.15 (s, 1H). The sodium salt of the title compound was prepared according to the procedure of Example 1D. $^1$H NMR (300 MHz, DMSO-d$_6$) δ 5.53 (s, 2H), 7.18 (dd, J=7.72, 4.41 Hz, 1H), 7.29 (m, 3H), 7.56 (m, 1H), 7.65 (m, 2H), 8.40 (m, 2H), 8.51 (dd, J=4.60, 2.02 Hz, 1H), 8.57 (d, J=1.47 Hz, 1H), 15.78 (s, 1H).

EXAMPLE 34

1-(1-adamantylmethyl)-3-(1,1-dioxido-4H-1,2,4-benzothiadiazin-3-yl)-4-hydroxy-1,8-naphthyridin-2(1H)-one

EXAMPLE 34A

2-[(1-adamantylmethyl)amino]nicotinic acid

The title compound was prepared according to the procedure of Example 3A substituting 2-chloronicotinic acid for ethyl 2-chloronicotinate and 1-adamantanemethylamine for 2-ethylbutylamine (0.185 g, 79%). MS (ESI+) m/z 287.1 (M+H)⁺; $^1$H NMR (300 MHz, DMSO-d$_6$) δ 1.74 (m, 12H), 2.00 (s, 3H), 3.31 (m, 2H), 6.60 (dd, J=7.35, 5.52 Hz, 1H), 7.96 (dd, J=5.33, 2.02 Hz, 1H), 8.26 (dd, J=7.35, 1.84 Hz, 1H).

EXAMPLE 34B 1-(1-adamantylmethyl)-2H-pyrido[2,3-d][1,3]oxazine-2,4(1H)-dione The title compound was prepared according to the procedure of Example 3B substituting the product of Example 34A for the product of Example 3A (0.025 g, 20%). $^1$H NMR (300 MHz, CDCl$_3$) δ 1.74 (m, 12H), 2.04 (s, 3H), 3.65 (d, J=5.88 Hz, 2H), 6.91 (dd, J=7.72, 5.52 Hz, 1H), 8.51 (d, J=4.78 Hz, 1H), 8.77 (d, J=7.72 Hz, 1H).

EXAMPLE 34C 1-(1-adamantylmethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 34B for the product of Example 1B (0.018 g, 47%). MS (ESI+) m/z 491.1 (M+H)⁺; $^1$H NMR (300 MHz, DMSO-d$_6$) δ 1.59 (s, 12H), 1.90 (m, 3H), 4.41 (br s, 2H), 7.48 (m, 1H), 7.56 (t, J=7.54 Hz, 1H), 7.69 (m, 1H), 7.77 (m, 1H), 7.94 (d, J=7.72 Hz, 1H), 8.56 (dd, J=8.09, 1.84 Hz, 1H), 8.85 (dd, J=4.60, 1.65 Hz, 1H). The sodium salt of the title compound was prepared according to the procedure of Example 1D. MS (ESI+) m/z 491.1 (M+H)$^+$; $^1$H NMR (300 MHz, DMSO-d$_6$) δ 1.56 (m, 12H), 1.87 (s, 3H), 4.21 (br s, 2H), 7.10 (dd, J=7.72, 4.78 Hz, 1H), 7.28 (m, 2H), 7.55 (m, 1H), 7.66 (dd, J=7.72, 1.47 Hz, 1H), 8.35 (dd, J=7.72, 1.84 Hz, 1H), 8.48 (dd, J=4.60, 2.02 Hz, 1H), 15.97 (br s, 1H).

EXAMPLE 35

3-(1,1-dioxido-4H-1,2,4-benzothiadiazin-3-yl)-4-hydroxy-1-[3-(trifluoromethyl)benzyl]-1,8-naphthyridin-2(1H)-one

EXAMPLE 35A

1-[3-(trifluoromethyl)benzyl]-2H-pyrido[2,3-d][1,3]oxazine-2,4(1H)-dione

The title compound was prepared according to the procedure of Example 1B substituting 3-(trifluoromethyl)benzyl bromide for n-butyl bromide (0.250 g, 42%). $^1$H NMR (300 MHz, DMSO-d$_6$) δ 5.43 (s, 2H), 7.40 (dd, J=7.72, 4.78 Hz, 1H), 7.55 (m, 1H), 7.64 (m, 1H), 7.73 (d, J=7.72 Hz, 1H), 7.81 (s, 1H), 8.43 (dd, J=7.72, 1.84 Hz, 1H), 8.72 (dd, J=4.78, 1.84 Hz, 1H).

EXAMPLE 35B 3-(1,1-dioxido-4H-1,2,4-benzothiadiazin-3-yl)-4-hydroxy-1-[3-(trifluoromethyl)benzyl]-1,8-naphthyridin-2(1H)-one The title compound was prepared according to the procedure of Example 1D substituting the product of Example 35A for the product of Example 1B (0.22 g, 57%). MS (ESI–) m/z 499 (M–H)$^-$; $^1$H NMR (300 MHz, DMSO-d$_6$) δ 5.77 (s, 2H), 7.54 (m, 6H), 7.66 (d, J=7.72 Hz, 1H), 7.76 (m, 2H), 7.92 (d, J=8.09 Hz, 1H), 8.61 (dd, J=8.09, 1.84 Hz, 1H), 8.83 (dd, J=4.41, 1.84 Hz, 1H), 13.91 (br s, 1H). The sodium salt of the title compound was prepared according to the procedure of Example 1D. MS (ESI–) m/z 499 (M–H)$^-$; $^1$H NMR (300 MHz, DMSO-d$_6$) δ 5.58 (s, 2H), 7.18 (dd, J=7.72, 4.78 Hz, 1H), 7.29 (m, 2H), 7.54 (m, 4H), 7.66 (m, 2H), 8.42 (dd, J=7.72, 1.84 Hz, 1H), 8.49 (dd, J=4.60, 2.02 Hz, 1H), 15.78 (m, 1H).

EXAMPLE 36

3-(1,1-dioxido-4H-1,2,4-benzothiadiazin-3-yl)-4-hydroxy-1-[(2-methyl-1,3-thiazol-5-yl)methyl]-1,8-naphthyridin-2(1H)-one

EXAMPLE 36A

1-[(2-methyl-1,3-thiazol-5-yl)methyl]-2H-pyrido[2,3-d][1,3]oxazine-2,4(1H)-dione The title compound was prepared according to the procedure of Example 1B substituting 2-methyl-5-chloromethylthiazole for n-butyl bromide (0.300 g, 54%).

EXAMPLE 36B 3-(1,1-dioxido-4H-1,2,4-benzothiadiazin-3-yl)-4-hydroxy-1-[(2-methyl-1,3-thiazol-5-yl)methyl]-1,8-naphthyridin-2(1H)-one The title compound was prepared according to the procedure of Example 1D substituting the product of Example 36A for the product of Example 1B (0.123 g, 25%). MS (ESI–) m/z 452 (M–H)$^-$; $^1$H NMR (300 MHz, DMSO-d$_6$) δ 2.54 (s, 3H), 5.76 (s, 1H), 7.53 (m, 1H), 7.52 (d, J=7.72 Hz, 1H), 7.65 (m, 2H), 7.76 (t, J=7.72 Hz, 1H), 7.91 (d, J=7.72 Hz, 1H), 8.57 (d, J=7.72 Hz, 1H), 8.90 (d, J=4.04 Hz, 1H), 13.92 (s, 1H). The sodium salt of the title compound was prepared according to the procedure of Example 1D.

EXAMPLE 37

1-(2-cyclohexylethyl)-3-(1,1-dioxido-4H-1,2,4-benzothiadiazin-3-yl)-4-hydroxy-1,8-naphthyridin-2(1H)-one

EXAMPLE 37A 1-(2-cyclohexylethyl)-2H-pyrido[2,3-d][1,3]oxazine-2,4(1H)-dione The title compound was prepared according to the procedure of Example 1B substituting 1-bromo-2-cyclohexylethane for n-butyl bromide (0.196 g, 39%).

EXAMPLE 37B 1-(2-cyclohexylethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 37A for the product of Example 1B (0.030 g, 18% after colum purification). MS (ESI–) m/z 451 (M–H)$^-$. The sodium salt of the title compound was prepared according to the procedure of Example 1D. MS (ESI–) m/z 451 (M–H)$^-$; $^1$H NMR (300 MHz, DMSO-d$_6$/TFA) δ 0.78 (m, 2H), 0.98 (m, 3H), 1.18 (m, 1H), 1.40 (m, 5H), 1.59 (d, J=12.50 Hz, 2H), 4.33 (m, 2H), 7.23 (m, 3H), 7.47 (t, J=7.54 Hz, 1H), 7.67 (d, J=7.72 Hz, 1H), 8.43 (m, 1H), 8.57 (dd, J=4.78, 1.47 Hz, 1H).

EXAMPLE 38

3-(1,1-dioxido-4H-1,2,4-benzothiadiazin-3-yl)-4-hydroxy-1-(4-methoxybenzyl)-1,8-naphthyridin-2(1H)-one

EXAMPLE 38A 1-(4-methoxybenzyl)-2H-pyrido[2,3-d][1,3]oxazine-2,4(1H)-dione

The title compound was prepared according to the procedure of Example 1B substituting 4-methoxybenzyl chloride for n-butyl bromide (0.364 g, 70%). MS (DCI) m/z 285 (M+H)$^+$.

EXAMPLE 38B 3-(1,1-dioxido-4H-1,2,4-benzothiadiazin-3-yl)-4-hydroxy-1-(4-methoxybenzyl)-1,8-naphthyridin-2(1H)-one The title compound was prepared according to the procedure of Example 1D substituting the product of Example 38A for the product of Example 1B (0.098 g, 51%). MS (ESI−) m/z 461 (M−H)⁻. The sodium salt of the title compound was prepared according to the procedure of Example 1D. $^1$H NMR (300 MHz, DMSO-$d_6$) δ 3.68 (s, 3H), 5.45 (s, 2H), 6.80 (dt, J=8.82, 2.21 Hz, 2H), 7.15 (dd, J=7.72, 4.78 Hz, 1H), 7.26 (m, 4H), 7.55 (td, J=7.72, 1.47 Hz, 1H), 7.67 (dd, J=7.91, 1.65 Hz, 1H), 8.39 (dd, J=7.72, 2.21 Hz, 1H), 8.50 (dd, J=4.78, 1.84 Hz, 1H), 15.86 (s, 1H).

EXAMPLE 39

3-(1,1-dioxido-4H-1,2,4-benzothiadiazin-3-yl)-4-hydroxy-1-(2-methylbenzyl)-1,8-naphthyridin-2(1H)-one

EXAMPLE 39A 1-(2-methylbenzyl)-2H-pyrido[2,3-d][1,3]oxazine-2,4(1H)-dione

The title compound was prepared according to the procedure of Example 1B substituting 2-methylbenzyl bromide for n-butyl bromide (0.353 g, 72%). MS (DCI) m/z 269 (M+H)⁺.

EXAMPLE 39B 3-(1,1-dioxido-4H-1,2,4-benzothiadiazin-3-yl)-4-hydroxy-1-(2-methylbenzyl)-1,8-naphthyridin-2(1H)-one The title compound was prepared according to the procedure of Example 1D substituting the product of Example 39A for the product of Example 1B (0.165 g, 62%). MS (ESI−) m/z 445 (M−H)⁻. The sodium salt of the title compound was prepared according to the procedure of Example 1D. $^1$H NMR (300 MHz, DMSO-$d_6$) δ 2.44 (s, 3H), 5.45 (s, 2H), 6.59 (d, J=7.35 Hz, 1H), 6.96 (t, J=7.17 Hz, 1H), 7.06 (t, J=6.80 Hz, 1H), 7.16 (m, 2H), 7.29 (t, J=7.54 Hz, 2H), 7.56 (td, J=7.72, 1.47 Hz, 1H), 7.66 (d, J=7.72 Hz, 1H), 8.43 (d, J=6.25 Hz, 2H), 15.84 (s, 1H).

EXAMPLE 40

1-(cyclopropylmethyl)-3-(1,1-dioxido-4H-1,2,4-benzothiadiazin-3-yl)-4-hydroxy-1,8-naphthyridin-2(1H)-one

EXAMPLE 40A 1-(cyclopropylmethyl)-2H-pyrido[2,3-d][1,3]oxazine-2,4(1H)-dione The title compound was prepared according to the procedure of Example 1B substituting (bromomethyl)cyclopropane for n-butyl bromide (0.278 g, 70%). MS (APCI+) m/z 219 (M+H). $^1$H NMR (300 MHz, DMSO-$d_6$) δ 0.46 (m, 4H), 1.27 (m, 1H), 4.04 (d, J=6.99 Hz, 2H), 7.39 (dd, J=7.91, 4.96 Hz, 1H), 8.40 (dd, J=7.72, 1.84 Hz, 1H), 8.78 (dd, J=4.78, 1.84 Hz, 1H).

EXAMPLE 40B 1-(cyclopropylmethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 40A for the product of Example 1B (0.06 g, 20% after column purification). MS (ESI−) m/z 395 (M−H)⁻. The sodium salt of the title compound was prepared according to the procedure of Example 1D. MS (ESI−) m/z 395 (M−H)⁻; $^1$H NMR (300 MHz, DMSO-$d_6$) δ 0.40 (m, 4H), 1.32 (m, 1H), 4.19 (d, J=6.99 Hz, 2H), 7.14 (dd, J=7.54, 4.60 Hz, 1H), 7.28 (m, 2H), 7.55 (t, J=7.35 Hz, 1H), 7.67 (dd, J=7.72, 1.10 Hz, 1H), 8.38 (dd, J=7.72, 1.84 Hz, 1H), 8.52 (dd, J=4.60, 2.02 Hz, 1H), 15.93 (s, 1H).

EXAMPLE 41

3-(1,1-dioxido-4H-1,2,4-benzothiadiazin-3-yl)-4-hydroxy-1-(1,3-thiazol-4-ylmethyl)-1,8-naphthyridin-2(1H)-one

EXAMPLE 41A 1-(1,3-thiazol-4-ylmethyl)-2H-pyrido[2,3-d][1,3]oxazine-2,4(1H)-dione The title compound was prepared according to the procedure of Example 1B substituting 4-(chloromethyl)thiazole for n-butyl bromide (0.049 g, 15%). $^1$H NMR (300 MHz, DMSO-$d_6$) δ 5.48 (s, 2H), 7.40 (dd, J=7.72, 4.78 Hz, 1H), 7.66 (s, 1H), 8.45 (dd, J=7.72, 1.84 Hz, 1H), 8.72 (dd, J=4.78, 1.84 Hz, 1H), 9.06 (d, J=2.21 Hz, 1H).

EXAMPLE 41B 3-(1,1-dioxido-4H-1,2,4-benzothiadiazin-3-yl)-4-hydroxy-1-(1,3-thiazol-4-ylmethyl)-1,8-naphthyridin-2(1H)-one The title compound was prepared according to the procedure of Example 1D substituting the product of Example 41A for the product of Example 1B (0.046 g, 59%). MS (ESI−) m/z 438 (M−H)⁻. The sodium salt of the title compound was prepared according to the procedure of Example 1D. $^1$H NMR (300 MHz, DMSO-$d_6$) δ 5.65 (s, 2H), 7.04 (d, J=2.21 Hz, 1H), 7.16 (dd, J=7.72, 4.78 Hz, 1H), 7.29 (m, 2H), 7.56 (m, 1H), 7.66 (d, J=7.35 Hz, 1H), 8.42 (dd, J=7.72, 2.21 Hz, 1H), 8.46 (dd, J=4.78, 2.20 Hz, 1H), 8.98 (d, J=1.84 Hz, 1H), 15.85 (s, 1H).

EXAMPLE 42

3-(1,1-dioxido-4H-1,2,4-benzothiadiazin-3-yl)-4-hydroxy-1-[(5-phenyl-2-thienyl)methyl]-1,8-naphthyridin-2(1H)-one The product of Example 4B (100 mg, 0.193 mmol), phenylboronic acid (49 mg, 0.387 mmol), 2M aqueous $Na_2CO_3$ (0.45 mL), absolute ethanol (0.5 mL), and tetrakis(triphenylphosphine)palladium (14 mg, 0.012 mmol) in $N_2$-sparged DMF (2 mL) was heated to reflux for 2.5 hours, cooled to 0° C., diluted with $H_2O$ (15 mL), adjusted to pH 3 with 1N HCl, and extracted with ethyl acetate (3×25 mL). The combined extracts were washed with saturated NaCl, dried over anhydrous $Na_2SO_4$, filtered, and concentrated. The residue was purified by flash column chromatography on silica gel with 3% ethyl acetate/dichloromethane to give the title compound (0.039 g, 40%). MS (ESI−) m/z 513 (M−H)⁻. The sodium salt of the title compound was prepared according to the procedure of Example 1D. $^1$H NMR (300 MHz, DMSO-$d_6$) δ 5.64 (s, 2H), 7.12 (d, J=3.68 Hz, 1H), 7.20 (dd, J=7.72, 4.78 Hz, 1H), 7.31 (m, 6H), 7.57 (m, 3H), 7.68 (d, J=7.72 Hz, 1H), 8.41 (dd, J=7.72, 1.84 Hz, 1H), 8.60 (dd, J=4.78, 1.84 Hz, 1H), 15.80 (s, 1H).

EXAMPLE 43

3-(1,1-dioxido-4H-1,2,4-benzothiadiazin-3-yl)-4-hydroxy-1-(4-methyl-3-pentenyl)-1,8-naphthyridin-2(1H)-one

EXAMPLE 43A 1-(4-methyl-3-pentenyl)-2H-pyrido[2,3-d][1,3]oxazine-2,4(1H)-dione The title compound was prepared according to the procedure of Example 1B substituting 5-bromo-2-methyl-2-pentene for n-butyl bromide (0.157 g, 35%). MS (DCI+) m/z 247 (M+H)$^+$; $^1$H NMR (300 MHz, DMSO-d) δ 1.59 (s, 3H), 1.66 (s, 3H), 2.35 (m, 2H), 4.09 (m, 2H), 5.18 (t, J=7.54 Hz, 1H), 7.39 (dd, J=7.72, 5.15 Hz, 1H), 8.40 (dd, J=7.72, 1.84 Hz, 1H), 8.79 (dd, J=5.15, 1.84 Hz, 1H).

EXAMPLE 43B 3-(1,1-dioxido-4H-1,2,4-benzothiadiazin-3-yl)-4-hydroxy-1-(4-methyl-3-pentenyl)-1,8-naphthyridin-2(1H)-one The title compound was prepared according to the procedure of Example 1D substituting the product of Example 43A for the product of Example 1B (0.030 g, 20% after recrystallization). MS (ESI−) m/z 423 (M−H)$^-$. The sodium salt of the title compound was prepared according to the procedure of Example 1D. MS (ESI−) m/z 423 (M−H)$^-$; $^1$H NMR (300 MHz, DMSO-d$_6$) δ 1.63 (s, 3H), 1.67 (s, 3H), 2.26 (m, 2H), 4.23 (m, 2H), 5.21 (m, 1H), 7.14 (dd, J=7.72, 4.78 Hz, 1H), 7.28 (m, 2H), 7.55 (t, J=7.35 Hz, 1H), 7.67 (d, J=7.72 Hz, 1H), 8.37 (dd, J=7.72, 2.21 Hz, 1H), 8.53 (dd, J=4.60, 2.02 Hz, 1H), 15.92 (s, 1H).

EXAMPLE 44

4-{[3-(1,1-dioxido-4H-1,2,4-benzothiadiazin-3-yl)-4-hydroxy-2-oxo-1,8-naphthyridin-1(2H)-yl]methyl}benzonitrile

EXAMPLE 44A

4-[(2,4-dioxo-2H-pyrido[2,3-d][1,3]oxazin-1(4H)-yl)methyl]benzonitrile

The title compound was prepared according to the procedure of Example 1B substituting 4-cyanobenzyl bromide for n-butyl bromide (1.02 g, 60%). MS (DCI) m/z 280 (M+H)$^+$.

EXAMPLE 44B

4-{[3-(1,1-dioxido-4H-1,2,4-benzothiadiazin-3-yl)-4-hydroxy-2-oxo-1,8-naphthyridin-1(2H)-yl]methyl}benzonitrile The title compound was prepared according to the procedure of Example 1D substituting the product of Example 44A for the product of Example 1B (0.197 g, 60%). MS (ESI−) m/z 456 (M−H)$^-$. The sodium salt of the title compound was prepared according to the procedure of Example 1D. $^1$H NMR (300 MHz, DMSO-d$_6$) δ 5.58 (s, 2H), 7.18 (dd, J=7.54, 4.60 Hz, 1H), 7.29 (td, J=8.46, 1.84 Hz, 2H), 7.41 (d, J=8.46 Hz, 2H), 7.56 (td, J=7.81, 1.65 Hz, 1H), 7.67 (dd, J=7.91, 1.29 Hz, 1H), 7.72 (d, J=8.46 Hz, 2H), 8.42 (dd, J=7.72, 1.84 Hz, 1H), 8.46 (dd, J=4.60, 2.02 Hz, 1H), 15.77 (s, 1H).

EXAMPLE 45

1-[2-(1-cyclohexen-1-yl)ethyl]-3-(1,1-dioxido-4H-1,2,4-benzothiadiazin-3-yl)-4-hydroxy-1,8-naphthyridin-2(1H)-one

EXAMPLE 45A ethyl 2-{[2-(1-cyclohexen-1-yl)ethyl]amino}nicotinate

The title compound was prepared according to the procedure of Example 3A substituting 2-(1-cyclohexenyl)ethylamine for 2-ethylbutylamine (2.2 g, 80%). MS (DCI) m/z 275 (M+H)$^+$.

EXAMPLE 45B

1-[2-(1-cyclohexen-1-yl)ethyl]-2H-pyrido[2,3-d][1,3]oxazine-2,4(1H)-dione

The title compound was prepared according to the procedure of Example 3B substituting the product of Example 45A for the product of Example 3A (0.493 g, 91%). MS (DCI) m/z 290 (M+NH$_4$)$^+$.

EXAMPLE 45C

1-[2-(1-cyclohexen-1-yl)ethyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 45B for the product of Example 1B (0.048 g, 14%). MS (ESI−) m/z 449 (M−H)$^-$. The sodium salt of the title compound was prepared according to the procedure of Example 1D. $^1$H NMR (300 MHz, DMSO-d$_6$) δ 1.53 (m, 4H), 1.90 (m, 2H), 2.05 (m, 2H), 2.18 (t, J=7.54 Hz, 2H), 4.36 (m, 2H), 5.38 (s, 1H), 7.13 (dd, J=7.72, 4.78 Hz, 1H), 7.28 (m, 2H), 7.55 (td, J=7.72, 1.47 Hz, 1H), 7.66 (dd, J=7.72, 1.47 Hz, 1H), 8.37 (dd, J=7.54, 2.02 Hz, 1H), 8.52 (dd, J=4.60, 2.02 Hz, 1H), 15.91 (s, 1H).

EXAMPLE 46

3-(1,1-dioxido-4H-1,2,4-benzothiadiazin-3-yl)-4-hydroxy-1-[(2-methyl-1,3-thiazol-4-yl)methyl]-1,8-naphthyridin-2(1H)-one

EXAMPLE 46A

1-[(2-methyl-1,3-thiazol-4-yl)methyl]-2H-pyrido[2,3-d][1,3]oxazine-2,4(1H)-dione The title compound was prepared according to the procedure of Example 1B substituting 4-chloromethyl-2-methylthiazole for n-butyl bromide (0.087 g, 26%). $^1$H NMR (300 MHz, DMSO-d$_6$) δ 2.63 (s, 3H), 5.37 (d, J=1.47 Hz, 2H), 7.39 (s, 1H), 7.40 (dd, J=7.72, 4.78 Hz, 1H), 8.44 (dd, J=7.72, 1.84 Hz, 1H), 8.72 (dd, J=4.78, 1.84 Hz, 1H).

EXAMPLE 46B 3-(1,1-dioxido-4H-1,2,4-benzothiadiazin-3-yl)-4-hydroxy-1-[(2-methyl-1,3-thiazol-4-yl)methyl]-1,8-naphthyridin-2(1H)-one The title compound was prepared according to the procedure of Example 1D substituting the product of Example 46A for the product of Example 1B (0.078 g, 56%). MS (DCI/NH$_3$) m/z 454 (M+H)$^+$. The sodium salt of the title compound was prepared according to the procedure of Example 1D. $^1$H NMR (300 MHz, DMSO-d$_6$) δ 2.61 (s, 3H), 5.55 (s, 2H), 6.74 (s, 1H), 7.16 (dd, J=7.73, 4.78 Hz, 1H), 7.29 (m, 2H), 7.55 (m, 1H), 7.67 (d, J=7.72 Hz, 1H), 8.41 (dd, J=7.72, 1.84 Hz, 1H), 8.47 (dd, J=4.78, 2.21 Hz, 1H), 15.85 (s, 1H).

EXAMPLE 47

2-{[3-(1,1-dioxido-4H-1,2,4-benzothiadiazin-3-yl)-4-hydroxy-2-oxo-1,8-naphthyridin-1(2H)-yl]methyl}benzonitrile

EXAMPLE 47A

2-[(2,4-dioxo-2H-pyrido[2,3-d][1,3]oxazin-1(4H)-yl)methyl]benzonitrile

The title compound was prepared according to the procedure of Example 1B substituting 2-cyanobenzyl bromide for n-butyl bromide (0.332 g, 65%). MS (DCI) m/z 280 (M+H)$^+$.

EXAMPLE 47B

2-{[3-(1,1-dioxido-4H-1,2,4-benzothiadiazin-3-yl)-4-hydroxy-2-oxo-1,8-naphthyridin-1(2H)-yl]methyl}benzonitrile The title compound was prepared according to the procedure of Example 1D substituting the product of Example 47A for the product of Example 1B (0.183 g, 66%). MS (ESI–) m/z 456 (M–H)$^-$. The sodium salt of the title compound was prepared according to the procedure of Example 1D. $^1$H NMR (300 MHz, DMSO-d$_6$) δ 5.68 (s, 2H), 7.00 (d, J=8.09 Hz, 1H), 7.19 (dd, J=7.35, 4.78 Hz, 1H), 7.30 (t, J=8.09 Hz, 2H), 7.39 (t, J=7.54 Hz, 1H), 7.56 (t, J=7.85 Hz, 2H), 7.67 (d, J=7.72 Hz, 1H), 7.84 (d, J=7.72 Hz, 1H), 8.44 (m, 2H), 15.75 (s, 1H).

EXAMPLE 48

3-(1,1-dioxido-4H-1,2,4-benzothiadiazin-3-yl)-4-hydroxy-1-[(5-methyl-3-isoxazolyl)methyl]-1,8-naphthyridin-2(1H)-one

EXAMPLE 48A

1-[(5-methyl-3-isoxazolyl)methyl]-2H-pyrido[2,3-d][1,3]oxazine-2,4(1H)-dione

The title compound was prepared according to the procedure of Example 1B substituting 3-chloromethyl-5-methylisoxazole for n-butyl bromide (0.047 g, 15%). $^1$H NMR (300 MHz, DMSO-d$_6$) δ 2.34 (s, 3H), 5.35 (s, 2H), 6.26 (d, J=1.10 Hz, 1H), 7.42 (dd, J=7.72, 4.78 Hz, 1H), 8.44 (dd, J=7.72, 1.84 Hz, 1H), 8.75 (dd, J=5.15, 1.84 Hz, 1H).

EXAMPLE 48B 3-(1,1-dioxido-4H-1,2,4-benzothiadiazin-3-yl)-4-hydroxy-1-[(5-methyl-3-isoxazolyl)methyl]-1,8-naphthyridin-2(1H)-one The title compound was prepared according to the procedure of Example 1D substituting the product of Example 48A for the product of Example 1B (0.051 g, 67%). MS (ESI–) m/z 436 (M–H)$^-$. The sodium salt of the title compound was prepared according to the procedure of Example 1D. $^1$H NMR (300 MHz, DMSO-d$_6$) δ 2.29 (s, 3H), 5.50 (s, 2H), 5.94 (s, 1H), 7.18 (dd, J=7.72, 4.78 Hz, 1H), 7.29 (m, 2H), 7.56 (t, J=8.09 Hz, 1H), 7.67 (d, J=8.09 Hz, 1H), 8.41 (dd, J=7.72, 1.84 Hz, 1H), 8.49 (dd, J=4.78, 2.21 Hz, 1H), 15.76 (s, 1H).

EXAMPLE 49

3-(1,1-dioxido-4H-1,2,4-benzothiadiazin-3-yl)-4-hydroxy-1-(1-naphthylmethyl)-1,8-naphthyridin-2(1H)-one

EXAMPLE 49A 1-(2-naphthylmethyl)-2H-pyrido[2,3-d][1,3]oxazine-2,4(1H)-dione

The title compound was prepared according to the procedure of Example 1B substituting 1-(bromomethyl)naphthalene for n-butyl bromide (0.391 g, 71%). MS (DCI) m/z 305 (M+H)$^+$.

EXAMPLE 49B 3-(1,1-dioxido-4H-1,2,4-benzothiadiazin-3-yl)-4-hydroxy-1-(1-naphthylmethyl)-1,8-naphthyridin-2(1H)-one The title compound was prepared according to the procedure of Example 1D substituting the product of Example 49A for the product of Example 1B (0.087 g, 60%). MS (ESI–) m/z 481 (M–H)$^-$; $^1$H NMR (300 MHz, DMSO-d$_6$) δ 5.88 (s, 2H), 7.45 (m, 2H), 7.54 (t, J=7.72 Hz, 3H), 7.65 (d, J=7.72 Hz, 1H), 7.75 (m, 2H), 7.81 (dd, J=6.07, 3.49 Hz, 1H), 7.86 (d, J=8.46 Hz, 2H), 7.93 (d, J=7.35 Hz, 1H), 8.63 (dd, J=7.72, 1.84 Hz, 1H), 8.83 (dd, J=4.78, 1.84 Hz, 1H), 14.04 (s, 1H). The sodium salt of the title compound was prepared according to the procedure of Example 1D. $^1$H NMR (300 MHz, DMSO-d$_6$) δ 5.69 (s, 2H), 7.16 (dd, J=7.54, 4.60 Hz, 1H), 7.29 (t, J=7.72 Hz, 2H), 7.43 (m, 2H), 7.49 (dd, J=8.64, 1.65 Hz, 1H), 7.56 (td, J=7.72, 1.47 Hz, 1H), 7.67 (d, J=7.35 Hz, 2H), 7.83 (m, 3H), 8.42 (dd, J=7.54, 2.02 Hz, 1H), 8.48 (dd, J=4.60, 2.02 Hz, 1H), 15.86 (s, 1H).

EXAMPLE 50

3-(1,1-dioxido-4H-1,2,4-benzothiadiazin-3-yl)-4-hydroxy-1-(2-pyridinylmethyl)-1,8-naphthyridin-2(1H)-one

EXAMPLE 50A 1-(2-pyridinylmethyl)-2H-pyrido[2,3-d][1,3]oxazine-2,4(1H)-dione The title compound was prepared according to the procedure of Example 1B substituting 2-(bromomethyl)pyridine for n-butyl bromide (0.060 g, 19%). $^1$H NMR (300 MHz, DMSO-d$_6$) δ 5.45 (s, 2H), 7.26 (m, 1H), 7.39 (dd, J=7.72, 4.78 Hz, 1H), 7.45 (d, J=8.09 Hz, 1H), 7.73 (m, 1H), 8.46 (dd, J=7.72, 1.84 Hz, 1H), 8.47 (m, 1H), 8.68 (dd, J=4.78, 1.47 Hz, 1H).

EXAMPLE 50B 3-(1,1-dioxido-4H-1,2,4-benzothiadiazin-3-yl)-4-hydroxy-1-(2-pyridinylmethyl)-1,8-naphthyridin-2(1H)-one The title compound was prepared according to the procedure of Example 1D substituting the product of Example 50A for the product of Example 1B (0.072 g, 72%). MS (ESI−) m/z 432 (M−H)$^−$. The sodium salt of the title compound was prepared according to the procedure of Example 1D. $^1$H NMR (300 MHz, DMSO-d$_6$) δ 5.62 (s, 2H), 6.97 (d, J=8.09 Hz, 1H), 7.18 (m, 2H), 7.31 (m, 2H), 7.62 (m, 3H), 8.44 (d, J=6.62 Hz, 3H), 15.71 (s, 1H).

EXAMPLE 51

1-(4-tert-butylbenzyl)-3-(1,1-dioxido-4H-1,2,4-benzothiadiazin-3-yl)-4-hydroxy-1,8-naphthyridin-2(1H)-one

EXAMPLE 51A 1-(4-tert-butylbenzyl)-2H-pyrido[2,3-d][1,3]oxazine-2,4(1H)-dione The title compound was prepared according to the procedure of Example 1B substituting 4-(tert-butyl)benzyl bromide for n-butyl bromide (0.410 g, 72%). MS (DCI) m/z 311 (M+H)$^+$.

EXAMPLE 51B 1-(4-tert-butylbenzyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 51A for the product of Example 1B (0.109 g, 70%). MS (ESI−) m/z 487 (M−H)$^−$. The sodium salt of the title compound was prepared according to the procedure of Example 1D. $^1$H NMR (300 MHz, DMSO-d$_6$) δ 1.23 (s, 9H), 5.49 (s, 2H), 7.16 (m, 3H), 7.28 (m, 4H), 7.55 (td, J=7.91, 1.47 Hz, 1H), 7.66 (d, J=6.25 Hz, 1H), 8.40 (dd, J=7.72, 2.21 Hz, 1H), 8.49 (dd, J=4.60, 2.02 Hz, 1H), 15.84 (s, 1H).

EXAMPLE 52 ethyl [3-(1,1-dioxido-4H-1,2,4-benzothiadiazin-3-yl)-4-hydroxy-2-oxo-1,8-naphthyridin-1(2H)-yl] acetate

EXAMPLE 52A ethyl (2,4-dioxo-2H-pyrido[2,3-d][1,3]oxazin-1(4H)-yl)acetate

The title compound was prepared according to the procedure of Example 1B substituting ethyl bromoacetate for n-butyl bromide (0.174 g, 43%). $^1$H NMR (300 MHz, DMSO-d$_6$) δ 1.21 (t, J=7.17 Hz, 3H), 4.18 (q, J=7.11 Hz, 2H), 4.92 (s, 2H), 7.45 (dd, J=7.72, 4.78 Hz, 1H), 8.47 (dd, J=7.91, 1.65 Hz, 1H), 8.77 (dd, J=4.78, 1.84 Hz, 1H).

EXAMPLE 52B ethyl [3-(1,1-dioxido-4H-1,2,4-benzothiadiazin-3-yl)-4-hydroxy-2-oxo-1,8-naphthyridin-1(2H)-yl] acetate The title compound was prepared according to the procedure of Example 1D substituting the product of Example 52A for the product of Example 1B (0.200 g, 52%). MS (ESI−) m/z 427 (M−H)$^−$; $^1$H NMR (300 MHz, DMSO-d$_6$/CF$_3$COOD) δ 1.26 (t, J=6.99 Hz, 3H), 4.22 (q, J=7.11 Hz, 2H), 5.34 (s, 2H), 7.44 (dd, J=7.91, 4.60 Hz, 1H), 7.54 (m, 2H), 7.74 (m, 1H), 7.96 (m, 1H), 8.63 (dd, J=8.09, 1.84 Hz, 1H), 8.79 (dd, J=4.78, 1.84 Hz, 1H).

EXAMPLE 53

[3-(1,1-dioxido-4H-1,2,4-benzothiadiazin-3-yl)-4-hydroxy-2-oxo-1,8-naphthyridin-1(2H)-yl]acetic acid To a suspension of the product of Example 52B in 1:1 THF:methanol (6 mL) was added 0.5 N aqueous lithium hydroxide (6 mL). The mixture was stirred at room temperature for 2 hours, adjusted to pH 3 with 1.0 N HCl, and filtered. The filter cake was washed with water and dried to give the title compound (0.133 g, 86%). MS (ESI−) m/z 399 (M−H)$^−$; $^1$H NMR (300 MHz, DMSO-d$_6$) δ 5.16 (s, 2H), 7.54 (m, 2H), 7.67 (d, J=7.72 Hz, 1H), 7.77 (t, J=7.72 Hz, 1H), 7.92 (d, J=7.72 Hz, 1H), 8.60 (dd, J=8.09, 1.84 Hz, 1H), 8.84 (dd, J=4.60, 1.65 Hz, 1H), 13.11 (br s, 1H), 13.79 (br s, 1H).

EXAMPLE 54

3-(1,1-dioxido-4H-1,2,4-benzothiadiazin-3-yl)-4-hydroxy-1-(3-phenoxybenzyl)-1,8-naphthyridin-2(1H)-one

EXAMPLE 54A 1-(3-phenoxybenzyl)-2H-pyrido[2,3-d][1,3]oxazine-2,4(1H)-dione

The title compound was prepared according to the procedure of Example 1B substituting 3-phenoxybenzyl chloride for n-butyl bromide (0.190 g, 31%). MS (DCI) m/z 347 (M+H)$^+$.

EXAMPLE 54B 3-(1,1-dioxido-4H-1,2,4-benzothiadiazin-3-yl)-4-hydroxy-1-(3-phenoxybenzyl)-1,8-naphthyridin-2(1H)-one The title compound was prepared according to the procedure of Example 1D substituting the product of Example 54A for the product of Example 1B (0.063 g, 52%). MS (ESI−) m/z 523 (M−H)$^−$. The sodium salt of the title compound was prepared according to the procedure of Example 1D. $^1$H NMR (300 MHz, DMSO-d$_6$) δ 5.51 (s, 2H), 6.77 (dd, J=8.09, 1.47 Hz, 1H), 6.91 (s, 1H), 6.99 (t, J=8.46 Hz, 2H), 7.10 (t, J=7.35 Hz, 1H), 7.19 (m, 1H), 7.31 (m, 6H), 7.57 (t, J=7.72

Hz, 1H), 7.68 (d, J=7.72 Hz, 1H), 8.41 (dd, J=7.72, 1.84 Hz, 1H), 8.48 (d, J=2.94 Hz, 1H), 15.74 (s, 1H).

EXAMPLE 55

1-allyl-3-(1,1-dioxido-4H-1,2,4-benzothiadiazin-3-yl)-4-hydroxy-1,8-naphthyridin-2(1H)-one

EXAMPLE 55A 1-allyl-2H-pyrido[2,3-d][1,3]oxazine-2,4(1H)-dione

The title compound was prepared according to the procedure of Example 1B substituting allyl bromide for n-butyl bromide (5.12 g, 82%). MS (DCI/NH$_3$) m/z 205 (M+H)$^+$. $^1$H NMR (300 MHz, DMSO-d$_6$) δ 4.75 (m, 2H), 5.14 (dd, J=10.66, 1.47 Hz, 1H), 5.27 (dd, J=17.28, 1.47 Hz, 1H), 5.92 (m, 1H), 7.39 (dd, J=7.72, 4.78 Hz, 1H), 8.40 (dd, J=7.91, 2.02 Hz, 1H), 8.75 (dd, J=4.78, 1.84 Hz, 1H).

EXAMPLE 55B 1-allyl-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 55A for the product of Example 1B (1.4 g, 34.5%). MS (DCI/NH$_3$) m/z 383 (M+H)$^+$. $^1$H NMR (300 MHz, DMSO-d$_6$) δ 5.03 (m, 1H), 5.11-5.15 (m, 3H), 5.93-6.07 (m, 1H), 7.45-7.60 (m, 2H), 7.65-7.72 (m, J=8.46 Hz, 1H), 7.73-7.80 (t, J=7.72 Hz, 1H), 7.92 (d, J=7.35 Hz, 1H), 8.58 (dd, J=8.09, 1.84 Hz, 1H), 8.85 (dd, J=4.60, 1.65 Hz, 1H).

EXAMPLE 56

3-(1,1-dioxido-4H-1,2,4-benzothiadiazin-3-yl)-4-hydroxy-1-(2-naphthylmethyl)-1,8-naphthyridin-2(1H)-one

EXAMPLE 56A 1-(2-naphthylmethyl)-2H-pyrido[2,3-d][1,3]oxazine-2,4(1H)-dione

The title compound was prepared according to the procedure of Example 1B substituting 2-(bromomethyl)naphthalene for n-butyl bromide (0.417 g, 75%). MS (DCI) m/z 305 (M+H)$^+$.

EXAMPLE 56B 3-(1,1-dioxido-4H-1,2,4-benzothiadiazin-3-yl)-4-hydroxy-1-(2-naphthylmethyl)-1,8-naphthyridin-2(1H)-one The title compound was prepared according to the procedure of Example 1D substituting the product of Example 56A for the product of Example 1B (0.022 g, 42%). MS (ESI−) m/z 481 (M−H)$^−$; $^1$H NMR (300 MHz, DMSO-d$_6$) δ 6.18 (s, 2H), 6.83 (d, J=6.62 Hz, 1H), 7.28 (m, 1H), 7.53 (t, J=7.54 Hz, 2H), 7.68 (m, 4H), 7.81 (d, J=8.09 Hz, 1H), 7.92 (d, J=7.35 Hz, 1H), 8.00 (d, J=8.09 Hz, 1H), 8.32 (d, J=8.46 Hz, 1H), 8.66 (dd, J=8.09, 1.84 Hz, 1H), 8.74 (dd, J=4.78, 1.84 Hz, 1H), 14.04 (s, 1H). The sodium salt of the title compound was prepared according to the procedure of Example 1D. $^1$H NMR (300 MHz, DMSO-d$_6$) δ 6.00 (s, 2H), 6.76 (d, J=6.25 Hz, 1H), 7.18 (dd, J=7.54, 4.96 Hz, 1H), 7.30 (m, 3H), 7.63 (m, 4H), 7.75 (d, J=8.09 Hz, 1H), 7.97 (d, J=6.99 Hz, 1H), 8.31 (d, J=8.46 Hz, 1H), 8.40 (d, J=3.68 Hz, 1H), 8.47 (dd, J=7.72, 1.84 Hz, 1H), 15.78 (s, 1H).

EXAMPLE 57

3-(1,1-dioxido-4H-1,2,4-benzothiadiazin-3-yl)-4-hydroxy-1-[(1R)-1-phenylethyl]-1,8-naphthyridin-2(1H)-one

EXAMPLE 57A ethyl 2-{[(1R)-1-phenylethyl]amino}nicotinate

The title compound was prepared according to the procedure of Example 3A substituting (R)-(+)-α-methylbenzylamine for 2-ethylbutylamine (2.23 g, 82%). MS (DCI) m/z 271 (M+H)$^+$.

EXAMPLE 57B

1-[(1R)-1-phenylethyl]-2H-pyrido[2,3-d][1,3]oxazine-2,4(1H)-dione

The title compound was prepared according to the procedure of Example 3B substituting the product of Example 57A for the product of Example 3A (0.250 g, 62%). $^1$H NMR (300 MHz, DMSO-d$_6$) δ 1.86 (d, J=6.99 Hz, 3H), 6.65 (q, J=6.99 Hz, 1H), 7.27 (m, 3H), 7.40 (m, 3H), 8.43 (dd, J=7.72, 1.84 Hz, 1H), 8.73 (dd, J=4.96, 2.02 Hz, 1H).

EXAMPLE 57C 3-(1,1-dioxido-4H-1,2,4-benzothiadiazin-3-yl)-4-hydroxy-1-[(1R)-1-phenylethyl]-1,8-naphthyridin-2(1H)-one The title compound was prepared according to the procedure of Example 1D substituting the product of Example 57B for the product of Example 1B (0.080 g, 36%). MS (ESI−) m/z 445 (M−H)$^−$. The sodium salt of the title compound was prepared according to the procedure of Example 1D. $^1$H NMR (300 MHz, DMSO-d$_6$) δ 1.90 (d, J=7.35 Hz, 3H), 6.87 (m, 1H), 7.12 (m, 2H), 7.25 (m, 6H), 7.55 (m, 1H), 7.65 (d, J=7.72 Hz, 1H), 8.40 (d, J=6.25 Hz, 2H), 15.92 (s, 1H).

EXAMPLE 58

1-[(5-tert-butyl-2-thienyl)methyl]-3-(1,1-dioxido-4H-1,2,4-benzothiadiazin-3-yl)-4-hydroxy-1,8-naphthyridin-2(1H)-one

EXAMPLE 58A

1-[(5-tert-butyl-2-thienyl)methyl]-2H-pyrido[2,3-d][1,3]oxazine-2,4(1H)-dione

The title compound was prepared according to the procedure of Example 1B substituting 2-bromomethyl-5-tert-butylthiophene for n-butyl bromide (0.098 g, 25%). $^1$H NMR (300 MHz, DMSO-d$_6$) δ 1.28 (s, 9H), 5.39 (s, 2H), 6.71 (d, J=3.68 Hz, 1H), 7.00 (d, J=3.68 Hz, 1H), 7.42 (dd, J=7.72, 4.78 Hz, 1H), 8.40 (dd, J=7.72, 1.47 Hz, 1H), 8.83 (dd, J=4.78, 1.84 Hz, 1H).

EXAMPLE 58B

1-[(5-tert-butyl-2-thienyl)methyl]-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 58A for the product of Example 1B (0.082 g, 54%). MS (ESI−) m/z 493 (M−H)⁻. The sodium salt of the title compound was prepared according to the procedure of Example 1D. $^1$H NMR (300 MHz, DMSO-$d_6$) δ 1.25 (s, 9H), 5.55 (s, 2H), 6.63 (d, J=3.31 Hz, 1H), 6.89 (d, J=3.31 Hz, 1H), 7.18 (dd, J=7.72, 4.78 Hz, 1H), 7.28 (m, 2H), 7.56 (m, 1H), 7.67 (d, J=7.72 Hz, 1H), 8.39 (dd, J=7.72, 1.84 Hz, 1H), 8.57 (dd, J=4.78, 1.84 Hz, 1H), 15.83 (s, 1H).

EXAMPLE 59

1-(1,1'-biphenyl-4-ylmethyl)-3-(1,1-dioxido-4H-1,2,4-benzothiadiazin-3-yl)-4-hydroxy-1,8-naphthyridin-2(1H)-one

EXAMPLE 59A 1-(1,1'-biphenyl-4-ylmethyl)-2H-pyrido[2,3-d][1,3]oxazine-2,4(1H)-dione The title compound was prepared according to the procedure of Example 1B substituting 4-phenylbenzyl chloride for n-butyl bromide (0.119 g, 20%). MS (DCI) m/z 331 (M+H)⁺.

EXAMPLE 59B 1-(1,1'-biphenyl-4-ylmethyl)-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 59A for the product of Example 1B (0.061 g, 50%). MS (ESI−) m/z 507 (M−H)⁻. The sodium salt of the title compound was prepared according to the procedure of Example 1D. $^1$H NMR (300 MHz, DMSO-$d_6$) δ 5.57 (s, 2H), 7.17 (dd, J=7.72, 4.78 Hz, 1H), 7.31 (m, 5H), 7.42 (t, J=7.54 Hz, 2H), 7.57 (m, 5H), 7.67 (d, J=8.09 Hz, 1H), 8.42 (dd, J=7.72, 1.84 Hz, 1H), 8.50 (dd, J=4.60, 2.02 Hz, 1H), 15.84 (s, 1H).

EXAMPLE 60

3-(1,1-dioxido-4H-1,2,4-benzothiadiazin-3-yl)-4-hydroxy-1-[2-(1H-indol-3-yl)ethyl]-1,8-naphthyridin-2(1H)-one

EXAMPLE 60A ethyl 2-{[2-(1H-indol-3-yl)ethyl]amino}nicotinate

The title compound was prepared according to the procedure of Example 3A substituting tryptamine for 2-ethylbutylamine (1.24 g, 80%). MS (DCI) m/z 310 (M+H)⁺.

EXAMPLE 60B

1-[2-(1H-indol-3-yl)ethyl]-2H-pyrido[2,3-d][1,3]oxazine-2,4(1H)-dione

The title compound was prepared according to the procedure of Example 3B substituting the product of Example 60A for the product of Example 3A (0.164 g, 53%). MS (DCI) m/z 325 (M+NH₄)⁺.

EXAMPLE 60C 3-(1,1-dioxido-4H-1,2,4-benzothiadiazin-3-yl)-4-hydroxy-1-[2-(1H-indol-3-yl)ethyl]-1,8-naphthyridin-2(1H)-one The title compound was prepared according to the procedure of Example 1D substituting the product of Example 60B for the product of Example 1B (0.140 g, 54%). MS (ESI−) m/z 484 (M−H)⁻. The sodium salt of the title compound was prepared according to the procedure of Example 1D. $^1$H NMR (300 MHz, DMSO-$d_6$) δ 3.09 (m, 2H), 4.75 (m, 2H), 7.08 (m, 2H), 7.27 (d, J=2.57 Hz, 1H), 7.36 (d, J=6.99 Hz, 1H), 7.54 (m, 2H), 7.77 (m, 3H), 7.94 (d, J=7.72 Hz, 1H), 8.60 (dd, J=8.09, 1.84 Hz, 1H), 8.95 (dd, J=4.78, 1.84 Hz, 1H), 10.88 (s, 1H).

EXAMPLE 61

3-(1,1-dioxido-4H-1,2,4-benzothiadiazin-3-yl)-1-[(6-ethoxy-2-pyridinyl)methyl]-4-hydroxy-1,8-naphthyridin-2(1H)-one

EXAMPLE 61A

1-[(6-chloro-2-pyridinyl)methyl]-2H-pyrido[2,3-d][11,3]oxazine-2,4(1H)-dione

The title compound was prepared according to the procedure of Example 1B substituting 2-bromomethyl-6-chloropyridine for n-butyl bromide (0.159 g, 45%). $^1$H NMR (300 MHz, DMSO-$d_6$) δ 5.40 (s, 2H), 7.41 (m, 2H), 7.49 (d, J=7.72 Hz, 1H), 7.80 (t, J=7.72 Hz, 1H), 8.46 (dd, J=7.72, 1.84 Hz, 1H), 8.68 (dd, J=5.15, 1.84 Hz, 1H).

EXAMPLE 61B 3-(1,1-dioxido-4H-1,2,4-benzothiadiazin-3-yl)-1-[(6-ethoxy-2-pyridinyl)methyl]-4-hydroxy-1,8-naphthyridin-2(1H)-one The title compound was prepared according to the procedure of Example 1D substituting the product of Example 61A for the product of Example 1B (0.109 g, 42%). MS (ESI−) m/z 476 (M−H)⁻. The sodium salt of the title compound was prepared according to the procedure of Example 1D. $^1$H NMR (300 MHz, DMSO-$d_6$) δ 1.19 (t, J=6.99 Hz, 3H), 4.17 (q, J=6.99 Hz, 2H), 5.52 (s, 2H), 6.45 (d, J=7.35 Hz, 1H), 6.54 (d, J=7.72 Hz, 1H), 7.15 (m, 1H), 7.29 (t, J=7.72 Hz, 2H), 7.54 (m, 2H), 7.66 (d, J=8.09 Hz, 1H), 8.42 (m, 2H), 15.83 (s, 1H).

EXAMPLE 62

1-benzyl-3-(1,1-dioxido-4H-1,2,4-benzothiadiazin-3-yl)-4-hydroxy-7-methyl-1,8-naphthyridin-2(1H)-one

EXAMPLE 62A phenylmethanaminium 2-(benzylamino)-6-methylnicotinate

The title compound was prepared as a benzylamine salt according to the procedure of Example 3A substituting 2-chloro-6-methyl-nicotinic acid for 2-chloro-nicotinic acid ethyl ester and benzyl amine for 2-ethylbutylamine (0.480 g, 46%). MS (ESI+) m/z 243.03 (M+H)$^+$; $^1$H NMR (300 MHz, CDCl$_3$) δ 2.35 (s, 3H), 3.67 (s, 2H), 4.65 (s, 2H), 5.73 (br s, 3H), 6.16 (d, J=7.72 Hz, 1H), 7.17 (m, 10H), 7.76 (d, J=7.35 Hz, 1H), 8.66 (br s, 1H).

EXAMPLE 62B 1-benzyl-7-methyl-2H-pyrido[2,3-d][1,3]oxazine-2,4(1H)-dione

The title compound was prepared according to the procedure of Example 3B substituting the product of Example 62A for the product of Example 3A (0.150 g, 50%). $^1$H NMR (300 MHz, CDCl$_3$) δ 2.66 (s, 3H), 5.47 (s, 2H), 7.10 (d, J=8.09 Hz, 1H), 7.31 (m, 3H), 7.55 (dd, J=7.54, 1.65 Hz, 2H), 8.26 (d, J=8.09 Hz, 1H).

EXAMPLE 62C 1-benzyl-3-(1,1-dioxido-4H-1,2,4-benzothiadiazin-3-yl)-4-hydroxy-7-methyl-1,8-naphthyridin-2(1H)-one The title compound was prepared according to the procedure of Example 1D substituting the product of Example 62B for the product of Example 1B (0.53 g, 51%). $^1$H NMR (300 MHz, DMSO-d$_6$) δ 2.61 (s, 3H), 5.69 (s, 2H), 7.30 (m, 6H), 7.53 (m, 1H), 7.64 (m, J=7.35 Hz, 1H), 7.74 (t, J=7.54 Hz, 1H), 7.90 (d, J=8.82 Hz, 1H), 8.46 (d, J=8.46 Hz, 1H). The sodium salt of the title compound was prepared according to the procedure of Example 1D. MS (ESI+) m/z 447.0 (M+H)$^+$; $^1$H NMR (300 MHz, DMSO-d$_6$) δ 2.48 (s, 3H), 5.50 (s, 2H), 7.25 (m, 7H), 7.54 (m, 1H), 7.66 (d, J=6.25 Hz, 1H), 8.28 (d, J=7.72 Hz, 1H), 15.95 (s, 1H).

EXAMPLE 63

3-(1,1-dioxido-4H-1,2,4-benzothiadiazin-3-yl)-4-hydroxy-1-[(6-methyl-2-pyridinyl)methyl]-1,8-naphthyridin-2(1H)-one

EXAMPLE 63A

1-[(6-methyl-2-pyridinyl)methyl]-2H-pyrido[2,3-d][1,3]oxazine-2,4(1H)-dione

The title compound was prepared according to the procedure of Example 1B substituting 2-bromomethyl-6-methylpyridine for n-butyl bromide (0.088 g, 27%). $^1$H NMR (300 MHz, DMSO-d$_6$) δ 2.42 (s, 3H), 5.38 (s, 2H), 7.19 (d, J=7.72 Hz, 1H), 7.37 (m, 2H), 7.58 (t, J=7.72 Hz, 1H), 8.45 (dd, J=7.72, 1.84 Hz, 1H), 8.67 (dd, J=4.78, 1.84 Hz, 1H).

EXAMPLE 63B 3-(1,1-dioxido-4H-1,2,4-benzothiadiazin-3-yl)-4-hydroxy-1-[(6-methyl-2-pyridinyl)methyl]-1,8-naphthyridin-2(1H)-one The title compound was prepared according to the procedure of Example 1D substituting the product of Example 63A for the product of Example 1B (0.081 g, 40%). MS (ESI−) m/z 446 (M−H)$^-$. The sodium salt of the title compound was prepared according to the procedure of Example 1D. $^1$H NMR (300 MHz, DMSO-d$_6$) δ 2.45 (s, 3H), 5.54 (s, 2H), 6.57 (d, J=7.72 Hz, 1H), 7.04 (d, J=7.35 Hz, 1H), 7.16 (dd, J=7.17, 4.96 Hz, 1H), 7.29 (t, J=7.72 Hz, 2H), 7.47 (t, J=7.72 Hz, 1H), 7.56 (m, 1H), 7.66 (d, J=7.72 Hz, 1H), 8.43 (m, 2H), 15.82 (s, 1H).

EXAMPLE 64

3-(1,1-dioxido-4H-1,2,4-benzothiadiazin-3-yl)-1-(1-ethylpropyl)-4-hydroxy-1,8-naphthyridin-2(1H)-one

EXAMPLE 64A ethyl 2-[(1-ethylpropyl)amino]nicotinate

The title compound was prepared according to the procedure of Example 3A substituting 2-ethyl-propylamine for 2-ethylbutylamine (1.45 g, 88%). MS (ESI+) 237.1 (M+H)$^+$. $^1$H NMR (300 MHz, CDCl$_3$) δ 0.93 (t, J=7.35 Hz, 6H), 1.38 (t, J=7.17 Hz, 3H), 1.60 (m, 4H), 4.17 (m, 1H), 4.32 (q, J=7.11 Hz, 2H), 6.45 (dd, J=7.72, 4.78 Hz, 1H), 7.89 (br d, J=8.09 Hz, 1H), 8.10 (dd, J=7.72, 1.84 Hz, 1H), 8.24 (dd, J=4.78, 2.21 Hz, 1H).

EXAMPLE 64B 1-(1-ethylpropyl)-2H-pyrido[2,3-d][1,3]oxazine-2,4(1H)-dione

The title compound was prepared according to the procedure of Example 3B substituting the product of Example 64A for the product of Example 3A (0.120 g, 57%). MS (ESI+) m/z 223.1 (M+H)$^+$; $^1$H NMR (300 MHz, CDCl$_3$) δ 0.87 (t, J=7.54 Hz, 6H), 1.88 (m, 2H), 2.21 (s, 2H), 5.43 (s, 1H), 7.24 (dd, J=6.99, 4.04 Hz, 1H), 8.42 (dd, J=7.72, 1.84 Hz, 1H), 8.68 (dd, J=4.78, 1.84 Hz, 1H).

EXAMPLE 64C 3-(1,1-dioxido-4H-1,2,4-benzothiadiazin-3-yl)-1-(1-ethylpropyl)-4-hydroxy-1,8-naphthyridin-2(1H)-one The title compound was prepared according to the procedure of Example 1D substituting the product of Example 64B for the product of Example 1B (0.030 g, 15%). MS (ESI+) m/z 413.04 (M+H)$^+$; $^1$H NMR (300 MHz, DMSO-d$_6$) δ 0.76 (t, J=7.54 Hz, 6H), 1.90 (m, 2H), 2.29 (m, 2H), 5.37 (m, 0.5H), 5.92 (m, 0.5H), 7.50 (m, 1H), 7.56 (t, J=7.54 Hz, 1H), 7.69 (m, 1H), 7.78 (t, J=7.17 Hz, 1H), 7.93 (d, J=7.35 Hz, 1H), 8.58 (d, J=8.09 Hz, 1H), 8.84 (m, 1H), 14.11 (s, 1H). The sodium salt of the title compound was prepared according to the procedure of Example 1D. MS (ESI+) m/z 413.07 (M+H−Na)$^+$; $^1$H NMR (300 MHz, DMSO-d$_6$) δ 0.74 (t, J=7.35 Hz, 6H), 1.88 (br s, 2H), 2.30 (br s, 2H), 5.35 (br s, 0.5H), 5.78 (br s, 0.5H), 7.28 (br s, 1H), 7.42 (m, J=7.35 Hz, 2H), 7.66 (m, 1H), 7.79 (br d, J=7.35 Hz, 1H), 8.47 (br d, J=7.35 Hz, 1H), 8.64 (br s, 1H).

EXAMPLE 65

3-(1,1-dioxido-4H-1,2,4-benzothiadiazin-3-yl)-4-hydroxy-1-[(1S)-1-phenylethyl]-1,8-naphthyridin-2(1H)-one

EXAMPLE 65A ethyl 2-{[(1S)-1-phenylethyl]amino}nicotinate

The title compound was prepared according to the procedure of Example 3A substituting (S)-(−)-α-methylbenzylamine for 2-ethylbutylamine (2.2 g, 81%). MS (DCI) m/z 271 (M+H)$^+$.

EXAMPLE 65B

1-[(1S)-1-phenylethyl]-2H-pyrido[2,3-d][1,3]oxazine-2,4(1H)-dione

The title compound was prepared according to the procedure of Example 3B substituting the product of Example 65A for the product of Example 3A (0.320 g, 80%). $^1$H NMR (300 MHz, DMSO-d$_6$) δ 1.86 (d, J=6.99 Hz, 3H), 6.65 (q, J=6.99 Hz, 1H), 7.27 (m, 3H), 7.40 (m, 3H), 8.43 (dd, J=7.72, 1.84 Hz, 1H), 8.73 (dd, J=4.96, 2.02 Hz, 1H).

EXAMPLE 65C 3-(1,1-dioxido-4H-1,2,4-benzothiadiazin-3-yl)-4-hydroxy-1-[(1S)-1-phenylethyl]-1,8-naphthyridin-2(1H)-one The title compound was prepared according to the procedure of Example 1D substituting the product of Example 65B for the product of Example 1B (0.122 g, 36%). MS (ESI−) m/z 445 (M−H)$^-$. The sodium salt of the title compound was prepared according to the procedure of Example 1D. $^1$H NMR (300 MHz, DMSO-d$_6$) δ 1.90 (d, J=7.35 Hz, 3H), 6.87 (m, 1H), 7.12 (m, 2H), 7.25 (m, 6H), 7.55 (m, 1H), 7.65 (d, J=7.72 Hz, 1H), 8.40 (d, J=6.25 Hz, 2H), 15.92 (s, 1H).

EXAMPLE 66

2-{2-[3-(1,1-dioxido-4H-1,2,4-benzothiadiazin-3-yl)-4-hydroxy-2-oxo-1,8-naphthyridin-1(2H)-yl]ethyl}-1H-isoindole-1,3(2H)-dione

EXAMPLE 66A

1-[2-(1,3-dioxo-1,3-dihydro-2H-isoindol-2-yl)ethyl]-2H-pyrido[2,3-d][1,3]oxazine-2,4(1H)-dione The title compound was prepared according to the procedure of Example 1B substituting N-(2-bromoethyl)phthalimide for n-butyl bromide (0.121 g, 20%). $^1$H NMR (300 MHz, DMSO-d$_6$) δ 4.00 (t, J=5.52 Hz, 2H), 4.46 (t, J=5.52 Hz, 2H), 7.28 (dd, J=7.72, 4.78 Hz, 1H), 7.80 (s, 4H), 8.38 (dd, J=7.72, 1.84 Hz, 1H), 8.53 (dd, J=4.78, 1.84 Hz, 1H).

EXAMPLE 66B

2-{2-[3-(1,1-dioxido-4H-1,2,4-benzothiadiazin-3-yl)-4-hydroxy-2-oxo-1,8-naphthyridin-1(2H)-yl]ethyl}-1H-isoindole-1,3(2H)-dione The title compound was prepared according to the procedure of Example 1D substituting the product of Example 65B for the product of Example 1B (0.085 g, 46%). MS (ESI−) m/z 514 (M−H)$^-$; $^1$H NMR (300 MHz, DMSO-d$_6$/TFA) δ 4.09 (t, J=5.15 Hz, 2H), 4.87 (m, 2H), 7.11 (dd, J=7.91, 4.60 Hz, 1H), 7.19 (d, J=8.09 Hz, 1H), 7.44 (t, J=7.72 Hz, 1H), 7.58 (m, 5H), 7.84 (d, J=8.09 Hz, 1H), 8.34 (dd, J=4.41, 1.84 Hz, 1H), 8.42 (dd, J=7.91, 1.65 Hz, 1H).

EXAMPLE 67

3-(1,1-dioxido-4H-1,2,4-benzothiadiazin-3-yl)-4-hydroxy-1-(3-hydroxypropyl)-1,8-naphthyridin-2(1H)-one A solution of the product of Example 73 in THF (5 mL) was reacted with sodium borohydride (0.022 g, 0.58 mmol) at 0° C. for 30 minutes. The solution was poured into water and extracted with ethyl acetate. The extract was dried over sodium sulfate, filtered, concentrated and purified by preparative HPLC on a Waters Symmetry C8 column (40 mm×100 mm, 7 μm particle size) using a gradient of 10% to 100% acetonitrile/0.1% aqueous TFA over 12 minutes (15 minute run time) at a flow rate of 70 mL/min to produce the title compound. MS (DCI/NH$_3$) m/z 401 (M+H)$^+$; $^1$H NMR (300 MHz, DMSO-d$_6$) δ 1.87 (m, 2H), 3.54 (t, J=6.43 Hz, 2H), 4.55 (m, 2H), 7.52 (dd, J=8.09, 4.78 Hz, 1H), 7.56 (m, 1H), 7.71 (d, J=8.09 Hz, 1H), 7.79 (m, 1H), 7.94 (d, J=8.09 Hz, 1H), 8.58 (dd, J=8.09, 1.84 Hz, 1H), 8.90 (dd, J=4.60, 1.65 Hz, 1H), 14.13 (s, 1H).

EXAMPLE 68

1-cyclopentyl-3-(1,1-dioxido-4H-1,2,4-benzothiadiazin-3-yl)-4-hydroxy-1,8-naphthyridin-2(1H)-one

EXAMPLE 68A ethyl 2-(cyclopentylamino)nicotinate

The title compound was prepared according to the procedure of Example 3A substituting cyclopentylamine for 2-ethylbutylamine (0.231 g, 67%). MS (ESI+) m/z 235.1 (M+H)$^+$; $^1$H NMR (300 MHz, CDCl$_3$) δ 1.37 (t, J=7.17 Hz, 3H), 1.64 (m, 6H), 2.08 (m, 2H), 4.31 (q, J=7.23 Hz, 2H), 4.45 (m, 1H), 6.48 (dd, J=7.72, 4.78 Hz, 1H), 8.02 (d, J=5.88 Hz, 1H), 8.10 (dd, J=7.91, 2.02 Hz, 1H), 8.28 (dd, J=4.78, 1.84 Hz, 1H).

EXAMPLE 68B 1-cyclopentyl-2H-pyrido[2,3-d][1,3]oxazine-2,4(1H)-dione

The title compound was prepared according to the procedure of Example 3B substituting the product of Example 68A for the product of Example 3A (0.130 g, 56%). MS (ESI+) m/z 221.08 (M+H)$^+$; $^1$H NMR (300 MHz, CDCl$_3$) δ 1.66 (m, 1H), 1.99 (m, 4H), 2.21 (m, 2H), 5.79 (m, 1H), 7.25 (dd, J=8.09, 4.78 Hz, 1H), 8.42 (dd, J=7.72, 2.21 Hz, 1H), 8.70 (dd, J=4.78, 1.84 Hz, 1H).

EXAMPLE 68C 1-cyclopentyl-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 68B for the product of Example 1B (0.133 g, 60%). MS (ESI+) m/z 433.06 (M+H)$^+$; $^1$H NMR (300 MHz, DMSO-d$_6$) δ 1.70 (m, 2H), 1.85 (m, 2H), 2.07 (s, 2H), 2.28 (m, 2H), 6.17 (m, J=8.64, 8.64 Hz, 1H), 7.52 (m, 2H), 7.65 (d, J=7.72 Hz, 1H), 7.77 (m, 1H), 7.93 (d, J=6.99 Hz, 1H), 8.57 (dd, J=7.91, 2.02 Hz, 1H), 8.86 (dd, J=4.78, 1.84 Hz, 1H), 14.05 (br s, 1H). The sodium salt of the title compound was prepared according to the procedure of Example 1D. $^1$H NMR (300 MHz, DMSO-d$_6$) δ 1.63 (m, 2H), 1.79 (br s, 2H), 2.04 (m, 2H), 2.23 (m, 2H), 6.08 (m, 1H), 7.31 (br s, 1H), 7.43 (br s, 2H), 7.65 (d, J=6.25 Hz, 1H), 7.80 (br s, 1H), 8.48 (d, J=7.72 Hz, 1H), 8.69 (br s, 1H).

EXAMPLE 69

3-(1,1-dioxido-4H-1,2,4-benzothiadiazin-3-yl)-1-[2-(1,3-dioxolan-2-yl)ethyl]-4-hydroxy-1,8-naphthyridin-2(1H)-one

EXAMPLE 69A

1-[2-(1,3-dioxolan-2-yl)ethyl]-2H-pyrido[2,3-d][1,3]oxazine-2,4(1H)-dione

The title compound was prepared according to the procedure of Example 1B substituting 2-(2-bromomethyl)-1,3-dioxolane for n-butyl bromide (0.86 g, 53%). MS (DCI/NH$_3$) m/z 265 (M+H)$^+$; $^1$H NMR (300 MHz, DMSO-d$_6$) δ 1.98 (m, 2H), 3.83 (m, 4H), 4.25 (m, 2H), 4.92 (m, 1H), 7.38 (m, 1H), 8.39 (dd, J=7.72, 1.84 Hz, 1H), 8.78 (dd, J=4.96, 2.02 Hz, 1H).

EXAMPLE 69B 3-(1,1-dioxido-4H-1,2,4-benzothiadiazin-3-yl)-1-[2-(1,3-dioxolan-2-yl)ethyl]-4-hydroxy-1,8-naphthyridin-2(1H)-one The title compound was prepared according to the procedure of Example 1D substituting the product of Example 69A for the product of Example 1B (0.89 g, 62%). MS (DCI/NH$_3$) m/z 443 (M+H)$^+$; $^1$H NMR (300 MHz, DMSO-d$_6$) δ 2.03 (m, 2H), 2.50 (m, 2H), 3.84 (m, 2H), 4.59 (m, 2H), 4.97 (t, J=4.60 Hz, 1H), 7.51 (dd, J=7.91, 4.60 Hz, 1H), 7.56 (m, 1H), 7.77 (m, 2H), 7.94 (m, 1H), 8.56 (dd, J=8.09, 1.84 Hz, 1H), 8.89 (dd, J=4.78, 1.84 Hz, 1H), 14.09 (s, 1H).

EXAMPLE 70

1-(2,3-dihydroxypropyl)-3-(1,1-dioxido-4H-1,2,4-benzothiadiazin-3-yl)-4-hydroxy-1,8-naphthyridin-2(1H)-one The product of Example 55B (1.08 g, 0.028 mol) was reacted with osmium tetroxide (0.0007 mol) and N-methylmorpholine N-oxide (4.96 g, 0.043 mol) in a 1:1 mixture of water and THF (50 mL) at room temperature for 18 hours. The reaction mixture was treated with sodium bisulfite and diluted with water. The product precipitated from the aqueous mixture and was collected by vacuum filtration to give the title compound as a a white solid (1.09 g, 93%). MS (DCI/NH$_3$) m/z 417 (M+H)$^+$; $^1$H NMR (300 MHz, DMSO-d$_6$) δ 3.33 (m, 2H), 3.87 (m, 1H), 4.37 (m, 2H), 4.52 (t, J=6.07 Hz, 1H), 4.78 (d, J=5.52 Hz, 1H), 7.17 (dd, J=7.72, 4.78 Hz, 1H), 7.29 (m, 2H), 7.56 (m, 1H), 7.67 (d, J=6.99 Hz, 1H), 8.40 (dd, J=7.72, 1.84 Hz, 1H), 8.53 (dd, J=4.78, 1.84 Hz, 1H), 15.80 (m, 1H).

EXAMPLE 71

1-cycloheptyl-3-(1,1-dioxido-4H-1,2,4-benzothiadiazin-3-yl)-4-hydroxy-1,8-naphthyridin-2(1H)-one

EXAMPLE 71A ethyl 2-(cycloheptylamino)nicotinate

The title compound was prepared according to the procedure of Example 3A substituting cycloheptylamine for 2-ethylbutylamine (1.01 g, 83%). MS (ESI+) m/z 263.1 (M+H)$^+$. $^1$H NMR (300 MHz, CDCl$_3$) δ 1.37 (t, J=7.17 Hz, 3H), 1.62 (m, 10H), 2.02 (m, 2H), 4.29 (m, 1H), 4.31 (q, J=7.35 Hz, 2H), 6.45 (dd, J=7.72, 4.78 Hz, 1H), 8.05 (d, J=6.99 Hz, 1H), 8.10 (dd, J=7.91, 2.02 Hz, 1H), 8.26 (dd, J=4.78, 1.84 Hz, 1H).

EXAMPLE 71B 1-cycloheptyl-2H-pyrido[2,3-d][1,3]oxazine-2,4(1H)-dione

The title compound was prepared according to the procedure of Example 3B substituting the product of Example 71A for the product of Example 3A (0.205 g, 55%). MS (ESI+) m/z 249.1 (M+H)$^+$; $^1$H NMR (300 MHz, CDCl$_3$) δ 1.63 (m, 6H), 1.84 (m, 4H), 2.43 (m, 2H), 5.39 (s, 1H), 7.24 (dd, J=7.72, 4.78 Hz, 1H), 8.40 (m, 1H), 8.71 (dd, J=4.78, 1.84 Hz, 1H).

EXAMPLE 71C 1-cycloheptyl-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 71B for the product of Example 1B (0.041 g, 15%). MS (ESI+) m/z 439.07 (M+H)$^+$. $^1$H NMR (300 MHz, DMSO-d$_6$) δ 1.23 (m, 6H), 1.58 (m, 4H), 1.79 (m, 2H), 5.90 (m, 1H), 7.45 (m, 1H), 7.53 (m, 1H), 7.66 (m, J=9.56 Hz, 1H), 7.74 (d, J=7.72 Hz, 1H), 7.90 (d, J=6.25 Hz, 1H), 8.54 (d, J=7.35 Hz, 1H), 8.85 (s, 1H). The sodium salt of the title compound was prepared according to the procedure of Example 1D. $^1$H NMR (300 MHz, DMSO-d$_6$) δ 1.61 (m, 8H), 1.77 (m, 4H), 1.94 (m, 2H), 5.60 (m, 1H), 7.10 (dd, J=7.54, 4.60 Hz, 1H), 7.54 (m, 1H), 7.66 (dd, J=7.72, 1.47 Hz, 1H), 8.36 (dd, J=7.72, 2.21 Hz, 1H), 8.51 (dd, J=4.78, 2.21 Hz, 1H), 15.99 (s, 1H).

EXAMPLE 72

1-(3-anilinopropyl)-3-(1,1-dioxido-4H-1,2,4-benzothiadiazin-3-yl)-4-hydroxy-1,8-naphthyridin-2(1H)-one A solution of the product of Example 73 (0.090 g, 0.23 mmol) and aniline (0.15 mL, 0.23 mmol) in THF (6 mL) was treated with sodium triacetoxyborohydride (0.08 g, 0.38 mmol) and glacial acetic acid (0.025 mL, 0.43 mmol) at ambient temperature for 24 hours. The solvent was removed under vacuum and the resulting solid was purified by preparative HPLC on a Waters Symmetry C8 column (40 mm×100 mm, 7 μm particle size) using a gradient of 10% to 100% acetonitrile/0.1% aqueous TFA over 12 minutes (15 minutes run time) at a flow rate of 70 mL/min to give the title compound. MS (DCI/NH$_3$) m/z 476 (M+H)$^+$. The title compound was dissolved in 1,4-dioxane (6 mL) and 4M HCl in dioxane (2 mL). After stirring at room temperature for 3 hours, the mixture was filtered and the filter cake was dried to yield the hydrochloride salt. $^1$H NMR (300 MHz, DMSO-d$_6$) δ 2.11 (m, 2H), 3.32 (m, 2H), 4.59 (t, J=6.80 Hz, 2H), 7.18 (s, 3H), 7.34 (d, J=7.35 Hz, 2H), 7.52 (m, 1H), 7.57 (m, 1H), 7.67 (d, J=7.35 Hz, 1H), 7.80 (m, 1H), 7.94 (d, J=7.72 Hz, 1H), 8.59 (dd, J=7.72, 1.84 Hz, 1H), 8.89 (dd, J=4.78, 1.84 Hz, 1H), 13.96 (s, 1H).

EXAMPLE 73

3-[3-(1,1-dioxido-4H-1,2,4-benzothiadiazin-3-yl)-4-hydroxy-2-oxo-1,8-naphthyridin-1(2H)-yl]propanal A stirred suspension of the product of Example 69B (0.65 g, 0.15 mmol) in water (3 mL) and glacial acetic acid (12 mL) at ambient temperature was treated dropwise with sulfuric acid (1 mL). The mixture was heated to 60° C. for 1 hour, and then diluted with water. The mixture was filtered and the filter cake was washed with water and dried to produce the title compound (0.455 g, 78%). MS (DCI/NH$_3$) m/z 399 (M+H)$^+$; $^1$H NMR (300 MHz, DMSO-d$_6$) δ 2.72 (m, 2H), 4.59 (t, J=6.62 Hz, 2H), 7.17 (dd, J=7.72, 4.78 Hz, 1H), 7.28 (m, 1H), 7.55 (m, 1H), 7.67 (d, J=7.72 Hz, 1H), 8.39 (dd, J=7.72, 1.84 Hz, 1H), 8.52 (dd, J=4.78, 1.84 Hz, 1H), 9.76 (t, J=2.21 Hz, 1H), 9.76 (t, J=2.21 Hz, 1H).

EXAMPLE 74 methyl 4-{[3-(1,1-dioxido-4H-1,2,4-benzothiadiazin-3-yl)-4-hydroxy-2-oxo-1,8-naphthyridin-1(2H)-yl]methyl}benzoate

EXAMPLE 74A methyl 4-[(2,4-dioxo-2H-pyrido[2,3-d][1,3]oxazin-1(4H)-yl)methyl]benzoate The title compound was prepared according to the procedure of Example 1B substituting methyl 4-(bromomethyl)benzoate for n-butyl bromide (1.5 g, 75%). MS (DCI) m/z 313 (M+H)$^+$.

EXAMPLE 74B methyl 4-{[3-(1,1-dioxido-4H-1,2,4-benzothiadiazin-3-yl)-4-hydroxy-2-oxo-1,8-naphthyridin-1(2H)-yl]methyl}benzoate The title compound was prepared according to the procedure of Example 1D substituting the product of Example 74A for the product of Example 1B (0.130 g, 37%). MS (ESI–) m/z 489 (M–H)$^−$; $^1$H NMR (300 MHz, DMSO-d$_6$) δ 3.82 (s, 3H), 5.76 (s, 2H), 7.42 (d, J=8.09 Hz, 2H), 7.50 (m, 2H), 7.63 (d, J=7.72 Hz, 1H), 7.74 (t, J=7.72 Hz, 1H), 7.88 (d, J=8.46 Hz, 2H), 7.93 (m, 1H), 8.60 (dd, J=8.09, 1.84 Hz, 1H), 8.78 (d, J=3.31 Hz, 1H), 14.12 (br s, 1H).

EXAMPLE 75 ethyl 5-{[3-(1,1-dioxido-4H-1,2,4-benzothiadiazin-3-yl)-4-hydroxy-2-oxo-1,8-naphthyridin-1(2H)-yl]methyl}-2-furoate

EXAMPLE 75A ethyl 5-[(2,4-dioxo-2H-pyrido[2,3-d][1,3]oxazin-1(4H)-yl)methyl]-2-furoate The title compound was prepared according to the procedure of Example 1B substituting ethyl 5-chloromethyl-2-furancarboxylate for n-butyl bromide (0.073 g, 19%). $^1$H NMR (300 MHz, DMSO-d$_6$) δ 1.34 (t, J=7.17 Hz, 3H), 4.32 (q, J=7.35 Hz, 2H), 5.56 (s, 2H), 6.49 (d, J=3.68 Hz, 1H), 7.09 (d, J=3.31 Hz, 1H), 7.31 (dd, J=7.72, 4.78 Hz, 1H), 8.44 (dd, J=7.72, 1.84 Hz, 1H), 8.76 (dd, J=4.78, 1.84 Hz, 1H).

EXAMPLE 75B ethyl 5-{[3-(1,1-dioxido-4H-1,2,4-benzothiadiazin-3-yl)-4-hydroxy-2-oxo-1,8-naphthyridin-1(2H)-yl]methyl}-2-furoate The title compound was prepared according to the procedure of Example 1D substituting the product of Example 75A for the product of Example 1B (0.074 g, 69%). MS (DCI/NH$_3$) m/z 495 (M+H)$^+$. $^1$H NMR (300 MHz, DMSO-d$_6$) δ 1.26 (t, J=7.17 Hz, 3H), 4.26 (q, J=7.23 Hz, 2H), 5.73 (s, 2H), 6.45 (d, J=3.68 Hz, 1H), 7.19 (d, J=3.68 Hz, 1H), 7.55 (m, 2H), 7.75 (m, 2H), 7.93 (d, J=7.72 Hz, 1H), 8.60 (dd, J=7.91, 1.83 Hz, 1H), 8.86 (dd, J=4.78, 1.84 Hz, 1H), 13.80 (s, 1H). The sodium salt of the title compound was prepared according to the procedure of Example 1D. $^1$H NMR (300 MHz, DMSO-d$_6$) δ 1.27 (t, J=7.17 Hz, 3H), 4.25 (q, J=7.23 Hz, 2H), 5.55 (s, 2H), 6.22 (d, J=3.31 Hz, 1H), 7.14 (d, J=3.31 Hz, 1H), 7.20 (dd, J=7.72, 4.60 Hz, 1H), 7.29 (m, 2H), 7.56 (m, 1H), 7.67 (d, J=8.09 Hz, 1H), 8.42 (dd, J=7.72, 2.20 Hz, 1H), 8.52 (dd, J=4.60, 2.21 Hz, 1H), 15.73 (s, 1H).

EXAMPLE 76

1-[3-(dimethylamino)propyl]-3-(1,1-dioxido-4H-1,2,4-benzothiadiazin-3-yl)-4-hydroxy-1,8-naphthyridin-2(1H)-one A solution of the product of Example 73 (0.085 g, 0.21 mmol) and dimethylamine (2.0 M in THF, 0.110 mL, 0.22 mmol) in tetrahyrofuran (4 mL) was reacted with sodium triacetoxyborohydride (0.06 g, 0.28 mmol) at room temperature for 1 hour. The solvent was removed under vacuum and the resulting solid was triturated with methanol and dimethylsulfoxide (1:1), filtered, and dried to product the title compound (0.56 g, 61%). (DCI/NH$_3$) m/z 428 (M+H)$^+$.

The sodium salt of the title compound was prepared according to the procedure of Example 1D. $^1$H NMR (300 MHz, DMSO-d$_6$) δ 1.72 (m, 2H), 2.15 (s, 6H), 2.29 (t, J=7.17 Hz, 2H), 4.28 (m, 2H), 7.14 (dd, J=7.72, 4.78 Hz, 1H), 7.27 (m, 2H), 7.55 (ddd, J=8.27, 7.17, 1.47 Hz, 1H), 7.67 (dd, J=8.09, 1.47 Hz, 1H), 8.37 (dd, J=7.54, 2.02 Hz, 1H), 8.53 (dd, J=4.78, 1.84 Hz, 1H), 15.93 (s, 1H).

EXAMPLE 77

1-{3-[[2-(dimethylamino)ethyl](methyl)amino]propyl}-3-(1,1-dioxido-4H-1,2,4-benzothiadiazin-3-yl)-4-hydroxy-1,8-naphthyridin-2(1H)-one The title compound was prepared according to the procedure of Example 72 substituting N,N,N-trimethylethylenediamine for aniline. MS (DCI/NH$_3$) m/z 485 (M+H)$^+$. The dihydrochloride salt of the title compound was prepared according to the procedure of Example 72. $^1$H NMR (300 MHz, DMSO-d$_6$) δ 2.20 (s, 2H), 2.84 (m, J=4.41 Hz, 6H), 3.50 (m, 9H), 4.54 (m, 2H), 7.54 (m, 3H), 7.77 (m, 1H), 7.91 (d, J=8.09 Hz, 1H), 8.59 (dd, J=8.09, 1.84 Hz, 1H), 8.85 (dd, J=4.60, 1.65 Hz, 1H), 10.43 (s, 1H), 14.25 (s, 1H).

EXAMPLE 78

3-(1,1-dioxido-4H-1,2,4-benzothiadiazin-3-yl)-4-hydroxy-1-[3-(4-methyl-1-piperazinyl)propyl]-1,8-naphthyridin-2(1H)-one The title compound was prepared according to the procedure of Example 72 substituting 4-methylpiperazine for aniline. MS (ESI-) m/z 450 (M-H)$^-$. The dihydrochloride salt of the title compound was prepared according to the procedure of Example 72. $^1$H NMR (300 MHz, DMSO-d$_6$) δ 2.03 (m, 2H), 3.10 (m, 4H), 3.69 (m, 4H), 3.90 (m, 2H), 4.39 (s, 2H), 7.20 (dd, J=7.72, 4.41 Hz, 1H), 7.30 (m, 2H), 7.58 (m, 1H), 7.68 (d, J=7.72 Hz, 1H), 8.42 (dd, J=7.72, 1.84 Hz, 1H), 8.55 (dd, J=4.41, 1.84 Hz, 1H), 15.71 (s, 1H).

EXAMPLE 79

1-(2-aminoethyl)-3-(1,1-dioxido-4H-1,2,4-benzothiadiazin-3-yl)-4-hydroxy-1,8-naphthyridin-2(1H)-one A solution of Example 66 (45.0 mg, 0.087 mmol) in a mixture of absolute ethanol (1.5 mL), N,N-dimethylformamide (0.8 mL) and dimethyl sulfoxide (1.0 mL) was treated with hydrazine monohydrate (13.42 mg, 0.261 mmol) at room temperature. The mixture was then heated to reflux at 80° C. for 5 hours, cooled to room temperature, and concentrated. The concentrate was purified by a C8 HPLC column eluting with 20% to 80% acetonitrile in water with 1% trifluoroacetic acid to give the TFA salt of the title compound (0.010 g, 23%). MS (APCI+) m/z 386 (M+H)$^-$; $^1$H NMR (300 MHz, DMSO-d$_6$) δ 3.20 (dd, J=11.95, 6.80 Hz, 2H), 4.62 (t, J=5.52 Hz, 2H), 7.27 (m, 1H), 7.39 (m, 2H), 7.65 (t, J=7.35 Hz, 1H), 7.75 (d, J=7.72 Hz, 1H), 7.82 (br s, 3H), 8.42 (d, J=9.56 Hz, 1H), 8.61 (d, J=3.31 Hz, 1H), 15.18 (br s, 1H).

EXAMPLE 80

1-[3-(diethylamino)propyl]-3-(1,1-dioxido-4H-1,2,4-benzothiadiazin-3-yl)-4-hydroxy-1,8-naphthyridin-2(1H)-one The title compound was prepared according to the procedure of Example 72 substituting diethylamine for aniline. MS (DCI/NH$_3$) m/z 456 (M+H)$^+$. The hydrochloride salt of the title compound was prepared according to the procedure of Example 72. $^1$H NMR (300 MHz, DMSO-d$_6$) δ 1.19 (t, J=7.17 Hz, 6H), 2.15 (m, 2H), 3.12 (m, 6H), 4.55 (t, J=6.62 Hz, 2H), 7.57 (m, 2H), 7.66 (m, 1H), 7.80 (m, 1H), 7.95 (d, J=8.09 Hz, 1H), 8.61 (dd, J=7.72, 1.84 Hz, 1H), 8.90 (dd, J=4.60, 1.65 Hz, 1H), 10.05 (s, 1H), 13.92 (s, 1H).

EXAMPLE 81

1-cyclohexyl-3-(1,1-dioxido-4H-1,2,4-benzothiadiazin-3-yl)-4-hydroxy-1,8-naphthyridin-2(1H)-one

EXAMPLE 81A ethyl 2-(cyclohexylamino)nicotinate

The title compound was prepared according to the procedure of Example 3A substituting cyclohexylamine for 2-ethylbutylamine (1.92 g, 61%). MS (ESI+) m/z 249.1 (M+H)$^+$; $^1$H NMR (300 MHz, CDCl$_3$) δ 1.38 (m, 7H), 1.61 (m, 2H), 1.75 (m, 2H), 2.02 (m, 2H), 4.08 (m, 1H), 4.31 (q, J=7.11 Hz, 2H), 6.46 (dd, J=7.72, 4.78 Hz, 1H), 7.99 (d, J=7.72 Hz, 1H), 8.10 (dd, J=7.72, 2.21 Hz, 1H), 8.25 (dd, J=4.78, 1.84 Hz, 1H).

EXAMPLE 81B 1-cyclohexyl-2H-pyrido[2,3-d][1,3]oxazine-2,4(1H)-dione

The title compound was prepared according to the procedure of Example 3B substituting the product of Example 81A for the product of Example 3A (0.171 g, 35%). $^1$H NMR (300 MHz, CDCl$_3$) δ 1.37 (m, 4H), 1.73 (m, 2H), 1.91 (m, 2H), 2.47 (ddd, J=24.82, 12.32, 3.31 Hz, 2H), 5.28 (tt, J=12.27, 3.72 Hz, 1H), 7.24 (dd, J=6.99, 4.04 Hz, 1H), 8.41 (dd, J=7.72, 2.21 Hz, 1H), 8.70 (dd, J=4.78, 2.21 Hz, 1H).

EXAMPLE 81C 1-cyclohexyl-3-(1,1-dioxido-4H-1,2,4-benzothiadiazin-3-yl)-4-hydroxy-1,8-naphthyridin-2(1H)-one The title compound was prepared according to the procedure of Example 1D substituting the product of Example 81B for the product of Example 1B (0.073 g, 26%). MS (ESI+) m/z 425.04 (M+H)$^+$; $^1$H NMR (300 MHz, DMSO-d$_6$) δ 1.25 (m, 4H), 1.76 (m, 4H), 1.91 (s, 2H), 5.64 (s, 1H), 7.48 (dd, J=8.09, 4.78 Hz, 1H), 7.55 (t, J=7.54 Hz, 1H), 7.69 (m, J=8.09 Hz, 1H), 7.77 (m, 1H), 7.92 (d, J=8.09 Hz, 1H), 8.56 (m, J=8.09, 1.84 Hz, 1H), 8.86 (d, J=2.21 Hz, 1H), 14.12 (s, 1H). The sodium salt of the title compound was prepared according to the procedure of Example 1D. MS (ESI+) m/z 425.04 (M+H)$^+$, 447.1 (M+Na)$^+$; $^1$H NMR (300 MHz, DMSO-d$_6$) δ 1.31 (m, 4H), 1.52 (d, J=10.66 Hz, 2H), 1.63 (m, 2H), 1.83 (m, J=12.50 Hz, 2H), 5.41 (t, J=11.03 Hz, 1H), 7.11 (dd, J=7.72, 4.78 Hz, 1H), 7.27 (m, 2H), 7.55 (m, 1H), 7.66 (d, J=6.62 Hz, 1H), 8.37 (dd, J=7.72, 2.21 Hz, 1H), 8.50 (dd, J=4.60, 2.02 Hz, 1H), 15.94 (s, 1H).

EXAMPLE 82

3-(1,1-dioxido-4H-1,2,4-benzothiadiazin-3-yl)-4-hydroxy-1-[3-(4-morpholinyl)propyl]-1,8-naphthyridin-2(1H)-one The title compound was prepared according to the procedure of Example 72 substituting morpholine for aniline (0.053 g 60%). MS (ESI-) m/z 450 (M-H)$^-$. The sodium salt of the title compound was prepared according to the procedure of Example 1D. $^1$H NMR (300 MHz, DMSO-d$_6$) δ 2.03 (m, 2H), 3.10 (m, 4H), 3.69 (m, 4H), 3.90 (m, 2H), 4.39 (s, 2H), 7.20 (dd, J=7.72, 4.41 Hz, 1H), 7.30 (m, 2H), 7.58 (m, 1H), 7.68 (d, J=7.72 Hz, 1H), 8.42 (dd, J=7.72, 1.84 Hz, 1H), 8.55 (dd, J=4.41, 1.84 Hz, 1H), 15.71 (s, 1H).

EXAMPLE 83

5-{[3-(1,1-dioxido-4H-1,2,4-benzothiadiazin-3-yl)-4-hydroxy-2-oxo-1,8-naphthyridin-1(2H)-yl]methyl}-2-furoic acid A solution of the product of Example 75B (23 mg, 0.046 mmol) in THF (1 mL) was treated with 1N NaOH (0.2 mL) at room temperature. After 3 hours, the mixture was treated with H$_2$O (5 mL), adjusted to pH 4 with 1N HCl, and extracted with ethyl acetate (2×25 mL). The extracts were washed with saturated NaCl, dried over anhydrous Na$_2$SO$_4$, filtered, and concentrated. The resulting solid was purified by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min to give the title compound (0.039 g, 83%). MS (ESI−) m/z 465 (M−H)$^−$; $^1$H NMR (300 MHz, DMSO-d$_6$) δ 5.72 (s, 2H), 6.42 (d, J=3.68 Hz, 1H), 7.11 (d, J=3.31 Hz, 1H), 7.53 (m, 2H), 7.68 (d, J=7.72 Hz, 1H), 7.76 (m, 1H), 7.92 (d, J=7.72 Hz, 1H), 8.60 (dd, J=8.09, 1.84 Hz, 1H), 8.86 (dd, J=4.78, 1.84 Hz, 1H), 13.90 (s, 1H).

EXAMPLE 84

1-benzyl-3-(7-bromo-1,1-dioxido-4H-1,2,4-benzothiadiazin-3-yl)-4-hydroxy-1,8-naphthyridin-2(1H)-one

EXAMPLE 84A 2-amino-5-bromobenzenesulfonamide

The title compound was prepared from 4-bromoaniline using the procedure described in *JCS Perkin* 1, 1979, 1043.

EXAMPLE 84B ethyl 1-benzyl-4-hydroxy-2-oxo-1,2-dihydro-1,8-naphthyridine-3-carboxylate To a slurry of sodium hydride (60%, 0.118 g, 2.95 mmol) in anhydrous dimethylacetamide (6 mL) at 0° C. under N$_2$ was added diethyl malonate (0.472 g, 2.95 mmol) dropwise over 5 minutes. The mixture was stirred at ambient temperature for 1 hour, reacted with the product of Example 15A (0.50 g, 1.97 mmol), and heated at 120° C. for 3 hours. The mixture was cooled to ambient temperature and partitioned between ethyl acetate and cold water, and adjusted to pH to 5 with 1 M HCl. The aqueous layer was extracted with ethyl acetate (2×100 mL) and the combined extracts were washed with brine, dried over magnesium sulfate, filtered, and concentrated under vacuum. The residue was recrystallized from methanol to give the title compound as a white solid (0.439 g, 68%). MS (ESI+) m/z 325.0 (M+H)$^+$, 347.0 (M+Na)$^+$; $^1$H NMR (300 MHz, DMSO-d$_6$) δ 1.30 (t, J=7.17 Hz, 3H), 4.32 (q, J=7.23 Hz, 2H), 5.55 (s, 2H), 7.23 (m, 5H), 7.37 (dd, J=7.91, 4.60 Hz, 1H), 8.45 (dd, J=7.91, 2.02 Hz, 1H), 8.71 (dd, J=4.78, 1.84 Hz, 1H), 13.00 (s, 1H).

EXAMPLE 84C

N-[2-(aminosulfonyl)-4-bromophenyl]-1-benzyl-4-hydroxy-2-oxo-1,2-dihydro-1,8-naphthyridine-3-carboxamide The product of Example 84B (0.065 g, 0.20 mmol) was reacted with the product of Example 84A (0.050 g, 0.20 mmol) in toluene (4 mL) at reflux for 3 hours. The reaction was cooled and the resulting precipitate was collected by filtration and dried to give to give the title compound as an off-white solid (0.074 g, 70%). MS (ESI+) m/z 528.9 (M+H)$^+$, 530.9 (M+H)$^+$, 551.1 (M+Na)$^+$, 552.9 (M+Na)$^+$; $^1$H NMR (300 MHz, DMSO-d$_6$) δ 5.67 (s, 2H), 7.23 (m, 2H), 7.29 (m, 3H), 7.48 (dd, J=8.09, 4.78 Hz, 1H), 7.69 (s, 2H), 7.87 (dd, J=8.82, 2.21 Hz, 1H), 7.97 (m, 1H), 8.01 (d, J=2.21 Hz, 1H), 8.55 (dd, J=7.91, 1.65 Hz, 1H), 8.82 (dd, J=4.60, 1.65 Hz, 1H), 12.44 (s, 1H), 16.45 (s, 1H).

EXAMPLE 84D 1-benzyl-3-(7-bromo-1,1-dioxido-4H-1,2,4-benzothiadiazin-3-yl)-4-hydroxy-1,8-naphthyridin-2(1H)-one A mixture of the product of Example 84C (0.074 g, 0.14 mmol) in aqueous potassium hydroxide (10%, 5 mL) was heated to reflux for 16 hours, cooled to room temperature and adjusted to pH 3 with 6 M HCl. The mixture was filtered and the filter cake was washed with water, triturated with tetrahydrofuran/water, filtered, and dried under vacuum to give the title compound (0.060 g, 84%). MS (ESI+) m/z 511.0 (M+H)$^+$, 512.9 (M+H)$^+$; $^1$H NMR (300 MHz, DMSO-d$_6$) δ 5.62 (s, 2H), 7.21 (m, 1H), 7.27 (m, J=4.41 Hz, 5H), 7.36 (m, 1H), 7.50 (d, J=8.82 Hz, 1H), 7.84 (dd, J=8.82, 1.84 Hz, 1H), 7.95 (s, 1H), 8.51 (dd, J=7.91, 1.65 Hz, 1H), 8.68 (m, 1H). The sodium salt of the title compound was prepared according to the procedure of Example 1D. MS (ESI+) m/z 511.0 (M+H−Na)$^+$, 512.9 (M+H−Na)$^+$; $^1$H NMR (300 MHz, DMSO-d$_6$) δ 5.52 (s, 2H), 7.17 (m, 2H), 7.24 (m, 5H), 7.71 (m, 1H), 7.76 (d, J=2.21 Hz, 1H), 8.40 (dd, J=7.72, 1.84 Hz, 1H), 8.49 (dd, J=4.60, 2.02 Hz, 1H), 16.09 (s, 1H).

EXAMPLE 85

1-benzyl-3-(1,1-dioxido-7-phenyl-2H-1,2,4-benzothiadiazin-3-yl)-4-hydroxy-1,8-naphthyridin-2(1H)-one

EXAMPLE 85A

N-[3-(aminosulfonyl)-1,1'-biphenyl-4-yl]-1-benzyl-4-hydroxy-2-oxo-1,2-dihydro-1,8-naphthyridine-3-carboxamide The title compound was prepared according to the procedure of Example 84C substituting 2-amino-5-phenylbenzenesulfonamide for 2-amino-5-bromobenzenesulfonamide (0.084 g, 79%). MS (ESI+) m/z 527.1 (M+H)$^+$, 549.1 (M+Na)$^+$; $^1$H NMR (300 MHz, DMSO-d$_6$) δ 5.68 (s, 2H), 7.2-7.8 (m, 13H), 7.98 (s, 1H), 8.09 (s, 1H), 8.17 (s, 1H), 8.54 (s, 1H), 8.81 (s, 1H), 12.49 (s, 1H), 16.67 (s, 1H).

EXAMPLE 85B 1-benzyl-3-(1,1-dioxido-7-phenyl-2H-1,2,4-benzothiadiazin-3-yl)-4-hydroxy-1,8-naphthyridin-2(1H)-one The title compound was prepared according to the procedure of Example 84D substituting the product of Example 85A for the product of Example 84C (0.055 g, 69%). MS (ESI+) m/z 509.1 (M+H)$^+$; $^1$H NMR (300 MHz, DMSO-d$_6$) δ 5.71 (s, 2H), 7.24 (m, 1H), 7.30 (m, 3H), 7.49 (m, 4H), 7.79 (m, J=7.35 Hz, 3H), 8.07 (m, J=11.03, 2.21 Hz, 2H), 8.60 (dd, J=7.91, 1.65 Hz, 1H), 8.81 (m, J=3.68 Hz, 1H). The sodium salt of the title compound was prepared according to the procedure of Example 1D. MS (ESI+) m/z 531.0 (M+), 509.1 (M−Na+H)$^+$; $^1$H NMR (300 MHz, DMSO-d$_6$) δ 5.53 (s, 2H), 7.17 (m, 2H), 7.25 (m, J=4.41 Hz, 4H), 7.39 (m, 2H), 7.49 (t, J=7.54 Hz, 2H), 7.71 (d, J=6.99 Hz, 2H), 7.89 (m, 2H), 8.42 (dd, J=7.72, 1.84 Hz, 1H), 8.49 (dd, J=4.60, 2.02 Hz, 1H), 15.99 (s, 1H).

EXAMPLE 86

1-benzyl-3-(7-cyclohexyl-1,1-dioxido-4H-1,2,4-benzothiadiazin-3-yl)-4-hydroxy-1,8-naphthyridin-2(1H)-one

EXAMPLE 86A 2-amino-5-cyclohexylbenzenesulfonamide

A solution of 4-cyclohexylaniline (0.877 g, 5.0 mmol, 1.0 eq) in nitroethane (5 mL) was cooled to −40° C., treated dropwise with chlorosulfonyl isocyanate (0.87 g, (0.523 mL, 6.15 mmol, 1.23 eq), warmed to 0° C., treated with aluminum trichloride (0.85 g, 6.35 mmol, 1.27 eq), heated in a 110° C. oil bath for 30 minutes, cooled to ambient temperature, and poured into 200 mL of ice water. The mixture was filtered and the filter cake was rinsed with cold water, dissolved in 50% H$_2$SO$_4$ (25 mL), heated to reflux for 4 hours, cooled to ambient temperature, poured into 200 mL of ice water, and carefully neutralized to pH 7 with 40% NaOH. The reaction mixture was extracted with ethyl acetate (3×100 mL) and the combined extracts were washed with brine, dried (MgSO$_4$), filtered, and concentrated to give 0.40 g of the desired product (31% yield). MS (ESI+) m/z 255.0 (M+H)$^+$, 272.1 (M+H$_2$O)$^+$, 277.0 (M+Na)$^+$; $^1$H NMR (300 MHz, DMSO-d$_6$) δ 1.32 (m 4H), 1.71 (m, 6H), 2.36 (m, 1H), 5.64 (s, 2H), 6.72 (d, J=8.09 Hz, 1H), 7.11 (dd, J=8.46, 2.21 Hz, 1H), 7.16 (s, 2H), 7.38 (d, J=2.21 Hz, 1H).

EXAMPLE 86B

N-[2-(aminosulfonyl)-4-cyclohexylphenyl]-1-benzyl-4-hydroxy-2-oxo-1,2-dihydro-1,8-naphthyridine-3-carboxamide The title compound was prepared according to the procedure of Example 84C substituting the product of Example 86A for 2-amino-5-bromobenzenesulfonamide (0.081 g, 76%). MS (ESI+) m/z 533.1 (M+H)$^+$, 555.2 (M+Na)$^+$; $^1$H NMR (300 MHz, DMSO-d$_6$) δ 1.27 (m, 1H), 1.45 (m, 4H), 1.72 (m, 1H), 1.85 (m, 4H), 2.61 (m, 1H), 5.68 (s, 2H), 7.26 (m, 4H), 7.50 (m, 4H), 7.76 (d, J=1.84 Hz, 1H), 7.86 (d, J=8.46 Hz, 2H), 8.54 (dd, J=8.09, 1.47 Hz, 1H), 8.80 (s, 1H), 12.31 (s, 1H), 16.78 (s, 1H).

EXAMPLE 86C 1-benzyl-3-(7-cyclohexyl-1,1-dioxido-4H-1,2,4-benzothiadiazin-3-yl)-4-hydroxy-1,8-naphthyridin-2(1H)-one The title compound was prepared according to the procedure of Example 84D substituting the product of Example 86B for the product of Example 84C (0.040 g, 53%). MS (ESI+) m/z 533.1 (M+H+H$_2$O)$^+$, 555.1 (M+H$_2$O+Na)$^+$, 515.1 (M+H)$^+$; $^1$H NMR (300 MHz, DMSO-d$_6$) δ 1.34 (m, 5H), 1.77 (m, 5H), 2.60 (m, 1H), 5.66 (s, 2H), 7.25 (m, 4H), 7.51 (m, J=9.56 Hz, 4H), 7.88 (s, 1H), 8.54 (s, 1H), 8.80 (s, 1H), 12.31 (s, 1H), 16.78 (s, 1H). The sodium salt of the title compound was prepared according to the procedure of Example 1D. $^1$H NMR (300 MHz, DMSO-d$_6$) δ 1.41 (m, 5H), 1.70 (m, 5H), 3.79 (m, 1H), 5.52 (s, 2H), 7.12 (dd, J=7.54, 4.60 Hz, 1H), 7.17 (m, 1H), 7.23 (m, 4H), 7.41 (dd, J=8.64, 2.02 Hz, 1H), 7.67 (d, J=2.21 Hz, 1H), 8.33 (d, J=8.46 Hz, 1H), 8.38 (dd, J=7.72, 1.84 Hz, 1H), 8.43 (dd, J=4.60, 2.02 Hz, 1H), 11.15 (s, 1H).

EXAMPLE 87

1-benzyl-3-(7-tert-butyl-1,1-dioxido-4H-1,2,4-benzothiadiazin-3-yl)-4-hydroxy-1,8-naphthyridin-2(1H)-one

EXAMPLE 87A

N-[2-(aminosulfonyl)-4-tert-butylphenyl]-1-benzyl-4-hydroxy-2-oxo-1,2-dihydro-1,8-naphthyridine-3-carboxamide The title compound was prepared according to the procedure of Example 84C substituting 2-amino-5-tert-butylbenzenesulfonamide for 2-amino-5-bromobenzenesulfonamide (0.072 g, 79%). MS (ESI+) m/z 507.12 (M+H)$^+$, 524.2 (M+H$_2$O)$^+$, 529.1 (M+Na)$^+$; $^1$H NMR (300 MHz, DMSO-d$_6$) δ 1.33 (s, 9H), 5.68 (s, 2H), 7.22 (m, 1H), 7.29 (m, J=3.68 Hz, 4H), 7.47 (m, 3H), 7.70 (dd, J=8.64, 2.39 Hz, 1H), 7.88 (d, J=8.82 Hz, 1H), 7.91 (d, J=2.21 Hz, 1H), 8.54 (dd, J=8.09, 1.84 Hz, 1H), 8.81 (dd, J=4.60, 1.65 Hz, 1H), 12.33 (s, 1H), 16.79 (s, 1H).

EXAMPLE 87B 1-benzyl-3-(7-tert-butyl-1,1-dioxido-4H-1,2,4-benzothiadiazin-3-yl)-4-hydroxy-1,8-naphthyridin-2(1H)-one The title compound was prepared according to the procedure of Example 84D substituting the product of Example 87A for the product of Example 84C (0.040 g, 100%). MS (ESI+) m/z 489.1 (M+H)$^+$, 511.1 (M+Na)$^+$; $^1$H NMR (300 MHz, DMSO-d$_6$) δ 1.34 (s, 9H), 5.70 (s, 2H), 7.22 (m, 1H), 7.29 (m, J=4.41 Hz, 4H), 7.48 (m, 1H), 7.59 (d, J=8.82 Hz, 1H), 7.75 (s, 1H), 7.81 (d, J=10.66 Hz, 1H), 8.58 (d, J=6.62 Hz, 1H), 8.79 (s, 1H). The sodium salt of the title compound was prepared according to the procedure of Example 1D. $^1$H NMR (300 MHz, DMSO-d$_6$) δ 1.32 (s, 9H), 5.53 (s, 2H), 7.18

(m, 2H), 7.25 (m, J=4.41 Hz, 5H), 7.59 (s, 1H), 7.65 (m, 1H), 8.42 (d, J=7.35 Hz, 1H), 8.50 (m, J=3.86, 2.02 Hz, 1H).

EXAMPLE 88

1-benzyl-4-hydroxy-3-(7-methyl-1,1-dioxido-4H-1, 2,4-benzothiadiazin-3-yl)-1,8-naphthyridin-2(1H)-one

EXAMPLE 88A

N-[2-(aminosulfonyl)-4-methylphenyl]-1-benzyl-4-hydroxy-2-oxo-1,2-dihydro-1,8-naphthyridine-3-carboxamide The title compound was prepared according to the procedure of Example 84C substituting 2-amino-5-methylbenzenesulfonamide for 2-amino-5-bromobenzenesulfonamide (0.075 g, 90%). MS (ESI+) m/z 465.1 (M+H)$^+$, 482.0 (M+H$_2$O)$^+$, 487.1 (M+Na)$^+$. $^1$H NMR (300 MHz, DMSO-d$_6$) δ 2.39 (s, 3H), 5.68 (s, 2H), 7.23 (m, 1H), 7.29 (m, 4H), 7.47 (m, 4H), 7.73 (d, J=1.47 Hz, 1H), 7.84 (d, J=8.09 Hz, 1H), 8.54 (dd, J=7.72, 1.84 Hz, 1H), 8.81 (dd, J=4.60, 1.65 Hz, 1H), 12.30 (s, 1H), 16.78 (s, 1H).

EXAMPLE 88B 1-benzyl-4-hydroxy-3-(7-methyl-1,1-dioxido-4H-1, 2,4-benzothiadiazin-3-yl)-1,8-naphthyridin-2(1H)-one The title compound was prepared according to the procedure of Example 84D substituting the product of Example 88A for the product of Example 84C (0.031 g, 42%). MS (ESI+) m/z 447.0 (M+H)$^+$, 469.1 (M+Na)$^+$. $^1$H NMR (300 MHz, DMSO-d$_6$) δ 2.41 (s, 3H), 5.65 (s, 2H), 7.24 (m, 5H), 7.45 (m, 3H), 7.66 (s, 1H), 8.54 (d, J=7.72 Hz, 1H), 8.72 (s, 1H). The sodium salt of the title compound was prepared according to the procedure of Example 1D. $^1$H NMR (300 MHz, DMSO-d$_6$) δ 2.37 (s, 3H), 5.55 (s, 2H), 7.21 (m, 7H), 7.41 (d, J=8.46 Hz, 1H), 7.51 (s, 1H), 8.43 (d, J=8.09 Hz, 1H), 8.53 (s, 1H).

EXAMPLE 89

1-butyl-3-(6-chloro-1,1-dioxido-4H-1,2,4-benzothiadiazin-3-yl)-4-hydroxy-1,8-naphthyridin-2(1H)-one

EXAMPLE 89A ethyl 1-butyl-4-hydroxy-2-oxo-1,2-dihydro-1,8-naphthyridine-3-carboxylate To a slurry of NaH (95%, 0.44 g, 18.2 mmol) in 15 mL anhydrous DMA at 10° C. under N$_2$ was added diethyl malonate (2.9 g, 18.2 mmol) dropwise over 10 minutes. The mixture was stirred at ambient temperature for 30 minutes, treated with the product of Example 1B (2.0 g, 9.1 mmol) and heated at 120° C. for 3 hours. The mixture was cooled to ambient temperature and partitioned between ethyl acetate and cold water adjusting the pH to with 1 M HCl. The organic layer was washed 2×100 mL with water, 2×100 mL with saturated brine, dried (Na$_2$SO$_4$), filtered and the filtrate was concentrated under vacuum. The residue was recrystallized from hexane/ethyl acetate to give the desired compound as a white solid (1.84 g, 70% yield). MS (APCI+) m/z 291 (M+H)$^+$.

EXAMPLE 89B

N-[2-(aminosulfonyl)-4-chlorophenyl]-1-butyl-4-hydroxy-2-oxo-1,2-dihydro-1,8-naphthyridine-3-carboxamide A mixture of the product of Example 89A (87 mg, 0.3 mmol) and 2-amino-4-chlorobenzenesulfonamide (62 mg, 0.3 mmol) in toluene (5 mL) was refluxed for 16 hours, cooled, and the resulting precipitate was collected by filtration and dried to give the desired amide as an off-white solid (80 mg, 59% yield). MS (APCI+) m/z 451 (M+H)$^+$.

EXAMPLE 89C ethyl 1-butyl-4-hydroxy-2-oxo-1,2-dihydro-1,8-naphthyridine-3-carboxylate The title compound was prepared according to the procedure of Example 84C substituting the product of Example 89B for the product of Example 84B (0.037 g, 53%). MS (ESI−) m/z 431 (M−H)$^−$. The sodium salt of the title compound was prepared according to the procedure of Example 1D. $^1$H NMR (300 MHz, DMSO-d$_6$) δ 0.93 (t, J=7.17 Hz, 3H), 1.34 (m, 2H), 1.58 (m, 2H), 4.27 (m, 2H), 7.14 (dd, J=7.72, 4.78 Hz, 1H), 7.32 (dd, J=8.27, 2.02 Hz, 1H), 7.42 (d, J=1.84 Hz, 1H), 7.68 (d, J=8.46 Hz, 1H), 8.37 (dd, J=7.54, 2.02 Hz, 1H), 8.54 (dd, J=4.78, 1.84 Hz, 1H), 16.09 (s, 1H).

EXAMPLE 90

1-benzyl-3-(8-bromo-5-methyl-1,1-dioxido-4H-1,2, 4-benzothiadiazin-3-yl)-4-hydroxy-1,8-naphthyridin-2(1H)-one

EXAMPLE 90A

N-[2-(aminosulfonyl)-3-bromo-6-methylphenyl]-1-benzyl-4-hydroxy-2-oxo-1,2-dihydro-1,8-naphthyridine-3-carboxamide The title compound was prepared according to the procedure of Example 84C substituting 2-amino-6-bromo-3-methylbenzenesulfonamide for 2-amino-5-bromobenzenesulfonamide to give the crude title compound (0.1 g, 98%).

EXAMPLE 90B 1-benzyl-3-(8-bromo-5-methyl-1,1-dioxido-4H-1,2, 4-benzothiadiazin-3-yl)-4-hydroxy-1,8-naphthyridin-2(1H)-one The title compound was prepared according to the procedure of Example 84D substituting the product of Example 90A for the product of Example 84C. The crude product was purified by column chromatography with silica gel eluting with dichloromethane and methanol (98:2) to give the title compound as a white solid, (0.03 g, 31% yield). MS (ESI−) m/z 525 (M−H)$^−$. The sodium salt of the title compound was prepared according to the procedure of Example 1D. $^1$H NMR (300 MHz, DMSO-d$_6$) δ 16.0 (br s, 1H), 8.49 (dd, J=4.8, 1.8 Hz, 1H), 8.44 (dd, J=7.7, 1.8 Hz, 1H), 7.45 (br s, 1H), 7.37 (m, 1H), 7.23 (m, 3H), 7.16 (dd, J=4.8, 3.3 Hz, 1H), 7.01 (m, 1H), 6.85 (d, J=7.7 Hz, 1H), 5.53 (br s, 2H), 2.43 (s, 3H).

EXAMPLE 91

1-benzyl-3-(8-fluoro-5-methyl-1,1-dioxido-4H-1,2,4-benzothiadiazin-3-yl)-4-hydroxy-1,8-naphthyridin-2(1H)-one

EXAMPLE 91A

N-[2-(aminosulfonyl)-3-fluoro-6-methylphenyl]-1-benzyl-4-hydroxy-2-oxo-1,2-dihydro-1,8-naphthyridine-3-carboxamide The title compound was prepared according to the procedure of Example 84C substituting 2-amino-6-fluoro-3-methylbenzenesulfonamide for 2-amino-5-bromobenzenesulfonamide to give the crude title compound (0.120 g, 100%).

EXAMPLE 91B 1-benzyl-3-(8-fluoro-5-methyl-1, 1-dioxido-4H-1,2,4-benzothiadiazin-3-yl)-4-hydroxy-1,8-naphthyridin-2(1H)-one The title compound was prepared according to the procedure of Example 84D substituting the product of Example 91A for the product of Example 84C. The crude product was purified by column chromatography with silica gel eluting with dichloromethane and methanol (98:2) as a white solid, (0.05 g, 44% yield). MS (ESI−) m/z 463 (M−H)−. The sodium salt of the title compound was prepared according to the procedure of Example 1D. $^1$H NMR (300 MHz, DMSO-$d_6$) δ 16.1 (br s, 1H), 8.49 (dd, J=4.6, 2.0 Hz, 1H), 8.44 (dd, J=7.7, 1.8 Hz, 1H), 7.59 (m, 1H), 7.47 (dd, J=7.3, 5.8 Hz, 1H), 7.38 (m, 1H), 7.21 (m, 3H), 7.16 (dd, J=7.7, 5.8 Hz, 1H), 6.99 (t, J=8.8 Hz, 1H), 5.53 (s, 2H), 2.42 (s, 3H).

EXAMPLE 92

1-benzyl-4-hydroxy-3-(5-isopropyl-1,1-dioxido-4H-1,2,4-benzothiadiazin-3-yl)-1,8-naphthyridin-2(1H)-one

EXAMPLE 92A

N-[2-(aminosulfonyl)-6-isopropylphenyl]-1-benzyl-4-hydroxy-2-oxo-1,2-dihydro-1,8-naphthyridine-3-carboxamide The title compound was prepared according to the procedure of Example 84C substituting 2-amino-3-isopropylbenzenesulfonamide for 2-amino-5-bromobenzenesulfonamide (0.050 g, 55%) after chromatrography on silica gel (eluting with 4:1 hexane/ethyl acetate). $^1$H NMR (300 MHz, DMSO-$d_6$) δ $^1$H NMR (300 MHz, DMSO-$d_6$) δ 1.12 (d, J=6.62 Hz, 3H), 1.26 (d, J=6.99 Hz, 3H), 3.06 (m, 1H), 5.69 (m, 2H), 7.27 (m, 5H), 7.39 (s, 2H), 7.48 (dd, J=7.72, 4.78 Hz, 1H), 7.55 (t, J=7.72 Hz, 1H), 7.71 (d, J=8.09 Hz, 1H), 7.80 (dd, J=7.72, 1.10 Hz, 1H), 8.53 (dd, J=7.91, 1.65 Hz, 1H), 8.83 (dd, J=4.78, 1.84 Hz, 1H), 11.75 (s, 1H), 16.83 (s, 1H).

EXAMPLE 92B 1-benzyl-4-hydroxy-3-(5-isopropyl-1,1-dioxido-4H-1,2,4-benzothiadiazin-3-yl)-1,8-naphthyridin-2(1H)-one The title compound was prepared according to the procedure of Example 84D substituting the product of Example 92a for the product of Example 84C (0.038 g, 75%). MS (ESI+) m/z 475.1 (M+H)$^+$, 492.1 (M+H$_2$O)$^+$, 497.1 (M+Na)$^+$. $^1$H NMR (300 MHz, DMSO-$d_6$) δ 1.34 (d, J=6.62 Hz, 6H), 3.30 (m, 1H), 5.73 (s, 2H), 7.27 (m, 5H), 7.54 (m, 2H), 7.78 (m, J=16.18, 7.72 Hz, 2H), 8.62 (dd, J=7.91, 1.65 Hz, 1H), 8.84 (s, 1H), 14.64 (s, 1H). The sodium salt of the title compound was prepared according to the procedure of Example 1D. $^1$H NMR (300 MHz, DMSO-$d_6$) δ 1.32 (d, J=6.62 Hz, 6H), 3.42 (m, 1H), 5.53 (s, 2H), 7.15 (m, 2H), 7.25 (m, J=4.41 Hz, 4H), 7.29 (m, 1H), 7.53 (m, J=7.72, 1.84 Hz, 2H), 8.46 (m, 2H), 16.06 (s, 1H).

EXAMPLE 93

1-benzyl-4-hydroxy-3-(5-methyl-1,1-dioxido-4H-1,2,4-benzothiadiazin-3-yl)-1,8-naphthyridin-2(1H)-one

EXAMPLE 93A

N-[2-(aminosulfonyl)-6-methylphenyl]-1-benzyl-4-hydroxy-2-oxo-1,2-dihydro-1,8-naphthyridine-3-carboxamide The title compound was prepared according to the procedure of Example 84C substituting 2-amino-3-methylbenzenesulfonamide for 2-amino-5-bromobenzenesulfonamide (0.059 g, 100%). $^1$H NMR (300 MHz, DMSO-d6) δ 2.27 (s, 3 H) 5.68 (m, 2 H) 7.24 (m, 5 H) 7.46 (m, 4 H) 7.59 (d, J=6.99 Hz, 1 H) 7.79 (d, J=7.72 Hz, 1 H) 8.54 (dd, J=8.09, 1.84 Hz, 1 H) 8.83 (dd, J=4.78, 1.84 Hz, 1 H) 11.90 (s, 1 H) 16.79 (s, 1 H).

EXAMPLE 93B 1-benzyl-4-hydroxy-3-(5-methyl-1,1-dioxido-4H-1,2,4-benzothiadiazin-3-yl)-1,8-naphthyridin-2(1H)-one The title compound was prepared according to the procedure of Example 84D substituting the product of Example 93A for the product of Example 84C (0.015 g, 25%) after silica gel chromatography (eluting with 98:2 dichloromethane/methanol). MS (ESI+) m/z 447.0 (M+H)$^+$, 469.1 (M+Na)$^+$. $^1$H NMR (300 MHz, -d6) δ 2.52 (m, 3 H) 5.75 (m, 2 H) 7.23 (m, 1 H) 7.30 (m, 4 H) 7.47 (t, J=7.72 Hz, 1 H) 7.53 (dd, J=8.09, 4.78 Hz, 1 H) 7.69 (d, J=7.35 Hz, 1 H) 7.79 (d, J=8.09 Hz, 1 H) 8.63 (dd, J=7.72, 1.84 Hz, 1 H) 8.85 (dd, J=4.78, 1.84 Hz, 1 H) 14.41 (s, 1 H). The sodium salt of the title compound was prepared according to the procedure of Example 1d. $^1$H NMR (300 MHz, DMSO-d6) δ 2.48 (s, 3 H) 5.56 (s, 2 H) 7.21 (m, 6 H) 7.49 (d, J=7.35 Hz, 1 H) 7.56 (d, J=7.35 Hz, 1 H) 8.47 (d, J=7.72 Hz, 1 H) 8.53 (s, 1 H) 11.98 (s, 1 H).

EXAMPLE 94

1-benzyl-3-(5-bromo-1,1-dioxido-4H-1,2,4-benzothiadiazin-3-yl)-4-hydroxy-1,8-naphthyridin-2(1H)-one

EXAMPLE 94A

N-[2-(aminosulfonyl)-6-bromophenyl]-1-benzyl-4-hydroxy-2-oxo-1,2-dihydro-1,8-naphthyridine-3-carboxamide The title compound was prepared according to the procedure of Example 84C substituting 2-amino-3-methylbenzenesulfonamide for 2-amino-5-bromobenzenesulfonamide (0.080 g, 25%) after silica gel chromatography (eluting with 2:1 hexane/ethyl acetate). MS (ESI+) m/z 529.0 (M+H)$^+$, 530.9 (M+H)$^+$. $^1$H NMR (300 MHz, DMSO-d6) δ 5.71 (m, 2H) 7.23 (m, 1H) 7.32 (m, 4 H) 7.50 (m, 2 H) 7.62 (s, 2 H) 7.96 (dd, J=7.91, 1.29 Hz, 1 H) 8.02 (dd, J=7.91, 1.29 Hz, 1 H) 8.55 (dd, J=7.91, 1.65 Hz, 1 H) 8.85 (dd, J=4.78, 1.84 Hz, 1 H) 11.95 (s, 1 H) 16.51 (s, 1 H).

EXAMPLE 94B 1-benzyl-3-(5-bromo-1,1-dioxido-4H-1,2,4-benzothiadiazin-3-yl)-4-hydroxy-1,8-naphthyridin-2(1H)-one The title compound was prepared according to the procedure of Example 84D substituting the product of Example 94A for the product of Example 84C (0.040 g, 54%). MS (ESI+) m/z 510.9 (M+H)$^+$, 512.9 (M+H)$^+$. $^1$H NMR (300 MHz, DMSO-d6) δ 5.56 (s, 2 H) 7.23 (m, 8 H) 7.76 (d, J=8.46 Hz, 1 H) 7.94 (d, J=8.09 Hz, 1 H) 8.46 (dd, J=7.72, 1.84 Hz, 1 H) 8.55 (m, 1 H) 16.17 (s, 1 H). The sodium salt of the title compound was prepared according to the procedure of Example 1d. $^1$H NMR (300 MHz, DMSO-d6) δ 5.53 (s, 2 H) 7.17 (m, 2 H) 7.25 (m, 5 H) 7.71 (d, J=6.99 Hz, 1 H) 7.90 (m, 1 H) 8.43 (dd, J=7.72, 1.84 Hz, 1 H) 8.49 (dd, J=4.60, 2.02 Hz, 1 H) 16.38 (s, 1 H).

EXAMPLE 95

1-benzyl-3-(1,1-dioxido-5-propyl-2H-1,2,4-benzothiadiazin-3-yl)-4-hydroxy-1,8-naphthyridin-2(1H)-one

EXAMPLE 95A

N-[2-(aminosulfonyl)-6-propylphenyl]-1-benzyl-4-hydroxy-2-oxo-1,2-dihydro-1,8-naphthyridine-3-carboxamide The title compound was prepared according to the procedure of Example 84C substituting 2-amino-3-propylbenzenesulfonamide for 2-amino-5-bromobenzenesulfonamide (0.062 g, 59%). MS (DCI/NH$_3$) m/z 493 (M+H)$^+$. $^1$H NMR (300 MHz, DMSO-d$_6$) δ 0.83 and 0.93 (two t, J=7.35 Hz, 3H), 1.57 (m, 2H), 2.57 (m, 2H), 5.66 (m, 2H), 7.28 (m, 5H), 7.41 (s, 2H), 7.48 (m, 2H), 7.61 (m, 1H), 7.81 (dd, J=7.72, 1.47 Hz, 1H), 8.53 (dd, J=7.91, 1.65 Hz, 1H), 8.83 (dd, J=4.78, 1.84 Hz, 1H), 11.82 (s, 1H), 16.80 (s, 1H).

EXAMPLE 95B 1-benzyl-3-(1,1-dioxido-5-propyl-2H-1,2,4-benzothiadiazin-3-yl)-4-hydroxy-1,8-naphthyridin-2(1H)-one The title compound was prepared according to the procedure of Example 84D substituting the product of Example 95A for the product of Example 84C (0.029 g, 50%). MS (ESI−) m/z 473 (M−H)$^−$. The sodium salt of the title compound was prepared according to the procedure of Example 1D. $^1$H NMR (300 MHz, DMSO-d$_6$) δ 1.03 (t, J=7.17 Hz, 3H), 1.68 (m, 2H), 2.83 (t, J=7.72 Hz, 2H), 5.53 (s, 2H), 7.19 (m, 7H), 7.44 (d, J=6.25 Hz, 1H), 7.53 (d, J=7.35 Hz, 1H), 8.43 (dd, J=7.54, 1.84 Hz, 1H), 8.48 (dd, J=4.78, 1.84 Hz, 1H), 16.02 (s, 1H).

EXAMPLE 96

1-benzyl-3-(5-ethyl-1,1-dioxido-4H-1,2,4-benzothiadiazin-3-yl)-4-hydroxy-1,8-naphthyridin-2(1H)-one

EXAMPLE 96A

N-[2-(aminosulfonyl)-6-ethylphenyl]-1-benzyl-4-hydroxy-2-oxo-1,2-dihydro-1,8-naphthyridine-3-carboxamide The title compound was prepared according to the procedure of Example 84C substituting 2-amino-3-ethylbenzenesulfonamide for 2-amino-5-bromobenzenesulfonamide (0.070 g, 74%). MS (ESI−) m/z 479 (M+H)$^+$. $^1$H NMR (300 MHz, DMSO-d$_6$) δ 1.17 (t, J=7.54 Hz, 3H), 2.61 (q, J=7.60 Hz, 2H), 5.70 (m, 2H), 7.27 (m, 5H), 7.42 (s, 2H), 7.49 (m, 2H), 7.63 (m, 1H), 7.81 (dd, J=7.91, 1.29 Hz, 1H), 8.53 (dd, J=7.91, 1.65 Hz, 1H), 8.83 (dd, J=4.41, 1.84 Hz, 1H), 11.82 (s, 1H), 16.80 (s, 1H).

EXAMPLE 96B 1-benzyl-3-(5-ethyl-1,1-dioxido-4H-1,2,4-benzothiadiazin-3-yl)-4-hydroxy-1,8-naphthyridin-2(1H)-one The title compound was prepared according to the procedure of Example 84D substituting the product of Example 96A for the product of Example 84C (0.060 g, 93%). MS (ESI−) m/z 459 (M−H)$^−$. The sodium salt of the title compound was prepared according to the procedure of Example 1D. $^1$H NMR (300 MHz, DMSO-d$_6$) δ 1.30 (t, J=7.54 Hz, 3H), 2.86 (q, J=7.35 Hz, 2H), 5.53 (s, 2H), 7.14 (dd, J=7.72, 4.78 Hz, 1H), 7.22 (m, 6H), 7.46 (d, J=7.72 Hz, 1H), 7.53 (d, J=7.72 Hz, 1H), 8.44 (dd, J=7.72, 1.84 Hz, 1H), 8.48 (dd, J=4.78, 1.83 Hz, 1H), 15.98 (s, 1H).

EXAMPLE 97

3-(1-benzyl-4-hydroxy-2-oxo-1,2-dihydro-1,8-naphthyridin-3-yl)-2H-1,2,4-benzothiadiazine-5-carbonitrile 1,1-dioxide The product of Example 94B (0.329 g, 0.643 mmol) and CuCN (0.29 g, 3.21 mmol) in anhydrous DMF (5 mL) were heated under N$_2$ at 145° for 22 hrs. The reaction was cooled to room temperature, diluted with CH$_2$Cl$_2$ (50 mL) and 1N aq HCl (10 mL), and vigorously stirred for 15 minutes. The layers were separated and the aqueous phase extracted with CH$_2$Cl$_2$ (2×50 mL). The organic extracts were washed with 1N aqueous HCl (20 mL) and saturated aqueous NaCl, then dried over anhydrous Na$_2$SO$_4$. After filtration and concentration by rotary evaporation, the residue was purified by silica gel flash chromatography (2.5×14 cm, 5% EtOAc/CH$_2$Cl$_2$) to give the title compound (0.136 g, 46%). MS (ESI−) m/z 456 (M−H)$^−$. $^1$H NMR (300 MHz, DMSO-d6) δ 5.69 (s, 2 H) 7.26 (m, 5 H) 7.47 (dd, J=7.91, 4.60 Hz, 1 H) 7.62 (t, J=7.91 Hz, 1 H) 8.25 (m, 2 H) 8.59 (dd, J=7.91, 2.02 Hz, 1 H) 8.80 (dd, J=4.60, 1.65 Hz, 1 H) 15.67 (s, 1 H). The sodium salt of the title compound was prepared according to the procedure of Example 1D. $^1$H NMR (300 MHz, DMSO-d$_6$) δ 5.53 (s, 2 H) 7.20 (m, 6 H) 7.41 (t, J=7.91 Hz, 1 H) 8.00 (d, J=7.35 Hz, 1 H)

8.07 (d, J=7.72 Hz, 1 H) 8.43 (dd, J=7.54, 1.65 Hz, 1 H) 8.51 (dd, J=4.60, 1.65 Hz, 1 H) 17.35 (s, 1 H).

EXAMPLE 98

1-butyl-3-(1,1-dioxido-4H-pyrido[3,2-e][1,2,4]thiadiazin-3-yl)-4-hydroxy-2(1H)-quinolinone

EXAMPLE 98A 3-nitropyridine-2-thiol 2-mercapto-3-nitropyridine was prepared by treating 3-nitro-2-chloro-pyridine (50 g, 0.0317 mol) with thiourea (24 g, 0.0317 mol) in 200 mL of ethanol at reflux for several hours. After the reaction mixture was allowed to cool, 7.19 mL solution of KOH (42.8 g in 115 mL of water) was added and the resulting mixture was heated at reflux for 3 hours. The crude reaction mixture was cooled to room temperature and then concentrated to 50% of its volume in vacuo. After diluting with 300 mL of water, the product was isolated by vacuum filtration as an orange solid that was used without further purification. MS (DCI/NH$_3$) m/z 157 (M+H)$^+$. $^1$H NMR (300 MHz, DMSO-d$_6$) δ 5.76 (m, 1H), 7.67 (dd, J=8.46, 4.78 Hz, 1H), 8.63 (dd, J=8.46, 1.47 Hz, 1H), 8.73 (dd, J=4.60, 1.65 Hz, 1H).

EXAMPLE 98B 3-aminopyridine-2-sulfonamide

The title compound, (3-aminopyrid-2-yl)sulfonamide was prepared in 3 steps (80% yield) from 2-mercapto-3-nitropyridine according to the procedure of R. Lejeune and coworkers as described in *J. pharm. Belg*, 39, 217-224, 1984. MS (DCI/NH$_3$) m/z 174 (M+H)$^+$. $^1$H NMR (300 MHz, DMSO-d$_6$) δ 6.00 (s, 2H), 7.25 (m, 2H), 7.34 (s, 2H), 7.82 (dd, J=4.04, 1.47 Hz, 1H).

EXAMPLE 98C

N-[2-(aminosulfonyl)pyridin-3-yl]-1-butyl-4-hydroxy-2-oxo-1,2-dihydroquinoline-3-carboxamide The title compound was prepared according to the procedure of Example 89B substituting 3-amino-pyridine-2-sulfonamide for 2-amino-4-chlorobenzenesulfonamide.

EXAMPLE 98D 1-butyl-3-(1,1-dioxido-4H-pyrido[3,2-e][1,2,4]thiadiazin-3-yl)-4-hydroxy-2(1H)-quinolinone The title compound was prepared according to the procedure of Example 84D substituting the product of Example 98C for the product of Example 84C as a white solid (0.065 g, 22%). MS (ESI−) m/z 397 (M−H)$^−$; $^1$H NMR (300 MHz, DMSO-d$_6$) δ 0.96 (t, J=7.35 Hz, 3H), 1.46 (m, 2H), 1.66 (m, 2H), 4.34 (m, 2H), 7.46 (t, J=7.54 Hz, 1H), 7.82 (m, 3H), 8.23 (d, J=6.99 Hz, 1H), 8.26 (d, J=7.72 Hz, 1H), 8.70 (d, J=3.68 Hz, 1H), 14.38 (s, 1H), 15.12 (s, 1H).

EXAMPLE 99

1-benzyl-3-(1,1-dioxido-4H-pyrido[3,2-e][1,2,4]thiadiazin-3-yl)-4-hydroxy-2(1H)-quinolinone

EXAMPLE 99A ethyl 1-benzyl-4-hydroxy-2-oxo-1,2-dihydroquinoline-3-carboxylate The title compound was prepared according to the procedure of Example 84B substituting 1-benzyl-1H-benzo[d][1,3]oxazine-2,4-dione for the product of Example 15A.

EXAMPLE 99B

N-[2-(aminosulfonyl)pyridin-3-yl]-1-benzyl-4-hydroxy-2-oxo-1,2-dihydroquinoline-3-carboxamide The title compound was prepared according to the procedure of Example 84C substituting the product of Example 99A for the product of Example 84B and substituting (3-amino-pyrid-2-yl)sulfonamide for 2-amino-5-bromobenzenesulfonamide to give the crude product as an off white solid.

EXAMPLE 99C 1-benzyl-3-(1,1-dioxido-4H-pyrido[3,2-e][1,2,4]thiadiazin-3-yl)-4-hydroxy-2(1H)-quinolinone The title compound was prepared according to the procedure of Example 84D substituting the product of Example 99B for the product of Example 84C (0.076 g, 38%). $^1$H NMR (300 MHz, DMSO-d$_6$) δ 5.64 (s, 2H), 7.29 (m, 5H), 7.43 (m, J=7.72, 7.72 Hz, 1H), 7.54 (d, J=8.46 Hz, 1H), 7.80 (m, 2H), 8.23 (m, 2H), 8.69 (d, J=3.31 Hz, 1H).

EXAMPLE 100

1-benzyl-3-(1,1-dioxido-4H-pyrido[3,2-e][1,2,4]thiadiazin-3-yl)-4-hydroxy-1,8-naphthyridin-2(1H)-one

EXAMPLE 100A

N-[2-(aminosulfonyl)pyridin-3-yl]-1-benzyl-4-hydroxy-2-oxo-1,2-dihydro-1,8-naphthyridine-3-carboxamide The title compound was prepared according to the procedure of Example 84C substituting 3-amino-pyridine-2-sulfonamide for 2-amino-5-bromobenzenesulfonamide. MS (ESI−) m/z 452 (M+H)$^+$. $^1$H NMR (300 MHz, DMSO-d$_6$) δ 5.66 (s, 2H), 7.22 (m, 1H), 7.28 (m, 3H), 7.43 (m, 1H), 7.70 (m, 3H), 8.52 (m, 2H), 8.77 (s, 3H), 12.56 (s, 1H), 16.34 (s, 1H).

EXAMPLE 100B 1-benzyl-3-(1,1-dioxido-4H-pyrido[3,2-e][1,2,4]thiadiazin-3-yl)-4-hydroxy-1,8-naphthyridin-2(1H)-one The title compound was prepared according to the procedure of Example 84D substituting the product of Example 100A for the product of Example 84C to give after purification by reverse phase HPLC (water/acetonitrile/0.1% NH$_4$OAc gradient) the title compound as a white solid (0.053 g, 10%). MS (ESI−) m/z 432 (M−H)$^-$; $^1$H NMR (300 MHz, DMSO-d$_6$) δ 5.70 (m, 2H), 7.25 (m, 7H), 7.50 (dd, J=7.91, 4.60 Hz, 1H), 7.80 (dd, J=8.46, 4.41 Hz, 1H), 8.17 (d, J=8.46 Hz, 1H), 8.60 (m, J=5.79, 1.88, 1.88 Hz, 1H), 8.68 (dd, J=4.41, 1.10 Hz, 1H), 8.82 (dd, J=4.78, 1.84 Hz, 1H).

EXAMPLE 101

5-chloro-3-(1,1-dioxido-4H-pyrido[3,2-e][1,2,4]thiadiazin-3-yl)-4-hydroxy-1-(3-methylbutyl)-2(1H)-quinolinone

EXAMPLE 101A 5-chloro-2H-3,1-benzoxazine-2,4(1H)-dione

A solution of potassium hydroxide (1.68 g, 30 mmol) and 2-amino-6-chlorobenzoic acid (3.43 g, 20 mmol) in water (25 mL) at 0° C. was treated dropwise with 20% phosgene in toluene (16.8 mL, 32 mmol) resulting in a precipitate. The mixture was stirred for 1 hour and the solid was collected by filtration, washed with water and dried to give the title compound (3.6 g, 91%). $^1$H NMR (300 MHz, DMSO-d$_6$) δ 7.11 (d, J=7.35 Hz, 1H), 7.31 (d, J=6.99 Hz, 1H), 7.66 (t, J=8.09 Hz, 1H), 11.83 (s, 1H).

EXAMPLE 101B 5-chloro-1-(3-methylbutyl)-2H-3,1-benzoxazine-2,4(1H)-dione

The title compound was prepared according to the procedure of Example 1B substituting 1-bromo-3-methylbutane for n-butyl bromide and substituting the product of Example 101A for the product of Example 1A (0.610 g, 45%). MS (DCI) m/z 285 (M+NH$_4$)$^+$.

EXAMPLE 101C ethyl 5-chloro-4-hydroxy-1-(3-methylbutyl)-2-oxo-1,2-dihydroquinoline-3-carboxylate The title compound was prepared according to the procedure of Example 89A substituting the product of Example 101B for the product of Example 1B (0.600 g, 80%). $^1$H NMR (300 MHz, DMSO-d$_6$) δ 0.96 (d, J=6.62 Hz, 6H), 1.32 (t, J=7.17 Hz, 3H), 1.44 (m, 2H), 1.70 (m, J=13.24, 6.62 Hz, 1H), 4.18 (m, 2H), 4.35 (q, J=6.99 Hz, 2H), 7.35 (d, J=6.99 1H), 7.48 (d, J=8.09 Hz, 1H), 7.67 (m, 1H), 13.88 (s, 1H).

EXAMPLE 101D

N-[2-(aminosulfonyl)pyridin-3-yl]-5-chloro-4-hydroxy-1-(3-methylbutyl)-2-oxo-1,2-dihydroquinoline-3-carboxamide The product of Example 101C (0.170 g, 0.50 mmol) was reacted with the product of Example 98A (0.086 g, 0.50 mmol) in toluene (6 mL) at reflux for 16 hours. The reaction was cooled and the resulting precipitate was collected by filtration and dried to give the title compound (0.200 g, 86%). MS (DCI) m/z 465 (M+H)$^+$. 1 $^1$H NMR (300 MHz, DMSO-d$_6$) δ 0.99 (d, J=6.62 Hz, 6H), 1.51 (m, 2H), 1.76 (m, 1H), 4.32 (m, 2H), 7.45 (d, J=7.35 Hz, 1H), 7.61 (d, J=8.82 Hz, 1H), 7.71 (s, 2H), 7.77 (m, 2H), 8.45 (dd, J=8.46, 1.47 Hz, 1H), 8.53 (dd, J=4.60, 1.29 Hz, 1H), 12.84 (s, 1H), 17.22 (s, 1H).

EXAMPLE 101E 5-chloro-3-(1,1-dioxido-4H-pyrido[3,2-e][1,2,4]thiadiazin-3-yl)-4-hydroxy-1-(3-methylbutyl)-2(1H)-quinolinone The title compound was prepared according to the procedure of Example 84D substituting the product of Example 101D for the product of Example 84C (0.200 g, 98%). MS (ESI−) m/z 445 (M−H)$^-$. The sodium salt of the title compound was prepared according to the procedure of Example 1D. $^1$H NMR (300 MHz, DMSO-d$_6$) δ 0.98 (d, J=6.62 Hz, 6H), 1.45 (m, 2H), 1.71 (m, 1H), 4.11 (m, 2H), 7.08 (d, J=7.35 Hz, 1H), 7.23 (d, J=8.09 Hz, 1H), 7.43 (t, J=8.27 Hz, 1H), 7.57 (dd, J=8.46, 4.41 Hz, 1H), 7.78 (d, J=8.09 Hz, 1H), 8.45 (d, J=4.41 Hz, 1H), 15.77 (s, 1H).

EXAMPLE 102

1-benzyl-3-(1,1-dioxido-4H-pyrido[3,2-e][1,2,4]thiadiazin-3-yl)-4-hydroxy-5-methyl-2(1H)-quinolinone

EXAMPLE 102A

1-Benzyl-(4-methyl)benzo[2,3-d][1,3]oxazine-2,4-dione

The title compound was prepared according to the procedure of Example 1B substituting benzyl bromide for n-butyl bromide and substituting (4-methyl)benzo[2,3-d][1,3]oxazine-2,4-dione for the product of Example 1A (0.67 g, 60%). MS (DCI+) m/z 268 (M+H)$^-$; $^1$H NMR (300 MHz, DMSO-d$_6$) δ 2.66 (s, 3H), 5.28 (s, 2H), 7.07 (d, J=8.48 Hz, 1H), 7.14 (d, J=7.80 Hz, 1H), 7.33 (m, 5H), 7.57 (t, J=7.46 Hz, 1H).

EXAMPLE 102B ethyl 1-benzyl-4-hydroxy-5-methyl-2-oxo-1,2-dihydroquinoline-3-carboxylate The title compound was prepared according to the procedure of Example 84A substituting the product of Example 102A for the product of Example 15A (0.71 g, 89%). MS (DCI+) m/z 338 (M+H)$^-$; $^1$H NMR (300 MHz, DMSO-d$_6$) δ 1.33 (t, J=7.17 Hz, 3H), 2.77 (s, 3H), 4.39 (q, J=7.23 Hz, 2H), 5.47 (s, 2H), 7.05 (d, J=7.35 Hz, 1H), 7.20 (m, 4H), 7.31 (m, 2H), 7.47 (t, J=8.09 Hz, 1H), 14.43 (s, 1H).

EXAMPLE 102C

N-[2-(aminosulfonyl)pyridin-3-yl]-1-benzyl-4-hydroxy-5-methyl-2-oxo-1,2-dihydroquinoline-3-carboxamide The title compound was prepared according to the procedure of Example 84C substituting the product of Example 102B for the product of Example 84B and substituting the product of Example 98A for 2-amino-5-bromobenzenesulfonamide (0.163 g, 41%). MS (ESI+) m/z 465 (M+H)$^-$; $^1$H NMR (300 MHz, DMSO-d$_6$) δ 2.82 (s, 3H), 5.59 (s, 2H), 7.15

(d, J=7.35 Hz, 1H), 7.24 (m, 3H), 7.33 (m, 3H), 7.56 (t, J=7.91 Hz, 1H), 7.72 (m, 3H), 8.51 (m, 1H), 8.53 (s, 1H), 12.93 (s, 1H), 17.16 (m, 1H).

EXAMPLE 102D 1-benzyl-3-(1,1-dioxido-4H-pyrido[3,2-e][1,2,4]thiadiazin-3-yl)-4-hydroxy-5-methyl-2(1H)-quinolinone The title compound was prepared according to the procedure of Example 84D substituting the product of Example 102C for the product of Example 84C (0.064 g, 41%). MS (ESI+) m/z 447 (M+H)⁻. The sodium salt of the title compound was prepared according to the procedure of Example 1D. MS (ESI−) m/z 445 (M−H)⁻; $^1$H NMR (300 MHz, DMSO-d$_6$) δ 2.81 (s, 3H), 5.37 (dd, J=6.07, 2.02 Hz, 2H), 6.80 (d, J=7.35 Hz, 1H), 6.95 (d, J=8.09 Hz, 1H), 7.20 (m, 4H), 7.29 (m, 2H), 7.57 (dd, J=8.46, 4.41 Hz, 1H), 7.75 (dd, J=8.46, 1.47 Hz, 1H), 8.44 (dd, J=4.41, 1.47 Hz, 1H), 16.29 (s, 1H).

EXAMPLE 103

3-(1,1-dioxido-4H-pyrido[3,2-e][1,2,4]thiadiazin-3-yl)-4-hydroxy-1-[(2-methyl-1,3-thiazol-5-yl)methyl]-2(1H)-quinolinone

EXAMPLE 103A

1-[(2-methyl-1,3-thiazol-5-yl)methyl]-2H-3,1-benzoxazine-2,4(1H)-dione

The title compound was prepared according to the procedure of Example 1B substituting isatoic anhydride for the product of Example 1A and 2-methyl-5-chloromethylthiazole for n-butyl bromide to give (0.410 g, 73%).

EXAMPLE 103B ethyl 1-[(2-methyl-1,3-thiazol-5-yl)methyl]-2,4-dioxo-1,2,3,4-tetrahydroquinoline-3-carboxylate The title compound was prepared according to the procedure of Example 84A substituting the product of Example 103A for the product of Example 15B (0.132 g, 25%). MS (ESI−) m/z 343 (M−H)⁻; $^1$H NMR (300 MHz, CDCl$_3$) δ 1.49 (t, J=6.99 Hz, 3H), 2.61 (s, 3H), 4.53 (q, J=7.23 Hz, 2H), 5.54 (s, 2H), 7.27 (t, J=8.09 Hz, 1H), 7.41 (d, J=8.46 Hz, 1H), 7.62 (s, 1H), 7.67 (m, 1H), 8.21 (dd, J=8.09, 1.47 Hz, 1H), 14.32 (s, 1H).

EXAMPLE 103C

N-[2-(aminosulfonyl)pyridin-3-yl]-1-[(2-methyl-1,3-thiazol-5-yl)methyl]-2,4-dioxo-1,2,3,4-tetrahydroquinoline-3-carboxamide The title compound was prepared as described in the procedure of Example 84C substituting the product of Example 99A for the product of Example 84B and substituting 3-amino-pyridine-2-sulfonamide for 2-amino-5-bromobenzenesulfonamide (0.148 g, 79%). MS (APCI) m/z 472 (M+H)⁺. $^1$H NMR (300 MHz, DMSO-d$_6$) 6.2.55 (s, 3H), 5.69 (s, 2H), 7.25 (m, 1H), 7.35 (s, 1H), 7.42 (t, J=6.62 Hz, 1H), 7.81 (m, 4H), 8.17 (d, J=7.72 Hz, 1H), 8.52 (d, J=2.57 Hz, 1H), 8.54 (s, 1H), 12.67 (s, 1H), 16.28 (s, 1H).

EXAMPLE 103D 3-(1,1-dioxido-4H-pyrido[3,2-e][1,2,4]thiadiazin-3-yl)-4-hydroxy-1-[(2-methyl-1,3-thiazol-5-yl)methyl]-2(1H)-quinolinone The title compound was prepared according to the procedure of Example 84D substituting the product of Example 103C for the product of Example 84C (0.033 g, 68%). MS (APCI) m/z 454 (M+H)⁺. $^1$H NMR (300 MHz, DMSO-d$_6$) δ 2.56 (s, 3H), 5.74 (s, 2H), 7.48 (t, J=6.80 Hz, 1H), 7.82 (s, 1H), 7.88 (m, 4H), 8.24 (m, 2H), 8.71 (dd, J=4.41, 1.47 Hz, 1H), 14.01 (s, 1H).

EXAMPLE 104

1-benzyl-4-hydroxy-3-(7-methyl-1,1-dioxido-4H-pyrido[2,3-e][1,2,4]thiadiazin-3-yl)-2(1H)-quinolinone

EXAMPLE 104A (2-Amino-5-methylpyrid-3-yl)sulfonyl chloride (2-Amino-5-methylpyrid-3-yl)sulfonyl chloride was prepared from 2-amino-5-picoline by the method described by Weller, H. N. in U.S. Pat. No. 5,378,704. $^1$H NMR (300 MHz, DMSO-d$_6$) δ 2.20 (s, 3H), 7.70 (br. s., 2H), 7.85 (d, J=5.52 Hz, 1H), 8.07 (d, J=2.21 Hz, 1H).

EXAMPLE 104B 2-amino-5-methylpyridine-3-sulfonamide

The product of Example 104A was reacted with concentrated ammonium hydroxide at ambient temperature overnight. The reaction mixture was concentrated to give the title compound as a light yellow solid in quantitative yield. MS (DCI/NH$_3$) m/z 188 (M+H)⁺. $^1$H NMR (300 MHz, DMSO-d$_6$) δ 2.17 (m, 3H), 6.28 (s, 2H), 7.43 (s, 2H), 7.70 (d, J=1.84 Hz, 1H), 8.00 (d, J=2.21 Hz, 1H).

EXAMPLE 104C

N-[3-(aminosulfonyl)-5-methylpyridin-2-yl]-1-benzyl-4-hydroxy-2-oxo-1,2-dihydroquinoline-3-carboxamide The title compound was prepared according to the procedure of Example 84C substituting product of Example 104B for 2-amino-5-bromobenzenesulfonamide.

EXAMPLE 104D 1-benzyl-4-hydroxy-3-(7-methyl-1,1-dioxido-4H-pyrido[2,3-e][1,2,4]thiadiazin-3-yl)-2(1H)-quinolinone The title compound was prepared according to the procedure of Example 84D substituting the product of Example 104C for the product of Example 84C (0.20 g, 35%). $^1$H NMR (300 MHz, DMSO-d$_6$) δ 3.32 (m, 3H), 5.45 (s, 2H), 5.97 (s, 1H), 7.22 (m, 9H), 7.50 (m, 1H), 7.91 (dd, J=7.91, 1.65 Hz, 1H), 11.50 (m, 1H). The sodium salt of the title compound was prepared according to the procedure of Example 1D. $^1$H NMR (300 MHz, DMSO-d$_6$) δ 2.37 (m, 3H), 5.39 (m, 2H), 7.07 (m, 1H), 7.24 (m, 6H), 7.39 (m, 1H), 7.94 (d, J=1.47 Hz, 1H), 8.13 (dd, J=7.91, 1.65 Hz, 1H), 8.43 (d, J=1.84 Hz, 1H), 16.49 (m, 1H)

EXAMPLE 105

1-butyl-4-hydroxy-3-(7-methyl-1,1-dioxido-4H-pyrido[2,3-e][1,2,4]thiadiazin-3-yl)-1,8-naphthyridin-2(1H)-one

EXAMPLE 105A ethyl 3-{[3-(aminosulfonyl)-5-methylpyridin-2-yl]amino}-3-oxopropanoate The product of Example 104B (1.0 g, 0.0053 mol) in 10 mL of THF containing 5 mL of pyridine was treated with ethyl 3-chloro-3-oxopropionate (0.97 g, 0.0064 mol) at ambient temperature for several hours. The reaction mixture was concentrated to half its original volume and then diluted with water. The resulting precipitate was collected by filtration and washed with water and dried under vacuum to give the title compound as an off white solid (1.19 g, 75% yield). MS (ESI) m/z 300 (M–H)$^-$. $^1$H NMR (300 MHz, DMSO-d$_6$) δ 1.19 (t, J=7.17 Hz, 3H), 2.35 (s, 3H), 3.65 (s, 2H), 4.11 (q, J=7.23 Hz, 2H), 7.60 (s, 2H), 8.06 (d, J=1.47 Hz, 1H), 8.41 (d, J=1.84 Hz, 1H), 9.79 (s, 1H).

EXAMPLE 105C ethyl (7-methyl-1,1-dioxido-4H-pyrido[2,3-e][1,2,4]thiadiazin-3-yl)acetate The product of Example 105A (0.363 g, 0.0012 mol) in 20 mL of ethanol was reacted with sodium carbonate (0.350 g, 0.0033 mol). The reaction mixture was heated at reflux for 2 hours. After cooling, the reaction mixture was diluted with dichloromethane, filtered to remove the excess sodium carbonate, and concentrated. The residue was purified chromatography on silica gel with ethyl acetate in hexanes (1:1) followed by 4% methanol in dichloromethane as the mobile phase to give the title compound as a white solid (0.296 g, 87% yield). MS (ESI) m/z 282 (M–H)$^-$; $^1$H NMR (300 MHz, DMSO-d$_6$) δ 1.21 (t, J=6.99 Hz, 3H), 2.40 (s, 3H), 3.73 (s, 2H), 4.15 (q, J=7.11 Hz, 2H), 8.20 (s, 1H), 8.58 (d, J=1.84 Hz, 1H), 12.79 (s, 1H).

EXAMPLE 105D 1-butyl-4-hydroxy-3-(7-methyl-1,1-dioxido-4H-pyrido[2,3-e][1,2,4]thiadiazin-3-yl)-1,8-naphthyridin-2(1H)-one The title compound was prepared according to the procedure of Example 1D substituting the product of Example 105C for the product of Example 1C (0.065 g, 58% yield). $^1$H NMR (300 MHz, DMSO-d$_6$) δ 0.94 (t, J=7.35 Hz, 3H), 1.40 (m, 2H), 1.67 (m, 2H), 2.44 (m, 3H), 4.46 (dd, J=7.91, 7.17 Hz, 2H), 7.48 (dd, J=8.09, 4.78 Hz, 1H), 8.29 (s, 1H), 8.56 (dd, J=7.91, 1.65 Hz, 1H), 8.64 (d, J=1.47 Hz, 1H), 8.87 (d, J=5.52 Hz, 1H). The sodium salt of the title compound was prepared according to the procedure of Example 1D. $^1$H NMR (300 MHz, DMSO-d$_6$) δ 0.93 (t, J=7.35 Hz, 3H), 1.34 (m, 2H), 1.58 (m, 2H), 2.36 (s, 3H), 4.26 (d, J=7.72 Hz, 2H), 4.29 (d, J=6.99 Hz, 1H), 7.13 (dd, J=7.72, 4.78 Hz, 1H), 7.95 (s, 1H), 8.37 (d, J=7.72, 2.21 Hz, 1H), 8.42 (d, J=1.84 Hz, 1H), 8.53 (dd, J=4.60, 2.02 Hz, 1H), 16.11 (s, 1H).

EXAMPLE 106

3-(1,1-dioxido-4H-1,2,4-benzothiadiazin-3-yl)-4-hydroxy-1-(2-thienylmethyl)-1,8-naphthyridin-2(1H)-one

EXAMPLE 106A 1-(thien-2-ylmethyl)-2H-pyrido[2,3-d][1,3]oxazine-2,4(1H)-dione The title compound was prepared according to the procedure of Example 1B substituting 2-(bromomethyl)-thiophene for n-butyl bromide (0.165 g, 51%). $^1$H NMR (300 MHz, DMSO-d$_6$) δ 5.48 (s, 2H), 6.97 (dd, J=5.15, 3.31 Hz, 1H), 7.21 (d, J=3.31 Hz, 1H), 7.43 (m, 2H), 8.41 (dd, J=7.72, 1.84 Hz, 1H), 8.83 (dd, J=5.15, 1.84 Hz, 1H).

EXAMPLE 106B 3-(1,1-dioxido-4H-1,2,4-benzothiadiazin-3-yl)-4-hydroxy-1-(2-thienylmethyl)-1,8-naphthyridin-2(1H)-one The title compound was prepared according to the procedure of Example 1D substituting the product of Example 106A for the product of Example 1B (0.162 g, 60%). MS (ESI–) m/z 437 (M–H)$^-$. The sodium salt of the title compound was prepared according to the procedure of Example 1D. $^1$H NMR (300 MHz, DMSO-d$_6$) δ 5.64 (s, 2H), 6.90 (m, J=5.15, 3.68 Hz, 1H), 7.11 (m, J=3.49, 0.92 Hz, 1H), 7.18 (dd, J=7.72, 4.78 Hz, 1H), 7.29 (m, 3H), 7.56 (m, 1H), 7.67 (dd, J=7.72, 1.10 Hz, 1H), 8.39 (dd, J=7.72, 2.21 Hz, 1H), 8.57 (dd, J=4.78, 1.84 Hz, 1H), 15.80 (s, 1H).

EXAMPLE 107

1-(benzyloxy)-3-(1,1-dioxido-4H-1,2,4-benzothiadiazin-3-yl)-4-hydroxy-1,8-naphthyridin-2(1H)-one

EXAMPLE 107A ethyl 2-[(benzyloxy)amino]nicotinate

2-Chloro-nicotinic acid ethyl ester (4.55 g, 24.6 mmol), O-benzylhydroxyamine hydrochloride (7.85 g, 49.2 mmol) and N,N-diisopropylethylamine (6.36 g, 49.2 mmol) in 10 mL 1,4-dioxane were reacted in a sealed tube at 120° C. for 48 hours. The reaction mixture was partitioned between ethyl acetate and 5% aqueous sodium bicarbonate. The aqueous layer was re-extracted with ethyl acetate (2×50 mL). The organic layers were combined and dried over sodium sulfate, filtered, and concentrated. The residue was purified by column chromatography on silica gel eluting with hexane and ethyl acetate (9:1) to provide the title compound (3.5 g, 53%). MS (DCI) m/z 273 (M+H)$^+$.

EXAMPLE 107B ethyl 2-[(benzyloxy)(3-ethoxy-3-oxopropanoyl)amino]nicotinate

A solution of the product of Example 107a (1.2 g, 4.4 mmol) and triethylamine (0.49 g, 4.8 mmol) in dichloromethane (25 mL) was treated dropwise with ethyl chloromalonate (0.73 g, 4.8 mmol), stirred for 2 hr and partitioned between ethyl acetate and water and the layers were separated. The ethyl acetate layer was washed with brine, dried (Na$_2$SO$_4$), and concentrated. The residue was purified by column chromatography on silica gel eluting with hexane and ethyl acetate (3:1) to provide the title compound (1.1 g, 65%). MS (DCI) m/z 387 (M+H)$^+$.

EXAMPLE 107C ethyl 1-(benzyloxy)-4-hydroxy-2-oxo-1,2-dihydro-1, 8-naphthyridine-3-carboxylate A solution of the product of Example 107b (0.386 g, 1.0 mmol) in ethanol (5 mL) was treated with 21% sodium ethoxide in ethanol (0.324 g, 1.0 mmol), stirred for 30 minutes and partitioned between ethyl acetate and 5% aqueous HCl and the layers were separated. The ethyl acetate layer was washed with brine, dried (Na$_2$SO$_4$), and concentrated to provide the title compound (0.28 g, 82%). MS (DCI) m/z 341(M+H)$^+$.

EXAMPLE 107D

N-[2-(aminosulfonyl)phenyl]-1-(benzyloxy)-4-hydroxy-2-oxo-1,2-dihydro-1,8-naphthyridine-3-carboxamide A mixture of the product of Example 107c (340 mg, 0.82 mmol) and 2-aminobenzenesulfonamide (141 mg, 0.82 mmol) in toluene (10 mL) was refluxed for 16 hours, cooled, and the resulting precipitate was collected by filtration and dried to give the title compound (340 mg, 89%). MS (DCI) m/z 467 (M+H)$^+$.

EXAMPLE 107E 1-(benzyloxy)-3-(1,1-dioxido-4H-1,2,4-benzothiadiazin-3-yl)-4-hydroxy-1,8-naphthyridin-2(1H)-one The title compound was prepared according to the procedure of Example 84d substituting the product of Example 107d for the product of Example 84c to give the title compound (0.082 g, 87%). MS (ESI−) m/z 447 (M−H)$^−$. The sodium salt of the title compound was prepared according to the procedure of Example 1d. $^1$H NMR (300 MHz, DMSO-d$_6$) δ 5.12 (s, 2H) 7.22 (dd, J=7.72, 4.78 Hz, 1H) 7.30 (m, 2H) 7.44 (m, 3H) 7.57 (m, 1H) 7.70 (m, 3H) 8.41 (dd, J=7.72, 1.84 Hz, 1H) 8.61 (dd, J=4.78, 1.84 Hz, 1H) 15.70 (s, 1H).

EXAMPLE 108

6-(1,1-dioxido-4H-1,2,4-benzothiadiazin-3-yl)-8-(2-ethylbutyl)-5-hydroxy-2-(methylsulfanyl)pyrido[2,3-d]pyrimidin-7(8H)-one

EXAMPLE 108A methyl 4-[(2-ethylbutyl)amino]-2-(methylthio)pyrimidine-5-carboxylate Ethyl 4-chloro-2-methylthio-5-pyrimidinecarboxylate (0.40 g, 1.72 mmol) was reacted with 1-amino-2-ethyl butane (0.175 g, 1.72 mmol) and triethylamine (0.60 mL, 4.32 mmol) at ambient temperature for 18 hours. The reaction was partitioned between water and dichloromethane. The organic layer was dried over sodium sulfate, filtered, and the concentrated to give the title compound (0.50 g, 98%).

EXAMPLE 108B

4-[(2-ethylbutyl)amino]-2-(methylthio)pyrimidine-5-carboxylic acid

The product of Example 108A (0.50 g, 1.68 mmol)) in water and ethanol (1:2) was reacted with sodium hydroxide (0.22 g, 5.50 mmol) at ambient temperature for 3 hours. The reaction was concentrated under vacuum to remove the ethanol and neutralized with aqueous hydrochloric acid (1 M). The resulting precipitate was collected by filtration and dried to yield the title compound (0.41 g, 91%). MS (DCI/NH$_3$) m/z 270 (M+H)$^+$; $^1$H NMR (300 MHz, DMSO-d$_6$) δ 0.88 (t, J=7.54 Hz, 6H), 1.31 (dt, J=14.25, 7.03 Hz, 4H), 1.53 (m, 1H), 2.47 (s, 3H), 3.46 (t, J=6.07 Hz, 2H), 8.50 (s, 1H), 13.22 (s, 1H).

EXAMPLE 108C 1-(2-ethylbutyl)-7-(methylthio)-2H-pyrimido[4,5-][1,3]oxazine-2,4(1H)-dione The product of Example 108B (0.41 g, 1.52 mmol) was reacted with ethyl chloroformate (0.445 mL, 4.65 mmol) and pyridine (0.405 mL, 5.56 mmol) in toluene (8 ML) at 90° C. for 24 hours. The reaction was concentrated under vacuum. The residue was extracted with ethyl acetate and filtered. Concentration of the filtrate gave the title compound (0.394 g, 88%).

EXAMPLE 108D 6-(1,1-dioxido-4H-1,2,4-benzothiadiazin-3-yl)-8-(2-ethylbutyl)-5-hydroxy-2-(methylsulfanyl)pyrido[2,3-d]pyrimidin-7(8H)-one The title compound was prepared according to the procedure of Example 1D substituting the product of Example 108C for the product of Example 1B (0.153 g, 24%). MS (ESI−) m/z 472 (M−H)$^−$. The sodium salt of the title compound was prepared according to the procedure of Example 1D. $^1$H NMR (300 MHz, DMSO-d$_6$) δ 0.87 (t, J=7.54 Hz, 6H), 1.28 (m, 4H), 1.87 (ddd, J=13.05, 6.80, 6.62 Hz, 1H), 2.56 (s, 3H), 4.15 (d, J=7.35 Hz, 2H), 7.26 (d, J=8.46 Hz, 1H), 7.31 (m, 1H), 7.56 (ddd, J=8.27, 7.17, 1.47 Hz, 1H), 7.67 (dd, J=7.72, 1.47 Hz, 1H), 8.89 (s, 1H), 15.52 (s, 1H).

EXAMPLE 109

6-(1,1-dioxido-4H-1,2,4-benzothiadiazin-3-yl)-8-(2-ethylbutyl)-5-hydroxypyrido[2,3-d]pyrimidin-7(8H)-one The product of Example 108D (0.15 g, 0.30 mmol) was reacted with an excess of Raney nickel (slurry in water, 2 mL) in ethanol (5 mL) and heated at 60° C. for 1 hour. The mixture was filtered through celite, rinsed with ethanol, and the filtrate concentrated under vacuum to yield the title compound. MS (ESI−) m/z 448 (M−H)$^−$; $^1$H NMR (300 MHz, DMSO-d$_6$) δ 0.86 (t, J=7.35 Hz, 6H), 1.28 (m, 4H), 1.87 (m, 1H), 4.18 (d, J=7.35 Hz, 2H), 7.30 (m, 2H), 7.57 (ddd, J=8.27, 7.17, 1.47 Hz, 1H), 7.68 (dd, J=7.91, 1.29 Hz, 1H), 8.94 (s, 1H), 9.09 (s, 1H), 15.43 (s, 1H).

EXAMPLE 110

4-benzyl-6-(1,1-dioxido-4H-1,2,4-benzothiadiazin-3-yl)-7-hydroxythieno[3,2-b]pyridin-5(4H)-one

EXAMPLE 110A 2H-thieno[3,2-d][1,3]oxazine-2,4(1H)-dione

The title compound was prepared according to the procedure of Fabis, and co-workers as described in *Tetrahedron*, 1998, 54, 10789-10800. MS (DCI/NH$_3$) m/z 186.9 (M+NH$_4$)$^+$; $^1$H NMR (300 MHz, DMSO-d$_6$) δ 6.95 (d, J=6 Hz, 1 H) 8.25 (d, J=6 Hz, 1 H) 12.22 (brs, 1 H).

EXAMPLE 110B 1-benzyl-2H-thieno[3,2-d][1,3]oxazine-2,4(1H)-dione

The product of Example 110A (0.137 g, 0.81 mmol) was reacted with benzyl bromide (0.10 mL, 0.85 mmol), and potassium carbonate (0.134 g, 0.97 mmol) in dimethylformamide (5 mL) at ambient temperature for 20 hours. The reaction mixture was diluted with water and the resulting precipitate was collecte by filtration, and dried to give the title compound (0.165 g, 80%). MS (DCI/NH$_3$) m/z 277 (M+NH$_4$)$^+$; $^1$H NMR (300 MHz, DMSO-d$_6$) δ 5.21 (s, 2 H) 7.25 (d, J=5.52 Hz, 1 H) 7.35 (m, 5 H) 8.28 (d, J=5.52 Hz, 1 H).

EXAMPLE 110C 4-benzyl-6-(1,1-dioxido-4H-1,2,4-benzothiadiazin-3-yl)-7-hydroxythieno[3,2-b]pyridin-5(4H)-one The title compound was prepared according to the procedure of Example 1D substituting the product of Example 110B for the product of Example 1B (0.137 g, 49%). MS (ESI-) m/z 438 (M-H)$^-$. The sodium salt of the title compound was prepared according to the procedure of Example 1D. $^1$H NMR (300 MHz, DMSO-d$_6$) δ 5.26 (s, 2 H) 7.03 (d, J=5.52 Hz, 1 H) 7.21 (m, 2 H) 7.28 (m, 5 H) 7.54 (ddd, J=8.27, 7.17, 1.47 Hz, 1 H) 7.65 (dd, J=7.91, 1.29 Hz, 1 H) 7.73 (d, J=5.52 Hz, 1 H) 15.89 (s, 1 H).

EXAMPLE 111

4-butyl-6-(1,1-dioxido-4H-1,2,4-benzothiadiazin-3-yl)-7-hydroxythieno[3,2-b]pyridin-5(4H)-one

EXAMPLE 111A 1-butyl-2H-thieno[3,2-d][1,3]oxazine-2,4(1H)-dione

The title compound was prepared according to the procedure of Example 110B substituting n-butyl bromide for benzyl bromide (0.059 g, 22%). MS (DCI) m/z 226 (M+H)$^+$; $^1$H NMR (300 MHz, DMSO-d$_6$) δ 0.91 (t, J=7.17 Hz, 3 H) 1.36 (dt, J=22.70, 7.22 Hz, 2 H) 1.62 (m, 2 H) 3.94 (m, 2 H) 7.39 (d, J=5.52 Hz, 1 H) 8.34 (d, J=5.15 Hz, 1 H).

EXAMPLE 111B 4-butyl-6-(1,1-dioxido-4H-1,2,4-benzothiadiazin-3-yl)-7-hydroxythieno[3,2-b]pyridin-5(4H)-one The title compound was prepared according to the procedure of Example 1D substituting the product of Example 111A for the product of Example 1B (0.050 g, 47%). MS (DCI/NH$_3$) m/z 404 (M+H)$^+$; $^1$H NMR (300 MHz, DMSO-d$_6$) δ 0.93 (m, 3 H) 1.40 (td, J=14.98, 7.17 Hz, 2 H) 1.67 (m, 2 H) 4.27 (m, 2 H) 7.54 (m, 1 H) 7.60 (d, J=5.52 Hz, 1 H) 7.67 (d, J=7.72 Hz, 1 H) 7.77 (ddd, J=8.36, 7.08, 1.47 Hz, 1 H) 7.92 (d, J=7.72 Hz, 1 H) 8.39 (d, J=5.52 Hz, 1 H) 14.46 (s, 1 H) 14.90 (s, 1 H).

EXAMPLE 112

6-(1,1-dioxido-4H-1,2,4-benzothiadiazin-3-yl)-7-hydroxy-4-(4-pyridinylmethyl)thieno[3,2-b]pyridin-5(4H)-one

EXAMPLE 112A 1-(pyridin-4-ylmethyl)-2H-thieno[3,2-d][1,3]oxazine-2,4(1H)-dione The title compound was prepared according to the procedure of Example 1B substituting the product of Example 110A for the product of Example 1A and substituting 4-bromomethylpyridine hydrobromide for n-butyl bromide (0.205 g, 80%).

EXAMPLE 112B 6-(1,1-dioxido-4H-1,2,4-benzothiadiazin-3-yl)-7-hydroxy-4-(4-pyridinylmethyl)thieno[3,2-b]pyridin-5(4H)-one The title compound was prepared according to the procedure of Example 1D substituting the product of Example 112A for the product of Example 1B (0.155 g, 45%). MS (DCI/NH$_3$) m/z 439 (M+H)$^+$; $^1$H NMR (300 MHz, DMSO-d$_6$) δ 5.78 (s, 2 H) 7.49 (d, J=5.52 Hz, 1 H) 7.55 (t, J=7.54 Hz, 1 H) 7.62 (d, J=7.35 Hz, 1 H) 7.76 (m, 4 H) 7.93 (d, J=7.72 Hz, 1 H) 8.38 (d, J=5.52 Hz, 1 H) 8.75 (d, J=6.25 Hz, 1 H) 14.06 (s, 1 H).

EXAMPLE 113

1-(3-bromobenzyl)-3-(1,1-dioxido-4H-1,2,4-benzothiadiazin-3-yl)-4-hydroxy-5,6,7,8-tetrahydro-2(1H)-quinolinone

EXAMPLE 113A 5,6,7,8-tetrahydro-2H-3,1-benzoxazine-2,4(1H)-dione

The title compound was prepared according to the procedure of Example 3B substituting ethyl 2-aminocyclohex-1-ene-1-carboxylate for the product of Example 3A (0.960 g, 97%). MS (ESI-) m/z 166 (M-H)$^+$.

EXAMPLE 113B 1-(3-bromobenzyl)-5,6,7,8-tetrahydro-2H-3,1-benzoxazine-2,4(1H)-dione The title compound was prepared according to the procedure of Example 1B substituting the product of Example 113A for the product of Example 1A and substituting 3-bromobenzyl bromide for n-butyl bromide (0.049 g, 46%). MS (ESI-) m/z 334 (M-H)$^+$.

EXAMPLE 113C 1-(3-bromobenzyl)-3-(1,1-dioxido-4H-1,2,4-benzothiadiazin-3-yl)-4-hydroxy-5,6,7,8-tetrahydro-2(1H)-quinolinone The title compound was prepared according to the procedure of Example 1D substituting the product of Example 113B for the product of Example 1B (0.021 g, 34%). MS (ESI−) m/z 514 (M−H)+; $^1$H NMR (300 MHz, DMSO-$d_6$) δ 1.68 (m, 4 H), 2.51 (m, 2 H), 2.67 (m, 2 H), 5.40 (s, 2 H), 7.13 (d, J=7.72 Hz, 1 H), 7.30 (t, J=7.91 Hz, 1 H), 7.51 (m, 3 H), 7.61 (d, J=8.09 Hz, 1 H), 7.73 (t, J=7.17 Hz, 1 H), 7.90 (d, J=8.46 Hz, 1 H), 14.40 (s, 1 H), 14.56 (s, 1 H). The sodium salt of the title compound was prepared according to the procedure of Example 1D. $^1$H NMR (300 MHz, DMSO-$d_6$) δ 1.59 (m, 4 H), 2.33 (t, J=5.70 Hz, 2 H), 2.41 (m, 2 H), 5.14 (s, 2 H), 7.11 (d, J=8.09 Hz, 1 H), 7.18 (d, J=8.09 Hz, 1 H), 7.25 (m, 3 H), 7.41 (d, J=7.72 Hz, 1 H), 7.50 (td, J=7.72, 1.47 Hz, 1 H), 7.62 (dd, J=7.72, 1.47 Hz, 1 H), 17.13 (s, 1 H).

EXAMPLE 114

5-(1,1-dioxido-4H-1,2,4-benzothiadiazin-3-yl)-4-hydroxy-7-(4-pyridinylmethyl)thieno[2,3-b]pyridin-6(7H)-one

EXAMPLE 114A 2H-thieno[2,3-d][1,3]oxazine-2,4(1H)-dione

The title compound was prepared by the method of Fabis, and coworkers in *Tetrahedron* 1998 54 10789-10800. MS (DCI/NH$_3$) m/z 187 (M+NH$_4$)+; $^1$H NMR (300 MHz, DMSO-$d_6$) δ 7.17 (d, J=16.8 Hz, 1 H) 7.21 (d, J=16.8 Hz 1 H) 12.56 (brs, 1 H).

EXAMPLE 114B 1-(pyridin-4-ylmethyl)-2H-thieno[2,3-d][1,3]oxazine-2,4(1H)-dione The title compound was prepared according to the procedure of Example 1B substituting the product of Example 114A for the product of Example 1A and substituting 4-bromomethylpyridine hydrobromide for n-butyl bromide (0.22 g, 95%).

EXAMPLE 114C 5-(1,1-dioxido-4H-1,2,4-benzothiadiazin-3-yl)-4-hydroxy-7-(4-pyridinylmethyl)thieno[2,3-b]pyridin-6(7H)-one The title compound was prepared according to the procedure of Example 1D substituting the product of Example 114B for the product of Example 1B (0.047 g, 13%). MS (DCI/NH$_3$) m/z 439 (M+H)+; $^1$H NMR (300 MHz, DMSO-$d_6$) δ 5.62 (s, 2 H) 7.48 (m, 2 H) 7.55 (t, J=7.54 Hz, 1 H) 7.62 (d, J=7.72 Hz, 1 H) 7.68 (d, J=6.25 Hz, 1 H) 7.76 (ddd, J=8.55, 7.26, 1.47 Hz, 1 H) 7.93 (d, J=8.09 Hz, 1 H) 8.71 (d, J=6.62 Hz, 1 H) 13.87 (s, 1 H).

EXAMPLE 115

6-(1,1-dioxido-4H-1,2,4-benzothiadiazin-3-yl)-7-hydroxy-4-(3-pyridinylmethyl)thieno[3,2-b]pyridin-5(4H)-one

EXAMPLE 115A 1-(pyridin-3-ylmethyl)-2H-thieno[3,2-d][1,3]oxazine-2,4(1H)-dione The title compound was prepared according to the procedure of Example 1B substituting the product of Example 110A for the product of Example 1A and substituting 3-bromomethylpyridine hydrobromide for n-butyl bromide (0.28 g, 90%). MS (DCI/NH$_3$) m/z 261 (M+H)+; $^1$H NMR (300 MHz, DMSO-$d_6$) δ 5.24 (s, 2 H) 7.34 (d, J=5.52 Hz, 1 H) 7.38 (m, 1 H) 7.81 (dt, J=8.00, 1.88 Hz, 1 H) 8.30 (d, J=5.15 Hz, 1 H) 8.51 (dd, J=4.78, 1.47 Hz, 1 H) 8.67 (d, J=1.84 Hz, 1 H).

EXAMPLE 115B 6-(1,1-dioxido-4H-1,2,4-benzothiadiazin-3-yl)-7-hydroxy-4-(3-pyridinylmethyl)thieno[3,2-b]pyridin-5(4H)-one The title compound was prepared according to the procedure of Example 1D substituting the product of Example 115A for the product of Example 1B (0.237 g, 50%). MS (DCI/NH$_3$) m/z 439 (M+H)+. The sodium salt of the title compound was prepared according to the procedure of Example 1D. $^1$H NMR (300 MHz, DMSO-$d_6$) δ 5.49 (s, 2 H) 7.34 (dd, J=7.91, 4.60 Hz, 1 H) 7.45 (m, 3 H) 7.68 (m, 2 H) 7.83 (d, J=8.09 Hz, 1 H) 8.16 (s, 1 H) 8.47 (d, J=3.68 Hz, 1 H) 8.62 (s, 1 H) 14.83 (brs, 1 H).

EXAMPLE 116

7-benzyl-5-(1,1-dioxido-4H-1,2,4-benzothiadiazin-3-yl)-4-hydroxythieno[2,3-b]pyridin-6(7H)-one

EXAMPLE 116A 1-benzyl-2H-thieno[2,3-d][1,3]oxazine-2,4(1H)-dione

The title compound was prepared according to the procedure of Example 110B substituting the product of Example 114A for the product of Example 110A (0.26 g, 100%).

EXAMPLE 116B 7-benzyl-5-(1,1-dioxido-4H-1,2,4-benzothiadiazin-3-yl)-4-hydroxythieno[2,3-b]pyridin-6(7H)-one The title compound was prepared according to the procedure of Example 1D substituting the product of Example 116A for the product of Example 1B (0.144 g, 38%). MS (ESI−) m/z 436 (M−H)−. The sodium salt of the title compound was prepared according to the procedure of Example 1D. MS (ESI−) m/z 436 (M−H—); 6 $^1$H NMR (300 MHz, DMSO-d$_6$) δ 5.14 (s, 2 H) 6.90 (d, J=5.52 Hz, 1 H) 7.20 (m, 2 H) 7.30 (m, 6 H) 7.54 (m, 1 H) 7.65 (dd, J=7.72, 1.47 Hz, 1 H) 16.25 (s, 1 H).

EXAMPLE 117

4-(cyclopropylmethyl)-6-(1,1-dioxido-4H-1,2,4-benzothiadiazin-3-yl)-7-hydroxythieno[3,2-b]pyridin-5(4H)-one

EXAMPLE 117A 1-(cyclopropylmethyl)-2H-thieno[3,2-d][1,3]oxazine-2,4(1H-dione The title compound was prepared according to the procedure of Example 1B substituting the product of Example 110A for the product of Example 1A and substituting bromomethyl cyclopropane for n-butyl bromide (0.23 g, 87%). MS (DCI/NH$_3$) m/z 241 (M+NH$_4$)$^+$; $^1$H NMR (300 MHz, DMSO-d$_6$) δ 0.47 (m, 4 H) 1.21 (m, 1 H) 3.89 (d, J=6.99 Hz, 2 H) 7.45 (d, J=5.15 Hz, 1 H) 8.35 (d, J=5.15 Hz, 1 H).

EXAMPLE 117B 4-(cyclopropylmethyl)-6-(1,1-dioxido-4H-1,2,4-benzothiadiazin-3-yl)-7-hydroxythieno[3,2-b]pyridin-5(4H)-one The title compound was prepared according to the procedure of Example 1D substituting the product of Example 117A for the product of Example 1B (0.252 g, 60%). MS (ESI−) m/z 400 (M−H)$^−$. The sodium salt of the title compound was prepared according to the procedure of Example 1D. $^1$H NMR (300 MHz, DMSO-d$_6$) δ 0.41 (m, 4 H) 1.20 (m, 1 H) 3.92 (d, J=6.99 Hz, 2 H) 7.19 (m, 2 H) 7.26 (t, J=7.54 Hz, 1 H) 7.53 (m, 1 H) 7.64 (d, J=6.62 Hz, 1 H) 7.79 (d, J=5.52 Hz, 1 H) 15.97 (s, 1 H).

EXAMPLE 118

5-(1,1-dioxido-4H-1,2,4-benzothiadiazin-3-yl)-4-hydroxy-7-(3-methylbutyl)thieno[2,3-b]pyridin-6(7H)-one

EXAMPLE 118A 1-(3-methylbutyl)-2H-thieno[2,3-d][1,3]oxazine-2,4(1H)-dione

The title compound was prepared according to the procedure of Example 1B substituting the product of Example 114A for the product of Example 1A and substituting isobutyl bromide for n-butyl bromide (0.074 g, 35%).

EXAMPLE 118B 5-(1,1-dioxido-4H-1,2,4-benzothiadiazin-3-yl)-4-hydroxy-7-(3-methylbutyl)thieno[2,3-b]pyridin-6(7H)-one The title compound was prepared according to the procedure of Example 1D substituting the product of Example 118A for the product of Example 1B (0.063 g, 49%). MS (ESI−) m/z 416 (M−H)$^−$ The sodium salt of the title compound was prepared according to the procedure of Example 1D. $^1$H NMR (300 MHz, DMSO-d$_6$) δ 0.96 (s, 3 H) 0.98 (s, 3 H) 1.53 (m, 2 H) 1.66 (m, 1 H) 3.87 (m, 2 H) 6.95 (d, J=5.52 Hz, 1 H) 7.19 (m, 2 H) 7.25 (m, 1 H) 7.52 (ddd, J=8.27, 7.17, 1.47 Hz, 1 H) 7.64 (dd, J=7.72, 1.47 Hz, 1 H) 16.30 (s, 1 H).

EXAMPLE 119

4-benzyl-6-(1,1-dioxido-4H-1,2,4-benzothiadiazin-3-yl)-7-hydroxy-2-phenylthieno[3,2-b]pyridin-5(4H)-one

EXAMPLE 119A 6-phenyl-2H-thieno[3,2-d][1,3]oxazine-2,4(1H)-dione

Methyl-3-amino-5-phenylthiophene-2-carboxylate (0.25 g, 1.07 mmol) in water (6 mL) was reacted with potassium hydroxide (0.12 g, 2.14 mmol) at 90° C. for 24 hours. The reaction was cooled to 0° C. and phosgene (1.9M in toluene, 0.70 mL, 1.40 mmol) was added dropwise. After stirring at room temperature for 1 hour, the resulting solid was collected by filtration, washed with excess water and dried to give the title compound as a tan solid (0.175 g, 65%).

EXAMPLE 119B 1-benzyl-6-phenyl-2H-thieno[3,2-d][1,3]oxazine-2,4(1H)-dione

The title compound was prepared according to the procedure of Example 1B substituting the product of Example 119A for the product of Example 1A (0.19 g, 80%). MS (DCI/NH$_3$) m/z 353 (M+NH$_4$)$^+$; $^1$H NMR (300 MHz, DMSO-d$_6$) δ 5.26 (s, 2 H) 7.43 (m, 8 H) 7.82 (m, 3 H).

EXAMPLE 119C 4-benzyl-6-(1,1-dioxido-4H-1,2,4-benzothiadiazin-3-yl)-7-hydroxy-2-phenylthieno[3,2-b]pyridin-5(4H)-one The title compound was prepared according to the procedure of Example 1D substituting the product of Example 119B for the product of Example 1B (0.062 g, 22%). MS (ESI−) m/z 512 (M−H)$^−$. The sodium salt of the title compound was prepared according to the procedure of Example 1D. $^1$H NMR (300 MHz, DMSO-d$_6$) δ 5.34 (s, 2H) 7.24 (m, 2 H) 7.33 (m, 5 H) 7.43 (m, 4 H) 7.56 (t, J=7.35 Hz, 1 H) 7.71 (m, 3 H) 15.82 (m, 1 H).

EXAMPLE 120

4-benzyl-6-(1,1-dioxido-4H-1,2,4-benzothiadiazin-3-yl)-7-hydroxy-3-methylthieno[3,2-b]pyridin-5(4H)-one

EXAMPLE 120A 7-methyl-2H-thieno[3,2-d][1,3]oxazine-2,4(1H)-dione

The title compound was prepared according to the procedure of Example 119A substituting methyl-3-amino-4-methylthiophene-2-carboxylate for methyl-3-amino-5-phenylthiophene-2-carboxylate.

EXAMPLE 120B 1-benzyl-7-methyl-2H-thieno[3,2-d][1,3]oxazine-2,4 (1H)-dione

The title compound was prepared according to the procedure of Example 110B substituting the product of Example 120A for the product of Example 110A (0.22 g, 73%). MS (DCI/NH$_3$) m/z 291 (M+NH$_4$)+

EXAMPLE 120C 4-benzyl-6-(1,1-dioxido-4H-1,2,4-benzothiadiazin-3-yl)-7-hydroxy-3-methylthieno[3,2-b]pyridin-5 (4H)-one The title compound was prepared according to the procedure of Example 1D substituting the product of Example 120B for the product of Example 1B (0.110 g, 30%). MS (ESI−) m/z 450 (M−H)$^-$. The sodium salt of the title compound was prepared according to the procedure of Example 1D. $^1$H NMR (300 MHz, DMSO-d$_6$) δ 2.21 (s, 3 H) 5.47 (s, 2 H) 7.05 (m, 1 H) 7.25 (m, 6 H) 7.37 (d, J=0.74 Hz, 1 H) 7.54 (ddd, J=8.27, 7.17, 1.47 Hz, 1 H) 7.64 (dd, J=7.91, 1.29 Hz, 1 H) 15.92 (s, 1 H).

EXAMPLE 121

1-benzyl-3-(1,1-dioxido-4H-1,2,4-benzothiadiazin-3-yl)-4-hydroxy-5,6,7,8-tetrahydro-2(1H)-quinolinone

EXAMPLE 121A 1-benzyl-5,6,7,8-tetrahydro-2H-3,1-benzoxazine-2,4 (1H)-dione

The title compound was prepared according to the procedure of Example 1B substituting the product of Example 113A for the product of Example 1A and substituting benzyl bromide for n-butyl bromide (0.620 g, 67%). MS (ESI−) m/z 256 (M−H)$^-$.

EXAMPLE 121B 1-benzyl-3-(1,1-dioxido-4H-1,2,4-benzothiadiazin-3-yl)-4-hydroxy-5,6,7,8-tetrahydro-2(1H)-quinolinone The title compound was prepared according to the procedure of Example 1D substituting the product of Example 121A for the product of Example 1B (0.039 g, 37%). MS (ESI−) m/z 434 (M−H)$^-$. The sodium salt of the title compound was prepared according to the procedure of Example 1D. $^1$H NMR (300 MHz, DMSO-d$_6$) δ 1.54 (m, 4 H), 2.33 (t, J=5.88 Hz, 2 H), 2.42 (m, 2 H), 5.15 (s, 2 H), 7.10 (d, J=6.99 Hz, 2 H), 7.20 (m, 3 H), 7.30 (t, J=7.35 Hz, 2 H), 7.50 (td, J=7.72, 1.47 Hz, 1 H), 7.61 (dd, J=7.72, 1.10 Hz, 1 H), 17.20 (s, 1 H).

EXAMPLE 122

1-benzyl-3-(1,1-dioxido-4H-1,2,4-benzothiadiazin-3-yl)-4-hydroxy-2(1H)-pyridinone

EXAMPLE 122A 2H-1,3-oxazine-2,6(3H)-dione

The title compound was prepared by the method described by Warren, and coworkers in *Journal of Organic Chemistry* 1975 40(6) 743-746. MS (DCI/NH$_3$) m/z 131 (M+NH$_4$)$^+$; $^1$H NMR (300 MHz, DMSO-d$_6$) δ 5.61 (d, J=7.72 Hz, 1 H) 7.65 (d, J=7.35 Hz, 1 H) 11.55 (s, 1 H).

EXAMPLE 122B 3-benzyl-2H-1,3-oxazine-2,6(3H)-dione

The title compound was prepared according to the procedure of Example 110B substituting the product of Example 122A for the product of Example 110A (0.156 g, 25%). MS (DCI/NH$_3$) m/z 221 (M+NH$_4$)$^+$; $^1$H NMR (300 MHz, DMSO-d$_6$) δ 4.89 (s, 2 H) 5.78 (d, J=7.72 Hz, 1 H) 7.37 (m, 5 H) 7.97 (d, J=8.09 Hz, 1 H).

EXAMPLE 122C 1-benzyl-3-(1,1-dioxido-4H-1,2,4-benzothiadiazin-3-yl)-4-hydroxy-2(1H)-pyridinone The title compound was prepared according to the procedure of Example 1D substituting the product of Example 122B for the product of Example 1B (0.13 g, 5%). MS (ESI−) m/z 380 (M−H)$^-$; $^1$H NMR (300 MHz, DMSO-d$_6$) δ 4.89 (s, 2 H) 5.53 (d, J=7.35 Hz, 1 H) 7.11 (d, J=7.72 Hz, 1 H) 7.28 (m, 6 H) 7.39 (d, J=7.72 Hz, 1 H) 7.50 (m, 1 H) 7.61 (dd, J=7.72, 1.0 Hz, 1 H) 16.83 (s, 1 H).

EXAMPLE 123

1-benzyl-3-(1,1-dioxido-4H-1,2,4-benzothiadiazin-3-yl)-4-hydroxy-5,6-dimethyl-2(1H)-pyridinone

EXAMPLE 123A 4,5-dimethyl-2H-1,3-oxazine-2,6(3H)-dione

The title compound was prepared by the method described by. Washburne, et. al. *Tetrahedron Letters* 1976 17(4) 243-246. MS (DCI/NH$_3$) m/z 204 (M+H)+

EXAMPLE 123B 3-benzyl-4,5-dimethyl-2H-1,3-oxazine-2,6(3H)-dione

The title compound was prepared according to the procedure of Example 1B substituting the product of Example 123A for the product of Example 1A and substituting benzyl bromide for n-butyl bromide (0.109 g, 27%). MS (DCI/NH$_3$) m/z 249 (M+NH$_4$)$^+$; $^1$H NMR (300 MHz, DMSO-d$_6$) δ 1.86 (s, 3 H) 2.14 (s, 3 H) 5.09 (s, 2 H) 7.32 (m, 5 H).

EXAMPLE 123C 1-benzyl-3-(1,1-dioxido-4H-1,2,4-benzothiadiazin-3-yl)-4-hydroxy-5,6-dimethyl-2(1H)-pyridinone The title compound was prepared according to the procedure of Example 1D substituting the product of Example 123B for the product of Example 1B (0.070 g, 36%). MS (ESI−) m/z 408 (M−H)$^-$. The sodium salt of the title compound was prepared according to the procedure of Example 1D. $^1$H NMR (300 MHz, DMSO-d$_6$) δ 1.88 (s, 3 H) 2.10 (s, 3 H) 5.20 (s, 2 H) 7.13 (m, 2 H) 7.21 (m, 2 H) 7.31 (m, J=7.17, 7.17 Hz, 3 H) 7.50 (m, 1 H) 7.62 (dd, J=7.91, 1.29 Hz, 1 H) 17.28 (s, 1 H).

EXAMPLE 124

7-benzyl-5-(1,1-dioxido-4H-1,2,4-benzothiadiazin-3-yl)-4-hydroxy-3-methylthieno[2,3-b]pyridin-6(7H)-one

EXAMPLE 124A 5-methyl-2H-thieno[2,3-d][1,3]oxazine-2,4(1H)-dione

The title compound was prepared according to the procedure of Fabis, and co-workers as described in *Tetrahedron*, 1998, 54, 10789-10800. MS (ESI−) m/z 182 (M−H)⁻.

EXAMPLE 124B 1-benzyl-5-methyl-2H-thieno[2,3-d][1,3]oxazine-2,4(1H)-dione

The title compound was prepared according to the procedure of Example 1B substituting the product of Example 124A for the product of Example 1A and substituting benzyl bromide for n-butyl bromide (0.075 g, 50%). MS (DCI/NH₃) m/z 291 (M+NH₄)⁺.

EXAMPLE 124C 7-benzyl-5-(1,1-dioxido-4H-1,2,4-benzothiadiazin-3-yl)-4-hydroxy-3-methylthieno[2,3-b]pyridin-6(7H)-one The title compound was prepared according to the procedure of Example 1D substituting the product of Example 124B for the product of Example 1B (0.025 g, 23%). MS (ESI−) m/z 450 (M−H)⁻. The sodium salt of the title compound was prepared according to the procedure of Example 1D. ¹H NMR (300 MHz, DMSO-d₆) δ 2.46 (s, 3 H), 5.12 (s, 2 H), 6.47 (d, J=1.10 Hz, 1 H), 7.28 (m, 7 H), 7.52 (td, J=7.72, 1.47 Hz, 1 H), 7.64 (dd, J=7.72, 1.47 Hz, 1 H), 16.31 (s, 1 H).

EXAMPLE 125

6-(1,1-dioxido-4H-1,2,4-benzothiadiazin-3-yl)-7-hydroxy-4-(3-methylbutyl)thieno[3,2-b]pyridin-5(4H)-one

EXAMPLE 125A 1-(3-methylbutyl)-2H-thieno[3,2-d][1,3]oxazine-2,4(1H)-dione

The title compound was prepared according to the procedure of Example 1B substituting the product of Example 110A for the product of Example 1A and substituting 1-bromo-3-methyl butane for n-butyl bromide (0.246 g, 68%).

EXAMPLE 125B 6-(1,1-dioxido-4H-1,2,4-benzothiadiazin-3-yl)-7-hydroxy-4-(3-methylbutyl)thieno[3,2-b]pyridin-5(4H)-one The title compound was prepared according to the procedure of Example 1D substituting the product of Example 125A for the product of Example 1B (0.223 g, 52%). MS (ESI−) m/z 416 (M−H)⁻. The sodium salt of the title compound was prepared according to the procedure of Example 1D. ¹H NMR (300 MHz, DMSO-d₆) δ 0.96 (d, J=6.90 Hz, 6 H) 1.45 (m, 2 H) 1.67 (m, 1 H) 3.99 (m, 2 H) 7.09 (d, J=5.52 Hz, 1 H) 7.19 (d, J=7.72 Hz, 1 H) 7.26 (m, 1H) 7.53 (ddd, J=8.55, 7.26, 1.47 Hz, 1H) 7.64 (dd, J=7.72, 1.47 Hz, 1 H) 7.80 (d, J=5.52 Hz, 1 H) 15.95 (s, 1 H).

EXAMPLE 126

6-(1,1-dioxido-4H-1,2,4-benzothiadiazin-3-yl)-4-(2-ethylbutyl)-7-hydroxythieno[3,2-b]pyridin-5(4H)-one

EXAMPLE 126A 1-(2-ethylbutyl)-2H-thieno[3,2-d][1,3]oxazine-2,4(1H)-dione

The title compound was prepared according to the procedure of Example 1B substituting the product of Example 110A for the product of Example 1A and substituting 1-bromo-2-ethyl butane for n-butyl bromide (0.116 g, 31%). MS (DCI/NH₃) m/z 271 (M+NH₄)⁺.

EXAMPLE 126B 6-(1,1-dioxido-4H-1,2,4-benzothiadiazin-3-yl)-4-(2-ethylbutyl)-7-hydroxythieno[3,2-b]pyridin-5(4H)-one The title compound was prepared according to the procedure of Example 1D substituting the product of Example 126A for the product of Example 1B (0.052 g, 26%). MS (ESI−) m/z 430 (M−H)⁻. The sodium salt of the title compound was prepared according to the procedure of Example 1D. ¹H NMR (300 MHz, DMSO-d₆) δ 0.87 (t, J=7.35 Hz, 6 H) 1.29 (m, 4 H) 1.73 (m, J=13.24, 6.99 Hz, 1 H) 3.91 (d, J=7.35 Hz, 2 H) 7.08 (d, J=5.52 Hz, 1 H) 7.18 (d, J=8.09 Hz, 1 H) 7.25 (m, J=7.54, 7.54 Hz, 1 H) 7.53 (ddd, J=8.55, 7.26, 1.47 Hz, 1 H) 7.64 (dd, J=7.72, 1.47 Hz, 1 H) 7.78 (d, J=5.15 Hz, 1 H) 15.99 (s, 1 H).

EXAMPLE 127

1-benzyl-3-(1,1-dioxido-4H-1,2,4-benzothiadiazin-3-yl)-4-hydroxy-6-methyl-5-phenyl-2(1H)-pyridinone

EXAMPLE 127A 4-methyl-5-phenyl-2H-1,3-oxazine-2,6(3H)-dione

Ethyl 2-phenylacetoacetate (1.0 g, 4.85 mmol) and urethane (0.43 g, 4.85 mmol) were heated, neat, with Phosphorous oxychloride (3 mL) at 90° C. for 3 hours. The excess reagents were removed under vacuum and the resulting residue was triturated with benzene and filtered. This solid was triturated with diethyl ether, filtered, and dried to yield 0.818 g (83%). MS (DCI/NH₃) m/z 204 (M+H)⁺; ¹H NMR (300 MHz, DMSO-d₆) δ 1.98 (s, 3 H) 7.28 (m, 2 H) 7.39 (m, 3 H) 11.65 (s, 1 H).

EXAMPLE 127B 3-benzyl-4-methyl-5-phenyl-2H-1,3-oxazine-2,6(3H)-dione

The title compound was prepared according to the procedure of Example 1B substituting the product of Example 127A for the product of Example 1A and substituting benzyl bromide for n-butyl bromide (0.257 g, 71%). MS (DCI/NH$_3$) m/z 311 (M+NH$_4$)$^+$; $^1$H NMR (300 MHz, DMSO-d$_6$) δ 2.03 (s, 3 H) 5.16 (s, 2 H) 7.34 (m, 10 H).

EXAMPLE 127C 1-benzyl-3-(1,1-dioxido-4H-1,2,4-benzothiadiazin-3-yl)-4-hydroxy-6-methyl-5-phenyl-2(1H)-pyridinone The title compound was prepared according to the procedure of Example 1D substituting the product of Example 127B for the product of Example 1B (0.022 g, 5%). MS (ESI–) m/z 470 (M–H)$^-$. The sodium salt of the title compound was prepared according to the procedure of Example 1D. $^1$H NMR (300 MHz, DMSO-d$_6$) δ 1.92 (s, 3 H) 5.24 (s, 2 H) 7.19 (m, 10 H) 7.33 (m, 2 H) 7.46 (ddd, J=8.27, 7.17, 1.47 Hz, 1 H) 7.61 (dd, J=7.91, 1.29 Hz, 1 H) 16.97 (s, 1 H).

EXAMPLE 128

3-(1,1-dioxido-4H-1,2,4-benzothiadiazin-3-yl)-4-hydroxy-5,6-dimethyl-1-(3-methylbutyl)-2(1H)-pyridinone

EXAMPLE 128A 4,5-dimethyl-3-(3-methylbutyl)-2H-1,3-oxazine-2,6(3H)-dione

The title compound was prepared according to the procedure of Example 1B substituting the product of Example 123A for the product of Example 1A and substituting 1-bromo-3-methyl butane for n-butyl bromide (0.224 g, 60%). MS (DCI/NH$_3$) m/z 255 (M+NH$_4$)$^+$; $^1$H NMR (300 MHz, DMSO-d$_6$) δ 0.92 (d, J=6.62 Hz, 6 H) 1.46 (m, 2 H) 1.59 (dt, J=13.14, 6.48 Hz, 1 H) 1.85 (s, 3 H) 2.26 (s, 3 H) 3.77 (m, 2 H).

EXAMPLE 128B 3-(1,1-dioxido-4H-1,2,4-benzothiadiazin-3-yl)-4-hydroxy-5,6-dimethyl-1-(3-methylbutyl)-2(1H)-pyridinone The title compound was prepared according to the procedure of Example 1D substituting the product of Example 128A for the product of Example 1B (0.132 g, 32%). MS (ESI–) m/z 388 (M–H)$^-$. The sodium salt of the title compound was prepared according to the procedure of Example 1D. $^1$H NMR (300 MHz, DMSO-d$_6$) δ 0.94 (d, J=2.5 Hz, 6H) 1.87 (s, 3H) 2.24 (s, 3H) 3.84 (m, 2H) 7.16 (m, 1H) 7.21 (m, 1H) 7.49 (m, 1H) 7.61 (m, 1H) 17.41 (s, 1H).

EXAMPLE 129

3-(1,1-dioxido-4H-1,2,4-benzothiadiazin-3-yl)-1-(2-ethylbutyl)-4-hydroxy-5,6-dimethyl-2(1H)-pyridinone

EXAMPLE 129A 3-(2-ethylbutyl)-4,5-dimethyl-2H-1,3-oxazine-2,6(3H)-dione

The title compound was prepared according to the procedure of Example 1B substituting the product of Example 123A for the product of Example 1A and substituting 1-bromo-2-ethyl-butane for n-butyl bromide (0.181 g, 45%). $^1$H NMR (300 MHz, DMSO-d$_6$) δ 0.85 (t, J=7.35 Hz, 6 H) 1.29 (m, 4 H) 1.65 (m, 1 H) 1.86 (s, 3 H) 2.25 (s, 3 H) 3.73 (d, J=7.35 Hz, 2 H).

EXAMPLE 129B 3-(1,1-dioxido-4H-1,2,4-benzothiadiazin-3-yl)-1-(2-ethylbutyl)-4-hydroxy-5,6-dimethyl-2(1H)-pyridinone The title compound was prepared according to the procedure of Example 1D substituting the product of Example 129A for the product of Example 1B (0.027 g, 9%). MS (ESI–) m/z 402 (M–H)$^-$. The sodium salt of the title compound was prepared according to the procedure of Example 1D. $^1$H NMR (300 MHz, DMSO-d$_6$) δ 0.85 (t, J=7.35 Hz, 6 H) 1.25 (m, 4 H) 1.62 (m, 1 H) 1.88 (s, 3 H) 2.22 (s, 3 H) 3.82 (m, 2 H) 7.14 (d, J=7.72 Hz, 1 H) 7.21 (m, 1 H) 7.48 (ddd, J=8.46, 7.17, 1.65 Hz, 1 H) 7.60 (dd, J=7.91, 1.29 Hz, 1 H) 17.42 (s, 1 H).

EXAMPLE 130

1-benzyl-3-(1,1-dioxido-4H-1,2,4-benzothiadiazin-3-yl)-4-hydroxy-6-phenyl-2(1H)-pyridinone

EXAMPLE 130A 4-phenyl-2H-1,3-oxazine-2,6(3H)-dione

The title compound was prepared according to the procedure of Example 127A, substituting ethyl benzoylacetate for ethyl 2-phenylacetoacetate to yield the desired product (0.99 g, 47%). MS (DCI/NH$_3$) m/z 188 (M+H)$^+$; $^1$H NMR (300 MHz, DMSO-d$_6$) δ 6.03 (s, 1 H) 7.56 (m, 3 H) 7.79 (m, 2 H) 11.80 (s, 1 H).

EXAMPLE 130B 3-benzyl-4-phenyl-2H-1,3-oxazine-2,6(3H)-dione

The title compound was prepared according to the procedure of Example 1B substituting the product of Example 130A for the product of Example 1A and benzyl bromide for n-butyl bromide (0.223 g, 78%).

EXAMPLE 130C 1-benzyl-3-(1,1-dioxido-4H-1,2,4-benzothiadiazin-3-yl)-4-hydroxy-6-phenyl-2(1H)-pyridinone The title compound was prepared according to the procedure of Example 1D substituting the product of Example 130B for the product of Example 1B (0.021 g, 6%). MS (ESI–) m/z 456 (M–H)$^-$. The sodium salt of the title compound was prepared according to the procedure of Example 1D. $^1$H NMR (300 MHz, DMSO-d$_6$) δ 4.89 (s, 2 H) 5.44 (s, 1 H) 6.87 (d, J=6.99 Hz, 1 H) 7.20 (m, 9 H) 7.35 (m, 2 H) 7.52 (ddd, J=8.55, 7.26, 1.47 Hz, 1 H) 7.63 (dd, J=7.72, 1.47 Hz, 1 H) 16.78 (s, 1 H).

EXAMPLE 131

5-(1,1-dioxido-4H-1,2,4-benzothiadiazin-3-yl)-4-hydroxy-7-(3-methyl-2-butenyl)thieno[2,3-b]pyridin-6(7H)-one

EXAMPLE 131A 1-(3-methylbut-2-enyl)-2H-thieno[2,3-d][1,3]oxazine-2,4(1H)-dione The title compound was prepared according to the procedure of Example 1B substituting the product of Example 114A for the product of Example 1A and substituting 1-bromo-3-methyl-but-2-ene for n-butyl bromide (0.23 g, 82%). MS (DCI/NH$_3$) m/z 255 (M+NH$_4$)$^+$; $^1$H NMR (300 MHz, DMSO-d$_6$) δ 1.72 (d, J=1.10 Hz, 3 H) 1.79 (d, J=0.74 Hz, 3 H) 4.50 (d, J=6.62 Hz, 2 H) 5.23 (m, 1 H) 7.28 (d, J=1.10 Hz, 2 H).

EXAMPLE 131B 5-(1,1-dioxido-4H-1,2,4-benzothiadiazin-3-yl)-4-hydroxy-7-(3-methyl-2-butenyl)thieno[2,3-b]pyridin-6(7H)-one The title compound was prepared according to the procedure of Example 1D substituting the product of Example 131A for the product of Example 1B (0.178 g, 44%). MS (ESI-) m/z 414 (M-H)$^-$. The sodium salt of the title compound was prepared according to the procedure of Example 1D. $^1$H NMR (300 MHz, DMSO-d$_6$) δ 1.69 (s, 3 H) 1.82 (s, 3 H) 4.51 (d, J=6.62 Hz, 2 H) 5.13 (m, 1 H) 6.94 (d, J=5.52 Hz, 1 H) 7.20 (m, 2 H) 7.25 (m, 1 H) 7.53 (ddd, J=8.27, 7.17, 1.47 Hz, 1 H) 7.64 (dd, J=7.72, 1.47 Hz, 1 H) 16.30 (s, 1 H).

EXAMPLE 132

1,5-dibenzyl-3-(1,1-dioxido-4H-1,2,4-benzothiadiazin-3-yl)-4-hydroxy-6-methyl-2(1H)-pyridinone

EXAMPLE 132A 5-benzyl-4-methyl-2H-1,3-oxazine-2,6(3H)-dione

The title compound was prepared according to the procedure of in Example 127A, substituting ethyl 2-benzyl-3-oxobutyric acid ethyl ester for ethyl 2-phenylacetoacetate to yield the desired product. MS (DCI/NH$_3$) m/z 218 (M+H)+

EXAMPLE 132B 3,5-dibenzyl-4-methyl-2H-1,3-oxazine-2,6(3H)-dione

The title compound was prepared according to the procedure of Example 1B substituting the product of Example 132A for the product of Example 1A and benzyl bromide for n-butyl bromide (0.215 g, 76%).

EXAMPLE 132C 1,5-dibenzyl-3-(1,1-dioxido-4H-1,2,4-benzothiadiazin-3-yl)-4-hydroxy-6-methyl-2(1H)-pyridinone The title compound was prepared according to the procedure of Example 1D substituting the product of Example 132B for the product of Example 1B (0.051 g, 15%). MS (ESI-) m/z 484 (M-H)$^-$. The sodium salt of the title compound was prepared according to the procedure of Example 1D. $^1$H NMR (300 MHz, DMSO-d$_6$) δ 2.05 (s, 3 H) 3.84 (s, 2 H) 5.21 (s, 2 H) 7.21 (m, 12 H) 7.49 (m, 1 H) 7.62 (dd, J=7.91, 1.29 Hz, 1 H) 17.10 (s, 1 H).

EXAMPLE 133

3-(1,1-dioxido-4H-1,2,4-benzothiadiazin-3-yl)-1-(2-ethylbutyl)-4-hydroxy-6-methyl-5-phenyl-2(1H)-pyridinone

EXAMPLE 133A 3-(2-ethylbutyl)-4-methyl-5-phenyl-2H-1,3-oxazine-2,6(3H)-dione The title compound was prepared according to the procedure of Example 1B substituting the product of Example 127A for the product of Example 1A and substituting 1-bromo-2-ethyl butane for n-butyl bromide (0.145 g, 41%). MS (DCI/NH$_3$) m/z 288 (M+H)+

EXAMPLE 133B 3-(1,1-dioxido-4H-1,2,4-benzothiadiazin-3-yl)-1-(2-ethylbutyl)-4-hydroxy-6-methyl-5-phenyl-2(1H)-pyridinone The title compound was prepared according to the procedure of Example 1D substituting the product of Example 133A for the product of Example 1B (0.019 g, 8%).

MS (ESI-) m/z 464 (M-H)$^-$. The sodium salt of the title compound was prepared according to the procedure of Example 1D. $^1$H NMR (300 MHz, DMSO-d$_6$) δ 0.88 (t, J=7.35 Hz, 6 H) 1.30 (m, 4 H) 1.71 (m, 1 H) 2.03 (s, 3 H) 3.83 (m, 2 H) 7.10 (m, 3 H) 7.22 (m, 2 H) 7.34 (t, J=7.17 Hz, 2 H) 7.45 (ddd, J=8.27, 7.17, 1.47 Hz, 1 H) 7.60 (dd, J=7.91, 1.29 Hz, 1 H) 17.10 (s, 1 H).

EXAMPLE 134

6-(1,1-dioxido-4H-1,2,4-benzothiadiazin-3-yl)-7-hydroxy-4-pentylthieno[3,2-b]pyridin-5(4H)-one

EXAMPLE 134A 1-pentyl-2H-thieno[3,2-d][1,3]oxazine-2,4(1H)-dione

The title compound was prepared according to the procedure of Example 1B substituting the product of Example 110A for the product of Example 1A and substituting n-pentyl bromide for n-butyl bromide (0.205 g, 72%).

EXAMPLE 134B 6-(1,1-dioxido-4H-1,2,4-benzothiadiazin-3-yl)-7-hydroxy-4-pentylthieno[3,2-b]pyridin-5(4H)-one The title compound was prepared according to the procedure of Example 1D substituting the product of Example 134A for the product of Example 1B (0.189 g, 53%). MS (ESI-) m/z 416 (M-H)$^-$ The sodium salt of the title compound was prepared according to the procedure of Example 1D. $^1$H NMR (300 MHz, DMSO-d$_6$) δ 0.88 (m, 3H) 1.33 (m, 4 H) 1.57 (m, 2 H) 3.97 (m, 2 H) 7.14 (d, J=5.52 Hz, 1 H) 7.18

(d, J=8.09 Hz, 1 H) 7.25 (m, 1 H) 7.53 (m, 1 H) 7.64 (dd, J=7.91, 1.29 Hz, 1 H) 7.79 (d, J=5.52 Hz, 1 H) 15.96 (s, 1 H).

EXAMPLE 135

5-(1,1-dioxido-4H-1,2,4-benzothiadiazin-3-yl)-4-hydroxy-3-methyl-7-(3-methylbutyl)thieno[2,3-b]pyridin-6(7H)-one

EXAMPLE 135A 5-methyl-2H-thieno[2,3-d][1,3]oxazine-2,4(1H)-dione

The title compound was prepared from 2-amino-4-methyl-thiophene-3-carboxylic acid ethyl ester according to the procedure of Fabis, and co-workers as described in *Tetrahedron*, 1998, 54, 10789-10800MS (ESI) m/z 182 (M−H)⁻; ¹H NMR (300 MHz, DMSO-D₆) δ ppm 2.30 (d, J=1.47 Hz, 3 H), 6.78 (s, 1 H), 12.51 (s, 1 H).

EXAMPLE 135B 5-methyl-1-(3-methylbutyl)-2H-thieno[2,3-d][1,3]oxazine-2,4(1H)-dione The title compound was prepared according to the procedure of Example 1B substituting the product of Example 135A for the product of Example 1A and substituting isopentyl bromide for n-butyl bromide (0.048 g, 30%). MS (DCI/NH₃) m/z 254 (M+H)⁺. ¹H NMR (300 MHz, DMSO-d₆) δ 0.94 (d, J=6.25 Hz, 6 H), 1.61 (m, 3 H), 2.33 (d, J=1.10 Hz, 3 H), 3.83 (m, 2 H), 6.92 (d, J=1.10 Hz, 1 H).

EXAMPLE 135C 5-(1,1-dioxido-4H-1,2,4-benzothiadiazin-3-yl)-4-hydroxy-3-methyl-7-(3-methylbutyl)thieno[2,3-b]pyridin-6(7H)-one The title compound was prepared according to the procedure of Example 1D substituting the product of Example 135B for the product of Example 1B (0.043 g, 52%). MS (DCI/NH₃) m/z 430 (M+H)⁺; ¹H NMR (300 MHz, DMSO-d₆) δ 0.98 (d, J=6.25 Hz, 6 H), 1.67 (m, 3 H), 2.50 (s, 3 H), 4.13 (m, 2 H), 7.08 (s, 1 H), 7.55 (t, J=7.54 Hz, 1 H), 7.68 (d, J=8.46 Hz, 1 H), 7.77 (t, J=7.17 Hz, 1 H), 7.92 (d, J=7.35 Hz, 1 H), 14.30 (s, 1 H), 15.22 (s, 1 H). The sodium salt of the title compound was prepared according to the procedure of Example 1D. ¹H NMR (300 MHz, DMSO-d₆) δ 0.97 (d, J=6.62 Hz, 6 H), 1.56 (m, 3 H), 3.89 (m, 2 H), 7.53 (m, 5 H), 16.37 (brs, 1 H).

EXAMPLE 136

6-(1,1-dioxido-4H-1,2,4-benzothiadiazin-3-yl)-7-hydroxy-4-(4-methylpentyl)thieno[3,2-b]pyridin-5(4H)-one

EXAMPLE 136A 1-(4-methylpentyl)-2H-thieno[3,2-d][1,3]oxazine-2,4(1H)-dione

The title compound was prepared according to the procedure of Example 1B substituting the product of Example 110A for the product of Example 1A and substituting 1-bromo-4-methyl-pentane for n-butyl bromide (0.110 g, 61%).

EXAMPLE 136B 6-(1,1-dioxido-4H-1,2,4-benzothiadiazin-3-yl)-7-hydroxy-4-(4-methylpentyl)thieno[3,2-b]pyridin-5(4H)-one The title compound was prepared according to the procedure of Example 1D substituting the product of Example 136A for the product of Example 1B (0.064 g, 34%). MS (ESI−) m/z 430 (M−H)⁻. The sodium salt of the title compound was prepared according to the procedure of Example 1D. ¹H NMR (300 MHz, DMSO-d₆) δ 0.86 (s, 3H) 0.88 (s, 3 H) 1.24 (m, J=15.81, 6.99 Hz, 2 H) 1.56 (m, 3 H) 3.96 (d, J=6.99 Hz, 2 H) 7.16 (m, 1 H) 7.26 (t, J=7.35 Hz, 1 H) 7.53 (t, J=7.72 Hz, 1 H) 7.64 (d, J=7.72 Hz, 1 H) 7.80 (d, J=5.15 Hz, 1 H) 15.96 (s, 1 H).

EXAMPLE 137

4-(3-butenyl)-6-(1,1-dioxido-4H-1,2,4-benzothiadiazin-3-yl)-7-hydroxythieno[3,2-b]pyridin-5(4H)-one

EXAMPLE 137A 1-but-3-enyl-2H-thieno[3,2-d][1,3]oxazine-2,4(1H)-dione

The title compound was prepared according to the procedure of Example 1B substituting the product of Example 110A for the product of Example 1A and substituting 4-bromo-but-1-ene for n-butyl bromide (0.09 g, 56%).

EXAMPLE 137B 4-(3-butenyl)-6-(1,1-dioxido-4H-1,2,4-benzothiadiazin-3-yl)-7-hydroxythieno[3,2-b]pyridin-5(4H)-one The title compound was prepared according to the procedure of Example 1D substituting the product of Example 137A for the product of Example 1B (0.062 g, 38%). MS (ESI−) m/z 399.9 (M−H)⁻. The sodium salt of the title compound was prepared according to the procedure of Example 1D. ¹H NMR (300 MHz, DMSO-d₆) δ 2.34 (q, J=7.23 Hz, 2 H) 4.04 (m, 2 H) 5.05 (m, 2 H) 5.87 (m, 1 H) 7.18 (m, 2 H) 7.25 (t, J=7.17 Hz, 1 H) 7.53 (m, 1 H) 7.64 (d, J=6.62 Hz, 1 H) 7.79 (d, J=5.52 Hz, 1 H) 15.93 (s, 1 H).

EXAMPLE 138

7-benzyl-5-(1,1-dioxido-4H-1,2,4-benzothiadiazin-3-yl)-4-hydroxy-1-phenyl-1,7-dihydro-6H-pyrazolo[3,4-b]pyridin-6-one

EXAMPLE 138A ethyl 5-(benzylamino)-1-phenyl-1H-pyrazole-4-carboxylate

The title compound was prepared according to the procedure of Example 1B substituting ethyl 5-amino-1-phenyl-4-pyrazole-carboxylate for the product of Example 1A and substituting benzyl bromide for n-butyl bromide (0.990 g, 83%). MS (ESI–) m/z 320(M–H)⁻.

EXAMPLE 138B ethyl 5-[benzyl(3-ethoxy-3-oxopropanoyl)amino]-1-phenyl-1H-pyrazole-4-carboxylate The title compound was prepared (51% yield) from the product of Example 138A and ethyl malonyl chloride according to the procedure of Rowley, and co-workers as described in *J. Med. Chem.*, 1993, 36, 3386-3396. MS (ESI–) m/z 434 (M–H)⁺.

EXAMPLE 138C methyl 7-benzyl-4-hydroxy-6-oxo-1-phenyl-6,7-dihydro-1H-pyrazolo[3,4-b]pyridine-5-carboxylate The title compound was prepared from the product of Example 138B and sodium methoxide according to the procedure of Rowley, and co-workers as described in *J. Med. Chem.*, 1993, 36, 3386-3396. MS (ESI–) m/z 374 (M–H)⁻.

EXAMPLE 138D

N-[2-(aminosulfonyl)phenyl]-7-benzyl-4-hydroxy-6-oxo-1-phenyl-6,7-dihydro-1H-pyrazolo[3,4-b]pyridine-5-carboxamide The title compound was prepared according to the procedure of Example 84C substituting the product of Example 138C for the product of Example 84B and 2-aminobenzenesulfonamide for 2-amino-5-bromobenzenesulfonamide (0.014 g, 61%). MS (ESI+) m/z 516 (M+H)⁺.

EXAMPLE 138E 7-benzyl-5-(1,1-dioxido-4H-1,2,4-benzothiadiazin-3-yl)-4-hydroxy-1-phenyl-1,7-dihydro-6H-pyrazolo[3,4-b]pyridin-6-one The title compound was prepared according to the procedure of Example 84D substituting the product of Example 138D for the product of Example 84C (0.061 g, 84%). MS (ESI–) m/z 496 (M–H)⁻. The sodium salt of the title compound was prepared according to the procedure of Example 1D. $^1$H NMR (300 MHz, DMSO-$d_6$) δ 4.92 (s, 2 H), 6.53 (m, 2 H), 7.21 (m, 9 H), 7.43 (t, J=7.35 Hz, 1 H), 7.54 (td, J=7.81, 1.65 Hz, 1 H), 7.64 (dd, J=7.91, 1.29 Hz, 1 H), 7.88 (s, 1 H), 16.05 (s, 1 H).

EXAMPLE 139

4-benzyl-6-(1,1-dioxido-4H-1,2,4-benzothiadiazin-3-yl)-2,7-dihydroxy[1,3]thiazolo[4,5-b]pyridin-5(4H)-one

EXAMPLE 139A methyl 4-(benzylamino)-2-(methylthio)-1,3-thiazole-5-carboxylate The title compound was prepared according to the procedure of Example 1B substituting 4-amino-2-methylthio-5-thiazolecarboxylic acid methyl ester for the product of Example 1A and substituting benzyl bromide for n-butyl bromide (0.411 g, 57%). MS (ESI+) m/z 295 (M+H)⁺.

EXAMPLE 139B methyl 4-[benzyl(3-ethoxy-3-oxopropanoyl)amino]-2-(methylthio)-1,3-thiazole-5-carboxylate The title compound was prepared according to the procedure of Example 138B substituting the product of Example 139A for the product of Example 138A (0.147 g, 30%). MS (ESI+) m/z 409 (M+H)⁺.

EXAMPLE 139C ethyl 4-benzyl-7-hydroxy-2-(methylthio)-5-oxo-4,5-dihydro[1,3]thiazolo[4,5-b]pyridine-6-carboxylate The title compound was prepared according to the procedure of Example 138C substituting the product of Example 139B for the product of Example 138B (0.11 μg, 82%). MS (ESI–) m/z 375 (M–H)⁻.

EXAMPLE 139D

N-[2-(aminosulfonyl)phenyl]-4-benzyl-7-hydroxy-2-(methylthio)-5-oxo-4,5-dihydro[1,3]thiazolo[4,5-b]pyridine-6-carboxamide The title compound was prepared according to the procedure of Example 84C substituting the product of Example 139C for the product of Example 84B and 2-aminobenzenesulfonamide for 2-amino-5-bromobenzenesulfonamide (0.114 g, 75%). MS (ESI–) m/z 501 (M–H)⁻.

EXAMPLE 139E 4-benzyl-6-(1,1-dioxido-4H-1,2,4-benzothiadiazin-3-yl)-2,7-dihydroxy[1,3]thiazolo[4,5-b]pyridin-5(4H)-one The title compound was prepared according to the procedure of Example 84D, substituting the product of Example 139D for the product of Example 84C (0.108 g, 60%). MS (ESI–) m/z 453 (M–H)⁻. $^1$H NMR (300 MHz, DMSO-$d_6$) δ 5.37 (s, 2 H), 7.29 (m, 5 H), 7.44 (t, J=7.72 Hz, 1 H), 7.50 (d, J=7.72 Hz, 1 H), 7.67 (td, J=7.72, 1.47 Hz, 1 H), 7.82 (d, J=7.72 Hz, 1 H), 14.01 (s, 1 H), 14.32 (s, 1 H). The sodium salt of the title compound was prepared according to the procedure of Example 1D. $^1$H NMR (300 MHz, DMSO-$d_6$) δ 5.13 (s, 2 H), 7.04 (d, J=8.09 Hz, 1 H), 7.20 (m, 6 H), 7.45 (t, J=7.35 Hz, 1 H), 7.56 (d, J=7.72 Hz, 1 H), 17.25 (s, 1H).

EXAMPLE 140

4-[(2-chloro-1,3-thiazol-5-yl)methyl]-6-(1,1-dioxido-4H-1,2,4-benzothiadiazin-3-yl)-7-hydroxythieno[3,2-b]pyridin-5(4H)-one

EXAMPLE 140A

1-[(2-chloro-1,3-thiazol-5-yl)methyl]-2H-thieno[3,2-d][1,3]oxazine-2,4(1H)-dione The title compound was prepared according to the procedure of Example 1B substituting the product of Example 104A for the product of Example 1A and substituting 2-chloro-5-bromomethylthiazole for n-butyl bromide (0.341 g, 75%). MS (DCI/NH$_3$) m/z 301 (M+H)$^+$. $^1$H NMR (300 MHz, DMSO-d$_6$) δ 5.35 (s, 2 H), 7.60 (d, J=5.15 Hz, 1 H), 7.89 (s, 1 H), 8.38 (d, J=5.52 Hz, 1 H),

EXAMPLE 140B

4-[(2-chloro-1,3-thiazol-5-yl)methyl]-6-(1,1-di-oxido-4H-1,2,4-benzothiadiazin-3-yl)-7-hydroxythieno[3,2-b]pyridin-5(4H)-one The title compound was prepared according to the procedure of Example 1D substituting the product of Example 140A for the product of Example 1B (0.134 g, 40%). MS (ESI−) m/z 477 (M−H)$^−$. $^1$H NMR (300 MHz, DMSO-d$_6$) δ 5.64 (s, 2 H), 7.55 (t, J=7.17 Hz, 1 H), 7.67 (d, J=7.72 Hz, 1 H), 7.78 (t, J=7.17 Hz, 1 H), 7.86 (d, J=5.52 Hz, 1 H), 7.93 (d, J=7.72 Hz, 1 H), 7.95 (s, 1 H), 8.43 (d, J=5.52 Hz, 1 H), 14.10 (s, 1 H). The sodium salt of the title compound was prepared according to the procedure of Example 1D.

EXAMPLE 141

6-(1,1-dioxido-4H-1,2,4-benzothiadiazin-3-yl)-7-hydroxy-4-[(5-methyl-3-pyridinyl)methyl]thieno[3,2-b]pyridin-5(4H)-one

EXAMPLE 141A

1-[(5-methylpyridin-3-yl)methyl]-2H-thieno[3,2-d][1,3]oxazine-2,4(1H)-dione

The title compound was prepared according to the procedure of Example 1B substituting the product of Example 110A for the product of Example 1A and substituting 3-methyl-5-chloromethylpyridine for n-butyl bromide (0.255 g, 38%). MS (DCI/NH$_3$) m/z 275 (M+H)$^+$. $^1$H NMR (300 MHz, DMSO-d$_6$) δ 2.27 (s, 3 H), 5.21 (s, 2 H), 7.31 (d, J=5.52 Hz, 1 H), 7.63 (s, 1 H), 8.29 (d, J=5.15 Hz, 1 H), 8.34 (d, J=1.47 Hz, 1 H), 8.47 (d, J=1.84 Hz, 1 H).

EXAMPLE 141B 6-(1,1-dioxido-4H-1,2,4-benzothiadiazin-3-yl)-7-hydroxy-4-[(5-methyl-3-pyridinyl)methyl]thieno[3,2-b]pyridin-5(4H)-one The title compound was prepared according to the procedure of Example 1D substituting the product of Example 141 A for the product of Example 1B (0.175 g, 43%). MS (ESI−) m/z 451 (M−H)$^−$. $^1$H NMR (300 MHz, DMSO-d$_6$) δ 2.25 (s, 3 H), 5.54 (s, 2 H), 7.53 (m, 3 H), 7.64 (d, J=7.72 Hz, 1 H), 7.75 (td, J=7.72, 1.47 Hz, 1 H), 7.92 (d, J=7.35 Hz, 1 H), 8.34 (d, J=5.15 Hz, 1 H), 8.34 (s, 1 H), 8.45 (d, J=1.47 Hz, 1 H), 14.30 (s, 1 H). The sodium salt of the title compound was prepared according to the procedure of Example 1D.

EXAMPLE 142

6-(1,1-dioxido-4H-1,2,4-benzothiadiazin-3-yl)-7-hydroxy-4-[(2-methyl-1,3-thiazol-5-yl)methyl]thieno[3,2-b]pyridin-5(4H)-one

EXAMPLE 142A

1-[(2-methyl-1,3-thiazol-5-yl)methyl]-2H-thieno[3,2-d][1,3]oxazine-2,4(1H)-dione The title compound was prepared according to the procedure of Example 1B substituting the product of Example 110A for the product of Example 1A and substituting 2-methyl-5-chloromethylthiazole for n-butyl bromide (0.308 g, 55%). MS (DCI/NH$_3$) m/z 281 (M+H)$^+$. $^1$H NMR (300 MHz, DMSO-d$_6$) δ 2.59 (s, 3 H), 5.34 (s, 2 H), 7.58 (d, J=5.52 Hz, 1 H), 7.81 (s, 1 H), 8.37 (d, J=5.52 Hz, 1 H).

EXAMPLE 142B 6-(1,1-dioxido-4H-1,2,4-benzothiadiazin-3-yl)-7-hydroxy-4-[(2-methyl-1,3-thiazol-5-yl)methyl]thieno[3,2-b]pyridin-5(4H)-one The title compound was prepared according to the procedure of Example 1D substituting the product of Example 142A for the product of Example 1B (0.151 g, 40%). MS (DCI/NH$_3$) m/z 459 (M+H)$^+$. $^1$H NMR (300 MHz, DMSO-d$_6$) δ 2.56 (s, 3 H), 5.65 (s, 2 H), 7.56 (t, J=7.17 Hz, 1 H), 7.68 (d, J=7.72 Hz, 1 H), 7.79 (m, 3 H), 7.93 (d, J=7.72 Hz, 1 H), 8.42 (d, J=5.52 Hz, 1 H), 14.18 (s, 1 H). The sodium salt of the title compound was prepared according to the procedure of Example 1D.

EXAMPLE 143

4-[(5-chloro-2-thienyl)methyl]-6-(1,1-dioxido-4H-1,2,4-benzothiadiazin-3-yl)-7-hydroxythieno[3,2-b]pyridin-5(4H)-one

EXAMPLE 143A

1-[(5-chlorothien-2-yl)methyl]-2H-thieno[3,2-d][1,3]oxazine-2,4(1H)-dione

The title compound was prepared according to the procedure of Example 1B substituting the product of Example 110A for the product of Example 1A and substituting 2-chloro-5-chloromethylthiophene for n-butyl bromide (0.601 g, 100%).

EXAMPLE 143B

4-[(5-chloro-2-thienyl)methyl]-6-(1,1-dioxido-4H-1,2,4-benzothiadiazin-3-yl)-7-hydroxythieno[3,2-b]pyridin-5(4H)-one The title compound was prepared according to the procedure of Example 1D substituting the product of Example 143A for the product of Example 1B (0.115 g, 12%). MS (APCI) m/z 478 (M+H)$^+$. $^1$H NMR (300 MHz, DMSO-D d$_6$) δ 5.59 (s, 2 H), 6.99 (d, J=3.68 Hz, 1 H), 7.23 (d, J=4.04 Hz, 1 H), 7.56 (t, J=7.72 Hz, 1 H), 7.68 (d, J=7.72 Hz, 1 H), 7.78 (m, 1 H), 7.80 (d, J=5.88 Hz, 1 H), 7.93 (d, J=8.09 Hz, 1 H), 8.41 (d, J=5.52 Hz, 1 H), 14.18 (s, 1 H). The sodium salt of the title compound was prepared according to the procedure of Example 1D.

EXAMPLE 144

6-(1,1-dioxido-4H-1,2,4-benzothiadiazin-3-yl)-7-hydroxy-4-[(2-methyl-1,3-thiazol-4-yl)methyl]thieno[3,2-b]pyridin-5(4H)-one

EXAMPLE 144A

1-[(2-methyl-1,3-thiazol-4-yl)methyl]-2H-thieno[3,2-d][1,3]oxazine-2,4(1H)-dione The title compound was prepared according to the procedure of Example 1B substituting the product of Example 110A for the product of Example 1A and substituting 2-methyl-4-chloromethylthiazole hydrochloride for n-butyl bromide (0.200 g, 36%).

EXAMPLE 144B 6-(1,1-dioxido-4H-1,2,4-benzothiadiazin-3-yl)-7-hydroxy-4-[(2-methyl-1,3-thiazol-4-yl)methyl]thieno [3,2-b]pyridin-5(4H)-one The title compound was prepared according to the procedure of Example 1D substituting the product of Example 144A for the product of Example 1B (0.127 g, 38%). MS (ESI+) m/z 459 (M+H)$^+$. $^1$H NMR (300 MHz, DMSO-d$_6$) δ 2.60 (s, 3 H), 5.55 (s, 2 H), 7.54 (t, J=6.99 Hz, 1 H), 7.54 (d, J=5.52 Hz, 1 H), 7.65 (d, J=7.72 Hz, 1 H), 7.76 (m, 1 H), 7.92 (d, J=6.62 Hz, 1 H), 8.34 (d, J=5.51 Hz, 1 H), 14.30 (s, 1 H),

EXAMPLE 145

4-benzyl-6-(1,1-dioxido-4H-1,2,4-benzothiadiazin-3-yl)-7-hydroxy-2-(methylsulfanyl)[1,3]thiazolo[4,5-b]pyridin-5(4H)-one

EXAMPLE 145A 4-benzyl-2-(methylthio)-5H-[1,3]thiazolo[4,5-d][1,3]oxazine-5,7(4H)-dione The title compound was prepared according to the procedure of Example 3B substituting the product of Example 139A for the product of Example 3A (0.048 g, 92%). MS (DCI/NH$_3$) m/z 324 (M+NH$_4$)$^+$.

EXAMPLE 145B 4-benzyl-6-(1,1-dioxido-4H-1,2,4-benzothiadiazin-3-yl)-7-hydroxy-2-(methylsulfanyl)[1,3]thiazolo[4,5-b]pyridin-5(4H)-one The title compound was prepared according to the procedure of Example 1D substituting the product of Example 145A for the product of Example 1B (0.037 g, 51%). MS (ESI) m/z 485 (M+H)$^+$. The sodium salt of the title compound was prepared according to the procedure of Example 1D. $^1$H NMR (300 MHz, DMSO-d$_6$) δ 2.73 (s, 3 H), 5.31 (s, 2 H), 7.25 (m, 7 H), 7.53 (td, J=7.72, 1.47 Hz, 1 H), 7.64 (dd, J=7.91, 1.29 Hz, 1 H), 15.52 (s, 1 H).

EXAMPLE 146

4-benzyl-6-(1,1-dioxido-4H-1,2,4-benzothiadiazin-3-yl)-7-hydroxy-2-(methylsulfonyl) [1,3]thiazolo[4,5-b]pyridin-5(4H)-one The title compound was prepared as a white solid from the product of Example 145B and 3-chloroperoxybenzoic acid according to the procedure of Leysen, and co-workers described in *J Heterocyclic Chem.*, 1984, 21, 401-406. MS (ESI) m/z 515 (M−H)$^-$; $^1$H NMR (300 MHz, DMSO-d$_6$) δ 3.59 (s, 3 H), 5.51 (s, 2 H), 7.32 (m, 5 H), 7.51 (m, 2 H), 7.69 (m, 1 H), 7.85 (d, J=7.72 Hz, 1 H), 13.95 (s, 1 H).

EXAMPLE 147

2-amino-4-benzyl-6-(1,1-dioxido-4H-1,2,4-benzothiadiazin-3-yl)-7-hydroxy[1,3]thiazolo[4,5-b]pyridin-5(4H)-one The product of Example 146 (0.011 g, 0.02 mmol) was reacted with ammonia (0.5 M in dioxane, 1.3 mL, 0.64 mmol) in a pressure tube at 70° C. for 17 hours. The reaction was cooled and the resulting precipitate was collected by filtration and dried to give the title compound as a white solid (0.009 g, 100%). MS (ESI) m/z 452 (M−H)$^-$; $^1$H NMR (300 MHz, DMSO-d$_6$) δ 5.43 (s, 2 H), 6.91 (s, 1 H), 7.07 (s, 1 H), 7.30 (m, 4 H), 7.52 (dd, J=24.27, 8.82 Hz, 2 H), 7.69 (t, J=7.54 Hz, 1 H), 7.85 (d, J=8.82 Hz, 1 H), 9.03 (br s, 1 H), 14.57 (brs, 1 H).

EXAMPLE 148

4-benzyl-6-(1,1-dioxido-4H-1,2,4-benzothiadiazin-3-yl)-7-hydroxy[1,3]thiazolo[4,5-b]pyridin-5(4H)-one The product of Example 147 (0.0085 g, 0.019 mmol) was reacted with tert-butyl nitrite (5 □L, 0.037 mmol) in DMF (0.3 mL) at 60° C. for 1 hour. The reaction was cooled, and the crude mixture was purified by column chromatography with silica gel eluting with hexane and ethyl acetate (1:1) to give the title compound as a yellow solid (0.0045 g, 54%). MS (ESI) m/z 437 (M−H)$^-$; $^1$H NMR (300 MHz, DMSO-d$_6$) δ 5.53 (s, 2 H), 7.25 (m, 1 H), 7.31 (m, 4 H), 7.43 (m, 2 H), 7.66 (m, 1 H), 7.80 (d, J=8.46 Hz, 1 H), 9.48 (s, 1 H), 14.56 (br s, 1 H).

759163 EXAMPLE 149

3-(1,1-dioxido-4H-1,2,4-benzothiadiazin-3-yl)-4-hydroxy-1-(2-phenylpropyl)-1,8-naphthyridin-2(1H)-one

EXAMPLE 149A ethyl 2-[(2-phenylpropyl)amino]nicotinate

The title compound was prepared according to the procedure of Example 3A substituting (+)-beta-methylphenethylamine for 2-ethyl-butylamine (0.44 g, 58%). MS (DCI+) m/z 285 (M+H)$^-$; $^1$H NMR (300 MHz, DMSO-d$_6$) δ 1.25 (m, 6H), 3.07 (m, 1H), 3.64 (m, 3H), 4.22 (q, J=6.99 Hz, 1H), 6.61 (dd, J=7.72, 4.78 Hz, 1H), 7.21 (m, 1H), 7.30 (m, 4H), 7.87 (t, J=5.52 Hz, 1H), 8.05 (m, 1H), 8.29 (m, 1H).

EXAMPLE 149B 1-(2-phenylpropyl)-2H-pyrido[2,3-d][1,3]oxazine-2,4(1H)-dione

The title compound was prepared according to the procedure of Example 3B substituting the product of Example 149A for the product of Example 3A (0.44 g, 99%). MS (DCI+) m/z 283 (M+H)$^-$; $^1$H NMR (300 MHz, DMSO-d$_6$) δ 1.26 (d, J=6.99 Hz, 3H), 3.37 (m, 1H), 4.21 (dd, J=13.24, 6.25

Hz, 1H), 4.36 (m, 1H), 7.21 (m, 1H), 7.29 (m, 4H), 7.38 (dd, J=7.72, 4.78 Hz, 1H), 8.39 (dd, J=7.72, 1.84 Hz, 1H), 8.77 (dd, J=4.78, 1.84 Hz, 1H).

EXAMPLE 149C 3-(1,1-dioxido-4H-1,2,4-benzothiadiazin-3-yl)-4-hydroxy-1-(2-phenylpropyl)-1,8-naphthyridin-2(1H)-one The title compound was prepared according to the procedure of Example 1D substituting the product of Example 149B for the product of Example 1B (0.045 g, 62%). MS (ESI−) m/z 459 (M−H)−; $^1$H NMR (300 MHz, DMSO-D$_6$) δ 1.23 (d, J=7.35 Hz, 3H), 3.47 (m, 1H), 4.59 (dd, J=12.50, 6.62 Hz, 1H), 4.75 (m, 1H), 7.16 (m, 1H), 7.28 (m, 4H), 7.45 (dd, J=7.91, 4.60 Hz, 1H), 7.56 (t, J=7.54 Hz, 1H), 7.69 (m, 1H), 7.78 (m, 1H), 7.93 (d, J=8.09 Hz, 1H), 8.53 (dd, J=8.09, 1.84 Hz, 1H), 8.80 (dd, J=4.60, 1.65 Hz, 1H), 14.13 (brs, 1H). The sodium salt of the title compound was prepared according to the procedure of Example 1d. $^1$H NMR (300 MHz, DMSO-D$_6$) δ 1.12 (d, J=6.99 Hz, 3H), 3.42 (m, 1H), 4.30 (dd, J=12.50, 5.52 Hz, 1H), 4.67 (dd, J=12.32, 9.74 Hz, 1H), 7.12 (dd, J=7.72, 4.78 Hz, 1H), 7.18 (m, 1H), 7.30 (m, 6H), 7.56 (m, 1H), 7.67 (d, J=7.72 Hz, 1H), 8.36 (dd, J=7.54, 2.02 Hz, 1H), 8.50 (dd, J=4.78, 1.84 Hz, 1H), 15.92 (s, 1H).

EXAMPLE 150

8-benzyl-6-(1,1-dioxido-4H-1,2,4-benzothiadiazin-3-yl)-5-hydroxy-2-(methylsulfanyl)pyrido[2,3-d]pyrimidin-7(8H)-one

EXAMPLE 150A ethyl 4-(benzylamino)-2-(methylthio)pyrimidine-5-carboxylate

The title compound was prepared according to the procedure of Example 108A substituting benzyl amine for 1-amino-2-ethyl-butane (0.97 g, 92%). MS (DCI/NH$_3$) m/z 304 (M+H)+$^1$H NMR (300 MHz, DMSO-d$_6$) δ 1.32 (q, J=7.48 Hz, 3 H) 2.41 (s, 3 H) 4.30 (q, J=7.11 Hz, 2 H) 4.73 (d, J=5.88 Hz, 2 H) 7.30 (m, 5 H) 8.58 (s, 1 H) 8.89 (t, J=5.70 Hz, 1 H)

EXAMPLE 150B 4-(benzylamino)-2-(methylthio)pyrimidine-5-carboxylic acid

The title compound was prepared according to the procedure of Example 108B substituting the product of Example 150A for the product of Example 108A. (0.185 g, 78%).

EXAMPLE 150C 1-benzyl-7-(methylthio)-2H-pyrimido[4,5-d][1,3]oxazine-2,4(1H)-dione The title compound was prepared according to the procedure of Example 108C substituting the product of Example 150B for the product of Example 108B (0.145 g, 72%). MS (DCI/NH$_3$) m/z 302 (M+H)+

EXAMPLE 150D 8-benzyl-6-(1,1-dioxido-4H-1,2,4-benzothiadiazin-3-yl)-5-hydroxy-2-(methylsulfanyl)pyrido[2,3-d]pyrimidin-7(8H)-one The title compound was prepared according to the procedure of Example 1D substituting the product of Example 150C for the product of Example 1B (0.042 g, 18%). MS (ESI−) m/z 478 (M−H)−. The sodium salt of the title compound was prepared according to the procedure of Example 1D. $^1$H NMR (300 MHz, DMSO-d$_6$) δ 2.48 (s, 3 H) 5.41 (s, 2 H) 7.26 (m, 7 H) 7.57 (m, 1 H) 7.67 (dd, J=7.54, 0.92 Hz, 1 H) 8.91 (s, 1 H) 15.42 (s, 1 H).

EXAMPLE 151

8-benzyl-6-(1,1-dioxido-4H-1,2,4-benzothiadiazin-3-yl)-5-hydroxypyrido[2,3-d]pyrimidin-7(8H)-one The title compound was prepared according to the procedure of Example 109 substituting the product of Example 151D for the product of Example 108D (0.019 g, 58%). MS (ESI−) m/z 432 (M−H)−; $^1$H NMR (300 MHz, DMSO-d6) δ 5.44 (s, 2 H) 7.20 (m, 1 H) 7.30 (m, 7 H) 7.57 (m, 1 H) 7.68 (d, J=8.09 Hz, 1 H) 8.94 (s, 1 H) 9.12 (s, 1 H) 15.32 (s, 1 H).

EXAMPLE 152

3-(1,1-dioxido-4H-1,2,4-benzothiadiazin-3-yl)-4-hydroxy-1-(3-hydroxybutyl)-2(1H)-quinolinone A solution of the product of Example 73 (0.12 g, 0.30 mmol) in tetrahydrofuran (6 mL) was treated with 3.0 M methyl magnesium bromide (0.11 mL, 0.33 mmol) at −50° C., then stirred at room temperature for 1 hour. The solution was diluted with 1N HCl and water then filtered. The resulting solid was triturated with dichloromethane and filtered. The filtrate was concentrated to give the title compound (0.050 g, 40%). MS (DCI/NH$_3$) m/z 415 (M+H)+; $^1$H NMR (300 MHz, DMSO-d$_6$) δ 1.14 (d, J=6.25 Hz, 3 H) 1.75 (dd, J=9.19, 5.52 Hz, 2 H) 3.78 (m, 1 H) 4.57 (m, 2 H) 7.54 (m, 2 H) 7.77 (m, 2 H) 7.94 (d, J=7.35 Hz, 1 H) 8.58 (dd, J=7.91, 2.02 Hz, 1 H) 8.90 (dd, J=4.78, 1.84 Hz, 1 H) 14.12 (s, 1 H).

EXAMPLE 153

1-benzyl-3-(1,1-dioxido-4H-1,2,4-benzothiadiazin-3-yl)-4-hydroxythieno[3,4-b]pyridin-2(1H)-one

EXAMPLE 153A 4H-thieno[3,4-d][1,3]oxazine-2,4(1H)-dione

The title compound was prepared according to procedure of Example 119A substituting ethyl 3-aminothiophene-5-carboxylate hydrochloride for methyl 3-amino-5-phenylthiophene-carboxylate (0.86 g, 50%). MS (DCI/NH$_3$) m/z 187 (M+NH$_4$)+; $^1$H NMR (300 MHz, DMSO-d$_6$) δ 6.90 (d, J=9.93 Hz, 1 H) 8.65 (d, J=9.93 Hz, 1 H) 11.57 (brs, 1 H).

EXAMPLE 153B 1-benzyl-4H-thieno[3,4-d][1,3]oxazine-2,4(1H)-dione

The title compound was prepared according to the procedure of Example 1B substituting the product of Example 153A for the product of Example 1A and substituting benzyl bromide for n-butyl bromide (0.33 g, 91%).

EXAMPLE 153C 1-benzyl-3-(1,1-dioxido-4H-1,2,4-benzothiadiazin-3-yl)-4-hydroxythieno[3,4-b]pyridin-2(1H)-one The title compound was prepared according to the procedure of Example 1D substituting the product of Example 153B for the product of Example 1B (0.028 g, 5%). MS (ESI−) m/z 436 (M−H)$^-$; $^1$H NMR (300 MHz, DMSO-d$_6$) δ 5.13 (s, 2 H) 6.68 (d, J=3.31 Hz, 1 H) 7.21 (m, 2 H) 7.28 (m, 5 H) 7.54 (m, 1 H) 7.64 (m, 1 H) 7.99 (d, J=3.31 Hz, 1 H) 15.83 (s, 1 H).

EXAMPLE 154

4-[(5-bromo-2-thienyl)methyl]-6-(1,1-dioxido-4H-1,2,4-benzothiadiazin-3-yl)-7-hydroxythieno[3,2-b]pyridin-5(4H)-one

EXAMPLE 154A

1-[(5-bromothien-2-yl)methyl]-2H-thieno[3,2-] [11,3]oxazine-2,4(1H)-dione

The title compound was prepared according to the procedure of Example 1B substituting the product of Example 110A for the product of Example 1A and substituting 2-bromo-5-bromomethyl-thiophene for n-butyl bromide (0.25 g, 82%).

EXAMPLE 154B

4-[(5-bromo-2-thienyl)methyl]-6-(1,1-dioxido-4H-1,2,4-benzothiadiazin-3-yl)-7-hydroxythieno[3,2-b]pyridin-5(4H)-one The title compound was prepared according to the procedure of Example 1D substituting the product of Example 154A for the product of Example 1B (0.219 g, 58%). MS (ESI−) m/z 521 (M−H)$^-$. The sodium salt of the title compound was prepared according to the procedure of Example 1D. $^1$H NMR (300 MHz, DMSO-d$_6$) δ 5.28 (s, 2 H) 7.02 (d, J=3.68 Hz, 1 H) 7.09 (d, J=3.68 Hz, 1 H) 7.20 (d, J=8.09 Hz, 1 H) 7.27 (m, 1 H) 7.37 (d, J=5.15 Hz, 1 H) 7.54 (ddd, J=8.55, 7.26, 1.47 Hz, 1 H) 7.66 (dd, J=7.72, 1.47 Hz, 1 H) 7.81 (d, J=5.15 Hz, 1 H) 15.80 (s, 1 H).

EXAMPLE 155

1-butyl-3-(1,1-dioxido-4H-1,2,4-benzothiadiazin-3-yl)-2(1H)-pyridinone

EXAMPLE 155A 1-butyl-2-oxo-1,2-dihydropyridine-3-carboxylic acid

To a solution of 2-hydroxy-nicotinic acid (0.50 g, 3.59 mmol) and potassium -hydroxide (0.40 g, 7.13 mmol) in 4:1 methanol: water (6 mL) at room temperature, was added 1-iodobutane (0.74 mL, 6.42 mmol). This solution was heated at 60° C. for 30 minutes, then cooled to room temperature and diluted with water and 1N HCl. The resulting solid was filtered and dried to give the title compound (0.27 g, 39%). MS (DCI/NH$_3$) m/z 196 (M+H)$^+$; $^1$H NMR (300 MHz, DMSO-d$_6$) δ 0.91 (m, 3 H) 1.30 (m, 2 H) 1.69 (m, 2 H) 4.10 (m, 2 H) 6.73 (m, 1 H) 8.27 (dd, J=6.62, 1.84 Hz, 1 H) 8.38 (dd, J=7.35, 2.21 Hz, 1 H) 14.68 (s, 1 H).

EXAMPLE 155B

N-[2-(aminosulfonyl)phenyl]-1-butyl-2-oxo-1,2-dihydropyridine-3-carboxamide

A solution of the product of Example 155A and 2-aminobenzene sulfonamide (0.24 g, 1.39 mmol) in tetrahydrofuran (8 mL) at room temperature and treated with TBTU (O-(1H-benzotriazol-1-yl)-N,N,N',N'-tetramethyluronium tetrafluoroborate) and triethylamine (0.58 mL, 4.15 mmol). After 18 hours, the mixture was poured into water, extracted with ethyl acetate, dried over sodium sulfate, filtered and the filtrate evaporated under vacuum and purified by preparative HPLC on a Waters Symmetry C8 column (40 mm×100 mm, 7 μm particle size) using a gradient of 10% to 100% acetonitrile:0.1% aqueous TFA over 12 min (15 min run time) at a flow rate of 70 mL/min to yield the title compound.

EXAMPLE 155C 1-butyl-3-(1,1-dioxido-4H-1,2,4-benzothiadiazin-3-yl)-2(1H)-pyridinone The title compound was prepared according to the procedure of Example 84D and purified by preparative HPLC on a Waters Symmetry C8 column (40 mm×100 mm, 7 μm particle size) using a gradient of 10% to 100% acetonitrile:0.1% aqueous TFA over 12 min (15 min run time) at a flow rate of 70 mL/min.
MS DCI/NH$_3$) m/z 332 (M+H)$^+$. The sodium salt of the title compound was prepared according to the procedure of Example 1D. $^1$H NMR (300 MHz, DMSO-d$_6$) δ 0.93 (t, J=7.35 Hz, 3 H) 1.34 (td, J=14.89, 7.35 Hz, 2 H) 1.73 (ddd, J=14.89, 7.72, 7.54 Hz, 2 H) 4.13 (m, 2 H) 6.73 (dd, J=7.35, 6.62 Hz, 1 H) 7.50 (m, 1 H) 7.59 (d, J=7.35 Hz, 1 H) 7.71 (m, 1 H) 7.85 (dd, J=7.91, 1.29 Hz, 1 H) 8.30 (dd, J=6.43, 2.02 Hz, 1 H) 8.62 (dd, J=7.54, 2.02 Hz, 1 H) 13.76 (s, 1 H).

EXAMPLE 156

3-(1,1-dioxido-4H-1,2,4-benzothiadiazin-3-yl)-1,8-naphthyridine-2,4-diol

The product of Example 73 (0.12 g, 0.30 mmol) in tetrahydrofuran (6 mL) was reacted with 3.0 M methyl magnesium bromide (0.11 mL, 0.33 mmol) at −50° C., and then stirred at room temperature for 1 hour. The solution was diluted with 1N HCl and filtered. The resulting solid was triturated with dichloromethane and filtered to yield the product. MS (DCI/NH$_3$) m/z 343 (M+H)$^+$; $^1$H NMR (300 MHz, DMSO-d$_6$) δ 7.46 (dd, J=7.91, 4.60 Hz, 1 H) 7.57 (m, 1 H) 7.64 (d, J=7.72 Hz, 1 H) 7.79 (ddd, J=8.36, 7.26, 1.29 Hz, 1 H) 7.94 (d, J=7.35 Hz, 1 H) 8.49 (dd, J=8.09, 1.84 Hz, 1 H) 8.80 (dd, J=4.60, 1.65 Hz, 1 H) 12.92 (s, 1 H) 14.28 (s, 1 H).

EXAMPLE 157

1-(benzyloxy)-3-(1,1-dioxido-4H-1,2,4-benzothiadiazin-3-yl)-4-hydroxy-1,8-naphthyridin-2(1H)-one

EXAMPLE 157A ethyl 2-[(benzyloxy)amino]nicotinate

2-Chloro-nicotinic acid ethyl ester (4.55 g, 24.6 mmol), O-benzylhydroxyamine hydrochloride (7.85 g, 49.2 mmol)

and N,N-diisopropylethylamine (6.36 g, 49.2 mmol) in 10 mL 1,4-dioxane were reacted in a sealed tube at 120° C. for 48 hours. The reaction mix was partitioned between ethyl acetate and 5% aqueous sodium bicarbonate. The aqueous layer was re-extracted with ethyl acetate (2×50 mL). The organic layers were combined and dried over sodium sulfate, filtered, and concentrated. The residue was purified by column chromatography on silica gel eluting with hexane and ethyl acetate (9:1) to provide the title compound (3.5 g, 53%). MS (DCI) m/z 273 (M+H)$^+$.

EXAMPLE 157B ethyl 2-[(benzyloxy)(3-ethoxy-3-oxopropanoyl) amino]nicotinate

A solution of the product of Example 157A (1.2 g, 4.4 mmol) and triethylamine (0.49 g, 4.8 mmol) in dichloromethane (25 mL) was treated dropwise with ethyl chloromalonate (0.73 g, 4.8 mmol), stirred for 2 hr and partitioned between ethyl acetate and water and the layers were separated. The ethyl acetate layer was washed with brine, dried (Na$_2$SO$_4$), and concentrated. The residue was purified by column chromatography on silica gel eluting with hexane and ethyl acetate (3:1) to provide the title compound (1.1 g, 65%). MS (DCI) m/z 387 (M+H)$^+$.

EXAMPLE 157C ethyl 1-(benzyloxy)-4-hydroxy-2-oxo-1,2-dihydro-1, 8-naphthyridine-3-carboxylate A solution of the product of Example 157B (0.386 g, 1.0 mmol) in ethanol (5 mL) was treated with 21% sodium ethoxide in ethanol (0.324 g, 1.0 mmol), stirred for 30 minutes and partitioned between ethyl acetate and 5% aqueous HCl and the layers were separated. The ethyl acetate layer was washed with brine, dried (Na$_2$SO$_4$), and concentrated to provide the title compound (0.28 g, 82%). MS (DCI) m/z 341(M+H)$^+$.

EXAMPLE 157D

N-[2-(aminosulfonyl)phenyl]-1-(benzyloxy)-4-hydroxy-2-oxo-1,2-dihydro-1,8-naphthyridine-3-carboxamide The title compound was prepared according to the procedure of Example 84C substituting the product of Example 157C for the product of Example 84B and substituting 2-aminosulfonamide for the product of Example 84A (340 mg, 89% yield). MS (DCI) m/z 467 (M+H)$^+$.

EXAMPLE 157E 1-(benzyloxy)-3-(1,1-dioxido-4H-1,2,4-benzothiadiazin-3-yl)-4-hydroxy-1,8-naphthyridin-2(1H)-one The title compound was prepared according to the procedure of Example 84D substituting the product of Example 157D for the product of Example 84C (0.082 g, 87%). MS (ESI–) m/z 447 (M–H)$^-$. The sodium salt of the title compound was prepared according to the procedure of Example 1d. $^1$H NMR (300 MHz, DMSO-d$_6$) δ 5.12 (s, 2 H) 7.22 (dd, J=7.72, 4.78 Hz, 1 H) 7.30 (m, 2 H) 7.44 (m, 3 H) 7.57 (m, 1 H) 7.70 (m, 3 H) 8.41 (dd, J=7.72, 1.84 Hz, 1 H) 8.61 (dd, J=4.78, 1.84 Hz, 1 H) 15.70 (s, 1 H).

EXAMPLE 158

3-(1,1-dioxido-4H-1,2,4-benzothiadiazin-3-yl)-4-hydroxy-1-isobutoxy-1,8-naphthyridin-2(1H)-one

EXAMPLE 158A ethyl 2-(isobutoxyamino)nicotinate

The title compound was prepared according to the procedure of Example 157A substituting O-isobutylhydroxylamine hydrochloride for O-benzylhydroxyamine hydrochloride (0.372 g, 34%). MS (DCI) m/z 239 (M+H)$^+$.

EXAMPLE 158B ethyl 2-[(3-ethoxy-3-oxopropanoyl)(isobutoxy) amino]nicotinate

The title compound was prepared according to the procedure of Example 157B substituting the product of Example 158A for the product of Example 157A (0.230 g, 42%). MS (DCI) m/z 353 (M+H)$^+$.

EXAMPLE 158C ethyl 4-hydroxy-1-isobutoxy-2-oxo-1,2-dihydro-1,8-naphthyridine-3-carboxylate The title compound was prepared according to the procedure of Example 157C substituting the product of Example 158B for the product of 157B (0.200 g, 99%). MS (DCI) m/z 307 (M+H)$^+$.

EXAMPLE 158D

N-[2-(aminosulfonyl)phenyl]-4-hydroxy-1-isobutoxy-2-oxo-1,2-dihydro-1,8-naphthyridine-3-carboxamide The title compound was prepared according to the procedure of Example 84C substituting the product of Example 158C for the product of Example 84B and substituting 2-aminosulfonamide for the product of Example 84A (0.225 g, 86%). MS (DCI) m/z 433 (M+H)$^+$.

EXAMPLE 158E 3-(1,1-dioxido-4H-1,2,4-benzothiadiazin-3-yl)-4-hydroxy-1-isobutoxy-1,8-naphthyridin-2(1H)-one The title compound was prepared according to the procedure of Example 84D substituting the product of Example 158D for the product of Example 84C (0.200 g, 93%). MS (ESI–) m/z 413 (M–H)$^-$. The sodium salt of the title compound was prepared according to the procedure of Example 1d. $^1$H NMR (300 MHz, DMSO-d$_6$) δ 1.05 (d, J=6.62 Hz, 6 H) 2.08 (m, 1 H) 3.88 (d, J=6.62 Hz, 2 H) 7.18 (dd, J=7.72, 4.78 Hz, 1 H) 7.29 (m, 2 H) 7.55 (m, 1 H) 7.67 (d, J=7.72 Hz, 1 H) 8.37 (dd, J=7.72, 1.84 Hz, 1 H) 8.55 (dd, J=4.78, 1.84 Hz, 1 H) 15.72 (s, 1 H).

EXAMPLE 159

1-butyl-3-(1,1-dioxido-4H-1,2,4-benzothiadiazin-3-yl)-4-hydroxy-1,5-naphthyridin-2(1H)-one

EXAMPLE 159A 2H-pyrido[3,2-d][1,3]oxazine-2,4(1H)-dione

The title compound was prepared as aminor bi-product (0.50 g, 4%) from 2,3-pyridinecarboxylic anhydride (11.4 g, 76 mmol) and trimethylsilyl azide (11.0 mL, 80 mmol) according to the procedure of Le Count, D. J. and co-workers described in *Synthesis*, 1982, 972-973. $^1$H NMR (300 MHz, DMSO-d$_6$) δ 7.56 (dd, J=8.46, 1.47 Hz, 1 H) 7.71 (dd, J=8.46, 4.41 Hz, 1 H) 8.51 (dd, J=4.41, 1.47 Hz, 1 H) 11.78 (s, 1 H).

EXAMPLE 159B 1-butyl-2H-pyrido[3,2-d][1,3]oxazine-2,4(1H)-dione

The title compound was prepared according to the procedure of Example 1B substituting the product of Example 159A for the product of Example 1A (0.12 g, 35%). $^1$H NMR (300 MHz, DMSO-d$_6$) δ 0.92 (t, J=7.35 Hz, 3 H) 1.40 (m, J=15.26, 7.17 Hz, 2 H) 1.60 (m, 2 H) 3.98 (m, 2 H) 7.81 (dd, J=8.82, 4.41 Hz, 1 H) 7.97 (dd, J=8.64, 1.29 Hz, 1 H) 8.55 (dd, J=4.23, 1.29 Hz, 1 H).

EXAMPLE 159C 1-butyl-3-(1,1-dioxido-4H-1,2,4-benzothiadiazin-3-yl)-4-hydroxy-1,5-naphthyridin-2(1H)-one The title compound was prepared according to the procedure of Example 1D substituting the product of Example 159B for the product of Example 1B (0.053 g, 25%). MS (ESI-) m/z 397 (M-H)$^-$. The sodium salt of the title compound was prepared according to the procedure of Example 1D. $^1$H NMR (300 MHz, DMSO-d$_6$) δ 0.94 (t, J=7.17 Hz, 3 H) 1.39 (m, 2 H) 1.54 (m, 2 H) 4.07 (t, J=7.72 Hz, 2 H) 7.28 (m, 2 H) 7.56 (m, 2 H) 7.68 (dd, J=7.91, 1.29 Hz, 1 H) 7.77 (d, J=8.46 Hz, 1 H) 8.39 (d, J=4.04 Hz, 1 H) 16.15 (s, 1 H).

EXAMPLE 160

1-benzyl-3-(1,1-dioxido-4H-1,2,4-benzothiadiazin-3-yl)-4-hydroxy-1,5-naphthyridin-2(1H)-one

EXAMPLE 160A 1-benzyl-2H-pyrido[3,2-d][1,3]oxazine-2,4(1H)-dione

The title compound was prepared according to the procedure of Example 1B substituting the product of Example 159A for the product of Example 1A and substituting benzyl bromide for n-butyl bromide (0.92 g, 60%). $^1$H NMR (300 MHz, DMSO-d$_6$) δ 5.28 (s, 2 H) 7.33 (m, 3 H) 7.43 (m, 2 H) 7.70 (m, 2 H) 8.54 (dd, J=3.86, 1.65 Hz, 1 H).

EXAMPLE 160B ethyl 1-benzyl-4-hydroxy-2-oxo-1,2-dihydro-1,5-naphthyridine-3-carboxylate The title compound was prepared according to the procedure of Example 89A substituting the product of Example 160A for the product of Example 1B (0.110 g, 23%). MS (DCI) m/z 325 (M+H)$^+$.

EXAMPLE 160C

N-[2-(aminosulfonyl)phenyl]-1-benzyl-4-hydroxy-2-oxo-1,2-dihydro-1,5-naphthyridine-3-carboxamide The title compound was prepared according to the procedure of Example 89B substituting the product of Example 160B for the product of Example 89A and 2-aminobenzenesulfonamide for 2-amino-4-chlorobenzenesulfonamide (0.12 g, 86%). MS (ESI-) m/z 449 (M-H)$^-$.

EXAMPLE 160D 1-benzyl-3-(1,1-dioxido-4H—1,2,4-benzothiadiazin-3-yl)-4-hydroxy-1,5-naphthyridin-2(1H)-one The title compound was prepared according to the procedure of Example 84C substituting the product of Example 160C for the product of Example 84B (0.120 g, 99%). MS (ESI-) m/z 431 (M-H)$^-$. The sodium salt of the title compound was prepared according to the procedure of Example 1D. $^1$H NMR (300 MHz, DMSO-d6) δ 5.39 (s, 2 H) 7.25 (m, 7 H) 7.40 (dd, J=8.46, 4.41 Hz, 1 H) 7.57 (m, 2 H) 7.68 (d, J=8.09 Hz, 1 H) 8.35 (d, J=4.04 Hz, 1 H) 16.11 (s, 1 H).

EXAMPLE 161

1-benzyl-4-chloro-3-(1,1-dioxido-4H-1,2,4-benzothiadiazin-3-yl)-1,8-naphthyridin-2(1H)-one The title compound was prepared from the product of Example 15B and phosphoryl chloride according to the procedure of Stadlbauer, W. and co-workers described in *Journal of Heterocyclic Chemistry*, 35, 1998, 627-636 (2.07 g, 88%). MS (ESI-) m/z 449 (M-H)$^-$; $^1$H NMR (300 MHz, DMSO-d$_6$) δ 5.68 (s, 2 H) 7.29 (m, 6 H) 7.57 (m, 2 H) 7.75 (m, 1 H) 7.92 (dd, J=7.91, 1.29 Hz, 1 H) 8.56 (dd, J=8.09, 1.47 Hz, 1 H) 8.87 (dd, J=4.60, 1.65 Hz, 1 H) 12.73 (s, 1 H).

EXAMPLE 162

3-(1,1-dioxido-4H-1,2,4-benzothiadiazin-3-yl)-4-hydroxy-1-{[(1E)-phenylmethylene]amino}-2(1H)-quinolinone

EXAMPLE 162A

2-[(2E)-2-benzylidenehydrazino]benzoic acid

The title compound was prepared from 2-hydrazinobenzoic acid hydrochloride (1.89 g, 10.0 mmol) and benzaldehyde (1.06 g, 10.0 mmol) according to the procedure of Fischer, E. and co-workers described in *Chem. Ber.*, 35, 1902, 2318 (2.4 g, quantitative yield). MS (DCI) m/z 241 (M+H)$^+$.

EXAMPLE 162B

1-{[(1E)-phenylmethylene]amino}-2H-3,1-benzoxazine-2,4(1H)-dione

A solution of the product of Example 162A (1.2 g, 5.0 mmol) and potassium hydroxide (0.336 g, 6.0 mmol) in 15 ml of water at 0° C. was treated dropwise with 20% phosgene in toluene (3.5 ml, 6.5 mmol), stirred for 1 hour, treated with 1M NaOH to reach a pH of 10 and extracted 3×30 mL with ethyl acetate. The ethyl acetate extracts were combined, washed with brine, dried (Na$_2$SO$_4$), and concentrated to provide the title compound (0.32 g, 24%). MS (DCI) m/z 267 (M+H)$^+$.

EXAMPLE 162C 3-(1,1-dioxido-4H-1,2,4-benzothiadiazin-3-yl)-4-hydroxy-1-{[(1E)-phenylmethylene]amino}-2(1H)-quinolinone The title compound was prepared according to the procedure of Example 1D substituting the product of Example 162B for the product of Example 1B (0.110 g, 49%). MS (ESI−) m/z 443 (M−H)⁻. The sodium salt of the title compound was prepared according to the procedure of Example 1D. $^1$H NMR (300 MHz, DMSO-d6) δ 7.16 (m, 1 H) 7.30 (m, 2 H) 7.54 (m, 6 H) 7.67 (dd, J=8.09, 1.47 Hz, 1 H) 7.99 (m, 2 H) 8.13 (dd, J=7.91, 1.29 Hz, 1 H) 9.04 (s, 1 H) 16.09 (s, 1 H).

EXAMPLE 163

1-amino-3-(1,1-dioxido-4H-1,2,4-benzothiadiazin-3-yl)-4-hydroxy-2(1H)-quinolinone A solution of the product of Example 162C (0.075 g, 0.17 mmol) in 10% aqueous potassium hydroxide (5 mL) was refluxed for 2 hours, cooled, treated with 12 M HCl to pH 3 which produced a precipitate. The solid was collected by filtration, washed repeatedly with water and dried to constant mass to give the desired product (0.050 g, 83%). MS (ESI−) m/z 355 (M−H)⁻. The sodium salt of the title compound was prepared according to the procedure of Example 1D. $^1$H NMR (300 MHz, DMSO-d$_6$) δ 5.31 (s, 2 H) 7.05 (t, J=8.09 Hz, 1 H) 7.27 (m, 2 H) 7.53 (m, 2 H) 7.67 (m, 2 H) 8.07 (dd, J=8.09, 1.47 Hz, 1 H) 16.38 (s, 1 H).

EXAMPLE 164

3-(1,1-dioxido-4H-1,2,4-benzothiadiazin-3-yl)-4-hydroxy-1-(2-phenylethyl)-1,8-naphthyridin-2(1H)-one

EXAMPLE 164A ethyl 2-[(2-phenylethyl)amino]nicotinate

The title compound was prepared according to the procedure of Example 3A substituting phenethylamine for 2-ethylbutylamine (1.98 g, 73%). MS (DCI) m/z 271 (M+H)⁺.

EXAMPLE 164B 1-(2-phenylethyl)-2H-pyrido[2,3-d][1,3]oxazine-2,4(1H)-dione

The title compound was prepared according to the procedure of Example 3B substituting the product of 164A for the product of Example 3A (0.53 g, 99%). MS (DCI) m/z 269 (M+H)⁺.

EXAMPLE 164C 3-(1,1-dioxido-4H-1,2,4-benzothiadiazin-3-yl)-4-hydroxy-1-(2-phenylethyl)-1,8-naphthyridin-2(1H)-one The title compound was prepared according to the procedure of Example 1D substituting the product of Example 164B for the product of Example 1B (0.132 g, 59%). MS (ESI−) m/z 445 (M−H)⁻. The sodium salt of the title compound was prepared according to the procedure of Example 1D. $^1$H NMR (300 MHz, DMSO-d$_6$) δ 2.87 (m, 2 H) 4.47 (m, 2 H) 7.16 (dd, J=7.72, 4.78 Hz, 1 H) 7.29 (m, 7 H) 7.57 (m, 1 H) 7.67 (d, J=7.72 Hz, 1 H) 8.40 (dd, J=7.72, 1.84 Hz, 1 H) 8.57 (dd, J=4.78, 1.84 Hz, 1 H) 15.90 (s, 1 H).

EXAMPLE 165

1-butyl-4-chloro-3-(1,1-dioxido-4H-1,2,4-benzothiadiazin-3-yl)-1,8-naphthyridin-2(1H)-one The title compound was prepared according to the procedure of Example 161 substituting the product of Example 1D for the product of Example 15B.

EXAMPLE 166

4-amino-1-butyl-3-(1,1-dioxido-4H-1,2,4-benzothiadiazin-3-yl)-1,8-naphthyridin-2(1H)-one A solution of the product of Example 165 (0.10 g, 0.24 mmol) and ammonia (2 ml of a 2 M solution in methanol, 4.0 mmol) was stirred in a sealed tube at 100° C. for 2 hours, allowed to cool to room temperature. The resulting solid collected by filtration and washed with methanol (2 ml) to give the title compound as a brown solid (0.019 g, 20%). MS (ESI−) m/z 396 (M−H)⁻; $^1$H NMR (300 MHz, DMSO-d$_6$) δ 0.94 (t, J=7.35 Hz, 3H), 1.38 (m, 2H), 1.66 (m, 2H), 4.44 (t, J=7.35 Hz, 2H), 7.48 (m, 2H), 7.55 (d, J=8.09 Hz, 1H), 7.70 (t, J=8.46 Hz, 1H), 7.84 (dd, J=7.72, 1.10 Hz, 1H), 8.77 (d, J=8.09 Hz, 1H), 8.82 (dd, J=4.78, 1.47 Hz, 1H), 9.84 (brs, 1H).

EXAMPLE 167

1-butyl-3-(1,1-dioxido-4H-1,2,4-benzothiadiazin-3-yl)-4-(methylamino)-1,8-naphthyridin-2(1H)-one The title compound was prepared according to the procedure of Example 166 substituting methylamine (2 M solution in methanol) for ammonia (2 M solution in methanol) as a brown solid (0.023 g, 23%). MS (ESI−) m/z 410 (M−H)⁻; $^1$H NMR (300 MHz, DMSO-d$_6$) δ 0.91 (t, J=7.17 Hz, 3H), 1.34 (m, 2H), 1.60 (m, 2H), 2.95 (d, J=5.15 Hz, 3H), 4.31 (m, J=7.36 Hz, 2H), 7.36 (dd, J=8.09, 4.78 Hz, 1H), 7.40 (d, J=8.46 Hz, 1H), 7.49 (t, J=8.09 Hz, 1H), 7.71 (m, 2H), 7.85 (dd, J=7.91, 1.29 Hz, 1H), 8.56 (dd, J=8.27, 1.29 Hz, 1H), 8.69 (dd, J=4.60, 1.29 Hz, 1H), 12.44 (brs, 1H).

EXAMPLE 168

1-butyl-4-(dimethylamino)-3-(1,1-dioxido-4H-1,2,4-benzothiadiazin-3-yl)-1,8-naphthyridin-2(1H)-one The title compound was prepared according to the procedure of Example 166 substituting dimethylamine (2 M solution in methanol) for ammonia (2 M solution in methanol) as a brown solid (0.015 g, 15%). MS (ESI−) m/z 424 (M−H)⁻; $^1$H NMR (300 MHz, DMSO-d$_6$) δ 0.93 (t, J=7.35 Hz, 3H), 1.36 (m, 2H), 1.63 (m, 2H), 2.99 (s, 6H), 4.36 (t, J=7.72 Hz, 2H), 7.38 (m, 2H), 7.51 (m, 1H), 7.73 (m, 1H), 7.88 (dd, J=8.09, 1.47 Hz, 1H), 8.36 (dd, J=8.09, 1.47 Hz, 1H), 8.71 (dd, J=4.78, 1.84 Hz, 1H), 12.45 (s, 1H).

EXAMPLE 169

1-butyl-3-(1,1-dioxido-4H-1,2,4-benzothiadiazin-3-yl)-4-hydrazino-1,8-naphthyridin-2(1H)-one The title compound was prepared according to the procedure of Example 166 substituting hydrazine for ammonia (2

M solution in methanol) as a brown solid (0.026 g, 26%). MS (ESI−) m/z 411 (M−H)−; $^1$H NMR (300 MHz, DMSO-d$_6$) δ 0.94 (t, J=7.35 Hz, 3H), 1.39 (m, 2H), 1.64 (m, 2H), 3.35 (brs, 3H), 4.41 (t, J=7.72 Hz, 2H), 7.04 (t, J=7.54 Hz, 1H), 7.42 (dd, J=7.72, 4.78 Hz, 1H), 7.57 (m, 1H), 7.83 (dd, J=7.91, 1.65 Hz, 1H), 8.49 (dd, J=7.72, 1.84 Hz, 1H), 8.64 (d, J=8.46 Hz, 1H), 8.68 (dd, J=4.78, 1.84 Hz, 1H), 9.65 (s, 1H).

EXAMPLE 170

4-azido-1-butyl-3-(1,1-dioxido-4H-1,2,4-benzothiadiazin-3-yl)-1,8-naphthyridin-2(1H)-one A solution of the product of Example 165 (0.1 g, 0.24 mmol) and sodium azide (0.037 g, 0.571 mmol) in dimethylformamide (2.5 ml) was stirred at 80° C. for 1.5 hours, allowed to cool to room temperature and concentrated under reduced pressure. The crude residue was purified by a C8 HPLC column eluting with 20% to 80% acetonitrile in water with 1% trifluoroacetic acid to give the title compound (0.025 g, 26% after column purification). MS (ESI−) m/z 422 (M−H)−; $^1$H NMR (300 MHz, DMSO-d$_6$) δ 0.94 (t, J=7.35 Hz, 3H), 1.38 (m, 2H), 1.67 (m, 2H), 4.42 (t, J=7.54 Hz, 2H), 7.41 (d, J=7.72 Hz, 1H), 7.46 (dd, J=7.91, 4.60 Hz, 1H), 7.56 (m, 1H), 7.76 (m, 1H), 7.91 (dd, J=8.09, 1.10 Hz, 1H), 8.41 (dd, J=8.09, 1.84 Hz, 1H), 8.84 (dd, J=4.41, 1.84 Hz, 1H), 12.74 (s, 1H).

EXAMPLE 171

1-butyl-3-(1,1-dioxido-4H-1,2,4-benzothiadiazin-3-yl)-4-[(2-hydroxyethyl)amino]-1,8-naphthyridin-2(1H)-one The title compound was prepared according to the procedure of Example 166 substituting ethanolamine (0.25 g, 4.0 mmol) and anhydrous methanol (2 ml) for ammonia (2 M solution in methanol) (0.02 g, 19%). MS (ESI−) m/z 440 (M−H)−; $^1$H NMR (300 MHz, DMSO-d$_6$) δ 0.92 (t, J=7.35 Hz, 3H), 1.35 (m, 2H), 1.61 (m, 2H), 2.71 (m, 1H), 3.40 (m, 1H), 3.47 (m, 2H), 3.57 (m, 2H), 4.32 (t, J=7.36 Hz, 2H), 7.35 (m, 1H), 7.39 (d, J=6.99 Hz, 1H), 7.44 (t, J=7.72 Hz, 1H), 7.51 (brs, 1H), 7.67 (m, 1H), 7.81 (dd, J=7.91, 1.29 Hz, 1H), 8.66 (dd, J=8.09, 1.47 Hz, 1H), 8.69 (dd, J=4.78, 1.47 Hz, 1H).

EXAMPLE 172

3-(1,1-dioxido-4H-1,2,4-benzothiadiazin-3-yl)-4-hydroxy-1-propoxyquinolin-2(1H)-one

EXAMPLE 172A ethyl 2-(hydroxyamino)benzoate

The title compound is prepared from ethyl-2-nitrobenzoate according to the procedure of Entwistle and Gilkerson described in *Tetrahedron*, 34, 1978, 213-215.

EXAMPLE 172B ethyl 2-(propoxyamino)benzoate

The title compound is prepared according to the procedure of Example 1B substituting the product of Example 172A for the product of Example 1A and substituting n-propyl bromide for n-butyl bromide.

EXAMPLE 172C ethyl 2-[(3-ethoxy-3-oxopropanoyl)(propoxy)amino]benzoate

The title compound is prepared according to the procedure of Example 157B substituting the product of Example 172B for the product of Example 157A.

EXAMPLE 172D ethyl 4-hydroxy-2-oxo-1-propoxy-1,2-dihydroquinoline-3-carboxylate The title compound is prepared according to the procedure of Example 157C substituting the product of Example 172C for the product of Example 157B.

EXAMPLE 172E

N-[2-(aminosulfonyl)phenyl]-4-hydroxy-2-oxo-1-propoxy-1,2-dihydroquinoline-3-carboxamide The title compound is prepared according to the procedure of Example 84C substituting the product of Example 172D for the product of Example 84B and substituting 2-aminosulfonamide for the product of Example 84A.

EXAMPLE 172F 3-(1,1-dioxido-4H-1,2,4-benzothiadiazin-3-yl)-4-hydroxy-1-propoxyquinolin-2(1H)-one The title compound is prepared according to the procedure of Example 84D substituting the product of Example 172E for the product of Example 84C. The sodium salt of the title compound is prepared according to the procedure of Example 1D.

EXAMPLE 173

7-benzyl-5-(1,1-dioxido-4H-1,2,4-benzothiadiazin-3-yl)-4-hydroxy-3-(hydroxymethyl)-7,7a-dihydrothieno[2,3-b]pyridin-6(3aH)-one

EXAMPLE 173A methyl 2-amino-4-(hydroxymethyl)thiophene-3-carboxylate

A solution of methyl cyanoacetate (1.18 mL, 13.28 mmol) and sodium sulfide nonahydrate (3.20 g, 13.28 mmol) in methanol (25 mL) at 0° C. was treated with 1-acetoxy-3-chloroacetone (2.0 g, 13.28 mmol). The cold bath was removed and triethylamine (1.86 mL, 13.28 mmol) was added dropwise. The solution was stirred at room temperature for 20 hours then diluted with water and extracted into ethyl acetate. The organic layer was dried over sodium sulfate, filtered, and the solvent removed under vacuum to provide the titled compound (1.25 g, 51%). MS (DCI/NH$_3$) M/Z 188

(M+H)+; 1H NMR (300 MHz, DMSO-d6) δ 3.68 (s, 3 H) 4.45 (dd, J=5.52, 1.47 Hz, 2 H) 4.88 (t, J=5.70 Hz, 1 H) 6.12 (s, 1 H) 7.28 (s, 2 H)

EXAMPLE 173B methyl 2-amino-4-({[tert-butyl(dimethyl)silyl]oxy}methyl)thiophene-3-carboxylate A solution of the product of Example 173A (1.25 g, 6.70 mmol) and N,N-diisopropylethylamine (0.71 mL, 7.35 mmol) in dichloromethane at 0° C. was treated with t-butyldimethylsilyl trifluoromethanesulfonate (0.85 mL, 6.70 mmol). After stirring at 0° C. for 1 hour, the solution was poured into water, extracted into dichloromethane, and dried over sodium sulfate. The solvent was removed under vacuum to provide the titled compound (0.87 g, 78%). MS (DCI/NH3) m/z 302 (M+H)+; 1H NMR (300 MHz, DMSO-d6) δ 0.00 (m, 6 H) 0.84 (s, 9 H) 3.62 (s, 3 H) 4.59 (d, J=1.47 Hz, 2 H) 6.03 (m, 1 H) 7.22 (s, 2 H).

EXAMPLE 173C methyl 2-(benzylamino)-4-({[tert-butyl(dimethyl)silyl]oxy}methyl)thiophene-3-carboxylate A solution of the product of Example 173B (0.36 g, 1.20 mmol) and potassium carbonate (0.185 g, 1.30 mmol) in acetonitrile (5 mL) was treated with benzyl bromide (0.16 mL, 1.25 mmol) at 45° C. for 24 hours. The solution was poured into water and extracted into ethyl acetate (2×). The combined organic layers were concentrated and purified by flash chromatography eluting with dichloromethane to provide the titled compound (0.17 g, 36%). MS (DCI/NH3) m/z 392 (M+H)+; 1H NMR (300 MHz, DMSO-d6) δ 0.00 (m, 6 H) 0.84 (s, 9 H) 3.67 (m, 3 H) 4.38 (d, J=5.88 Hz, 2 H) 4.62 (d, J=1.47 Hz, 2 H) 6.12 (s, 1 H) 7.28 (m, 5 H) 8.16 (t, J=6.07 Hz, 1 H).

EXAMPLE 173D 1-benzyl-5-({[tert-butyl(dimethyl)silyl]oxy}methyl)-2H-thieno[2,3-d][1,3]oxazine-2,4(1H)-dione The title compound was prepared according to the procedure of Example 3B substituting the product of Example 173C for the product of Example 3A (0.015 g, 83%). MS (DCI/NH3) m/z 404 (M+H)+

EXAMPLE 173E 7-benzyl-5-(1,1-dioxido-4H-1,2,4-benzothiadiazin-3-yl)-4-hydroxy-3-(hydroxymethyl)-7,7A-dihydrothieno[2,3-b]pyridin-6(3AH)-one The title compound was prepared according to the procedure of Example 1D substituting the product of Example 173D for the product of Example 1B. (0.013 g, 8%). MS (DCI/NH3) m/z 468 (M+H)+; 1H NMR (300 MHz, DMSO-d6) δ 4.78 (s, 2 H) 5.42 (s, 2 H) 7.13 (s, 1 H) 7.32 (m, 5 H) 7.53 (t, J=7.17 Hz, 1 H) 7.64 (d, J=9.93 Hz, 1 H) 7.75 (m, 1 H) 7.91 (d, J=6.99 Hz, 1 H).

EXAMPLE 174

1-benzyl-3-(6-chloro-1,1-dioxido-4H-thieno[3,2-e][1,2,4]thiadiazin-3-yl)-4-hydroxy-1,8-naphthyridin-2(1H)-one

EXAMPLE 174A 3-amino-5-chlorothiophene-2-sulfonamide

The title compound is prepared according to the procedure of Hansen, J. and coworkers as described in *J. of Medicinal Chemistry* 2002, 45, 4171-4187.

EXAMPLE 174B

N-[2-(aminosulfonyl)-5-chlorothien-3-yl]-1-benzyl-4-hydroxy-2-oxo-1,2-dihydro-1,8-naphthyridine-3-carboxamide The title compound is prepared according to the procedure of Example 84C substituting the product of Example 174A for the product of Example 84A and substituting 3-amino-5-chlorothiophene-2-sulfonamide for 2-amino-5-bromobenzenesulfonamide.

EXAMPLE 174C 1-benzyl-3-(6-chloro-1,1-dioxido-4H-thieno[3,2-e][1,2,4]thiadiazin-3-yl)-4-hydroxy-1,8-naphthyridin-2(1H)-one The title compound is prepared according to the procedure of Example 84D substituting the product of Example 174B for the product of Example 84C.

EXAMPLE 175

1-benzyl-3-(6-chloro-1,1-dioxido-4H-thieno[3,2-e][1,2,4]thiadiazin-3-yl)-4-hydroxyquinolin-2(1H)-one

EXAMPLE 175A

N-[2-(aminosulfonyl)-5-chlorothien-3-yl]-1-benzyl-4-hydroxy-2-oxo-1,2-dihydroquinoline-3-carboxamide The title compound is prepared according to the procedure of Example 84C substituting the product of Example 174A for the product of Example 84A and substituting the product of Example 99A for the product of example Example 84B.

EXAMPLE 175B 1-benzyl-3-(6-chloro-1,1-dioxido-4H-thieno[3,2-e][1,2,4]thiadiazin-3-yl)-4-hydroxyquinolin-2(1H)-one The title compound is prepared according to the procedure of Example 84D substituting the product of Example 175A for the product of Example 84C.

EXAMPLE 176

3-[5-(aminomethyl)-1,1-dioxido-4H-1,2,4-benzothiadiazin-3-yl]-1-benzyl-4-hydroxy-1,8-naphthyridin-2(1H)-one The product of Example 97 (91.6 mg, 0.2002 mmol) and Raney-nickel (0.94 g) in tetrahydrofuran (92 mL) and triethylamine (4.5 mL) was hydrogenated at 60 psi H$_2$ pressure at 50° for 2 days, with additional Raney-nickel (0.94 g) being added after 24 hrs. The reaction was cooled to room temperature, filtered, and concentrated by rotary evaporation to a greenish-yellow solid. The residue was purified by preparative HPLC on a Waters Symmetry C8 column (40 mm×100 mm, 7 μm particle size) using a gradient of 10% to 100% acetonitrile:0.1% aqueous TFA over 12 min (15 min run time) at a flow rate of 70 mL/min to give the title compound as a white solid (11 mg, 12%). MS (ESI–)⁻ m/z 460 (M–H)⁻; $^1$H NMR (300 MHz, DMSO-d$_6$) δ 4.31 (s, 2 H) 5.64 (s, 2 H) 7.28 (m, 6 H) 7.49 (m, 1 H) 7.74 (d, J=7.35 Hz, 1 H) 7.85 (d, J=7.72 Hz, 1 H) 8.48 (m, 3 H) 8.68 (m, 1 H). The sodium salt of the title compound was prepared according to the procedure of Example 1D. $^1$H NMR (300 MHz, DMSO-d$_6$) δ 4.16 (s, 2 H) 5.54 (s, 2 H) 7.24 (m, 7 H) 7.65 (d, J=7.72 Hz, 2 H) 8.43 (dd, J=7.54, 1.65 Hz, 1 H) 8.50 (dd, J=4.41, 1.84 Hz, 1 H).

EXAMPLE 177

8-benzyl-3-chloro-6-(1,1-dioxido-4H-1,2,4-benzothiadiazin-3-yl)-5-hydroxypyrido[2,3-c]pyridazin-7(8H)-one

EXAMPLE 177A 3-(benzylamino)-6-chloropyridazine-4-carboxylic acid 2,5-Dichloro-pyridizine-3-carboxylate (0.40 g, 2.07 mmol) in toluene (8 mL) was reacted with triethylamine (0.72 mL, 5.20 mmol) and benzyl amine (0.23 mL, 2.07 mmol) at 90° C. for 8 hours. The solution was partitioned between water and ethyl acetate. The organic layer was dried over sodium sulfate, filtered, and concentrated to yield the title compound (0.257 g, 47%). MS (DCI/NH$_3$) m/z 264 (M+H$^+$)$^+$.

EXAMPLE 177B 8-benzyl-3-chloro-5H-pyridazino[3,4-d][1,3]oxazine-5,7(8H)-dione The title compound is prepared according to the procedure of Example 108C substituting the product of Example 177A for the product of Example 108B.

EXAMPLE 177C 8-benzyl-3-chloro-6-(1,1-dioxido-4H-1,2,4-benzothiadiazin-3-yl)-5-hydroxypyrido[2,3-c]pyridazin-7(8H)-one The title compound is prepared according to the procedure of Example 1D substituting the product of Example 177B for the product of Example 1B.

EXAMPLE 178

8-benzyl-6-(1,1-dioxido-4H-1,2,4-benzothiadiazin-3-yl)-5-hydroxy-3-(methylthio)pyrido[2,3-c]pyridazin-7(8H)-one The product of Example 177 is reacted with methanethiol in toluene at elevated temperatures the reaction was concentrated give the title compound.

EXAMPLE 179

8-benzyl-6-(1,1-dioxido-4H-1,2,4-benzothiadiazin-3-yl)-5-hydroxypyrido[2,3-c]pyridazin-7(8H)-one The title compound is produced by the procedure of Example 109 substituting the product of Example 178 for the product of Example 108D.

EXAMPLE 180

1-benzyl-3-(1,1-dioxido-4H-1,2,4-benzothiadiazin-3-yl)-4-hydroxy-1,6-naphthyridin-2(1H)-one

EXAMPLE 180A methyl 4-(benzylamino)nicotinate

The title compound is prepared from 3-carbomethoxy-4-chloropyridine and benzylamine according to the procedure of Winn, et.al. as described in *J. Med. Chem.*, 36, 1993, 2676-2688.

EXAMPLE 180B 1-benzyl-2H-pyrido[4,3-d][1,3]oxazine-2,4(1H)-dione

The title compound is prepared according to the procedure of Example 3B substituting the product of Example 180A for the product of Example 3A.

EXAMPLE 180C 1-benzyl-3-(1,1-dioxido-4H-1,2,4-benzothiadiazin-3-yl)-4-hydroxy-1,6-naphthyridin-2(1 h)-one The title compound is prepared according to the procedure of Example 1D substituting the product of Example 180B for the product of Example 1B.

EXAMPLE 181

1-benzyl-3-(1,1-dioxido-4H-1,2,4-benzothiadiazin-3-yl)-4-hydroxy-1,7-naphthyridin-2(1H)-one

EXAMPLE 181A 2H-pyrido[3,4-dl 11,3]oxazine-2,4(1H)-dione

The title compound is prepared according to the procedure of Example 10A from 3-aminoisonicotinic acid.

EXAMPLE 181B 1-benzyl-2H-pyrido[3,4-d][1,3]oxazine-2,4(1H)-dione

The title compound is prepared according to the procedure of Example 1B substituting the product of Example 181 A for the product of Example 1A, substituting DMF for DMA, and substituting benzyl bromide for n-butyl bromide, respectively.

EXAMPLE 181C 1-benzyl-3-(1,1-dioxido-4H-1,2,4-benzothiadiazin-3-yl)-4-hydroxy-1,7-naphthyridin-2(1H)-one The title compound is prepared according to the procedure of Example 1D substituting the product of Example 181C for the product of Example 1B.

EXAMPLE 182

1-(benzylamino)-3-(1,1-dioxido-4H-1,2,4-benzothiadiazin-3-yl)-4-hydroxyquinolin-2(1H)-one A slurry of the product of Example 162 (0.133 g, 0.3 mmol) and 10% palladium on carbon (0.02 g, catalytic amount) in THF (25 mL) was hydrogenated under 1 atmosphere of hydrogen for 4 hours, filtered through Celite and the filtrate was concentrated. The residue was slurried in 1 mL DMSO/5 mL MeOH for 15 minutes and the solid was collected by filtration and dried under vacuum to give the title compound (0.08 g, 60%). MS (ESI−) m/z 445 (M−H)⁻. The sodium salt of the title compound was prepared according to the procedure of Example 1D. $^1$H NMR (300 MHz, DMSO-d$_6$) δ 3.93 (s, 2 H) 6.09 (t, J=6.99 Hz, 1 H) 7.09 (t, J=7.35 Hz, 1 H) 7.35 (m, 5 H) 7.54 (m, 4 H) 7.69 (t, J=8.82 Hz, 2 H) 8.10 (dd, J=7.91, 1.29 Hz, 1 H) 16.28 (s, 1 H).

EXAMPLE 183A 2-amino-5-methoxybenzenesulfonamide

The title compound was prepared from 4-methoxyaniline using the procedure described in *Journal of the Chemical Society, Perkin* 1, 1979, 1043.

EXAMPLE 183B

Ethyl (7-methoxy-1,1-dioxido-4H-1,2,4-benzothiadiazin-3-yl)acetate

To a solution of the product of Example 183A (0.534 g, 2.64 mmol) and triethylamine (0.44 mL, 3.17 mmol) in anhydrous dichloromethane (8 mL) under nitrogen at 0° C. was added dropwise ethyl malonyl chloride (0.39 mL, 3.04 mmol). The resulting mixture was stirred at 25° C. for 6 hours. The reaction mixture was diluted with 1 N HCl (30 mL), and the aqueous layer was extracted with ethyl acetate (2×30 mL). The combined organic extracts were washed with brine, dried over anhydrous magnesium sulfate and filtered. The filtrate was concentrated and the resulting brown solid was recrystallized from dichloromethane/methanol to give a pink solid (420 mg). The solid was treated with anhydrous sodium carbonate (700 mg, 6.65 mmol) in anhydrous ethanol (15 mL) and heated at reflux for 7 hours. The solid was filtered off, and the filtrate was concentrated to give the title compound as a white solid (420 mg, total yield for two steps 50%). MS (ESI) m/z 297 (M−H)⁻. $^1$H NMR (300 MHz, DMSO-d$_6$) δ ppm 1.19 (t, J=7.17 Hz, 3 H) 3.23 (s, 2 H) 3.75 (s, 3 H) 4.07 (q, J=6.99 Hz, 2 H) 6.99 (m, 3 H).

EXAMPLE 183C 4-hydroxy-3-(7-methoxy-1,1-dioxido-4H-1,2,4-benzothiadiazin-3-yl)-1-(3-methylbutyl)-1,8-naphthyridin-2(1H)-one To a solution of the product of Example 183B (0.5 g, 1.6 mmol) and the product of Example 12A (0.375 g, 1.6 mmol) in anhydrous THF (16 mL) under nitrogen at 0° C. was added sodium hydride (95%, 0.162 g, 6.4 mmol). The reaction was heated at reflux for 4 hours, cooled to 0° C., and treated dropwise with glacial acetic acid (3 mL). The resulting mixture was heated at reflux for 2 hours, cooled to 25°, and diluted with ice water (150 mL). The resulting precipitate was collected by filtration, washed with water and recrystallized from dioxane/water to give the title compound (566 mg, 80%). The sodium salt of the title compound was prepared according to the procedure of Example 1D. MS (ESI−) m/z 441 (M−H)⁻. $^1$H NMR (300 MHz, DMSO-d$_6$) δ ppm 0.96 (d, J=6.62 Hz, 6 H) 1.48 (m, 2 H) 1.64 (m, 1 H) 3.82 (s, 3 H) 4.29 (m, 2 H) 7.16 (m, 4 H) 8.36 (dd, J=7.54, 2.02 Hz, 1 H) 8.52 (dd, J=4.60, 2.02 Hz, 1 H) 15.86 (s, 1 H).

EXAMPLE 184

4-hydroxy-3-(7-hydroxy-1,1-dioxido-4H-1,2,4-benzothiadiazin-3-yl)-1-(3-methylbutyl)-1,8-naphthyridin-2(1H)-one The product of Example 183C (0.027 g, 0.061 mmol) in dichloromethane (0.6 mL) was reacted with boron tribromide (1.0 M, 0.37 mL, 0.37 mmol) in dichloromethane at 25° C. for 18 hours. The reaction was quenched with methanol and stirred for 30 minutes at 25° C. The reaction was concentrated under reduced pressure to give the title compound as a solid (20.4 mg, 78%). The disodium salt of the title compound was prepared according to the procedure of Example 1D using two equivalents of sodium hydroxide. MS (ESI−) m/z 427 (M−H)⁻. $^1$H NMR (300 MHz, DMSO-d$_6$) δ ppm 0.96 (d, J=6.62 Hz, 6 H) 1.47 (m, 2 H) 1.64 (m, 1 H) 4.29 (m, 2 H) 6.51 (m, 2 H) 6.78 (m, 1 H) 7.09 (dd, J=7.72, 4.78 Hz, 1 H) 8.34 (dd, J=7.35, 1.84 Hz, 1 H) 8.48 (dd, J=4.60, 2.02 Hz, 1 H) 15.23 (br s, 1 H).

EXAMPLE 185

({3-[4-hydroxy-1-(3-methylbutyl)-2-oxo-1,2-dihydro-1,8-naphthyridin-3-yl]-1,1-dioxido-4H-1,2,4-benzothiadiazin-7-yl}oxy)acetonitrile The product of Example 184 (0.050 g, 0.12 mmol) in N,N-dimethylformamide (1 mL) was reacted with 2-bromoacetonitrile (14 μL, 0.2 mmol), potassium carbonate (0.029 g, 0.22 mmol) and tetrabutylammonium iodide (catalytic) at 25° C. for 30 hours. The reaction mixture was diluted with water (50 mL) and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was triturated with hexanes and dichloromethane to give the title compound as a pale yellow solid (16.8 mg, 30%). The sodium salt of the title compound was prepared according to the procedure of Example 1D. (ESI−) m/z 466 (M−H)⁻. $^1$H NMR (300 MHz, DMSO-d$_6$) δ ppm 0.96 (d, J=6.62 Hz, 6 H) 1.47 (m, 2 H) 1.64 (m, 1 H) 4.29 (m, 2 H)

5.27 (s, 2 H) 7.13 (dd, J=7.72, 4.78 Hz, 1 H) 7.31 (m, 3 H) 8.36 (dd, J=7.72, 1.84 Hz, 1 H) 8.53 (dd, J=4.78, 1.84 Hz, 1 H) 15.99 (s, 1 H).

EXAMPLE 186

3-(1,1-dioxido-7-propoxy-4H-1,2,4-benzothiadiazin-3-yl)-4-hydroxy-1-(3-methylbutyl)-1,8-naphthyridin-2(1H)-one The product of Example 184 (0.030 g, 0.07 mmol) in N,N-dimethylformamide (1 mL) was reacted with 1-bromopropane (0.025 mL, 0.28 mmol), potassium carbonate (60 mg, 0.42 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was recrystallized from dichloromethane:hexanes to give the title compound (14 mg, 43%). The sodium salt of the title compound was prepared according to the procedure of Example 1D. $^1$H NMR (300 MHz, DMSO-$d_6$) δ ppm 0.96 (d, J=6.62 Hz, 6 H) 0.99 (t, J=7.35 Hz, 3 H) 1.48 (m, 2 H) 1.75 (m, 3 H) 3.98 (t, J=6.43 Hz, 2 H) 4.29 (m, 2 H) 7.16 (m, 4 H) 8.36 (dd, J=7.72, 1.84 Hz, 1 H) 8.52 (dd, J=4.60, 2.02 Hz, 1 H) 15.85 (s, 1 H). (ESI−) m/z 469 (M−H)$^−$.

EXAMPLE 187

4-hydroxy-3-[7-(methoxymethoxy)-1,1-dioxido-4H-1,2,4-benzothiadiazin-3-yl]-1-(3-methylbutyl)-1,8-naphthyridin-2(1H)-one The product of Example 184 (30 mg, 0.07 mmol) in N,N-dimethylformamide (1 mL) was reacted with bromo(methoxy)methane (0.021 mL, 0.28 mmol), potassium carbonate (38 mg, 0.28 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was chromatographed on silica gel eluting with 3:1 hexanes/ethyl acetate to give the title compound. $^1$H NMR (300 MHz, DMSO-$d_6$) δ ppm 0.98 (d, J=6.62 Hz, 6 H) 1.56 (m, 2 H) 1.70 (m, 1 H) 3.42 (s, 3 H) 4.47 (m, 2 H) 5.31 (s, 2 H) 7.44 (m, 3 H) 7.66 (m, 1 H) 8.54 (d, J=8.09 Hz, 1 H) 8.85 (s, 1 H). (ESI−) m/z 471 (M−H)$^−$. The sodium salt of the title compound was prepared according to the procedure of Example 1D.

EXAMPLE 188

4-Hydroxy-1-(3-methylbutyl)-3-{7-[(2-methylprop-2-enyl)oxy]-1,1-dioxido-4H-1,2,4-benzothiadiazin-3-yl}-1,8-naphthyridin-2(1H)-one The product of Example 184 (30 mg, 0.07 mmol) in N,N-dimethylformamide (1 mL) was reacted with 3-bromo-2-methylprop-1-ene (8 μL, 0.077 mmol), potassium carbonate (60 mg, 0.42 mmol) and tetrabutylammonium iodide (catalytic) at 25° C. for 24 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was recrystallized from dichloromethane:hexanes to give the title compound (17.4 mg, 50%). The sodium salt of the title compound was prepared according to the procedure of Example 1D. $^1$H NMR (300 MHz, DMSO-$d_6$) δ ppm 0.96 (d, J=6.62 Hz, 6 H) 1.47 (m, 2 H) 1.64 (m, 1 H) 1.78 (s, 3 H) 4.29 (m, 2 H) 4.54 (s, 2 H) 4.98 (s, 1 H) 5.08 (s, 1 H) 7.12 (m, 2 H) 7.22 (m, 2 H) 8.36 (dd, J=7.54, 2.02 Hz, 1 H) 8.52 (dd, J=4.60, 2.02 Hz, 1 H) 15.86 (s, 1 H). (ESI−) m/z 481 (M−H)$^−$.

EXAMPLE 189 tert-butyl ({3-[4-hydroxy-1-(3-methylbutyl)-2-oxo-1,2-dihydro-1,8-naphthyridin-3-yl]-1,1-dioxido-4H-1,2,4-benzothiadiazin-7-yl}oxy)acetate The product of Example 184 (30 mg, 0.07 mmol) in N,N-dimethylformamide (1 mL) was reacted with tert-butyl bromoacetate (0.04 mL, 0.28 mmol), potassium carbonate (0.04 g, 0.28 mmol) and tetrabutylammonium iodide (catalytic) at 25° C. for 24 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was chromatographed on silica gel eluting with 3:1 hexanes/ethyl acetate to give the title compound (20 mg, 53%). $^1$H NMR (300 MHz, DMSO-$d_6$) δ ppm 0.97 (d, J=6.62 Hz, 6 H) 1.43 (s, 9 H) 1.51 (m, 2 H) 1.66 (m, 1 H) 4.35 (m, 2 H) 4.77 (s, 2 H) 7.33 (m, 4 H) 8.42 (d, J=8.09 Hz, 1 H) 8.63 (s, 1 H). (ESI−) m/z 541 (M−H)$^−$. The sodium salt of the title compound was prepared according to the procedure of Example 1D.

EXAMPLE 190

2-({3-[4-hydroxy-1-(3-methylbutyl)-2-oxo-1,2-dihydro-1,8-naphthyridin-3-yl]-1,1-dioxido-4H-1,2,4-benzothiadiazin-7-yl}oxy)acetamide The product of Example 184 (30 mg, 0.07 mmol) in N,N-dimethylformamide (1 mL) was reacted with 2-bromoacetamide (16 mg, 0.12 mmol), potassium carbonate 24 mg, 0.17 mmol) and tetrabutylammonium iodide (catalytic) at 25° C. for 48 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was triturated with dichloromethane:hexanes to give the title compound. The sodium salt of the title compound was prepared according to the procedure of Example 1D. $^1$H NMR (300 MHz, DMSO-$d_6$) δ ppm 0.96 (d, J=6.62 Hz, 6 H) 1.48 (m, 2 H) 1.64 (m, 1 H) 4.29 (m, 2 H) 4.49 (s, 2 H) 7.13 (m, 2 H) 7.24 (m, 2 H) 7.40 (m, 1 H) 7.62 (m, 1 H) 8.36 (dd, J=7.54, 2.02 Hz, 1 H) 8.52 (dd, J=4.60, 2.02 Hz, 1 H) 15.89 (s, 1 H). (ESI−) m/z 484 (M−H)$^−$.

EXAMPLE 191

3-[7-(benzyloxy)-1,1-dioxido-4H-1,2,4-benzothiadiazin-3-yl]-4-hydroxy-1-(3-methylbutyl)-1,8-naphthyridin-2(1H)-one The product of Example 184 (30 mg, 0.07 mmol) in N,N-dimethylformamide (1 mL) was reacted with (bromomethyl)

benzene (0.0138 mL, 0.11 mmol), cesium carbonate (50 mg, 0.15 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was triturated with ethyl acetate to give the title compound (13 mg, 36%). The sodium salt of the title compound was prepared according to the procedure of Example 1D. $^1$H NMR (300 MHz, DMSO-d$_6$) δ ppm 0.96 (d, J=6.25 Hz, 6 H) 1.48 (m, 2 H) 1.64 (m, 1 H) 4.29 (m, 2 H) 5.17 (s, 2 H) 7.12 (dd, J=7.72, 4.78 Hz, 1 H) 7.23 (m, 3 H) 7.41 (m, 5 H) 8.36 (dd, J=7.35, 1.84 Hz, 1 H) 8.52 (dd, J=4.78, 1.84 Hz, 1 H) 15.87 (s, 1 H). (ESI−) m/z 517 (M−H)$^-$.

EXAMPLE 192

3-[1,1-dioxido-7-(2-pyrrolidin-1-ylethoxy)-4H-1,2,4-benzothiadiazin-3-yl]-4-hydroxy-1-(3-methylbutyl)-1,8-naphthyridin-2(1H)-one The product of Example 184 (30 mg, 0.07 mmol) in N,N-dimethylformamide (1 mL) was reacted with 1-(2-chloroethyl)pyrrolidine hydrochloride (19 mg, 0.11 mmol), potassium carbonate (96 mg, 0.69 mmol) and tetrabutylammonium iodide (catalytic) at 25° C. for 72 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was chromatographed on silica gel eluting with 5% methanol/dichloromethane to give the title compound. The potassium salt of the title compound was prepared according to the procedure of Example 1D substituting potassium hydroxide for sodium hydroxide. $^1$H NMR (300 MHz, DMSO-d$_6$) δ ppm 0.96 (d, J=6.62 Hz, 6 H) 1.48 (m, 2 H) 1.64 (m, 1 H) 1.91 (m, 4 H) 3.16 (m, 4 H) 3.47 (m, 1 H) 4.30 (m, 4 H) 7.13 (dd, J=7.54, 4.60 Hz, 1 H) 7.24 (m, 3 H) 8.36 (dd, J=7.72, 1.84 Hz, 1 H) 8.53 (dd, J=4.60, 2.02 Hz, 1 H) 15.90 (s, 1 H). (ESI−) m/z 524 (M−H)$^-$.

EXAMPLE 193

3-[1,1-dioxido-7-(2-oxo-2-phenylethoxy)-4H-1,2,4-benzothiadiazin-3-yl]-4-hydroxy-1-(3-methylbutyl)-1,8-naphthyridin-2(1H)-one The product of Example 184 (30 mg, 0.07 mmol) in N,N-dimethylformamide (1 mL) was reacted with 2-bromo-1-phenylethanone (30 mg, 0.15 mmol), potassium carbonate (60 mg, 0.42 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was chromatographed on silica gel eluting with 0.2% methanoudichloromethane to give the title compound. The sodium salt of the title compound was prepared according to the procedure of Example 1D. $^1$H NMR (300 MHz, DMSO-d$_6$) δ ppm 0.96 (d, J=6.62 Hz, 6 H) 1.48 (m, 2 H) 1.65 (m, 1 H) 4.31 (m, 2 H) 5.70 (s, 2 H) 7.14 (m, 1 H) 7.24 (d, J=9.93 Hz, 3 H) 7.59 (t, J=7.35 Hz, 2 H) 7.71 (t, J=7.35 Hz, 1 H) 8.05 (m, 2 H) 8.38 (dd, J=7.91, 1.65 Hz, 1 H) 8.54 (m, 1 H) 15.85 (s, 1 H). (ESI−) m/z 545 (M−H)$^-$.

EXAMPLE 194

3-[7-(allyloxy)-1,1-dioxido-4H-1,2,4-benzothiadiazin-3-yl]-4-hydroxy-1-(3-methylbutyl)-1,8-naphthyridin-2(1H)-one The product of Example 184 (30 mg, 0.07 mmol) in N,N-dimethylformamide (1 mL) was reacted with 3-iodoprop-1-ene (0.007 mL , 0.077 mmol), potassium carbonate 60 mg, 0.42 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was triturated with hexanes to give the title compound. $^1$H NMR (300 MHz, DMSO-d$_6$) δ ppm 0.98 (d, J=6.25 Hz, 6 H) 1.55 (m, 2 H) 1.68 (m, 1 H) 4.42 (m, 2 H) 4.69 (d, J=5.52 Hz, 2 H) 5.30 (dd, J=10.66, 1.47 Hz, 1 H) 5.43 (dd, J=17.28, 1.84 Hz, 1 H) 6.06 (m, 1 H) 7.29 (m, 3 H) 7.53 (m, 1 H) 8.49 (d, J=6.62 Hz, 1 H) 8.76 (m, 1 H) 15.29 (brs, 1 H). (ESI−) m/z 467 (M−H)$^-$.

EXAMPLE 195

4-Hydroxy-3-(7-isobutoxy-1,1-dioxido-4H-1,2,4-benzothiadiazin-3-yl)-1-(3-methylbutyl)-1,8-naphthyridin-2(1H)-one The product of Example 184 (30 mg, 0.07 mmole) in N,N-dimethylformamide (1 mL) was reacted with 1-bromo-2-methylpropane (0.034 mL, 0.3 mmol), potassium carbonate (60 mg, 0.42 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue recrystallized from hexanes:dichloromethane to give the title compound (10.5 mg, 31%). The sodium salt of the title compound was prepared according to the procedure of Example 1D. $^1$H NMR (300 MHz, DMSO-d$_6$) δ ppm 0.96 (d, J=6.25 Hz, 6 H) 0.99 (d, J=6.62 Hz, 6 H) 1.47 (m, 2 H) 1.64 (m, 1 H) 2.03 (m, 1 H) 3.80 (d, J=6.62 Hz, 2 H) 4.29 (m, 2 H) 7.15 (m, 4 H) 8.36 (dd, J=7.72, 1.84 Hz, 1 H) 8.52 (dd, J=4.78, 1.84 Hz, 1 H) 15.85 (s, 1 H). (ESI−) m/z 483 (M−H)$^-$.

EXAMPLE 196

4-({3-[4-hydroxy-1-(3-methylbutyl)-2-oxo-1,2-dihydro-1,8-naphthyridin-3-yl]-1,1-dioxido-4H-1,2,4-benzothiadiazin-7-yl}oxy)butanenitrile The product of Example 184 (30 mg, 0.07 mmol) in N,N-dimethylformamide 1 mL) was reacted with 4-bromobutanenitrile (0.0154 mL, 0.15 mmol), potassium carbonate (60 mg, 0.42 mmol) and tetrabutylammonium iodide (catalytic) at 25° C. for 96 hours. The reaction mixture was diluted with water and acidified to pH 5 with concentrated acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was recrystallized with hexanes:dichloromethane to give the title compound (21.8 mg, 62%). The sodium salt of the title compound was prepared according to the procedure of Example 1D. $^1$H NMR (300 MHz, DMSO-d$_6$) δ ppm 0.96 (d, J=6.62 Hz, 6 H) 1.47 (m, 2 H) 1.62 (m, 1 H) 2.04 (m, 2 H) 2.68 (t, J=7.17 Hz, 2 H) 4.10 (t, J=5.88 Hz, 2 H) 4.29 (m, 2 H) 7.17 (m, 4 H) 8.36 (dd, J=7.91, 1.29 Hz, 1 H) 8.52 (dd, J=4.60, 1.65 Hz, 1 H) 15.88 (s, 1 H). (ESI−) m/z 494 (M−H)$^−$.

EXAMPLE 197

({3-[1-(3-methylbutyl)-4-oxido-2-oxo-1,2-dihydro-1, 8-naphthyridin-3-yl]-1,1-dioxido-4H-1,2,4-benzothiadiazin-7-yl}oxy)acetate The product of Example 189 (15 mg, 0,028 mmol) in a mixture of trifluoroacetic acid (0.8 mL) and dichloromethane (0.2 mL) was stirred for two hours at 25° C. The solvents were removed under reduced pressure to give a yellow solid that was partitioned between ethyl acetate and water. The aqueous layer was extracted with ethyl acetate (2×20 mL). The aqueous layer was acidified to pH 2 with 1N HCl and extracted with ethyl acetate (3×20 mL). The combined organic extracts were washed with brine, dried over anhydrous magnesium sulfate, filtered, and concentrated under reduced pressure to give the title compound as a white solid (8 mg, 62%). The disodium salt was prepared according to the procedure of Example 1D using two equivalents of sodium hydroxide. $^1$H NMR (300 MHz, DMSO-d$_6$) δ ppm 0.99 (d, J=6.62 Hz, 6 H) 1.58 (m, 2 H) 1.70 (m, 1 H) 3.17 (s, 1 H) 4.49 (m, 2 H) 4.88 (s, 2 H) 7.36 (m, 2 H) 7.49 (m, 1 H) 7.70 (d, J=9.56 Hz, 1 H) 8.56 (dd, J=7.91, 1.65 Hz, 1 H) 8.88 (d, J=2.94 Hz, 1 H). (ESI−) m/z 485 (M−H)$^−$.

EXAMPLE 198

3-[7-(2-aminoethoxy)-1,1-dioxido-4H-1,2,4-benzothiadiazin-3-yl]-4-hydroxy-1-(3-methylbutyl)-1,8-naphthyridin-2(1H)-one A solution of the product of Example 185 (21.8 mg, 62%). in anhydrous tetrahydrofuran (0.5 mL) was treated with LiBH4 (10 mg, 0.46 mmol), stirred at ambient temperature for 16 hours, diluted with water (30 mL) and extracted with ethyl acetate (2×30 mL). The combined organic layers were washed with water, brine and dried over anhydrous magnesium sulfate. The slurry was filtered and the solvent removed under reduced pressure yielding the title compound as a yellow solid (10.1 mg, 97%). The sodium salt of the title compound was prepared according to the procedure of Example 1D. $^1$H NMR (300 MHz, DMSO-d$_6$) δ ppm 0.96 (d, J=6.62 Hz, 6 H) 1.48 (m, 2 H) 1.64 (m, 1 H) 2.82 (m, 2 H) 4.13 (t, J=5.33 Hz, 2 H) 4.29 (m, 2 H) 5.40 (m, 2 H) 7.17 (m, 4 H) 8.36 (dd, J=7.72, 1.84 Hz, 1 H) 8.52 (dd, J=4.60, 2.02 Hz, 1 H) 15.88 (s, 1 H). (ESI−) m/z 470 (M−H)$^−$.

EXAMPLE 199

2-({3-[4-hydroxy-1-(3-methylbutyl)-2-oxo-1,2-dihydro-1,8-naphthyridin-3-yl]-1,1-dioxido-4H-1,2,4-benzothiadiazin-7-yl}oxy)-N-methylacetamide A mixture of Example 197 (4.7 mg, 0.0097 mmol), 1-(3-dimethylaminopropyl)-3-ethylcarbodiimide hydrochloride (1.4 mg, 0.01 mmol), methylamine in tetrahydrofuran (2.0 M, 10 µL, 0.02 mmol) and 1-hydroxybenzotriazole (1.4 mg, 0.01 mmol) in N,N-dimethylformamide (0.2 mL) was stirred at 25° C. for 5 hours. The reaction mixture was diluted with ethyl acetate (40 mL), washed with saturated sodium bicarbonate, water and brine, and dried over anhydrous magnesium sulfate. The drying agent was removed by filtration and the solvent removed under reduced pressure to give the title compound as a pale yellow solid (4 mg, 83%). The sodium salt of the title compound was prepared according to the procedure of Example 1D. $^1$H NMR (300 MHz, DMSO-d$_6$) δ ppm 0.96 (d, J=6.62 Hz, 6 H) 1.47 (m, 2 H) 1.64 (m, 1 H) 2.67 (d, J=4.78 Hz, 3 H) 4.30 (m, 2 H) 4.53 (s, 2 H) 7.18 (m, 4 H) 8.11 (m, 1 H) 8.36 (dd, J=7.54, 2.02 Hz, 1 H) 8.52 (dd, J=4.78, 1.84 Hz, 1 H) 15.90 (s, 1 H). (ESI−) m/z 498 (M−H)$^−$.

EXAMPLE 200

3-[4-hydroxy-1-(3-methylbutyl)-2-oxo-1,2-dihydro-1,8-naphthyridin-3-yl]-1,1-dioxido-4H-1,2,4-benzothiadiazin-7-yl acetate A mixture of Example 184 (30 mg, 0.07 mmol), triethylamine (12 µL, 0.084 mmol) and acetic anhydride (8 µL, 0.084 mmol) in anhydrous dichloromethane (1 mL) was stirred at 25° C. for 16 hours. The reaction mixture was diluted with ethyl acetate and water, acidified to pH 5 with acetic acid and partitioned. The aqueous layer was extracted with ethyl acetate (2×20 mL). The combined organic extracts were washed with saturated sodium bicarbonate, water, brine, dried over anhydrous magnesium sulfate, filtered, and the solvent removed under reduced pressure to give the title compound as a white solid (29.5 mg, 89%). $^1$H NMR (300 MHz, DMSO-d$_6$) δ ppm 0.98 (d, J=6.25 Hz, 6 H) 1.56 (m, 2 H) 1.69 (m, 1 H) 2.30 (s, 3 H) 4.46 (m, 2 H) 7.44 (m, 1 H) 7.52 (d, J=8.82 Hz, 1 H) 7.72 (m, 2 H) 8.53 (dd, J=7.72, 1.47 Hz, 1 H) 8.83 (s, 1 H). (ESI−) m/z 469 (M−H)$^−$.

EXAMPLE 201

3-[1,1-dioxido-7-(pyridin-2-yloxy)-4H-1,2,4-benzothiadiazin-3-yl]-4-hydroxy-1-(3-methylbutyl)-1,8-naphthyridin-2(1H)-one The product of Example 184 (10 mg, 0.023 mmol) was reacted with 2-bromopyridine (2.4 µL, 0.025 mmol), cesium carbonate (15 mg, 0.046 mmol) and copper metal (40 mg) in dimethylsulfoxide (0.1 mL) at 110° C. in a microwave reactor for 2 hours. The mixture was cooled to 25° C., poured into water (20 mL) and extracted with ethyl acetate (2×20 mL). The combined organic extracts were washed with brine, dried over anhydrous magnesium sulfate, filtered, and the solvent removed under reduced pressure leaving a tan solid. The solid was chromatographed on silica gel, eluting first with methylene chloride, then 1% methanol in methylene chloride gave the title compound as a light brown solid (5 mg, 42%). The sodium salt of the title compound was prepared according to the procedure of Example 1D. $^1$H NMR (300 MHz, DMSO-d$_6$) δ ppm 0.96 (s, 3H) 0.98 (s, 3 H) 1.48 (m, 2 H) 1.65 (m, 1 H) 4.30 (t, J=7.50 Hz, 2 H) 7.14 (m, 3 H) 7.35 (s, 3 H) 7.89 (m, 1 H) 8.17 (m, 1 H) 8.38 (dd, J=7.72, 2.21 Hz, 1 H) 8.53 (dd, J=4.78, 1.84 Hz, 1 H) 16.07 (s, 1 H). (ESI−) m/z 504 (M−H)$^−$.

EXAMPLE 202

3-[1,1-dioxido-7-(pyrimidin-2-yloxy)-4H-1,2,4-benzothiadiazin-3-yl]-4-hydroxy-1-(3-methylbutyl)-1,8-naphthyridin-2(1H)-one The product of Example 184 (10 mg, 0.023 mmole) was reacted with 2-bromopyrimidine (4.5 mg, 0.028 mmole), cesium carbonate (15 mg, 0.046 mmole) and tetrabutylammonium iodide (1 mg) in dimethylsulfoxide (0.1 mL) in a microwave reaction apparatus at 110° C. for 1 hour. The mixture was cooled to 25° C., poured into water (20 mL) and extracted with ethyl acetate (2×50 mL). The combined organic extracts were washed with brine, dried over anhydrous magnesium sulfate, filtered and the solvent removed under reduced pressure leaving a tan solid. The solid was chromatographed on silica gel, eluting first with methylene chloride, followed by 2% methanol in methylene chloride, affording the title compound as a white solid (6 mg, 51%). The sodium salt of the title compound was prepared according to the procedure as described in Example 1D. $^1$H NMR (300 MHz, DMSO-d$_6$) δ ppm 0.96 (s, 3 H) 0.98 (s, 3 H) 1.48 (m, 2 H) 1.65 (m, 1 H) 4.30 (t, J=7.50 Hz, 2 H) 7.14 (dd, J=7.54, 4.60 Hz, 1 H) 7.30 (t, J=4.78 Hz, 1 H) 7.42 (m, 3 H) 8.38 (dd, J=7.72, 1.84 Hz, 1 H) 8.54 (dd, J=4.78, 1.84 Hz, 1 H) 8.67 (s, 1 H) 8.68 (s, 1 H) 16.10 (s, 1 H). (ESI-)$^-$. m/z 505 (M–H)$^-$.

EXAMPLE 203

2-({3-[4-hydroxy-1-(3-methylbutyl)-2-oxo-1,2-dihydro-1,8-naphthyridin-3-yl]-1,1-dioxido-4H-1,2,4-benzothiadiazin-7-yl}oxy)-N,N-dimethylacetamide The title compound was prepared according to the procedure of Example 185 substituting 2-chloro-N,N-dimethylacetamide for 2-bromoacetonitrile. The compound was purified by trituration with methanol. The sodium salt of the title compound was prepared according to the procedure of Example 1D. $^1$H NMR (300 MHz, DMSO-d$_6$) δ ppm 0.96 (d, J=6.62 Hz, 6 H) 1.47 (m, 2 H) 1.64 (m, 1 H) 2.86 (s, 3 H) 3.01 (s, 3 H) 4.30 (m, 2 H) 4.90 (s, 2 H) 7.16 (m, 4 H) 8.36 (dd, J=7.72, 1.84 Hz, 1 H) 8.52 (d, J=4.78 Hz, 1 H) 15.86 (s, 1 H). (ESI-) m/z 512 (M–H)$^-$.

EXAMPLE 204

4-hydroxy-1-(3-methylbutyl)-3-(7-nitro-1,1-dioxido-4H-1,2,4-benzothiadiazin-3-yl)-1,8-naphthyridin-2(1H)-one The product of Example 12B (0.229 g, 0.56 mmol) at 0° C. was reacted with ammonium nitrate (0.058 g, 0.72 mmol) in concentrated sulfuric acid (1.5 mL), stirred at 0° C. for 30 minutes. The reaction mixture was poured onto crushed ice and the pH was adjusted to 9 with aqueous sodium hydroxide. The resulting solid was isolated by filtration to give the title compound (0.21 g, 81%). The sodium salt of the title compound was prepared according to the procedure of Example 1D. (ESI-) m/z 456 (M–H)$^-$. $^1$H NMR (300 MHz, DMSO-d$_6$) δ ppm 0.96 (d, J=6.62 Hz, 6 H) 1.47 (m, 2 H) 1.64 (m, 1 H) 4.29 (m, 2 H) 7.14 (m, 1 H) 7.52 (m, 1 H) 8.40 (m, 3 H) 8.54 (m, 1 H) 16.77 (s, 1 H).

EXAMPLE 205 RZ 3-(7-amino-1,1-dioxido-4H-1,2,4-benzothiadiazin-3-yl)-4-hydroxy-1-(3-methylbutyl)-1,8-naphthyridin-2(1H)-one A mixture of the product of Example 204 (0.198 g, 0.43 mmol), iron powder (0.121 g, 2.16 mmol), and NH$_4$Cl (0.031 g, 0.58 mmol) in methanol:tetrahydrofuran:water (3:3:1,7 mL) was stirred at reflux for nine hour. The reaction mixture was cooled to 25° C. and the iron was removed by filtration and washed with methanol. The filtrate was concentrated under reduced pressure, diluted with water and extracted with ethyl acetate. The organic layer was washed with water, brine and dried over anhydrous magnesium sulfate filtered and concentrated under reduced pressure to give the title compound as a yellow solid (0.121 g, 66%). (ESI-) m/z 426 (M–H)$^-$. $^1$H NMR (300 MHz, DMSO-d$_6$) δ ppm 0.98 (d, J=6.62 Hz, 6 H) 1.58 (m, 2 H) 1.69 (m, 1 H) 4.46 (m, 2 H) 5.86 (s, 2 H) 6.96 (m, 2 H) 7.46 (m, 2 H) 8.52 (d, J=6.99 Hz, 1 H) 8.84 (m, 1 H) 13.90 (s, 1 H).

EXAMPLE 206

({3-[4-hydroxy-1-(3-methylbutyl)-2-oxo-1,2-dihydro-1,8-naphthyridin-3-yl]-1,1-dioxido-4H-1,2,4-benzothiadiazin-7-yl}amino)acetonitrile To the solution of the product from Example 205 (10 mg, 0.023 mmol) in N,N-dimethylformamide (0.2 mL) was added bromoacetonitrile (2.5 μL, 0.035 mmol) and potassium carbonate (5 mg, 0.035 mmol). The mixture was stirred while heating at 100° C. in a microwave reactor for 1 h. After cooling to 25° C., the orange solution was diluted with water and the pH of the aqueous layer was adjusted to pH 5 with acetic acid. The aqueous layer was extracted with ethyl acetate (3×20 mL). The combined organic layer was washed with water and brine, dried over magnesium sulfate, filtered, concentrated and purified by flash column chromatography on silica gel eluting with 1% methanol/dichloromethane to give the title compound as a yellow solid (6.0 mg, 55%). MS (ESI-) m/z 465 (M–H)$^-$. $^1$H NMR (300 MHz, DMSO-d$_6$) δ ppm 0.99 (d, J=6.62 Hz, 6 H) 1.58 (m, 2 H) 1.68 (m, 1 H) 4.46 (m, 4 H) 6.92 (m, 1 H) 7.16 (m, 2 H) 7.49 (m, 1 H) 7.61 (d, J=9.19 Hz, 1 H) 8.56 (dd, J=7.90, 1.65 Hz, 1 H) 8.89 (m, 1 H) 14.00 (br s, 1 H) 15.39 (br s, 1 H). The sodium salt of the title compound was prepared according to the procedure of Example 1D. $^1$H NMR (300 MHz, DMSO-d$_6$) δ ppm 0.96 (d, J=6.62 Hz, 6 H) 1.48 (m, 2 H) 1.64 (m, 1 H) 4.31 (m, 4 H) 6.49 (t, J=6.62 Hz, 1 H) 6.99 (m, 2 H) 7.13 (m, 2 H) 8.35 (dd, J=7.72, 1.84 Hz, 1 H) 8.51 (dd, J=4.41, 1.84 Hz, 1 H) 15.73 (s, 1 H).

EXAMPLE 207

7-hydroxy-6-(7-methoxy-1,1-dioxido-4H-1,2,4-benzothiadiazin-3-yl)-4-(3-methylbutyl)thieno[3,2-b]pyridin-5(4H)-one The title compound was prepared according to the procedure of Example 1D substituting the product of Example 125A for the product of Example 1B and substituting the product of Example 183B for the product of Example 1C. The sodium salt was prepared according to the procedure of example 1D. $^1$H NMR (300 MHz, DMSO-d$_6$) δ ppm 0.96 (d, J=6.62 Hz, 6 H) 1.44 (m, 2 H) 1.66 (m, 1 H) 3.81 (s, 3 H) 3.99 (m, 2 H) 7.09 (m, 2 H) 7.16 (m, 2 H) 7.79 (d, J=5.15 Hz, 1 H) 15.87 (s, 1 H). (ESI-) m/z 446 (M–H)$^-$.

EXAMPLE 208

4-benzyl-7-hydroxy-6-(7-methoxy-1,1-dioxido-4H-1,2,4-benzothiadiazin-3-yl)thieno[3,2-b]pyridin-5(4H)-one The title compound was prepared according to the procedure of Example 1D substituting the product of Example 110B for the product of Example 1B and substituting the product of Example 183B for the product of Example 1C. The sodium salt was prepared according to the procedure of Example 1D. $^1$H NMR (300 MHz, DMSO-d$_6$) δ ppm 3.81 (s, 3 H) 5.26 (s, 2 H) 7.02 (d, J=5.15 Hz, 1 H) 7.11 (m, 1 H) 7.17 (m, 2 H) 7.24 (m, 5 H) 7.71 (d, J=5.15 Hz, 1 H) 15.80 (s, 1 H). (ESI–) m/z 466 (M–H)$^-$.

EXAMPLE 209A 2-amino-6-methoxy-3-methylbenzenesulfonamide

The title compound was prepared from 3-methoxy-6-methyl-aniline using the procedure described in *JCS Perkin* 1, 1979, 1043.

EXAMPLE 209B

N-[2-(aminosulfonyl)-3-methoxy-6-methylphenyl]-1-benzyl-4-hydroxy-2-oxo-1,2-dihydro-1,8-naphthyridine-3-carboxamide The title compound was prepared according to the procedure of Example 84C substituting the product of Example 209A for product of Example 84A to give the title compound (0.22 g, 100%).

EXAMPLE 209C 1-benzyl-3-(8-methoxy-5-methyl-1,1-dioxido-4H-1,2,4-benzothiadiazin-3-yl)-4-hydroxy-1,8-naphthyridin-2(1H)-one The title compound was prepared according to the procedure of Example 84D substituting the product of Example 209B for the product of Example 84C. The solution was then acidified with 6N aqueous HCl (10 mL), filtered and the solid washed with methanol (10 mL) to give the title compound as a white solid, (0.12 g, 56% yield). MS (ESI–) m/z 477 (M–H)$^+$. The sodium salt of the title compound was prepared according to the procedure of Example 1D. $^1$H NMR (300 MHz, DMSO-d$_6$) δ 2.37 (s, 3 H) 3.83 (s, 3 H) 5.52 (s, 2 H) 6.76 (d, J=8.5 Hz, 1 H) 7.16 (m, 2 H) 7.23 (m, 4 H) 7.37 (d, J=8.9 Hz, 1 H) 8.45 (m, 2 H), 15.67 (s, 1 H).

EXAMPLE 210

1-benzyl-3-(8-hydroxy-5-methyl-1,1-dioxido-4H-1,2,4-benzothiadiazin-3-yl)-4-hydroxy-1,8-naphthyridin-2(1H)-one A mixture of the product of Example 209C (20 mg, 0.042 mmol) and boron tribromide (1.0M in dichloromethane) (840 µL, 0.84 mmol) in dichloroethane (5 mL) was stirred at 70° C. for 16 hrs. The reaction mixture was cooled to 25° C., quenched with water (10 mL) and extracted with ethyl acetate (20 mL). The resulting organic layer was dried over MgSO$_4$, filtered, and concentrated under reduced pressure to provide the title compound as a white solid (0.019 g, 98% yield). MS (ESI–) m/z 463 (M–H)$^-$. The disodium salt of the title compound was prepared according to the procedure of Example 1D using two equivalents of sodium hydroxide. $^1$H NMR (300 MHz, DMSO-d$_6$) δ 2.16 (s, 3 H) 5.52 (s, 2 H) 5.92 (d, J=8.8 Hz, 1 H) 6.79 (d, J=8.8 Hz, 1 H) 7.11 (dd, J=7.8, 4.8 Hz, 1 H) 7.17 (m, 1 H) 7.23 (m, 4 H) 8.42 (m, 2 H), 14.77 (s, 1 H).

EXAMPLE 211

{[3-(1-benzyl-4-hydroxy-2-oxo-1,2-dihydro-1,8-naphthyridin-3-yl)-5-methyl-1,1-dioxido-4H-1,2,4-benzothiadiazin-8-yl]oxy}acetonitrile A mixture of the product of Example 210 (23 mg, 0.050 mmol), bromoacetonitrile (14 µL, 0.2 mmol) and potassium carbonate (15 mg, 0.11 mmol) in N,N-dimethylformamide (1 mL) was stirred at 25° C. for 3 days. The reaction mixture was concentrated under reduced pressure and the resulting oil was chromatographed on silica gel eluting with ethyl acetate to provide the title compound as a white solid (0.003 g, 12% yield). MS (ESI–) m/z 500 (M–H)$^-$. The sodium salt of the title compound was prepared according to the procedure of Example 1D. $^1$H NMR (300 MHz, DMSO-d$_6$) δ 2.38 (s, 3 H) 5.25 (m, 2H) 5.54 (s, 2 H) 6.93 (m, 1 H) 7.18 (m, 2 H) 7.23 (m, 4 H) 7.37 (m, 1 H) 8.46 (m, 2H).

EXAMPLE 212A 2-amino-3-methoxybenzenesulfonamide

The title compound was prepared from 2-methoxyaniline using the procedure as described in *Journal of the Chemical Society, Perkin* 1, 1979, 1043.

EXAMPLE 212B

Ethyl (5-methoxy-1,1-dioxido-4H-1,2,4-benzothiadiazin-3-yl)acetate

The title compound was prepared according to the procedure of Example 1C substituting the product of Example 212A for 2-aminobenzenesulfonamide. MS (DCI) m/z 299 (M+H)$^+$.

EXAMPLE 212C

1-Benzyl-4-hydroxy-3-(5-methoxy-1,1-dioxido-4H-1,2,4-benzothiadiazin-3-yl)-1,8-naphthyridin-2(1H)-one The title compound was prepared according to the procedure as described in Example 1D substituting the product of Example 15A for the product of Example 1B and substituting the product of Example 212B for the product of Example 1C (187 mg, 41%). The sodium salt of the title compound was prepared according to the procedure of Example 1D. (ESI–) m/z 461 (M–H)$^-$. $^1$H NMR (300 MHz, DMSO-d$_6$) δ ppm 3.98 (s, 3 H) 5.52 (s, 2 H) 7.18 (m, 9 H) 8.42 (dd, J=7.54, 2.02 Hz, 1 H) 8.47 (dd, J=4.78, 1.84 Hz, 1 H) 15.71 (s, 1 H).

EXAMPLE 213

1-Benzyl-4-hydroxy-3-(5-hydroxy-1,1-dioxido-4H-1,2,4-benzothiadiazin-3-yl)-1,8-naphthyridin-2(1H)-one The title compound was prepared according to the procedure as described in Example 184 substituting the product of Example 212C for the product of Example 183C. (ESI–) m/z 447 (M–H)$^-$. The disodium salt of the title compound was prepared according to the procedure of Example 1D using two equivalents of sodium hydroxide. $^1$H NMR (300 MHz, DMSO-d$_6$) δ ppm 5.53 (s, 2 H) 6.25 (m, 2 H) 6.76 (t, J=7.91 Hz, 1 H) 7.17 (m, 6 H) 8.42 (dd, J=4.78, 1.84 Hz, 1 H) 8.48 (dd, J=7.54, 2.02 Hz, 1 H).

EXAMPLE 214A {[3-(1-benzyl-4-hydroxy-2-oxo-1,2-dihydro-1,8-naphthyridin-3-yl)-1,1-dioxido-4H-1,2,4-benzothiadiazin-5-yl]oxy}acetonitrile The title compound was prepared according to the procedure as described in Example 185 substituting the product of Example 213 for the product of Example 184. (ESI−) m/z 486 (M−H)$^−$. $^1$H NMR (300 MHz, DMSO-d$_6$) δ ppm 5.51 (s, 2 H) 5.72 (s, 2 H) 7.24 (m, 1 H) 7.28 (s, 1 H) 7.31 (m, 5 H) 7.51 (dd, J=7.91, 4.60 Hz, 1 H) 7.61 (m, 1 H) 8.61 (dd, J=7.72, 1.84 Hz, 1 H) 8.83 (m, 1 H) 14.52 (s, 1 H).

EXAMPLE 214B

3-[5-(2-aminoethoxy)-1,1-dioxido-4H-1,2,4-benzothiadiazin-3-yl]-1-benzyl-4-hydroxy-1,8-naphthyridin-2(1H)-one The title compound was prepared according to the procedure as described in Example 198 substituting the product of Example 214A for the product of Example 185. (ESI−) m/z 490 (M−H)$^−$. The sodium salt of the title compound was prepared according to the procedure of Example 1D. $^1$H NMR (300 MHz, DMSO-d$_6$) δ ppm 3.06 (s, br, 2 H) 4.30 (t, J=4.78 Hz, 2 H) 5.54 (s, 2 H) 5.72 (s, br, 2 H) 7.20 (m, 9 H) 8.50 (dd, J=4.78, 1.84 Hz, 1 H) 8.69 (dd, J=7.72, 2.21 Hz, 1 H) 16.05 (s, 1 H).

EXAMPLE 215

2-{[3-(1-benzyl-4-hydroxy-2-oxo-1,2-dihydro-1,8-naphthyridin-3-yl)-1,1-dioxido-4H-1,2,4-benzothiadiazin-5-yl]oxy}acetamide The title compound was prepared according to the procedure as described in Example 190 substituting the product of Example 213 for the product of Example 184. (ESI−) m/z 504 (M−H)$^−$. The sodium salt of the title compound was prepared according to the procedure of Example 1D. $^1$H NMR (300 MHz, DMSO-d$_6$) δ ppm 4.64 (s, 2 H) 5.53 (s, 2 H) 7.22 (m, 9 H) 7.88 (s, 1 H) 8.13 (s, 1 H) 8.46 (dd, J=7.72, 1.84 Hz, 1 H) 8.51 (dd, J=4.78, 1.84 Hz, 1 H) 16.15 (s, 1 H).

EXAMPLE 216

1-benzyl-4-hydroxy-3-{5-[(4-nitrobenzyl)oxy]-1,1-dioxido-4H-1,2,4-benzothiadiazin-3-yl}-1,8-naphthyridin-2(1H)-one The title compound was prepared according to the procedure as described in Example 185 substituting the product of Example 213 for the product of Example 184 and substituting para-nitrobenzyl bromide for 2-bromoacetonitrile. (ESI−) m/z 582 (M−H)$^−$. The sodium salt of the title compound was prepared according to the procedure of Example 1D. $^1$H NMR (300 MHz, DMSO-d$_6$) δ ppm 5.54 (s, 2 H) 5.55 (s, 2 H) 7.26 (m, 9 H) 8.08 (s, 1 H) 8.11 (s, 1 H) 8.28 (s, 1 H) 8.31 (s, 1 H) 8.48 (q, J=2.08 Hz, 1 H) 8.50 (s, 1 H) 16.01 (s, 1 H).

EXAMPLE 217A

N-[2-(aminosulfonyl)phenyl]-1-benzyl-6-chloro-4-hydroxy-2-oxo-1,2-dihydro-1,8-naphthyridine-3-carboxamide The title compound was prepared according to the procedure of Example 84C substituting ethyl 1-benzyl-6-chloro-4-hydroxy-2-oxo-1,2-dihydro-1,8-naphthyridine-3-carboxylate for the product of Example 84B and substituting 2-amino-benzenesulfonamide for the product of Example 84A. $^1$H NMR (300 MHz, DMSO-d$_6$) δ ppm 5.64 (s, 2 H) 7.25 (m, 5 H) 7.44 (t, J=7.72 Hz, 1 H) 7.52 (s, 2 H) 7.67 (m, 1 H) 7.93 (m, 2 H) 8.56 (d, J=2.57 Hz, 1 H) 8.87 (d, J=2.57 Hz, 1 H) 12.34 (s, 1 H) 16.76 (s, 1 H).

EXAMPLE 217B

1-Benzyl-6-chloro-3-(1,1-dioxido-4H-1,2,4-benzothiadiazin-3-yl)-4-hydroxy-1,8-naphthyridin-2(1H)-one The title compound was prepared according to the procedure of Example 84D substituting the product of Example 217A for the product of Example 84C. The sodium salt of the title compound was prepared according to the procedure as described in Example 1D. MS (DCI/NH$_3$) m/z 465 (M+H)$^+$, 483 (M+NH$_3$)$^+$. $^1$H NMR (300 MHz, DMSO-d$_6$) δ ppm 5.49 (s, 2 H) 7.17 (m, 6 H) 7.48 (t, J=7.35 Hz, 1 H) 7.83 (dd, J=7.72, 1.47 Hz, 1 H) 8.32 (d, J=2.57 Hz, 1 H) 8.46 (m, 2 H) 11.20 (s, 1 H).

EXAMPLE 218A

N-[2-(aminosulfonyl)phenyl]-1-benzyl-4-hydroxy-2-oxo-6-phenyl-1,2-dihydro-1,8-naphthyridine-3-carboxamide The title compound was prepared according to the procedure of Example 84C substituting ethyl 1-benzyl-6-phenyl-4-hydroxy-2-oxo-1,2-dihydro-1,8-naphthyridine-3-carboxylate for the product of Example 84B and substituting 2-amino-benzenesulfonamide for the product of Example 84A. $^1$H NMR (300 MHz, DMSO-d$_6$) δ ppm 5.72 (s, 2 H) 7.28 (m, 6 H) 7.44 (m, 2 H) 7.54 (m, 3 H) 7.67 (m, 1 H) 7.85 (d, J=6.99 Hz, 2 H) 7.92 (dd, J=8.09, 1.47 Hz, 1 H) 7.99 (d, J=8.09 Hz, 1 H) 8.70 (d, J=2.21 Hz, 1 H) 9.17 (d, J=2.21 Hz, 1 H) 12.41 (s, 1 H) 16.80 (s, 1 H).

EXAMPLE 218B 1-benzyl-3-(1,1-dioxido-4H-1,2,4-benzothiadiazin-3-yl)-4-hydroxy-6-phenyl-1,8-naphthyridin-2(1H)-one The title compound was prepared according to the procedure of Example 84D substituting the product of Example 218A for the product of Example 84C. MS (ESI−) m/z 507 (M−H)$^−$. The sodium salt of the title compound was prepared to the procedure as described in Example 1D. $^1$H NMR (300 MHz, DMSO-d$_6$) δ ppm 5.53 (s, 2 H) 7.04 (m, 2 H) 7.26 (m, 7 H) 7.48 (t, J=7.54 Hz, 2 H) 7.58 (d, J=8.09 Hz, 1 H) 7.70 (d, J=7.35 Hz, 2 H) 8.51 (d, J=2.21 Hz, 1 H) 8.65 (d, J=2.57 Hz, 1 H)

EXAMPLE 219A 2-amino-4-methoxybenzenesulfonamide

The title compound was prepared according to the procedure as described in Topliss et al, J. Med. Chem. 6, 1963, 122.

EXAMPLE 219B

Ethyl (6-methoxy-1,1-dioxido-4H-1,2,4-benzothiadiazin-3-yl)acetate

The title compound was prepared according to the procedure of Example 1C substituting the product of Example 219A for 2-aminobenzenesulfonamide. MS (DCI) m/z 299 $(M+H)^+$.

EXAMPLE 219C 1-benzyl-4-hydroxy-3-(6-methoxy-1,1-dioxido-4H-1,2,4-benzothiadiazin-3-yl)-1,8-naphthyridin-2(1H)-one The title compound was prepared according to the procedure as described in Example 1D substituting the product of Example 15A for the product of Example 1B and substituting the product of Example 219B for the product of Example 1C. The sodium salt of the title compound was prepared according to the procedure of Example 1D. MS (ESI−) m/z 461 $(M-H)^-$. $^1H$ NMR (300 MHz, DMSO-$d_6$) δ ppm 3.90 (m, 3 H) 5.72 (s, 2 H) 7.08 (dd, J=8.82, 2.21 Hz, 1 H) 7.26 (m, 6 H) 7.51 (dd, J=8.09, 4.78 Hz, 1 H) 7.82 (d, J=9.19 Hz, 1 H) 8.61 (dd, J=8.09, 1.84 Hz, 1 H) 8.83 (dd, J=4.60, 2.02 Hz, 1 H) 13.97 (s, 1 H).

EXAMPLE 220A

N-[3-amino-4-(aminosulfonyl)phenyl]acetamide

The title compound was prepared according to the procedure as described in Topliss et al, J. Med. Chem. 6, 1963, 122.

EXAMPLE 220B

Ethyl [6-(acetylamino)-1,1-dioxido-4H-1,2,4-benzothiadiazin-3-yl]acetate

The title compound was prepared according to the procedure as described in Example 1C substituting the product of Example 220A for 2-aminobenzenesulfonamide. MS(DCI) m/z 326 $(M+H)^+$.

EXAMPLE 220C

N-[3-(1-benzyl-4-hydroxy-2-oxo-1,2-dihydro-1,8-naphthyridin-3-yl)-1,1-dioxido-4H-1,2,4-benzothiadiazin-6-yl]acetamide The title compound was prepared according to the procedure as described in Example 1D substituting the product of Example 15A for the product of Example 1B and substituting the product of Example 220B for the product of Example 1C. The sodium salt of the title compound was prepared according to the procedure of Example 1D. $^1H$ NMR (300 MHz, DMSO-$d_6$) δ ppm 6.82 (d, J=1.84 Hz, 2 H) 6.95 (dd, J=8.64, 2.02 Hz, 2 H) 7.29 (d, J=4.04 Hz, 1 H) 7.44 (dd, J=8.09, 4.78 Hz, 2 H) 7.74 (m, 2 H) 8.47 (m, 1 H) 8.78 (m, 1 H) 10.81 (s, 1 H) 12.86 (s, 1 H) 14.06 (s, 1 H). MS (ESI−) m/z 447 $(M-H)^-$.

EXAMPLE 221

1-benzyl-4-hydroxy-3-(6-hydroxy-1,1-dioxido-4H-1,2,4-benzothiadiazin-3-yl)-1,8-naphthyridin-2(1H)-one A mixture of the product of Example 219C (20 mg, 0.043 mmole) and boron tribromide (1.0 M in dichloromethane, 20 equivalents) in 1,2 dichloroethane (5 mL) was stirred at reflux for 28 hours. The reaction mixture was cooled to 25° C., diluted with tetrahydrofuran and aqueous 1N HCl, and refluxed for 2 hours. The resulting solid was collected by filtration and dried to give the title compound (11.3 mg). The disodium salt of the title compound was prepared according to the procedure of Example 1D using two equivalents of sodium hydroxide. MS (ESI−) m/z 447 $(M-H)^-$. $^1H$ NMR (300 MHz, DMSO-$d_6$) δ ppm 6.82 (d, J=1.84 Hz, 2 H) 6.95 (dd, J=8.64, 2.02 Hz, 2 H) 7.29 (d, J=4.04 Hz, 1 H) 7.44 (dd, J=8.09, 4.78 Hz, 2 H) 7.74 (m, 2 H) 8.47 (m, 1 H) 8.78 (m, 1 H) 10.81 (s, 1 H) 12.86 (s, 1 H) 14.06 (s, 1 H).

EXAMPLE 222A 2-amino-6-methylbenzenesulfonamide

The title compound was prepared according to the procedure as described in Topliss et al, J. Med. Chem. 6, 1963, 122.

EXAMPLE 222B

Ethyl (8-methyl-1,1-dioxido-4H-1,2,4-benzothiadiazin-3-yl)acetate

The title compound was prepared according to the procedure of Example 1C substituting the product of Example 222A for 2-aminobenzenesulfonamide.

EXAMPLE 222C 1-benzyl-4-hydroxy-3-(8-methyl-1,1-dioxido-4H-1,2,4-benzothiadiazin-3-yl)-1,8-naphthyridin-2(1H)-one The title compound was prepared according to the procedure as described in Example 1D substituting the product of Example 15A for the product of Example 1B and substituting the product of Example 222B for the product of Example 1C. (35.8 mg, 10%). The sodium salt of the title compound was prepared according to the procedure of Example 1D. MS (ESI−) m/z 446 $(M-H)^-$. $^1H$ NMR (300 MHz, DMSO-$d_6$) δ ppm 2.56 (s, 3 H) 5.52 (s, 2 H) 7.06 (dd, J=7.72, 3.31 Hz, 2 H) 7.13 (m, 2 H) 7.23 (m, 4 H) 7.41 (t, J=7.72 Hz, 2 H) 8.39 (d, J=1.84 Hz, 1 H) 8.48 (dd, J=4.60, 2.02 Hz, 1 H) 15.70 (s, 1 H).

EXAMPLE 223

4-hydroxy-3-(5-methoxy-1,1-dioxido-4H-1,2,4-benzothiadiazin-3-yl)-1-(3-methylbutyl)-1,8-naphthyridin-2(1H)-one The title compound was prepared according to the procedure of Example 1D substituting the product of Example 12A for the product of Example 1B and substituting the product of Example 212B for the product of Example 1C. The sodium salt of the title compound was prepared according to the procedure of Example 1D. MS (ESI–) m/z 441 (M–H)⁻. $^1$H NMR (300 MHz, DMSO-$d_6$) δ ppm 0.95 (s, 3 H) 0.98 (s, 3 H) 1.47 (m, 2 H) 1.64 (m, 1 H) 3.98 (s, 3 H) 4.29 (t, J=7.50 Hz, 2 H) 7.11 (dd, J=7.72, 4.78 Hz, 1 H) 7.23 (m, 3 H) 8.38 (dd, J=7.35, 1.84 Hz, 1 H) 8.51 (dd, J=4.41, 1.84 Hz, 1 H) 15.80 (s, 1 H).

EXAMPLE 224

7-hydroxy-6-(5-methoxy-1,1-dioxido-4H-1,2,4-benzothiadiazin-3-yl)-4-(3-methylbutyl)thieno[3,2-b]pyridin-5(4H)-one The title compound was prepared according to the procedure of Example 1D substituting the product of Example 125A for the product of Example 1B and substituting the product of Example 212B for the product of Example 1C. The sodium salt of the title compound was prepared according to the procedure as described in Example 1D. (ESI–) m/z 446 (M–H)⁻. $^1$H NMR (300 MHz, DMSO-$d_6$) δ ppm 0.95 (s, 3 H) 0.97 (s, 3 H) 1.44 (m, 2 H) 1.67 (m, 1 H) 3.99 (m, 5 H) 7.08 (d, J=5.52 Hz, 1 H) 7.19 (m, 3 H) 7.79 (d, J=5.15 Hz, 1 H) 15.75 (s, 1 H).

EXAMPLE 225

4-Benzyl-7-hydroxy-6-(5-methoxy-1,1-dioxido-4H-1,2,4-benzothiadiazin-3-yl)thieno[3,2-b]pyridin-5(4H)-one The title compound was prepared according to the procedure of Example 1D substituting the product of Example 110B for the product of Example 1B and substituting the product of Example 212B for the product of Example 1C. The sodium salt of the title compound was prepared according to the procedure of Example 1D. $^1$H NMR (300 MHz, DMSO-$d_6$) δ ppm 3.97 (s, 3 H) 5.26 (s, 2 H) 7.01 (d, J=5.52 Hz, 1 H) 7.25 (m, 8 H) 7.70 (d, J=5.52 Hz, 1 H) 15.69 (s, 1 H). MS (ESI–) m/z 466 (M–H)⁻.

EXAMPLE 226A methyl 2-[2-benzylidenehydrazino]benzoate 2-(N'-Benzylidene-hydrazino)-benzoic acid (5.0 g, 20.81 mmol) in 1:1 tetrahydrofuran and methanol (50 mL) was reacted with a solution of trimethylsilyl diazomethane in hexanes (2.0M, 12 mL, 25.0 mmol) at 0° C. for 1 hour then stirred at 25° C. for 48 hours. The solvent was removed under vacuum to give the title compound as a solid (6.00 g, 100%). $^1$H NMR (300 MHz, DMSO-$d_6$) δ ppm 3.87 (s, 3 H) 6.84 (td, J=7.54, 1.10 Hz, 1 H) 7.41 (m, 3 H) 7.54 (m, 1 H) 7.74 (m, 3 H) 7.86 (dd, J=8.09, 1.47 Hz, 1 H) 8.21 (s, 1 H) 11.02 (s, 1 H).

EXAMPLE 226B methyl 2-[2-benzylidene-1-(3-ethoxy-3-oxopropanoyl)hydrazino]benzoate The product of Example 226A (5.29 g, 20.81 mmol) in toluene (80 mL) was reacted with ethyl chloromalonate (2.68 mL, 25.0 mmol) at reflux for 4 hours. The reaction mixture was cooled to 25° C. and concentrated under vacuum. The residue was triturated with diethyl ether and hexanes (3:1) to give the title compound (5.17 g, 70%). MS (DCI) m/z 355 (M+H)⁺. $^1$H NMR (300 MHz, DMSO-$d_6$) δ ppm 3.32 (s, 2 H) 3.69 (s, 3 H) 3.73 (s, 3 H) 7.16 (s, 1 H) 7.32 (dd, J=7.72, 1.10 Hz, 1 H) 7.40 (m, 3 H) 7.63 (m, 2 H) 7.70 (td, J=7.63, 1.29 Hz, 1 H) 7.85 (td, J=7.72, 1.47 Hz, 1 H) 8.10 (dd, J=7.72, 1.47 Hz, 1 H).

EXAMPLE 226C

Ethyl 4-hydroxy-2-oxo-1-{[phenylmethylene]amino}-1,2-dihydroquinoline-3-carboxylate The product of Example 226B (5.17 g, 14.59 mmol) in ethanol (100 mL) was reacted with sodium ethoxide (21% by weight in ethanol, 5.50 mL, 14.60 mmol) at 25° C. then heated at 50° C. for 1 hour. After cooling to 25° C., the reaction mixture was poured into water, acidified to pH 4 with 1M hydrochloric acid and extracted with ethyl acetate. The organic layer was dried over anhydrous sodium sulfate, filtered and the solvent removed under vacuum to give the title compound (4.51 g, 96%). MS (DCI) m/z 323 (M+H)⁺. $^1$H NMR (300 MHz, DMSO-$d_6$) δ ppm 3.73 (s, 3 H) 7.21 (m, 1 H) 7.56 (m, 5 H) 7.95 (m, 2 H) 8.03 (d, J=7.72 Hz, 1 H) 9.08 (s, 1 H).

767087 Example 226D PKD 1-amino-3-(1,1-dioxido-4H-1,2,4-benzothiadiazin-3-yl)-4-hydroxyquinolin-2(1H)-one The product of Example 226C (4.51 g, 14.00 mmol) was reacted with 2-amino benzenesulfonamide (2.41 g, 14.00 mmol) in toluene (65 mL) at reflux for 6 hours. After cooling to 25° C., the solid (5.52 g) was collected by filtration and reacted further with aqueous 10% potassium hydroxide (100 mL) for 8 hours at 130° C. After cooling to 25° C., the reaction was poured into ice and acidified to pH 2 with 1 M hydrochloric acid. The resulting solid was isolated by filtration and dried to give the title compound (3.50 g, 71%). The sodium salt of the title compound was prepared according to the procedure of Example 1D. $^1$H NMR (300 MHz, DMSO-$d_6$) δ 5.31 (s, 2 H) 7.05 (t, J=8.09 Hz, 1 H) 7.27 (m, 2 H) 7.53 (m, 2 H) 7.67 (m, 2 H) 8.07 (dd, J=8.09, 1.47 Hz, 1 H) 16.38 (s, 1 H).

EXAMPLE 227A 3-(1,1-Dioxido-4H-1,2,4-benzothiadiazin-3-yl)-4-hydroxy-1-[(1-propylbutylidene)amino]quinolin-2(1H)-one The product of Example 226D (0.080 g, 0.22 mmol) was reacted with 4-heptanone (0.63 mL, 4.49 mmol) in N,N-dimethylacetamide (1 mL) in a sealed tube at 135° C. for 45 minutes in a microwave reactor. The reaction mixture was cooled to 25° C. and concentrated. The resulting residue was triturated with diethyl ether and filtered to give the title compound as a solid (0.032 g, 32%). MS (ESI–) m/z 453 (M–H)⁻.

EXAMPLE 227B 1-(1-propyl-butylamino)-3-(1,1-dioxido-4H-1,2,4-benzothiadiazin-3-yl)-4-hydroxyquinolin-2(1H)-one The product of Example 227A (0.032 g, 0.07 mmol) in tetrahydrofuran (2 mL) and methanol (0.010 mL, 0.14 mmol) at 0° C. was treated with dropwise addition of a 2.0M solution of lithium borohydride in tetrahydrofuran (0.055 mL, 0.11

EXAMPLE 228A 3-(1,1-dioxido-4H-1,2,4-benzothiadiazin-3-yl)-4-hydroxy-1-{[2-methylpropylidene]amino}quinolin-2(1H)-one The product of Example 226D (0.178 g, 0.50 mmol) was reacted with 2-methylpropanal (0.9 mL, 10.0 mmol) in N,N-dimethylacetamide (3 mL) in a sealed tube at 135° C. for 45 minutes in a microwave reactor. The reaction mixture was cooled to 25° C. and concentrated. The resulting residue was triturated with diethyl ether and filtered to give the title compound.

EXAMPLE 228B 3-(1,1-dioxido-4H-1,2,4-benzothiadiazin-3-yl)-4-hydroxy-1-(isobutylamino)quinolin-2(1H)-one The product of Example 228A (0.132 g, 0.32 mmol) in tetrahydrofuran (6 mL) and methanol (0.026 mL, 0.64 mmol) at 0° C. was treated with dropwise addition of a 2.0M solution of lithium borohydride in tetrahydrofuran (0.24 mL, 0.48 mmol). The reaction was stirred at 25° C. for 1 hour, acidified with 1 M hydrochloric acid to a pH of approximately 2-4, diluted with water (12 mL), and the resulting precipitate was collected by filtration and dried. The crude product was triturated with 1:1 ethyl acetate:hexane (10 ml) and filtered to give the title compound. The sodium salt of the title compound was prepared according to the procedure of Example 1D. $^1$H NMR (300 MHz, DMSO-$d_6$) δ ppm 1.03 (d, J=6.62 Hz, 6 H) 1.86 (m, 1 H) 2.73 (m, 2 H) 5.94 (t, J=7.35 Hz, 1 H) 7.07 (t, J=7.35 Hz, 1 H) 7.27 (m, 2 H) 7.54 (m, 2 H) 7.60 (d, J=6.99 Hz, 1 H) 7.66 (d, J=6.99 Hz, 1 H) 8.08 (d, J=8.09 Hz, 1 H) 16.27 (s, 1 H). MS (ESI−) (M−H)$^−$ m/z 411.

EXAMPLE 229A 3-(1,1-dioxido-4H-1,2,4-benzothiadiazin-3-yl)-1-[(1-ethylpropylidene)amino]-4-hydroxyquinolin-2(1H)-one The product of Example 226D (0.178 g, 0.5 mmol) was reacted with pentan-3-one (0.53 mL, 5.0 mmol) in N,N-dimethylacetamide (4 mL) in a sealed tube at 135° C. for 60 minutes in a microwave reactor. The reaction mixture was cooled to 25° C. and concentrated. The resulting residue was triturated with diethyl ether and filtered to give the title compound.

EXAMPLE 229B 3-(1,1-dioxido-4H-1,2,4-benzothiadiazin-3-yl)-1-[(1-ethylpropyl)amino]-4-hydroxyquinolin-2(1H)-one The product of Example 229A (0.122 g, 0.287 mmol) in tetrahydrofuran (8 mL) and methanol (0.023 mL, 0.57 mmol) at 0° C. was treated with dropwise addition of a 2.0M solution of lithium borohydride in tetrahydrofuran (0.215 mL, 0.43 mmol). The reaction was stirred at 25° C. for 2 hour, acidified with 1 M hydrochloric acid to a pH of approximately 2-4, diluted with water (15 mL), and the resulting precipitate was collected by filtration and dried. The crude product was chromatographed on silica gel with 98:2 dichloromethane/methanol to give the title compound The sodium salt of the title compound was prepared according to the procedure of Example 1D. $^1$H NMR (300 MHz, DMSO-$d_6$) δ ppm 0.83 (s, 3 H) 0.98 (s, 3 H) 1.31 (m, 2 H) 1.48 (m, 2 H) 2.99 (m, 1 H) 5.70 (d, J=4.04 Hz, 1 H) 7.05 (t, J=7.17 Hz, 1 H) 7.28 (m, 2 H) 7.51 (m, 2 H) 7.66 (d, J=8.09 Hz, 1 H) 7.72 (d, J=8.09 Hz, 1 H) 8.06 (d, J=7.72 Hz, 1 H) 16.32 (s, 1 H). MS (ESI−) (M−H)$^−$ m/z 425.

EXAMPLE 230A 3-(1,1-dioxido-4H-1,2,4-benzothiadiazin-3-yl)-4-hydroxy-1-[pentylideneamino]quinolin-2(1H)-one The product of Example 226D (0.05 g, 0.14 mmol) was reacted with pentanal (0.015 mL, 1.4 mmol) in N,N-dimethylacetamide (2 mL) in a sealed tube at 135° C. for 45 minutes in a microwave reactor. The reaction mixture was cooled to 25° C. and concentrated. The resulting residue was triturated with diethyl ether and filtered to give the title compound.

EXAMPLE 230B 3-(1,1-dioxido-4H-1,2,4-benzothiadiazin-3-yl)-4-hydroxy-1-(pentylamino)quinolin-2(1H)-one The product of Example 230A (0.034 g, 0.08 mmol) in tetrahydrofuran (2 mL) and methanol (0.0064 mL, 0.16 mmol) at 0° C. was treated with dropwise addition of a 2.0M solution of lithium borohydride in tetrahydrofuran (0.06 mL, 0.12 mmol). The reaction was stirred at 25° C. for 1 hour, acidified with 1 M hydrochloric acid to a pH of approximately 2-4, diluted with water (5 mL), and the resulting precipitate was collected by filtration and dried. The crude product was chromatographed on silica gel with 98:2 dichloromethane/methanol to give the title compound. The sodium salt of the title compound was prepared according to the procedure of Example 1D. $^1$H NMR (300 MHz, DMSO-$d_6$) δ ppm 0.90 (t, J=6.99 Hz, 3 H) 1.37 (m, 4 H) 1.55 (m, 2 H) 2.73 (m, 2 H) 5.90 (t, J=6.80 Hz, 1 H) 7.07 (t, J=7.72 Hz, 1 H) 7.26 (m, 2 H) 7.52 (m, 2 H) 7.60 (d, J=8.09 Hz, 1 H) 7.66 (d, J=8.09 Hz, 1 H) 8.09 (d, J=8.09 Hz, 1 H) 16.27 (s, 1 H). MS (ESI−) (M−H)$^−$ m/z 425.

EXAMPLE 231A 1-(cyclohexylideneamino)-3-(1,1-dioxido-4H-1,2,4-benzothiadiazin-3-yl)-4-hydroxyquinolin-2(1H)-one The product of Example 226D (0.155 g, 0.60 mmol) was reacted with cyclohexanone (20 mole equivalents) in N,N-dimethylacetamide (2 mL) in a sealed tube at 135° C. for 60 minutes in a microwave reactor. The reaction mixture was

--- mmol). The reaction was stirred at 25° C. for 1 hour, acidified with 1M hydrochloric acid to a pH of approximately 2-4, diluted with water (10 mL), and the resulting precipitate was collected by filtration and dried. The crude product was suspended in tetrahydrofuran (2 mL) and adsorbed onto approximately 0.5 g of silica gel and evaporated. A slurry of the crude product and silica in dichloromethane was loaded onto a 2 g Alltech Sep-pack and eluted with dichloromethane. Product containing fractions were combined and concentrated under vacuum to give the title compound (0.013 g, 40%). MS (ESI−) m/z 453 (M−H)$^−$. The sodium salt of the title compound was prepared according to the procedure of Example 1D. $^1$H NMR (300 MHz, DMSO-$d_6$) δ ppm 0.85 (m, 6 H) 1.33 (m, 8 H) 3.13 (m, 1 H) 5.66 (d, J=4.04 Hz, 1 H) 7.05 (m, 1 H) 7.28 (m, 2 H) 7.51 (m, 2 H) 7.68 (m, 2 H) 8.06 (dd, J=7.72, 1.47 Hz, 1 H) 16.32 (s, 1 H).

EXAMPLE 231B 1-(cyclohexylamino)-3-(1,1-dioxido-4H-1,2,4-benzothiadiazin-3-yl)-4-hydroxyquinolin-2(1H)-one The product of Example 231 A (0.087 g, 0.2 mmol) in tetrahydrofuran (4 mL) and methanol (0.016 mL, 0.4 mmol) at 0° C. was treated with dropwise addition of a 2.0M solution of lithium borohydride in tetrahydrofuran (0.15 mL, 0.3 mmol). The reaction was stirred at 25° C. for 1 hour, acidified with 1 M hydrochloric acid to a pH of approximately 2-4, diluted with water (5 mL), and the resulting precipitate was collected by filtration and dried to give the title compound. The sodium salt of the title compound was prepared according to the procedure of Example 1D. $^1$H NMR (300 MHz, DMSO-$d_6$) δ ppm 1.13 (m, 6 H) 1.58 (m, 2 H) 1.75 (m, 2 H) 2.97 (m, 1 H) 5.68 (d, J=3.68 Hz, 1 H) 7.05 (t, J=7.54 Hz, 1 H) 7.27 (d, J=8.09 Hz, 1 H) 7.30 (d, J=8.09 Hz, 1 H) 7.49 (t, J=7.72 Hz, 1 H) 7.55 (t, J=7.72 Hz, 1 H) 7.67 (d, J=8.09 Hz, 1 H) 7.76 (d, J=8.46 Hz, 1 H) 8.06 (d, J=7.72 Hz, 1 H) 16.30 (s, 1 H). MS (ESI−) (M−H)$^-$ m/z 437.

EXAMPLE 232A 3-(1,1-dioxido-4H-1,2,4-benzothiadiazin-3-yl)-4-hydroxy-1-{[(2-methyl-1,3-thiazol-4-yl)methylene]amino}quinolin-2(1H)-one The product of Example 226D (0.119 g, 0.33 mmol) was reacted with 2-methyl-1,3-thiazole-4-carbaldehyde 5 mol equivalents) in N,N-dimethylacetamide (3 mL) in a sealed tube at 135° C. for 60 minutes in a microwave reactor. The reaction mixture was cooled to 25° C. and concentrated. The resulting residue was triturated with diethyl ether and filtered to give the title compound.

EXAMPLE 232B 3-(1,1-dioxido-4H-1,2,4-benzothiadiazin-3-yl)-4-hydroxy-1-{[(2-methyl-1,3-thiazol-4-yl)methyl]amino}quinolin-2(1H)-one The product of Example 232A (0.097 g, 0.208 mmol) in tetrahydrofuran (5 mL) and methanol (0.016 mL, 0.40 mmol) at 0° C. was treated with dropwise addition of a 2.0M solution of lithium borohydride in tetrahydrofuran (0.15 mL, 0.3 mmol). The reaction was stirred at 25° C. for 3 hour, acidified with 1M hydrochloric acid to a pH of approximately 2-4, diluted with water (10 mL), and the resulting precipitate was collected by filtration and dried. The crude product was chromatographed on C-18 reverse phase column eluting with water:acetonitrile 90:10-0:100 to give the title compound. The sodium salt of the title compound was prepared according to the procedure of Example 1D. $^1$H NMR (300 MHz, DMSO-$d_6$) δ ppm 2.68 (s, 3 H) 3.24 (m, 2 H) 6.33 (m, 1 H) 7.10 (m, 1 H) 7.31 (m, 2 H) 7.43 (s, 1 H) 7.61 (m, 4 H) 8.08 (d, J=7.72 Hz, 1 H) 16.24 (s, 1 H). MS (ESI−) (M−H)$^-$ m/z 466.

EXAMPLE 233A 3-(1,1-dioxido-4H-1,2,4-benzothiadiazin-3-yl)-4-hydroxy-1-[(1-methylethylidene)amino]quinolin-2(1H)-one The product of Example 226D (0.080 g, 0.22 mmol) was reacted with acetone (0.34 mL, 4.50 mmol) in N,N-dimethylacetamide (1.0 mL) in a sealed tube at 125° C. for 25 minutes in a microwave reactor. The reaction mixture was cooled to 25° C. and concentrated. The resulting residue was triturated with diethyl ether and filtered to give the title compound.

EXAMPLE 233B 3-(1,1-dioxido-4H-1,2,4-benzothiadiazin-3-yl)-4-hydroxy-1-(isopropylamino)quinolin-2(1H)-one The product of Example 233A (0.044 g, 0.11 mmol) in tetrahydrofuran (2.0 mL) and methanol (0.010 mL, 0.28 mmol) at 0° C. was treated with dropwise addition of a 2.0M solution of lithium borohydride in tetrahydrofuran 0.085 mL, 0.17 mmol). The reaction was stirred at 25° C. for 1 hour, acidified with 1 M hydrochloric acid to a pH of approximately 2-4, diluted with water and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 0.99 (m, 6 H) 3.94 (m, 1 H) 5.65 (d, J=4.41 Hz, 1 H) 7.04 (t, J=7.35 Hz, 1 H) 7.28 (m, 2 H) 7.51 (m, 2 H) 7.66 (d, J=7.72 Hz, 1 H) 7.75 (d, J=8.46 Hz, 1 H) 8.06 (dd, J=8.09, 1.47 Hz, 1 H) 16.28 (s, 1 H). (ESI−) m/z 397 (M−H)$^-$.

EXAMPLE 234A 1-(cyclobutylideneamino)-3-(1,1-dioxido-4H-1,2,4-benzothiadiazin-3-yl)-4-hydroxyquinolin-2(1H)-one The product of Example 226D (0.080 g, 0.22 mmol) was reacted with cyclobutanone (0.50 mL, 7.10 mmol) in N,N-dimethylacetamide (0.50 mL) in a sealed tube at 125° C. for 40 minutes in a microwave reactor. The reaction mixture was cooled to 25° C. and concentrated. The resulting residue was triturated with diethyl ether and filtered to give the title compound.

EXAMPLE 234B 1-(cyclobutylamino)-3-(1,1-dioxido-4H-1,2,4-benzothiadiazin-3-yl)-4-hydroxyquinolin-2(1H)-one The product of Example 234A (0.032 g, 0.078 mmol) in tetrahydrofuran (2.0 mL) and methanol (0.010 mL, 0.28 mmol) at 0° C. was treated with dropwise addition of a 2.0M solution of lithium borohydride in tetrahydrofuran (0.025 mL, 0.050 mmol). The reaction was stirred at 25° C. for 1 hour, acidified with 1M hydrochloric acid to a pH of approximately 2-4, diluted with water, and the resulting precipitate was collected by filtration and dried.

The crude product was chromatographed on silica gel with dichloromethane to give the title compound. The sodium salt of the title compound was prepared according to the procedure of Example 1D. $^1$H NMR (300 MHz, DMSO-$d_6$) δ ppm 1.54 (m, 1 H) 1.98 (m, 4 H) 3.61 (m, 2 H) 6.09 (d, J=6.25 Hz, 1 H) 7.06 (td, J=7.35, 1.10 Hz, 1 H) 7.27 (m, 2 H) 7.53 (m, 2 H) 7.65 (m, 2 H) 8.06 (dd, J=7.91, 1.65 Hz, 1 H) 16.28 (s, 1 H). MS (ESI−) m/z 409 (M−H)$^-$.

EXAMPLE 235A 1-(cyclopentylideneamino)-3-(1,1-dioxido-4H-1,2,4-benzothiadiazin-3-yl)-4-hydroxyquinolin-2(1H)-one The product of Example 226D (0.079 g, 0.22 mmol) was reacted with cyclopentanone (0.195 mL, 2.22 mmol) in N,N- dimethylacetamide (1.50 mL) in a sealed tube at 130° C. for 30 minutes in a microwave reactor. The reaction mixture was cooled to 25° C. and concentrated.

The resulting residue was triturated with ethyl acetate and filtered to give the title compound.

EXAMPLE 235B 1-(cyclopentylamino)-3-(1,1-dioxido-4H-1,2,4-benzothiadiazin-3-yl)-4-hydroxyquinolin-2(1H)-one The product of Example 235A (0.030 g, 0.071 mmol) in tetrahydrofuran (2.0 mL) and methanol (0.010 mL, 0.28 mmol) at 0° C. was treated with dropwise addition of a 2.0M solution of lithium borohydride in tetrahydrofuran (0.060 mL, 0.12 mmol). The reaction was stirred at 25° C. for 1 hour, acidified with 1 M hydrochloric acid to a pH of approximately 2-4, diluted with water, and the resulting precipitate was collected by filtration and dried to give the title compound. The sodium salt of the title compound was prepared according to the procedure of Example 1D. $^1$H NMR (300 MHz, DMSO-$d_6$) δ ppm 1.61 (m, 8 H) 3.70 (m, 1 H) 5.68 (d, J=4.41 Hz, 1 H) 7.05 (t, J=7.35 Hz, 1 H) 7.28 (t, J=8.27 Hz, 2 H) 7.54 (m, 2 H) 7.69 (dd, J=15.81, 8.09 Hz, 2 H) 8.06 (dd, J=8.09, 1.47 Hz, 1 H) 16.28 (s, 1 H). MS (ESI−) m/z 423 (M−H)$^−$.

EXAMPLE 236A 3-(1,1-dioxido-4H-1,2,4-benzothiadiazin-3-yl)-4-hydroxy-1-{[3-methylcyclopentylidene]amino}quinolin-2(1H)-one The product of Example 226D (0.080 g, 0.22 mmol) was reacted with 3-methylcyclopentanone (0.50 mL, 5.09 mmol) in N,N-dimethylacetamide (1.0 mL) in a sealed tube at 135° C. for 40 minutes in a microwave reactor. The reaction mixture was cooled to 25° C. and concentrated. The resulting residue was triturated with diethyl ether and filtered to give the title compound.

EXAMPLE 236B 3-(1,1-dioxido-4H-1,2,4-benzothiadiazin-3-yl)-4-hydroxy-1-{[3-methylcyclopentyl]amino}quinolin-2(1H)-one The product of Example 236A (0.068 g, 0.16 mmol) in tetrahydrofuran (2.0 mL) and methanol (0.010 mL, 0.28 mmol) at 0° C. was treated with dropwise addition of a 2.0M solution of lithium borohydride in tetrahydrofuran (0.100 mL, 0.20 mmol). The reaction was stirred at 25° C. for 1 hour, acidified with 1M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 1.03 (m, 3 H) 1.35 (m, 1 H) 1.78 (m, 4 H) 2.56 (m, J=5.52 Hz, 2 H) 3.69 (m, 1 H) 5.78 (m, 1 H) 7.05 (m, 1 H) 7.27 (m, 2 H) 7.52 (m, 2 H) 7.69 (m, 2 H) 8.06 (dd, J=7.72, 1.47 Hz, 1 H) 16.28 (s, 1 H). MS (ESI−) m/z 437 (M−H)$^−$.

EXAMPLE 237A 3-(1,1-dioxido-4H-1,2,4-benzothiadiazin-3-yl)-4-hydroxy-1-(tetrahydro-4H-pyran-4-ylideneamino)quinolin-2(1H)-one The product of Example 226D (0.080 g, 0.22 mmol) was reacted with tetrahydro-4H-pyran-4-one (0.215 mL, 2.33 mmol) in N,N-dimethylacetamide (1.0 mL) in a sealed tube at 130° C. for 35 minutes in a microwave reactor. The reaction mixture was cooled to 25° C. and concentrated. The resulting residue was triturated with diethyl ether and filtered to give the title compound.

EXAMPLE 237B 3-(1,1-dioxido-4H-1,2,4-benzothiadiazin-3-yl)-4-hydroxy-1-(tetrahydro-2H-pyran-4-ylamino)quinolin-2(1H)-one The product of Example 237A (0.082 g, 0.19 mmol) in tetrahydrofuran (2.0 mL) and methanol (0.015 mL, 0.42 mmol) at 0° C. was treated with dropwise addition of a 2.0M solution of lithium borohydride in tetrahydrofuran (0.140 mL, 0.28 mmol). The reaction was stirred at 25° C. for 1 hour, acidified with 1 M hydrochloric acid to a pH of approximately 2-4, diluted with water, and , and the resulting precipitate was collected by filtration and dried. The crude product was chromatographed on silica gel with dichloromethaneto give the title compound. The sodium salt of the title compound was prepared according to the procedure of Example 1D. $^1$H NMR (300 MHz, DMSO-$d_6$) δ ppm 0.86 (m, 1 H) 1.24 (m, 2 H) 1.48 (m, 2 H) 3.20 (m, J=18.02, 10.66 Hz, 2 H) 3.81 (m, 2 H) 5.82 (d, J=4.04 Hz, 1 H) 7.04 (m, J=7.72 Hz, 1 H) 7.27 (m, J=8.46, 8.46 Hz, 2 H) 7.52 (m, 2 H) 7.66 (d, J=7.72 Hz, 1 H) 7.76 (d, J=8.09 Hz, 1 H) 8.04 (d, J=1.47 Hz, 1 H). MS (ESI−) m/z 439 (M−H)$^−$.

EXAMPLE 238A 3-(1,1-dioxido-4H-1,2,4-benzothiadiazin-3-yl)-1-{[1-ethylbutylidene]amino}-4-hydroxyquinolin-2(1H)-one The product of Example 226D (0.085 g, 0.24 mmol) was reacted with hexan-3-one (0.55 mL, 4.48 mmol) in N,N-dimethylacetamide (1.0 mL) in a sealed tube at 140° C. for 60 minutes in a microwave reactor. The reaction mixture was cooled to 25° C. and concentrated. The resulting residue was triturated with diethyl ether and filtered to give the title compound.

EXAMPLE 238B 3-(1,1-dioxido-4H-1,2,4-benzothiadiazin-3-yl)-1-{[1-ethylbutyl]amino}-4-hydroxyquinolin-2(1H)-one The product of Example 238A (0.049 g, 0.11 mmol) in tetrahydrofuran (2.0 mL) and methanol (0.015 mL, 0.42 mmol) at 0° C. was treated with dropwise addition of a 2.0M solution of lithium borohydride in tetrahydrofuran (0.152 mL, 0.30 mmol). The reaction was stirred at 25° C. for 1 hour, acidified with 1M hydrochloric acid to a pH of approximately 2-4, diluted with water, and the resulting precipitate was collected by filtration and dried to give the title compound. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 0.88 (m, 6 H) 1.37 (m, 6 H) 3.05 (m, 1 H) 5.68 (m, 1 H) 7.05 (m, 1 H) 7.28 (m, 2 H) 7.52 (m, 2 H) 7.66 (d, J=7.72 Hz, 1 H) 7.71 (m, 1 H) 8.06 (dd, J=7.72, 1.47 Hz, 1 H) 16.32 (s, 1 H). MS (ESI−) m/z 439 (M−H)$^−$.

EXAMPLE 239A 3-(1,1-dioxido-4H-1,2,4-benzothiadiazin-3-yl)-4-hydroxy-1-{[(3R)-3-methylcyclohexylidene]amino}quinolin-2(1H)-one The product of Example 226D (0.080 g, 0.22 mmol) was reacted with (3R)-3-methylcyclohexanone 0.275 mL, 2.25 mmol) in N,N-dimethylacetamide (1.0 mL) in a sealed tube at 130° C. for 35 minutes in a microwave reactor. The reaction mixture was cooled to 25° C. and concentrated. The resulting residue was triturated with diethyl ether and filtered to give the title compound.

EXAMPLE 239B 3-(1,1-dioxido-4H-1,2,4-benzothiadiazin-3-yl)-4-hydroxy-1-{[(3R)-3-methylcyclohexyl]amino}quinolin-2(1H)-one The product of Example 239A (0.045 g, 0.10 mmol) in tetrahydrofuran (2.0 mL) and methanol (0.010 mL, 0.28 mmol) at 0° C. was treated with dropwise addition of a 2.0M solution of lithium borohydride in tetrahydrofuran (0.075 mL, 0.15 mmol). The reaction was stirred at 25° C. for 1 hour, acidified with 1M hydrochloric acid to a pH of approximately 2-4, diluted with water, and the resulting precipitate was collected by filtration and dried to give the title compound. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 0.83 (m, 3 H) 1.22 (m, 3 H) 1.73 (m, 3 H) 2.99 (m, 1 H) 5.67 (d, J=4.04 Hz, 1 H) 7.04 (t, J=6.99 Hz, 1 H) 7.28 (t, J=8.27 Hz, 2 H) 7.53 (m, 2 H) 7.66 (d, J=7.72 Hz, 1 H) 7.74 (d, J=8.09 Hz, 1 H) 8.06 (m, 1 H). MS (ESI−) m/z 451 (M−H)$^−$.

EXAMPLE 240A 2-(2-cycloheptylidenehydrazino)benzoic acid

The title compound was prepared according to the prodecure as described in Example 162A, substituting cycloheptanone for benzaldehyde.

EXAMPLE 240B 1-(cycloheptylideneamino)-2H-3,1-benzoxazine-2,4(1H)-dione

The title compound was prepared according to the procedure as described in Example 162B, substituting the product of Example 240A for the product of Example 162A.

EXAMPLE 240C 1-(cycloheptylideneamino)-3-(1,1-dioxido-4H—1,2,4-benzothiadiazin-3-yl)$_4$-hydroxyquinolin-2(1H)-one The title compound was prepared according to the procedure as described in Example 1D, substituting the product of Example 240B for the product of Example 1B.

EXAMPLE 240D 1-(cycloheptylamino)-3-(1,1-dioxido-4H-1,2,4-benzothiadiazin-3-yl)-4-hydroxyquinolin-2(1H)-one The product of Example 240C (0.099 g, 0.22 mmol) in tetrahydrofuran (4.0 mL) (0.099 g, 0.22 mmol) in tetrahydrofuran (4.0 mL) and methanol (0.020 mL, 0.49 mmol) at 0° C. was treated with dropwise addition of a 2.0M solution of lithium borohydride in tetrahydrofuran (0.16 mL, 0.32 mmol). The reaction was stirred at 25° C. for 1 hour, acidified with 1 M hydrochloric acid to a pH of approximately 2-4, diluted with water, and the resulting precipitate was collected by filtration and dried to give the title compound. The sodium salt of the title compound was prepared according to the procedure of Example 1D. $^1$H NMR (300 MHz, DMSO-$d_6$) δ ppm 1.43 (m, 11 H) 1.87 (m, 1 H) 3.25 (m, 1 H) 5.53 (d, J=3.68 Hz, 1 H) 7.04 (m, 1 H) 7.28 (m, 2 H) 7.51 (m, 2 H) 7.66 (d, J=7.72 Hz, 1 H) 7.73 (d, J=8.46 Hz, 1 H) 8.05 (dd, J=7.72, 1.47 Hz, 1 H) 16.30 (s, 1 H). MS (ESI−) m/z 451 (M−H)$^−$.

EXAMPLE 241A 3-(1,1-dioxido-4H-1,2,4-benzothiadiazin-3-yl)-1-{[3-ethylcyclopentylidene]amino}-4-hydroxyquinolin-2(1H)-one The product of Example 226D (0.080 g, 0.22 mmol) was reacted with 3-ethylcyclopentanone (0.380 mL, 3.30 mmol) in N,N-dimethylacetamide (1.0 mL) in a sealed tube at 135° C. for 35 minutes in a microwave reactor. The reaction mixture was cooled to 25° C. and concentrated. The resulting residue was triturated with diethyl ether and filtered to give the title compound.

EXAMPLE 241B 3-(1,1-dioxido-4H-1,2,4-benzothiadiazin-3-yl)-1-{[3-ethylcyclopentyl]amino}-4-hydroxyquinolin-2(1H)-one The product of Example 241 A (0.031 g, 0.068 mmol) in tetrahydrofuran (2.0 mL) and methanol (0.010 mL, 0.25 mmol) at 0° C. was treated with dropwise addition of a 2.0M solution of lithium borohydride in tetrahydrofuran (0.055 mL, 0.11 mmol). The reaction was stirred at 25° C. for 1 hour, acidified with 1 M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 0.85 (m, 3 H) 1.56 (m, 8 H) 3.65 (m, 2 H) 5.75 (m, 1 H) 7.05 (t, J=6.99 Hz, 1 H) 7.28 (m, 2 H) 7.52 (m, 2 H) 7.69 (m, 2 H) 8.06 (dd, J=7.90, 1.65 Hz, 1 H) 16.28 (s, 1 H). MS (ESI−) m/z 451 (M−H)$^−$.

EXAMPLE 242A 3-(1,1-dioxido-4H-1,2,4-benzothiadiazin-3-yl)-4-hydroxy-1-{[1-isopropylbutylidene]amino}quinolin-2(1H)-one The product of Example 226D (0.080 g, 0.22 mmol) was reacted with 2-methylhexan-3-one (0.620 mL, 4.48 mmol) in N,N-dimethylacetamide (1.0 mL) in a sealed tube at 135° C. for 60 min then at 145° C. for 60 minutes in a microwave reactor. The reaction mixture was cooled to 25° C. and concentrated. The resulting residue was triturated with diethyl ether and filtered to give the title compound.

EXAMPLE 242B 3-(1,1-dioxido-4H-1,2,4-benzothiadiazin-3-yl)-4-hydroxy-1-{[1-isopropylbutyl]amino}uinolin-2(1H)-one The product of Example 242A (0.049 g, 0.11 mmol) in tetrahydrofuran (2.0 mL) and methanol (0.010 mL, 0.25 mmol) at 0° C. was treated with dropwise addition of a 2.0M solution of lithium borohydride in tetrahydrofuran (0.085 mL, 0.17 mmol). The reaction was stirred at 25° C. for 1 hour, acidified with 1 M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 0.68 (m, 1 H) 1.18 (m, 9 H) 2.49 (m, 4 H) 3.00 (m, J=44.49 Hz, 1 H) 5.73 (d, J=20.22 Hz, 1 H) 7.04 (m, 1 H) 7.27 (m, 2 H) 7.52 (m, 2 H) 7.71 (m, 2 H) 8.06 (dd, J=8.09, 1.47 Hz, 1 H) 16.33 (s, 1 H). MS (ESI−) m/z 453 (M−H)⁻.

EXAMPLE 243A 3-(1,1-dioxido-4H-1,2,4-benzothiadiazin-3-yl)-4-hydroxy-1-{[1-phenylethylidene]amino}quinolin-2(1H)-one The product of Example 226D (0.080 g, 0.22 mmol) was reacted with 1-phenylethanone (0.49 mL, 4.20 mmol) in N,N-dimethylacetamide (1.0 mL) in a sealed tube at 135° C. for 40 minutes in a microwave reactor. The reaction mixture was cooled to 25° C. and concentrated. The resulting residue was triturated with diethyl ether and filtered to give the title compound.

EXAMPLE 243B 3-(1,1-dioxido-4H-1,2,4-benzothiadiazin-3-yl)-4-hydroxy-1-{[1-phenylethyl]amino}quinolin-2(1H)-one The product of Example 243A (0.093 g, 0.20 mmol) in tetrahydrofuran (2.0 mL) and methanol (0.015 mL, 0.42 mmol) at 0° C. was treated with dropwise addition of a 2.0M solution of lithium borohydride in tetrahydrofuran (0.152 mL, 0.30 mmol). The reaction was stirred at 25° C. for 1 hour, acidified with 1M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 1.31 (m, 3 H) 4.41 (d, J=68.76 Hz, 1 H) 5.85 (m, 1 H) 7.28 (m, J=7.54, 7.54 Hz, 7 H) 7.59 (m, 4 H) 8.07 (m, 2 H) 16.30 (s, 1 H). MS (ESI−) m/z 459 (M−H)⁻.

EXAMPLE 244A 3-(1,1-dioxido-4H-1,2,4-benzothiadiazin-3-yl)-4-hydroxy-1-{[1-thien-3-ylethylidene]amino}quinolin-2(1H)-one The product of Example 226D (0.080 g, 0.22 mmol) was reacted with 1-thien-3-ylethanone (0.14 g, 1.11 mmol) in N,N-dimethylacetamide (0.50 mL) in a sealed tube at 135° C. for 45 minutes in a microwave reactor. The reaction mixture was cooled to 25° C. and concentrated. The resulting residue was triturated with diethyl ether and filtered to give the title compound.

EXAMPLE 244B 3-(1,1-dioxido-4H-1,2,4-benzothiadiazin-3-yl)-4-hydroxy-1-{[1-thien-3-ylethyl]amino}quinolin-2(1H)-one The product of Example 244A (0.070 g, 0.15 mmol) in tetrahydrofuran (2.0 mL) and methanol (0.015 mL, 0.42 mmol) at 0° C. was treated with dropwise addition of a 2.0M solution of lithium borohydride in tetrahydrofuran (0.090 mL, 0.18 mmol). The reaction was stirred at 25° C. for 1 hour, acidified with 1M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 1.26 (m, 3 H) 4.58 (m, 1 H) 5.74 (s, 1 H) 7.07 (m, 1 H) 7.18 (m, 1 H) 7.28 (m, 3 H) 7.37 (s, 1 H) 7.55 (m, 2 H) 7.66 (m, 1 H) 7.96 (d, J=6.62 Hz, 1 H) 8.07 (s, 1 H) 16.30 (s, 1 H). MS (ESI−) m/z 465 (M−H)⁻.

EXAMPLE 245A

1-{[3,5-dimethylcyclohexylidene]amino}-3-(1,1-dioxido-4H-1,2,4-benzothiadiazin-3-yl)-4-hydroxyquinolin-2(1H)-one The product of Example 226D (0.080 g, 0.22 mmol) was reacted with 3,5-dimethylcyclohexanone (0.57 g, 4.52 mmol) in N,N-dimethylacetamide (1.0 mL) in a sealed tube at 135° C. for 40 minutes in a microwave reactor. The reaction mixture was cooled to 25° C. and concentrated. The resulting residue was triturated with diethyl ether and filtered to give the title compound.

EXAMPLE 245B

1-{[3,5-dimethylcyclohexyl]amino}-3-(1,1-dioxido-4H-1,2,4-benzothiadiazin-3-yl)-4-hydroxyquinolin-2(1H)-one The product of Example 245A (0.064 g, 0.14 mmol) in tetrahydrofuran (2.0 mL) and methanol (0.010 mL, 0.25 mmol) at 0° C. was treated with dropwise addition of a 2.0M solution of lithium borohydride in tetrahydrofuran (0.100 mL, 0.20 mmol). The reaction was stirred at 25° C. for 1 hour, acidified with 1 M hydrochloric acid to a pH of approximately 2-4, diluted with water, and the resulting precipitate was collected by filtration and dried. The crude product was chromatographed on silica gel with dichlrormethane to give the title compound. The sodium salt of the title compound was prepared according to the procedure of Example 1D. $^1$H NMR (300 MHz, DMSO-$d_6$) δ ppm 0.55 (m, 2 H) 0.87 (m, 6 H) 1.67 (m, 6 H) 3.05 (m, 1 H) 5.66 (dd, J=5.70, 3.86 Hz, 1 H) 7.05 (m, 1 H) 7.28 (t, J=8.27 Hz, 2 H) 7.51 (m, 2 H) 7.66 (d, J=7.72 Hz, 1 H) 7.73 (t, J=7.54 Hz, 1 H) 8.06 (dd, J=7.91, 1.29 Hz, 1 H). MS (ESI−) m/z 465 (M−H)⁻.

EXAMPLE 246A 3-(1,1-dioxido-4H-1,2,4-benzothiadiazin-3-yl)-4-hydroxy-1-{[4-isopropylcyclohexylidene]amino}quinolin-2(1H)-one The product of Example 226D (0.080 g, 0.22 mmol) was reacted with 4-isopropylcyclohexanone (0.63 mL, 4.11 mmol) in N,N-dimethylacetamide (1.0 mL) in a sealed tube at 135° C. for 45 minutes in a microwave reactor. The reaction mixture was cooled to 25° C. and concentrated. The resulting residue was triturated with diethyl ether and filtered to give the title compound.

EXAMPLE 246B 3-(1,1-dioxido-4H-1,2,4-benzothiadiazin-3-yl)-4-hydroxy-1-[(4-isopropylcyclohexyl)amino]quinolin-2(1H)-one The product of Example 246A (0.095 g, 0.20 mmol) in tetrahydrofuran (2.0 mL) and methanol (0.015 mL, 0.42 mmol) at 0° C. was treated with dropwise addition of a 2.0M solution of lithium borohydride in tetrahydrofuran (0.150 mL, 0.30 mmol). The reaction was stirred at 25° C. for 1 hour, acidified with 1M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 0.86 (m, 6 H) 1.43 (m, 7 H) 1.87 (m, 1 H) 2.94 (m, 1 H) 3.14 (m, 1 H) 5.71 (m, 1 H) 7.04 (t, J=7.54 Hz, 1 H) 7.28 (t, J=8.46 Hz, 2 H) 7.50 (m, 2 H) 7.70 (m, 2 H) 8.06 (m, 1 H) 16.30 (s, 1 H). MS (ESI−) m/z 479 (M−H)$^-$.

EXAMPLE 247A

1-[3,4-dihydronaphthalen-2(1H)-ylideneamino]-3-(1,1-dioxido-4H-1,2,4-benzothiadiazin-3-yl)-4-hydroxyquinolin-2(1H)-one The product of Example 226D (0.080 g, 0.22 mmol) was reacted with 3,4-dihydronaphthalen-2(1H)-one (0.60 mL, 4.54 mmol) in N,N-dimethylacetamide (1.0 mL) in a sealed tube at 135° C. for 45 minutes in a microwave reactor. The reaction mixture was cooled to 25° C. and concentrated. The resulting residue was triturated with diethyl ether and filtered to give the title compound.

EXAMPLE 247B 3-(1,1-dioxido-4H-1,2,4-benzothiadiazin-3-yl)-4-hydroxy-1-[1,2,3,4-tetrahydronaphthalen-2-ylamino]quinolin-2(1H)-one The product of Example 247A (0.070 g, 0.14 mmol) in tetrahydrofuran (2.0 mL) and methanol (0.010 mL, 0.25 mmol) at 0° C. was treated with dropwise addition of a 2.0M solution of lithium borohydride in tetrahydrofuran (0.110 mL, 0.22 mmol). The reaction was stirred at 25° C. for 1 hour, acidified with 1 M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 2.73 (s, 2 H) 3.27 (d, J=12.50 Hz, 4 H) 5.93 (d, J=3.68 Hz, 1 H) 7.07 (m, 6 H) 7.28 (t, J=7.54 Hz, 3 H) 7.55 (m, 2 H) 7.66 (d, J=7.72 Hz, 1 H) 8.07 (dd, J=7.72, 1.47 Hz, 1 H) 16.28 (s, 1 H). MS (ESI−) m/z 485 (M−H)$^-$.

EXAMPLE 248A 3-(1,1-dioxido-4H-1,2,4-benzothiadiazin-3-yl)-4-hydroxy-1-{[3-(trifluoromethyl)cyclohexylidene]amino}quinolin-2(1H)-one The product of Example 226D (0.080 g, 0.22 mmol) was reacted with 3-(trifluoromethyl)cyclohexanone (0.75 mL, 4.54 mmol) in N,N-dimethylacetamide (1.0 mL) in a sealed tube at 135° C. for 40 minutes in a microwave reactor. The reaction mixture was cooled to 25° C. and concentrated. The resulting residue was triturated with diethyl ether and filtered to give the title compound.

EXAMPLE 248B 3-(1,1-dioxido-4H-1,2,4-benzothiadiazin-3-yl)-4-hydroxy-1-{[3-(trifluoromethyl)cyclohexyl]amino}quinolin-2(1H)-one The product of Example 248A (0.103 g, 0.20 mmol) in tetrahydrofuran (2.0 mL) and methanol (0.015 mL, 0.42 mmol) at 0° C. was treated with dropwise addition of a 2.0M solution of lithium borohydride in tetrahydrofuran (0.15 mL, 0.30 mmol). The reaction was stirred at 25° C. for 1 hour, acidified with 1M hydrochloric acid to a pH of approximately 2-4, diluted with water, and the resulting precipitate was collected by filtration and dried. The crude product was chromatographed on silica gel with dichloromethane to give the title compound. The sodium salt of the title compound was prepared according to the procedure of Example 1D. $^1$H NMR (300 MHz, DMSO-$d_6$) δ ppm 1.21 (m, 4 H) 1.76 (m, 2 H) 2.31 (m, 1 H) 3.11 (m, 2 H) 3.97 (m, 1 H) 5.81 (d, J=19.85 Hz, 1 H) 7.05 (m, 1 H) 7.28 (m, 2 H) 7.53 (m, 2 H) 7.66 (d, J=8.09 Hz, 1 H) 7.75 (d, J=7.72 Hz, 1 H) 8.06 (dd, J=8.09, 1.47 Hz, 1 H). MS (ESI−) m/z 505 (M−H)$^-$.

EXAMPLE 249A

1-[butylideneamino]-3-(1,1-dioxido-4H-1,2,4-benzothiadiazin-3-yl)-4-hydroxyquinolin-2(1H)-one The product of Example 226D (0.060 g, 0.168 mmol) was reacted with butyraldehyde (0.135 mL, 1.50 mmol) in N,N-dimethylacetamide (1.0 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 249B 1-(butylamino)-3-(1,1-dioxido-4H-1,2,4-benzothiadiazin-3-yl)-4-hydroxyquinolin-2(1H)-one The product of Example 249A (0.040 g, 0.097 mmol) in tetrahydrofuran (2.0 mL) and methanol (0.008 mL, 0.194 mmol) at 0° C. was treated with dropwise addition of a 2.0M solution of lithium borohydride in tetrahydrofuran (0.074 mL, 0.148 mmol). The reaction was stirred at 25° C. for 1 hour, acidified with 1 M hydrochloric acid to a pH of approximately 2-4, diluted with water (5.0 mL), and the resulting precipitate was collected by filtration and washed with water (2×5.0 ml) and dried. The crude product was triturated with diethyl ether and filtered to give the title compound. The sodium salt of the title compound was prepared according to the procedure of Example 1D. $^1$H NMR (300 MHz, DMSO-d$_6$) δ ppm 0.93 (t, J=7.17 Hz, 3 H) 1.48 (m, 4 H) 2.77 (m, 2 H) 5.90 (t, J=6.99 Hz, 1 H) 7.07 (m, 1 H) 7.27 (m, 2 H) 7.58 (m, 3 H) 7.66 (d, J=8.09 Hz, 1 H) 8.08 (dd, J=8.09, 1.47 Hz, 1 H) 16.28 (s, 1 H). MS (ESI−) m/z 411 (M−H)$^-$.

EXAMPLE 250A 3-(1,1-dioxido-4H-1,2,4-benzothiadiazin-3-yl)-4-hydroxy-1-{[3-methylbutylidene]amino}quinolin-2(1H)-one The product of Example 226D (0.060 g, 0.168 mmol) was reacted with 3-methylbutanal (0.161 mL, 1.50 mmol) in N,N-dimethylacetamide (1.0 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 250B 3-(1,1-dioxido-4H-1,2,4-benzothiadiazin-3-yl)-4-hydroxy-1-[(3-methylbutyl)amino]quinolin-2(1H)-one The product of Example 250A (0.041 g, 0.097 mmol) in tetrahydrofuran (2.0 mL) and methanol (0.008 mL, 0.194 mmol) at 0° C. was treated with dropwise addition of a 2.0M solution of lithium borohydride in tetrahydrofuran (0.074 mL, 0.148 mmol). The reaction was stirred at 25° C. for 1 hour, acidified with 1 M hydrochloric acid to a pH of approximately 2-4, diluted with water (5.0 mL), and the resulting precipitate was collected by filtration and dried. The crude product was triturated with diethyl ether and filtered to give the title compound. The sodium salt of the title compound was prepared according to the procedure of Example 1D. $^1$H NMR (300 MHz, DMSO-d$_6$) δ ppm 0.92 (s, 3 H) 0.94 (s, 3 H) 1.45 (q, J=7.11 Hz, 2 H) 1.73 (m, 1 H) 2.79 (m, 2 H) 5.87 (t, J=6.80 Hz, 1 H) 7.07 (t, J=7.35 Hz, 1 H) 7.28 (t, J=8.46 Hz, 2 H) 7.55 (m, 3 H) 7.66 (d, J=7.72 Hz, 1 H) 8.08 (dd, J=7.91, 1.29 Hz, 1 H) 16.28 (s, 1 H). MS (ESI−) m/z 425 (M−H)$^-$.

EXAMPLE 251A 3-(1,1-dioxido-4H-1,2,4-benzothiadiazin-3-yl)-1-{[3-furylmethylene]amino}-4-hydroxyquinolin-2(1H)-one The product of Example 226D (0.070 g, 0.196 mmol) was reacted with 3-furaldehyde (0.147 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 251B 3-(1,1-dioxido-4H-1,2,4-benzothiadiazin-3-yl)-1-[(3-furylmethyl)amino]-4-hydroxyquinolin-2(1H)-one The product of Example 251A (0.028 g, 0.064 mmol) in tetrahydrofuran (1.3 mL) and methanol (0.005 mL, 0.128 mmol) at 0° C. was treated with dropwise addition of a 2.0M solution of lithium borohydride in tetrahydrofuran (0.050 mL, 0.100 mmol). The reaction was stirred at 25° C. for 1 hour, acidified with 1M hydrochloric acid to a pH of approximately 2-4, diluted with water (6.0 mL), and the resulting precipitate was collected by filtration and dried. The crude product was triturated with diethyl ether and filtered to give the title compound. The sodium salt of the title compound was prepared according to the procedure of Example 1D. $^1$H NMR (300 MHz, DMSO-d$_6$) δ ppm 3.79 (m, 2 H) 6.03 (t, J=6.80 Hz, 1 H) 6.65 (s, 1 H) 7.08 (t, J=7.35 Hz, 1 H) 7.27 (m, 3 H) 7.54 (m, 2 H) 7.68 (m, 3 H) 8.08 (d, J=7.72 Hz, 1 H) 16.26 (s, 1 H). MS (ESI−) m/z 435 (M−H)$^-$.

EXAMPLE 252A 3-(1,1-dioxido-4H-1,2,4-benzothiadiazin-3-yl)-1-{[2-furylmethylene]amino}-4-hydroxyquinolin-2(1H)-one The product of Example 226D (0.070 g, 0.196 mmol) was reacted with 2-furaldehyde (0.147 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 252B 3-(1,1-dioxido-4H-1,2,4-benzothiadiazin-3-yl)-1-[(2-furylmethyl)amino]-4-hydroxyquinolin-2(1H)-one The product of Example 252A (0.058 g, 0.134 mmol) in tetrahydrofuran (3.0 mL) and methanol (0.010 mL, 0.268 mmol) at 0° C. was treated with dropwise addition of a 2.0M solution of lithium borohydride in tetrahydrofuran (0.105 mL, 0.210 mmol). The reaction was stirred at 25° C. for 1 hour, acidified with 1 M hydrochloric acid to a pH of approximately 2-4, diluted with water (6.0 mL), and the resulting precipitate was collected by filtration and dried. The crude product was triturated with diethyl ether and filtered to give the title compound. The sodium salt of the title compound was prepared according to the procedure of Example 1D. $^1$H NMR (300 MHz, DMSO-d$_6$) δ ppm 4.03 (s, 2 H) 6.20 (t, J=6.07 Hz, 1 H) 6.35 (m, 1 H) 7.05 (t, J=7.72 Hz, 1 H) 7.29 (t, J=7.72 Hz, 3 H) 7.46 (t, J=7.72 Hz, 1 H) 7.56 (m, 2 H) 7.67 (d, J=7.72 Hz, 2 H) 8.06 (d, J=8.09 Hz, 1 H) 16.24 (s, 1 H). MS (ESI−) m/z 435 (M−H)$^-$.

EXAMPLE 253A 3-(1,1-dioxido-4H-1,2,4-benzothiadiazin-3-yl)-4-hydroxy-1-{[thien-2-ylmethylene]amino}quinolin-2(1H)-one The product of Example 226D (0.070 g, 0.196 mmol) was reacted with thiophene-2-carbaldehyde (0.166 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 253B 3-(1,1-dioxido-4H-1,2,4-benzothiadiazin-3-yl)-4-hydroxy-1-[(thien-2-ylmethyl)amino]quinolin-2(1H)-one The product of Example 253A (0.025 g, 0.055 mmol) in tetrahydrofuran (1.2 mL) and methanol (0.005 mL, 0.110 mmol) at 0° C. was treated with dropwise addition of a 2.0M solution of lithium borohydride in tetrahydrofuran (0.044 mL, 0.088 mmol). The reaction was stirred at 25° C. for 1 hour, acidified with 1M hydrochloric acid to a pH of approximately 2-4, diluted with water (5.0 mL), and the resulting precipitate was collected by filtration and dried. The crude product was triturated with diethyl ether and filtered to give the title compound. The sodium salt of the title compound was prepared according to the procedure of Example 1D. $^1$H NMR (300 MHz, DMSO-$d_6$) δ ppm 4.18 (s, 2 H) 6.16 (t, J=6.62 Hz, 1 H) 7.01 (dd, J=5.15, 3.31 Hz, 1 H) 7.07 (d, J=7.72 Hz, 1 H) 7.12 (m, 1 H) 7.29 (t, J=7.54 Hz, 2 H) 7.53 (m, 3 H) 7.67 (d, J=7.72 Hz, 2 H) 8.08 (d, J=8.09 Hz, 1 H) 16.24 (s, 1 H). MS (ESI-) m/z 451 (M-H)$^-$.

EXAMPLE 254A 3-(1,1-dioxido-4H-1,2,4-benzothiadiazin-3-yl)-4-hydroxy-1-{[1,3-thiazol-2-ylmethylene]amino}uinolin-2(1H)-one The product of Example 226D (0.060 g, 0.168 mmol) was reacted with 1,3-thiazole-2-carbaldehyde (0.132 mL, 1.5 mmol) in N,N-dimethylacetamide (1.0 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 254B 3-(1,1-dioxido-4H-1,2,4-benzothiadiazin-3-yl)-4-hydroxy-1-[(1,3-thiazol-2-ylmethyl)amino]quinolin-2(1H)-one The product of Example 254A (0.030 g, 0.066 mmol) in tetrahydrofuran (1.3 mL) and methanol (0.005 mL, 0.132 mmol) at 0° C. was treated with dropwise addition of a 2.0M solution of lithium borohydride in tetrahydrofuran (0.050 mL, 0.100 mmol). The reaction was stirred at 25° C. for 1 hour, acidified with 1 M hydrochloric acid to a pH of approximately 2-4, diluted with water (5.0 mL), and the resulting precipitate was collected by filtration and dried. The crude product was triturated with diethyl ether and filtered to give the title compound. The sodium salt of the title compound was prepared according to the procedure of Example 1D. $^1$H NMR (300 MHz, DMSO-$d_6$) δ ppm 4.36 (m, 2 H) 6.57 (t, J=6.62 Hz, 1 H) 7.09 (dd, J=13.60, 6.62 Hz, 2 H) 7.29 (t, J=7.54 Hz, 2 H) 7.56 (m, 2 H) 7.68 (m, 2 H) 7.97 (d, J=8.46 Hz, 1 H) 8.08 (d, J=7.35 Hz, 1 H) 16.20 (s, 1 H). MS (ESI-) m/z 452 (M-H)$^-$.

EXAMPLE 255A 3-(1,1-dioxido-4H-1,2,4-benzothiadiazin-3-yl)-1-{[(2-ethyl-3-methylbutylidene]amino}-4-hydroxyquinolin-2(1H)-one The product of Example 226D (0.070 g, 0.196 mmol) was reacted with 2-ethyl-3-methylbutanal (0.110 mL, 0.733 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 255B 3-(1,1-dioxido-4H-1,2,4-benzothiadiazin-3-yl)-1-{[2-ethyl-3-methylbutyl]amino}-4-hydroxyquinolin-2(1H)-one The product of Example 255A (0.031 g, 0.069 mmol) in tetrahydrofuran (1.5 mL) and methanol (0.006 mL, 0.138 mmol) at 0° C. was treated with dropwise addition of a 2.0M solution of lithium borohydride in tetrahydrofuran (0.054 mL, 0.108 mmol). The reaction was stirred at 25° C. for 1 hour, acidified with 1 M hydrochloric acid to a pH of approximately 2-4, diluted with water (5.0 mL), and the resulting precipitate was collected by filtration and dried. The crude product was chromatographed on silica gel eluted with 30% ethyl acetate/hexane to give the title compound. The sodium salt of the title compound was prepared according to the procedure of Example 1D. $^1$H NMR (300 MHz, DMSO-$d_6$) δ ppm 0.94 (m, 18 H) 1.36(dd, J=11.58, 5.33 Hz, 2 H) 1.47 (m, 4 H) 1.91 (s, 2 H) 3.32 (s, 4 H) 5.87 (t, J=7.54 Hz, 2 H) 6.98 (t, J=7.54 Hz, 1 H) 7.08 (m, 2 H) 7.26 (m, 4 H) 7.38 (t, J=8.27 Hz, 1 H) 7.56 (m, 4 H) 7.66 (m, 2 H). MS (ESI-) m/z 453 (M-H)$^-$.

EXAMPLE 256A 3-(1,1-dioxido-4H-1,2,4-benzothiadiazin-3-yl)-4-hydroxy-1-{[(4-methylphenyl)methylene]amino}quinolin-2(1H)-one The product of Example 226D (0.070 g, 0.196 mmol) was reacted with 4-methylbenzaldehyde (0.210 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 256B 3-(1,1-dioxido-4H-1,2,4-benzothiadiazin-3-yl)-4-hydroxy-1-[(4-methylbenzyl)amino]quinolin-2(1H)-one The product of Example 256A (0.065 g, 0.142 mmol) in tetrahydrofuran (3.0 mL) and methanol (0.012 mL, 0.284 mmol) at 0° C. was treated with dropwise addition of a 2.0M solution of lithium borohydride in tetrahydrofuran (0.111 mL, 0.222 mmol). The reaction was stirred at 25° C. for 1 hour, acidified with 1 M hydrochloric acid to a pH of approximately 2-4, diluted with water (8.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 2.32 (s, 3 H) 3.87 (s, 2 H) 6.03 (s, 1 H) 7.10 (m, 1 H) 7.21 (d, J=7.72 Hz, 2 H) 7.30 (t, J=7.17 Hz, 2 H) 7.42 (d, J=7.72 Hz, 2 H) 7.56 (t, J=8.64 Hz, 2 H) 7.70 (t, J=9.38 Hz, 2 H) 8.10 (d, J=7.72 Hz, 1 H) 16.28 (m, 1 H). MS (ESI-) m/z 459 (M-H)$^-$.

EXAMPLE 257A 3-(1,1-dioxido-4H-1,2,4-benzothiadiazin-3-yl)-4-hydroxy-1-{[(3-methylphenyl)methylene]amino}quinolin-2(1H)-one The product of Example 226D (0.070 g, 0.196 mmol) was reacted with 3-methylbenzaldehyde (0.210 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 257B 3-(1,1-dioxido-4H-1,2,4-benzothiadiazin-3-yl)-4-hydroxy-1-[(3-methylbenzyl)amino]quinolin-2(1H)-one The product of Example 257A (0.038 g, 0.083 mmol) in tetrahydrofuran (1.7 mL) and methanol (0.007 mL, 0.166 mmol) at 0° C. was treated with dropwise addition of a 2.0M solution of lithium borohydride in tetrahydrofuran (0.065 mL, 0.130 mmol). The reaction was stirred at 25° C. for 1 hour, acidified with 1 M hydrochloric acid to a pH of approximately 2-4, diluted with water (5.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 2.35 (s, 3 H) 3.87 (s, 2 H) 6.05 (t, J=6.62 Hz, 1 H) 7.12 (m, 2 H) 7.31 (m, 5 H) 7.56 (t, J=7.54 Hz, 2 H) 7.70 (dd, J=11.95, 7.91 Hz, 2 H) 8.10 (d, J=7.72 Hz, 1 H) 16.28 (s, 1 H). MS (ESI-) m/z 459 (M-H)$^-$.

EXAMPLE 258A 3-(1,1-dioxido-4H-1,2,4-benzothiadiazin-3-yl)-4-hydroxy-1-{[(2-methylphenyl)methylene]amino}quinolin-2(1H)-one The product of Example 226D (0.070 g, 0.196 mmol) was reacted with 2-methylbenzaldehyde (0.206 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 258B 3-(1,1-dioxido-4H-1,2,4-benzothiadiazin-3-yl)-4-hydroxy-1-[(2-methylbenzyl)amino]quinolin-2(1H)-one The product of Example 258A (0.026 g, 0.057 mmol) in tetrahydrofuran (1.2 mL) and methanol (0.005 mL, 0.114 mmol) at 0° C. was treated with dropwise addition of a 2.0M solution of lithium borohydride in tetrahydrofuran (0.045 mL, 0.090 mmol). The reaction was stirred at 25° C. for 1 hour, acidified with 1 M hydrochloric acid to a pH of approximately 2-4, diluted with water (5.0 mL), and the resulting precipitate was collected by filtration, washed with water and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 3.29 (s, 3 H) 3.97 (s, 2 H) 6.02 (t, J=6.62 Hz, 1 H) 7.08 (t, J=7.35 Hz, 1 H) 7.23 (s, 3 H) 7.29 (t, J=7.54 Hz, 2 H) 7.47 (m, 1 H) 7.55 (d, J=7.72 Hz, 2 H) 7.67 (m, 2 H) 8.10 (d, J=7.72 Hz, 1 H) 16.31 (s, 1 H). MS (ESI-) m/z 459 (M-H)$^-$.

EXAMPLE 259A 3-(1,1-dioxido-4H-1,2,4-benzothiadiazin-3-yl)-4-hydroxy-1-{[(3-methylthien-2-yl)methyl]amino}quinolin-2(1H)-one The product of Example 226D (0.060 g, 0.168 mmol) was reacted with 3-methylthiophene-2-carbaldehyde (0.180 mL, 1.50 mmol) in N,N-dimethylacetamide (1.0 mL) in a sealed tube at 135° C. for 45 minutes in a microwave reactor. The reaction mixture was cooled to 25° C. and concentrated. The resulting residue was triturated with ethyl acetate and filtered to give the title compound.

EXAMPLE 259B 3-(1,1-dioxido-4H-1,2,4-benzothiadiazin-3-yl)-4-hydroxy-1-{[(3-methylthien-2-yl)methyl]amino}quinolin-2(1H)-one The product of Example 259A (0.020 g, 0.043 mmol) in tetrahydrofuran (1.0 mL) and methanol (0.004 mL, 0.086 mmol) at 0° C. was treated with dropwise addition of a 2.0M solution of lithium borohydride in tetrahydrofuran (0.033 mL, 0.065 mmol). The reaction was stirred at 25° C. for 1 hour, acidified with 1M hydrochloric acid to a pH of approximately 2-4, diluted with water (5.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 2.42 (s, 3 H) 4.10 (brs, 2 H) 7.09 (d, J=5.15 Hz, 1 H) 7.19 (brs, 1 H) 7.37 (m, 3 H) 7.58 (m, 2 H) 7.72 (m, 2 H) 8.04 (m, 1 H) 8.14 (d, J=8.09 Hz, 1 H) 16.10 (brs, 1 H). MS (ESI-) m/z 465 (M-H)$^-$.

EXAMPLE 260A 3-(1,1-dioxido-4H-1,2,4-benzothiadiazin-3-yl)-4-hydroxy-1-{[(4-methoxyphenyl)methylene]amino}quinolin-2(1H)-one The product of Example 226D (0.070 g, 0.196 mmol) was reacted with 4-methoxybenzaldehyde (0.217 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 260B 3-(1,1-dioxido-4H-1,2,4-benzothiadiazin-3-yl)-4-hydroxy-1-[(4-methoxybenzyl)amino]quinolin-2(1H)-one The product of Example 260A (0.045 g, 0.095 mmol) in tetrahydrofuran (2.0 mL) and methanol (0.008 mL, 0.19 mmol) at 0° C. was treated with dropwise addition of a 2.0M solution of lithium borohydride in tetrahydrofuran (0.074 mL, 0.148 mmol). The reaction was stirred at 25° C. for 1 hour, acidified with 1M hydrochloric acid to a pH of approximately 2-4, diluted with water (5.0 mL), and the resulting precipitate was collected by filtration and dried. The crude product was triturated with methanol/diethyl ether and filtered to give the title compound. The sodium salt of the title compound was prepared according to the procedure of Example 1D. $^1$H NMR (300 MHz, DMSO-$d_6$) δ ppm 3.77 (s, 3 H) 3.82 (s, 2 H) 5.98 (s, 1 H) 6.95 (d, J=8.46 Hz, 2 H) 7.10 (t, J=7.54 Hz, 1 H) 7.30 (m, 2 H) 7.45 (d, J=8.46 Hz, 2 H) 7.56 (s, 2 H) 7.70 (t, J=9.38 Hz, 2 H) 8.10 (d, J=7.72 Hz, 1 H) 16.29 (m, 1 H). MS (ESI−) m/z 475 (M−H)−.

EXAMPLE 261A

1-{[(5-chlorothien-2-yl)methylene]amino}-3-(1,1-dioxido-4H-1,2,4-benzothiadiazin-3-yl)-4-hydroxyquinolin-2(1H)-one The product of Example 226D (0.060 g, 0.168 mmol) was reacted with 5-chlorothiophene-2-carbaldehyde (0.160 mL, 1.50 mmol) in N,N-dimethylacetamide (1.0 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 261B

1-{[(5-chlorothien-2-yl)methyl]amino}-3-(1,1-dioxido-4H-1,2,4-benzothiadiazin-3-yl)-4-hydroxyquinolin-2(1H)-one The product of Example 261A (0.048 g, 0.099 mmol) in tetrahydrofuran (2.0 mL) and methanol (0.008 mL, 0.198 mmol) at 0° C. was treated with dropwise addition of a 2.0M solution of lithium borohydride in tetrahydrofuran (0.074 mL, 0.149 mmol). The reaction was stirred at 25° C. for 1 hour, acidified with 1 M hydrochloric acid to a pH of approximately 2-4, diluted with water (6.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 4.10 (s, 2 H) 6.24 (t, J=6.43 Hz, 1 H) 7.19 (m, 1 H) 7.30 (m, 3 H) 7.43 (d, J=8.46 Hz, 1 H) 7.56 (m, 3 H) 7.67 (d, J=8.09 Hz, 1 H) 8.12 (d, J=7.72 Hz, 1 H) 15.95 (s, 1 H). MS (ESI−) m/z 485 (M−H)−.

EXAMPLE 262A

1-{[(2-chloro-1,3-thiazol-5-yl)methylene]amino}-3-(1,1-dioxido-4H-1,2,4-benzothiadiazin-3-yl)-4-hydroxyquinolin-2(1H)-one The product of Example 226D (0.070 g, 0.196 mmol) was reacted with 2-chloro-1,3-thiazole-5-carbaldehyde (0.157 mL, 1.06 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 262B

1-{[(2-chloro-1,3-thiazol-5-yl)methyl]amino}-3-(1,1-dioxido-4H-1,2,4-benzothiadiazin-3-yl)-4-hydroxyquinolin-2(1H)-one The product of Example 262A (0.040 g, 0.082 mmol) in tetrahydrofuran (1.7 mL) and methanol (0.007 mL, 0.164 mmol) at 0° C. was treated with dropwise addition of a 2.0M solution of lithium borohydride in tetrahydrofuran (0.064 mL, 0.128 mmol). The reaction was stirred at 25° C. for 1 hour, acidified with 1 M hydrochloric acid to a pH of approximately 2-4, diluted with water (5.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 4.22 (m, 2 H) 6.38 (t, J=6.25 Hz, 1 H) 7.07 (t, J=7.54 Hz, 1 H) 7.28 (t, J=8.09 Hz, 2 H) 7.59 (m, 5 H) 8.08 (dd, J=8.09, 1.47 Hz, 1 H) 16.19 (s, 1 H). MS (ESI−) m/z 486 (M−H)−.

EXAMPLE 263A

1-{1 [(3-bromophenyl)methylene]amino}-3-(1,1-dioxido-4H-1,2,4-benzothiadiazin-3-yl)-4-hydroxyquinolin-2(1H)-one The product of Example 226D (0.059 g, 0.165 mmol) was reacted with 3-bromobenzaldehyde (0.175 mL, 1.5 mmol) in N,N-dimethylacetamide (1.0 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 263B

1-[(3-bromobenzyl)amino]-3-(1,1-dioxido-4H-1,2,4-benzothiadiazin-3-yl)-4-hydroxyquinolin-2(1H)-one The product of Example 263A (0.048 g, 0.091 mmol) in tetrahydrofuran (2.0 mL) and methanol (0.008 mL, 0.182 mmol) at 0° C. was treated with dropwise addition of a 2.0M solution of lithium borohydride in tetrahydrofuran (0.130 mL, 0.260 mmol). The reaction was stirred at 25° C. for 1 hour, acidified with 1M hydrochloric acid to a pH of approximately 2-4, diluted with water (8.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 3.93 (brs, 2 H) 6.17 (t, J=6.99 Hz, 1 H) 7.09 (t, J=7.54 Hz, 1 H) 7.28 (d, J=8.09 Hz, 2 H) 7.37 (d, J=7.72 Hz, 1 H) 7.54 (m, 4 H) 7.68 (m, 2 H) 7.74 (t, J=1.65 Hz, 1 H) 8.09 (dd, J=7.91, 1.29 Hz, 1 H) 16.26 (s, 1 H). MS (ESI−) m/z 524 (M−H)−.

EXAMPLE 264A

1-{[(4-bromophenyl)methylene]amino}-3-(1,1-dioxido-4H-1,2,4-benzothiadiazin-3-yl)-4-hydroxyquinolin-2(1H)-one The product of Example 226D (0.060 g, 0.168 mmol) was reacted with 4-bromobenzaldehyde (0.278 mL, 1.50 mmol) in N,N-dimethylacetamide (1.0 mL) in a sealed tube at 110°

C. for 35 minutes in a microwave reactor. The reaction mixture was cooled to 25° C. and concentrated. The resulting residue was triturated with ethyl acetate and filtered to give the title compound.

EXAMPLE 264B

1-[(4-bromobenzyl)amino]-3-(1,1-dioxido-4H-1,2,4-benzothiadiazin-3-yl)-4-hydroxyquinolin-2(1H)-one The product of Example 264A (0.049 g, 0.094 mmol) in tetrahydrofuran (2.0 mL) and methanol (0.008 mL, 0.188 mmol) at 0° C. was treated with dropwise addition of a 2.0M solution of lithium borohydride in tetrahydrofuran (0.134 mL, 0.268 mmol). The reaction was stirred at 25° C. for 1 hour, acidified with 1M hydrochloric acid to a pH of approximately 2-4, diluted with water (6.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 3.92 (brs, 2 H) 7.09 (t, J=6.99 Hz, 1 H) 7.28 (m, 3 H) 7.54 (m, 5 H) 7.68 (d, J=8.09 Hz, 2 H) 8.09 (dd, J=8.09, 1.47 Hz, 1 H) 16.25 (brs, 1 H). MS (ESI−) m/z 524 (M−H)$^-$.

EXAMPLE 265A

1-{[(2-bromophenyl)methylene]amino}-3-(1,1-dioxido-4H-1,2,4-benzothiadiazin-3-yl)-4-hydroxyquinolin-2(1H)-one The product of Example 226D (0.060 g, 0.168 mmol) was reacted with 2-bromobenzaldehyde (0.175 mL, 1.50 mmol) in N,N-dimethylacetamide (1.0 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 265B

1-[(2-bromobenzyl)amino]-3-(1,1-dioxido-4H-1,2,4-benzothiadiazin-3-yl)-4-hydroxyquinolin-2(1H)-one The product of Example 265A (0.068 g, 0.129 mmol) in tetrahydrofuran (3.0 mL) and methanol (0.011 mL, 0.258 mmol) at 0° C. was treated with dropwise addition of a 2.0M solution of lithium borohydride in tetrahydrofuran (0.184 mL, 0.368 mmol). The reaction was stirred at 25° C. for 1 hour, acidified with 1M hydrochloric acid to a pH of approximately 2-4, diluted with water (8.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 4.11 (brs, 2 H) 6.24 (t, J=6.80 Hz, 1 H) 7.06 (t, J=7.54 Hz, 1 H) 7.28 (m, 3 H) 7.56 (m, 3 H) 7.67 (m, 4 H) 8.08 (dd, J=7.91, 1.29 Hz, 1 H) 16.27 (s, 1 H). (ESI−) m/z 524 (M−H)$^-$.

EXAMPLE 266A 3-(1,1-dioxido-4H-1,2,4-benzothiadiazin-3-yl)-4-hydroxy-1-{[pyridin-3-ylmethylene]amino}quinolin-2(1H)-one The product of Example 226D (0.070 g, 0.196 mmol) was reacted with nicotinaldehyde (0.168 mL, 1.78 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 266B 3-(1,1-dioxido-4H-1,2,4-benzothiadiazin-3-yl)-4-hydroxy-1-[(pyridin-3-ylmethyl)amino]quinolin-2(1H)-one The product of Example 266A (0.062 g, 0.14 mmol) in tetrahydrofuran (2.5 mL) and methanol (0.012 mL, 0.280 mmol) at 0° C. was treated with dropwise addition of a 2.0M solution of lithium borohydride in tetrahydrofuran (0.105 mL, 0.210 mmol). The reaction was stirred at 25° C. for 1 hour, acidified with 1M hydrochloric acid to a pH of approximately 2-4, diluted with water (8.0 mL), and the resulting precipitate was collected by filtration and dried. The crude product was triturated with methanol/diethyl ether and filtered to give the title compound. The sodium salt of the title compound was prepared according to the procedure of Example 1D. $^1$H NMR (300 MHz, DMSO-$d_6$) δ ppm 3.99 (s, 2 H) 6.22 (t, J=6.62 Hz, 1 H) 7.08 (t, J=7.35 Hz, 1 H) 7.27 (m, 2 H) 7.40 (dd, J=7.54, 4.96 Hz, 1 H) 7.54 (m, 2 H) 7.68 (d, J=8.09 Hz, 2 H) 7.93 (m, 1 H) 8.08 (dd, J=7.72, 1.47 Hz, 1 H) 8.51 (dd, J=4.78, 1.47 Hz). (ESI−) m/z 446 (M−H)

EXAMPLE 267A 3-({[3-(1,1-dioxido-4H-1,2,4-benzothiadiazin-3-yl)-4-hydroxy-2-oxoquinolin-1(2H)-yl]imino}methyl)benzonitrile The product of Example 226D (0.070 g, 0.196 mmol) was reacted with 3-formylbenzonitrile (0.080 mL, 0.610 mmol) in N,N-dimethylacetamide (1.2 mL) in a sealed tube at 110° C. for 35 minutes in a microwave reactor. The reaction mixture was cooled to 25° C. and concentrated. The resulting residue was triturated with ethyl acetate and filtered to give the title compound.

EXAMPLE 267B 3-({[3-(1,1-dioxido-4H-1,2,4-benzothiadiazin-3-yl)-4-hydroxy-2-oxoquinolin-1(2H)-yl]amino}methyl)benzonitrile The product of Example 267A (0.055 g, 0.117 mmol) in tetrahydrofuran (2.0 mL) and methanol (0.010 mL, 0.234 mmol) at 0° C. was treated with dropwise addition of a 2.0M solution of lithium borohydride in tetrahydrofuran (0.088 mL, 0.176 mmol). The reaction was stirred at 25° C. for 1 hour, acidified with 1M hydrochloric acid to a pH of approximately 2-4, diluted with water (6.0 mL), and the resulting precipitate was collected by filtration and dried. The crude product was triturated with dichloromethane/diethyl ether and filtered to give the title compound. The sodium salt of the title compound was prepared according to the procedure of Example 1D. $^1$H NMR (300 MHz, DMSO-$d_6$) δ ppm 4.01 (s, 2 H) 6.25 (t, J=6.80 Hz, 1 H) 7.08 (t, J=7.35 Hz, 1 H) 7.28 (m, 2 H) 7.56 (m, 3 H) 7.68 (dd, J=8.09, 2.21 Hz, 2 H) 7.79 (d, J=8.09 Hz, 1 H) 7.86 (d, J=7.72 Hz, 1 H) 7.99 (s, 1 H) 8.09 (dd, J=7.91, 1.29 Hz, 1 H). (ESI−) m/z 470 (M−H)$^-$.

EXAMPLE 268A methyl 3-[(2E)-2-benzylidenehydrazino]thiophene-2-carboxylate

A solution of methyl 3-hydrazinothiophene-2-carboxylate (Maybridge technical grade, 2.0 g, 0.11 mol) in ethanol (250 mL) at 25° C. was reacted with a solution of benzaldehyde (12.32 g, 0.11 mol) in ethanol (100 mL). The mixture was stirred at 25° C. for 1.5 hours and concentrated to yield 30 g of a white solid. HPLC/MS show a single peak with retention time of 2.35 min. and a M+1 peak of 261. $^1$H NMR (300 MHz, CDCl$_3$) δ ppm 3.85 (s, 3 H) 7.35 (m, 4 H) 7.64 (dd, J=8.09, 1.47 Hz, 2 H) 7.77 (s, 1 H) 10.10 (s, 1 H).

EXAMPLE 268B

Methyl 3-[2-benzylidene-1-(3-ethoxy-3-oxopropanoyl)hydrazino]thiophene-2-carboxylate The product of Example 185A (26.4 g, 0.101 mol) was reacted with ethyl chloromalonate (18.3 g, 0.121 mol) in toluene (400 mL), stirred at reflux for 4 hours, allowing HCl gas to bubble out of the condenser. The reaction was cooled to 25° C. and concentrated under vacuum. The resulting residue was chromatographed on silica gel eluting with 3:1 hexanes/ethyl acetate to give the title compound (37.1 g, 98%).

EXAMPLE 268C

Ethyl 7-hydroxy-5-oxo-4-{[phenylmethylene]amino}-4,5-dihydrothieno[3,2-b]pyridine-6-carboxylate A solution of the product of Example 268B (37.8 g, 0.101 mol) in ethanol (0.5 L) under nitrogen was reacted with sodium ethoxide in ethanol (21% by weight, 32.8 g, 0.104 mol) at room temperature. The mixture was slowly warmed to 50° C. and stirred for 1 hour at 40-50° C., cooled to 25° C., partitioned between ethyl acetate and water, and acidified to pH 4 with 1 M hydrochloric acid. The ethyl acetate layer was washed with brine, dried over anhydrous sodium sulfate, filtered, and concentrated to give the title compound (12.0 g, 35%). $^1$H NMR (300 MHz, CDCl$_3$) δ ppm 1.47 (t, J=7.17 Hz, 3 H) 4.52 (q, J=7.23 Hz, 2 H) 7.33 (d, J=5.15 Hz, 1 H) 7.50 (m, 3 H) 7.75 (d, J=5.52 Hz, 1 H) 7.88 (dd, J=7.72, 1.84 Hz, 2 H) 9.44 (s, 1 H) 14.16 (s, 1 H).

EXAMPLE 268D 4-amino-6-(1,1-dioxido-4H-1,2,4-benzothiadiazin-3-yl)-7-hydroxythieno[3,2-b]pyridin 5(4H)-one The product of Example 268C (2.29 g, 6.69 mmol) was reacted with 2-aminobenzenesulfonamide (1.15 g, 6.69 mmol) in toluene (60 mL), and stirred at reflux for 5 hours. The reaction was cooled to 25° C. and the resulting precipitate was collected by filtration and dried (1.95 g, 62%). The resulting solid (1.95 g, 4.2 mmol) was reacted with 10% aqueous KOH (60 mL) at reflux for 24 hours, cooled to 25° C. and acidified with concentrated hydrochloric acid to pH 2. The resulting solid was collected by filtration, washed repeatedly with water and dried to provide the title compound (1.5 g, 98%).(Any sodium salt made?) $^1$H NMR (300 MHz, DMSO-d$_6$) δ ppm 6.12 (s, 2 H) 7.49 (d, J=5.52 Hz, 1 H) 7.57 (m, 2 H) 7.79 (t, J=7.17 Hz, 1 H) 7.93 (d, J=7.72 Hz, 1 H) 8.34 (d, J=5.52 Hz, 1 H) 14.33 (s, 1 H) 14.68 (s, 1 H).

EXAMPLE 269A 6-(1,1-dioxido-4H-1,2,4-benzothiadiazin-3-yl)-7-hydroxy-4-{[2-methylpropylidene]amino}thieno[3,2-b]pyridin-5(4H)-one The product of Example 268D (0.10 g, 0.27 mmol) was reacted with 2-methyl-propionaldehyde (0.20 g, 2.77 mmol) in N,N-dimethylacetamide (3 mL) in a sealed tube at 135° C. for 40 minutes in a microwave reactor. The reaction was cooled to 25° C. and concentrated under vacuum. The resulting residue was triturated with a mixture of 25% ethyl acetate in hexanes and filtered to give the title compound as a solid (0.073 g, 65%). MS (APCI+) m/z 417 (M+H)$^+$.

EXAMPLE 269B 6-(1,1-Dioxido-4H-1,2,4-benzothiadiazin-3-yl)-7-hydroxy-4-(isobutylamino)thieno[3,2-b]pyridin-5(4H)-one The product of Example 269A (0.073 g, 0.18 mmol) in tetrahydrofuran (4 mL) and methanol (0.020 mL, 0.5 mmol) at 0° C. was treated dropwise with a 2.0M solution of lithium borohydride in tetrahydrofuran (0.20 mL, 0.40 mmol). The reaction was stirred at 25° C. for 1 hour, acidified with 1 M hydrochloric acid a pH of approximately 2-4, diluted with water (10 mL), and the resulting precipitate was collected by filtration and dried. The crude product was suspended in tetrahydrofuran (10 mL) and adsorbed onto approximately 5 g of silica gel and evaporated. The product was eluted with methanol in chloroform. Product containing fractions were combined and evaporated under vacuum to give the title compound (0.032 g, 42%). MS (ESI−) m/z 417 (M−H)$^-$. The sodium salt of the title compound was prepared according to the procedure of Example 1D. $^1$H NMR (300 MHz, DMSO-d$_6$) δ ppm 1.01 (d, J=6.62 Hz, 6 H) 1.88 (m, 1 H) 2.83 (s, 2 H) 6.60 (s, 1 H) 7.41 (d, J=4.04 Hz, 1 H) 7.55 (t, J=7.54 Hz, 1 H) 7.65 (d, J=8.46 Hz, 1 H) 7.77 (t, J=7.91 Hz, 1 H) 7.93 (d, J=7.72 Hz, 1 H) 8.35 (d, J=4.78 Hz, 1 H) 14.21 (s, 1 H) 14.82 (s, 1 H).

EXAMPLE 270A 6-(1,1-dioxido-4H-1,2,4-benzothiadiazin-3-yl)-7-hydroxy-4-{[(3S)-3-methylcyclopentylidene]amino}thieno[3,2-b]pyridin-5(4H)-one The product of Example 268D (0.065 g, 0.18 mmol) was reacted with (3S)-3-methylcyclopentanone (0.54 g, 5.6 mmol) in N,N-dimethylacetamide (2 mL) in a sealed tube at 135° C. for 90 minutes in a microwave reactor. The reaction was cooled to 25° C. and concentrated under vacuum. The resulting residue was triturated with ethyl acetate/hexane (2:1) and filtered to give the title compound.

EXAMPLE 270B 6-(1,1-dioxido-4H-1,2,4-benzothiadiazin-3-yl)-7-hydroxy-4-{[(3S)-3-methylcyclopentyl]amino}thieno[3,2-b]pyridin-5(4H)-one The product of Example 269A (0.060 g, 0.14 mmol) in tetrahydrofuran (4 mL) and methanol (0.012 mL, 0.3 mmol) at 0° C. was treated dropwise with a 2.0M solution of lithium borohydride in tetrahydrofuran (0.12 mL, 0.24 mmol). The reaction was stirred at 25° C. for 2 hour, acidified with 1 M hydrochloric acid a pH of approximately 2-4, diluted with water (20 mL), and the resulting precipitate was collected by filtration and dried. The crude product was chromatographed on silica gel with dichloromethane to dichloromethane/methanol (99:1). The sodium salt of the title compound was prepared according to the procedure of Example 1D. $^1$H NMR (300 MHz, DMSO-$d_6$) δ ppm 1.01 (m, 3 H) 1.69 (m, 7 H) 3.76 (m, 1 H) 5.75 (s, 1 H) 7.19 (m, 3 H) 7.54 (m, 1 H) 7.65 (d, J=7.72 Hz, 1 H) 7.74 (d, J=6.25 Hz, 1 H) 15.91 (s, 1 H). MS (ESI−) m/z 443 (M−H)$^-$.

EXAMPLE 271A

4-{[1-cyclopropylethylidene]amino}-6-(1,1-dioxido-4H-1,2,4-benzothiadiazin-3-yl)-7-hydroxythieno[3,2-b]pyridin-5(4H)-one The product of Example 268D (0.065 g, 0.18 mmol) was reacted with 1-cyclopropylethanone (0.54 g, 6.4 mmol) in N,N-dimethylacetamide (2 mL) in a sealed tube at 135° C. for 120 minutes in a microwave reactor. The reaction was cooled to 25° C. and concentrated under vacuum. The resulting residue was triturated with ethyl acetate/hexane (2:1) and filtered to give the title compound.

EXAMPLE 271B

4-{[1-cyclopropylethyl]amino}-6-(1,1-dioxido-4H-1,2,4-benzothiadiazin-3-yl)-7-hydroxythieno[3,2-b]pyridin-5(4H)-one The product of Example 269A (0.058 g, 0.14 mmol) in tetrahydrofuran (4 mL) and methanol (0.012 mL, 0.3 mmol) at 0° C. was treated dropwise with a 2.0M solution of lithium borohydride in tetrahydrofuran (0.12 mL, 0.24 mmol). The reaction was stirred at 25° C. for 2 hour, acidified with 1 M hydrochloric acid a pH of approximately 2-4, diluted with water (20 mL), and the resulting precipitate was collected by filtration and dried. The crude product was chromatographed on silica gel with dichloromethane to dichloromethane/methanol (99:1) to give the title compound. The sodium salt of the title compound was prepared according to the procedure of Example 1D. $^1$H NMR (300 MHz, DMSO-$d_6$) δ ppm 1.05 (m, 8 H) 2.44 (m, 1 H) 5.81 (d, J=2.57 Hz, 1 H) 7.23 (m, 3 H) 7.53 (m, 1 H) 7.64 (d, 1=7.72 Hz, 1 H) 7.74 (s, br, 1 H) 15.95 (s, 1 H). MS (ESI−) m/z 429 (M−H)$^-$.

EXAMPLE 272A

4-[(butylideneamino]-6-(1,1-dioxido-4H-1,2,4-benzothiadiazin-3-yl)-7-hydroxythieno[3,2-b]pyridin-5(4H)-one The product of Example 268D (0.10 g, 0.27 mmol) was reacted with butyraldehyde (0.5 g, 6.9 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.075 g, 65%).

EXAMPLE 272B 4-(butylamino)-6-(1,1-dioxido-4H-1,2,4-benzothiadiazin-3-yl)-7-hydroxythieno[3,2-b]pyridin-5(4H)-one The product of Example 269A (0.075 g, 0.18 mmol) in tetrahydrofuran (4 mL) and methanol (0.029 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-$d_6$) δ ppm 0.90 (t, J=7.17 Hz, 3 H) 1.39 (dd, J=15.08, 7.35 Hz, 2 H) 1.50 (m, 2 H) 3.02 (t, J=6.43 Hz, 2 H) 6.65 (s, 1 H) 7.43 (d, J=5.15 Hz, 1 H) 7.55 (t, J=7.72 Hz, 1 H) 7.64 (d, J=8.09 Hz, 1 H) 7.77 (t, J=7.72 Hz, 1 H) 7.92 (d, J=8.09 Hz, 1 H) 8.34 (d, J=5.15 Hz, 1 H) 14.21 (s, 1 H) 14.83 (s, 1 H). MS (ESI−) m/z 417 (M−H)$^-$.

EXAMPLE 273A 6-(1,1-dioxido-4H-1,2,4-benzothiadiazin-3-yl)-4-{[2-ethylbutylidene]amino}-7-hydroxythieno[3,2-b]pyridin-5(4H)-one The product of Example 268D (0.10 g, 0.27 mmol) was reacted with 2-ethylbutanal (0.5 g, 5.2 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.082 g, 68%).

EXAMPLE 273B 6-(1,1-dioxido-4H-1,2,4-benzothiadiazin-3-yl)-4-[(2-ethylbutyl)amino]-7-hydroxythieno[3,2-b]pyridin-5(4H)-one The product of Example 269A (0.82 g, 0.18 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-$d_6$) δ ppm 0.90 (t, J=7.17 Hz, 6 H) 1.45 (m, 5 H) 2.94 (m, J=4.78 Hz, 2 H) 6.53 (s, 1 H) 7.38 (d, J=5.52 Hz, 1 H) 7.55 (t, J=7.54 Hz, 1 H) 7.65 (d, J=8.09 Hz, 1 H) 7.77 (t, J=8.46 Hz, 1 H) 7.92 (d, J=7.72 Hz, 1 H) 8.36 (d, J=5.52 Hz, 1 H) 14.19 (s, 1 H) 14.83 (s, 1 H). MS (ESI−) m/z 445(M−H)$^-$.

EXAMPLE 274A 6-(1,1-dioxido-4H-1,2,4-benzothiadiazin-3-yl)-7-hydroxy-4-[pentylideneamino]thieno[3,2-b]pyridin-5(4H)-one The product of Example 268D (0.10 g, 0.27 mmol) was reacted with pentanal (0.5 g, 5.0 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.081 g, 70%).

EXAMPLE 274B 6-(1,1-dioxido-4H-1,2,4-benzothiadiazin-3-yl)-7-hydroxy-4-(pentylamino)thieno[3,2-b]pyridin-5(4H)-one The product of Example 269A (0.081 g, 0.19 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 1% methanol in chloroform to give the title compound. The sodium salt of the title compound was prepared according to the procedure of Example 1D. $^1$H NMR (300 MHz, DMSO-$d_6$) δ ppm 0.88 (t, J=6.99 Hz, 3 H) 1.34 (m, 4 H) 1.53 (m, 2 H) 3.01 (t, J=6.62 Hz, 2 H) 6.64 (s, 1 H) 7.43 (d, J=5.15 Hz, 1 H) 7.55 (t, J=7.72 Hz, 1 H) 7.64 (d, J=8.09 Hz, 1 H) 7.78 (t, J=7.91 Hz, 1 H) 7.93 (d, J=8.09 Hz, 1 H) 8.35 (d, J=5.52 Hz, 1 H) 14.21 (s, 1 H) 14.81 (s, 1 H). MS (ESI–) m/z 431 (M–H)⁻.

EXAMPLE 275A 6-(1,1-dioxido-4H-1,2,4-benzothiadiazin-3-yl)-7-hydroxy-4-{[3-methylbutylidene]amino}thieno[3,2-b]pyridin-5(4H)-one The product of Example 268D (0.10 g, 0.27 mmol) was reacted with 3-methylbutanal (0.5 g, 5.8 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.083 g, 71%).

EXAMPLE 275B 6-(1,1-dioxido-4H-1,2,4-benzothiadiazin-3-yl)-7-hydroxy-4-[(3-methylbutyl)amino]thieno[3,2-b]pyridin-5(4H)-one The product of Example 269A (0.083 g, 0.19 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1M hydrochloric acid to a pH of approximately 2-4, diluted with water (15 mL), and the resulting precipitate was collected by filtration and dried. The crude product was chromatographed on silica gel with 1% methanol in chloroform to give the title compound. The sodium salt of the title compound was prepared according to the procedure of Example 1D. $^1$H NMR (300 MHz, DMSO-$d_6$) δ ppm 0.90 (d, J=6.62 Hz, 6 H) 1.44 (q, J=7.11 Hz, 2 H) 1.70 (m, 1 H) 3.03 (t, J=6.99 Hz, 2 H) 6.61 (s, 1 H) 7.43 (d, J=5.15 Hz, 1 H) 7.55 (t, J=7.54 Hz, 1 H) 7.65 (d, J=8.09 Hz, 1 H) 7.77 (t, J=7.72 Hz, 1 H) 7.92 (d, J=7.72 Hz, 1 H) 8.35 (d, J=5.52 Hz, 1 H) 14.20 (s, 1 H) 14.81 (s, 1 H). MS (ESI–) m/z 431 (M–H)⁻.

EXAMPLE 276A

4-{[3,3-dimethylbutylidene]amino}-6-(1,1-dioxido-4H-1,2,4-benzothiadiazin-3-yl)-7-hydroxythieno[3,2-b]pyridin-5(4H)-one The product of Example 268D (0.10 g, 0.27 mmol) was reacted with 3,3-dimethylbutanal (0.5 g, 5.0 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.072 g, 77%).

EXAMPLE 276B

4-[(3,3-dimethylbutyl)amino]-6-(1,1-dioxido-4H-1,2,4-benzothiadiazin-3-yl)-7-hydroxythieno[3,2-b]pyridin-5(4H)-one The product of Example 269A (0.072 g, 0.21 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-$d_6$) δ ppm 0.89 (s, 9 H) 1.49 (dd, J=9.56, 6.99 Hz, 2 H) 3.03 (m, 2 H) 6.61 (s, 1 H) 7.43 (d, J=5.52 Hz, 1 H) 7.55 (t, J=7.54 Hz, 1 H) 7.66 (d, J=7.72 Hz, 1 H) 7.77 (m, 1 H) 7.92 (d, J=8.09 Hz, 1 H) 8.35 (d, J=5.52 Hz, 1 H) 14.19 (s, 1 H) 14.83 (s, 1 H). MS (ESI–) m/z 445 (M–H)⁻.

EXAMPLE 277A 6-(1,1-dioxido-4H-1,2,4-benzothiadiazin-3-yl)-7-hydroxy-4-{[(3-methylphenyl)methylene]amino}thieno[3,2-b]pyridin-5(4H)-one The product of Example 268D (0.10 g, 0.27 mmol) was reacted with 3-methylbenzaldehyde (0.5 g, 4.2 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.092, 73%).

EXAMPLE 277B 6-(1,1-dioxido-4H-1,2,4-benzothiadiazin-3-yl)-7-hydroxy-4-[(3-methylbenzyl)amino]thieno[3,2-b]pyridin-5(4H)-one The product of Example 269A (0.090 g, 0.2 mmol) in tetrahydrofuran (4 mL) and methanol (0.015 mL, 0.4 mmol) at 0° C. was treated dropwise with a 2.0M solution of lithium borohydride in tetrahydrofuran (0.150 mL, 0.3 mmol). The reaction was stirred at 25° C. for 1 hour, acidified with 1M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-$d_6$) δ ppm 2.29 (s, 3 H) 4.15 (s, 2 H) 6.94 (s, 1 H) 7.22 (m, 4 H) 7.30 (d, J=5.15 Hz, 1 H) 7.56 (t, J=7.72 Hz, 1 H) 7.68 (d, J=8.46 Hz, 1 H) 7.79 (t, J=6.99 Hz, 1 H) 7.94 (d, J=7.72 Hz, 1 H) 8.24 (d, J=5.15 Hz, 1 H) 14.26 (s, 1 H) 14.84 (s, 1 H). MS (ESI–) m/z 465(M–H)⁻.

EXAMPLE 278A 6-(1,1-dioxido-4H-1,2,4-benzothiadiazin-3-yl)-7-hydroxy-4-{[(2-methylphenyl)methylene]amino}thieno[3,2-b]pyridin-5(4H)-one The product of Example 268D (0.10 g, 0.27 mmol) was reacted with 2-methylbenzaldehyde (0.5 g, 4.2 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.072 g, 57%).

EXAMPLE 278B 6-(1,1-dioxido-4H-1,2,4-benzothiadiazin-3-yl)-7-hydroxy-4-[(2-methylbenzyl)amino]thieno[3,2-b]pyridin-5(4H)-one The product of Example 269A (0.072 g, 0.15 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-$d_6$) δ ppm 2.45 (s, 3 H) 4.21 (s, 2 H) 6.92 (s, 1 H) 7.15 (m, 5 H) 7.56 (t, J=7.72 Hz, 1 H) 7.67 (d, J=8.09 Hz, 1 H) 7.79 (t, J=7.72 Hz, 1 H) 7.94 (d, J=7.72 Hz, 1 H) 8.17 (d, J=5.52 Hz, 1 H) 14.22 (s, 1 H) 14.82 (s, 1 H). MS (ESI–) m/z 465 (M–H)$^-$.

EXAMPLE 279A 6-(1,1-dioxido-4H-1,2,4-benzothiadiazin-3-yl)-7-hydroxy-4-{[(4-methylphenyl)methylene]amino}thieno[3,2-b]pyridin-5(4 h)-one The product of Example 268D (0.10 g, 0.27 mmol) was reacted with 4-methylbenzaldehyde (0.5 g, 4.2 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.10 g, 81%).

EXAMPLE 279B 6-(1,1-dioxido-4H-1,2,4-benzothiadiazin-3-yl)-7-hydroxy-4-[(4-methylbenzyl)amino]thieno[3,2-b]pyridin-5(4H)-one The product of Example 269A (0.10 g, 0.22 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-d6) δ ppm 2.27 (s, 3 H) 4.14 (s, 2 H) 6.92 (s, 1 H) 7.13 (d, J=8.09 Hz, 2 H) 7.28 (d, J=2.94 Hz, 1 H) 7.30 (d, J=5.88 Hz, 2 H) 7.56 (t, J=7.72 Hz, 1 H) 7.67 (d, J=8.46 Hz, 1 H) 7.79 (t, J=7.72 Hz, 1 H) 7.94 (d, J=7.72 Hz, 1 H) 8.22 (d, J=5.52 Hz, 1 H) 14.21 (s, 1 H) 14.82 (s, 1 H). MS (ESI–) m/z 465 (M–H)$^-$.

EXAMPLE 280A 6-(1,1-dioxido-4H-1,2,4-benzothiadiazin-3-yl)-7-hydroxy-4-{[3-methylbut-2-enylidene]amino}thieno[3,2-b]pyridin-5(4H)-one The product of Example 268D (0.10 g, 0.27 mmol) was reacted with 3-methylbut-2-enal (0.5 g, 5.9 mmol) in N,N-dimethylacetamide (3 mL) in a sealed tube at 130° C. for 40 minutes in a microwave reactor. The reaction was cooled to 25° C. and concentrated under vacuum. The resulting residue was triturated with diethyl ether and filtered to give the title compound (0.093 g, 80%).

EXAMPLE 280B 6-(1,1-dioxido-4H-1,2,4-benzothiadiazin-3-yl)-7-hydroxy-4-[(3-methylbut-2-enyl)amino]thieno[3,2-b]pyridin-5(4H)-one The product of Example 269A (0.093 g, 0.22 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in choroform to give the title compound. The sodium salt of the title compound was prepared according to the procedure of Example 1D. $^1$H NMR (300 MHz, DMSO-$d_6$) δ ppm 1.51 (s, 3 H) 1.61 (s, 3 H) 3.64 (d, J=6.99 Hz, 2 H) 5.32 (t, J=8.09 Hz, 1 H) 6.65 (s, 1 H) 7.43 (d, J=5.52 Hz, 1 H) 7.55 (t, J=7.54 Hz, 1 H) 7.64 (d, J=8.46 Hz, 1 H) 7.78 (t, J=7.17 Hz, 1 H) 7.92 (d, J=7.72 Hz, 1 H) 8.32 (m, 1 H) 14.21 (s, 1 H) 14.82 (s, 1 H). MS (ESI–) m/z 429 (M–H)$^-$.

EXAMPLE 281A 6-(1,1-dioxido-4H-1,2,4-benzothiadiazin-3-yl)-7-hydroxy-4-[propylideneamino]thieno[3,2-b]pyridin-5(4H)-one The product of Example 268D (0.10 g, 0.27 mmol) was reacted with propionaldehyde (0.5 g, 8.6 mmol) in N,N-dimethylacetamide (3 mL) in a sealed tube at 120° C. for 90 minutes in a microwave reactor. The reaction was cooled to 25° C. and concentrated under vacuum. The resulting residue was triturated with diethyl ether and filtered to give the title compound (0.073 g, 67%).

EXAMPLE 281B 6-(1,1-dioxido-4H-1,2,4-benzothiadiazin-3-yl)-7-hydroxy-4-(propylamino)thieno[3,2-b]pyridin-5(4H)-one The product of Example 269A (0.073 g, 0.18 mmol) in tetrahydrofuran (4 mL) and methanol (0.020 mL, 0.5 mmol)

at 0° C. was treated dropwise with a 2.0M solution of lithium borohydride in tetrahydrofuran (0.150 mL, 0.3 mmol). The reaction was stirred at 25° C. for 1 hour, acidified with 1M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. 1H NMR (300 MHz, DMSO-$d_6$) δ ppm 0.95 (t, J=7.35 Hz, 3 H) 1.54 (m, 2 H) 2.99 (t, J=6.99 Hz, 2 H) 6.66 (s, 1 H) 7.44 (d, J=5.15 Hz, 1 H) 7.55 (t, J=7.54 Hz, 1 H) 7.64 (d, J=8.09 Hz, 1 H) 7.78 (t, J=7.17 Hz, 1 H) 7.93 (d, J=7.72 Hz, 1 H) 8.35 (d, J=5.15 Hz, 1 H) 14.20 (s, 1 H) 14.81 (s, 1 H). MS (ESI−) m/z 403 (M−H)−.

EXAMPLE 282A 6-(1,1-dioxido-4H-1,2,4-benzothiadiazin-3-yl)-7-hydroxy-4-{[pyridin-4-ylmethylene]amino}thieno[3,2-b]pyridin-5(4H)-one The product of Example 268D (0.10 g, 0.27 mmol) was reacted with isonicotinaldehyde (0.5 g, 4.7 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.093 g, 76%).

EXAMPLE 282B 6-(1,1-dioxido-4H-1,2,4-benzothiadiazin-3-yl)-7-hydroxy-4-[(pyridin-4-ylmethyl)amino]thieno[3,2-b]pyridin-5(4H)-one The product of Example 269A (0.093 g, 0.21 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. $^1$H NMR (300 MHz, DMSO-$d_6$) δ ppm 4.39 (s, 2 H) 7.34 (d, J=5.15 Hz, 1 H) 7.42 (s, 1 H) 7.56 (t, J=7.72 Hz, 1 H) 7.63 (d, J=8.09 Hz, 1 H) 7.79 (m, J=7.72, 7.72 Hz, 3 H) 7.94 (d, J=7.72 Hz, 1 H) 8.27 (d, J=5.15 Hz, 1 H) 8.52 (d, J=6.62 Hz, 2 H) 14.15 (s, 1 H) 14.87 (s, 1 H). MS (ESI−) m/z 452 (M−H)−.

EXAMPLE 283A 6-(1,1-dioxido-4H-1,2,4-benzothiadiazin-3-yl)-7-hydroxy-4-{[pyridin-3-ylmethylene]amino}thieno[3,2-b]pyridin-5(4H)-one The product of Example 268D (0.10 g, 0.27 mmol) was reacted with nicotinaldehyde (0.5 g, 4.7 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.102 g, 84%).

EXAMPLE 283B 6-(1,1-dioxido-4H-1,2,4-benzothiadiazin-3-yl)-7-hydroxy-4-[(pyridin-3-ylmethyl)amino]thieno[3,2-b]pyridin-5(4H)-one The product of Example 269A (0.102 g, 0.23 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. 1H NMR (300 MHz, DMSO-$d_6$) δ ppm 4.33 (s, 2 H) 7.28 (d, J=5.52 Hz, 1 H) 7.36 (s, 1 H) 7.61 (m, 3 H) 7.79 (t, J=7.17 Hz, 1 H) 7.94 (d, J=8.09 Hz, 1 H) 8.20 (d, J=11.03 Hz, 1 H) 8.27 (d, J=5.51 Hz, 1 H) 8.49 (d, J=5.51 Hz, 1 H) 8.64 (s, 1 H) 14.14 (s, 1 H) 14.83 (s, 1 H). MS (ESI−) m/z 452 (M−H)−.

EXAMPLE 284A 6-(1,1-dioxido-4H-1,2,4-benzothiadiazin-3-yl)-7-hydroxy-4-{[pyridin-2-ylmethylene]amino}thieno[3,2-b]pyridin-5(4H)-one The product of Example 268D (0.10 g, 0.27 mmol) was reacted with 2-pyridinecarboxaldehyde (0.5 g, 4.7 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.071 g, 58%).

EXAMPLE 284B 6-(1,1-dioxido-4H-1,2,4-benzothiadiazin-3-yl)-7-hydroxy-4-[(pyridin-2-ylmethyl)amino]thieno[3,2-b]pyridin-5(4H)-one The product of Example 269A (0.071 g, 0.16 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 5% methanol in chloroform to give the title compound. The sodium salt of the title compound was prepared according to the procedure of Example 1D. $^1$H NMR (300 MHz, DMSO-$d_6$) δ ppm 4.65 (s, 2 H) 7.25 (d, J=5.15 Hz, 1 H) 7.45 (s, 1 H) 7.59 (m, 3 H) 7.78 (t, J=7.91 Hz, 1 H) 7.93 (d, J=7.72 Hz, 2 H) 8.16 (t, J=7.72 Hz, 1 H) 8.24 (d, J=5.15 Hz, 1 H) 8.72 (d, J=5.51 Hz, 1 H) 14.10 (s, 1 H) 14.87 (s, 1 H). MS (ESI−) m/z 452(M−H)−.

EXAMPLE 285A 6-(1,1-dioxido-4H-1,2,4-benzothiadiazin-3-yl)-7-hydroxy-4-{[(3-methoxyphenyl)methylene]amino}thieno[3,2-b]pyridin-5(4H)-one The product of Example 268D (0.10 g, 0.27 mmol) was reacted with 3-methoxybenzaldehyde (0.5 g, 3.7 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.093 g 72%).

EXAMPLE 285B 6-(1,1-dioxido-4H-1,2,4-benzothiadiazin-3-yl)-7-hydroxy-4-[(3-methoxybenzyl)amino]thieno[3,2-b]pyridin-5(4H)-one The product of Example 269A (0.093 g, 0.19 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to a pH of approximately 2-4, diluted with water (15 mL), and the resulting precipitate was collected by filtration and dried. The crude product was chromatographed on silica gel with 1% methanol in chloroform to give the title compound. The sodium salt of the title compound was prepared according to the procedure of Example 1D. 1H NMR (300 MHz, DMSO-$d_6$) δ ppm 3.73 (s, 3 H) 4.17 (s, 2 H) 6.84 (m, 1 H) 6.98 (m, 3 H) 7.22 (d, J=8.09 Hz, 1 H) 7.26 (d, J=5.15 Hz, 1 H) 7.56 (t, J=7.17 Hz, 1 H) 7.67 (d, J=8.09 Hz, 1 H) 7.79 (t, J=8.46 Hz, 1 H) 7.94 (d, J=7.72 Hz, 1 H) 8.22 (d, J=5.15 Hz, 1 H) 14.21 (s, 1 H) 14.84 (s, 1 H). MS (ESI−) m/z 481 (M−H)−.

EXAMPLE 286A 6-(1,1-dioxido-4H-1,2,4-benzothiadiazin-3-yl)-4-{[3-furylmethylene]amino}-7-hydroxythieno[3,2-b]pyridin-5(4H)-one The product of Example 268D (0.10 g, 0.27 mmol) was reacted with 3-furaldehyde (0.5 g, 5.2 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.103 g, 87%).

EXAMPLE 286B 6-(1,1-dioxido-4H-1,2,4-benzothiadiazin-3-yl)-4-[(3-furylmethyl)amino]-7-hydroxythieno[3,2-b]pyridin-5(4H)-one The product of Example 269A (0.103 g, 0.23 mmol) in tetrahydrofuran (4 mL) and methanol (0.030 mL, 0.8 mmol) at 0° C. was treated dropwise with a 2.0M solution of lithium borohydride in tetrahydrofuran (0.200 mL, 0.4 mmol). The reaction was stirred at 25° C. for 1 hour, acidified with 1M hydrochloric acid to a pH of approximately 2-4, diluted with water (15 mL), and the resulting precipitate was collected by filtration and dried. The crude product was chromatographed on silica gel with 2% methanol in chloroform to give the title compound. The sodium salt of the title compound was prepared according to the procedure of Example 1D. 1H NMR (300 MHz, DMSO-$d_6$) δ ppm 4.08 (s, 2 H) 6.59 (s, 1 H) 6.95 (s, 1 H) 7.32 (d, J=5.15 Hz, 1 H) 7.58 (m, 3 H) 7.66 (d, J=8.09 Hz, 1 H) 7.79 (t, J=8.46 Hz, 1 H) 7.93 (d, J=7.72 Hz, 1 H) 8.24 (d, J=5.52 Hz, 1 H) 14.21 (s, 1 H) 14.83 (s, 1 H). MS (ESI−) m/z 441 (M−H)−.

EXAMPLE 287A 3-({[6-(1,1-dioxido-4H-1,2,4-benzothiadiazin-3-yl)-7-hydroxy-5-oxothieno[3,2-b]pyridin-4(5H)-yl]imino}methyl)benzonitrile The product of Example 268D (0.100 g, 0.27 mmol) was reacted with 3-formylbenzonitrile (0.362 g, 2.75 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.088 g, 69%).

EXAMPLE 287B 3-({[6-(1,1-dioxido-4H-1,2,4-benzothiadiazin-3-yl)-7-hydroxy-5-oxothieno[3,2-b]pyridin-4(5H)-yl]amino}methyl)benzonitrile The product of Example 269A (0.088 g, 0.19 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1 M hydrochloric acid to pH of approximately 2-4, diluted with water (15 mL), and the resulting precipitate was collected by filtration and dried. The crude product was chromatographed on silica gel with 1% methanol in chloroform to give the title compound. The sodium salt of the title compound was prepared according to the procedure of Example 1D. $^1$H NMR (300 MHz, DMSO-$d_6$) δ ppm 4.26 (s, 2 H) 7.21 (s, 1 H) 7.29 (d, J=5.15 Hz, 1 H) 7.55 (m, 2 H) 7.65 (d, J=8.09 Hz, 1 H) 7.78 (m, 3 H) 7.94 (m, 2 H) 8.22 (d, J=5.52 Hz, 1 H) 14.19 (s, 1 H) 14.83 (s, 1 H). MS (ESI−) m/z 476(M−H)−.

EXAMPLE 288A 6-(1,1-dioxido-4H-1,2,4-benzothiadiazin-3-yl)-7-hydroxy-4-{[thien-3-ylmethylene]amino}thieno[3,2-b]pyridin-5(4H)-one The product of Example 268D (0.10 g, 0.27 mmol) was reacted with thiophene-3-carbaldehyde (0.5 g, 4.5 mmol) in N,N-dimethylacetamide (3 mL) in a sealed tube at 135° C. for 60 minutes in a microwave reactor. The reaction was cooled to 25° C. and concentrated under vacuum. The resulting residue was triturated with diethyl ether and filtered to give the title compound (0.077 g, 63%).

EXAMPLE 288B 6-(1,1-dioxido-4H-1,2,4-benzothiadiazin-3-yl)-7-hydroxy-4-[(thien-3-ylmethyl)amino]thieno[3,2-b]pyridin-5(4H)-one The product of Example 269A (0.077 g, 0.17 mmol) in tetrahydrofuran (4 mL) and methanol (0.020 mL, 0.5 mmol) at 0° C. was treated dropwise with a 2.0M solution of lithium borohydride in tetrahydrofuran (0.150 mL, 0.3 mmol). The reaction was stirred at 25° C. for 1 hour, acidified with 1M hydrochloric acid to pH of approximately 2-4, diluted with water (25 mL), and the resulting precipitate was collected by filtration and dried. The crude product was chromatographed on silica gel with 2% methanol in chloroform to give the title compound. The sodium salt of the title compound was prepared according to the procedure of Example 1D. 1H NMR (300 MHz, DMSO-d$_6$) δ ppm 4.22 (s, 2 H) 7.01 (s, 1 H) 7.20 (dd, J=4.96, 1.29 Hz, 1 H) 7.23 (d, J=5.52 Hz, 1 H) 7.40 (d, J=1.84 Hz, 1 H) 7.48 (dd, J=4.78, 2.94 Hz, 1 H) 7.56 (t, J=7.17 Hz, 1 H) 7.67 (d, J=7.72 Hz, 1 H) 7.79 (t, J=7.72 Hz, 1 H) 7.94 (d, J=7.72 Hz, 1 H) 8.21 (d, J=5.15 Hz, 1 H) 14.21 (s, 1 H) 14.82 (s, 1 H). MS (ESI−) m/z 457 (M−H)−.

EXAMPLE 289A 4-(cyclobutylideneamino)-6-(1,1-dioxido-4H-1,2,4-benzothiadiazin-3-yl)-7-hydroxythieno[3,2-b]pyridin-5(4H)-one The product of Example 268D (0.10 g, 0.27 mmol) was reacted with cyclobutanone (1.0 g, 14.3 mmol) in N,N-dimethylacetamide (2 mL) in a sealed tube at 135° C. for 60 minutes in a microwave reactor. The reaction was cooled to 25° C. and concentrated under vacuum. The resulting residue was triturated with diethyl ether and filtered to give the title compound (0.086 g 77%).

EXAMPLE 289B 4-(cyclobutylamino)-6-(1,1-dioxido-4H-1,2,4-benzothiadiazin-3-yl)-7-hydroxythieno[3,2-b]pyridin-5(4H)-one The product of Example 269A (0.077 g, 0.21 mmol) in tetrahydrofuran (4 mL) and methanol (0.030 mL, 0.8 mmol) at 0° C. was treated dropwise with a 2.0M solution of lithium borohydride in tetrahydrofuran (0.200 mL, 0.4 mmol). The reaction was stirred at 25° C. for 1 hour, acidified with 1M hydrochloric acid to pH of approximately 2-4, diluted with water (15 mL), and the resulting precipitate was collected by filtration and dried. The crude product was chromatographed on silica gel with 1% methanol in chloroform to give the title compound. The sodium salt of the title compound was prepared according to the procedure of Example 1D. $^1$H NMR (300 MHz, DMSO-d$_6$) δ ppm 1.81 (m, 6 H) 3.85 (m, 1 H) 6.84 (s, 1 H) 7.49 (d, J=5.15 Hz, 1 H) 7.55 (t, J=7.91 Hz, 1 H) 7.62 (d, J=8.09 Hz, 1 H) 7.78 (t, J=7.91 Hz, 1 H) 7.93 (d, J=8.09 Hz, 1 H) 8.33 (d, J=5.15 Hz, 1 H) 14.21 (s, 1 H) 14.82 (s, 1 H). MS (ESI−) m/z 415 (M−H)−.

EXAMPLE 290A 6-(1,1-dioxido-4H-1,2,4-benzothiadiazin-3-yl)-7-hydroxy-4-{[phenylmethylene]amino}thieno[3,2-b]pyridin-5(41H)-one The product of Example 268D (0.115 g, 0.30 mmol) was reacted with benzaldehyde (0.32 g, 3.0 mmol) in N,N-dimethylacetamide (2 mL) in a sealed tube at 135° C. for 50 minutes in a microwave reactor. The reaction was cooled to 25° C. and concentrated under vacuum. The resulting residue was triturated with 0.1 M HCl (20 mL) and filtered to give the title compound.

EXAMPLE 290B 4-(benzylamino)-6-(1,1-dioxido-4H-1,2,4-benzothiadiazin-3-yl)-7-hydroxythieno[3,2-b]pyridin-5(4H)-one The product of Example 269A (0.116 g, 0.257 mmol) in tetrahydrofuran (5 mL) and methanol (0.021 mL, 0.514 mmol) at 0° C. was treated dropwise with a 2.0M solution of lithium borohydride in tetrahydrofuran (0.19 mL, 0.386 mmol). The reaction was stirred at 25° C. for 2 hour, acidified with 1M hydrochloric acid a pH of approximately 2-4, diluted with water (20 mL), and the resulting precipitate was collected by filtration and dried to give the title compound. The sodium salt of the title compound was prepared according to the procedure of Example 1D. $^1$H NMR (300 MHz, DMSO-d$_6$) δ ppm 3.97 (d, J=5.54 Hz, 2 H) 6.17 (t, J=6.43 Hz, 1 H) 7.08 (d, J=5.52 Hz, 1 H) 7.21 (d, J=8.09 Hz, 1 H) 7.33 (m, 4 H) 7.47 (d, J=6.62 Hz, 2 H) 7.55 (t, J=6.99 Hz, 1 H) 7.66 (d, J=7.35 Hz, 1 H) 7.73 (d, J=5.52 Hz, 1 H) 15.92 (s, 1 H). MS (ESI−) m/z 451 (M−H)−.

EXAMPLE 291A

4-{[cyclohexylmethylene]amino}-6-(1,1-dioxido-4H-1,2,4-benzothiadiazin-3-yl)-7-hydroxythieno[3,2-b]pyridin-5(4H)-one The product of Example 268D (0.115 g, 0.30 mmol) was reacted with cyclohexanecarbaldehyde (0.336 g, 3.0 mmol) in N,N-dimethylacetamide (3 mL) in a sealed tube at 135° C. for 60 minutes in a microwave reactor. The reaction was cooled to 25° C. and concentrated under vacuum. The resulting residue was triturated with 0.1 M HCl (20 mL) and filtered to give the title compound.

EXAMPLE 291B

4-[(cyclohexylmethyl)amino]-6-(1,1-dioxido-4H-1,2,4-benzothiadiazin-3-yl)-7-hydroxythieno[3,2-b]pyridin-5(4H)-one The product of Example 269A (0.12 g, 0.26 mmol) in tetrahydrofuran (5 mL) and methanol (0.021 mL, 0.52 mmol) at 0° C. was treated dropwise with a 2.0M solution of lithium borohydride in tetrahydrofuran (0.195 mL, 0.39 mmol). The reaction was stirred at 25° C. for 1 hour, acidified with 1M hydrochloric acid a pH of approximately 2-4, diluted with water (15 mL), and the resulting precipitate was collected by filtration and dried. The crude product was chromatographed on silica gel with 97:3 dichloromethane/methanol to give the title compound. The sodium salt of the title compound was prepared according to the procedure of Example 1D. $^1$H NMR (300 MHz, DMSO-d$_6$) δ ppm 1.04 (m, 2 H) 1.23 (m, 3 H) 1.52 (m, 1 H) 1.68 (m, 3 H) 1.87 (m, 2 H) 2.69 (m, 2 H) 5.95 (t, J=7.17 Hz, 1 H) 7.07 (d, J=5.52 Hz, 1 H) 7.19 (d, J=8.09 Hz, 1 H) 7.26 (t, J=7.72 Hz, 1 H) 7.53 (t, J=7.17 Hz, 1 H) 7.65 (d, J=6.99 Hz, 1 H) 7.78 (d, J=5.15 Hz, 1 H) 15.91 (s, 1 H). MS (APCI$^+$) m/z 459 (M+H)$^+$.

EXAMPLE 292A 6-(1,1-dioxido-4H-1,2,4-benzothiadiazin-3-yl)-7-hydroxy-4-{[1,3-thiazol-5-ylmethylene]amino}thieno[3,2-b]pyridin-5(4H)-one The product of Example 268D (0.115 g, 0.30 mmol) was reacted with 1,3-thiazole-5-carbaldehyde (0.35 g, 3.0 mmol) in N,N-dimethylacetamide (3 mL) in a sealed tube at 140° C. for 80 minutes in a microwave reactor. The reaction was cooled to 25° C. and concentrated under vacuum. The resulting residue was triturated with 0.1 M HCl (20 mL) and filtered to give the title compound.

EXAMPLE 292B 6-(1,1-dioxido-4H-1,2,4-benzothiadiazin-3-yl)-7-hydroxy-4-[(1,3-thiazol-5-ylmethyl)amino]thieno[3,2-b]pyridin-5(4H)-one The product of Example 269A (0.137 g, 0.30 mmol) in tetrahydrofuran (7 mL) and methanol (0.025 mL, 0.6 mmol)

EXAMPLE 293A

4-{[(3-bromophenyl)methylene]amino}-6-(1,1-di-oxido-4H-1,2,4-benzothiadiazin-3-yl)-7-hydroxythieno[3,2-b]pyridin-5(4H)-one The product of Example 268D (0.115 g, 0.30 mmol) was reacted with 3-bromobenzaldehyde (0.555 g, 3.0 mmol) in N,N-dimethylacetamide (2 mL) in a sealed tube at 135° C. for 30 minutes in a microwave reactor. The reaction was cooled to 25° C. and concentrated under vacuum. The resulting residue was triturated with ethyl acetate (3 mL) and filtered to give the title compound.

EXAMPLE 293B

4-[(3-bromobenzyl)amino]-6-(1,1-dioxido-4H-1,2,4-benzothiadiazin-3-yl)-7-hydroxythieno[3,2-b]pyridin-5(4H)-one The product of Example 269A (0.13 g, 0.245 mmol) in tetrahydrofuran (4 mL) and methanol (0.015 mL, 0.36 mmol) at 0° C. was treated dropwise with a 2.0M solution of lithium borohydride in tetrahydrofuran (0.15 mL, 0.30 mmol). The reaction was stirred at 25° C. for 2 hour, acidified with 1M hydrochloric acid a pH of approximately 2-4, diluted with water (15 mL), and the resulting precipitate was collected by filtration and dried to give the title compound. The sodium salt of the title compound was prepared according to the procedure of Example 1D. $^1$H NMR (300 MHz, DMSO-$d_6$) δ ppm 4.02 (m, 2 H) 6.27 (t, J=6.25 Hz, 1 H) 7.08 (d, J=5.15 Hz, 1 H) 7.20 (d, J=8.46 Hz, 1 H) 7.28 (t, J=7.72 Hz, 1 H) 7.32 (t, J=6.99 Hz, 1 H) 7.46 (d, J=7.72 Hz, 1 H) 7.54 (m, 2 H) 7.67 (m, 2 H) 7.73 (d, J=5.15 Hz, 1 H) 15.90 (s, 1 H). MS (ESI−) m/z 529/531 (M−H)⁻.

EXAMPLE 294A 4-(cyclohexylideneamino)-6-(1,1-dioxido-4H-1,2,4-benzothiadiazin-3-yl)-7-hydroxythieno[3,2-b]pyridin-5(4H)-one The product of Example 268D (0.054 g, 0.15 mmol) was reacted with cyclohexanone (0.44 g, 4.5 mmol) in N,N-dimethylacetamide (1mL) in a sealed tube at 135° C. for 45 minutes in a microwave reactor. The reaction was cooled to 25° C. and concentrated under vacuum. The resulting residue was triturated with diethyl ether (3 mL) and filtered to give the title compound.

EXAMPLE 294B 4-(cyclohexylamino)-6-(1,1-dioxido-4H-1,2,4-benzothiadiazin-3-yl)-7-hydroxythieno[3,2-b]pyridin-5(4H)-one The product of Example 269A (0.051 g, 0.115 mmol) in tetrahydrofuran (5 mL) and methanol (0.01 mL, 0.23 mmol) at 0° C. was treated dropwise with a 2.0M solution of lithium borohydride in tetrahydrofuran (0.090 mL, 0.175 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 97:3 dichloromethane/methanolto give the title compound. The sodium salt of the title compound was prepared according to the procedure of Example 1D. $^1$H NMR (300 MHz, DMSO-$d_6$) δ ppm 1.16 (m, 5 H) 1.59 (m, 5 H) 3.01 (m, 1 H) 5.75 (d, J=3.31 Hz, 1 H) 7.15 (d, J=5.52 Hz, 1 H) 7.19 (d, J=7.72 Hz, 1 H) 7.26 (t, J=7.54 Hz, 1 H) 7.54 (m, 1 H) 7.65 (d, J=7.72 Hz, 1 H) 7.72 (d, J=5.52 Hz, 1 H) 15.93 (s, 1 H). MS (ESI−) m/z 443 (M−H)⁻.

EXAMPLE 295A 4-(cyclopentylideneamino)-6-(1,1-dioxido-4H-1,2,4-benzothiadiazin-3-yl)-7-hydroxythieno[3,2-b]pyridin-5(4H)-one The product of Example 268D (0.054 g, 0.15 mmol) was reacted with cyclopentanone (0.95 g, 11.3 mmol) in N,N-dimethylacetamide (1 mL) in a sealed tube at 135° C. for 60 minutes in a microwave reactor. The reaction was cooled to 25° C. and concentrated under vacuum. The resulting residue was triturated with diethyl ether (3 mL) and filtered to give the title compound.

EXAMPLE 295B 4-(cyclopentylamino)-6-(1,1-dioxido-4H-1,2,4-benzothiadiazin-3-yl)-7-hydroxythieno[3,2-b]pyridin-5(4H)-one The product of Example 269A (0.040 g, 0.09 mmol) in tetrahydrofuran (3 mL) and methanol (0.008 mL, 0.19 mmol) at 0° C. was treated dropwise with a 2.0M solution of lithium borohydride in tetrahydrofuran (0.07 mL, 0.14 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 98:2 dichloromethane/methanol to give the title compound. The sodium salt of the title compound was prepared according to the procedure of Example 1D. $^1$H NMR (300 MHz, DMSO-$d_6$) δ ppm 1.54 (m, 6 H) 1.74 (m, 2 H) 3.75 (m, 1 H) 5.77 (d, J=3.68 Hz, 1 H) 7.12 (d, J=5.15 Hz, 1 H) 7.19 (d, J=7.72 Hz, 1 H) 7.26 (t, J=7.17 Hz, 1 H) 7.54 (m, 1 H) 7.64 (d, J=7.72 Hz, 1 H) 7.74 (d, J=5.52 Hz, 1 H) 15.91 (s, 1 H). MS (ESI−) m/z 429 (M−H)⁻.

EXAMPLE 296A 4-(cycloheptylideneamino)-6-(1,1-dioxido-4H-1,2,4-benzothiadiazin-3-yl)-7-hydroxythieno[3,2-b]pyridin-5(4H)-one The product of Example 268D (0.054 g, 0.15 mmol) was reacted with cycloheptanone (0.84 g, 7.5 mmol) in N,N-

---

(Continuation from previous page:)

at 0° C. was treated dropwise with a 2.0M solution of lithium borohydride in tetrahydrofuran (0.225 mL, 0.45 mmol). The reaction was stirred at 25° C. for 2 hour, acidified with 1M hydrochloric acid a pH of approximately 2-4, diluted with water (20 mL), and the resulting precipitate was collected by filtration and dried. The crude product was chromatographed on silica gel with 95:5 dichloromethane/methanol to give the title compound. The sodium salt of the title compound was prepared according to the procedure of Example 1D. $^1$H NMR (300 MHz, DMSO-$d_6$) δ ppm 4.34 (m, 2 H) 6.45 (t, J=5.52 Hz, 1 H) 6.97 (d, J=5.15 Hz, 1 H) 7.20 (d, J=8.09 Hz, 1 H) 7.27 (t, J=7.54 Hz, 1 H) 7.54 (t, J=7.17 Hz, 1 H) 7.66 (d, J=7.72 Hz, 1 H) 7.70 (d, J=5.52 Hz, 1 H) 7.79 (s, 1 H) 9.02 (s, 1 H) 15.87 (s, 1 H). MS (ESI−) m/z 458 (M−H)⁻.

dimethylacetamide (1mL) in a sealed tube at 135° C. for 45 minutes in a microwave reactor. The reaction was cooled to 25° C. and concentrated under vacuum. The resulting residue was triturated with diethyl ether (3 mL) and filtered to give the title compound.

EXAMPLE 296B 4-(cycloheptylamino)-6-(1,1-dioxido-4H-1,2,4-benzothiadiazin-3-yl)-7-hydroxythieno[3,2-b]pyridin-5(4H)-one The product of Example 269A (0.06 g, 0.13 mmol) in tetrahydrofuran (4 mL) and methanol (0.011 mL, 0.26 mmol) at 0° C. was treated dropwise with a 2.0M solution of lithium borohydride in tetrahydrofuran (0.10 mL, 0.2 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 98:2 dichloromethane/methanol to give the title compound. The sodium salt of the title compound was prepared according to the procedure of Example 1D. $^1$H NMR (300 MHz, DMSO-$d_6$) δ ppm 1.35 (m, 4 H) 1.50 (m, 4 H) 1.64 (m, 3 H) 1.86 (m, 1 H) 2.56 (m, 1 H) 5.62 (d, J=2.94 Hz, 1 H) 7.12 (d, J=5.52 Hz, 1 H) 7.19 (d, J=8.09 Hz, 1 H) 7.26 (t, J=7.54 Hz, 1 H) 7.53 (m, 1 H) 7.64 (d, J=7.72 Hz, 1 H) 7.72 (d, J=5.15 Hz, 1 H) 15.92 (s, 1 H). MS (ESI–) m/z 457 (M–H)$^-$.

EXAMPLE 297A 6-(1,1'-dioxido-4H-1,2,4-benzothiadiazin-3-yl)-7-hydroxy-4-{[3-methylcyclohexylidene]amino}thieno[3,2-b]pyridin-5(4H)-one The product of Example 268D (0.054 g, 0.15 mmol) was reacted with 3-methylcyclohexanone (1.26 g, 11.25 mmol) in N,N-dimethylacetamide (1 mL) in a sealed tube at 135° C. for 45 minutes in a microwave reactor. The reaction was cooled to 25° C. and concentrated under vacuum. The resulting residue was triturated with diethyl ether (3 mL) and filtered to give the title compound.

EXAMPLE 297B 6-(1,1-dioxido-4H-1,2,4-benzothiadiazin-3-yl)-7-hydroxy-4-{[3-methylcyclohexyl]amino}thieno[3,2-b]pyridin-5(4H)-one The product of Example 269A (0.060 g, 0.13 mmol) in tetrahydrofuran (4 mL) and methanol (0.011 mL, 0.26 mmol) at 0° C. was treated dropwise with a 2.0M solution of lithium borohydride in tetrahydrofuran (0.1 mL, 0.20 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 98:2 dichloromethane/methanol to give the title compound. The sodium salt of the title compound was prepared according to the procedure of Example 1D. $^1$H NMR (300 MHz, DMSO-$d_6$) δ ppm 0.86 (m, 4 H) 1.08 (m, 1 H) 1.29 (m, 3 H) 1.60 (m, 3 H) 1.93 (m, 1 H) 3.04 (m, 1 H) 5.76 (d, J=3.31 Hz, 1 H) 7.14 (d, J=5.52 Hz, 1 H) 7.19 (d, J=8.46 Hz, 1 H) 7.26 (t, J=7.54 Hz, 1 H) 7.52 (dt, J=8.46, 1.47 Hz, 1 H) 7.65 (d, J=8.09 Hz, 1 H) 7.73 (t, J=5.15 Hz, 1 H) 15.93 (s, 1 H). MS (ESI–) m/z 457 (M–H)$^-$.

EXAMPLE 298A 6-(1,1-dioxido-4H-1,2,4-benzothiadiazin-3-yl)-7-hydroxy-4-{[(3R)-3-methylcyclohexylidene]amino}thieno[3,2-b]pyridin-5(4H)-one The product of Example 268D (0.073 g, 0.2 mmol) was reacted with (3R)-3-methylcyclohexanone (1.12 g, 10.0 mmol) in N,N-dimethylacetamide (2 mL) in a sealed tube at 135° C. for 45 minutes in a microwave reactor. The reaction was cooled to 25° C. and concentrated under vacuum. The resulting residue was triturated with diethyl ether (3 mL) and filtered to give the title compound.

EXAMPLE 298B 6-(1,1-dioxido-4H-1,2,4-benzothiadiazin-3-yl)-7-hydroxy-4-{[(3R)-3-methylcyclohexyl]amino}thieno[3,2-b]pyridin-5(4H)-one The product of Example 269A (0.06 g, 0.13 mmol) in tetrahydrofuran (6 mL) and methanol (0.011 mL, 0.26 mmol) at 0° C. was treated dropwise with a 2.0M solution of lithium borohydride in tetrahydrofuran (0.1 mL, 0.2 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 98:2 dichloromethane/methanol to give the title compound. The sodium salt of the title compound was prepared according to the procedure of Example 1D. $^1$H NMR (300 MHz, DMSO-$d_6$) δ ppm 0.86 (m, 4 H) 1.08 (m, 1 H) 1.29 (m, 3 H) 1.60 (m, 3 H) 1.93 (m, 1 H) 3.04 (m, 1 H) 5.76 (d, J=3.31 Hz, 1 H) 7.14 (d, J=5.52 Hz, 1 H) 7.19 (d, J=8.46 Hz, 1 H) 7.26 (t, J=7.54 Hz, 1 H) 7.52 (dt, J=8.46, 1.47 Hz, 1 H) 7.65 ((d, J=8.09 Hz, 1 H) 7.73 (t, J=5.15 Hz, 1 H) 15.93 (s, 1 H). MS (ESI–) m/z 457 (M–H)$^-$.

EXAMPLE 299A 6-(1,1-dioxido-4H-1,2,4-benzothiadiazin-3-yl)-4-[(1-ethylpropylidene)amino]-7-hydroxythieno[3,2-b]pyridin-5(4H)-one The product of Example 268D (0.073 g, 0.2 mmol) was reacted with pentan-3-one (0.86 g, 10.0 mmol) in N,N-dimethylacetamide (2 mL) in a sealed tube at 135° C. for 40 minutes in a microwave reactor. The reaction was cooled to 25° C. and concentrated under vacuum. The resulting residue was triturated with diethyl ether (3 mL) and filtered to give the title compound.

EXAMPLE 299B 6-(1,1-dioxido-4H-1,2,4-benzothiadiazin-3-yl)-4-[(1-ethylpropyl)amino]-7-hydroxythieno[3,2-b]pyridin-5(4H)-one The product of Example 269A (0.08 g, 0.18 mmol) in tetrahydrofuran (7 mL) and methanol (0.015 mL, 0.36 mmol) at 0° C. was treated dropwise with a 2.0M solution of lithium borohydride in tetrahydrofuran (0.135 mL, 0.27 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 98:2 dichloromethane/methanol to give the title compound. The sodium salt of the title compound was prepared according to the procedure of Example 1D. $^1$H NMR (300 MHz, DMSO-d$_6$) δ ppm 0.87 (m, 6 H) 1.29 (m, 4 H) 3.03 (m, 1 H) 5.76 (d, J=3.68 Hz, 1 H) 7.12 (d, J=5.52 Hz, 1 H) 7.19 (d, J=8.46 Hz, 1 H) 7.26 (t, J=6.99 Hz, 1 H) 7.54 (m, 1 H) 7.65 (d, J=7.72 Hz, 1 H) 7.74 (d, J=5.15 Hz, 1 H) 15.95 (s, 1 H). MS (ESI−) m/z 431 (M−H)⁻.

EXAMPLE 300A 6-(1,1-dioxido-4H-1,2,4-benzothiadiazin-3-yl)-7-hydroxy-4-{[1-phenylethylidene]amino}thieno[3,2-b]pyridin-5(4H)-one The product of Example 268D (0.073 g, 0.2 mmol) was reacted with 1-phenylethanone (1.2 g, 10.0 mmol) in N,N-dimethylacetamide (2 mL) in a sealed tube at 135° C. for 75 minutes in a microwave reactor. The reaction was cooled to 25° C. and concentrated under vacuum. The resulting residue was triturated with diethyl ether (3 mL) and filtered to give the title compound.

EXAMPLE 300B 6-(1,1-dioxido-4H-1,2,4-benzothiadiazin-3-yl)-7-hydroxy-4-{[-phenylethyl]amino}thieno[3,2-b]pyridin-5(4H)-one The product of Example 269A (0.046 g, 0.10 mmol) in tetrahydrofuran (5 mL) and methanol (0.005 mL, 0.12 mmol) at 0° C. was treated dropwise with a 2.0M solution of lithium borohydride in tetrahydrofuran (0.06 mL, 0.12 mmol). The reaction was stirred at 25° C. for 3 hour, acidified with 1M hydrochloric acid a pH of approximately 2-4, diluted with water (10 mL), and the resulting precipitate was collected by filtration and dried. The crude product was chromatographed on silica gel with 99:1 dichloromethane/methanol to give the title compound. The sodium salt of the title compound was prepared according to the procedure of Example 1D. $^1$H NMR (300 MHz, DMSO-d$_6$) δ ppm 1.26 (m, 3 H) 4.49 (m, 1 H) 5.90 (m, 1 H) 7.20 (d, J=8.09 Hz, 1 H) 7.27 (t, J=8.46 Hz, 2 H) 7.30 (m, 5 H) 7.54 (m, 2 H) 7.66 (d, J=8.09 Hz, 1 H) 15.93 (s, 1 H). MS (ESI−) m/z 465 (M−H)⁻.

EXAMPLE 301A 6-(1,1-dioxido-4H-1,2,4-benzothiadiazin-3-yl)-7-hydroxy-4-{[1-methylbutylidene]amino}thieno[3,2-b]pyridin-5(4H)-one The product of Example 268D (0.073 g, 0.2 mmol) was reacted with pentan-2-one (0.9 g, 10.4 mmol) in N,N-dimethylacetamide (2 mL) in a sealed tube at 135° C. for 60 minutes in a microwave reactor. The reaction was cooled to 25° C. and concentrated under vacuum. The resulting residue was triturated with diethyl ether (3 mL) and filtered to give the title compound.

EXAMPLE 301B 6-(1,1-dioxido-4H-1,2,4-benzothiadiazin-3-yl)-7-hydroxy-4-{[-methylbutyl]amino}thieno[3,2-b]pyridin-5(4H)-one The product of Example 269A (0.070 g, 0.16 mmol) in tetrahydrofuran (mL) and methanol (0.013 mL, 0.32 mmol) at 0° C. was treated dropwise with a 2.0M solution of lithium borohydride in tetrahydrofuran (0.12 mL, 0.24 mmol). The reaction was stirred at 25° C. for 1 hour, acidified with 1M hydrochloric acid a pH of approximately 2-4, diluted with water (10 mL), and the resulting precipitate was collected by filtration and dried. The crude product was chromatographed on silica gel with 99:1 dichloromethane/methanol to give the title compound. The sodium salt of the title compound was prepared according to the procedure of Example 1D. $^1$H NMR (300 MHz, DMSO-d$_6$) δ ppm 0.87 (m, 6 H) 1.30 (m, 4 H) 3.25 (m, 1 H) 5.74 (d, J=3.68 Hz, 1 H) 7.13 (d, J=5.15 Hz, 1 H) 7.19 (d, J=8.09 Hz, 1 H) 7.26 (t, J=7.54 Hz, 1 H) 7.54 (dd, J=8.09, 1.47 Hz, 1 H) 7.65 (d, J=7.72 Hz, 1 H) 7.73 (d, J=5.52 Hz, 1 H) 15.94 (s, 1 H). MS (ESI−) m/z 431 (M−H)⁻.

EXAMPLE 303A

4-{[cyclopropylmethylene]amino}-6-(1,1-dioxido-4H-1,2,4-benzothiadiazin-3-yl)-7-hydroxythieno[3,2-b]pyridin-5(4H)-one The product of Example 268D (0.15 g, 0.41 mmol) was reacted with cyclopropanecarbaldehyde (1.0 g, 14 mmol) in N,N-dimethylacetamide (3 mL) in a sealed tube at 120° C. for 90 minutes in a microwave reactor. The reaction was cooled to 25° C. and concentrated under vacuum. The resulting residue was triturated with diethyl ether and filtered to give the title compound (0.104 g, 60%).

EXAMPLE 303B

4-[(cyclopropylmethyl)amino]-6-(1,1-dioxido-4H-1,2,4-benzothiadiazin-3-yl)-7-hydroxythieno[3,2-b]pyridin-5(4H)-one The product of Example 269A (0.104 g, 0.25 mmol) in tetrahydrofuran (4 mL) and methanol (0.020 mL, 0.5 mmol) at 0° C. was treated dropwise with a 2.0M solution of lithium borohydride in tetrahydrofuran (0.200 mL, 0.4 mmol). The reaction was stirred at 25° C. for 1 hour, acidified with 1M hydrochloric acid to pH of approximately 2-4, diluted with water (20 mL), and the resulting precipitate was collected by filtration and dried. The crude product was chromatographed on silica gel with 1% methanol in chloroform to give the title compound. The sodium salt of the title compound was prepared according to the procedure of Example 1D. 1H NMR (300 MHz, DMSO-d$_6$) δ ppm 0.06 (m, 2 H) 0.36 (m, 2 H) 0.96 (m, 1 H) 2.92 (d, J=6.99 Hz, 2 H) 6.75 (s, 1 H) 7.53 (d, J=5.52 Hz, 1 H) 7.55 (m, 1 H) 7.63 (d, J=8.09 Hz, 1 H) 7.77 (m, 1 H) 7.92 (d, J=7.72 Hz, 1 H) 8.33 (d, J=5.52 Hz, 1 H) 14.19 (s, 1 H) 14.82 (s, 1 H). MS (ESI−) m/z 415 (M−H)⁻.

EXAMPLE 304A 4-(benzyloxy)-2-fluoro-1-nitrobenzene

3-Fluoro-4-nitro-phenol (10 g, 0.064 mol) was reacted with benzyl bromide (8.3 ml, 0.070 mol), cesium carbonate (22.7 g, 0.07 mol), and tetrabutyl ammonium iodide (0.05 g) in N,N-dimethylformamide (100 mL) at 25° C. for 18 hr. The reaction mixture was poured into distilled water (500 mL) and stirred for 10 minutes. The reaction mixture was extracted with ethyl acetate (3×200 mL). The combined organic extracts were washed with brine, dried over anhydrous sodium sulfate, filtered and solvent removed under reduced pressure to give the title compound as a light yellow solid (15 g). $^1$H NMR (300 MHz, DMSO-d$_6$) δ ppm 5.27 (s, 2 H) 7.06

(dd, J=9.56, 2.57 Hz, 1 H) 7.29 (dd, J=13.60, 2.57 Hz, 1 H) 7.44 (m, 5 H) 8.17 (t, J=9.19 Hz, 1 H). ESI m/z (M+H)$^+$: 248

EXAMPLE 304B 4-(benzyloxy)-2-(benzylthio)-1-nitrobenzene

A slurry of the product of Example 304A (15 g, 0.061 mol) in ethanol (100 mL), was treated with sodium carbonate (6.41 g, 0.061 mol) and benzyl mercaptan (7.5 mL, 0.058 mol) in water (50 mL). The reaction mixture was refluxed for 5 hours, cooled to 25° C. and poured into of distilled water (800 mL). The resulting slurry was stirred for1 hour at 25° C. and filtered. The resulting yellow solid was washed with water and dried in a vacuum oven at 50° C. to give the title compound (20.53 g). $^1$H NMR (300 MHz, DMSO-d$_6$) δ ppm 4.35 (s, 2 H) 5.27 (s, 2 H) 7.02 (dd, J=9.19, 2.57 Hz, 1 H) 7.16 (d, J=2.57 Hz, 1 H) 7.40 (m, 10 H) 8.24 (d, J=9.19 Hz, 1 H). ESI m/z (M+H)$^+$: 352

EXAMPLE 304C 5-(benzyloxy)-2-nitrobenzenesulfonamide

A slurry of the product of Example 304B (5 g, 0.014 mol) in glacial acetic acid (50 mL) and water (5.5 mL) at 0° C. was bubbled with chlorine gas for 10 minutes, and stirred for an additional 30-45 minutes. The reaction mixture was poured into ice water (200 g), stirred for 30 minutes, and extracted with dichloromethane (2×100 mL). The combined dichloromethane extracts were cooled in an ice bath to approximately 5° C. and concentrated aqueous ammonium hydroxide (40 mL) was added slowly resulting in foaming and bubbling as the ammonia was added. After 30 minutes, the bubbling subsided, and the organic layer was separated and the aqueous layer was extracted with dichloromethane (100 ml). The combined organic extracts were washed with 1N phosphoric acid (50 mL), brine, dried over anhydrous magnesium sulfate, filtered and the solvent removed under reduced pressure to give the title compound as a white solid (3.85 g). $^1$H NMR (300 MHz, DMSO-d$_6$) δ ppm 5.28 (s, 2H) 7.44 (m, 6H) 7.63 (d, J=2.94 Hz, 1 H) 7.79 (s, 2 H) 8.01 (d, J=8.82 Hz, 1 H). ESI m/z (M+H)$^+$309.

EXAMPLE 304D 2-amino-5-(benzyloxy)benzenesulfonamide

The product of Example 304C (3.85 g, 0.0125 mol) was treated with iron powder (4.3 g, 0.077 mol, 6.15 equivalent) and ammonium chloride (4.4 g, 0.082 mol) in methanol (100 mL) and water (50 mL), and stirred at reflux for 1 hour. The hot reaction mixture was filtered through fluted filter paper and washed with hot methanol. The filtrate was concentrated under reduced pressure to a white semi-solid that was partitioned between ethyl acetate and water. The organic layer was washed with brine, dried over anhydrous sodium sulfate, filtered and the solvent removed under reduced pressure to give the title compound as a off white solid (2.5 g). $^1$H NMR (300 MHz, DMSO-d$_6$) δ ppm 4.98 (s, 2 H) 5.46 (s, 2 H) 6.76 (d, J=8.82 Hz, 1 H) 7.01 (dd, J=8.82, 2.94 Hz, 1 H) 7.21 (d, J=2.94 Hz, 1 H) 7.23 (s, 2 H) 7.37 (m, 5 H). ESI m/z (M+H)$^+$ 279. ESI m/z (M−H)$^-$277.

EXAMPLE 304E 1-amino-N-[2-(aminosulfonyl)-4-(benzyloxy)phenyl]-4-hydroxy-2-oxo-1,2-dihydroquinoline-3-carboxamide The products of Example 304D (4.0 g, 14.37 mmol) and Example 226C (2.42 g, 7.20 mmol) in toluene (50 mL) were reacted at 118° C. for 4 hours. The mixture was filtered while still warm and the solid dried to yield the title compound (3.13 g, 90%). MS (ESI−) m/z 479 (M−H)$^-$. $^1$H NMR (300 MHz, DMSO-d$_6$) δ ppm 5.20 (s, 2 H) 5.76 (s, 2 H) 7.40 (m, 10 H) 7.84 (m, 2 H) 8.02 (d, J=8.46 Hz, 1 H) 8.10 (dd, J=8.09, 1.47 Hz, 1 H) 12.31 (s, 1 H) 16.41 (s, 1 H).

EXAMPLE 304F 1-amino-3-[7-(benzyloxy)-1,1-dioxido-4H-1,2,4-benzothiadiazin-3-yl]-4-hydroxyquinolin-2(1H)-one The product of Example 304E (3.13 g, 6.51 mmol) was suspended in 10% potassium hydroxide solution (50 mL), heated at 125° C. for 24 hours then at 140° C. for 24 hours. The mixture was poured into ice and 1 M hydrochloric acid, filtered, and dried to give the title compound (2.03 g, 67%). MS (ESI−) m/z 461 (M−H)$^-$. $^1$H NMR (300 MHz, DMSO-d$_6$) δ ppm 5.18 (s, 2 H) 5.33 (s, 2 H) 7.06 (m, 1 H) 7.25 (m, 3 H) 7.43 (m, 6 H) 7.69 (d, J=7.72 Hz, 1 H) 8.06 (d, J=8.09 Hz, 1 H) 16.31 (s, 1 H).

EXAMPLE 304G

3-[7-(benzyloxy)-1,1-dioxido-4H-1,2,4-benzothiadiazin-3-yl]-1-(cyclobutylideneamino)-4-hydroxyquinolin-2(1H)-one The product of Example 304F (0.285 g, 0.62 mmol) in N,N-dimethylacetamide (1.5 mL) was reacted with cyclobutanone (0.85 mL, 10.9 mmol) in a sealed tube in a microwave reactor at 130° C. for 45 minutes. The reaction was cooled to 25° C., concentrated under a stream of nitrogen warmed through a manifold heated to 165° C. and the resulting residue was triturated with diethyl ether to give the title compound (0.178 g, 56%).

EXAMPLE 304H

3-[7-(benzyloxy)-1,1-dioxido-4H-1,2,4-benzothiadiazin-3-yl]-1-(cyclobutylamino)-4-hydroxyquinolin-2(1H)-one The product of Example 304G (0.178 g, 0.35 mmol) in tetrahydrofuran (3 mL) at 0° C. was treated with methanol (0.025 mL, 0.70 mmol), followed by dropwise addition of a 2.0 M solution of lithium borohydride in tetrahydrofuran (0.260 mL, 0.52 mmol), stirred at 25° C. for one hour, and diluted with 1 N HCl. The resulting precipitate was filtered and dried. The solid was dissolved in tetrahydrofuran and absorbed onto silica gel by evaporating to dryness. The resulting silica was loaded onto a 2 g Alltech sep pack and eluted with dichloromethane to give the title compound (0.059 g, 33%). MS (ESI−) m/z 515 (M−H)$^-$. $^1$H NMR (300 MHz, DMSO-d$_6$) δ ppm 1.55 (m, 1 H) 1.71 (m, 1 H) 2.04 (m, 4 H) 3.77 (m, 1 H) 5.26 (s, 2 H) 6.57 (d, J=5.15 Hz, 1 H) 7.45 (m, 8 H) 7.64 (d, J=9.56 Hz, 1 H) 7.88 (m, 1 H) 8.05 (d, J=8.46 Hz, 1 H) 8.17 (m, 1 H).

EXAMPLE 304I 1-(cyclobutylamino)-4-hydroxy-3-(7-hydroxy-1,1-dioxido-4H-1,2,4-benzothiadiazin-3-yl)quinolin-2(1H)-one The product of Example 304H (0.059 g, 0.11 mmol) in tetrahydrofuran (4 mL) was reacted with platinum oxide (50 mg) under hydrogen atmosphere at 25° C. for 20 hours. The catalyst was filtered off and the filtrate evaporated to give the title compound (0.048 g, 100%). MS (ESI−) m/z 425 (M−H)−.

EXAMPLE 304J 2-({3-[1-(cyclobutylamino)-4-hydroxy-2-oxo-1,2-dihydroquinolin-3-yl]-1,1-dioxido-4H-1,2,4-benzothiadiazin-7-yl}oxy)acetamide The product of Example 304I (0.048 g, 0.11 mmol) in N,N-dimethylformamide (2 mL) was reacted with cesium carbonate (0.15 g, 0.45 mmol), bromoacetamide (0.026 mL, 0.18 mmol), and a catalytic amount of tetrabutylammonium iodide at 25° C. for 3 hours. The reaction was concentrated under a stream of nitrogen stream of nitrogen warmed through a manifold heated to 165° C. and the resulting residue was triturated with water, filtered and dried. The resulting solid was triturated in hot ethyl acetate, filtered, and dried to give the title compound (0.020 g, 37%). MS (ESI−) m/z 482 (M−H)−. $^1$H NMR (300 MHz, DMSO-$d_6$) δ ppm 1.59 (m, 2 H) 1.99 (m, 4 H) 3.60 (m, 1 H) 4.49 (s, 2 H) 6.08 (d, J=6.62 Hz, 1 H) 7.05 (t, J=7.17 Hz, 1 H) 7.20 (m, 3 H) 7.40 (s, 1 H) 7.50 (m, 1 H) 7.65 (m, 2 H) 8.05 (d, J=7.72 Hz, 1 H) 16.25 (s, 1 H). The sodium salt of the title compound was prepared according to the procedure of Example 1D. $^1$H NMR (300 MHz, DMSO-$d_6$) δ ppm 1.59 (m, 1 H) 1.99 (m, 4 H) 3.61 (m, 2 H) 4.49 (s, 2 H) 6.08 (d, J=6.62 Hz, 1 H) 7.05 (m, 1 H) 7.21 (m, 2 H) 7.40 (s, 2 H) 7.50 (m, 1 H) 7.64 (m, 2 H) 8.06 (dd, J=7.91, 1.29 Hz, 1 H) 8.32 (s, 1 H).

EXAMPLE 305A

3-[7-(benzyloxy)-1,1-dioxido-4H-1,2,4-benzothiadiazin-3-yl]-1-(cyclopentylideneamino)-4-hydroxyquinolin-2(1H)-one The product of Example 304F (0.284 g, 0.61 mmol) and cyclopentanone (0.80 mL, 9.04 mmol) in N,N-dimethylacetamide (2 mL) were reacted at 130° C. for 40 minutes in a microwave reactor in a sealed tube. The reaction was concentrated under a stream of nitrogen warmed through a manifold heated to 165° C. The resulting residue was triturated with diethyl ether and filtered to give the title compound (0.210 g, 65%). $^1$H NMR (300 MHz, DMSO-$d_6$) δ ppm 1.72 (m, 2 H) 1.87 (m, 2 H) 2.16 (m, 2 H) 2.71 (m, 2 H) 5.18 (s, 2 H) 7.31 (m, 11 H) 8.10 (d, J=8.46 Hz, 1 H) 16.22 (s, 1 H).

EXAMPLE 305B

3-[7-(benzyloxy)-1,1-dioxido-4H-1,2,4-benzothiadiazin-3-yl]-1-(cyclopentylamino)-4-hydroxyquinolin-2(1H)-one The produce of Example 305A (0.21 g, 0.40 mmol) in tetrahydrofuran (3 mL) and methanol (0.030 mL) at 0° C. was reacted with lithium borohydride (2.0 M solution in tetrahydrofuran, 0.30 mL, 0.60 mmol). The reaction was stirred at 25° C. for 1 hour then diluted with 1 M aqueous hydrochloric acid and filtered. The product was purified by dissolving in tetrahydrofuran, absorbing onto silica gel, loading onto a 2 g Alltech Sep-pack and eluting with dicholomethane. The filtrate was evaporated to dryness under reduced pressure to give the title compound (0.124 g. 59%). $^1$H NMR (300 MHz, DMSO-$d_6$) δ ppm 1.54 (m, 4 H) 1.79 (m, 2 H) 2.55 (m, 2 H) 3.94 (m, 1 H) 5.26 (s, 2 H) 6.23 (m, J=6.99, 4.04 Hz, 1 H) 7.43 (m, 8 H) 7.69 (d, J=6.99 Hz, 1 H) 7.87 (m, 1 H) 8.09 (d, J=8.09 Hz, 1 H) 8.16 (d, J=6.62 Hz, 1 H) 14.08 (s, 1 H) 15.18 (s, 1 H).

EXAMPLE 305C 1-(cyclopentylamino)-4-hydroxy-3-(7-hydroxy-1,1-dioxido-4H-1,2,4-benzothiadiazin-3-yl)quinolin-2(1H)-one The product of Example 305B (0.122 g, 0.23 mmol) in tetrahyrofuran (15 mL) was reacted with a catalytic amount of palladium hydroxide on carbon, a catalytic amount of 5% palladium on carbon, and ammonium formate (0.080 g, 1.27 mmol) at 60° C. for 2 hours. The warm reaction mixture was filtered through celite and the filtrate was evaporated under reduced pressure to give the title compound (0.10 g, 100%). MS (ESI−) m/z 439 (M−H)−. $^1$H NMR (300 MHz, DMSO-$d_6$) δ ppm 1.54 (m, 4 H) 1.78 (m, J=2.94 Hz, 2 H) 2.58 (m, 2 H) 3.91 (m, 1 H) 6.25 (m, 1 H) 7.13 (m, 2 H) 7.45 (m, 1 H) 7.54 (d, J=9.19 Hz, 1 H) 7.85 (m, 1 H) 8.12 (m, 2 H) 10.45 (s, 1 H) 14.00 (s, 1 H) 15.25 (s, 1 H).

EXAMPLE 305D 2-({3-[1-(cyclopentylamino)-4-hydroxy-2-oxo-1,2-dihydroquinolin-3-yl]-1,1-dioxido-4H-1,2,4-benzothiadiazin-7-yl}oxy)acetamide The product of Example 305C (0.10 g, 0.23 mmol) was reacted with cesium carbonate (0.30 g, 0.92 mmol), 2-bromoacetamide (0.050 g, 0.37 mmol) and a catalytic amount of tetrabuylammonium iodide in N,N-dimethylformamide (5 mL) at 25° C. for 2 hours. The reaction was concentrated to half the volume under a stream of nitrogen warmed through a manifold heated to 165° C. The resulting solution was diluted with water and the precipitate was collected by filtration and dried to give the title compound (0.095 g, 85%). MS (ESI−) m/z 496 (M−H)−. The sodium salt of the title compound was prepared according to the procedure of Example 1D. $^1$H NMR (500 MHz, DMSO-$d_6$) δ ppm 1.52 (m, 6 H) 1.76 (m, 2 H) 3.70 (m, 1 H) 4.47 (s, 2 H) 5.68 (d, J=4.88 Hz, 1 H) 7.03 (t, J=7.63 Hz, 1 H) 7.20 (m, 5 H) 7.46 (t, J=7.32 Hz, 1 H) 7.70 (d, J=8.54 Hz, 1 H) 8.06 (d, J=7.32 Hz, 1 H) 16.15 (s, 1 H).

EXAMPLE 306A

3-[7-(benzyloxy)-1,1-dioxido-4H-1,2,4-benzothiadiazin-3-yl]-1-(cyclohexylideneamino)-4-hydroxyquinolin-2(1H)-one The title compound was prepared according to the procedure as described in Example 304G, substituting cyclohexanone for cyclobutanone.

EXAMPLE 306B

3-[7-(benzyloxy)-1,1-dioxido-4H-1,2,4-benzothiadiazin-3-yl]-1-(cyclohexylamino)-4-hydroxyquinolin-2(1H)-one The title compound was prepared according to the procedure described in Example 304H, substituting the product of Example 306A for the product of Example 304G (0.11 g, 78%).

EXAMPLE 306C 1-(cyclohexylamino)-4-hydroxy-3-(7-hydroxy-1,1-dioxido-4H-1,2,4-benzothiadiazin-3-yl)quinolin-2(1H)-one The title compound was prepared according to the procedure of Example 305C substituting the product of Example 306B for the product of Example 305B (39 mg, 42%).

EXAMPLE 306D 2-({3-[1-(cyclohexylamino)-4-hydroxy-2-oxo-1,2-dihydroquinolin-3-yl]-1,1-dioxido-4H-1,2,4-benzothiadiazin-7-yl}oxy)acetamide The product of Example 306C (13 mg, 0.028 mmol) in N,N-dimethylformamide (5 mL) was reacted with cesium carbonate (0.0137 g, 0.114 mol) and 2-bromoacetamide (0.008 g, 0.058 mmol) according to the procedure as described in Example 304J to give the title compound. The sodium salt was prepared according to the procedure of Example 1D (7 mg, 48%). $^1$H NMR (300 MHz, DMSO-$d_6$) δ ppm 1.36 (m, 10 H) 2.96 (bs, 1 H) 4.49 (s, 2 H) 5.67 (d, J=4.04 Hz, 1 H) 7.04 (t, J=7.54 Hz, 1 H) 7.20 (m, 3 H) 7.40 (s, 1 H) 7.47 (m, 1 H) 7.62 (s, 1 H) 7.74 (d, J=8.46 Hz, 1 H) 8.05 (d, J=6.62 Hz, 1 H) 16.26 (s, 1 H). (ESI−) m/z 510 (M−H)$^-$, m/z 532 (M+Na−H)$^{-1}$.

EXAMPLE 307

4-[(2-chloro-1,3-thiazol-5-yl)methyl]-7-hydroxy-6-(7-hydroxy-1,1-dioxido-4H-1,2,4-benzothiadiazin-3-yl)thieno[3,2-b]pyridin-5(4H)-one

EXAMPLE 307A

Ethyl [7-(benzyloxy)-1,1-dioxido-4H-1,2,4-benzothiadiazin-3-yl]acetate

The title compound was prepared according to the procedure of Example 1C substituting the product of Example 304D for 2-amino-benzenesulfonamide.

EXAMPLE 307B

Ethyl (7-hydroxy-1,1-dioxido-4H-1,2,4-benzothiadiazin-3-yl)acetate

The product of Example 307A (1.42 g, 3.79 mmol) in tetrahydrofuran (60 mL) was reacted with 10% palladium on carbon (0.2 g) under hydrogen atmosphere for 16 hours at 25° C. The reaction mixture was filtered and concentrated under reduced pressure to an oil. The residue was purified on silica gel eluting with ethyl acetate to give the title compound as of a white solid (0.8 g).

EXAMPLE 307C

Ethyl {1,1-dioxido-7-[(triisopropylsilyl)oxy]-4H-1,2,4-benzothiadiazin-3-yl}acetate The product of Example 307B (0.1 g, 0.352 mmol) was reacted with 2,6-lutidine (0.045 mL, 0.387 mmol) and triisopropyl trifluoromethanesulfonate (0.1 mL, 0.387 mmol) in dichloromethane (10 mL) at 5° C. for 3 hours. The reaction was diluted with dichloromethane and extracted with aqueous 1N phosphoric acid. The organic layer was washed with brine and dried over anhydrous magnesium sulfate, filtered and concentrated under reduced pressure to give the title compound as a light yellow solid (0.13 g, 84%).

EXAMPLE 307D

4-[(2-Chloro-1,3-thiazol-5-yl)methyl]-6-{1,1-dioxido-7-[(triisopropylsilyl)oxy]-4H-1,2,4-benzothiadiazin-3-yl}-7-hydroxythieno[3,2-b]pyridin-5(4H)-one The title compound was prepared according to the procedure of Example 1D substituting the product of Example 140A for the product of Example 1B and substituting the product of Example 307C for the product of Example 1C (0.29 g, 66%). MS (ESI−) m/z 649 (M−H)$^-$. $^1$H NMR (300 MHz, DMSO-$d_6$) δ ppm 1.09 (d, J=7.35 Hz, 18 H) 1.28 (m, 3 H) 5.63 (s, 2 H) 7.22 (d, J=2.57 Hz, 1 H) 7.31 (dd, J=8.82, 2.94 Hz, 1 H) 7.65 (d, J=8.82 Hz, 1 H) 7.86 (d, J=5.52 Hz, 1 H) 7.95 (s, 1 H) 8.42 (d, J=5.52 Hz, 1 H) 14.05 (s, 1 H) 14.96 (s, 1 H).

EXAMPLE 307E

4-[(2-chloro-1,3-thiazol-5-yl)methyl]-7-hydroxy-6-(7-hydroxy-1,1-dioxido-4H-1,2,4-benzothiadiazin-3-yl)thieno[3,2-b]pyridin-5(4H)-one The product of Example 307D (0.235 g 0.36 mmol.) in tetrahydrofuran (10 mL) was reacted with tetrabutylamonium fluoride in tetrahydrofuran (1M, 0.43 mL) at 25° C. for 2 hours. The reaction mixture was diluted with water (50 mL) and adjusted to pH 2 with 1 M HCl and extracted with ethyl acetate. The organic layer was concentrated under reduced pressure to give the title compound (0.15 g, 84%). MS (ESI−) m/z 493 (M−H)$^-$. The sodium salt of the title compound was prepared according to the procedure of Example 1D. $^1$H NMR (300 MHz, DMSO-$d_6$) δ ppm 5.63 (s, 2 H) 7.17 (s, 1 H) 7.20 (d, J=2.57 Hz, 1 H) 7.57 (d, J=8.82 Hz, 1 H) 7.85 (d, J=5.52 Hz, 1 H) 7.95 (s, 1 H) 8.42 (d, J=5.15 Hz, 1 H) 10.42 (s, 1 H) 13.95 (s, 1H) 15.10 (s, 1 H).

EXAMPLE 308

2-[(3-{4-[(2-chloro-1,3-thiazol-5-yl)methyl]-7-hydroxy-5-oxo-4,5-dihydrothieno[3,2-b]pyridin-6-yl}-1,1-dioxido-4H-1,2,4-benzothiadiazin-7-yl)oxy]acetamide The product of Example 307E (0.065 g, 0.13 mmol.) in N,N-dimethylformamide (5 mL) was reacted with cesium carbonate (0.171 g, 0.53 mmol) and 2-bromoacetamide (0.036 g, 0.26 mmol) at 25° C. for 24 hrs. The reaction mixture was diluted with water and the resulting precipitate was collected by filtration to give the title compound (0.036 g, 50%). MS (ESI−) m/z 550 (M−H)$^-$. The sodium salt of the title compound was prepared according to the procedure of Example 1D. $^1$H NMR (300 MHz, DMSO-$d_6$) δ ppm 4.60 (s, 2 H) 5.63 (s, 2 H) 7.38 (t, J=2.21 Hz, 1 H) 7.42 (d, J=2.94 Hz, 1 H) 7.44 (s, 1 H) 7.69 (d, J=8.46 Hz, 1 H) 7.66 (s, 1 H) 7.85 (d, J=5.52 Hz, 1 H) 7.95 (s, 1 H) 8.42 (d, J=5.52 Hz, 1 H) 14.04 (s, 1 H) 14.99 (s, 1 H).

EXAMPLE 309A

1-Benzyl-4-hydroxy-1H-quinolin-2-one

The title compound was prepared according to the procedure as described in D. R. Buckle, B. C. Cantello, H. Smith, B. A. Spicer, *Journal of Medicinal Chemistry,* 18, 726-732 (1975).

EXAMPLE 309B

1-Benzyl-3-(bis-methylsulfanyl-methylene)-1H-quinoline-2,4-dione

A suspension of sodium hydride (0.75 g, 16 mmol.) in N,N-dimethylformamide (20 mL) at 0° C. was added a solution of the product of Example 309A (2 g, 7.97 mmol) in N,N-dimethylformamide (30 mL) over 30 minutes. The red-orange mixture was warmed to 25° C. and stirred for 30 minutes as a violet color developed. The reaction was then heated at 50° C. for 2 hours and cooled to 25° C. over 30 minutes. Carbon disulfide (1.13 mL, 16 mmol) was added to the mixture. The mixture was heated at 50° C. for 2 hrs (red-brown color developed) and cooled to 25° C. Methyl iodide (1.2 mL, 16 mmol) was added and the reaction was stirred at 25° C. for 30 minutes. The reaction was quenched with phosphate buffer (10 mL, pH=7) and the reaction was concentrated under reduced pressure. The residue was triturated with pH 7 phosphate buffer and ethyl acetate/hexanes (1:1), the resulting orange solids were collected by filtration, washed with hexanes and dried under reduced pressure to give the title compound (1.76 g, 62%). $^1$H NMR (300 MHz, CDCl$_3$) δ ppm 2.65 (s, 6 H) 5.43 (s, 2 H) 7.06 (d, J=8.46 Hz, 1 H) 7.14 (m, 1 H) 7.28 (m, 5 H) 7.43 (m, 1 H) 8.24 (dd, J=7.72, 1.47 Hz, 1 H).

EXAMPLE 309C methyl 4-(benzylthio)-5-nitrothiophene-3-carboxylate

The title compound was prepared according to the procedure as described in Stanetty, P. et. al., *Journal of Heterocyclic Chemistry,* 36, 761-765 (1999).

EXAMPLE 309D

[4-(benzylthio)-5-nitrothien-3-yl]methanol

The product of Example 309C (5 g, 16.2 mmol) in dichloromethane (150 mL) at −40° C. was reacted with diisobutylaluminum hydride (1M in dichloromethane, 36 mL, 2.2 equivalents) added dropwise. The reaction was stirred for 15 minutes after complete addition, quenched with 10% aqueous sodium potassium tartrate solution and stirred at 25° C. for 1 hour. The organic layer was separated, filtered through celite® (diatomaceous earth) and the filtrate was concentrated under reduced pressure. The resulting oil was purified by flash chromatography on silica gel with a Biotage-40s column eluting with 2:98 methanol/dichloromethane to give the title compound as an oil, (4.32 g, 95%). $^1$H NMR (300 MHz, CDCl$_3$) δ ppm 4.21 (s, 2 H), 4.39 (s, 2 H), 7.11 (m, 3 H), 7.23 (m, 2 H) 7.40 (s, 1 H).

EXAMPLE 309E 3-(benzylthio)-4-[(methoxymethoxy)methyl]-2-nitrothiophene

The product of Example 309D (3.9 g, 13.9 mmol) in dichloromethane (8 mL) was reacted with diisopropylethylamine (7.42 mL, 3 equivalents) and methoxymethyl chloride (2.38 mL, 2.25 equivalents) at 25° C. 16 hours. The reaction was concentrated under reduced pressure and the residue purified by flash chromatography on silica gel using a Biotage-40 m column eluting with dichloromethane to give the title compound as a yellowish oil, (4.32 g, 94%). $^1$H NMR (300 MHz, CDCl$_3$) δ ppm 3.36 (s, 3 H), 4.20 (s, 2 H), 4.34 (s, 2 H), 4.62 (s, 2 H), 7.13 (m, 3 H), 7.21 (m, 2 H), 7.40 (s, 1 H).

EXAMPLE 309F

4-[(methoxymethoxy)methyl]-2-nitrothiophene-3-sulfonamide

The product of Example 309E (4 g, 12.3 mmol) in dichloromethane (70 mL) and 1 N aqueous hydrochloric acid (35 mL) at 0° C. was reacted with chlorine gas bubbled in slowly over a period of 0.5 hour, then stirred for an additional 1 hour. The reaction mixture was purged with nitrogen gas to remove excess chlorine and treated with solid sodium bisulfite (11 g) added slowly to the mixture with stirring for 5 minutes. Dichloromethane (15 mL) and water (15 mL) were added, the organic layer was separated and eluted through 40 g of 50:50 mixture of MgSO$_4$/Na$_2$SO$_4$. The filtrate was concentrated under reduced pressure. A solution of the concentrate (4.7 g) in dichloromethane (100 mL) at −40° C. was bubbled with ammonia gas over a period of 10 minutes. The reaction mixture was stirred for an additional 15 minutes, purged with nitrogen gas to dispel the excess ammonia and concentrated under reduced pressure. The concentrate was purified by flash chromatography on silica gel using a Biotage-40s column eluting with 5:95 methanol/dichloromethane to give the title compound as an oil (2.3 g, 66%). $^1$H NMR (300 MHz, CDCl$_3$) δ ppm 3.31 (m, 3 H), 4.70 (s, 2 H), 4.73 (s, 2 H), 7.85 (m, 2 H), 7.88 (s, 1 H).

EXAMPLE 309G 2-amino-4-[(methoxymethoxy)methyl]thiophene-3-sulfonamide

The product of Example 309F (1.8 g, 6.4 mmol) was reacted with iron powder (1.43 g, 4 equivalents) in acetic acid (70 mL) at 50° C. for 7.5 hours then concentrated under reduced pressure. A slurry of the residue in 5% methanol/dichloromethane (60 mL) and water (6 mL) was filtered through silica gel (20 g) and further rinsed with 5% methanol/dichloromethane (300 mL). The filtrate was concentrated under reduced pressure and the residue purified by flash chromatography on silica gel using a Biotage-12s column eluting with 2.5:97.5 methanol: dichloromethane to give the title compound (1 g, 62%). $^1$H NMR (300 MHz, DMSO-d$_6$) δ ppm 3.30 (s, 3 H), 4.53 (s, 2 H), 4.66 (s, 2 H), 6.28 (s, 1 H), 6.61 (s, 2 H), 6.94 (s, 2 H).

EXAMPLE 309H

1-Benzyl-4-hydroxy-3-{7-[(methoxymethoxy)methyl]-1,1-dioxido-4H-thieno[2,3-e][1,2,4]thiadiazin-3-yl}quinolin-2(1H)-one The product of Example 309G (35 mg, 0.14 mmol) and the product of Example 309B (50 mg, 0.14 mmol) were reacted in toluene (3 mL) at 100° C. for 3 hours. The resulting precipitate was collected by filtration and washed with toluene and diethyl ether to give the title compound (52 mg, 73.3%). The sodium salt of the title compound was prepared according to the procedure of Example 1D. $^1$H NMR (300 MHz, DMSO-d$_6$) δ ppm 3.26 (s, 3 H), 4.65 (s, 2 H), 4.72 (s, 2 H), 5.62 (s, 2 H), 7.28 (m, 7 H), 7.43 (s, 2 H), 7.51 (d, J=8.09 Hz, 1 H), 7.75 (m, 1 H), 8.22 (d, J=8.09 Hz, 1 H).

EXAMPLE 310

1-Benzyl-4-hydroxy-3-[7-(hydroxymethyl)-1,1-dioxido-4H-thieno[2,3-e][1,2,4]thiadiazin-3-yl]quinolin-2(1H)-one A suspension of the product of Example 309H (46 mg, 0.09 mmol) in 6N aqueous hydrochloric acid (2.5 mL) and tetrahydrofuran (5 mL) was heated at 70° C. for 4 hours, cooled to 25° C. and let stand for 18 hours at room temperature. The resulting precipitate was collected by filtration and washed with water and diethyl ether to give the title compound (39 mg, 92.8%). The sodium salt of the title compound was prepared according to the procedure of Example 1D. $^1$H NMR (300 MHz, DMSO-d$_6$) δ ppm 4.63 (s, 2 H), 5.62 (s, 2 H), 7.31 (m, 6 H), 7.41 (t, J=7.72 Hz, 1 H), 7.53 (d, J=8.46 Hz, 1 H), 7.76 (t, J=7.91 Hz, 1 H), 8.22 (dd, J=8.09, 1.47 Hz, 1 H).

EXAMPLE 311A

N-(tert-butyl)-5-chlorothiophene-2-sulfonamide

The title compound was prepared according to the procedure as described in Unterhalt, B, Moghaddam, S. *Pharmazie*, 1994, 49, 115-117.

EXAMPLE 311B 3-azido-N-(tert-butyl)-5-chlorothiophene-2-sulfonamide

A solution of Example 311A (1.01 g, 3.99 mmol) in tetrahydrofuran (32 mL) at −78° C. was treated with dropwise addition of sec-BuLi (1.4 M in hexane, 2.1 equivalents). The reaction was warmed to −20° C. and stirred for 30 minutes, treated with a solution of tosyl azide (1.1 equivalent) in tetrahydrofuran (7 mL) at −20° C., stirred at 25° C. for 18 hours. The reaction mixture was quenched with water and extracted with ethyl acetate. The organic layer was washed with brine, dried over anhydrous sodium sulfate, filtered and concentrated. The residue was purified by column chromatography on silica gel, eluting with a gradient of 30% dichloromethane in hexane to 100% dichloromethane to give approximately a 2:1 mixture of starting material to the title compound.

EXAMPLE 311C

3-Amino-5-chloro-N-isopropylthiophene-2-sulfonamide

A solution of the product of Example 311B (0.739 g) in toluene (20 mL) and hexadecyltributylphosphonium bromide (0.128 g, 0.25 mmol) at 0° C. was treated dropwise with a solution of sodium borohydride (0.109 g, 2.9 mmol) in water (0.80 mL). The reaction was stirred at 25° C. for 18 hours and at 5° C. for 72 hours. The reaction was extracted with ethyl acetate. The organic layer was washed with 1N aqueous sodium hydroxide, water, and brine and dried over anhydrous sodium sulfate, filtered and concentrated. The residue was purified by column chromatography on silica gel, eluting with a gradient of 1:1 hexanes/dichloromethane to 100% dichloromethane to give the title compound (0.252 g, 23%). $^1$H NMR (300 MHz, CDCl$_3$) δ ppm 6.36 (s, 1 H) 4.93 (br s, 2 H) 4.60 (br s, 1 H) 1.30 (s, 9 H).

EXAMPLE 311D

3-Amino-5-chloro-N-isopropylthiophene-2-sulfonamide, trifluoroacetate salt

The product of Example 311C (0.0998 g) in trifluoroacetic acid (3.9 mL) was stirred at 25° C. for 18 hours. The reaction was concentrated under reduced pressure and azeotroped three times with ethyl acetate to give the title compound as a trifluoroacetate salt (0.160 g). $^1$H NMR (300 MHz, CDCl$_3$) δ ppm 6.41 (s, 1 H) 5.22 (br s, 2 H) 4.84 (br s, 2 H).

EXAMPLE 311E

1-Benzyl-3-(6-chloro-1,1-dioxido-4H-thieno[3,2-e][1,2,4]thiadiazin-3-yl)-4-hydroxyquinolin-2(1H)-one The title compound was prepared according to the procedure of Example 309H, substituting the product of Example 311D for the product of Example 309G, in the presence of diisopropylethylamine (3 equivalents). The sodium salt of the title compound was prepared according to the procedure of Example 1D. $^1$H NMR (300 MHz, DMSO-d$_6$) δ ppm 16.97 (s, 1 H) 8.11 (d, J=8.09 Hz, 1 H) 7.20 (m, 9 H) 5.40 (s, 2 H).

EXAMPLE 312A

5-Bromo-4-nitro-1H-imidazole

4-Bromo-1H-imidazole (2.0 g, 13.6 mmol) was reacted with concentrated nitric acid (0.947 mL, 14.96 mmol) in concentrated sulfuric acid (20 mL) at 110° C. for 1 hour. The reaction was cooled to 25° C. and poured into 200 mL of ice water. The resulting white precipitate formed was collected by filtration to give the title compound (2.3 g, 87%). MS (ESI−) m/z 191 (M−H)$^-$. $^1$H NMR (300 MHz, DMSO-d$_6$) δ ppm 7.99 (s, 1H).

EXAMPLE 312B

1-Benzyl-5-bromo-4-nitro-1H-imidazole

A solution of the product of Example 312A (2.3 g, 11.98 mmol) in anhydrous N,N-dimethylformamide (40 mL) at 25° C. was reacted with sodium bicarbonate (2.0 g, 24 mmol) and dropwise addition of benzyl bromide (1.58 mL, 13.17 mmol). The reaction was stirred for an additional 12 hours at 25° C. The reaction was concentrated under reduced pressure and the residue was partitioned between ethyl acetate and water. The organic layer was dried over MgSO$_4$, filtered, and concentrated under reduced pressure. The residue was purified by reverse phase column chromatography on a C18 column, eluting with a gradient of acetonitrile in water containing 0.1% trifluoroacetic acid (5:95 to 100) to give the title compound (1.63 g, 48%). MS (ESI+) m/z 284 (M+H)$^+$. 1H NMR (300 MHz, DMSO-d$_6$) δ ppm 5.38 (s, 2H), 7.24-7.42 (m, 5H), 8.28 (s, 1H).

EXAMPLE 312C ammonium 1-benzyl-4-nitro-1H-imidazole-5-thiolate

A solution of the product of Example 312B in 5N ammonium hydroxide (16 mL) and dioxane (10 mL) at 35° C. was bubbled with hydrogen sulfide gas for 15 minutes. The reaction flask was then sealed and stirring was continued for 1 hour. The reaction was purged with nitrogen gas for 10 minutes and concentrated under reduced pressure to give the title compound.

EXAMPLE 312D 1-benzyl-4-nitro-1H-imidazole-5-sulfonyl chloride

A solution of the product of Example 312C in 1N HCl (20 mL) and dioxane (10 mL) at 30° C. was bubbled with chlorine gas for 15 minutes. The reaction flask was sealed and the reaction mixture stirred for 1 hour. The chlorine addition was repeated as above and the reaction mixture stirred for an additional 1 hour. The reaction was cooled in an ice bath. Cold water was added to the reaction and the resulting precipitate was collected by filtration to give the title compound (1.51 g, 87% for 2 steps). 1H NMR (300 MHz, DMSO-$d_6$) δ ppm 5.57 (s, 2H), 7.27-7.40 (m, 5H), 7.74 (s, 1H).

EXAMPLE 312E 1-benzyl-4-nitro-1H-imidazole-5-sulfonamide

A solution of the product of Example 312D (1.5 g, 4.97 mmol) in dioxane (25 mL) at 25° C. was bubbled with ammonia gas for 10 minutes. The reaction flask was sealed and the reaction mixture was stirred an additional 30 minutes. This above process was repeated. The reaction mixture was concentrated under reduced pressure and the residue was washed with cold water several times to give the title compound (1.27 g, 90%). MS (ESI−) m/z 281 (M−H)$^-$. $^1$H NMR (300 MHz, DMSO-$d_6$) δ ppm 5.61 (s, 2H), 7.26-7.42 (m, 5H), 8.17 (s, 1H).

EXAMPLE 312F 4-amino-1-benzyl-1H-imidazole-5-sulfonamide

A solution of the product of Example 312E (434 mg, 1.54 mmol) in acetic acid (4.3 mL) and dioxane (4.3 mL) was reacted with iron powder (343 mg, 6.15 mmol) at 50° C. for 3 hours. The reaction mixture was cooled to 25° C., filtered through a pad of celite® (diatomaceous earth) and the filtrate was concentrated under reduced pressure. The residue was dissolved in dichloromethane and washed with a saturated aqueous sodium bicarbonate solution. The aqueous layer was extracted with dichloromethane (2×) and the combined organic layers were dried over magnesium sulfate, filtered, and concentrated under reduced pressure. The residue was chromatographed on silica gel using a gradient of methanol in dichloromethane (0-5%) to give the title compound (180 mg, 46%). MS (ESI+) m/z 253 (M+H)$^+$. $^1$H NMR (300 MHz, DMSO-$d_6$) δ ppm 5.24 (s, 2H), 7.22-7.39 (m, 5H), 7.43 (s, 1H).

EXAMPLE 312G 1-benzyl-3-(7-benzyl-1,1-dioxido-4,7-dihydroimidazo[4,5-e][1,2,4]thiadiazin-3-yl)-4-hydroxyquinolin-2(1H)-one The product of Example 312F (152 mg, 0.602 mmol) was reacted with the product of Example 309B (214 mg, 0.602 mmol) in toluene (8 mL) at 100° C. for 3 hours. The reaction was allowed to cool to 25° C. and diluted with hexanes. The resulting precipitate was collected by filtration. The residue was chromatographed on silica gel, eluting with gradient of 0-2% methanol in dichloromethane to give the title compound (155 mg, 50%). MS (ESI+) m/z 512 (M+H)$^+$. 1H NMR (300 MHz, DMSO-$d_6$) δ ppm 5.42 (s, 2H), 5.63 (s, 2H), 7.22-7.44 (m, 11H), 7.53-7.56 (m, 1H), 7.74-7.79 (m, 1H), 8.20-8.23 (dd, J=8.1, 1.5 Hz, 1H), 8.32 (s, 1H).

EXAMPLE 313

1-benzyl-3-(1,1-dioxido-4,7-dihydroimidazo[4,5-e][1,2,4]thiadiazin-3-yl)-4-hydroxyquinolin-2(1H)-one The product of Example 312 (19.35 mg, 0.0378 mmol) in anhydrous dimethyl sulfoxide (2.5 mL) was reacted with a solution of potassium tert-butoxide in tetrahydrofuran (1M, 0.265 mL, 0.265 mmol) at 25° C. for 12 hours. The reaction was quenched by adding saturated aqueous ammonium chloride solution and extracted with dichloromethane. The aqueous layer was made basic with a sodium bicarbonate solution and extracted twice with dichloromethane. The combined organic layers were combined, dried over magnesium sulfate, filtered, and concentrated under reduced pressure. The residue was chromatographed on a reverse phase C18 column eluting with 5%-100% acetonitrile in water containing 0.1% trifluoroacetic acid to give the title compound (17 mg, 81%). MS (ESI−) m/z 420 (M−H)$^-$. 1H NMR (300 MHz, DMSO-$d_6$)/CF$_3$COOD) δ ppm 5.6 (s, 2H), 7.17-7.27 (m, 5H), 7.35-7.40 (t, J=7.64 Hz, 1H), 7.51-7.63 (d, J=8.3 Hz, 1H), 7.69-7.73 (t, J=8.8 Hz, 1H), 8.0-8.01 (m, 1H), 8.18-8.20 (dd, J=8.3, 1.2 Hz, 1H).

EXAMPLE 314

N$^2$-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}glycinamide A solution of the product of Example 206 (10.8 mg, 0.023 mmol) in concentrated sulfuric acid (0.6 mL) was treated with a slow addition of water (0.1 mL) and the yellow solution was stirred at 25° C. for 18 hours. The reaction mixture was poured onto ice, the pH was adjusted to pH 9 with 50% NaOH and aqueous sodium bicarbonate solution. The mixture was extracted with ethyl acetate (3×20 mL). The combined organic layers were washed with water, brine, dried over magnesium sulfate and filtered. The filtrate concentrated under reduced pressure to give the title compound as a yellow solid (9.1 mg, 83%). MS (ESI−) m/z 483 (M−H)$^-$. $^1$H NMR (300 MHz, DMSO-$d_6$) δ ppm 0.96 (d, J=6.62 Hz, 6H) 1.49 (m, 2 H) 1.64 (m, 1 H) 3.63 (d, J=5.52 Hz, 2 H) 4.30 (m, 2 H) 6.23 (br s, 1 H) 6.69 (s, 1 H) 6.87 (d, J=7.35 Hz, 1 H) 7.12 (s, 3 H) 7.42 (s, 1 H) 8.36 (d, J=7.35 Hz, 1 H) 8.52 (s, 1 H) 15.62 (br s, 1 H). The sodium salt of the title compound was prepared according to the procedure of Example 1D. $^1$H NMR (300 MHz, DMSO-$d_6$) δ ppm 0.96 (d, J=6.62 Hz, 6 H) 1.48 (m, 2 H) 1.64 (m, 1 H) 3.62 (d, J=5.88 Hz, 2 H) 4.29 (m, 2 H)

6.20 (m, 1 H) 6.68 (d, J=2.57 Hz, 1 H) 6.86 (m, 1 H) 7.41 (m, 3 H) 8.35 (dd, J=7.72, 1.84 Hz, 1 H) 8.50 (dd, J=4.78, 1.84 Hz, 1 H) 15.63 (s, 1 H).

EXAMPLE 315A 1-butyl-4-hydroxy-1,8-naphthyridin-2(1H)-one

A slurry of the product of Example 89A (3.24 g, 11.16 mmol) in 2 N sodium hydroxide (100 mL) was heated at reflux for 3 hours, cooled to 11° C. and treated dropwise with concentrated hydrochloric acid to a constant pH of 3. The resulting white solid was collected by filtration, washed with water and dried to give the title compound (2.47 g, quantitative). MS (APCI+) m/z 219 (M+H)$^+$. 1H NMR (300 MHz, DMSO-d$_6$) δ ppm 0.90 (t, J=7.35 Hz, 3 H) 1.32 (m, 2 H) 1.57 (m, 2 H) 4.31 (m, 2 H) 5.89 (s, 1 H) 7.27 (dd, J=7.72, 4.78 Hz, 1 H) 8.23 (dd, J=7.72, 1.84 Hz, 1 H) 8.64 (dd, J=4.78, 1.84 Hz, 1 H) 11.61 (s, 1 H).

EXAMPLE 315B

3-[bis(methylthio)methylene]-1-butyl-1,8-naphthyridine-2,4(1H,3H)-dione

The title compound was prepared according to the procedure of Example 309B substituting the product of Example 315A for the product of Example 309A. $^1$H NMR (300 MHz, CDCCl$_3$) δ ppm 0.97 (t, J=7.35 Hz, 3 H) 1.44 (dd, J=15.44, 7.35 Hz, 2 H) 1.69 (m, 2 H) 2.64 (s, 6 H) 4.39 (m, 2 H) 7.10 (dd, J=7.72, 4.78 Hz, 1 H) 8.45 (dd, J=7.72, 1.84 Hz, 1 H) 8.56 (dd, J=4.60, 2.02 Hz, 1 H).

EXAMPLE 315C 1-butyl-4-hydroxy-3-{7-[(methoxymethoxy)methyl]-1,1-dioxido-4H-thieno[2,3-e][1,2,4]thiadiazin-3-yl}-1,8-naphthyridin-2(1H)-one The product of Example 309G (110 mg, 0.43 mmol) and the product of Example 315B (140.6 mg, 0.43 mmol) were reacted in toluene (5 mL) at 100° C. for 3 hours. The reaction was concentrated under reduced pressure and the residue was purified by chromatography on silica gel using a Biotage-12 m column eluting with 1:99 methanol:dichloromethane to give the title compound as a white solid (114 mg, 54.6%). The sodium salt of the title compound was prepared according to the procedure of Example 1D. $^1$H NMR (300 MHz,CDCCl$_3$) δ ppm 1.00 (t, J=7.35 Hz, 3 H), 1.46 (m, 2 H), 1.74 (m, 2 H), 3.45 (s, 3 H), 4.56 (m, 2 H), 4.80 (s, 2 H), 4.84 (s, 2 H), 7.09 (s, 1 H), 7.26 (s, 1 H), 7.36 (dd, J=8.09, 4.41 Hz, 1 H), 8.57 (dd, J=8.09, 1.84 Hz, 1 H), 8.81 (dd, J=4.78, 1.84 Hz, 1 H), 15.06 (s, 1 H), 15.11 (s, 1 H).

EXAMPLE 316

1-butyl-4-hydroxy-3-[7-(hydroxymethyl)-1,1-dioxido-4H-thieno[2,3-e][1,2,4]thiadiazin-3-yl]-1,8-naphthyridin-2(1H)-one The product of Example 315C (92 mg, 0.19 mmol) was reacted with 6N aqueous hydrochloric acid (4 mL) and tetrahydrofran (8 mL) at 70° C. for 3 hours. The reaction was concentrated under reduced pressure to remove the tetrahydrofuran, and treated with methanol (5 mL). The resulting precipitate was collected by filtration and washed with water and diethylether to give the title compound as a white solid (65 mg, 77.8%). The sodium salt of the title compound was prepared according to the procedure of Example 1D. $^1$H NMR (300 MHz, CDCl$_3$) δ ppm 1.00 (t, J=7.35 Hz, 3 H), 1.47 (dd, J=15.26, 7.54 Hz, 2 H), 1.73 (m, 2 H) 4.57 (m, 2 H), 4.86 (s, 2 H), 7.07 (s, 1 H), 7.37 (dd, J=8.09, 4.78 Hz, 1 H), 8.58 (dd, J=8.09, 1.84 Hz, 1 H), 8.82 (dd, J=4.60, 2.02 Hz, 1 H), 14.94 (s, 1 H), 15.24 (s, 1 H).

EXAMPLE 317A methyl 4-(aminosulfonyl)-5-nitrothiophene-3-carboxylate

A solution of the product of Example 309A (2 g, 6.5 mmol) in dichloromethane (38 mL) and 1.5 N aqueous hydrochloric acid (21 mL) at 0° C. was bubbled with chlorine gas over 30 minutes. The reaction flask was sealed and stirred for an additional 1 hour. Nitrogen gas was bubbled through the reaction to dispel the chlorine, followed by the addition of solid sodium bisulfite (5.12 g) with stirring for 5 minutes. Dichloromethane (10 mL) and water (10 mL) were added to the reaction. The organic layer was separated and eluted through 20 g of 1:1 mixture of magnesium sulfate and sodium sulfate. The filtrate was concentrated under reduced pressure, and the residue triturated with hexanes to give the sulfonyl chloride as a white solid (1.8 g, 97%). A solution of the crude sulfonyl chloride (1.5 g) in dichloromethane (15 mL) at −40° C. was bubbled with ammonia gas over a period of 5 minutes. The reaction flask was sealed and stirred for another 15 minutes. Nitrogen gas was bubbled into the reaction mixture to dispel the ammonia. The reaction was concentrated under reduced pressure while maintaining the temperature under 0° C. The residue was chromatographed on silica gel using a Biotage-40s column eluting with 5:95 methanol:dichloromethane to give an oil. This oil was triturated with a mixture of 5% methanol:dichloromethane (20 mL) and hexanes (20 mL), to give the title compound as a yellow solid (0.75 g, 54%). $^1$H NMR (300 MHz, DMSO-d$_6$) δ ppm 3.81 (s, 3 H), 7.88 (s, 2 H), 8.31 (s, 1 H).

methyl 5-amino-4-(aminosulfonyl)thiophene-3-carboxylate

The product of Example 317A (0.75 g, 2.86 mmol) was reacted with iron powder (0.64 g, 4 equivalents) in acetic acid (30 mL) at 50° C. for 7.5 hours. The reaction was concentrated under reduced pressure and the residue was slurried in 5% methanol:dichloromethane (20 mL) and water (2 mL) and filtered through a short column of silica gel (20 g) that was washed with 5% methanol:dichloromethane (200 mL). The filtrate was concentrated under reduced pressure and residue was chromatographed on silica gel using a Biotage-12s column eluting with 1:1 ethyl acetate/hexane to give the title compound as a yellow solid (0.527 g, 78%). $^1$H NMR (300 MHz, DMSO-d$_6$) δ ppm 3.77 (s, 3 H), 6.84 (s, 2 H), 6.88 (s, 2 H), 7.28 (s, 1 H).

EXAMPLE 317C methyl 3-(1-benzyl-4-hydroxy-2-oxo-1,2-dihydroquinolin-3-yl)-4H-thieno[2,3-e][1,2,4]thiadiazine-7-carboxylate 1,1-dioxide The product of Example 317B (180 mg, 0.76 mmol) and the product of Example 309B (270 mg, 0.76 mmol) were reacted in toluene (15 mL) at 100° C. for 3 hours. The reaction was cooled to 25° C. and the resulting precipitate was collected by filtration, washed with toluene and and diethyl ether to give the title compound (302 mg, 80%). The sodium salt of the title compound was prepared according to the procedure of Example 1D. $^1$H NMR (300 MHz, DMSO-$d_6$) δ ppm 3.85 (s, 3 H), 5.61 (s, 2 H), 7.29 (m, 5 H), 7.40 (m, 1 H), 7.52 (m, 1 H), 7.74 (m, 1 H), 8.21 (d, J=7.72 Hz, 1 H), 8.26 (s, 1 H).

EXAMPLE 318

3-(1-benzyl-4-hydroxy-2-oxo-1,2-dihydroquinolin-3-yl)-4H-thieno[2,3-e][1,2,4]thiadiazine-7-carboxylic acid 1,1-dioxide The product of Example 317C (90 mg, 0.09 mmol) was reacted with a solution of 1N aqueous sodium hydroxide (0.8 mL, 4.4 equivalents) in ethanol (2 mL) at 70° C. for 1.5 hours. The reaction was filtered and the filtrate was acidified with 1N aqueous hydrochloric acid (0.8 mL). The resulting precipitate was collected by filtration and washed with water, methanol, and diethyl ether to give the title compound (80 mg, 91.5%). $^1$H NMR (300 MHz, DMSO-$d_6$) δ ppm 5.62 (s, 2 H), 7.29 (m, 5 H), 7.42 (t, J=7.54 Hz, 1 H), 7.53 (d, J=8.82 Hz, 1 H), 7.76 (t, J=7.17 Hz, 1 H), 8.19 (s, 1 H), 8.22 (dd, J=8.09, 1.47 Hz, 1 H). The disodium salt of the title compound was prepared according to the procedure of Example 1D substituting two equivalent of sodium hydroxide for one equivalent of sodium hydroxide.

EXAMPLE 319

3-(1-benzyl-4-hydroxy-2-oxo-1,2-dihydroquinolin-3-yl)-4H-thieno[2,3-e][1,2,4]thiadiazine-7-carboxamide 1,1-dioxide The product of Example 317C (25 mg, 0.05 mmol) was suspended in ammonium hydroxide (1mL) and heated at 40° C. for 16 hours. The reaction mixture was cooled to 25° C., concentrated under reduced pressure to remove the excess ammonia, and a solution of 1N HCl (0.8 mL), MeOH (1mL), and water (3 mL) was added to the reaction mixture. The resulting precipitate was collected by filtration and washed with water, methanol, and diethyl ether to give the title compound (19 mg, 78.4%). $^1$H NMR (300 MHz, DMSO-$d_6$) δ ppm 5.62 (s, 2 H), 7.30 (m, 7 H), 7.41 (t, J=7.54 Hz, 1 H), 7.53 (m, 2 H), 7.76 (m, 2 H), 7.98 (s, 1 H), 8.22 (m, 1 H). The sodium salt of the title compound was prepared according to the procedure of Example 1D.

EXAMPLE 320A

3-[7-(benzyloxy)-1,1-dioxido-4H-1,2,4-benzothiadiazin-3-yl]-1-{[cyclopropylmethylene]amino}-4-hydroxyquinolin-2(1H)-one The product of Example 304F (0.800 g, 1.73 mmol) and cyclopropane carboxaldehyde (1.60 mL, 20.76 mmol) in N,N-dimethylacetamide (2 mL) were reacted at 120° C. for 60 minutes in a microwave reactor in a sealed tube. The reaction was concentrated under a stream of nitrogen warmed through a manifold heated to 165° C. The resulting residue was triturated with diethyl ether and filtered to give the title compound (0.750 g, 84%).

EXAMPLE 320B

3-[7-(benzyloxy)-1,1-dioxido-4H-1,2,4-benzothiadiazin-3-yl]-1-[(cyclopropylmethyl)amino]-4-hydroxyquinolin-2(1H)-one The produce of Example 320A (0.75 g, 1.46 mmol) in tetrahydrofuran (8 mL) and methanol (0.100 mL) at 0° C. was reacted with lithium borohydride (2.0 M solution in tetrahydrofuran, 1.0 mL, 2.0 mmol). The reaction was stirred at 25° C. for 1 hour then diluted with 1M aqueous hydrochloric acid and filtered. The product was purified by trituration with methyl sulfoxide, filtered and dried to give the title compound (0.296 g, 40%).

EXAMPLE 320C

1-[(cyclopropylmethyl)amino]-4-hydroxy-3-(7-hydroxy-1,1-dioxido-4H-1,2,4-benzothiadiazin-3-yl)quinolin-2(1H)-one The product of Example 320B (0.296 g, 0.57 mmol) in tetrahyrofuran (15 mL) was reacted with a catalytic amount of palladium hydroxide on carbon, a catalytic amount of 5% palladium on carbon, and ammonium formate (0.180 g, 2.85 mmol) at 60° C. for 2 hours. The warm reaction mixture was filtered through celite® (diatomaceous earth) and the filtrate was diluted with diethyl ether and the precipitate filtered and dried to give the title compound (0.127 g, 53%).

EXAMPLE 320D

2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetamide The product of Example 320C (0.125 g, 0.29 mmol) was reacted with cesium carbonate (0.38 g, 1.17 mmol), 2-bromoacetamide (0.060 g, 0.43 mmol) and a catalytic amount of tetrabuylammonium iodide in N,N-dimethylformamide (3 mL) at 25° C. for 2 hours. The reaction was concentrated to half the volume under a stream of nitrogen warmed through a manifold heated to 165° C. The resulting solution was diluted with water and the precipitate was collected by filtration and dried to give the title compound (0.134 g, 95%). MS (ESI–) m/z 482 (M–H)⁻. The sodium salt of the title compound was prepared according to the procedure of Example 1D. $^1$H NMR (300 MHz, DMSO-$d_6$) δ ppm 0.21 (m, J=3.86, 2.39 Hz, 2 H) 0.46 (m, 2 H) 0.99 (m, 1 H) 2.55 (m, 2 H) 4.49 (s, 2 H) 5.96 (t, J=6.43 Hz, 1 H) 7.06 (m, 1 H) 7.21 (m, 2 H) 7.40 (m, 2 H) 7.53 (m, 1 H) 7.62 (m, J=1.84 Hz, 1 H) 7.67 (d, J=8.46 Hz, 1 H) 8.07 (dd, J=8.09, 1.47 Hz, 1H) 16.25 (s, 1 H).

EXAMPLE 321A

3-[7-(benzyloxy)-1,1-dioxido-4H-1,2,4-benzothiadiazin-3-yl]-4-hydroxy-1-{[2-methylpropylidene]amino}quinolin-2(1H)-one The product of Example 304F (0.150 g, 0.32 mmol) and isobutyrlaldehyde (0.44 mL, 4.84 mmol) in N,N-dimethylacetamide (1.5 mL) were reacted at 125° C. for 40 minutes in a microwave reactor in a sealed tube. The reaction was concentrated under a stream of nitrogen warmed through a manifold heated to 165° C. The resulting residue was triturated with diethyl ether and filtered to give the title compound (0.140 g, 84%).

EXAMPLE 321B

3-[7-(benzyloxy)-1,1-dioxido-4H-1,2,4-benzothiadiazin-3-yl]-4-hydroxy-1-(isobutylamino)quinolin-2(1H)-one The produce of Example 321A (0.140 g, 0.27 mmol) in tetrahydrofuran (3 mL) and methanol (0.020 mL) at 0° C. was reacted with lithium borohydride (2.0 M solution in tetrahydrofuran, 0.20 mL, 0.40 mmol). The reaction was stirred at 25° C. for 1 hour then diluted with 1M aqueous hydrochloric acid and filtered. The product was purified by dissolving in tetrahydrofuran, absorbing onto silica gel, loading onto a silica gel column and eluting with dichloromethane. The filtrate was evaporated to dryness under reduced pressure to give the title compound (0.081 g, 58%).

EXAMPLE 321C 4-hydroxy-3-(7-hydroxy-1,1-dioxido-4H-1,2,4-benzothiadiazin-3-yl)-1-(isobutylamino)quinolin-2(1H)-one The product of Example 321B (0.081 g, 0.16 mmol) in tetrahyrofuran (10 mL) was reacted with a catalytic amount of palladium hydroxide on carbon, a catalytic amount of 5% palladium on carbon, and ammonium formate (0.040 g, 0.64 mmol) at 60° C. for 30 minutes. The warm reaction mixture was filtered through celite® (diatomaceous earth) and the filtrate was evaporated under reduced pressure to give the title compound (0.048 g, 72%).

EXAMPLE 321D 2-({3-[4-hydroxy-1-(isobutylamino)-2-oxo-1,2-dihydroquinolin-3-yl]-1,1-dioxido-4H-1,2,4-benzothiadiazin-7-yl}oxy)acetamide The product of Example 321C (0.048 g, 0.11 mmol) was reacted with cesium carbonate (0.11 g, 0.34 mmol), 2-bromoacetamide (0.023 g, 0.17 mmol) and a catalytic amount of tetrabuylammonium iodide in N,N-dimethylformamide (3 mL) at 25° C. for 2 hours. The reaction was concentrated to half the volume under a stream of nitrogen warmed through a manifold heated to 165° C. The resulting solution was diluted with water and the precipitate was collected by filtration and dried to give the title compound (0.042 g, 77%). MS (ESI–) m/z 484 (M–H)⁻. The sodium salt of the title compound was prepared according to the procedure of Example 1D. $^1$H NMR (300 MHz, DMSO-$d_6$) δ ppm 1.03 (m, 6 H) 1.86 (m, 1 H) 3.25 (m, 2 H) 4.50 (m, 2 H) 5.94 (t, J=7.35 Hz, 1 H) 7.07 (t, J=7.72 Hz, 1 H) 7.21 (m, 2 H) 7.40 (s, 1 H) 7.58 (m, 2 H) 8.07 (dd, J=7.72, 1.47 Hz, 1 H) 16.23 (s, 1 H).

EXAMPLE 322A

3-[7-(benzyloxy)-1,1-dioxido-4H-1,2,4-benzothiadiazin-3-yl]-1-[butylideneamino]-4-hydroxyquinolin-2(1H)-one The product of Example 304F (0.150 g, 0.32 mmol) and butyrlaldehyde (0.29 mL, 3.24 mmol) in N,N-dimethylacetamide (1.5 mL) were reacted at 120° C. for 25 minutes in a microwave reactor in a sealed tube. The reaction was concentrated under a stream of nitrogen warmed through a manifold heated to 165° C. The resulting residue was triturated with diethyl ether and filtered to give the title compound (0.134 g, 80%).

EXAMPLE 322B

3-[7-(benzyloxy)-1,1-dioxido-4H-1,2,4-benzothiadiazin-3-yl]-1-(butylamino)-4-hydroxyquinolin-2(1H)-one The produce of Example 322A (0.134 g, 0.26 mmol) in tetrahydrofuran (3 mL) and methanol (0.020 mL) at 0° C. was reacted with lithium borohydride (2.0 M solution in tetrahydrofuran, 0.195 mL, 0.39 mmol). The reaction was stirred at 25° C. for 1 hour then diluted with 1 M aqueous hydrochloric acid and filtered. The product was purified by dissolving in tetrahydrofuran, absorbing onto silica gel, loading onto a silica gel column and eluting with dichloromethane. The filtrate was evaporated to dryness under reduced pressure to give the title compound (0.045 g, 33%).

EXAMPLE 322C 1-(butylamino)-4-hydroxy-3-(7-hydroxy-1,1-dioxido-4H-1,2,4-benzothiadiazin-3-yl)quinolin-2(1H)-one The product of Example 322B (0.045 g, 0.087 mmol) in tetrahyrofuran (8 mL) was reacted with a catalytic amount of palladium hydroxide on carbon, a catalytic amount of 5% palladium on carbon, and ammonium formate (0.03 g, 0.48 mmol) at 60° C. for 4 hours. The warm reaction mixture was filtered through celite® (diatomaceous earth) and the filtrate was evaporated under reduced pressure to give the title compound (0.038 g, 100%).

EXAMPLE 322D 2-({3-[1-(butylamino)-4-hydroxy-2-oxo-1,2-dihydroquinolin-3-yl]-1,1-dioxido-4H-1,2,4-benzothiadiazin-7-yl}oxy)acetamide The product of Example 322C (0.038 g, 0.089 mmol) was reacted with cesium carbonate (0.087 g, 0.27 mmol), 2-bromoacetamide (0.018 g, 0.13 mmol) and a catalytic amount of tetrabuylammonium iodide in N,N-dimethylformamide (3 mL) at 25° C. for 2 hours. The reaction was concentrated to half the volume under a stream of nitrogen warmed through a manifold heated to 165° C. The resulting solution was diluted with water and the precipitate was collected by filtration and dried to give the title compound (0.041 g, 95%). MS (ESI–) m/z 484 (M–H)⁻. The sodium salt of the title compound was prepared according to the procedure of Example 1D. $^1$H NMR (300 MHz, DMSO-$d_6$) δ ppm 0.93 (t, J=7.17 Hz, 3 H) 1.48 (m, 4 H) 2.76 (m, 2 H) 4.49 (s, 2 H) 5.90 (t, J=6.80 Hz, 1 H) 7.06 (t, J=6.99 Hz, 1 H) 7.21 (m, 2 H) 7.40 (m, 1 H) 7.54 (m, 2 H) 8.07 (dd, J=8.09, 1.10 Hz, 1 H) 16.24 (s, 1 H).

EXAMPLE 323A

3-[7-(benzyloxy)-1,1-dioxido-4H-1,2,4-benzothiadiazin-3-yl]-4-hydroxy-1-{[(1E)-3-methylbutylidene]amino}quinolin-2(1H)-one The product of Example 304F (0.220 g, 0.48 mmol) and isovaleraldehyde (0.77 mL, 7.18 mmol) in N,N-dimethylacetamide (1.5 mL) were reacted at 130° C. for 35 minutes in a microwave reactor in a sealed tube. The reaction was concentrated under a stream of nitrogen warmed through a manifold heated to 165° C. The resulting residue was triturated with diethyl ether and filtered to give the title compound (0.181 g, 72%).

EXAMPLE 323B

3-[7-(benzyloxy)-1,1-dioxido-4H-1,2,4-benzothiadiazin-3-yl]-4-hydroxy-1-[(3-methylbutyl)amino]quinolin-2(1H)-one The produce of Example 323A (0.061 g, 0.11 mmol) in tetrahydrofuran (3 mL) and methanol (0.010 mL) at 0° C. was reacted with lithium borohydride (2.0 M solution in tetrahydrofuran, 0.09 mL, 0.18 mmol). The reaction was stirred at 25° C. for 1 hour then diluted with 1M aqueous hydrochloric acid and filtered. The product was purified by dissolving in tetrahydrofuran, absorbing onto silica gel, loading onto a 2 g Alltech Sep-pack and eluting with dichloromethane. The filtrate was evaporated to dryness under reduced pressure to give the title compound (0.037 g. 62%).

EXAMPLE 323C 4-hydroxy-3-(7-hydroxy-1,1-dioxido-4H-1,2,4-benzothiadiazin-3-yl)-1-[(3-methylbutyl)amino]quinolin-2(1H)-one The product of Example 323B (0.037 g, 0.07 mmol) in tetrahyrofuran (8 mL) was reacted with a catalytic amount of palladium hydroxide on carbon, a catalytic amount of 5% palladium on carbon, and ammonium formate (0.018 g, 0.29 mmol) at 60° C. for 30 minutes. The warm reaction mixture was filtered through celite® (diatomaceous earth) and the filtrate was evaporated under reduced pressure to give the title compound (0.025 g, 80%).

EXAMPLE 323D

2-[(3-{4-hydroxy-1-[(3-methylbutyl)amino]-2-oxo-1,2-dihydroquinolin-3-yl}-1,1-dioxido-4H-1,2,4-benzothiadiazin-7-yl)oxy]acetamide The product of Example 323C (0.025 g, 0.057 mmol) was reacted with cesium carbonate (0.055 g, 0.17 mmol), 2-bromoacetamide (0.012 g, 0.087 mmol) and a catalytic amount of tetrabuylammonium iodide in N,N-dimethylformamide (3 mL) at 25° C. for 2 hours. The reaction was concentrated to half the volume under a stream of nitrogen warmed through a manifold heated to 165° C. The resulting solution was diluted with water and the precipitate was collected by filtration and dried to give the title compound (0.020 g, 72%). MS (ESI−) m/z 498 (M−H)⁻. The sodium salt of the title compound was prepared according to the procedure of Example 1D. $^1$H NMR (300 MHz, DMSO-$d_6$) δ ppm 0.90 (m, 3H) 1.33 (m, 6 H) 1.54 (m, 2 H) 4.49 (s, 2 H) 5.90 (m, 1 H) 7.06 (m, 1 H) 7.21 (m, 2 H) 7.40 (m, 1 H) 7.55 (m, 2 H) 8.07 (dd, J=8.27, 1.29 Hz, 1 H) 16.23 (s, 1 H).

EXAMPLE 324A 4-amino-N-[2-(aminosulfonyl)-4-(benzyloxy)phenyl]-7-hydroxy-5-oxo-4,5-dihydrothieno[3,2-b]pyridine-6-carboxamide and N-[2-(aminosulfonyl)-4-(benzyloxy)phenyl]-7-hydroxy-5-oxo-4-{[(1E)-phenylmethylene]amino}-4,5-dihydrothieno[3,2-b]pyridine-6-carboxamide The products of Example 304D (1.55 g, 5.57 mmol) and Example 268C (1.27 g, 3.71 mmol) in toluene (100 mL) were reacted at 118° C. for 5 hours. The cooled slurry was filtered, washed with 25 mL toluene and dried to give the title compounds.

EXAMPLE 324B 4-amino-6-[7-(benzyloxy)-1,1-dioxido-4H-1,2,4-benzothiadiazin-3-yl]-7-hydroxythieno[3,2-b]pyridin-5(4H)-one The product of Example 324A (1.95 g, 3.7 mmole) was reacted with 10% aqueous potassium hydroxide (100 mL) at reflux for 24 hours, cooled to 25° C. and acidified with concentrated hydrochloric acid to pH 2. The resulting solid was collected by filtration, washed repeatedly with water and dried to provide the title compound (2.05 g, 100%). MS (ESI−) m/z 467 (M−H)⁻.

EXAMPLE 324C

6-[7-(benzyloxy)-1,1-dioxido-4H-1,2,4-benzothiadiazin-3-yl]-4-(cyclohexylideneamino)-7-hydroxythieno[3,2-b]pyridin-5(4H)-one The product of Example 324B (0.20 g, 0.42 mmol) and cyclohexanone (2.0 g, 20 mmol) in N,N-dimethylacetamide (4 mL) were reacted at 130° C. for 60 minutes in a microwave reactor in a sealed tube. The solvent was removed under reduced pressure and the resulting residue was triturated with diethyl ether (8 mL), filtered and dried to give the title compound (0.167 g 73%).

EXAMPLE 324D

6-[7-(benzyloxy)-1,1-dioxido-4H-1,2,4-benzothiadiazin-3-yl]-4-(cyclohexylamino)-7-hydroxythieno[3,2-b]pyridin-5(4H)-one The product of Example 324C (0.167 g, 0.30 mmol) in tetrahydrofuran (6 mL) and methanol (0.030 mL, 0.8 mmol) at 0° C. was reacted with lithium borohydride (2.0 M solution in tetrahydrofuran, 0.250 mL, 0.50 mmol). The reaction was stirred at 25° C. for 1.5 hour, acidified to pH 2 with 1 M aqueous hydrochloric acid and diluted with water (25 mL). The resulting precipitate was collected by filtration and dried to constant weight to give the title compound (0.114 g, 69%). MS (APCI+) m/z 551 (M+H)⁺. $^1$H NMR (300 MHz, DMSO-$d_6$) δ ppm 1.36 (m, 10 H) 5.25 (s, 2 H) 6.50 (s, 1 H) 7.43 (m, 8 H) 7.69 (d, J=8.82 Hz, 1 H) 8.29 (d, J=5.15 Hz, 1 H) 14.10 (s, 1 H) 14.87 (s, 1 H).

EXAMPLE 324E 4-(cyclohexylamino)-7-hydroxy-6-(7-hydroxy-1,1-dioxido-4H-1,2,4-benzothiadiazin-3-yl)thieno[3,2-b]pyridin-5(4H)-one The product of Example 324D (0.114 g, 0.21 mmol) in dry acetonitrile (11 mL) at 25° C. was reacted with iodotrimethylsilane (0.29 mL, 2.1 mmol) at 50° C. for 4 hours. The reaction was cooled to 25° C. and diluted with water (50 mL). The resulting precipitate was collected by filtration and dried under reduced pressure to give the title compound (0.083 g, 87% yield). MS (ESI−) m/z 459 (M−H)⁻. $^1$H NMR (300 MHz, DMSO-$d_6$) δ ppm 1.20 (m, 5 H) 1.66 (m, 5 H) 6.51 (s, 1 H) 7.18 (m, 2 H) 7.48 (d, J=5.52 Hz, 1 H) 7.57 (d, J=9.56 Hz, 1 H) 8.29 (d, J=5.15 Hz, 1 H) 10.42 (s, 1 H) 14.04 (s, 1 H) 14.93 (s, 1 H).

EXAMPLE 324F 2-({3-[4-(cyclohexylamino)-7-hydroxy-5-oxo-4,5-dihydrothieno[3,2-b]pyridin-6-yl]-1,1-dioxido-4H-1,2,4-benzothiadiazin-7-yl}oxy)acetamide The product of Example 324E (0.209 g, 0.45 mmol) was reacted with cesium carbonate (0.589 g, 1.81 mmol), 2-bromoacetamide (0.125 g, 0.91 mmol) and a catalytic amount of tetrabutylammonium iodide in N,N-dimethylformamide (8 mL) at 25° C. for 18 hours. The reaction was diluted with 50 mL water, acidified to pH 2 with 1 M hydrochloric acid. The resulting precipitate was collected by filtration and purified by column chromatography on silica gel eluting with 5% methanol in chloroform to give the title compound (0.050 g, 21% yield). The sodium salt of the title compound was prepared according to the procedure of Example 1D. MS (ESI−) m/z 516 (M−H)⁻. ¹H NMR (300 MHz, DMSO-$d_6$) δ ppm 1.48 (m, 10 H) 4.59 (s, 2 H) 6.50 (s, 1 H) 7.39 (m, 2 H) 7.44 (s, 1 H) 7.48 (d, J=5.15 Hz, 1 H) 7.65 (s, 1 H) 7.70 (d, J=9.56 Hz, 1 H) 8.28 (d, J=5.15 Hz, 1 H) 14.13 (s, 1 H) 14.89 (s, 1 H).

EXAMPLE 325

3-(1-benzyl-4-hydroxy-2-oxo-1,2-dihydroquinolin-3-yl)-N-(2-hydroxyethyl)-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added ethanolamine (2.8 μL, 1.1 equivalents) followed by N-methylmorpholine (8 μL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (18.7 mg, 85.8%). The sodium salt of the title compound was prepared according to the procedure of Example 1D. ¹H NMR (300 MHz, DMSO-$d_6$) δ 3.34 (m, 2 H), 3.51 (m, 2 H), 5.61 (m, 2 H), 7.29 (m, 5 H), 7.42 (m, 1 H), 7.52 (m, 1 H), 7.75 (m, 1 H), 7.96 (s, 1 H), 8.23 (m, 1 H), 8.37 (m, 1 H). MS (DCI⁺) m/z 525 (M+H)⁺.

796523 EXAMPLE 326

3-(1-benzyl-4-hydroxy-2-oxo-1,2-dihydroquinolin-3-yl)-N-[(1S)-2-hydroxy-1-(aminocarbonyl)ethyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added L-serinamide hydrochloride (6.5 mg, 1.1 equivalents) followed by N-methylmorpholine (12.6 μL, 2.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (17 mg, 73%). The sodium salt of the title compound was prepared according to the procedure of Example 1D. ¹H NMR (300 MHz, DMSO-$d_6$) δ 3.69 (dd, J=4.96, 3.13 Hz, 2 H), 4.40 (m, 1 H), 5.62 (s, 2 H), 7.27 (m, 5 H), 7.41 (m, 1 H), 7.53 (m, 1 H), 7.75 (m, 1 H), 8.12 (s, 1 H), 8.22 (d, J=7.72 Hz, 1 H), 8.28 (d, J=7.72 Hz, 1 H). MS (DCI+) m/z 568 (M+H)⁺.

EXAMPLE 327

N-(2-amino-2-oxoethyl)-3-(1-benzyl-4-hydroxy-2-oxo-1,2-dihydroquinolin-3-yl)-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added glycinamide hydrochloride (5.1 mg, 1.1 equivalents) followed by N-methylmorpholine (14 μL, 3 equivalents) and the solution was stirred for 3 hours. A solution of 1 N hydrochloric acid (4 mL) was added and the resulting precipitate was collected by filtration and washed with water, methanol and diethyl ether to give the title compound as a white solid (17 mg, 76%). The sodium salt of the title compound was prepared according to the procedure of Example 1D. ¹H NMR (300 MHz, DMSO-$d_6$) δ 3.83 (d, J=5.52 Hz, 2 H), 5.61 (s, 2 H), 7.13 (s, 1 H), 7.32 (m, 6 H), 7.51 (d, J=8.09 Hz, 1 H), 7.75 (m, 1 H), 8.04 (s, 1 H), 8.21 (d, J=6.99 Hz, 1 H), 8.59 (t, J=5.88 Hz, 1 H). MS (DCI⁺) m/z 538 (M+H)⁺.

EXAMPLE 328

3-(1-benzyl-4-hydroxy-2-oxo-1,2-dihydroquinolin-3-yl)-N-[(1S)-2-hydroxy-1-methylethyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added (S)-(+)-2-amino-1-propanol (3.6 μL, 1.1 equivalents) followed by N-methylmorpholine (8 μL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (18.4 mg, 82%). The sodium salt of the title compound was prepared according to the procedure of Example 1D. ¹H NMR (300 MHz, DMSO-$d_6$) δ 3.46 (m, 2 H), 3.95 (m, 1 H), 5.62 (s, 2 H), 7.30 (m, 5 H), 7.41 (t, J=7.72 Hz, 1 H), 7.52 (d, J=8.82 Hz, 1 H), 7.74 (d, J=6.99 Hz, 1 H), 7.96 (s, 1 H), 8.10 (d, J=8.09 Hz, 1 H), 8.22 (d, J=6.99 Hz, 1 H). MS (DCI+) m/z 539 (M+H)⁺.

EXAMPLE 329

3-(1-benzyl-4-hydroxy-2-oxo-1,2-dihydroquinolin-3-yl)-N,N-bis(2-hydroxyethyl)-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added diethanolamine (4.43 μL, 1.1 equivalents) followed by N-methylmorpholine (8 μL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (6.85 mg, 29%). The sodium salt of the title compound was prepared according to the procedure of Example 1D. ¹H NMR (300 MHz, DMSO-$d_6$) δ 3.53 (m, 4 H), 5.62 (s, 2 H), 7.30 (m, 6 H), 7.41 (t, J=7.54 Hz, 1 H), 7.53 (d, J=8.46 Hz, 1 H), 7.59 (s, 1 H), 7.76 (m, 1 H), 8.22 (d, J=8.09 Hz, 1 H). MS (ESI⁺) m/z 569 (M+H)⁺.

EXAMPLE 330

3-(1-benzyl-4-hydroxy-2-oxo-1,2-dihydroquinolin-3-yl)-N-[2-hydroxy-1-(hydroxymethyl)ethyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added serinol (4.21 mg, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (18.2 mg, 79%). The sodium salt of the title compound was prepared according to the procedure of Example 1D. $^1$H NMR (300 MHz, DMSO-$d_6$) δ 3.51 (d, J=5.52 Hz, 4 H), 3.89 (m, J=6.25 Hz, 1 H), 5.63 (s, 2 H), 7.30 (m, 6 H), 7.42 (t, J=7.54 Hz, 1 H), 7.53 (d, J=8.82 Hz, 1 H), 7.75 (d, J=8.46 Hz, 1 H), 8.02 (m, 2 H), 8.22 (d, J=8.09 Hz, 1 H). MS (DCI+) m/z 555 (M+H)$^+$.

EXAMPLE 331

1-benzyl-4-hydroxy-3-(7-{[(3R)-3-hydroxypyrrolidin-1-yl]carbonyl}-1,1-dioxido-4H-thieno[2,3-e][1,2,4]thiadiazin-3-yl)quinolin-2(1H)-one A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added (R)-(+)-3-pyrrolidinol (3.84 µL, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (19.8 mg, 87%). The sodium salt of the title compound was prepared according to the procedure of Example 1D. $^1$H NMR (300 MHz, DMSO-$d_6$) δ 1.89 (m, 2 H), 3.55 (m, 2 H), 4.31 (d, 1 H), 4.99 (br. s., 1 H), 5.62 (s, 2 H), 7.31 (m, 6 H), 7.41 (t, J=7.54 Hz, 1 H), 7.53 (d, J=8.82 Hz, 1 H), 7.69 (d, J=6.99 Hz, 1 H), 7.76 (t, J=7.35 Hz, 1 H), 8.22 (d, J=6.99 Hz, 1 H). MS (ESI$^+$) m/z 551 (M+H)$^+$.

EXAMPLE 332

3-(1-benzyl-4-hydroxy-2-oxo-1,2-dihydroquinolin-3-yl)-N-(3-hydroxypropyl)-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added 2-(methylamino)-ethanol (2.8 µL, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (19.2 mg, 86%). The sodium salt of the title compound was prepared according to the procedure of Example 1D. $^1$H NMR (300 MHz, DMSO-$d_6$) δ 1.67 (m, 2 H), 3.28 (m, 2 H), 3.48 (t, J=6.25 Hz, 2 H), 5.61 (s, 2 H), 7.30 (m, 6 H), 7.41 (t, J=7.54 Hz, 1 H), 7.52 (d, J=8.46 Hz, 1 H), 7.75 (t, J=6.99 Hz, 1 H), 7.92 (s, 1 H), 8.21 (m, 1 H), 8.34 (t, J=5.33 Hz, 1 H). MS (DCI$^+$) m/z 539 (M+H)$^+$.

EXAMPLE 333

3-(1-benzyl-4-hydroxy-2-oxo-1,2-dihydroquinolin-3-yl)-N-[(2S)-2,3-dihydroxypropyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added (S)-(−)-3-amino-1,2-propanediol (4.21 mg, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (18.4 mg, 80%). The sodium salt of the title compound was prepared according to the procedure of Example 1D. $^1$H NMR (300 MHz, DMSO-$d_6$) δ 3.15 (m, 2 H), 3.60 (m, 2 H), 5.62 (s, 2 H), 7.30 (m, 6 H), 7.41 (t, J=7.54 Hz, 1 H), 7.52 (d, J=8.46 Hz, 1 H), 7.75 (m, 1 H), 7.98 (s, 1 H), 8.22 (d, J=6.62 Hz, 1 H), 8.32 (t, J=5.88 Hz, 1 H). MS (DCI$^+$) m/z 555 (M+H)$^+$.

EXAMPLE 334

3-(1-benzyl-4-hydroxy-2-oxo-1,2-dihydroquinolin-3-yl)-N-[(1S)-1-(hydroxymethyl)propyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added (S)-(+)-2-amino-1-butanol (4.36 µL, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (16.5 mg, 72%). The sodium salt of the title compound was prepared according to the procedure of Example 1D. $^1$H NMR (300 MHz, DMSO-$d_6$) δ 0.91 (t, J=7.35 Hz, 3 H), 1.54 (m, 2 H), 3.45 (m, 2 H), 3.81 (m, 1 H), 5.62 (s, 2 H) 7.31 (m, 6 H), 7.41 (t, J=7.72 Hz, 1 H), 7.52 (d, J=8.09 Hz, 1 H), 7.76 (t, J=7.91 Hz, 1 H), 7.98 (m, 1 H), 8.01 (d, J=8.46 Hz, 1 H), 8.22 (d, J=6.99 Hz, 1 H). MS (DCI$^+$) m/z 553 (M+H)$^+$.

EXAMPLE 335

3-(1-benzyl-4-hydroxy-2-oxo-1,2-dihydroquinolin-3-yl)-N-[(1S)-1-(hydroxymethyl)-2-methylpropyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added (S)-(+)-2-amino-3-methyl-1-butanol (5.15 µL, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (18.8 mg, 80%). The sodium salt of the title compound was prepared according to the procedure of Example 1D. $^1$H NMR (300 MHz, DMSO-$d_6$) δ 0.92 (dd, J=6.62, 5.15 Hz, 6 H), 1.95 (m, 1 H), 3.48 (d, J=5.88 Hz, 2 H), 3.80 (m, 1 H), 5.62 (s, 2 H), 7.30 (m, 6 H), 7.40 (t, J=7.72 Hz, 1 H), 7.51 (d, J=8.46 Hz, 1 H), 7.75 (m, 1 H), 7.95 (d, J=8.82 Hz, 1 H), 8.00 (s, 1 H), 8.22 (d, J=6.62 Hz, 1 H). MS (DCI$^+$) m/z 567 (M+H)$^+$.

EXAMPLE 336

3-(1-benzyl-4-hydroxy-2-oxo-1,2-dihydroquinolin-3-yl)-N-[2-hydroxybutyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added 1-amino-2-butanol (4.43 µL, 1.1 equivalents) followed by N-methylmorpholine (8 µL, 1.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (19.97 mg, 87%). The sodium salt of the title compound was prepared according to the procedure of Example 1D. $^1$H NMR (300 MHz, DMSO-$d_6$) δ 0.90 (t, J=7.35 Hz, 3 H), 1.41 (m, 2 H), 3.14 (m, 2 H), 3.50 (m, 1 H), 5.62 (s, 2 H), 7.29 (m, 6 H), 7.41 (t, J=7.72 Hz, 1 H), 7.52 (d, J=8.82 Hz, 1 H), 7.74 (m, J=8.09 Hz, 1 H), 7.97 (s, 1 H), 8.21 (m, 1 H), 8.31 (t, J=5.33 Hz, 1 H). MS (DCI$^+$) m/z 553 (M+H)$^+$.

EXAMPLE 337

3-(1-benzyl-4-hydroxy-2-oxo-1,2-dihydroquinolin-3-yl)-N-[2-hydroxy-2-(4-hydroxyphenyl)ethyl]-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added octopamine hydrochloride (8.6 mg, 1.1 equivalents) followed by N-methylmorpholine (12.6 µL, 2.72 equivalents) and the solution was stirred for 16 hours. A solution of 1 N hydrochloric acid (4 mL) was added and the resulting precipitate was collected by filtration and washed with water, methanol and diethyl ether to give the title compound as a white solid (13.58 mg, 53%). The sodium salt of the title compound was prepared according to the procedure of Example 1D. $^1$H NMR (300 MHz, DMSO-$d_6$) δ 4.63 (dd, J=7.72, 4.41 Hz, 1 H), 5.62 (s, 2 H), 6.72 (d, J=8.46 Hz, 2 H), 7.18 (d, J=8.46 Hz, 2 H), 7.31 (m, 6 H), 7.41 (t, J=7.54 Hz, 1 H), 7.52 (d, J=8.82 Hz, 1 H), 7.74 (t, J=6.99 Hz, 1 H), 7.94 (s, 1 H), 8.21 (m, 1 H), 8.42 (t, J=5.52 Hz, 1 H), 9.27 (s, 1 H). MS (ESI$^-$) m/z 615 (M−H)$^-$.

EXAMPLE 338

1-benzyl-3-[1,1-dioxido-7-(piperazin-1-ylcarbonyl)-4H-thieno[2,3-e][1,2,4]thiadiazin-3-yl]-4-hydroxyquinolin-2(1H)-one A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added piperazine (4 mg 1.1 equivalents) followed by N-methylmorpholine (8 µL, 1.72 equivalents) and the solution was stirred for 16 hours. Water (5 mL) was added and the resulting precipitate was collected by filtration and washed with water, methanol and diethyl ether to give the title compound as a white solid (18.3 mg, 80.16%). The sodium salt of the title compound was prepared according to the procedure of Example 1D. $^1$H NMR (300 MHz, DMSO-$d_6$) δ 3.14 (s, 4 H), 3.65 (m, 4 H), 5.43 (s, 2 H), 7.26 (m, 8 H), 7.46 (m, 2 H), 8.11 (t, J=7.72 Hz, 1 H), 8.70 (br.s, 1 H). MS (DCI$^+$) m/z 550 (M+H)$^+$.

EXAMPLE 339

N-[5-(aminocarbonyl)pyridin-2-yl]-3-(1-benzyl-4-hydroxy-2-oxo-1,2-dihydroquinolin-3-yl)-4H-thieno[2,3-e][1,2,4]thiadiazine-7-carboxamide 1,1-dioxide A solution of the product of Example 318 (20 mg, 0.042 mmol), 1-(3-dimethylaminopropyl)-3-ethylcarbodiimide hydrochloride (11.76 mg, 1.48 equivalents), and 1-hydroxybenzotriazole (8.66 mg, 1.54 equivalents) in N,N-dimethylformamide (0.4 mL) was stirred for 15 minutes at room temperature. To this mixture was added 6-aminonicotinamide (6.33 mg, 1.1 equivalents) followed by N-methylmorpholine (8 µL, 1.72 equivalents) and the solution was heated at 70° C. for 16 hours. A solution of 1 N hydrochloric acid (4 mL) was added and the resulting precipitate was collected by filtration and washed with water, and diethyl ether. The solid was dissolved in 5% methanol/dichloromethane with 2 drops of triethylamine and purified by flash chromatography on silica gel using a Biotage-12s column eluting with 10:90 methanol/dichloromethane to give the title compound as a white solid (5.4 mg, 21.6%). The sodium salt of the title compound was prepared according to the procedure of Example 1D. $^1$H NMR (300 MHz, DMSO-$d_6$) δ 5.64 (s, 2 H,) 7.30 (m, 6 H), 7.43 (t, J=7.54 Hz, 1 H), 7.50 (m, 1 H), 7.54 (d, J=8.46 Hz, 1 H), 7.76 (m, 1 H), 8.10 (s, 1 H), 8.24 (m, 2 H), 8.32 (m, 1 H), 8.38 (s, 1 H), 8.88 (d, J=1.84 Hz, 1 H), 11.17 (s, 1 H). MS (DCI$^+$) m/z 601 (M+H)$^+$.

EXAMPLE 340A ethyl 2-(isopentylamino)nicotinate

A mixture of ethyl 2-chloronicotinate (3.71 g, 20 mmol), isoamylamine (3.03 mL, 26 mmol) and triethylamine (3.62 mL, 26 mmol) was heated in a sealed tube at 140° C. for 8 hours, cooled to 25C, diluted with ethyl acetate and the mixture washed with water. The organic layer was extracted with 1N aqueous hydrochloric acid. The acidic aqueous layer was adjusted to pH 8.0 with saturated sodium bicarbonate solution then extracted with ethyl acetate (2 portions). The combined organic extracts were dried over sodium sulfate, filtered, and concentrated under reduced pressure to give the title compound (3.58 g, 76%). MS (DCI/NH$_3$) m/z 237 (M+H)$^+$. $^1$H NMR (300 MHz, DMSO-d$_6$) δ ppm 0.93 (d, J=6.25 Hz, 6 H) 1.31 (t, J=6.99 Hz, 3 H) 1.47 (q, J=6.99 Hz, 2 H) 1.64 (m, 1 H) 3.47 (m, 2 H) 4.28 (q, J=6.99 Hz, 2 H) 6.59 (dd, J=7.72, 4.78 Hz, 1 H) 7.90 (t, J=5.15 Hz, 1 H) 8.07 (dd, J=7.91, 2.02 Hz, 1 H) 8.28 (dd, J=4.78, 1.84 Hz, 1 H).

EXAMPLE 340B 2-(isopentylamino)nicotinic acid

A mixture of Example 340A (1.73 g, 7.31 mmol), 1 N aqueous sodium hydroxide (14.6 mL), and methanol (7 mL) was stirred for 18 hours and diluted with water. The aqueous mixture was washed with ethyl acetate followed by dichloromethane, and adjusted to pH 7.5 with 1N aqueous hydrochloric acid. The resulting precipitate was collected by vacuum filtration, washed with water and air dried to give the title compound (424.4 mg, 28%). MS (DCI/NH3) m/z 209 (M+H)$^+$. $^1$H NMR (300 MHz, DMSO-d$_6$) δ ppm 0.91 (d, J=6.62 Hz, 6 H) 1.46 (q, J=6.99 Hz, 2 H) 1.63 (m, 1 H) 3.45 (t, J=7.17 Hz, 2 H) 6.56 (dd, J=7.72, 4.78 Hz, 1 H) 8.04 (dd, J=7.72, 1.84 Hz, 1 H) 8.05 (m, 1 H) 8.25 (dd, J=4.78, 2.21 Hz, 1 H) 12.96 (s, 1 H).

EXAMPLE 340C 4-hydroxy-1-(3-methylbutyl)-1,8-naphthyridin-2(1H)-one

A mixture of Example 340B (1 g, 4.81 mmol), acetic anhydride (10 mL) and glacial acetic acid (10 mL) was heated at 130° C. for 2 hours. The mixture was cooled to 25C and concentrated under reduced pressure. The residue was partitioned between ethyl acetate and saturated aqueous sodium bicarbonate. The organic layer was washed with brine, dried over sodium sulfate, filtered and concentrated under reduced pressure. The residue was chromatographed on silica gel, eluting with 0-100% hexane in ethyl acetate step gradient to give the title compound (100 mg, 9%). MS (DCI/NH$_3$) m/z 233 (M+H)$^+$. $^1$H NMR (300 MHz, DMSO-D6) δ ppm 0.94 (d, J=6.62 Hz, 6 H) 1.46 (m, 2 H) 1.60 (m, 1 H) 4.33 (m, 2 H) 5.88 (s, 1 H) 7.27 (dd, J=7.72, 4.78 Hz, 1 H) 8.22 (dd, J=7.72, 1.84 Hz, 1 H) 8.65 (dd, J=4.78, 1.84 Hz, 1 H) 11.61 (s, 1 H).

EXAMPLE 340D

3-[bis(methylthio)methylene]-1-butyl-1,8-naphthyridine-2,4(1H,3H)-dione

A solution of the product of Example 340C (0.2 g, 0.86 mmol) in dimethylformamide (7 mL) was treated with sodium hydride (76 mg, 60% in mineral oil, 2.2 equivalents), stirred for 30 min at 25° C., treated with carbon disulfide (0.14 g, 2.2 eq.), heated at 50° C. for 6 hours, cooled to 25° C., and treated with methyl iodide (0.27 g, 2.2 eq.). The mixture was stirred at 25° C. for 18 hours and concentrated. The residue was triturated with water and the resulting solids were filtered and dried in vacuo to give the title compound (0.23 g, crude yield 80%). $^1$H NMR (300 MHz, DMSO-d$_6$) δ 1.00 (d, J=10 Hz, 6 H), 1.6 (m, 2H), 1.75 (m, 1H), 2.63 (s, 6H), 4.4 (m, 2H), 7.1 (dd, J=10 Hz, 7 Hz, 1H), 8.42 (dd, J=10 Hz, 3 Hz, 1H), 8.58 (dd, J=7 Hz, 3 Hz, 1H). MS (DCI+) m/z 337 (M+H)$^+$.

EXAMPLE 340E 4-hydroxy-3-{7-[(methoxymethoxy)methyl]-1,1-dioxido-4H-thieno[2,3-e][1,2,4]thiadiazin-3-yl}-1-(3-methylbutyl)-1,8-naphthyridin-2(1H)-one The product of Example 309G (37.5 mg, 0.15 mmol) and the product of Example 340D (50 mg, 0.15 mmol) were reacted in toluene (5 mL) at 100° C. for 3 hours. The reaction was concentrated under reduced pressure and the residue was purified by chromatography on silica gel using a Biotage-12 m column eluting with 2:98 methanol:dichloromethane to give the title compound as a yellow solid (36 mg, 49%). The sodium salt of the title compound was prepared according to the procedure of Example 1D. $^1$H NMR (300 MHz, DMSO-d$_6$) δ 0.98 (d, J=6.99 Hz, 6 H), 1.57 (m, 2 H), 1.66 (m, 1 H), 4.45 (d, J=7.35 Hz, 2 H), 4.64 (s, 3 H), 4.71 (s, 3 H), 7.43 (s, 1 H), 7.46 (m, 1 H), 8.54 (d, J=6.99 Hz, 1 H), 8.87 (s, 1 H), 14.45 (br.s, 1 H). MS (DCI$^+$) m/z 510 (M+NH$_4$)$^+$.

EXAMPLE 341

4-hydroxy-3-[7-(hydroxymethyl)-1,1-dioxido-4H-thieno[2,3-e][1,2,4]thiadiazin-3-yl]-1-(3-methylbutyl)-1,8-naphthyridin-2(1H)-one The product of Example 340C (23 mg, 0.05 mmol) was reacted with 6 N aqueous hydrochloric acid (1 mL) in tetrahydrofuran (2 mL) at 70° C. for 3 hours. The reaction was concentrated under reduced pressure to remove the tetrahydrofuran, and treated with methanol (5 mL). The resulting precipitate was collected by filtration and washed with water and diethyl ether to give the title compound as a white solid (13 mg, 62%). The sodium salt of the title compound was prepared according to the procedure of Example 1D. $^1$H NMR (300 MHz, DMSO-d$_6$) δ 0.98 (d, J=6.62 Hz, 6 H), 1.57 (m, 2 H), 1.67 (m, 1 H), 4.46 (m, 2 H), 4.62 (s, 2 H), 7.30 (s, 1 H), 7.47 (dd, J=8.09, 4.78 Hz, 1 H), 8.54 (d, J=7.72, 1.84 Hz, 1 H), 8.86 (m, 1 H), 14.39 (br.s, 1 H). MS (DCI$^+$) m/z 466 (M+NH$_4$)$^+$.

EXAMPLE 342

[3-(1-benzyl-4-hydroxy-2-oxo-1,2-dihydroquinolin-3-yl)-1,1- dioxido-4H-thieno[2,3e][1,2,4]thiadiazin-7-yl]methyl carbamate A suspension of the product of Example 310 (40 mg, 0.086 mmol) in a solution of N,N-dimethylformamide (2 mL) and acetonitrile (0.6 mL) at −20° C. was treated with chlorosulfonyl-isocyanate (16.4 μL, 2.2 equivalents). The mixture was stirred 0.5 hour at −20° C. and 2 hours at 0° C., 6N hydrochloric acid (2 mL) was added and the mixture was heated 2.5 hours at 70° C. The mixture was cooled and water (10 mL) was added, the resulting precipitate was collected by filtration and washed with water and diethyl ether. The solid was dissolved in 5% methanol/dichloromethane with a few drops of triethylamine and purified by flash chromatography on silica gel using a Biotage-12s column eluting with 6:94 methanol/dichloromethane to give the title compound as a white solid (23 mg, 52.6%). The sodium salt of the title compounds was prepared according to the procedure of Example 1D. $^1$H NMR (300 MHz, DMSO-d$_6$) δ 5.08 (s, 2 H), 5.62 (s, 2 H), 6.72 (s, 2 H,) 7.29 (m, 5 H), 7.42 (m, 2 H), 7.53 (d, J=8.82 Hz, 1 H), 7.77 (t, J=7.35 Hz, 1 H), 8.22 (d, J=6.99 Hz, 1 H). MS (DCI$^+$) m/z 528 (M+NH$_4$)$^+$.

EXAMPLE 343

[3-(1-benzyl-4-hydroxy-2-oxo-1,2-dihydroquinolin-3-yl)-1,1-dioxido-4H-thieno[2,3-e][1,2,4]thiadiazin-7-yl]methyl aminocarbonylcarbamate A suspension of the product of Example 310 (40 mg, 0.086 mmol) in a solution of N,N-dimethylformamide (2 mL) and acetonitrile (0.6 mL) at −20° C. was treated with chlorosulfonyl-isocyanate (16.4 µL, 2.2 equivalents). The mixture was stirred 0.5 hour at -20° C. and 2 hours at 0° C., 6N hydrochloric acid (2 mL) was added and the mixture was heated 2.5 hours at 70° C. The mixture was cooled and water (10 mL) was added, the resulting precipitate was collected by filtration and washed with water and diethyl ether. The solid was dissolved in 5% methanol/dichloromethane with a few drops of triethylamine and purified by flash chromatography on silica gel using a Biotage-12s column eluting with 6:94 methanol/dichloromethane to give the title compound (6 mg, 12.7%). The sodium salt of the title compound was prepared according to the procedure of Example 1D. $^1$H NMR (300 MHz, DMSO-$d_6$) δ 5.23 (s, 2 H), 5.61 (s, 2 H), 7.28 (m, 4 H), 7.35 (m, 2 H), 7.51 (m, 1 H), 8.20 (m, 2 H), 10.01 (s, 1 H). MS (ESI$^-$) m/z 552 (M–H)$^-$.

EXAMPLE 344

3-[7-(azidomethyl)-1,1-dioxido-4H-thieno[2,3-e][1,2,4]thiadiazin-3-yl]-1-benzyl-4-hydroxyquinolin-2(1H)-one To the solution of the product of Example 310 (156.4 mg, 0.33 mmol) in dichloromethane (3 mL) was added 1,8-diazabicyclo[5.4.0]undec-7-ene (0.37 mL, 2.47 mmol) and diphenylphosphoryl azide (0.54 mL, 2.50 mmol) at room temperature. The solution was stirred at room temperature overnight and concentrated in vacuo. The residue was diluted with ethanol and aqueous hydrogen chloride (1 N, 2 mL) was added slowly and precipitates appeared. The solid was filtered and rinsed with a solution of ethanol/water (2:1) to give the title compound as a light brown solid (124.47 mg, 76%). MS (ESI$^-$) m/z 491 (M–H)$^-$. 1H NMR (300 MHz, DMSO-$d_6$) δ 4.59 (s, 2 H) 5.62 (br s, 2 H) 7.30 (m, 5 H) 7.41 (t, J=7.54 Hz, 1 H) 7.52 (d, J=8.82 Hz, 1 H) 7.58 (s, 1 H) 7.76 (m, 1 H) 8.22 (dd, J=8.09, 1.47 Hz, 1 H).

EXAMPLE 345

3-[7-(aminomethyl)-1,1-dioxido-4H-thieno[2,3-e][1,2,4]thiadiazin-3-yl]-1-benzyl-4-hydroxyquinolin-2(1H)-one To the solution of the product of Example 344 (136.2 mg, 0.28 mmol) in pyridine (1.68 mL) and concentrated ammonium hydroxide (1.12 mL) was added triphenylphosphine (145 mg, 0.55 mmol) at room temperature. The solution was stirred at room temperature overnight and concentrated in vacuo. The residue was diluted with toluene and the solid was filtered to give the title compound as a light brown solid (100.78 mg, 78%). MS (ESI$^+$) m/z 467 (M+H)$^+$. 1H NMR (300 MHz, DMSO-$d_6$) δ 4.10 (s, 2 H) 5.41 (br s, 2 H) 7.07-7.32 (m, 8 H) 7.43 (m, 1 H) 8.10 (dd, J=7.91, 1.65 Hz, 1 H).

EXAMPLE 346

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}methanesulfonamide To a solution of the product of Example 345 (15 mg, 0.032 mmol) in tetrahydrofuran (0.4 mL) was added triethylamine (0.018 mL, 0.129 mmol) followed by 1,8-diazabicyclo[5.4.0]undec-7-ene (0.018 mL, 0.129 mmol). The mixture was cooled to 0° C. and methanesulfonyl chloride was added (0.003 mL, 0.032 mmol). The mixture was stirred at 0° C. for 2.5 hours and then warmed to 23° C. and stirred for 2.5 hours. Additional 1,8-diazabicyclo[5.4.0]undec-7-ene (0.010 mL 0.064 mmol) and methane sulfonyl chloride (0.003 mL, 0.032 mmol) were added and the mixture was stirred at 23° C. for 15 hours. A few drops of N,N-dimethylformamide were added to increase solubility. Additional methane sulfonyl chloride (0.003 mL, 0.032 mmol) was added and the reaction mixture was stirred at 23° C. for 3 hours. A few drops of N,N-dimethylformamide and methane sulfonyl chloride (0.003 mL, 0.032 mmol) were added and the reaction mixture was stirred at 23° C. for 1 hour. Additional methane sulfonyl chloride (0.006 mL, 0.064 mmol) was added and the reaction mixture was stirred at 23° C. for 72 hours. The reaction mixture was concentrated under reduced pressure. The concentrate was diluted with diethyl ether and 1 N hydrochloric acid was added until no further precipitation was observed. The precipitate was then washed with water followed by diethyl ether. The solid was dissolved in 1% triethylamine/dichloromethane and purified by preparative thin layer chromatography eluting with 5% (5% triethylamine/methanol)/dichloromethane. The silica gel was washed with 10% (5% triethylamine/methanol)/dichloromethane to give the triethylamine salt of the title compound (4.7 mg, 23%). $^1$H NMR (500 MHz, DMSO-$d_6$) δ 1.16 (t, J=6.71 Hz, 9H) 2.94 (s, 3 H) 3.08 (bs, 6 H) 4.26 (d, 2 H) 5.40 (bs, 2 H) 7.06 (m, 2 H) 7.12 (d, J=8.54 Hz, 1 H) 7.23 (m, 5 H) 7.40 (t, J=7.32 Hz, 1 H) 7.50 (t, J=6.41 Hz, 1 H) 8.10 (d, J=6.10 Hz, 1 H).

EXAMPLE 347

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}nicotinamide To the solution of the product of Example 345 (0.015 g, 0.032 mmol) in tetrahydrofuran (0.4 mL) was added triethylamine (0.022 mL, 0.160 mmol), and 1,8-diazabicyclo[5.4.0]undec-7-ene (0.020 mL, 0.129 mmol). The mixture was cooled to 0° C. and nicotinoylchloride hydrochloride (0.007 g, 0.035 mmol) was added. The mixture was stirred for 2.5 hours and then warmed to 23° C. and stirred for 2.5 hours. Additional 1,8 diazabicyclo[5.4.0]undec-7-ene (0.010 mL, 0.068 mmol) and nicotinoylchloride hydrochloride (0.006 g, 0.032 mmol) were added and the mixture was stirred at 23° C. for 15 hours. Added additional nicotinoyl chloride hydrochloride (0.006 g, 0.032 mmol) and stirred at 23° C. for 6 hours. A few drops of N,N-dimethylformamide were added to increase solubility. Added additional nicotinoyl chloride hydrochloride (0.006 g, 0.032 mmol) and stirred at 23° C. for 72 hours. Hydrochloric acid (4 M in dioxane) (0.095 mL, 0.370 mmol) was added and the reaction mixture was concentrated under reduced pressure. The resulting solid was then washed with diethyl ether and water. The solid was dissolved in 1% triethylamine/dichloromethane and purified by preparative thin layer chromatography eluting with 5%(5% triethylamine/methanol)/dichloromethane. The silica gel was washed with 10% (5% triethylamine/methanol)/dichloromethane to give the triethylamine salt of the title compound (0.0068 g, 31%). $^1$HNMR(500 MHz, DMSO-$d_6$) δ 1.17 (t, J=7.32 Hz, 9 H) 3.09 (q, J=7.32 Hz, 6 H) 4.60 (d, J=4.88 Hz, 2 H) 5.44 (bs, 2 H) 7.00 (bs, 1 H) 7.12 (m, 1 H) 7.26 (m, 5 H) 7.46 (m, 1H) 7.53

(dd, J=7.63, 4.58 Hz, 1 H) 8.12 (d, J=7.32 Hz, 1 H) 8.26 (m, J=7.93 Hz, 1 H) 8.72 (d, J=3.66 Hz, 1 H) 8.86 (bs, 1 H) 9.09 (s, 1 H) 9.16 (bs, 1 H).

EXAMPLE 348

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}morpholine-4-carboxamide To the solution of the product of Example 345 (0.015 g, 0.032 mmol) in tetrahydrofuran (0.4 mL) was added triethylamine (0.009 mL, 0.064 mmol). The mixture was cooled to 0° C. and 4-morpholinecarbonyl chloride (0.004 mL, 0.035 mmol) was added. The reaction mixture was warmed to 23° C. and stirred for 15 hours. 1 N hydrochloric acid (0.065 mL, 0.064 mmol) was added and the mixture was then concentrated under reduced pressure. The product was washed with diethyl ether and water to give the title compound (7.5 mg, 40%). The sodium salt of the title compound was prepared according to the procedure of Example 1D. $^1$H NMR (500 MHz, DMSO-$d_6$) δ 3.57 (t, 4 H) 4.38 (d, J=4.88 Hz, 2 H) 5.60 (bs, 2 H) 7.11 (m, 2 H) 7.27 (m, 6 H) 7.38 (m, J=7.32, 3.05 Hz, 1 H) 7.49 (m, J=7.32 Hz, 1 H) 7.73 (bs, 1 H) 8.21 (d, J=7.32 Hz, 1 H).

EXAMPLE 349

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}-2-hydroxyacetamide To the solution of the product of Example 345 (0.0226 g, 0.048 mmol) in N,N-dimethylformamide (0.5 mL) was added triethylamine (0.020 mL, 0.145 mmol), 4-(dimethylamino) pyridine (0.018 g, 0.145 mmol), glycolic acid (0.011 g, 0.145 mmol), and 1-(3-dimethylaminopropyl)-3-ethylcarbodiimide hydrochloride (0.028 g, 0.145 mmol). The mixture was stirred at 23° C. for 15 hours and then was heated to 60° C. and stirred for 20 hours. The reaction mixture was concentrated under reduced pressure. The concentrate was diluted with dichloromethane, cooled to 0° C., and hydrochloric acid (4 M in dioxane) was added (0.037 mL, 0.145 mmol). The mixture was concentrated under reduced pressure. The residue was purified by reverse phase chromatography, eluting with a gradient of 10% acetonitrile in 0.1% trifluoroacetic acid/water to 95% acetonitrile in 0.1% trifluoroacetic acid/water to give the title compound (10.8 mg, 42%). The sodium salt of the title compound was prepared according to the procedure of Example 1D. $^1$H NMR (300 MHz, DMSO-$d_6$) δ 3.91 (s, 2 H) 4.44 (d, J=5.88 Hz, 2 H) 5.61 (bs, 2 H) 7.14 (s, 1 H) 7.29 (m, 5 H) 7.41 (t, J=7.35 Hz, 1 H) 7.52 (d, J=9.19 Hz, 1 H) 7.75 (t, 1 H) 8.21 (dd, 1 H) 8.35 (t, 1 H).

EXAMPLE 350A 1-amino-4-hydroxyquinolin-2(1H)-one

To a solution of 25% by weight aqueous potassium hydroxide (200 mL) and 1,4-dioxane (50 mL) heated to 90-100° C. was added portion wise the product of Example 226C (6.72 g, 20.0 mmol). The reaction mixture was heated at reflux for 90 minutes allowing distillation to occur and additional water and dioxane (30 mL each) were added to the reaction vessel to reach the original volume. The mixture was refluxed for an additional 90 minutes with distillation, cooled, washed with 200 mL of 1:1 diethyl ether/ethyl acetate, acidified with concentrated hydrochloric acid to pH 2 and the resulting solid was collected by filtration, washed with water and dried to constant mass to give the title compound as a tan sold (3.22 g, 91% yield). MS (DCI) m/z 177 (M+H)$^+$. $^1$H NMR (300 MHz, DMSO-$d_6$) δ 5.56 (s, 2 H) 5.94 (s, 1 H) 7.20 (t, J=7.54 Hz, 1 H) 7.62 (m, 1 H) 7.85 (m, 2 H) 11.33 (s, 1 H).

EXAMPLE 350B 2-(4-hydroxy-2-oxoquinolin-1(2H)-yl)-1H-isoindole-1,3(2H)-dione A mixture of the product of Example 350A (0.54 g, 3 mmol), phthalic anhydride (1.36 g, 2.2 eq.) and diisopropylethylamine (1.97 g, 5 eq.) in dioxane (20 mL) was heated at 100° C. for 2 hours, cooled to 25C and concentrated. The residue was triturated with water and ether. The resulting solids were filtered and dried in vacuum to give the title compound (0.6 g, 64% crude yield) which was used directly for the next step. $^1$H NMR (300 MHz, DMSO-$d_6$) δ 5.95 (s, 1H), 7.37 (m, 1H), 7.6 (m, 2H), 7.95-8.1 (m, 5H), 12.18 (s, 1H). MS (DCI$^+$) m/z 306 (M+H)$^+$.

EXAMPLE 350C

3-[bis(methylthio)methylene]-1-(1,3-dioxo-1,3-dihydro-2H-isoindol-2-yl)quinoline-2,4(1H,3H)-dione A solution of the product of Example 350B (0.6 g, 1.96 mmol) in acetic acid:pyridine (5:1, 15 mL) was treated with tris(methylthio)methyl methyl sulfate (prepared using the procedures in *Synthesis*, 22-25, 1988; M. Barbero, S. Cadamuro, I. Degani, R. Fochi, A. Gatti, V. Regondi)(1.6 g, 3 eq.) and heated at 100° C. for 2 hours. The reaction mixture was treated with ice, and the precipitated solids were filtered and dried in vacuum to give 0.53 g (66%) of the title compound. $^1$H NMR (300 MHz, DMSO-$d_6$) δ 2.63 (s, 6H), 7.34 (m, 1H), 7.55 (d, 1H), 7.61 (m, 1H), 8.08 (m, 5H). MS (DCI+) m/z 411 (M+H)$^+$.

EXAMPLE 350D

2-[4-hydroxy-3-{7-[(methoxymethoxy)methyl]-1,1-dioxido-4H-thieno[2,3-e][1,2,4]thiadiazin-3-yl}-2-oxoquinolin-1(2H)-yl]-1H-isoindole-1,3(2H)-dione The product of Example 309G (32.6 mg, 0.13 mmol) and the product of Example 350C (53 mg, 0.13 mmol) were reacted in toluene (3 mL) at 100° C. for 3 hours. The resulting precipitate was collected by filtration and washed with methanol and diethyl ether to give the title compound (45 mg, 61.5%). $^1$H NMR (300 MHz, DMSO-$d_6$) δ 3.32 (s, 3 H), 4.61 (s, 2 H), 4.70 (s, 2 H), 7.28 (s, 1 H), 7.42 (m, 1 H), 7.70 (d, J=4.04 Hz, 2 H), 8.06 (m, 2 H), 8.11 (m, 2 H), 8.22 (d, J=8.09 Hz, 1 H). MS (ESI$^-$) m/z 565 (M−H)$^-$.

EXAMPLE 350E 1-amino-4-hydroxy-3-{7-[(methoxymethoxy)methyl]-1,1-dioxido-4H-thieno[2,3-e][1,2,4]thiadiazin-3-yl}quinolin-2(1H)-one A solution of the product of Example 350D (185 mg, 0.326 mmol), methylhydrazine (43.47 μL, 2.5 equivalents), and triethylamine (0.126 mL, 3 equivalents) in 1,4-dioxane (10 mL) was heated at 102° C. for 3 hours. The reaction was concentrated under reduced pressure, and treated with a solution of methanol (75 mL) and 1N hydrochloric acid (100 mL). The resulting precipitate was collected by filtration and washed with water and diethyl ether to give the title compound as a white solid (94 mg, 66%). ¹H NMR (300 MHz, DMSO-d₆) δ 4.65 (s, 2 H), 4.71 (s, 2 H), 5.84 (br.s, 1 H), 7.44 (m, 2 H), 7.88 (m, 1 H), 8.04 (d, 1 H), 8.15 (d, 1 H), 14.73 (br.s, 2 H). MS (ESI⁻) m/z 435 (M−H)⁻.

EXAMPLE 350F

1-{[cyclopropylmethylene]amino}-4-hydroxy-3-{7-[(methoxymethoxy)methyl]-1,1-dioxido-4H-thieno[2,3-e][1,2,4]thiadiazin-3-yl}quinolin-2(1H)-one The product of Example 350D (94 mg, 0.22 mmol) was reacted with cyclopropanecarbaldehyde (0.162 mL, 2.2 mmol) in N,N-dimethylacetamide (1 mL) in a sealed tube at 120° C. for 90 minutes in a microwave reactor. The reaction was cooled to 25° C. and concentrated under reduced pressure. The resulting residue was triturated with diethyl ether and filtered to give the title compound (78.9 mg, 75%).

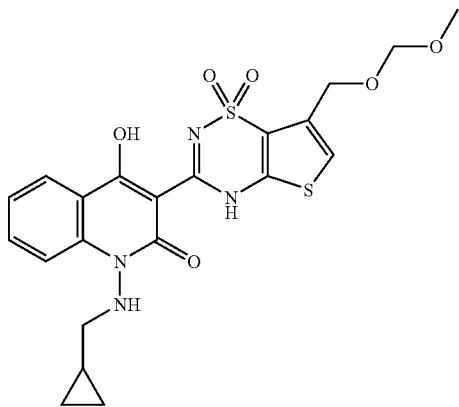

EXAMPLE 350G

1-[(cyclopropylmethyl)amino]-4-hydroxy-3-{7-[(methoxymethoxy)methyl]-1,1-dioxido-4H-thieno[2,3-e][1,2,4]thiadiazin-3-yl}quinolin-2(1H)-one The product of Example 350F (78.9 mg, 0.16 mmol) in tetrahydrofuran (4 mL) and methanol (0.013 mL, 0.32 mmol) at 0° C. was treated dropwise with a 2.0 M solution of lithium borohydride in tetrahydrofuran (0.131 mL, 0.24 mmol). The reaction was stirred at 25° C. for 1 hour, acidified with 1N hydrochloric acid to approximately pH 2-4, diluted with water (20 mL), and the resulting precipitate was collected by filtration and dried. The crude product was chromatographed on silica gel with 2% methanol/dichloromethane to give the title compound (41.6 mg, 52.5%). The sodium salt of the title compound was prepared according to the procedure of Example 1D. ¹H NMR (300 MHz, DMSO-d₆) δ 0.15 (d, J=4.41 Hz, 2 H), 0.42 (d, J=8.09 Hz, 2 H), 1.01 (m, 1 H), 2.84 (d, J=6.62 Hz, 2 H), 4.64 (s, 2 H), 4.71 (s, 2 H), 6.36 (br.s, 1 H), 7.41 (m, 2 H), 7.88 (t, J=7.35 Hz, 1 H), 8.07 (d, J=8.46 Hz, 1 H), 8.16 (d, J=8.09 Hz, 1 H). MS (ESI⁻) m/z 489 (M−H)⁻.

EXAMPLE 351

1-[(cyclopropylmethyl)amino]-4-hydroxy-3-[7-(hydroxymethyl)-1,1-dioxido-4H-thieno[2,3-e][1,2,4]thiadiazin-3-yl]quinolin-2(1H)-one The product of Example 350G (35 mg, 0.07 mmol) at 0° C. was treated with 4 N solution of hydrogen chloride in 1,4-dioxane (1 mL). The reaction was stirred at 0° C. for 2 hour and 25° C. for 3 hour, basified with 10% sodium bicarbonate (3 mL) and extracted with 2% methanol/dichloromethane. The solvent was concentrated and the residue was purified by flash column chromatography on silica gel eluting with 7% methanol/dichloromethane to give the title compound as a white solid (20 mg, 62.7%). The sodium salt of the title compound was prepared according to the procedure of Example 1D. ¹H NMR (300 MHz, DMSO-d₆) δ 0.15 (d, J=4.04 Hz, 2 H), 0.42 (d, J=8.09 Hz, 2 H), 1.01 (m, 1 H), 2.81 (d, 2 H), 4.62 (s, 2 H), 5.55 (br.s, 1 H), 6.35 (br.s, 1 H), 7.28 (s, 1 H), 7.39 (m, 1 H), 7.85 (m, 1 H), 8.03 (m, 1 H), 8.15 (d, J=7.35 Hz, 1 H). MS (ESI⁻) m/z 489 (M−H)⁻.

EXAMPLE 352A ethyl 3-{[2-(aminosulfonyl)-4-(benzyloxy)phenyl]amino}-3-oxopropanoate A suspension of the product of Example 304D (508.3 mg, 1.826 mmol) and triethylamine (0.47 mL, 3.394 mmol) in anhydrous dichloromethane (10 mL) was cooled to 0° C. under a nitrogen atmosphere. Ethyl malonyl chloride (0.43 mL, 3.023 mmol) was added dropwise and the resulting gold colored solution was stirred at 0° C. for 15 minutes, then at room temperature for 5 hours. The reaction was diluted with dichloromethane (50 mL) and washed with water (20 mL). The aqueous wash was extracted with dichloromethane (25 mL), and the combined organic layers were washed with 1N aqueous hydrochloric acid (20 mL), water (20 mL), and brine (20 mL). The organic layer was dried over anhydrous sodium sulfate, filtered and the solvent removed under reduced pressure. The yellow oil was purified by column chromatography on silica gel eluting with a gradient of 12% to 15% ethyl acetate/dichloromethane to give the title compound as a white solid (340 mg, 47%). MS (ESI⁻) m/z 391 (M−H)⁻. ¹H NMR (300 MHz, DMSO-d₆) δ 1.22 (t, J=7.17 Hz, 3 H) 3.56 (s, 2 H) 4.14 (q, J=6.99 Hz, 2 H) 5.15 (s, 2 H) 7.27 (dd, J=9.01, 3.13 Hz, 1 H) 7.42 (m, 8 H) 7.75 (d, J=8.82 Hz, 1 H) 9.42 (s, 1 H).

EXAMPLE 352B ethyl [7-(benzyloxy)-1,1-dioxido-4H-1,2,4-benzothiadiazin-3-yl]acetate The product of Example 352A (292 mg, 0.744 mmol) and sodium carbonate (394 mg, 3.722 mmol) in anhydrous ethanol (12 mL) was heated to reflux under a nitrogen atmosphere for 6.5 hours. The reaction was cooled to room temperature, filtered, and the filtrate concentrated under reduced pressure. The residue was purified by column chromatography on silica gel eluting with 3% methanol/dichloromethane to give the title compound as a white solid (237 mg, 85%). MS (ESI⁻) m/z 373 (M−H)⁻. ¹H NMR (300 MHz, DMSO-d₆) δ 1.21 (t, J=6.99 Hz, 3 H) 3.67 (s, 2 H) 4.16 (q, J=6.99 Hz, 2 H) 5.20 (s, 2 H) 7.39 (m, 8 H) 12.21 (s, 1 H).

EXAMPLE 352C ethyl (7-hydroxy-1,1-dioxido-4H-1,2,4-benzothiadiazin-3-yl)acetate The product of Example 352B (277 mg, 0.7398 mmol) in ethanol (20 mL) was hydrogenated at 1 atmosphere hydrogen pressure (balloon) with 10% palladium on carbon (28 mg, 10 weight %) for 1.25 hour. The reaction was filtered through a PTFE membrane filter (0.45 μm) and the catalyst thoroughly washed with ethanol (50 mL). The filtrate was concentrated under reduced pressure and the resulting oil triturated with dichloromethane/hexanes (1:1 v/v) to give the title compound as a crystalline white solid (194 mg, 92%). MS (ESI$^-$) m/z 283 (M–H)$^-$. $^1$H NMR (300 MHz, DMSO-d$_6$) δ 1.21 (t, J=7.17 Hz, 3 H) 3.64 (s, 2 H) 4.15 (q, J=7.23 Hz, 2 H) 7.06 (d, J=2.57 Hz, 1 H) 7.11 (dd, J=8.83, 2.57 Hz, 1 H) 7.20 (d, J=8.83 Hz, 1 H) 10.21 (s, 1 H) 12.11 (s, 1 H).

EXAMPLE 352D ethyl (7-hydroxy-8-nitro-1,1-dioxido-4H-1,2,4-benzothiadiazin-3-yl)acetate A suspension of the product of Example 352C (100 mg, 0.352 mmol) in glacial acetic acid (3 mL) was treated at room temperature with a solution of concentrated nitric acid in glacial acetic acid (1.43 M, 0.305 mL, 0.436 mmol) and stirred at this temperature for 19 hours. Added additional 1.43 M nitric acid/acetic acid (0.020 mL, 0.029 mmol) and let stir for 1.5 hours. The reaction was diluted with water (30 mL) and extracted with ethyl acetate (2×50 mL). The combined organic extracts were washed with brine, dried over anhydrous sodium sulfate, filtered, and concentrated under reduced pressure. The residue was purified by column chromatography on silica gel eluting with 8% methanol/dichloromethane to give the title compound as a light yellow solid (47 mg, 41%). MS (ESI$^-$) m/z 328 (M–H)$^-$. $^1$H NMR (300 MHz, PYRIDINE-d$_5$) δ 0.98 (t, J=7.17 Hz, 3 H) 3.86 (s, 2 H) 4.01 (q, J=7.23 Hz, 2 H) 7.11 (d, J=8.82 Hz, 1 H) 7.22 (d, J=8.82 Hz, 1 H).

EXAMPLE 352E ethyl (8-amino-7-hydroxy-1,1-dioxido-4H-1,2,4-benzothiadiazin-3-yl)acetate The product of Example 352D (61 mg, 0.1852 mmol) in methanol (5 mL) was hydrogenated at 1 atmosphere hydrogen pressure (balloon) with 10% palladium on carbon (9 mg, 15 weight %) for 45 minutes. The reaction was filtered through a PTFE membrane filter (0.45 μm) and the catalyst thoroughly washed with warm methanol (50 mL). The filtrate was concentrated under reduced pressure to give the title compound as a beige solid (55 mg, 99%). MS (ESI$^-$) m/z 298 (M–H)$^-$. $^1$H NMR (300 MHz, DMSO-d$_6$) δ 1.21 (t, J=7.17 Hz, 3 H) 3.61 (s, 2 H) 4.15 (q, J=6.99 Hz, 2 H) 5.22 (s, 2 H) 6.40 (d, J=8.46 Hz, 1 H) 6.93 (d, J=8.46 Hz, 1 H) 9.82 (s, 1 H) 11.86 (s, 1 H).

EXAMPLE 352F ethyl (8-methyl-1,1-dioxido-4H-[1,3]oxazolo[5,4-h][1,2,4]benzothiadiazin-3-yl)acetate A solution of the product of Example 352E (56.3 mg, 0.188 mmol) in anhydrous N,N-dimethylformamide (2 mL) was treated with trimethylorthoacetate (0.098 mL, 0.752 mmol) and p-toluenesulfonic acid monohydrate (1Mg) at room temperature for 3 hours under a nitrogen atmosphere. The solvent was removed under reduced pressure and the residue purified by column chromatography on silica gel eluting with 4% methanol/dichloromethane to give the title compound as a white crystalline solid (48 mg, 79%). MS (ESI$^-$) m/z 322 (M–H)$^-$. $^1$H NMR (300 MHz, DMSO-d$_6$) δ 1.22 (t, J=7.17 Hz, 3 H) 2.69 (s, 3 H) 3.71 (s, 2 H) 4.17 (q, J=7.11 Hz, 2 H) 7.27 (d, J=8.82 Hz, 1 H) 8.02 (d, J=8.82 Hz, 1 H) 12.33 (s, 1 H).

EXAMPLE 352G 4-hydroxy-1-(3-methylbutyl)-3-(8-methyl-1,1-dioxido-4H-[1,3]oxazolo[5,4-h][1,2,4]benzothiadiazin-3-yl)-1,8-naphthyridin-2(1H)-one To a solution of the product of Example 12A (16.7 mg, 0.0714 mmol) and the product of Example 352F (23.1 mg, 0.0714 mmol) in anhydrous tetrahydrofuran (2 mL) at 0° C. was added sodium hydride (60%, 11.4 mg, 0.286 mmol) under a nitrogen atmosphere. The reaction was heated at reflux for 3 hours, cooled to 0° C., and treated with glacial acetic acid (0.165 mL). The resulting yellow solution was heated at reflux for 2 hours, cooled to 0° C., diluted with water (5 mL), and acidified with 1N aqueous hydrochloric acid to pH 3. The resulting precipitate was collected by filtration, washed with water and dried to give the title compound as a yellow solid (20 mg, 60%). MS (ESI$^-$) m/z 466 (M–H)$^-$. $^1$H NMR (300 MHz, DMSO-d$_6$) δ 0.99 (d, J=6.25 Hz, 6 H) 1.58 (m, 2 H) 1.71 (m, 1 H) 2.73 (s, 3H) 4.50 (m, 2 H) 7.50 (dd, J=7.72, 4.41 Hz, 1 H) 7.64 (d, J=8.82 Hz, 1 H) 8.10 (d, J=8.82 Hz, 1 H) 8.57 (dd, J=7.91, 2.02 Hz, 1 H) 8.89 (dd, J=4.60, 2.02 Hz, 1 H) 14.18 (s, 1 H). A suspension of the product of Example 352G (14.6 mg, 0.0312 mmol) in anhydrous tetrahydrofuran (3 mL) and distilled water (1 mL) was treated with 0.998 N aqueous sodium hydroxide (0.0313 mL, 0.0312 mmol) and the yellow solution mixed for 15 minutes. The solvent was removed under reduced pressure and the residue dried to afford the sodium salt of Example 352G (15 mg, 98%). $^1$H NMR (300 MHz, DMSO-d$_6$) δ 0.97 (d, J=6.25 Hz, 6 H) 1.48 (m, 2 H) 1.65 (m, 1 H) 2.67 (s, 3 H) 4.30 (m, J=8.82, 6.25 Hz, 2 H) 7.13 (dd, J=7.91, 4.60 Hz, 1 H) 7.21 (d, J=8.82 Hz, 1 H) 7.86 (d, J=8.82 Hz, 1 H) 8.38 (dd, J=8.09, 1.47 Hz, 1 H) 8.53 (m, J=2.94 Hz, 1 H) 16.09 (s, 1 H).

EXAMPLE 353A

1-[(cyclopropylmethyl)amino]-4-hydroxyquinolin-2(1H)-one

To the suspension of the product of Example 350A (1.033 g, 5.86 mmol) in methanol (58 mL) was added acetic acid (0.29 mL) and cyclopropylcarboxaldehyde (482 μL, 6.45 mmol) followed by the addition of sodium cyanoborohydride (744.6 mg, 11.85 mmol) at room temperature. The suspension was stirred at room temperature overnight and quenched with half saturated brine (100 mL) and sodium bicarbonate (425 mg, 5.06 mmol). The mixture was extracted with ethyl acetate (300 mL) and the organic layer was separated and washed with half saturated brine (2×50 mL). The combined aqueous layers were extracted with dichloromethane (2×100 mL). The combined organic solution was dried with magnesium sulfate, filtered and concentrated. The residue was used without any purification. $^1$H NMR (300 MHz, DMSO-d$_6$) δ 0.09 (m, 2 H) 0.40 (m, 2 H) 0.95 (m, 1 H) 2.70 (t, J=6.43 Hz, 2 H) 5.91 (s, 1 H) 6.10 (t, J=6.07 Hz, 1 H) 7.21 (m, 1 H) 7.62 (t, J=7.17 Hz, 1 H) 7.87 (m, 2 H) 11.42 (br s, 1 H).

EXAMPLE 353B

3-[bis(methylthio)methylene]-1-[(cyclopropylmethyl)amino]quinoline-2,4(1H,3H)-dione To the suspension of the product of Example 353A (984.4 mg, 4.28 mmol) in 1,4-dioxane (40 mL) was added pyridine (2.8 mL, 34.6 mmol) and tris(methylthio)methyl methyl sulfate (prepared using the procedures in *Synthesis,* 22-25, 1988; M. Barbero, S. Cadamuro, I. Degani, R. Fochi, A. Gatti, V. Regondi) (2.26 g, 8.55 mmol) at room temperature. The suspension was put in a preheated oil bath at 55° C. and stirred for 15 minutes. To the solution was added another portion of tris(methylthio)methyl methyl sulfate (2.26 g, 8.55 mmol) and the mixture was stirred at 55° C. for 15 minutes and cooled to room temperature. The mixture was concentrated in vacuo and the residue was diluted with dichloromethane and loaded on a silica gel column and eluted with dichloromethane, 2% ethyl acetate/dichloromethane and then 5% ethyl acetate/dichloromethane to give the title compound (852.1 mg, 60%). $^1$H NMR (300 MHz, DMSO-$d_6$) δ 0.15 (m, 2 H) 0.42 (m, 2 H) 0.98 (m, 1 H) 2.61 (s, 6 H) 2.73 (t, J=6.43 Hz, 2 H) 6.05 (t, J=5.88 Hz, 1 H) 7.15 (m, 1 H) 7.64 (m, 1 H) 7.76 (d, J=8.09 Hz, 1 H) 7.98 (m, 1 H).

EXAMPLE 353C

1-[(cyclopropylmethyl)amino]-4-hydroxy-3-{7-[(methoxymethoxy)methyl]-1,1-dioxido-4H-thieno[2,3-e][1,2,4]thiadiazin-3-yl}quinolin-2(1H)-one A solution of the product of Example 353B (500.3, 1.5 mmol) and the product of Example 309G (377.62 mg, 1.5 mmol) in dioxane (15 mL) was stirred at reflux for 1.5 hours and concentrated under reduced pressure. The residue was purified by chromatography on silica gel eluting with 0% to 10% ethyl acetate/dichloromethane to give the title compound (384.7 mg, 52%). $^1$H NMR (300 MHz, DMSO-$d_6$) δ 0.15 (m, 2 H) 0.42 (m, 2 H) 1.01 (m, 1 H) 2.84 (d, J=6.99 Hz, 2 H) 4.64 (s, 2 H) 4.71 (s, 2 H) 6.36 (br s, 1 H) 7.42 (m, 2 H) 7.86 (m, 1 H) 8.07 (d, J=8.46 Hz, 1 H) 8.16 (m, 1 H).

EXAMPLE 353D

3-[7-(azidomethyl)-1,1-dioxido-4H-thieno[2,3-e][1,2,4]thiadiazin-3-yl]-1-[(cyclopropylmethyl)amino]-4-hydroxyquinolin-2(1H)-one To the product of Example 353C (384.7 mg, 0.78 mmol) was added a solution of hydrogen chloride in dioxane (4N, 7.8 mL) at 0° C. The solution warmed to room temperature and stirred for 5.5 hours and concentrated under reduced pressure. This solid was suspended in dichloromethane (7.8 mL) and to the suspension was added 1,8-diazabicyclo[5.4.0]undec-7-ene (0.6 mL, 4.01 mmol) and diphenylphosphoryl azide (0.85 mL, 3.94 mmol) at room temperature and stirred overnight. The solution was concentrated in vacuo. The residue was purified by chromatography, eluting with 1% triethylamine/dichloromethane to give a triethylamine salt of the title compound (357 mg, 79%). MS (ESI$^-$) m/z 470 (M−H)$^-$. 1H NMR (300 MHz, DMSO-$d_6$) δ 0.22 (m, 2 H) 0.46 (br d, J=7.35 Hz, 2 H) 1.01 (m, 1 H) 4.52 (s, 2 H) 5.98 (t, J=6.62 Hz, 1 H) 7.24 (s, 1 H) 7.40 (m, 1 H) 7.56 (m, 1 H) 8.05 (m, 1 H).

EXAMPLE 353E

3-[7-(aminomethyl)-1,1-dioxido-4H-thieno[2,3-e][1,2,4]thiadiazin-3-yl]-1-[(cyclopropylmethyl)amino]-4-hydroxyquinolin-2(1H)-one To the solution of the product of Example 353D (357 mg, 0.62 mmol) in pyridine (4.6 mL) and concentrated ammonium hydroxide (3 mL) was added triphenylphosphine (397 mg, 1.51 mmol) at room temperature. The solution was stirred at room temperature overnight and concentrated under reduced pressure. The residue was diluted with 30% hexane/toluene and the solid was filtered to give the title compound (250 mg, 90%). MS (ESI$^-$) m/z 446 (M+H)$^+$. $^1$H NMR (300 MHz, DMSO-$d_6$) δ 0.21 (m, 2 H) 0.46 (br d, J=8.09 Hz, 2 H) 1.00 (m, 1 H) 4.12 (s, 2 H) 5.98 (t, J=6.43 Hz, 1 H) 7.12 (m, 1 H) 7.22 (s, 1 H) 7.58 (m, 1 H) 7.72 (d, J=7.72 Hz, 1 H) 8.04 (m, 1 H).

EXAMPLE 353F

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]ethanesulfonamide To the suspension of the triethylamine salt of the product of Example 353E (85.26 mg, 0.16 mmol) in N,N-dimethylformamide (1.6 mL) was added triethylamine (48 μL, 0.34 mmol) and then methanesulfonyl chloride (13.3 μL, 0.17 mmol) at room temperature. The solution was stirred at room temperature for 20 minutes and concentrated in vacuo. The residue purified by reverse phase chromatography, eluting with 20% to 95% acetonitrile/0.1% triflouroacetic acid in water to give the title compound (39.86 mg, 49%). MS (ESI$^+$) m/z 524 (M+H)$^+$. $^1$H NMR (300 MHz, DMSO-$d_6$) δ 0.15 (m, 2 H) 0.42 (m, 2 H) 1.01 (m, 1 H) 2.84 (d, J=7.35 Hz, 2 H) 2.99 (s, 3 H) 4.29 (d, J=6.25 Hz, 2 H) 6.37 (br s, 1 H) 7.41 (m, 2 H) 7.75 (t, J=6.25 Hz, 1 H) 7.87 (m, 1 H) 8.08 (d, J=8.09 Hz, 1 H) 8.16 (m, 1 H) 14.46 (m, 1 H).

EXAMPLE 354

3-(8-amino-7-hydroxy-1,1-dioxido-4H-1,2,4-benzothiadiazin-3-yl)-4-hydroxy-1-(isobutylamino)quinolin-2(1H)-one A solution of the product of Example 321C (0.26 g, 0.61 mmol) in concentrated sulfuric acid (4 mL) at 0° C. was treated with ammonium nitrate (55 mg, 0.69 mmol). After stirring at room temperature for 30 minutes, the solution was poured into ice water and the precipitate was filtered, dried, and triturated with ethyl acetate to yield to nitrated intermediate (0.23 g, 79%). A solution of this solid (0.23 g, 0.48 mmol) in methanol:tetrahydrofuran:water (3:3:1) (2.3 mL) was treated with powdered iron (0.12 g, 2.15 mmol) and ammonium chloride (0.031 g, 0.58 mmol) at 60° C. for 1 hour. The warm solution was filtered through diatomaceous earth, rinsed with tetrahydrofuran. The filtrate was concentrated and the resulting solid was triturated with 1:1 dichloromethane: ethyl acetate to yield the title compound (0.088 g, 42%). MS (ESI$^-$) m/z 442 (M−H)$^-$. $^1$H NMR (300 MHz, DMSO-$d_6$) δ 1.04 (d, J=6.62 Hz, 6 H) 1.92 (m, 1 H) 2.76 (m, 2 H) 5.40 (s, 2 H) 6.34 (m, 1 H) 6.66 (d, J=7.72 Hz, 1 H) 7.00 (d, J=8.46 Hz, 1 H) 7.44 (m, 1 H) 7.94 (m, 2 H) 8.17 (d, J=6.99 Hz, 1 H) 10.12 (s, 1 H) 13.82 (s, 1 H) 15.19 (s, 1 H).

EXAMPLE 355

3-(1,1-dioxido-4H-[1,3]oxazolo[5,4-h][1,2,4]benzothiadiazin-3-yl)-4-hydroxy-1-(isobutylamino)quinolin-2(1H)-one A solution of Example 354 (0.036 g, 0.081 mmol) in dimethylformamide (2 mL) was treated with trimethyl orthoformate (1 mL) and a catalytic amount of para-toluenesulfonic acid at room temperature for 20 hours. The solvent was removed under a stream of warm nitrogen and the residue was triturated with 1:1 ethyl acetate: tetrahydrofuran, filtered, and dried to yield the title compound (8 mg, 22%). MS (ESI$^-$) m/z 452 (M–H)$^-$. $^1$H NMR (300 MHz, DMSO-d$_6$) δ 1.05 (d, J=6.62 Hz, 6 H) 1.93 (m, 1 H) 2.78 (m, 2 H) 6.33 (m, 1 H) 7.45 (t, J=7.54 Hz, 1 H) 7.73 (d, J=8.82 Hz, 1 H) 7.92 (t, J=7.72 Hz, 1 H) 8.00 (m, 1 H) 8.21 (m, 2 H) 9.04 (s, 1 H) 14.28 (s, 1 H).

EXAMPLE 356

2-({8-amino-3-[4-hydroxy-1-(isobutylamino)-2-oxo-1,2-dihydroquinolin-3-yl]-1,1-dioxido-4H-1,2,4-benzothiadiazin-7-yl}oxy)acetamide A solution of the product of Example 321C (0.49 g, 1.15 mmol) in concentrated sulfuric acid (6 mL) at 0° C. was treated with ammonium nitrate (100 mg, 1.25 mmol). After stirring at room temperature for 1 hour, the solution was poured into ice water and the precipitate was filtered, dried, and triturated with ethyl acetate to yield to nitrated intermediate (0.27 g, 49%). A solution of the nitrated intermediate (75 mg, 0.16 mmol) in N,N-dimethylformamide (3 mL) was treated with 2-bromoacetamide (33 mg, 0.24 mmol) and cesium carbonate (206 mg, 0.63 mmol) in the presence of a catalytic amount of tetrabutylammonium iodide at room temperature for 24 hours. The solvent was removed with a stream of warm nitrogen and the residue was triturated with water, filtered, and dried to yield the alkylated material (76 mg, 90%). A solution of this material in a 3:3:1 mixture of methanol:tetrahydrofuran:water (2.3 mL) was treated with powdered iron (36 mg, 0.64 mmol) and ammonium chloride (9 mg, 0.17 mmol) at 60° C. for 2 hours. The solution was filtered through diatomaceous earth, and rinsed with tetrahydrofuran. The filtrate was concentrated and purified by flash column, eluting with 1% methanol in dichloromethane to yield the title compound (16 mg, 22%). The sodium salt was prepared by the procedure of Example 1D. MS (ESI$^-$) m/z 499 (M–H)$^-$. $^1$H NMR (300 MHz, DMSO-d$_6$) δ 1.03 (d, J=6.62 Hz, 6 H) 1.86 (m, 1 H) 2.55 (m, 2 H) 4.39 (s, 2 H) 5.73 (s, 2 H) 5.93 (t, J=7.54 Hz, 1 H) 6.37 (d, J=8.46 Hz, 1 H) 7.04 (m, 2 H) 7.56 (m, 3 H) 7.84 (s, 1 H) 8.06 (d, J=8.46 Hz, 1 H) 15.91 (s, 1 H).

EXAMPLE 357

3-[8-(chloromethyl)-1,1-dioxido-4H-[1,3]oxazolo[5,4-h][1,2,4]benzothiadiazin-3-yl]-4-hydroxy-1-(isobutylamino)quinolin-2(1H)-one A solution of Example 354 (0.030 g, 0.067 mmol) in dimethylformamide (3 mL) was treated with 2-chloro-1,1,1-trimeth oxyethane (0.50 mL) and a catalytic amount of para-toluenesulfonic acid at 60° C. for 4 hours. The solvent was removed under a stream of warm nitrogen and the resulting residue was triturated with water and filtered, then triturated with methanol and filtered to yield the title compound (22 mg, 51%). The sodium salt was made by the procedure of Example 1D. MS (ESI$^-$) m/z 500 (M–H)$^-$. $^1$H NMR (300 MHz, DMSO-d$_6$) δ 1.04 (d, J=6.62 Hz, 6 H) 1.87 (m, J=20.04, 13.42, 6.99 Hz, 1 H) 2.63 (m, 2 H) 5.13 (s, 2 H) 5.95 (t, J=6.99 Hz, 1 H) 7.08 (t, J=7.54 Hz, 1 H) 7.36 (d, J=9.19 Hz, 1 H) 7.57 (m, 2 H) 7.99 (d, J=8.82 Hz, 1 H) 8.09 (dd, J=7.91, 1.29 Hz, 1 H) 16.59 (s, 1 H).

EXAMPLE 358A

3-[7-(benzyloxy)-1,1-dioxido-4H-1,2,4-benzothiadiazin-3-yl]-4-hydroxy-1-[propylideneamino]quinolin-2(1H)-one The product of Example 304F (0.1 g, 0.22 mmol) in N,N-dimethylacetamide (1 mL) was reacted with propionaldehyde diethylacetal (0.34 mL, 2.2 mmol) in a sealed tube in a microwave reactor at 100° C. for 60 minutes. The reaction was cooled to 25° C., concentrated under a stream of nitrogen warmed through a manifold heated to 165° C. and the resulting residue was triturated with diethyl ether to give the title compound (0.045 g, 42%).

EXAMPLE 358B

3-[7-(benzyloxy)-1,1-dioxido-4H-1,2,4-benzothiadiazin-3-yl]-4-hydroxy-1-(propylamino)quinolin-2(1H)-one The product of Example 358A (0.045 g, 0.09 mmol) in tetrahydrofuran (2 mL) at 0° C. was treated with methanol (0.005 mL, 0.35 mmol), followed by dropwise addition of a 2.0 M solution of lithium borohydride in tetrahydrofuran (0.07 mL, 0.13 mmol), stirred at 25° C. for one hour, and diluted with 1 N hydrochloric acid. The resulting precipitate was filtered and dried. The solid was dissolved in tetrahydrofuran and absorbed onto silica gel by evaporating to dryness. The resulting silica was loaded onto a 2 g Alltech sep pack and eluted with dichloromethane to give the title compound (0.020 g, 44%). MS (ESI$^-$) m/z 503 (M–H)$^-$.

EXAMPLE 358C 4-hydroxy-3-(7-hydroxy-1,1-dioxido-4H-1,2,4-benzothiadiazin-3-yl)-1-(propylamino)quinolin-2(1H)-one The product of Example 358B (0.020 g, 0.04 mmol) in tetrahydrofuran (5 mL) was treated with ammonium formate (13 mg, 0.19 mmole), palladium hydroxide (2 mg) and 10% Pd/C (1 mg) and the resulting mixture was refluxed for 1 hour. The catalyst was filtered off and the filtrate evaporated to give a white solid. The solid residue was partitioned between ethyl acetate (100 mL) and water (5 mL). The layers were separated and the organic solvent was removed under reduced pressure to give the title compound (0.016 g, 100%). MS (ESI$^-$) m/z 413 (M–H)$^-$.

EXAMPLE 358D 2-({3-[4-hydroxy-2-oxo-1-(propylamino)-1,2-dihydroquinolin-3-yl]-1,1-dioxido-4H-1,2,4-benzothiadiazin-7-yl}oxy)acetamide The product of Example 358C (0.016 g, 0.04 mmol) in N,N-dimethylformamide (2 mL) was reacted with cesium carbonate (0.015 g, 0.045 mmol), bromoacetamide (0.006 g, 0.18 mmol), and a catalytic amount of tetrabutylammonium iodide at 25° C. for 3 hours. The reaction was concentrated under a stream of nitrogen stream of nitrogen warmed through a manifold heated to 165° C. and the resulting residue was triturated with water, filtered and dried. The resulting solid was triturated in hot ethyl acetate, filtered, and dried to give the title compound (0.008 g, 37%). The sodium salt of the title compound was prepared according to the procedure of Example 1D. MS (ESI$^-$) m/z 470 (M−H)$^-$. $^1$H NMR (300 MHz, DMSO-d$_6$) δ 0.99 (m, 3 H)1.55 (t, 2 H) 2.73 (t, 2 H) 4.11 (d, 1 H) 4.41 (d, 1 H) 5.83 (d, 1 H) 7.05 (s, 3 H)7.39 (s, 1 H) 7.54 (s, 2 H) 7.98 (s, 1 H) 16.24 (s, 1 H).

EXAMPLE 359

3-{3-[4-hydroxy-1-(isobutylamino)-2-oxo-1,2-dihydroquinolin-3-yl]-1,1-dioxido-4H-[1,3]oxazolo[5,4-h][1,2,4]benzothiadiazin-8-yl}propanoic acid A solution of the product of Example 354 (15 mg, 0.033 mmol) and maleic anhydride (100 mg, 1.0 mmol) in pyridine (2 mL) was heated at 160° C. in a microwave reactor for 1 hour. The crude mixture was cooled to 25° C. and purified by preparative HPLC on a Waters Symmetry C8 column (25 mm×100 mm, 7 μm particle size) using a gradient of 10% to 100% acetonitrile:0.1% aqueous trifluoroacetic to yield the title compound (5.3 mg, 30%). The disodium salt was made by the procedure of Example 1D using 2 equivalents of sodium hydroxide. MS (ESI$^-$) m/z 524 (M−H)$^-$. $^1$H NMR (300 MHz, DMSO-d$_6$) δ 1.03 (d, J=6.25 Hz, 6 H) 1.86 (m, 1 H) 2.27 (m, 4 H) 2.66 (m, 2 H) 5.94 (t, J=7.54 Hz, 1 H) 6.81 (m, 2 H) 7.05 (t, J=7.91 Hz, 1 H) 7.53 (m, 2 H) 8.06 (d, J=6.62 Hz, 1 H) 15.74 (s, 1 H).

EXAMPLE 360

3-(8-{[(2-aminoethyl)amino]methyl}-1,1-dioxido-4H-[1,3]oxazolo[5,4-h][1,2,4]benzothiadiazin-3-yl)-4-hydroxy-1-(isobutylamino)quinolin-2(1H)-one A solution of the product from Example 357 (20 mg, 0.039 mmol) and tert-butyl-N-(2-aminoethyl)carbamate (7.7 mg, 0.046 mmol) in N,N-dimethylformamide (3 mL) was treated with cesium carbonate (39 mg, 0.117 mmol) at 50° C. for 2 hours. The solvent was removed with a stream of warm nitrogen and the resulting residue was triturated with water, filtered and dried. This solid was suspended in 1,4-dioxane (2 mL) and treated with a 4M solution of hydrochloric acid in 1,4-dioxane (2 mL) and stirred at room temperature for 20 hours. The solution was concentrated by half, filtered, and dried to yield the di-hydrochloride salt of the title compound (5.8 mg, (24%). MS (ESI$^-$) m/z 524 (M−H)$^-$. $^1$H NMR (500 MHz, benzene-d$_6$) δ 1.05 (d, J=6.71 Hz, 6 H) 1.93 (m, 1 H) 2.60 (m, 2 H) 2.81 (d, J=6.10 Hz, 2 H) 3.61 (m, 2 H) 4.67 (s, 2 H) 6.17 (m, 1 H) 7.05 (d, J=9.16 Hz, 1 H) 7.20 (d, J=8.54 Hz, 1 H) 7.44 (t, J=7.63 Hz, 1 H) 7.90 (m, 1 H) 7.99 (m, 2 H) 8.17 (d, J=7.93 Hz, 1 H) 8.24 (m, 2 H) 13.76 (s, 1 H).

EXAMPLE 361

2-({1,3-[4-hydroxy-1-(isobutylamino)-2-oxo-1,2-dihydroquinolin-3-yl]-1,1-dioxido-4H-1,2,4-benzothiadiazin-7-yl}oxy)propanamide To a solution of the product of Example 321C (20 mg, 0.0467 mmol) in N,N-dimethylformamide (2 mL) was added 2-bromopropionamide (10.6 mg, 0.070 mmol), tetra-n-butylammonium iodide (1.7 mg, 0.0047 mmol) and cesium carbonate (61 mg, 0.187 mmol). The mixture was stirred at 25° C. for 72 hours. To the solution was then treated with 1N aqueous hydrochloric acid (10 mL) and extracted with ethyl acetate (10 mL). The organic layer was separated and dried over magnesium sulfate, filtered, and concentrated under reduced pressure to provide the title compound (18.4 mg, 79%). The sodium salt of the title compound was prepared according to the procedure of Example 1D. MS (ESI$^-$) m/z 498 (M−Na)$^-$. $^1$H NMR (300 MHz, DMSO-d$_6$) δ 1.03 (d, J=6.6 Hz, 6H), 1.45 (d, J=6.6 Hz, 3H), 1.86 (m, 1H), 2.50 (m, 1H), 2.75 (m, 1H), 4.65(q, J=6.6 Hz, 1H), 5.94(t, J=7.3 Hz, 1H), 7.08 (m, 2H), 7.17 (m, 1H), 7.23 (m, 1H), 7.29 (s, 1H), 7.58 (m, 2H), 7.64 (s, 1H), 8.07 (d, J=6.6 Hz, 1H), 16.22 (s, 1H).

EXAMPLE 362

2-({3-[4-hydroxy-1-(isobutylamino)-2-oxo-1,2-dihydroquinolin-3-yl]-1,1-dioxido-4H-1,2,4-benzothiadiazin-7-yl}oxy)butanamide To a solution of the product of Example 321C (20 mg, 0.0467 mmol) in N,N-dimethylformamide (2 mL) was added 2-chlorobutyramide (8.5 mg, 0.070 mmol), tetra-n-butylammonium iodide (1.7 mg, 0.0047 mmol) and cesium carbonate (61 mg, 0.187 mmol). The mixture was stirred at 25° C. for 18 hours, then heated to 80° C. for 3 hours. After cooling to 25° C., 1N aqueous hydrochloric acid (10 mL) was added and the mixture extracted with ethyl acetate (10 mL). The resulting organic layer was separated and dried over magnesium sulfate, filtered, and concentrated under reduced pressure to provide the title compound (24 mg, 100%). The sodium salt of the title compound was prepared according to the procedure of Example 1D. MS (ESI$^-$) m/z 512 (M−Na)$^-$. $^1$H NMR (300 MHz, DMSO-d$_6$) δ 0.99 (t, J=7.7 Hz, 3H), 1.03 (d, J=6.3 Hz, 6H), 1.83 (m, 3H), 2.50 (m, 1H), 2.75 (m, 1H), 4.46 (m, 1H), 5.94 (m, 1H), 7.08 (m, 2H), 7.17 (m, 1H), 7.23 (m, 1H), 7.32 (s, 1H), 7.58 (m, 2H), 7.64 (s, 1H), 8.07 (d, J=7.8 Hz, 1H), 16.23 (bs, 1H).

EXAMPLE 363 methyl {3-[4-hydroxy-1-(isobutylamino)-2-oxo-1,2-dihydroquinolin-3-yl]-1,1-dioxido-4H-[1,3]oxazolo[5,4-h][1,2,4]benzothiadiazin-8-yl}acetate A solution of the product of Example 354 (67.5 mg, 0.015 mmol) in N,N-dimethylformamide (2 mL) was treated with p-toluenesulfonic acid monohydrate (1 mg) and monoorthomalonic acid tetramethyl ester (272 mg, 1.52 mmol). The mixture was heated at 50° C. in an oil bath under a nitrogen atmosphere and the resulting yellow solution was stirred for 3 hrs. At this time, additional ortho ester was added (272 mg, 1.52 mmol) and heating continued for another 5 hrs. The reaction was cooled to room temperature and the solution was concentrated by rotary evaporation in vacuo. The residue was further dried on a vacuum pump, then dissolved in dichloromethane (100 mL) and washed with water (2×50 mL) and brine. The organic layer was dried over anhydrous sodium sulfate, filtered, and concentrated under reduced pressure. The residue was chromatographed on silica gel, eluting with 1% methanol/dichloromethane. The resulting impure material was rechromatographed on silica gel, eluting with a gradient of 5% to 7% acetonitrile/dichloromethane to give the title compound (36 mg, 45%). MS (APCI$^+$) m/z 526 (M+H)$^+$. $^1$H NMR (300 MHz, DMSO-d$_6$) δ 1.05 (d, J=6.62 Hz, 6 H) 1.91 (m, 1 H) 2.77 (br m, 2 H) 3.72 (s, 3 H) 4.40 (s, 2 H) 6.36

(br m, 1 H) 7.45 (t, J=7.35 Hz, 1 H) 7.70 (d, J=9.19 Hz, 1 H) 7.94 (m, 2 H) 8.20 (d, J=8.82 Hz, 2 H) 14.25 (br s, 1 H). A suspension of the product of Example 363 (6.0 mg, 0.0114 mmol) in anhydrous tetrahydrofuran (3 mL) and distilled water (1 mL) was treated with 0.998 N aqueous sodium hydroxide (0.0114 mL, 0.0114 mmol) and the yellow solution mixed for 15 minutes. The solvent was removed under reduced pressure and the residue dried on a vacuum pump to afford the sodium salt of Example 363 (6.1 mg, 98%). $^1$H NMR (300 MHz, DMSO-d$_6$) δ 1.04 (d, J=5.15 Hz, 6 H) 1.88 (m, 1 H) 2.75 (m, 1 H) 3.72 (s, 3 H) 4.31 (s, 2 H) 5.95 (m, 1 H) 7.08 (m, 1 H) 7.30 (m, 1 H) 7.58 (m, 2 H) 7.95 (m, 1 H) 8.09 (m, 1 H) 16.55 (s, 1 H).

EXAMPLE 364

4-hydroxy-3-(8-{[3-hydroxypyrrolidin-1-yl]methyl}-1,1-dioxido-4H-[1,3]oxazolo[5,4-h][1,2,4]benzothiadiazin-3-yl)-1-(isobutylamino)quinolin-2(1H)-one A solution of the product from Example 357 (80 mg, 0.160 mmol) and 3-hydroxy pyrrolidine (20 mg, 0.240 mmol) in acetonitrile (4 mL) was treated with diisopropylethyl amine (0.115 mL, 0.640 mmol) at room temperature for 24 hours. The solvent was removed under a stream of with warm nitrogen and the residue was purified by preparative HPLC on a Waters Symmetry C8 column (25 mm×100 mm, 7 μm particle size) using a gradient of 10% to 100% acetonitrile:0.1% aqueous trifluoroacetic to yield the title compound (16.2 mg, 18%). The sodium salt was made by the procedure of Example 1D. MS (ESI$^-$) m/z 551 (M−H)$^-$. 1H NMR (300 MHz, DMSO-d$_6$) δ 1.04 (d, J=6.62 Hz, 6 H) 1.58 (m, 1 H) 1.88 (m, 1 H) 2.03 (m, 1 H) 2.60 (m, 2 H) 2.75 (m, 2 H) 2.88 (m, J=9.56, 6.25 Hz, 2 H) 3.97 (s, 2 H) 4.23 (m, 1 H) 4.76 (m, 1 H) 5.95 (t, J=7.35 Hz, 1 H) 7.08 (m, 1 H) 7.27 (d, J=8.82 Hz, 1 H) 7.56 (m, 2 H) 7.92 (d, J=8.82 Hz, 1 H) 8.09 (d, J=6.62 Hz, 1 H) 16.51 (s, 1 H).

EXAMPLE 365

3-[1,1-dioxido-8-(pyridinium-1-ylmethyl)-4H-[1,3]oxazolo[5,4-h][1,2,4]benzothiadiazin-3-yl]-1-(isobutylamino)-2-oxo-1,2-dihydroquinolin-4-olate A solution of the product of Example 357 (16.5 mg, 0.033 mmol) in pyridine (2 mL) was heated at 45° C. for 20 hours. The excess pyridine was removed with a stream of warm nitrogen and the residue was purified by preparative HPLC on a Waters Symmetry C8 column (25 mm×100 mm, 7 um particle size) using a gradient of 10% to 100% acetonitrile: 0.1% aqueous trifluoroacetic to yield the title compound (6 mg, 34%). MS (ESI$^-$) m/z 543 (M−H)$^-$. $^1$H NMR (300 MHz, DMSO-d$_6$) δ 1.03 (d, J=6.62 Hz, 6 H) 1.84 (m, J=13.42, 6.43 Hz, 1 H) 2.72 (m, 2 H) 5.93 (t, J=7.35 Hz, 1 H) 6.39 (s, 2 H) 7.07 (m, 1 H) 7.36 (d, J=8.82 Hz, 1 H) 7.56 (m, 2 H) 8.00 (d, J=8.82 Hz, 1 H) 8.08 (m, 1 H) 8.33 (m, 2 H) 8.78 (t, J=7.91 Hz, 1 H) 9.30 (d, J=5.52 Hz, 2 H) 16.59 (s, 1 H).

EXAMPLE 366

3-[1,1-dioxido-8-(pyrrolidin-1-ylmethyl)-4H-[1,3]oxazolo[5,4-h][1,2,4]benzothiadiazin-3-yl]-4-hydroxy-1-(isobutylamino)quinolin-2(1H)-one A solution of the product from Example 357 (80 mg, 0.160 mmol) and pyrrolidine (17 mg, 0.240 mmol) in acetonitrile (4 mL) was treated with diisopropylethyl amine (0.115 mL, 0.640 mmol) at ambient temperature for 24 hours. The solvent was removed under a stream of warm nitrogen and the residue was purified by preparative HPLC on a Waters Symmetry C8 column (25 mm×100 mm, 7 um particle size) using a gradient of 10% to 100% acetonitrile:0.1% aqueous trifluoroacetic to yield the title compound (12.4 mg, 15%). The sodium salt was made by the procedure of Example 1D. MS (ESI$^-$) m/z 535 (M−H)$^-$. $^1$H NMR (300 MHz, DMSO-d$_6$) δ 1.04 (d, J=6.62 Hz, 6 H) 1.73 (m, 4 H) 1.87 (m, 1 H) 2.63 (q, J=4.90 Hz, 4 H) 2.75 (m, 2 H) 3.99 (s, 2 H) 5.95 (t, J=7.35 Hz, 1 H) 7.08 (m, 1 H) 7.27 (d, J=8.82 Hz, 1 H) 7.56 (m, 2 H) 7.92 (d, J=8.82 Hz, 1 H) 8.09 (dd, J=7.90, 1.29 Hz, 1 H) 16.50 (s, 1 H).

EXAMPLE 367

8-amino-3-[4-hydroxy-1-(isobutylamino)-2-oxo-1,2-dihydroquinolin-3-yl]-1,1-dioxido-4H-1,2,4-benzothiadiazin-7-yl methanesulfonate A solution of the product of Example 354 (44 mg, 0.099 mmol) and methane sulfonyl chloride (0.010 mL, 0.011 mmol) in tetrahydrofuran (4 mL) was treated with diisopropylethylamine (0.075 mL, 0.040 mmol) at roo, temperature for 2 hours. The solution was poured into water. The resulting the precipitate was filtered, dried, and purified by flash column, eluting with 1% methanol in dichloromethane to yield the title compound (14.2 mg, 28%). The sodium salt was made by the procedure of Example 1D. MS (ESI$^-$) m/z 520 (M−H)$^-$. $^1$H NMR (300 MHz, DMSO-d$_6$) δ 1.03 (d, J=6.62 Hz, 6 H) 1.88 (m, 1 H) 2.71 (m, 2 H) 3.46 (s, 3 H) 5.94 (m, 1 H) 6.53 (m, 1 H) 7.16 (m, 1 H) 7.35 (m, 1 H) 7.64 (m, 2 H) 8.09 (d, J=7.35 Hz, 1 H) 16.23 (s, 1 H).

EXAMPLE 368

3-[8-(3-aminophenyl)-1,1-dioxido-4H-[1,3]oxazolo[5,4-h][1,2,4]benzothiadiazin-3-yl]-4-hydroxy-1-(isobutylamino)quinolin-2(1H)-one A mixture of the product of Example 354 (38 mg, 0.086 mmol) and 3-aminobenzoic acid (13 mg, 0.094 mmol) in polyphosphoric acid (1 mL) was heated to 190° C. for 1 hour. The solution was cooled to 25° C., triturated with water and a 10% solution of sodium carbonate. The solid was filtered, dried, and purified by flash column, eluting with 2% methanol in dichloromethane to yield the title compound (15 mg, 38%). The sodium salt was made by the procedure of Example 1D. MS (ESI$^-$) m/z 543 (M−H)$^-$. $^1$HNMR (300 MHz, DMSO-d$_6$) δ 1.04 (d, J=6.62 Hz, 6 H) 1.86 (m, 1 H) 2.56 (m, 2 H) 5.53 (s, 2 H) 5.96 (t, J=7.35 Hz, 1 H) 6.82 (ddd, J=8.09, 2.21, 1.10 Hz, 1 H) 7.08 (td, J=7.35, 1.47 Hz, 1 H) 7.27 (m, 2 H) 7.36 (dt, J=7.72, 1.29 Hz, 1 H) 7.57 (m, 3 H) 7.96 (d, J=8.82 Hz, 1 H) 8.10 (dd, J=8.09, 1.47 Hz, 1 H) 16.51 (s, 1 H).

EXAMPLE 369

3-[8-(aminomethyl)-1,1-dioxido-4H-[3]oxazolo[5,4-h][1,2,4]benzothiadiazin-3-yl]-4-hydroxy-1-(isobutylamino)quinolin-2(1H)-one A solution of the product of Example 357 (32 mg, 0.063 mmol) in tetrahydrofuran (2 mL) was treated with 20% ammonia in methanol (1 mL) and ammonium hydroxide (1 mL) and 1M sodium hydroxide solution (0.063 mL, 0.063 mmol) at room temperature of 16 hours. The mixture was blown dry with warm nitrogen and the resulting residue was partitioned between water and ethyl acetate. The organic layer was concentrated and purified by flash chromatography, eluting with a gradient of 100% dichloromethane to 2% methanol in dichloromethane, to yield the title compound (4 mg, 13%). MS (ESI⁻) m/z 481 (M–H)⁻. ¹H NMR (300 MHz, DMSO-d₆) δ 1.04 (d, J=6.62 Hz, 6 H) 1.91 (m, 1 H) 2.75 (m, 2 H) 4.55 (s, 2 H) 6.33 (m, 1 H) 6.98 (d, J=7.72 Hz, 1 H) 7.16 (d, J=8.46 Hz, 1 H) 7.44 (m, 1 H) 7.92 (m, 2 H) 8.17 (d, J=8.09 Hz, 1 H) 13.65 (s, 1 H) 15.60 (s, 1 H).

EXAMPLE 370

4-hydroxy-3-[8-(hydroxymethyl)-1,1-dioxido-4H-[1,3]oxazolo[5,4-h][1,2,4]benzothiadiazin-3-yl]-1-(isobutylamino)quinolin-2(1H)-one A solution of the product of Example 357 (32 mg, 0.063 mmol) in tetrahydrofuran (2 mL) was treated with 20% ammonia in methanol (1 mL) and ammonium hydroxide (1 mL) and 1M sodium hydroxide solution (0.063 mL, 0.063 mmol) at ambient temperature of 16 hours. The mixture was blown dry with warm nitrogen and the resulting residue was partitioned between water and ethyl acetate. The aqueous layer was adjusted to pH 1 with 1M hydrochloric acid and extracted with ethyl acetate. The organic layer was concentrated under reduced pressure to yield the title compound (5 mg, 16%). MS (ESI⁻) m/z 482 (M–H)⁻. ¹H NMR (300 MHz, DMSO-d₆) δ 1.04 (d, J=6.62 Hz, 6 H) 1.91 (m, 1 H) 2.76 (m, 2 H) 4.82 (s, 2 H) 6.34 (d, J=8.82 Hz, 1 H) 7.31 (d, J=8.82 Hz, 1 H) 7.43 (m, 2 H) 7.92 (m, 1 H) 8.18 (d, J=7.72 Hz, 1 H) 9.04 (s, 1 H) 14.31 (s, 1 H).

EXAMPLE 371

3-{8-[(butylamino)methyl]-1,1-dioxido-4H-[1,3]oxazolo[5,4-h][1,2,4]benzothiadiazin-3-yl}-4-hydroxy-1-(isobutylamino)quinolin-2(1H)-one A solution of the product of Example 357 (15.5 mg, 0.031 mmol) in pyridine (2 mL) was treated with n-butyl amine (0.030 mL, 0.31 mmol) at room temperature for 4 hours. The solvent was removed under a stream of warm nitrogen and the residue was purified by preparative HPLC on a Waters Symmetry C8 column (25 mm×100 mm, 7 μm particle size) using a gradient of 10% to 100% acetonitrile:0.1% aqueous trifluoroacetic to yield the title compound (1.2 mg, 7.2%). MS (ESI⁻) m/z 537 (M–H)⁻. ¹H NMR (300 MHz, DMSO-d₆) δ 0.91 (t, J=7.35 Hz, 3 H) 1.04 (d, J=6.62 Hz, 6 H) 1.36 (m, 2 H) 1.64 (m, 2 H) 1.87 (m, 1 H) 2.66 (m, 2 H) 3.05 (m, 2 H) 4.62 (s, 2 H) 5.96 (t, J=7.54 Hz, 1 H) 7.10 (t, J=6.80 Hz, 1 H) 7.39 (d, J=9.19 Hz, 1 H) 7.59 (m, 2 H) 8.02 (d, J=8.82 Hz, 1 H) 8.09 (d, J=8.09 Hz, 1 H) 16.54 (s, 1 H).

EXAMPLE 372 RZ

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}acetamide To the product of Example 205 (0.020 g, 0.047 mmol) in pyridine (0.5 mL) was added acetic anhydride (0.057 g, 0.0053 mL, 0.056 mmol). The reaction mixture was heated in a microwave reactor at 100° C. for 30 minutes. The reaction was poured into 30 mL of water. The solid was collected by filtration to give the title compound (15.8 mg, 72%). ¹H NMR (300 MHz, DMSO-d₆) δ 0.98 (d, J=6.62 Hz, 6 H) 1.57 (m, 2 H) 1.70 (m, 1 H) 2.10 (s, 3 H) 4.48 (m, 2 H) 7.48 (dd, J=8.09, 4.78 Hz, 1 H) 7.66 (d, J=8.82 Hz, 1 H) 7.78 (m, 1 H) 8.30 (d, J=1.84 Hz, 1 H) 8.55 (dd, J=7.72, 1.84 Hz, 1 H) 8.87 (dd, J=4.60, 1.65 Hz, 1 H) 10.39 (s, 1 H) 14.21 (br s, 1 H). MS (ESI⁻) m/z 468 (M–H)⁻.

EXAMPLE 373

2,2,2-trifluoro-N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}acetamide To a slurry of the product of Example 205 (0.043 g, 0.1 mmol) in 5 mL chloroform was added dropwise, trifluoroacetic anhydride (0.074 g, 0.35 mmol). The reaction mixture was stirred for 30 minutes and partitioned between ethyl acetate and water. The ethyl acetate layer was washed with brine, dried over sodium sulfate, filtered and concentrated under reduced pressure to give the title compound (0.048 g, 92% yield). MS (ESI⁻) m/z 522 (M–H)⁻. The sodium salt of the title compound was prepared according to the procedure of Example 1D. ¹H NMR (300 MHz, DMSO-d₆) δ 0.96 (d, J=6.62 Hz, 6 H) 1.48 (m, 2 H) 1.65 (m, 1 H) 4.30 (m, 2 H) 7.14 (dd, J=7.54, 4.60 Hz, 1 H) 7.35 (d, J=8.82 Hz, 1 H) 7.83 (dd, J=8.82, 2.57 Hz, 1 H) 8.07 (d, J=2.57 Hz, 1 H) 8.37 (dd, J=7.72, 1.84 Hz, 1 H) 8.54 (dd, J=4.78, 1.84 Hz, 1 H) 11.43 (s, 1 H) 16.09 (s, 1 H).

EXAMPLE 374

2,2,2-trifluoro-N-{3-[4-hydroxy-1-(3-methylbutyl)-2-oxo-1,2-dihydro-1,8-naphthyridin-3-yl]-8-nitro-1,1-dioxido-4H-1,2,4-benzothiadiazin-7-yl}acetamide To a solution of trifluoroacetic acid (2.5 mL) and trifluoroacetic anhydride (2.5 mL) at 0° C. was added portion wise the product of Example 205 (0.5 g, 1.17 mmol). The resulting red solution was stirred at 0° C. for 30 minutes, cooled to –20° C. and treated portion wise with potassium nitrate (0.13 g, 1.3 mmol). The mixture was stirred at –20° C. for 1 hour, poured onto ice and the resulting tan solid was collected by filtration, washed with water and dried to constant mass to give the title compound (0.628 g, 94% yield). MS (ESI⁻) m/z 567 (M–H)⁻. The sodium salt of the title compound was prepared according to the procedure of Example 1D. ¹H NMR (300 MHz, DMSO-d₆) δ 0.96 (d, J=6.62 Hz, 6 H) 1.49 (m, 2 H) 1.64 (m, 1 H) 4.30 (m, 2 H) 7.16 (dd, J=7.72, 4.78 Hz, 1 H) 7.67 (m, 2 H) 8.38 (dd, J=7.54, 2.02 Hz, 1 H) 8.57 (dd, J=4.41, 1.84 Hz, 1 H) 11.61 (s, 1 H) 16.67 (s, 1 H).

EXAMPLE 375

3-[1,1-dioxido-8-(trifluoromethyl)-4,7-dihydroimidazo[4,5-h][1,2,4]benzothiadiazin-3-yl]-4-hydroxy-1-(3-methylbutyl)-1,8-naphthyridin-2(1H)-one A mixture of the product of Example 374 (0.043 g, 0.075 mmol) and iron dust (0.025 g, 0.45 mmol) in acetic acid (2 mL) was heated at 80° C. for 1 hour, cooled, diluted with 20 mL ethyl acetate and filtered through a plug of Celite®. The ethyl acetate filtrate was washed with water, brine, dried over sodium sulfate, filtered and concentrated to give the title compound as an orange solid (0.035 g, 90% yield). MS (ESI⁻) m/z 519 (M–H)⁻. The sodium salt of the title compound was prepared according to the procedure of Example 1D. ¹H NMR (300 MHz, DMSO-d₆) δ 0.97 (d, J=6.25 Hz, 6 H) 1.48 (m, 2 H) 1.66 (m, 1 H) 4.31 (m, 2 H) 7.14 (m, 1 H) 7.25 (d, J=8.46 Hz, 1 H) 7.96 (d, J=9.19 Hz, 1 H) 8.38 (d, J=6.99 Hz, 1 H) 8.54 (m, 1 H) 14.46 (s, 1 H) 16.33 (s, 1 H).

EXAMPLE 376

3-(7-amino-8-nitro-1,1-dioxido-4H-1,2,4-benzothiadiazin-3-yl)-4-hydroxy-1-(3-methylbutyl)-1,8-naphthyridin-2(1H)-one A mixture of the product of Example 374 (0.500 g, 0.88 mmol) and potassium carbonate (1.4 g, 10.1 mmol) in methanol (20 mL), tetrahydrofuran (8 mL) and water (8 mL) was heated at 60° C. for 4 hours, cooled and concentrated. The resulting residue was dissolved in ethyl acetate, treated with 1M hydrochloric acid to a pH of about 1, washed with brine, dried over sodium sulfate, filtered and concentrated to give the title compound as a brown solid (0.4 g, 96% yield). MS (ESI$^-$) m/z 471 (M–H)$^-$. The sodium salt of the title compound was prepared according to the procedure of Example 1D. $^1$H NMR (300 MHz, DMSO-d$_6$) δ 0.96 (d, J=6.62 Hz, 6 H) 1.45 (m, 2 H) 1.64 (m, 1 H) 4.28 (m, 2 H) 6.37 (s, 2 H) 7.13 (dd, J=7.17, 4.23 Hz, 1 H) 7.16 (d, J=9.19 Hz, 1 H) 7.33 (d, J=9.19 Hz, 1 H) 8.35 (dd, J=7.72, 1.84 Hz, 1 H) 8.53 (dd, J=4.78, 1.84 Hz, 1 H) 16.02 (s, 1 H).

EXAMPLE 377

3-(7,8-diamino-1,1-dioxido-4H-1,2,4-benzothiadiazin-3-yl)-4-hydroxy-1-(3-methylbutyl)-1,8-naphthyridin-2(1H)-one A mixture of the product of Example 376 (2.1 g, 4.45 mmol), iron powder (1.24 g, 22.25 mmol) and ammonium chloride (0.29 g, 5.3 mmol) in methanol (50 mL), tetrahydrofuran (50 mL) and water (20 mL) was heated at 75° C. for 6 hours, cooled and filtered through a plug of Celite®. The filtrate was treated with 1M hydrochloric acid to a pH of about 2 and the solution was concentrated under vacuum. The resulting residue was stirred in 100 mL of water for 30 minutes and filtered to collect a solid which was then triturated with 50 mL of diethyl ether, filtered and dried to give the title compound (1.72 g, 87% yield). MS (ESI$^-$) m/z 441 (M–H)$^-$. The sodium salt of the title compound was prepared according to the procedure of Example 1D. $^1$H NMR (300 MHz, DMSO-d$_6$) δ 0.96 (d, J=6.62 Hz, 6 H) 1.49 (m, 2 H) 1.63 (m, 1 H) 4.28 (m, 2 H) 4.63 (s, 2 H) 5.20 (s, 2 H) 6.30 (d, J=8.09 Hz, 1 H) 6.74 (d, J=8.46 Hz, 1 H) 7.10 (dd, J=7.72, 4.78 Hz, 1 H) 8.34 (dd, J=7.72, 1.84 Hz, 1 H) 8.50 (dd, J=4.60, 2.02 Hz, 1 H) 15.41 (s, 1 H).

EXAMPLE 378

4-hydroxy-3-(8-hydroxy-1,1-dioxido-4,7-dihydroimidazo[4,5-h][1,2,4]benzothiadiazin-3-yl)-1-(3-methylbutyl)-1,8-naphthyridin-2(1H)-one A mixture of the product of Example 377 (0.022 g, 0.05 mmol) and urea (0.012 g, 0.2 mmol) in N,N-dimethylacetamide (0.5 mL) in a sealed tube was heated by microwave at 180° C. for 60 minutes. The mixture was cooled and partitioned between ethyl acetate and water adjusted to pH 3 with 1 M hydrochloric acid. The ethyl acetate layer was washed with water, brine, dried over sodium sulfate, filtered and concentrated. The residue was chromatographed on silica gel eluting first with dichloromethane and then 96:4 dichloromethane/methanol to give the title compound (0.022 g, 90% yield). MS (ESI$^-$) m/z 467 (M–H)$^-$. The sodium salt of the title compound was prepared according to the procedure of Example 1D. $^1$H NMR (300 MHz, DMSO-d$_6$) δ 0.97 (d, J=6.62 Hz, 6 H) 1.49 (m, 2 H) 1.65 (m, 1 H) 4.29 (m, 2 H) 6.69 (br. s, 1 H) 7.00 (br. s., 1 H) 7.12 (dd, J=7.72, 4.78 Hz, 1 H) 8.36 (m, 1 H) 8.51 (dd, J=4.41, 1.84 Hz, 1 H) 10.66 (s, 1 H) 15.76 (s, 1 H).

EXAMPLE 379

4-hydroxy-1-(3-methylbutyl)-3-(8-methyl-1,1-dioxido-4,7-dihydroimidazo[4,5-h][1,2,4]benzothiadiazin-3-yl)-1,8-naphthyridin-2(1H)-one A mixture of the product of Example 377 (0.022 g, 0.05 mmol) and acetic acid (1 mL) in a sealed tube was heated by microwave at 160° C. for 30 minutes, cooled and filtered to collect a solid which was washed repeatedly with diethyl ether and dried to give the title compound as a tan solid (0.006 g, 26% yield). MS (ESI$^-$) m/z 465 (M–H)$^-$. The sodium salt of the title compound was prepared according to the procedure of Example 1D. $^1$H NMR (300 MHz, DMSO-d$_6$) δ 0.97 (d, J=6.62 Hz, 6 H) 1.48 (m, 2 H) 1.64 (m, 1 H) 2.47 (s, 3 H) 4.31 (m, 2 H) 6.98 (d, J=8.46 Hz, 1 H) 7.13 (dd, J=7.54, 4.96 Hz, 1 H) 7.67 (d, J=8.46 Hz, 1 H) 8.38 (dd, J=7.54, 2.02 Hz, 1 H) 8.53 (dd, J=4.60, 1.65 Hz, 1 H) 12.57 (s, 1 H) 16.04 (s, 1 H).

EXAMPLE 380

3-[1,1-dioxido-8-(pentafluoroethyl)-4,7-dihydroimidazo[4,5-h][1,2,4]benzothiadiazin-3-yl]-4-hydroxy-1-(3-methylbutyl)-1,8-naphthyridin-2(1H)-one A mixture of the product of Example 377 (0.022 g, 0.05 mmol) and pentafluoropropionic acid (0.5 mL) in a sealed tube was heated by microwave at 130° C. for 30 minutes, cooled and concentrated under reduced pressure. The crude material was chromatographed on silica eluting first with dichloromethane and then 99:1 dichloromethane/methanol to give the title compound (0.011 g, 38% yield). MS (ESI$^-$) m/z 569 (M–H)$^-$. The sodium salt of the title compound was prepared according to the procedure of Example 1D. $^1$H NMR (300 MHz, DMSO-d$_6$) δ 0.98 (d, J=6.25 Hz, 6 H) 1.52 (m, 2 H) 1.69 (m, 1 H) 4.37 (m, 2 H) 7.30 (m, 2 H) 7.97 (m, 1 H) 8.54 (m, 2 H) 14.65 (m, 1 H).

EXAMPLE 381

1-[(cyclopropylmethyl)amino]-4-hydroxy-3-(7-hydroxy-8-nitro-1,1-dioxido-4H-1,2,4-benzothiadiazin-3-yl)quinolin-2(1H)-one A solution of the product of Example 320C (47 mg, 0.11 mmol) in concentrated sulfuric acid (2 mL) at 0° C. was treated with ammonium nitrate (10 mg, 0.13 mmol). After stirring at ambient temperature for 25 minutes, the solution was poured into ice water and the precipitate was filtered, dried, and purified by flash chromatography, eluting with 2% methanol in dichloromethane to yield the title compound (10 mg, 19%). MS (ESI$^-$) m/z 470 (M–H)$^-$. $^1$H NMR (300 MHz, DMSO-d$_6$) δ 0.14 (d, J=4.04 Hz, 2 H) 0.41 (m, 2 H) 1.01 (m, 1 H) 2.84 (d, J=6.99 Hz, 2 H) 7.44 (m, 2 H) 7.77 (d, J=9.56 Hz, 1 H) 7.88 (t, J=7.91 Hz, 1 H) 8.08 (d, J=8.46 Hz, 1 H) 8.16 (dd, J=8.09, 1.10 Hz, 1 H) 11.83 (s, 1 H).

EXAMPLE 382

3-(7-{2-[(3S)-3-aminopyrrolidin-1-yl]-2-oxoethoxy}-1,1-dioxido-4H-1,2,4-benzothiadiazin-3-yl)-1-[(cyclopropylmethyl)amino]-4-hydroxyquinolin-2 (1H)-one A mixture of the product of Example 384, 1-[3-(dimethylamino)propyl]-3-ethylcarbodiimide hydrochloride and 1-hydroxybenzotriazole in N,N-dimethylformamide is added pyrrolidin-3(S)-yl-carbamic acid tert-butyl ester. The mixture is stirred for 1 day. The solution is poured into ethyl acetate and washed with saturated sodium bicarbonate, water, brine and dried with magnesium sulfate. The solvent is removed by vacuo. The residue is triturated with methanol/water and filtered. The solid is added in hydrochloric acid (1 M in dioxane, 2 mL) and stirred overnight, filtered and washed with ethyl acetate/hexane (1:1) to give title compound.

EXAMPLE 383

2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]-N-ethylacetamide The product of Example 384 (24 mg, 0,05 mmole), 1-[3-(dimethylamino)propyl]-3 ethylcarbodiimide hydrochloride (16 mg, 0.08 mmol) and 1-hydroxybenzotriazole (14 mg, 0.1 mmol) in N,N-dimethylformamide (2 mL) was added ethylamine (100 µl, 2M in tetrahydrofuran, 0.2 mmol). The mixture was stirred for 1 day. The solution was poured into ethyl acetate (40 mL) and washed with saturated aqueous sodium bicarbonate, water, brine and dried with magnesium sulfate. The solvent was removed under reduced pressure. The residue was triturated with methanol/water and filtered to give title compound (6 mg, 24%). $^1$H NMR (500 MHz, DMSO-$d_6$) δ 0.20 (m, 2 H) 0.45 (m, 2 H) 1.00 (m, 1 H) 1.07 (t, J=7.08 Hz, 3 H) 2.70 (s, 2 H) 3.18 (m, 2 H) 4.49 (s, 2 H) 5.99 (s, br, 1 H) 7.08 (s, br, 1 H) 7.23 (s, br, 3 H) 7.52 (s, br, 1 H) 7.70 (s, br, 1 H) 7.88 (s, br, 1 H) 8.09 (d, J=7.81 Hz, 1 H). MS (ESI$^-$) m/z 510 (M–H)$^-$.

EXAMPLE 384A tert-butyl [(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetate The product of Example 320C (400 mg, 0.94 mmol) in N,N-dimethylformamide (10 mL) was reacted with tert-butyl bromoacetate (0.555 mL, 3.76 mmol), potassium carbonate (1.225 g, 3.76 mmol) and tetrabutylammonium iodide (catalytic) at 25° C. for overnight. The reaction mixture was diluted with water and adjusted to pH 7 with glacial acetic acid. The reaction was extracted with ethyl acetate and the organic layer was washed with aqueous sodium bicarbonate, water and brine, dried over anhydrous magnesium sulfate, filtered, and concentrated under reduced pressure. The resulting residue was chromatographed on silica gel eluting with a gradient of 3:1 hexanes:ethyl acetate to 1:1 hexanes:ethyl acetate to give the title compound (195 mg, 38%).

EXAMPLE 384B

[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetic acid The product of Example 384A (195 mg, 0.36 mmol) in a mixture of trifluoroacetic acid (5 mL) and dichloromethane (5 mL) was stirred for three hours at 25° C. The solvents were removed under reduced pressure. The residue was triturated with hexanes/ethyl acetate (1:1) and filtered to give title compound (114 mg, 65%). $^1$H NMR (300 MHz, DMSO-$d_6$) δ 0.14 (d, J=4.04 Hz, 2 H) 0.41 (d, J=7.35 Hz, 2 H) 1.02 (m, 1 H) 2.86 (d, J=6.25 Hz, 2 H) 4.88 (s, 2 H) 6.44 (s, 1 H) 7.39 (m, 3 H) 7.67 (d, J=8.82 Hz, 1 H) 7.89 (m, 1 H) 8.10 (d, J=8.46 Hz, 1 H) 8.17 (dd, J=1.47 Hz, J=6.62 Hz, 1 H) 13.16 (s, 1 H) 14.07 (s, 1 H) 15.12 (s, 1 H). MS (ESI$^-$) m/z 483 (M–H)$^-$.

EXAMPLE 385

3-{7-[2-(3-aminopyrrolidin-1-yl)-2-oxoethoxy]-1,1-dioxido-4H-1,2,4-benzothiadiazin-3-yl}-1-[(cyclopropylmethyl)amino]-4-hydroxyquinolin-2(1H)-one The product of Example 384B (24 mg, 0,05 mmole), 1-[3-(dimethylamino)propyl]-3-ethylcarbodiimide hydrochloride (16 mg, 0.08 mmol) and 1-hydroxybenzotriazole (14 mg, 0.1 mmol) in N,N-dimethylformamide (2 mL) was added pyrrolidin-3-yl-carbamic acid tert-butyl ester(19 mg, 0.1 mmol). The mixture was stirred for 1 day. The solution was poured into ethyl acetate (40 mL) and washed with saturated aqueous sodium bicarbonate, water, and brine, dried with magnesium sulfate, filtered and concentrated. The residue was triturated with methanol/water and filtered. The solid was treated with hydrochloric acid (1 M in dioxane, 2 mL) and stirred overnight, filtered and washed with ethyl acetate/hexane (1:1) to give title compound (15 mg, 51%). $^1$H NMR (500 MHz, BENZENE-d6) δ 0.16 (m, 2 H) 0.43 (m, 2 H) 1.01 (m, 1 H) 2.14 (m, 2 H) 2.29 (m, 1 H) 2.89 (d, J=6.84 Hz, 2 H) 3.36 (m, 2 H) 3.81 (m, 2 H) 4.88 (m, 2 H) 7.42 (m, 3 H) 7.61 (m, 1 H) 7.88 (m, 1 H) 8.09 (d, J=8.30 Hz, 1 H) 8.17 (d, J=8.30 Hz, 1 H) 8.28 (s, 3 H) 13.99 (s, 1 H). MS (ESI$^-$) m/z 551 (M–H)$^-$.

793695 EXAMPLE 386 DL2

3-(8-amino-7-hydroxy-1,1-dioxido-4H-1,2,4-benzothiadiazin-3-yl)-1-[(cyclopropylmethyl)amino]-4-hydroxyquinolin-2(1H)-one A mixture of the product of Example 381 (10 mg, 0.021 mmol), iron powder (5.9 mg, 0.105 mmol), and ammonium chloride (1.3 mg, 0.024 mmol) in methanol:tetrahydrofuran:water (2:2:1, 2 mL) was heated at 60° C. for 1 hour. The solution filtered through Celite® and washed with tetrahydrofuran. The solution was evaporated under reduced pressure and the residue was triturated with ethyl acetate, filtered and washed with water and dried to give title compound (5 mg, 53%). $^1$H NMR (300 MHz, DMSO-$d_6$) δ 0.13 (d, J=3.68 Hz, 2 H) 0.40 (d, J=7.72 Hz, 2 H) 1.02 (m, 1 H) 2.85 (d, J=5.52 Hz, 2 H) 5.40 (s, 2 H) 6.46 (s, 1 H) 6.65 (d, J=8.46 Hz, 1 H) 7.00 (d, J=8.09 Hz, 1 H) 7.45 (t, J=7.35 Hz, 1 H) 7.89 (t, J=7.17 Hz, 1 H) 8.10 (d, J=8.46 Hz, 1 H) 8.17 (d, J=8.82 Hz, 1 H) 10.13 (s, 1 H) 13.82 (s, 1 H) 15.17 (s, 1 H). MS (ESI$^-$) m/z 440 (M–H)$^-$.

EXAMPLE 387A

2-[(3-{1-[(cyclopropylmethyl)amino]-4-hydroxy-2-oxo-1,2-dihydroquinolin-3-yl}-8-nitro-1,1-dioxido-4H-1,2,4-benzothiadiazin-7-yl)oxy]acetamide The product of Example 381 (20 mg, 0.042 mmol) in N,N-dimethylformamide (2 mL) was treated with 2-bromoacetamide (11.6 mg, 0.084 mmol), potassium carbonate (54.7 mg, 0.168 mmol) and tetrabutylammonium iodide (catalytic) at 25° C., stirred at 25° C. for 18 hours. The solution was evaporated under reduced pressure and the residue was triturated with ethyl acetate, filtered and washed with water to give the title compound (12 mg, 54%).

A mixture of the product of Example 387A (12 mg, 0.023 mmol), iron powder (6.0 mg, 0.107 mmol), and ammonium chloride (1.4 mg, 0.026 mmol) in methanol:tetrahydrofuran:water (2:2:1,2 mL) was heated at 60° C. for 1 hour. The solution filtered through Celite® and washed with tetrahydrofuran. The solution was evaporated under reduced pressure and the residue was triturated with ethyl acetate, filtered washed with water and dried to give title compound (7 mg, 62%). $^1$H NMR (300 MHz, DMSO-$d_6$) δ 0.14 (d, J=3.31 Hz, 2 H) 0.41 (d, J=6.99 Hz, 2 H) 1.01 (m, 1 H) 2.85 (d, J=5.88 Hz, 2 H) 4.49 (s, 2 H) 5.98 (s, 2 H) 6.46 (s, 1 H) 6.73 (d, J=8.46 Hz, 1 H) 7.17 (d, J=8.46 Hz, 1 H) 7.44 (t, J=7.54 Hz, 1 H) 7.55 (s, 1 H) 7.89 (t, J=8.07, 1 H) 7.92 (s, 1 H) 8.10 (d, J=8.46 Hz, 1 H) 8.16 (d, J=8.09 Hz, 1 H) 13.86 (s, 1 H) 15.07 (s, 1 H). MS (ESI$^-$) m/z 497 (M–H)$^-$.

EXAMPLE 388A

[(3-{1-[(cyclopropylmethyl)amino]-4-hydroxy-2-oxo-1,2-dihydroquinolin-3-yl}-8-nitro-1,1-dioxido-4H-1,2,4-benzothiadiazin-7-yl)oxy]acetonitrile The product of Example 381 (20 mg, 0.042 mmol) in N,N-dimethylformamide (2 mL) was reacted with 2-bromoacetonitrile (6 µl, 0.086 mmol), potassium carbonate (54.7 mg, 0.168 mmol) and tetrabutylammonium iodide (catalytic) at 25° C. for 18 hours. The solution was evaporated under reduced pressure and the residue was triturated with ethyl acetate, filtered and washed with water to give the title compound (13 mg, 60%).

EXAMPLE 388B

[(8-amino-3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetonitrile A mixture of the product of Example 388A (13 mg, 0.025 mmol), iron powder (6.0 mg, 0.107 mmol), and ammonium chloride (1.5 mg, 0.028 mmol) in methanol:tetrahydrofuran:water (2:2:1, 2 mL) was heated at 60° C. for 1 hour. The solution filtered through Celite® and washed with tetrahydrofuran. The solution was evaporated under reduced pressure and the residue was triturated with ethyl acetate, filtered washed with water and dried to give title compound (5 mg, 41%). $^1$H NMR (300 MHz, DMSO-$d_6$) δ 0.14 (d, J=1.11 Hz, 2 H) 0.41 (d, J=5.88 Hz, 2 H) 1.01 (m, 1 H) 2.85 (d, J=5.40 Hz, 2 H) 5.23 (s, 2 H) 5.80 (s, 2 H) 6.45 (s, 1 H) 6.83 (d, J=8.46 Hz, 1 H) 7.38 (d, J=8.46 Hz, 1 H) 7.44 (t, J=7.02 Hz, 1 H) 7.90 (t, J=7.02 Hz, 1 H) 8.10 (d, J=8.46 Hz, 1 H) 8.16 (d, J=7.74 Hz, 1 H) 13.93 (s, 1 H) 14.94 (s, 1 H). MS (ESI$^-$) m/z 479 (M–H)$^-$.

EXAMPLE 389

1-[(cyclopropylmethyl)amino]-4-hydroxy-3-[7-(2-hydroxyethoxy)-1,1-dioxido-4H-1,2,4-benzothiadiazin-3-yl]quinolin-2(1H)-one Product of Example 384 (10 mg, 0.021 mmol) in tetrahydrofuran (10 mL) was added borane (0.8 mL, 1M in tetrahydrofuran, 0.8 mmol). The mixture was refluxed for 4 hours. Then poured into ice water (20 mL) and acidified to pH 2 with 1N hydrochloric acid. The solid was filtered and washed with water to give the title compound (5 mg, 51%). $^1$H NMR (300 MHz, DMSO-$d_6$) δ 0.14 (d, J=4.41 Hz, 2 H) 0.41 (d, J=7.72 Hz, 2 H) 1.01 (m, 1 H) 2.86 (d, J=5.52 Hz, 2 H) 3.74 (t, J=4.78 Hz, 2 H) 4.13 (t, J=4.78 Hz, 2 H) 4.89 (s, 1 H) 6.44 (s, 1 H) 7.41 (m, 3 H) 7.65 (d, J=9.84 Hz, 1 H) 7.89 (t, J=7.91 Hz, 1 H) 8.10 (d, J=8.46 Hz, 1 H) 8.17 (d, J=7.35 Hz, 1 H) 14.05 (s, 1 H) 15.14 (s, 1 H). MS (ESI$^-$) m/z 469 (M–H)$^-$.

EXAMPLE 390A

3-{7-[(1-benzyl-1H-imidazol-2-yl)methoxy]-1,1-dioxido-4H-1,2,4-benzothiadiazin-3-yl}-1-[(cyclopropylmethyl)amino]-4-hydroxyquinolin-2(1H)-one Product of Example 320C (20 mg, 0.047 mmol) in N,N-dimethylformamide (1 mL) was was heated with 1-benzyl-2-(chloromethyl)-1H-imidazole hydrochloride (23 mg, 0.095 mmol), potassium carbonate (0.061 g, 0.187 mmol) and tetrabutylammonium iodide (catalytic) at 120° C. for 2 hours in a microwave reactor. The solution was cooled to 25° C. and concentrated. The residue was triturated with ethyl acetate, filtered and washed with water to give title compound (21 mg, 75%).

EXAMPLE 390B

1-[(cyclopropylmethyl)amino]-4-hydroxy-3-[7-(1H-imidazol-2-ylmethoxy)-1,1-dioxido-4H-1,2,4-benzothiadiazin-3-yl]quinolin-2(1H)-one Product of Example 390A (16 mg, 0.027 mmol) in N,N-dimethylformamide (1 mL) was added 1,4-cyclodiene (25.5µl, 0.27 mmol) and palladium black (16 mg). The mixture was heated at 70° C. for 1 day. The mixture was filtered with Celite® and washed with N,N-dimethylformamide. The solution was evaporated under reduced pressure and the residue was chromatographed on silica gel eluting with dichloromethane:methanol (98:2) to give the title compound (6 mg, 44%). $^1$H NMR (300 MHz, DMSO-$d_6$) δ 0.16 (d, J=4.41 Hz, 2 H) 0.43 (d, J=7.35 Hz, 2 H) 0.99 (m, 1 H) 2.78 (s, br, 2 H) 5.25 (s, 2 H) 6.27 (s, br, 1 H) 7.22 (s, 2 H) 7.31 (m, 1 H) 7.39 (dd, J=9.01, 2.76 Hz, 1 H) 7.49 (d, J=2.57 Hz, 1 H) 7.54 (d, J=8.82 Hz, 1 H) 7.77 (m, 1 H) 7.95 (d, J=8.09 Hz, 1 H) 8.13 (dd, J=8.09 Hz, 1.47 Hz, 1 H) 14.83 (s, br, 1 H). MS (ESI$^-$) m/z 505 (M–H)$^-$.

EXAMPLE 391A 1,3-thiazol-2-ylmethanol

To thiazole-2-carbaldehyde (113 mg, 1Mmol) in methanol (10 mL) was added sodium borohydride (41 mg, 1.2 mmol) portion wise at 0° C. The mixture was stirred at room temperature for 2 hours. The mixture was diluted with water and acidified to pH 3 with 1M hydrochloric acid, and extracted with ethyl acetate (2×50 mL). The organic layers were washed with saturated aqueous sodium bicarbonate, water, brine, dried over magnesium sulfate, filtered and concentrated to give the title compound (69 mg, 60%).

EXAMPLE 391B 2-(chloromethyl)-1,3-thiazole

The product of Example 391A (66 mg, 0.57 mmol) was added dropwise into thionyl chloride (0.2 mL, 2.7 mmol) in

EXAMPLE 391C

1-[(cyclopropylmethyl)amino]-3-[1,1-dioxido-7-(1,3-thiazol-2-ylmethoxy)-4H-1,2,4-benzothiadiazin-3-yl]-4-hydroxyquinolin-2(1H)-one Product of Example 320C (15 mg, 0.035 mmol) in N,N-dimethylformamide (1 mL) was was heated with Example 391B (19 mg, 0.142 mmol), potassium carbonate (68 g, 0.209 mmol) and tetra-butylammonium iodide (catalytic) at 120° C. for 2 hours. The solution was evaporated under reduced pressure and the residue was triturated with ethyl acetate/hexane (1:1), filtered and washed with water to give title compound (17 mg, 92%). $^1$H NMR (500 MHz, DMSO-d$_6$) δ 0.21 (d, J=4.27 Hz, 2 H) 0.46 (d, J=7.32 Hz, 2 H) 0.99 (m, 1 H) 2.67 (s, br, 2 H) 5.49 (s, 2 H) 5.95 (t, J=6.71 Hz, 1 H) 7.04 (m, 1 H) 7.26 (m, 3 H) 7.50 (m, 1 H) 7.66 (d, J=8.54 Hz, 1 H) 7.75 (d, J=3.66 Hz, 1 H) 7.84 (d, J=3.05 Hz, 1 H) 8.07 (dd, J=7.93 Hz, 1.08 Hz, 1 H) 16.19 (s, 1 H). MS (ESI$^-$) m/z 522 (M−H)$^-$.

EXAMPLE 392A

[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]acetonitrile The product of Example 320C (0.050 g, 0.117 mmol) in N,N-dimethylformamide (2 mL) was reacted with 2-bromoacetonitrile (16 µL, 0.230 mmol), potassium carbonate (0.15 g, 0.46 mmol) and tetrabutylammonium iodide (catalytic) at 25° C. for 1 day. The solution was evaporated under reduced pressure and the residue was triturated with ethyl acetate/hexane (1:1), filtered and washed with water to give title compound (52 mg, 95%).

EXAMPLE 392B methyl 2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]ethanimidoate Hydrogen chloride gas was bubbled into a solution of the product of Example 392A (50 mg, 0.11 mmol) in methanol (10 mL) at 0° C. until saturation. The reaction was stirred at room temperature for 3 hours. The solution was evaporated under reduced pressure to give title compound (quantitative yield).

EXAMPLE 392C

1-[(cyclopropylmethyl)amino]-3-[7-(4,5-dihydro-1H-imidazol-2-ylmethoxy)-1,1-dioxido-4H-1,2,4-benzothiadiazin-3-yl]-4-hydroxyquinolin-2(1H)-one The product of Example of 392B (53 mg, 0.11 mmol) in methanol (10 mL) was added ethane-1,2-diamine (0.2 mL, 3 mmol) and refluxed overnight. The solvent was removed under reduced pressure and the residue was chromatographed on silica gel eluting with 4:1 dichloromethane/methanol to 3:2 dichloromethane/methanol 3:2 to give the title compound (11 mg, 20%). $^1$H NMR (500 MHz, DMSO-d$_6$) δ 0.18 (m, 2 H) 0.45 (m, 2 H) 1.00 (m, 1 H) 2.77 (d, J=6.71 Hz, 2 H) 3.91 (s, 4 H) 5.23 (s, 2 H) 6.11 (s, 1 H) 7.21 (m, 1 H) 7.42 (m, 3 H) 7.66 (m, 1 H) 7.85 (d, J=7.32 Hz, 1 H) 8.12 (d, J=7.93 Hz, 1 H) 10.70 (s, 1 H) 15.29 (s, 1 H). MS (ESI+) m/z 509 (M+H)$^+$.

EXAMPLE 393A 2-(bromomethyl)-1,3-thiazole-4-carbonitrile

To a solution of 2-methyl-1-thiazole-4-carbonitrile (248 mg, 2 mmol) in benzene (20 mL) was added N-bromosuccinimide (1.78 g, 10 mmol) and dibenzoyl peroxide (20 mg, 0.08 mmol). The mixture was refluxed for 2 days. The solution was evaporated under reduced pressure. The residue was partitioned between dichloromethane and water. The organic layer was concentrated under reduced pressure and the residue was chromatographed on silica gel eluting with 1:1 dichloromethane:hexane to give the title compound (190 mg, 47%).

EXAMPLE 393B

2-{[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]methyl}-1,3-thiazole-4-carbonitrile Product of Example 320C (20 mg, 0.047 mmol) in N,N-dimethylformamide (2 mL) was reacted with Example 393A (20 mg, 0.099 mmol), potassium carbonate (0.070 g, 0.215 mmol) and tetrabutylammonium iodide (catalytic) at room temperature for overnight. The solution was concentrated under reduced pressure and the residue was triturated with ethyl acetate/hexane (1:1), filtered and washed with water to give title compound (23 mg, 89%). $^1$H NMR (500 MHz, DMSO-d$_6$) δ 0.22 (m, 2 H) 0.46 (m, 2 H) 1.00 (m, 1 H) 2.69 (m, 2 H) 5.54 (s, 2 H) 5.96 (t, J=6.32 Hz, 1 H) 7.04 (m, 1 H) 7.28 (m, 3 H) 7.49 (m, 1 H) 7.67 (d, J=8.62 Hz, 1 H) 8.08 (dd, J=8.05 Hz, 1.70 Hz, 1 H) 8.81 (s, 1 H) 16.15 (s, 1 H), MS (ESI$^-$) m/z 547 (M−H)$^-$.

EXAMPLE 394

3-[7-(2-aminoethoxy)-1,1-dioxido-4H-1,2,4-benzothiadiazin-3-yl]-1-[(cyclopropylmethyl)amino]-4-hydroxyquinolin-2(1H)-one A solution of the product of Example 392A (39 mg, 0.084 mmol) in anhydrous tetrahydrofuran (2 mL) was treated with LiBH$_4$ (1mL, 2M in tetrahydrofuran, 0.2 mmol), stirred at ambient temperature for 30 minutes, then 18 µl water was added and stirred overnight. The solution was diluted with water (20 mL) and extracted with ethyl acetate (2×50 mL). The combined organic layers were washed with brine and dried over anhydrous magnesium sulfate. The slurry was filtered and the solvent removed under reduced pressure to give title compound (38 mg, 97%). 1H NMR (500 MHz, BENZENE-d$_6$) δ 0.20 (d, J=3.05 Hz, 2 H) 0.46 (d, J=7.32 Hz, 2 H) 1.01 (m, 1 H) 2.74 (s, br, 2 H) 2.86 (m, 2 H) 4.19 (t, J=4.90 Hz, 2 H) 5.21 (s, br, 2 H) 6.04 (s, br, 1 H) 7.15 (s, br, 1 H) 7.24 (s, br, 2 H) 7.32 (s, br, 1 H) 7.59 (s, br, 1 H) 7.78 (s, br, 1 H) 8.11 (d, J=7.32 Hz, 1 H) 15.65 (s, br, 1 H). MS (ESI$^-$) m/z 468 (M−H)$^-$.

EXAMPLE 395

N-{2-[(3-{1-[(cyclopropylmethyl)amino]-4-hydroxy-2-oxo-1,2-dihydroquinolin-3-yl}-1,1-dioxido-4H-1,2,4-benzothiadiazin-7-yl)oxy]ethyl}methanesulfonamide To the product of Example 394 (15 mg, 0.032 mmol) in pyridine (1 mL) was added methanesulfonyl chloride (12 µl, 0.156 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetate. The crude product was purified by chromatography on silica gel eluting with 199:1 dichloromethane:methanol to give the title compound (5 mg, 29%). $^1$H NMR (300 MHz, DMSO-d$_6$) δ 0.14 (d, J=4.04 Hz, 2 H) 0.41 (d, J=7.72 Hz, 2 H) 1.01 (m, 1 H) 2.86 (d, J=5.52 Hz, 2 H) 2.97 (s, 3 H) 3.38 (t, J=5.33 Hz, 2 H) 4.18 (t, J=5.33 Hz, 2 H) 6.44 (s, 1 H) 7.32 (t, J=5.88 Hz, 1 H) 7.41 (m, 3 H) 7.67 (d, J=9.93 Hz, 1 H) 7.89 (t, J=7.91 Hz, 1 H) 8.10 (d, J=8.46 Hz, 1 H) 8.17 (d, J=8.46 Hz, 1 H) 14.08 (s, 1 H) 15.11 (s, 1 H). MS (ESI$^-$) m/z 546 (M−H)$^-$.

EXAMPLE 396

3-[9-(butylamino)-1,1-dioxido-4H,8H-[1,4]oxazino[2,3-h][1,2,4]benzothiadiazin-3-yl]-4-hydroxy-1-(isobutylamino)quinolin-2(1H)-one A solution of the product of Example 357 (15.5 mg, 0.031 mmol) in pyridine (2 mL) was treated with n-butyl amine (0.030 mL, 0.31 mmol) at room temperature for 4 hours. The solvent was removed under a stream of warm nitrogen and the residue was purified by preparative HPLC on a Waters Symmetry C8 column (25 mm×100 mm, 7μm particle size) using a gradient of 10% to 100% acetonitrile:0.1% aqueous trifluoroacetic to yield the title compound (3.3 mg, 20%). MS (ESI$^-$) m/z 537 (M−H)$^-$. $^1$H NMR (300 MHz, DMSO-d$_6$) δ 0.92 (t, J=7.35 Hz, 3 H) 1.04 (d, J=6.62 Hz, 6 H) 1.36 (m, 2 H) 1.59 (m, 2 H) 1.90 (m, 1 H) 2.70 (m, 2 H) 3.41 (m, 2 H) 4.55 (s, 2 H) 6.32 (m, 1 H) 6.96 (m, 1 H) 7.15 (d, J=8.46 Hz, 1 H) 7.45 (m, 1 H) 7.93 (m, 2 H) 8.17 (d, J=6.62 Hz, 1 H) 13.66 (s, 1 H) 15.69 (s, 1 H).

EXAMPLE 397

3-{7-[(5-bromopyridin-2-yl)oxy]-1,1-dioxido-4H-1,2,4-benzothiadiazin-3-yl}-4-hydroxy-1-(isobutylamino)quinolin-2(1H)-one A mixture of the product of Example 321C (40.0 mg, 0.09 mmol), cesium carbonate (112 mg, 0.34 mmol), and 2,5-dibromopyridine (40.0 mg, 0.17 mmol) in dimethylsulfoxide (1.2 mL) was stirred while heating at 110° C. in a microwave reactor for 20 minutes. After cooling to 25° C., the purple mixture was partitioned between ethyl acetate and water. The aqueous layer was extracted with an additional portion of ethyl acetate. The combined organic layers were dried over sodium sulfate, filtered, concentrated under reduced pressure and purified by column chromatography on silica gel eluting with a step gradient (0-100%) of dichloromethane in hexanes to give the title compound as an off-white solid (34.0 mg, 63%). MS (ESI$^-$) m/z 582 (M−H)$^-$. $^1$H NMR (300 MHz, DMSO-d$_6$) δ 1.05 (d, J=6.62 Hz, 6 H) 1.93 (m, 1 H) 2.73 (m, 2 H) 6.35 (m, 1 H) 7.19 (d, J=8.82 Hz, 1 H) 7.45 (m, 1 H) 7.61 (dd, J=8.82, 2.57 Hz, 1 H) 7.77 (m, 2 H) 7.94 (m, 2 H) 8.13 (dd, J=8.82, 2.57 Hz, 1 H) 8.19 (m, 1 H) 8.31 (d, J=2.21 Hz, 1 H).

EXAMPLE 398

4-hydroxy-1-(isobutylamino)-3-{7-[(3-nitropyridin-2-yl)oxy]-1,1-dioxido-4H-1,2,4-benzothiadiazin-3-yl}quinolin-2(1H)-one A mixture the product of Example 321C (10.0 mg, 0.02 mmol), cesium carbonate (27.7 mg, 0.09 mmol), and 2-bromo-3-nitropyridine (8.4 mg, 0.04 mmol) in dimethylsulfoxide (0.3 mL) was stirred while heating at 110° C. in a microwave reactor for 20 minutes. After cooling to 25° C., the mixture was partitioned between ethyl acetate and water. The aqueous layer was extracted with an additional portion of ethyl acetate. The combined organic layers were dried over sodium sulfate, filtered, concentrated under reduced pressure and purified by column chromatography on silica gel eluting with a 0-100% dichloromethane in hexane step gradient to give the title compound as a yellow solid (8.6 mg, 68%). MS (ESI$^-$) m/z 549 (M−H)$^-$. $^1$H NMR (300 MHz, CDCl$_3$) δ 1.13 (d, J=6.62 Hz, 6 H) 2.00 (m, 1 H) 2.81 (m, 2 H) 5.73 (m, 1 H) 7.23 (m, 1 H) 7.40 (m, 2 H) 7.50 (dd, J=8.82, 2.57 Hz, 1 H) 7.82 (m, 2 H) 7.97 (m, 1 H) 8.27 (d, J=8.09, 1.10 Hz, 1 H) 8.35 (dd, J=4.78, 1.84 Hz, 1 H) 8.42 (dd, J=8.09, 1.84 Hz, 1 H) 14.39 (s, 1 H) 15.02 (s, 1 H).

EXAMPLE 399

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}methanesulfonamide To the product of Example 205 (0.020 g, 0.047 mmol) in pyridine (0.2 mL) was added methanesulfonyl chloride (0.0064 g, 0.0043 mL, 0.056 mmol). The reaction mixture was heated in a microwave reactor at 100° C. for 38 minutes. The reaction was diluted with ethyl acetate (40 mL), washed with 1 N hydrochloric acid, water, and brine. The organic layer was dried over magnesium sulfate and filtered. The filtrate was concentrated under reduced pressure to give a yellow solid, which was purified by chromatography on silica gel eluting with 99:1 dichloromethane:methanol to give the title compound (8.3 mg, 35%). $^1$H NMR (300 MHz, DMSO-d$_6$) δ 0.98 (d, J=6.62 Hz, 6 H) 1.57 (m, 2 H) 1.70 (m, 1 H) 3.10 (s, 3 H) 4.49 (m, 2 H) 7.50 (dd, J=7.91, 4.60 Hz, 1 H) 7.58 (dd, J=8.82, 2.57 Hz, 1 H) 7.64 (d, J=2.21 Hz, 1 H) 7.75 (d, J=8.82 Hz, 1 H) 8.56 (dd, J=8.09, 1.84 Hz, 1 H) 8.89 (dd, J=4.60, 1.65 Hz, 1 H) 10.29 (s, 1 H) 14.17 (s, 1 H). MS (ESI$^-$) m/z 504 (M−H)$^-$.

EXAMPLE 400

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}benzenesulfonamide To the product of Example 205 (0.020 g, 0.047 mmol) in pyridine (0.2 mL) was added benzenesulfonyl chloride (0.0099 g, 0.0072 mL, 0.056 mmol). The reaction mixture was heated in a microwave reactor at 100° C. for 35 minutes. The reaction was cooled to 25° C., diluted with ethyl acetate (40 mL), washed with 1 N hydrochloric acid, water, and brine. The organic layer was dried over magnesium sulfate, filtered and concentrated. The residue was chromatographed on silica gel eluting with 99:1 dichloromethane:methanol to give the title compound (18.6 mg, 69%). $^1$H NMR (300 MHz, DMSO-d$_6$) δ 0.97 (d, J=6.25 Hz, 6 H) 1.56 (m, 2 H) 1.68 (m, 1 H) 4.46 (m, 2 H) 7.47 (m, 3 H) 7.61 (m, 4 H) 7.80 (d, J=6.99 Hz, 2 H) 8.54 (dd, J=7.91, 1.65 Hz, 1 H) 8.87 (dd, J=4.23, 1.29 Hz, 1 H) 10.85 (s, 1 H) 14.08 (br s, 1 H). MS (ESI$^-$) m/z 566 (M−H)$^-$.

EXAMPLE 401

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}thiophene-2-sulfonamide To the product of Example 205 (21.5 mg, 0.05 mmol) in pyridine (1 mL) was added 2-thiophenesulfonyl chloride (44 mg, 0.24 mmol). The reaction mixture was heated in a microwave reactor at 120° C. for 120 minutes. The reaction was cooled to 25° C. and concentrated under reduced pressure. The residue was triturated with water (1 mL), filtered, and washed with hexane:ethyl acetate (1:1). The crude product was chromatographed on silica gel eluting with 199:1 dichloromethane:methanol to give the title compound (10 mg, 35%). $^1$H NMR (300 MHz, DMSO-d$_6$): δ 0.97 (d, J=6.25 Hz, 6 H) 1.55 (m, 2 H) 1.66 (m, 1 H) 4.46 (t, J=7.84 Hz, 2 H) 7.16 (dd, J=5.13 Hz, 3.66 Hz, 1 H) 7.48 (m, 2 H) 7.53 (d, J=2.21 Hz, 1 H) 7.56 (d, J=2.55 Hz, 1 H) 7.61 (dd, J=3.68, 1.47 Hz, 1 H) 7.68 (d, J=8.82 Hz, 1 H) 7.96 (dd, J=5.13 Hz, 1.47 Hz, 1 H) 8.53 (dd, J=8.09, 1.84 Hz, 1 H) 8.87 (dd, J=4.78, 1.84 Hz, 1 H) 10.98 (s, 1 H) 14.10 (s, 1 H). MS (ESI$^-$) m/z 572 (M–H)$^-$.

EXAMPLE 402

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}-1-methyl-1H-imidazole-4-sulfonamide To the product of Example 205 (21.5 mg, 0.05 mmol) in pyridine (1 mL) was added 1-methylimidazolesulfonyl chloride (44 mg, 0.24 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1hexane:ethyl acetate to give the title compound (21 mg, 73%). $^1$H NMR (300 MHz, DMSO-d$_6$): δ 0.98 (d, J=6.62 Hz, 6 H) 1.56 (m, 2 H) 1.68 (m, 1 H) 3.66 (s, 3 H) 4.48 (m, 2 H) 7.58 (m, 5 H) 7.78 (d, J=1.11 Hz, 1 H) 7.92 (d, J=1.47 Hz, 1 H) 8.55 (dd, J=8.09, 1.84 Hz, 1 H) 8.89 (dd, J=4.78, 1.84 Hz, 1 H) 10.80 (s, 1 H) 13.99 (s, 1 H). MS (ESI$^-$) m/z 570 (M–H)$^-$.

EXAMPLE 403

4,5-dichloro-N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}thiophene-2-sulfonamide To the product of Example 205 (0.020 g, 0.047 mmol) in pyridine (0.2 mL) was added 2,3-dichlorothiophene-5-sulfonyl chloride (0.015 g, 0.056 mmol). The reaction mixture was heated in a microwave reactor at 100° C. for 15 minutes. The reaction was diluted with ethyl acetate (40 mL), washed with 1 N hydrochloric acid, water, and brine. The organic layer was dried over magnesium sulfate, filtered and concentrated. The residue was chromatographed on silica gel eluting with 99:1 dichloromethane:methanol to give the title compound (14.8 mg, 50%). $^1$H NMR (300 MHz, DMSO-d$_6$) δ 0.98 (d, J=6.25 Hz, 6 H) 1.56 (m, 2 H) 1.69 (m, 1 H) 4.47 (m, 2 H) 7.50 (m, 2 H) 7.56 (s, 1 H) 7.71 (d, J=8.82 Hz, 1 H) 7.76 (s, 1 H) 8.55 (dd, J=7.91, 2.02 Hz, 1 H) 8.88 (dd, J=4.60, 1.65 Hz, 1 H) 11.28 (s, 1 H) 14.19 (br s, 1 H). MS (ESI$^-$) m/z 640 (M–H)$^-$.

EXAMPLE 404

2,2,2-trifluoro-N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}ethanesulfonamide To the product of Example 205 (21.5 mg, 0.05 mmol) in pyridine (1 mL) was added 2,-2,-2-trifluoroethanesulfonyl chloride (28 μl, 0.25 mmol). The reaction mixture was heated in a microwave reactor at 120° C. for 120 minutes. The reaction was cooled to 25° C. and concentrated under reduced pressure. The residue was triturated with water (1 mL), filtered, and washed with of 1:1 hexane:ethyl acetate. The crude product was chromatographed on silica gel eluting with 1:1 ethyl acetate/hexane to give the title compound (5 mg, 17%). $^1$H NMR (300 MHz, DMSO-d$_6$): δ 0.97 (d, J=6.62 Hz, 6 H) 1.49 (m, 2 H) 1.64 (m, 1 H) 4.31 (t, J=7.53 Hz, 2 H) 4.58 (q, J=9.93 Hz, 2 H) 7.17 (dd, J=7.35, 4.78 Hz, 1 H) 7.43 (m, 4 H) 8.38 (dd, J=7.72, 1.84 Hz, 1 H) 8.57 (d, J=2.94 Hz, 1 H) 10.63 (s, 1 H) 15.90 (s, 1 H). MS (ESI$^-$) m/z 572 (M–H)$^-$.

EXAMPLE 405 methyl [({3-[4-hydroxy-1-(3-methylbutyl)-2-oxo-1,2-dihydro-1,8-naphthyridin-3-yl]-1,1-dioxido-4H-1,2,4-benzothiadiazin-7-yl}amino)sulfonyl]acetate To product of example 205 (21.5 mg, 0.05 mmol) in methylene chloride (1 mL) was added chlorosulfonyl-acetic acid methyl ester (35 mg, 0.2 mmol) and triethylamine (30 μl, 0.22 mmol) and the resulting mixture was stirred at room temperature for 3 days. Upon completion of the reaction, the solvent was removed under reduced pressure. The residue was chromatographedon silica gel eluting with 199:1 dichloromethane:methanol. The product was dissolved in dichloromethane and added two drops of acetic acid, then stirred at rt for 10 min, washed with water. The organic layer was dried with magnesium sulfate and evaporated in vacuo to give the title compound (2 mg, 7%). $^1$H NMR (300 MHz, DMSO-d$_6$): δ 0.99 (d, J=6.62 Hz, 6 H) 1.57 (m, 2 H) 1.70 (m, 1 H) 3.65 (s, 3 H) 4.40 (s, 2 H) 4.49 (m, 2 H) 7.50 (dd, J=7.91, 4.60 Hz, 1 H) 7.59 (dd, J=8.82, 2.57 Hz, 1 H) 7.66 (d, J=2.57 Hz, 1 H) 7.76 (d, J=8.82 Hz, 1 H) 8.57 (dd, J=8.09, 1.84 Hz, 1 H) 8.90 (dd, J=4.41, 1.84 Hz, 1 H) 10.73 (s, 1 H) 14.15 (s, 1 H). MS (ESI$^-$) m/z 562 (M–H)$^-$.

EXAMPLE 406

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}ethanesulfonamide To the product of Example 205 (21.5 g, 0.05 mmol) in pyridine (1 mL) was added ethanesulfonyl chloride (19 μl, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetate. The crude product was chromatographed on silica gel eluting with 199:1 dichloromethane:methanol to give the title compound (3 mg, 11%). $^1$H NMR (300 MHz, DMSO-d$_6$): δ 0.98 (d, J=6.62 Hz, 6 H) 1.22 (t, J=7.35 Hz, 3 H) 1.58 (m, 2 H) 1.70 (m, 1 H) 3.20 (q, J=7.35 Hz, 2 H) 4.49 (m, 2 H) 7.50 (dd, J=7.91, 4.60 Hz, 1 H) 7.58 (dd, J=8.82, 2.57 Hz, 1 H) 7.65 (d, J=2.57 Hz, 1 H) 7.74 (d, J=9.19 Hz, 1 H) 8.56 (dd, J=8.09, 1.84 Hz, 1 H) 8.89 (dd, J=4.60, 1.65 Hz, 1 H) 10.35 (s, 1 H) 14.15 (s, 1 H). MS (ESI$^-$) m/z 518 (M–H)$^-$.

EXAMPLE 407

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}propane-2-sulfonamide To the product of Example 205 (21.5 g, 0.05 mmol) in pyridine (1 mL) was added isopropylsulfonyl chloride (22 μl, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetate. The crude product was chromatographed on silica gel eluting with 199:1 dichloromethane: methanol to give the title compound (2 mg, 7%). $^1$H NMR (300 MHz, DMSO-d$_6$): δ 0.98 (d, J=6.62 Hz, 6 H) 1.28 (d, J=6.99 Hz, 6 H) 1.57 (m, 2 H) 1.71 (m, 1 H) 3.29 (m, 1 H) 4.49 (m, 2 H) 7.50 (dd, J=7.91, 4.60 Hz, 1 H) 7.59 (dd, J=8.82, 2.57 Hz, 1 H) 7.67 (d, J=2.57 Hz, 1 H) 7.74 (d, J=9.18 Hz, 1 H) 8.56 (dd, J=8.09, 1.84 Hz, 1 H) 8.89 (dd, J=4.60, 1.65 Hz, 1 H) 10.33 (s, 1 H) 14.11 (s, 1 H). MS (ESI$^-$) m/z 532 (M−H)$^-$.

EXAMPLE 408

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}-1-phenylmethanesulfonamide A solution of the product of Example 205 (21.5 g, 0.05 mmol) in pyridine (1 mL) was treated with α-toluenesulfonyl chloride (38 mg, 0.2 mmol), heated in a microwave reactor at 120° C. for 120 minutes, cooled to 25C and concentrated under reduced pressure. The residue was triturated with water (1 ml), filtered, and washed with hexane:ethyl acetate (1:1). The crude product was chromatographed on silica gel, eluting with dichloromethane:methanol (399:1) to give the title compound (7 mg, 24%). $^1$H NMR (300 MHz, DMSO-d$_6$) δ 0.99 (d, J=6.62 Hz, 6 H) 1.58 (m, 2 H) 1.69 (m, 1 H) 4.49 (m, 2 H) 4.59 (s, 2 H) 7.32 (m, 5 H) 7.51 (m, 2 H) 7.57 (d, J=2.21 Hz, 1 H) 7.71 (d, J=8.82 Hz, 1 H) 8.57 (dd, J=8.09, 1.84 Hz, 1 H) 8.90 (dd, J=4.78, 1.84 Hz, 1 H) 10.38 (s, 1 H) 14.08 (s, 1 H) 15.14 (s, 1 H) (ESI$^-$) m/z 580 (M−H)$^-$

EXAMPLE 409A

N-[3-(4-hydroxy-1-isopentyl-2-oxo-1,2-dihydro-1,8-naphthyridin-3-yl)-1,1-dioxido-4H-1,2,4-benzothiadiazin-7-yl]-2-nitrobenzenesulfonamide To the product of Example 205 (21.5 g, 0.05 mmol) in pyridine (1 mL) was added 2-nitrobenzenesulfonyl chloride (44 mg, 0.2 mmol). The reaction mixture was heated in a microwave reactor at 120° C. for 120 minutes. The reaction was concentrated under reduced pressure. The residue was triturated with water (1 ml), filtered, and washed with of hexane:ethyl acetate (1:1). The crude product was chromatographed on silica gel, eluting with dichloromethane:methanol (399:1) to give the title compound (8 mg, 26%).

EXAMPLE 409B 2-amino-N-[3-(4-hydroxy-1-isopentyl-2-oxo-1,2-dihydro-1,8-naphthyridin-3-yl)-1,1-dioxido-4H-1,2,4-benzothiadiazin-7-yl]benzenesulfonamide A mixture of the product of Example 409A (8 mg, 0.013 mmol), iron powder (5.0 mg, 0.089 mmol), and NH$_4$Cl (1Mg, 0.019 mmol) in methanol:tetrahydrofuran:water (2:2:1,10 mL) was heated at 60° C. for 2 hour. The solution filtered through Celite® and washed with THF. The solution was concentrated and the residue was diluted with water, and extracted with ethyl acetate. The organic layer was washed with water, dried with MgSO$_4$, filtered and concentrated to give title compound (7 mg, 92%). $^1$H NMR (300 MHz, DMSO-d$_6$) δ 0.97 (d, J=6.62 Hz, 6 H) 1.54 (m, 2 H) 1.68 (m, 1 H) 4.46 (m, 2 H) 6.06 (s, 2 H) 6.59 (t, J=7.17 Hz, 1 H) 6.78 (d, J=8.46 Hz, 1 H) 7.23 (m, 1 H) 7.46 (m, 4 H) 7.63 (d, J=8.82 Hz, 1 H) 8.53 (dd, J=8.09, 1.84 Hz, 1 H) 8.87 (dd, J=4.41, 1.84 Hz, 1 H) 10.79 (s, 1 H) 14.00 (s, 1 H). (ESI$^-$) m/z 581 (M−H)$^-$.

EXAMPLE 410

3-[8-(chloromethyl)-1,1-dioxido-4,7-dihydroimidazo[4,5-h][1,2,4]benzothiadiazin-3-yl]-4-hydroxy-1-(3-methylbutyl)-1,8-naphthyridin-2(1H)-one A mixture of the product of Example 377 (0.022 g, 0.05 mmol) and chloroacetic acid (0.06 g, 0.63 mmol) in a sealed tube was heated in a microwave reactor at 120° C. for 30 minutes, cooled to 25° C. and partitioned between ethyl acetate and water. The ethyl acetate layer was washed with brine, dried over sodium sulfate, filtered and concentrated. The residue was chromatographed on silica gel eluting with dichloromethane and then 98:2 dichloromethane:methanol to give the title compound (0.010 g, 40% yield). MS (APCI$^+$) m/z 501 (M+H)$^+$. $^1$H NMR (300 MHz, DMSO-d$_6$) δ 0.99 (d, J=6.25 Hz, 6 H) 1.60 (m, 2 H) 1.71 (m, 1 H) 4.50 (m, 2 H) 5.00 (m, 2 H) 7.47 (m, 2 H) 7.95 (d, J=8.09 Hz, 1 H) 8.57 (dd, J=8.09, 1.84 Hz, 1 H) 8.90 (dd, J=4.41, 1.47 Hz, 1 H).

EXAMPLE 411

{3-[4-hydroxy-1-(3-methylbutyl)-2-oxo-1,2-dihydro-1,8-naphthyridin-3-yl]-1,1-dioxido-4,7-dihydroimidazo[4,5-h][1,2,4]benzothiadiazin-8-yl}acetonitrile A mixture of the product of Example 377 (0.044 g, 0.1 mmol) and cyanoacetic acid (0.085 g, 1.0 mmol) in a sealed tube was heated in a microwave reactor at 120° C. for 30 minutes, cooled and partitioned between ethyl acetate and water. The ethyl acetate layer was washed with brine, dried over sodium sulfate, filtered and concentrated to give a residue which was chromatographed on silica gel eluting first with dichloromethane and then 98:2 dichloromethane/methanol to give the title compound (0.007 g, 14% yield). MS (ESI$^-$) m/z 490 (M−H)$^-$. $^1$H NMR (300 MHz, DMSO-d$_6$) δ 0.99 (d, J=6.62 Hz, 6 H) 1.57 (m, 2 H) 1.71 (m, 1 H) 4.49 (m, 4 H) 7.50 (m, 2 H) 7.96 (m, 1 H) 8.57 (dd, J=7.72, 1.84 Hz, 1 H) 8.89 (dd, J=4.60, 1.29 Hz, 1 H).

EXAMPLE 412 methyl {3-[4-hydroxy-1-(3-methylbutyl)-2-oxo-1,2-dihydro-1,8-naphthyridin-3-yl]-1,1-dioxido-4,7-dihydroimidazo[4,5-h][1,2,4]benzothiadiazin-8-yl}acetate A mixture of the product of Example 377 (0.088 g, 0.2 mmol), 3,3,3-trimethoxy-propionic acid methyl ester (0.360 g, 2.0 mmol) and catalytic p-toluenesulfonic acid monohydrate in a sealed tube was heated in a microwave reactor at 60° C. for 30 minutes, cooled to 25° C. and partitioned between ethyl acetate and water. The ethyl acetate layer was washed with brine, dried over sodium sulfate, filtered and concentrated. The residue was chromatographed on silica gel eluting first with dichloromethane and then 97:3 dichloromethane/methanol to give the title compound (0.051 g, 49% yield). MS (ESI$^-$) m/z 523 (M−H)$^-$. $^1$H NMR (300 MHz, DMSO-d$_6$) δ 0.99 (d, J=6.25 Hz, 6 H) 1.58 (m, 2 H) 1.71 (m, 1 H) 3.68 (s, 3 H) 4.10 (s, 2 H) 4.49 (m, 2 H) 7.45 (d, J=8.46 Hz, 1 H) 7.51 (dd, J=7.91, 4.60 Hz, 1 H) 7.92 (d, J=8.82 Hz, 1 H) 8.57 (dd, J=7.91, 1.65 Hz, 1 H) 8.90 (dd, J=4.60, 1.65 Hz, 1 H) 13.07 (br. s., 1 H) 14.21 (br. s., 1 H) 15.31 (br. s., 1 H).

EXAMPLE 413

3-(9,9-dioxido-6H-[1,2,5]thiadiazolo[3,4-h][1,2,4] benzothiadiazin-7-yl)-4-hydroxy-1-(3-methylbutyl)-1,8-naphthyridin-2(1H)-one A mixture of the product of Example 377 (0.044 g, 0.11 mmol) and sulfamide (0.048 g, 0.5 mmol) in a sealed tube was heated in a microwave reactor at 190° C. for 4 minutes, cooled TO 25° C. and concentrated. The crude product was purified by chromatography on reverse phase gradient eluting with 0.1% trifluoroacetic acid in water/methanol (90/10) to 0.1% trifluoroacetic in water/methanol (5/95) to give the title compound (0.005 g, 11% yield). MS (ESI$^-$) m/z 469 (M–H)$^-$. $^1$H NMR (300 MHz, DMSO-d$_6$) δ 0.99 (d, J=6.25 Hz, 6 H) 1.59 (m, 2 H) 1.71 (m, 1 H) 4.49 (m, 2 H) 7.48 (dd, J=7.91, 4.60 Hz, 1 H) 7.93 (d, J=9.56 Hz, 1 H) 8.39 (d, J=9.19 Hz, 1 H) 8.57 (dd, J=7.72, 1.84 Hz, 1 H) 8.88 (dd, J=4.78, 1.84 Hz, 1 H) 14.38 (s, 1 H).

EXAMPLE 414A tert-butyl 4-amino-3-(aminosulfonyl)phenylcarbamate

A mixture of 2,5-diaminosulfonamide [prepared according to the procedure of *J. Amer. Chem. Soc.* 1943, 65, 738] (0.168 g, 0.896 mmol) and di-tert-butyl dicarbonate (0.196 g, 0.896 mmol) in tetrahydrofuran (10 mL) was stirred at room temperature for 16 hours. The reaction was concentrated under reduced pressure and the residue purified by chromatography on silica gel, eluting with 3:2 hexane/ethyl acetate, to provide the title compound (0.202 g, 78% yield).

EXAMPLE 414B tert-butyl 3-{1-[(cyclopropylmethyl)amino]-4-hydroxy-2-oxo-1,2-dihydroquinolin-3-yl}-1,1-dioxido-4H-1,2,4-benzothiadiazin-7-ylcarbamate A mixture of the product of Example 414A (78.1 mg, 0.272 mmol) and the product of Example 353B (91.0 mg, 0.272 mmol) in anhydrous dioxane (2.7 mL) was heated under reflux for 3 h. The reaction mixture was then cooled to 25° C. and concentrated under reduced pressure to yield an oily solid. The solid was triturated with methanol to yield the title compound (72.5 mg, 51%). $^1$H NMR (300 MHz, DMSO-d$_6$) δ 0.14 (d, J=4.04 Hz, 2 H) 0.42 (m, 2 H) 1.00 (m, 1 H) 1.51 (s, 9 H) 2.85 (bd, J=4.78 Hz, 2 H) 6.45 (bs, 1 H) 7.44 (t, J=7.54 Hz, 1 H) 7.62 (d, J=8.82 Hz, 1 H) 7.69 (dd, J=8.82, 2.20 Hz, 1 H) 7.89 (m, J=7.91, 7.91 Hz, 1 H) 8.10 (d, J=8.46 Hz, 1 H) 8.17 (m, 2 H) 9.93 (s, 1 H) 14.08 (s, 1 H) 15.15 (d, J=4.78 Hz, 1 H). MS (ESI$^-$) m/z 524.0 (M–H)$^-$. The sodium salt of the compound was prepared by reacting example 414B (3.9 mg, 0.0074 mmol) with 1 N sodium hydroxide solution (0.0074 mL, 0.0074 mmol) in 0.5 mL water and 0.5 mL tetrahydrofuran at room temperature for 1.2 h. The reaction mixture was then evaporated under a stream of nitrogen to provide the sodium salt (4.1 mg, 100% yield). $^1$H NMR (300 MHz, DMSO-d$_6$) δ 0.20 (m, J=5.52 Hz, 2 H) 0.46 (d, J=8.82 Hz, 2 H) 1.00 (m, 1 H) 1.50 (s, 9 H) 3.30 (m, 2 H) 5.96 (t, J=6.25 Hz, 1 H) 7.06 (t, J=7.17 Hz, 1 H) 7.20 (d, J=9.19 Hz, 1 H) 7.52 (m, 2 H) 7.67 (d, J=8.82 Hz, 1 H) 7.90 (s, 1 H) 8.06 (d, J=7.35 Hz, 1 H) 9.60 (s, 1 H) 16.22 (s, 1 H). MS (ESI+) m/z 543.1 (M+H+H2O-Na)$^+$, 526.1 (M–Na)$^+$, (ESI$^-$) m/z 524.1 (M–H)$^-$.

EXAMPLE 415

3-(7-amino-1,1-dioxido-4H-1,2,4-benzothiadiazin-3-yl)-1-[(cyclopropylmethyl)amino]-4-hydroxyquinolin-2(1H)-one A solution of the product of Example 414B (10.1 mg, 0.0192 mmol) in trifluoroacetic acid (0.5 mL) and dichloromethane (0.5 mL) was stirred at room temperature for 15 min. The solvent was then evaporated under a stream of nitrogen to provide the title compound (10.4 mg, quantitative yield.). $^1$H NMR (300 MHz, DMSO-d$_6$) δ 0.13 (d, J=4.04 Hz, 2 H) 0.41 (d, J=6.99 Hz, 2 H) 1.01 (m, 1 H) 2.85 (d, J=6.99 Hz, 2 H) 6.98 (m, 2 H) 7.38 (d, J=8.46 Hz, 1 H) 7.44 (t, J=7.72 Hz, 1 H) 7.89 (m, 1 H) 8.10 (d, J=8.46 Hz, 1 H) 8.16 (d, J=6.99 Hz, 1 H) 13.87 (s, 1 H) 15.40 (s, 1 H). MS (ESI$^+$) m/z 426.0 (M+H)$^+$, 448.0 (M+Na)$^+$, (ESI$^-$) m/z 424.1 (M–H)$^-$.

EXAMPLE 416

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}-4-(methylsulfonyl)benzenesulfonamide To the product of Example 205 (0.020 g, 0.047 mmol) in pyridine (0.2 mL) was added 4-methylsulfonylbenzenesulfonyl chloride (0.014 g, 0.056 mmol). The reaction mixture was heated in a microwave reactor at 100° C. for 30 minutes. The reaction was cooled to 25° C. and diluted with ethyl acetate (40 mL), washed with water and brine. The organic layer was dried over magnesium sulfate, filtered and concentrated. The residue was chromatographed on silica gel eluting with 99:1dichloromethane:methanol to give the title compound (15 mg, 50%). $^1$H NMR (300 MHz, DMSO-d$_6$) δ 0.97 (d, J=6.25 Hz, 6 H) 1.56 (m, 2 H) 1.68 (m, 1 H) 3.28 (s, 3 H) 4.46 (m, 2 H) 7.48 (m, 3 H) 7.65 (d, J=8.82 Hz, 1 H) 8.04 (d, J=8.82 Hz, 2 H) 8.15 (d, J=8.46 Hz, 2 H) 8.54 (dd, J=8.09, 1.84 Hz, 1 H) 8.86 (dd, J=4.60, 1.65 Hz, 1 H) 11.11 (s, 1 H) 14.14 (s, 1 H). MS (ESI$^-$) m/z 644 (M–H)$^-$.

EXAMPLE 417 methyl 3-[({3-[4-hydroxy-1-(3-methylbutyl)-2-oxo-1,2-dihydro-1,8-naphthyridin-3-yl]-1,1-dioxido-4H-1,2,4-benzothiadiazin-7-yl}amino)sulfonyl] thiophene-2-carboxylate To the product of Example 205 (0.020 g, 0.047 mmol) in pyridine (0.2 mL) was added 2-(methoxylcarbonyl) thiophene-3-sulfonyl chloride (0.014 g, 0.056 mmol). The reaction mixture was heated in a microwave reactor at 1001C for 30 minutes. The reaction was cooled to 25° C., diluted with ethyl acetate (40 mL), washed with water and brine. The organic layer was dried over magnesium sulfate, filtered and concentrated. The residue was chromatographed on silica gel eluting with 99:1 dichloromethane/methanol to give the title compound (15 mg, 50%). $^1$H NMR (300 MHz, DMSO-d$_6$) δ 0.97 (d, J=6.25 Hz, 6 H) 1.56 (m, 2 H) 1.69 (m, 1 H) 3.89 (s, 3 H) 4.46 (m, 2 H) 7.50 (m, 4 H) 7.65 (d, J=8.82 Hz, 1 H) 8.01 (d, J=5.15 Hz, 1 H) 8.54 (dd, J=7.91, 1.65 Hz, 1 H) 8.88 (dd, J=4.60, 1.65 Hz, 1 H) 10.74 (s, 1 H) 14.06 (s, 1 H). MS (ESI$^-$) m/z 630 (M–H)$^-$.

EXAMPLE 418

3-(8-amino-1,1-dioxido-4,7-dihydroimidazo[4,5-h] [1,2,4]benzothiadiazin-3-yl)-4-hydroxy-1-(3-methylbutyl)-1,8-naphthyridin-2(1H)-one The product of Example 377 (24 mg, 0.055 mmole) was suspended in water (0.1 mL) and cooled to 0° C. in an ice bath. To this slurry was added an acetonitrile solution of cyanogen bromide (0.1 mL, 0.067 mmole) and the mixture was stirred for 42 hours at room temperature. The reaction mixture was concentrated under reduced pressure to give the title compound (23.5 mg, 92%.) The compound was converted to the sodium salt as described in example 1D. MS (ESI$^-$) m/z 466 (M–H)$^-$. $^1$H NMR (300 MHz, DMSO-d$_6$) δ 0.97 (d, J=6.62 Hz, 6 H) 1.49 (s, 2 H) 1.65 (s, 1 H) 4.29 (d, J=8.46 Hz, 2 H) 6.01 (s, 2 H) 6.49 (s, 1 H) 6.78 (d, J=8.09 Hz, 1 H) 7.12 (dd, J=7.72, 4.41 Hz, 1 H) 7.30 (d, J=8.09 Hz, 1 H) 8.38 (m, 1 H) 8.51 (d, J=1.47 Hz, 1 H) 11.03 (s, 1 H).

EXAMPLE 419

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}propane-1-sulfonamide To the product of Example 205 (21.5 g, 0.05 mmol) in pyridine (1 mL) was added 1-propanesulfonyl chloride (22.5 mL, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetate. The crude product was chromatographed on reverse phase HPLC eluting with 0.1% aqueous trifluoroacetic acid/methanol (90/10) to 0.1% aqueous trifluoroacetic acid/methanol (5/95) to give the title compound (3 mg, 11%). $^1$H NMR (300 MHz, DMSO-d$_6$) δ 0.97 (m, 9 H) 1.57 (m, 2 H) 1.69 (m, 3 H) 3.17 (t, J=7.74 Hz, 2 H) 4.49 (t, J=7.74 Hz, 2 H) 7.50 (dd, J=7.91, 4.60 Hz, 1 H) 7.58 (dd, J=8.82, 2.57 Hz, 1 H) 7.64 (d, J=2.21 Hz, 1 H) 7.75 (d, J=8.82 Hz, 1 H) 8.56 (dd, J=7.72, 1.84 Hz, 1 H) 8.90 (dd, J=4.41, 1.84 Hz, 1 H) 10.35 (s, 1 H) 14.09 (s, 1 H). MS (ESI$^-$) m/z 532 (M–H)$^-$.

EXAMPLE 420

2-chloro-N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}benzenesulfonamide To the product of Example 205 (21.5 g, 0.05 mmol) in pyridine (1 mL) was added 2-chlorobenzenesulfonyl chloride (27 mL, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetate. The crude product was purified by chromatography on silica gel eluting with 199:1 dichloromethane:methanol to give the title compound (14 mg, 46%). $^1$H NMR (300 MHz, DMSO-d$_6$) δ 0.96 (d, J=6.25 Hz, 6 H) 1.54 (m, 2 H) 1.67 (m, 1 H) 4.44 (t, J=7.71 Hz, 2 H) 7.57 (m, 7 H) 8.11 (d, J=8.46 Hz, 1 H) 8.52 (dd, J=8.09, 1.84 Hz, 1 H) 8.86 (dd, J=4.78, 1.84 Hz, 1 H) 11.24 (s, 1 H) 13.99 (s, 1 H). MS (ESI$^-$) m/z 600 (M–H)$^-$.

EXAMPLE 421

1-chloro-N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}methanesulfonamide To the product of Example 205 (21.5 g, 0.05 mmol) in pyridine (1 mL) was added chloromethylsulfonyl chloride (18 mL, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with of 1:1 hexane:ethyl acetate. The crude product was purified by chromatography on reverse phase gradient eluting with 0.1% trifluoroacetic acid in water/methanol (90/10) to 0.1% trifluoroacetic in water/methanol (5/95) to give the title compound (6 mg, 22%). $^1$H NMR (300 MHz, DMSO-d$_6$) δ 0.99 (d, J=6.62 Hz, 6 H) 1.57 (m, 2 H) 1.69 (m, 1 H) 4.49 (t, J=7.74 Hz, 2 H) 5.18 (s, 2 H) 7.51 (dd, J=7.91, 4.60 Hz, 1 H) 7.62 (dd, J=8.82, 2.57 Hz, 1 H) 7.67 (d, J=2.57 Hz, 1 H) 7.77 (d, J=8.82 Hz, 1 H) 8.56 (dd, J=8.09, 1.84 Hz, 1 H) 8.90 (dd, J=4.41, 1.84 Hz, 1 H) 10.91 (s, 1 H) 14.10 (s, 1 H). MS (ESI$^-$) m/z 538 (M–H)$^-$.

EXAMPLE 422

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}butane-1-sulfonamide To the product of Example 205 (21.5 g, 0.05 mmol) in pyridine (1 mL) was added 1-butanesulfonyl chloride (26 mL, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetate. The crude product was chromatographed on silica gel eluting with 199:1 dichloromethane:methanol to give the title compound (8 mg, 29%). $^1$H NMR (300 MHz, DMSO-d$_6$) δ 0.84 (t, J=7.35 Hz, 3 H) 0.98 (d, J=6.62 Hz, 6 H) 1.37 (m, 2 H) 1.56 (m, 2 H) 1.69 (m, 3 H) 3.19 (t, J=7.74 Hz, 2 H) 4.48 (t, J=7.74 Hz, 2 H) 7.50 (dd, J=7.91, 4.60 Hz, 1 H) 7.58 (dd, J=9.01, 2.39 Hz, 1 H) 7.65 (d, J=2.21 Hz, 1 H) 7.75 (d, J=8.82 Hz, 1 H) 8.55 (dd, J=8.09, 1.84 Hz, 1 H) 8.89 (dd, J=4.41, 1.84 Hz, 1 H) 10.35 (s, 1 H) 14.07 (s, 1 H) 15.13 (s, 1 H). MS (ESI$^+$) m/z 548 (M+H)$^+$.

EXAMPLE 423

2,6-dichloro-N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}benzenesulfonamide To the product of Example 205 (21.5 g, 0.05 mmol) in pyridine (1 mL) was added 2,6-dichlorobenzenesulfonyl chloride (49, 0.2 mmol). The reaction mixture was heated in a microwave reactor at 120° C. for 120 minutes. The reaction was cooled to 25° C. and concentrated under reduced pressure. The residue was triturated with water (1 mL), filtered, and washed with 1:1 hexane:ethyl acetat. The crude product was chromatographed on silica gel eluting with 399:1 dichloromethane:methanol to give the title compound (5 mg, 16%). $^1$H NMR (300 MHz, DMSO-d$_6$) δ 0.97 (d, J=6.62 Hz, 6 H) 1.54 (m, 2 H) 1.67 (m, 1 H) 4.46 (m, 2 H) 7.47 (m, 2 H) 7.58 (m, 2 H) 7.68 (m, 3 H) 8.54 (dd, J=7.72, 1.84 Hz, 1 H) 8.88 (dd, J=4.78, 1.84 Hz, 1 H) 11.43 (s, 1 H) 14.02 (s, 1 H). MS (ESI$^-$) m/z 634 (M–H)$^-$.

EXAMPLE 424 methyl 2-chloro-6-({3-[4-hydroxy-1-(isobutylamino)-2-oxo-1,2-dihydroquinolin-3-yl]-1,1-dioxido-4H-1,2,4-benzothiadiazin-7-yl}oxy)isonicotinate A mixture of the product of Example 321C (40.0 mg, 0.138 mmol), potassium carbonate (19.1 mg, 0.138 mmol), copper (II)oxide (18.4 mg, 0.23 mmol)and methyl 2,6-dichloroisonicotinate (28.4 mg, 0.138 mmol) in pyridine (0.2 mL) was stirred while heating at 125° C. in a microwave reactor for 100 minutes. After cooling to 25° C., the mixture was loaded directly onto silica gel gel and eluted with a 0-5% methanol in dichloromethane step gradient. The fractions containing the desired product were combined and concentrated. The title compound was isolated by recrystallization of the residue using ethyl acetate/hexane (4.3 mg, 68%). MS (ESI$^-$) m/z 596 (M–H)$^-$. $^1$H NMR (300 MHz, CDCl$_3$) δ 1.13 (d, J=6.62 Hz, 6H) 2.00 (m, 1 H) 2.84 (br m, 2 H) 3.99 (s, 3 H) 5.73 (br s, 1 H) 7.43 (m, 4 H) 7.62 (d, J=8.46 Hz, 1 H) 7.80 (m, 2 H) 7.96 (d, J=8.46 Hz, 1 H) 8.28 (d, J=8.09 Hz, 1 H) 14.37 (s, 1 H) 15.04 (s, 1 H).

EXAMPLE 425A 4-(benzyloxy)-1-(3-methylbutyl)pyridin-2(1H)-one

A solution of 4-benzyloxy-1H-pyridin-2-one (1.0 g, 4.97 mmol) and 1-bromo-3-methyl butane (0.715 mL, 5.96 mmol) in N,N-dimethylformamide (20 mL) was treated with 1,8-diazabicyclo[5.4.0]undec-7-ene (1.86 mL, 12.43 mmol) at 65° C. for 5 days. The mixture was cooled to 25° C. and partitioned between water and dichloromethane. The organic layer was concentrated under reduced pressure. The residue was chromatographed on silica gel, eluting with 1% methanol in dichloromethane to give the title compound (0.57 g, 42%). MS (DCI/NH$_3$) m/z 272 (M+H)$^+$. $^1$H NMR (300 MHz, CDCl$_3$) δ 0.96 (d, J=6.25 Hz, 6 H) 1.61 (m, 3 H) 3.89 (m, 2 H) 4.99 (s, 2 H) 5.98 (dd, J=7.54, 2.76 Hz, 1 H) 6.06 (d, J=1.84 Hz, 1 H) 7.14 (d, J=7.72 Hz, 1 H) 7.39 (m, 5 H).

EXAMPLE 425B 4-hydroxy-1-(3-methylbutyl)pyridin-2(1H)-one

A solution of the product of Example 425A (0.55 g, 2.03 mmol) in tetrahydrofuran (10 mL) was treated with ammonium formate (0.37 g, 5.87 mmol) and a catalytic amount of 20% palladium hydroxide on carbon at 60° C. for 3 hours. The solution was filtered through diatomaceous earth and the filtrate was concentrated to yield the title compound (0.21 g, 57%). MS (DCI/NH$_3$) m/z 182 (M+H)$^+$. $^1$H NMR (300 MHz, CDCl$_3$) δ 0.95 (d, J=6.25 Hz, 6 H) 1.60 (m, 3 H) 3.90 (m, 2 H) 6.09 (dd, J=7.35, 2.57 Hz, 1 H) 6.15 (d, J=2.21 Hz, 1 H) 7.17 (d, J=7.35 Hz, 1 H).

EXAMPLE 425C

3-[bis(methylthio)methylene]-1-(3-methylbutyl)pyridine-2,4(1H,3H)-dione

A solution of the product of Example 425B (0.038 g, 0.21 mmol) in 1,4-dioxane (3 mL) was treated with pyridine (0.135 mL, 1.68 mmol) and tris(methylthio)methyl methyl sulfate (prepared using the procedures in *Synthesis*, 22-25, 1988; M. Barbero, S. Cadamuro, I. Degani, R. Fochi, A. Gatti, V. Regondi) (0.11 g, 0.42 mmol) at 40° C. for 1 hour. Another portion of tris(methylthio)methyl methyl sulfate (0.11 g, 0.42 mmol) was added and the solution was heated at 85° C. for 1 hour. The reaction mixture was cooled to 25° C. and the solvent was removed under a stream of with warm nitrogen. The residue was chromatographed on a 1 gram Alltech seppack cartridge eluting with 100% dichloromethane followed by 30% ethyl acetate in dichloromethane to yield the title compound (19 mg, 33%). $^1$H NMR (300 MHz, CHLOROFORM-D) δ 0.96 (d, J=6.25 Hz, 6 H) 1.58 (m, 3 H) 2.66 (s, 6 H) 3.78 (m, 2 H) 5.99 (d, J=7.35 Hz, 1 H) 7.06 (d, J=7.72 Hz, 1 H).

EXAMPLE 425D 2-amino-5-[(methylsulfonyl)amino]benzenesulfonamide

A mixture of 2,5-diamino-benzenesulfonamide (0.288 g, 0.0015 mol, 1 eq.), dichloromethane (5 mL), and pyridine (5 mL) was stirred at 0° C. Methanesulfonyl chloride (119 μL, 0.0015 mol, 1 eq.) was added dropwise over 3 minutes. The reaction mixture was warmed to 25° and stirred for 18 hours. The reaction mixture was evaporated under reduced pressure and the residue was chromatographed on silica gel using a step gradient of 0-4% methanol in dichloromethane to yield the title compound (68% yield). $^1$H NMR (300 MHz, DMSO-d$_6$) δ 2.87 (s, 3 H) 3.39 (s, 1 H) 5.80 (s, 1 H) 6.78 (d, J=8.82 Hz, 1 H) 7.13 (dd, J=8.64, 2.39 Hz, 1 H) 7.29 (s, 2 H) 7.45 (d, J=2.57 Hz, 1 H) 9.21 (m, 1 H). MS (ESI$^+$) m/z=266 (M+H)$^+$.

EXAMPLE 425E

N-{3-[4-hydroxy-1-(3-methylbutyl)-2-oxo-1,2-dihydropyridin-3-yl]-1,1-dioxido-4H-1,2,4-benzothiadiazin-7-yl}methanesulfonamide A solution of the product of Example 425C (0.019 g, 0.067 mmol) and the product of Example 425D (0.018 g, 0.067 mmol) in 1,4-dioxane was heated at 100° C. for 1 hour. The solvent was removed under a stream of with warm nitrogen and the residue was purified by preparative HPLC on a Waters Symmetry C8 column (25 mm×100 mm, 7 um particle size) using a gradient of 10% to 100% acetonitrile:0.1% aqueous trifluoroacetic acid to yield the title compound (0.007 g, 23%). MS (ESI$^-$) m/z 453 (M–H)$^-$. $^1$H NMR (300 MHz, DMSO-d$_6$) δ 0.93 (d, J=6.25 Hz, 6 H) 1.58 (m, 3 H) 3.08 (s, 3 H) 3.99 (m, 2 H) 6.33 (d, J=6.62 Hz, 1 H) 7.57 (m, 2 H) 7.67 (d, J=8.82 Hz, 1 H) 8.07 (d, J=6.62 Hz, 1 H) 10.25 (s, 1 H) 13.84 (s, 1 H) 14.28 (s, 1 H).

EXAMPLE 426A 1-benzyl-4-hydroxypyridin-2(1H)-one

The title compound was prepared by the method of Eschenhof, et. al., Tetrahedron, v 48, 30, p 6225-6230, 1992.

EXAMPLE 426B 1-benzyl-3-[bis(methylthio)methylene]pyridine-2,4(1H,3H)-dione

A solution of the product of Example 426A (0.124 g, 0.62 mmol) in 1,4-dioxane (6 mL) was treated with pyridine (0.400 mL, 4.96 mmol) and tris(methylthio)methyl methyl sulfate (prepared using the procedures in *Synthesis*, 22-25, 1988; M. Barbero, S. Cadamuro, I. Degani, R. Fochi, A. Gatti, V. Regondi) (0.32 g, 1.24 mmol) at 40° C. for 15 minutes. Another portion of tris(methylthio)methyl methyl sulfate (0.32 g, 1.24 mmol) was added and the solution was heated at 90° C. for 1 hour. The solvent was removed under a stream of with warm nitrogen and the residue was purified using a 1 gram Alltech sep-pack cartridge eluting with 100% dichloromethane followed by 30% ethyl acetate in dichloromethane to yield the title compound (79 mg, 42%). $^1$H NMR (300 MHz, CHLOROFORM-D) δ 2.68 (s, 6 H) 4.99 (s, 2 H) 6.11 (d, J=7.72 Hz, 1 H) 7.17 (d, J=8.09 Hz, 1 H) 7.33 (m, 5 H).

EXAMPLE 426C

N-[3-(1-benzyl-4-hydroxy-2-oxo-1,2-dihydropyridin-3-yl)-1,1-dioxido-4H-1,2,4-benzothiadiazin-7-yl]methanesulfonamide A solution of the product of Example 426B (0.028 g, 0.092 mmol) and the product of Example 425D (0.025 g, 0.092 mmol) in 1,4-dioxane was heated at 100° C. for 40 minutes. The solvent was removed under a stream of with warm nitrogen and the residue was triturated with water and ethyl acetate. The precipitate in the organic layer was filtered and dried to yield the title compound (0.006 g, 12%). MS (ESI$^-$) m/z 473 (M–H)$^-$. $^1$H NMR (500 MHz, DMSO-D6) δ 3.06 (s, 3 H) 5.21 (s, 2 H) 6.38 (d, J=4.88 Hz, 1 H) 7.34 (m, 5 H) 7.55 (m, 3 H) 8.18 (d, J=3.05 Hz, 1 H) 10.25 (s, 1 H) 13.87 (s, 1 H) 14.05 (s, 1 H).

EXAMPLE 427

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]ethanesulfonamide To a solution of the product of Example 353E (16.1 mg, 0.036 mmol) in N,N-dimethylformamide (0.4 mL) was added triethylamine (0.011 mL, 0.079 mmol). The mixture was cooled to 0° C. and ethanesulfonyl chloride was added (0.0036 mL, 0.038 mmol). The mixture was warmed to 23° C. and stirred for 2 hours. The reaction mixture was concentrated under reduced pressure. The residue was purified by reverse phase chromatography, eluting with a gradient of 10% acetonitrile in 0.1% trifluoroacetic acid in water to 95% acetonitrile/0.1% trifluoroacetic acid in water to give the title compound (7.7 mg, 40%). The sodium salt of the title compound was prepared by adding 1 N sodium hydroxide (0.029 mL, 0.0029 mmol) to a solution of the title compound (7.7 mg, 0.014 mmol) in water (0.4 mL) and stirring for thirty minutes. The reaction mixture was concentrated under reduced pressure. $^1$H NMR (300 MHz, DMSO-d$_6$) δ 0.21 (bs, 2 H) 0.46 (d, 2 H) 0.99 (m, 1 H) 1.19 (t, 3 H) 3.01 (q, 2 H) 4.23 (s, 2 H) 5.85 (t, J=6.62 Hz, 1 H) 6.79 (s, 1 H) 6.93 (t, J=7.54 Hz, 1 H) 7.35 (t, J=6.99 Hz, 2 H) 7.59 (d, J=8.09 Hz, 1 H) 7.95 (d, J=6.62 Hz, 1 H).

EXAMPLE 428

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]propane-1-sulfonamide To a solution of the product of Example 353E (16.7 mg, 0.037 mmol) in N,N-dimethylformamide (0.4 mL) was added triethylamine (0.011 mL, 0.079 mmol). The mixture was cooled to 0° C. and 1-propane sulfonyl chloride was added (0.005 mL, 0.041 mmol). The mixture was warmed to 23° C. and stirred for 1.5 hours. The reaction mixture was concentrated under reduced pressure. The residue was purified by reverse phase chromatography, eluting with a gradient of 10% acetonitrile/0.1% trifluoroacetic acid in water to 95% acetonitrile/0.1% trifluoroacetic acid in water to give the title compound (9.9 mg, 48%). $^1$H NMR (300 MHz, DMSO-d$_6$) δ 0.15 (d, J=4.04 Hz, 2 H) 0.42 (d, J=7.35 Hz, 2 H) 0.99 (m, 4 H) 1.69 (m, 2 H) 2.84 (d, J=7.35 Hz, 2 H) 3.06 (m, 2 H) 4.27 (d, J=6.25 Hz, 2 H) 6.35 (bs, 1 H) 7.37 (s, 1 H) 7.42 (t, J=7.54 Hz, 2 H) 7.75 (t, J=6.07 Hz, 1 H) 7.87 (t, J=7.17 Hz, 1 H) 8.07 (d, J=8.46 Hz, 1 H) 8.15 (dd, 1 H) 14.52 (bs, 1 H).

EXAMPLE 429

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]propane-2-sulfonamide To a solution of the product of Example 353E (16.2 mg, 0.036 mmol) in N,N-dimethylformamide (0.4 mL) was added triethylamine (0.011 mL, 0.079 mmol). The mixture was cooled to 0° C. and isopropyl sulfonyl chloride was added (0.0043 mL, 0.038 mmol). The mixture was warmed to 23° C. and stirred for 3 hours. Additional isopropyl sulfonyl chloride (0.006 mL, 0.055 mmol) was added and the reaction mixture was stirred at 23° C. for 15 hours. The reaction mixture was stirred at 50° C. for 2 hours. Additional triethylamine (0.040 mL, 0.287 mmol) and isopropyl sulfonyl chloride (0.010 mL, 0.091 mmol) were added and the reaction mixture was stirred at 50° C. for 2 hours. The reaction mixture was cooled to 25° C. and concentrated under reduced pressure. The residue was purified by reverse phase chromatography, eluting with a gradient of 10% acetonitrile/0.1% trifluoroacetic acid in water to 95% acetonitrile/0.1% trifluoroacetic acid in water to give the title compound (6.7 mg, 33%). The sodium salt of the title compound was prepared according to the procedure of Example 1D. $^1$H NMR (300 MHz, DMSO-d$_6$) δ 0.21 (bs, 2 H) 0.48 (d, 2 H) 0.98 (m, 1 H) 1.24 (d, J=6.99 Hz, 6 H) 3.19 (m, 1 H) 4.25 (s, 2 H) 5.85 (t, 1 H) 6.76 (s, 1 H) 6.92 (t, 1 H) 7.34 (m, 2 H) 7.57 (d, 1 H) 7.96 (d, 1 H).

EXAMPLE 430

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]benzenesulfonamide To a solution of the product of Example 353E (16.9 mg, 0.038 mmol) in N,N-dimethylformamide (0.4 mL) was added triethylamine (0.012 mL, 0.083 mmol) and benzene sulfonyl chloride (0.006 mL, 0.042 mmol). The reaction mixture was stirred at 23° C. for 0.75 hours. The reaction mixture was concentrated under reduced pressure. The residue was purified by reverse phase chromatography, eluting with a gradient of 10% acetonitrile/0.1% trifluoroacetic acid in water to 95% acetonitrile/0.1% trifluoroacetic acid in water to give the title compound (10.7 mg, 48%). $^1$H NMR (300 MHz, DMSO-d$_6$) δ 0.14 (d, J=4.04 Hz, 2 H) 0.41 (d, J=7.72 Hz, 2 H) 1.01 (m, J=7.54, 7.54 Hz, 1 H) 2.83 (d, J=6.99 Hz, 2 H) 4.07 (d, J=6.25 Hz, 2 H) 6.38 (bs, 1 H) 7.30 (s, 1 H) 7.41 (t, J=7.54 Hz, 1 H) 7.65 (m, 3 H) 7.86 (m, 3 H) 8.06 (d, J=8.82 Hz, 1 H) 8.15 (d, J=6.99 Hz, 1 H) 8.42 (t, J=6.25 Hz, 1 H) 14.43 (bs, 1 H).

EXAMPLE 431

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]-1-phenylmethanesulfonamide To a solution of the product of Example 353E (16.5 mg, 0.037 mmol) in N,N-dimethylformamide (0.4 mL) was added triethylamine (0.011 mL, 0.079 mmol). The mixture was cooled to 0° C. and α-toluene sulfonyl chloride was added (0.008 g, 0.041 mmol). The reaction mixture was warmed to 23° C. and stirred for 0.5 hours. The reaction mixture was then heated to 50° C. and stirred for 1.75 hours. Additional triethylamine (0.010 mL, 0.074 mmol) and α-toluene sulfonyl chloride (0.007 g, 0.037 mmol) were added and the reaction mixture was stirred at 23° C. for 1 hour. The reaction mixture was concentrated under reduced pressure. The residue was purified by reverse phase chromatography, eluting with a gradient of 10% acetonitrile/0.1% trifluoroacetic acid in water to 95% acetonitrile/0.1% trifluoroacetic acid in water to give the title compound (7.7 mg, 35%). $^1$H NMR (300 MHz, DMSO-$d_6$) δ 0.15 (d, J=4.04 Hz, 2 H) 0.42 (d, J=7.72 Hz, 2 H) 1.00 (m, 1 H) 2.84 (d, J=7.35 Hz, 2 H) 4.23 (d, J=5.52 Hz, 2 H) 4.44 (s, 2 H) 6.37 (bs, 1 H) 7.32 (s, 1 H) 7.42 (m, 6 H) 7.86 (m, 2 H) 8.07 (d, J=8.46 Hz, 1 H) 8.16 (dd, 1 H) 14.50 (bs, 1 H).

EXAMPLE 432A 1-(cyclobutylamino)-4-hydroxyquinolin-2(1H)-one

A solution of the product of Example 350A (0.516 g, 2.9 mmol) and cyclobutanone (1.05 g, 15.0 mmol) in acetic acid (0.90 g, 15.0 mmol) and methanol (20 mL) was treated portion wise with sodium cyanoborohydride (0.94 g, 15.0 mmol), stirred for 48 hours and concentrated. The residue was treated with 0.5 M aqueous sodium bicarbonate, acidified to pH 2 with 1M hydrochloric acid and extracted with ethyl acetate. The ethyl acetate was washed with brine, dried over sodium sulfate, filtered and concentrated. The crude material was chromatographed on silica gel eluting with 3:2 hexane/ethyl acetate to give the title compound (0.400 g, 60%). MS (ESI+) m/z 231 (M+H)$^+$. $^1$H NMR (300 MHz, DMSO-$d_6$) δ 1.52 (m, 1 H) 1.63 (m, 1 H) 1.96 (m, 4 H) 3.64 (m, 1 H) 5.91 (s, 1 H) 6.26 (d, J=6.62 Hz, 1 H) 7.20 (t, J=8.09 Hz, 1 H) 7.61 (m, 1 H) 7.84 (m, 2 H) 11.42 (s, 1 H).

EXAMPLE 432B

3-[bis(methylthio)methylene]-1-(cyclobutylamino)quinoline-2,4(1H,3H)-dione

A solution of the product of Example 432A (0.115 g, 0.5 mmol) and tris(methylthio)methyl methyl sulfate (prepared using the procedures in *Synthesis*, 22-25, 1988; M. Barbero, S. Cadamuro, I. Degani, R. Fochi, A. Gatti, V. Regondi) (0.27 g, 1.0 mmol) in pyridine (0.316 g, 4.0 mmol) and dioxane (5.0 mL) was heated at 60° C. for 30 minutes. Additional tris(methylthio)methyl methyl sulfate was added (0.27 g, 1.0 mmol) and heating continued for 30 minutes. The mixture was cooled to 25° C. and partitioned between ethyl acetate and water. The ethyl acetate layer was washed with water, brine, dried over sodium sulfate, filtered and concentrated. The crude material was chromatographed on silica gel eluting with 95/5 dichloromethane/ethyl acetate to give the title compound (0.146 g, 87% yield). MS (ESI$^+$) m/z 335 (M+H)$^+$. $^1$H NMR (300 MHz, DMSO-$d_6$) δ 1.54 (m, 1 H) 1.66 (m, 1 H) 1.99 (m, 4 H) 2.61 (s, 6 H) 3.62 (m, 1 H) 6.18 (d, J=6.25 Hz, 1 H) 7.15 (t, J=7.54 Hz, 1 H) 7.63 (m, 1 H) 7.72 (d, J=8.09 Hz, 1 H) 7.98 (dd, J=7.91, 1.29 Hz, 1 H).

EXAMPLE 432C

N-{3-[1-(cyclobutylamino)-4-hydroxy-2-oxo-1,2-dihydroquinolin-3-yl]-1,1-dioxido-4H-1,2,4-benzothiadiazin-7-yl}methane sulfonamide A mixture of the product of Example 425D (0.195 g, 0.585 mmol, 1.5 eq.) and the product of Example 432B (0.100 g, 0.390 mmol, 1.5 eq.) in anhydrous dioxane (10 mL) was heated for 1 hour at 120° C. After cooling to 25° C., the reaction mixture was treated with methanol (20 mL) and diethyl ether (20 mL) and the precipitated product collected by vacuum filtration to yield the title compound (25 mg, 12% yield). $^1$H NMR (300 MHz, DMSO-$d_6$) δ 1.69 (m, 2 H) 2.13 (m, 4 H) 3.10 (s, 3 H) 3.77 (m, 1 H) 6.57 (s, 1 H) 7.44 (t, J=7.35 Hz, 1 H) 7.65 (m, 3 H) 7.89 (t, J=7.35 Hz, 1 H) 8.06 (d, J=8.46 Hz, 1 H) 8.16 (d, J=7.72 Hz, 1 H) 10.31 (s, 1 H) 14.16 (s, 1 H) 15.03 (s, 1 H). MS (ESI$^+$) m/z=504 (M+H)$^+$.

EXAMPLE 433

N-(3-{1-[(cyclopropylmethyl)amino]-4-hydroxy-2-oxo-1,2-dihydroquinolin-3-yl}-1,1-dioxido-4H-1,2,4-benzothiadiazin-7-yl)methanesulfonamide A solution of the product of Example 353B (0.090 g, 0.269 mmol, 1 eq.), and the product of Example 425D (0.071 g, 0.269 mmol, 1 eq.), in anhydrous dioxane (5 mL) was heated for 1 hour at 120° C. After cooling the reaction mixture to 25° C., methanol (20 mL) and diethyl ether (20 mL) were added and the precipitated product collected by vacuum filtration to give the title compound (21 mg, 15.5% yield). $^1$H NMR (300 MHz, DMSO-$d_6$) δ 0.16 (m, 2 H) 0.41 (m, 2 H) 1.07 (m, 1 H) 2.85 (m, 2 H) 3.10 (s, 3 H) 6.44 (m, 1 H) 7.44 (t, J=7.54 Hz, 1 H) 7.62 (m, 2 H) 7.71 (m, 1 H) 7.90 (t, J=7.91 Hz, 1 H) 8.10 (d, J=8.46 Hz, 1 H) 8.17 (d, J=6.99 Hz, 1 H) 10.30 (m, 1 H) 14.15 (m, 1 H). MS (ESI$^+$) m/z=504 (M+H)$^+$.

EXAMPLE 434

4-hydroxy-3-[8-(hydroxymethyl)-1,1-dioxido-4,9-dihydroimidazo[4,5-h][1,2,4]benzothiadiazin-3-yl]-1-(3-methylbutyl)-1,8-naphthyridin-2(1H)-one The product of Example 377 (14 mg, 0.033 mmole) was treated with 4N HCl (0.5 mL) and glycolic acid (4 mg, 0.052 mmole) and the resulting mixture was heated 24 hours at reflux. The mixture was concentrated under reduced pressure to a white pasty solid. The solid was purified by chromatography on silica gel eluting with 95:5 dichloromethane:methanol to give the title compound (10 mg, 63%). The title compound was converted to the sodium salt as described in Example 1D. MS (ESI$^+$) m/z: 483. $^1$H NMR (300 MHz, DMSO-$d_6$) δ 0.97 (d, J=6.25 Hz, 6 H) 1.50 (s, 1 H) 1.64 (d, J=6.99 Hz, 1 H) 3.87 (s, 1 H) 4.08 (d, J=6.62 Hz, 1 H) 4.30 (d, J=6.99 Hz, 1 H) 4.54 (s, 1 H) 4.66 (d, J=6.62 Hz, 1 H) 4.73 (s, 1 H) 5.33 (d, J=6.62 Hz, 1 H) 7.04 (d, J=8.82 Hz, 1 H) 7.14

(dd, J=7.35, 4.78 Hz, 1 H) 7.76 (d, J=8.82 Hz, 1 H) 8.39 (dd, J=7.54, 2.02 Hz, 1 H) 8.53 (m, 1 H) 12.49 (s, 1 H).

EXAMPLE 435A 2-chloroethyl ({3-[4-hydroxy-1-(3-methylbutyl)-2-oxo-1,2-dihydro-1,8-naphthyridin-3-yl]-1,1-dioxido-4H-1,2,4-benzothiadiazin-7-yl}amino)sulfonylcarbamate A solution of chlorosulfonyl isocyanate (33 mg, 0.23 mmol) in dichloromethane (8 mL) was cooled to 0° C. and 2-chloroethanol (18.8 mg, 0.23 mmol) was added dropwise. The mixture was stirred at 0° C. for 90 minutes followed by the addition of a solution containing the product of Example 205 (100 mg, 0.23 mmol) and triethylamine (71 mg, 0.70 mmol) in dichloromethane (2 mL). The mixture was stirred for 24 hrs at 25° C. then partititioned between dichloromethane (25 mL) and 1N aqueous hydrochloric acid (20 mL). The resulting organic layer was separated and dried over magnesium sulfate, filtered, and concentrated under reduced pressure to provide the title compound (96 mg, 67%). MS (ESI$^-$) m/z 611 (M–H)$^-$. $^1$H NMR (300 MHz, DMSO-d$_6$) δ 0.98 (d, J=6.62 Hz, 6 H) 1.57 (m, 2 H) 1.69 (m, 1 H) 3.78 (m, 2 H) 4.32 (m, 2 H) 4.49 (m, 2 H) 7.51 (m, 2 H) 7.63 (s, 1 H) 7.77 (d, J=9.19 Hz, 1 H) 8.56 (dd, J=7.72, 1.10 Hz, 1 H) 8.90 (dd, J=4.41, 1.47 Hz, 1 H) 11.15 (s, 1 H) 12.26 (s, 1 H) 14.10 (s, 1 H).

EXAMPLE 435B

N-{3-[4-hydroxy-1-(3-methylbutyl)-2-oxo-1,2-dihydro-1,8-naphthyridin-3-yl]-1,1-dioxido-4H-1,2,4-benzothiadiazin-7-yl}-2-oxo-1,3-oxazolidine-3-sulfonamide To a solution of the product of Example 435A (90 mg, 0.147 mmol) in dichloromethane (10 mL) was added triethylamine (1 mL). The mixture was stirred at 25° C. for 6 hours. The reaction was treated with 1N aqueous hydrochloric acid (10 mL) and extracted with dichloromethane (20 mL). The organic layer was separated and dried over magnesium sulfate, filtered, and concentrated under reduced pressure to provide the title compound as a colorless solid (70 mg, 82%). $^1$H NMR (300 MHz, DMSO-d$_6$) δ 0.98 (d, J=6.62 Hz, 6 H) 1.57 (m, 2 H) 1.69 (m, 1 H) 3.98 (m, 2 H) 4.36 (m, 2 H) 4.48 (m, 2 H) 7.49 (dd, J=7.72, 4.78 Hz, 1 H) 7.60 (m, 1 H) 7.62 (s, 1 H) 7.75 (d, J=8.82 Hz, 1 H) 8.56 (m, 1 H) 8.89 (m, 1 H) 11.59 (s, 1 H) 14.15 (s, 1 H).

EXAMPLE 435C

N-[3-(4-hydroxy-1-isopentyl-2-oxo-1,2-dihydro-1,8-naphthyridin-3-yl)-1,1-dioxido-4H-1,2,4-benzothiadiazin-7-yl]-N'-(2-phenylethyl)sulfamide A mixture of the product of Example 435B (28 mg, 0.05 mmole) and phenethylamine (6 mg, 0.05 mmol) in acetonitrile (10 mL) and triethylamine (0.5 mL) was heated at reflux for 18 hours. The reaction mixture was cooled to 25C, diluted with ethyl acetate, extracted with 10 mL 1 N HCl, followed by 10 mL brine. The organic layer was dried over anhydrous Na$_2$SO$_4$, filtered, and concentrated under vacuum. The product was isolated by preparative thin layer chromatography on silica gel eluting with 25% ethyl acetate in dichloromethane to provide 2 mg of the title compound (10% yield). $^1$H NMR (300 MHz, DMSO-d$_6$) δ 0.98 (d, J=6.62 Hz, 6 H) 1.57 (m, 2 H) 1.69 (m, 1 H) 2.68 (m, 2 H) 3.09 (m, 2 H) 4.49 (m, 2 H) 7.20 (m, 5 H) 7.46 (m, 1 H) 7.51 (m, 1 H) 7.60 (d, J=2.21 Hz, 1 H) 7.68 (d, J=8.82 Hz, 1 H) 7.97 (m, 1 H) 8.56 (dd, J=8.09, 1.84 Hz, 1 H) 8.89 (m, 1 H) 10.28 (s, 1 H) 14.13 (s, 1 H) 15.23 (s, 1 H).

EXAMPLE 436 benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide A solution of chlorosulfonyl isocyanate (24.5 μL, 0.281 mmol) in dichloromethane (2 mL) was treated dropwise with benzyl alcohol (29 μL, 0.281 mmol) at 25° C., stirred at 25° C. for 30 min, treated with a solution of the product of Example 205 (100 mg, 0.234 mmol) and triethylamine (130 μL, 0.936 mmol) in dichloromethane (3 mL)and stirred for 2 hrs at 25° C. The reaction mixture was treated with dichloromethane (10 mL) and 1N aqueous hydrochloric acid (10 mL). The resulting organic layer was separated and dried over magnesium sulfate, filtered, and concentrated under reduced pressure to provide the title compound (122 mg, 81%). MS (ESI$^-$) m/z 639 (M–H)$^-$. $^1$H NMR (300 MHz, DMSO-d$_6$) δ 0.99 (d, J=6.6 Hz, 6H), 1.59 (m, 2H), 1.66 (m, 1H), 4.49 (m, 2H), 5.12 (s, 2H), 7.32 (m, 5H), 7.48 (m, 2H), 7.65 (d, J=2.2 Hz, 1H), 7.75 (d, J=8.8 Hz, 1H), 8.57 (dd, J=7.7, 1.8 Hz, 1H), 8.90 (dd, J=0.8, 1.8 Hz, 1H), 11.17 (s, 1H), 12.19 (bs, 1H), 14.11 (bs, 1H).

EXAMPLE 437

N-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide A solution of the product of Example 436 (40 mg, 0.0625 mmol) in methanol (5 mL) was treated with 10% palladium on carbon (20 mg), and stirred at 25° C. for 5 hours under hydrogen atmosphere. The resulting solution was then filtered and the filtrate concentrated under reduced pressure to provide the title compound (25 mg, 78%). MS (ESI$^-$) m/z 505 (M–H)$^-$. $^1$H NMR (300 MHz, DMSO-d$_6$) δ ppm 0.98 (d, J=6.3 Hz, 6H), 1.57 (m, 2H), 1.66 (m, 1H), 4.42 (m, 2H), 7.38 (m, 1H), 7.43 (m, 2H), 7.59 (m, 1H), 8.52 (m, 1H), 8.82 (bs, 1H), 9.99 (bs, 1H).

EXAMPLE 438 benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]-1-propyldiazathiane-1-carboxylate 2,2-dioxide A solution of triphenylphosphine (1.5 eq) in dichloromethane is treated dropwise with diethyl azodicarboxylate (1.5 eq) at 25° C. The solution is allowed to stir for 10 min followed by the dropwise addition of a solution containing the product of Example 436 (1 eq) and n-propanol (1.1 eq) in dichloromethane. The resulting solution is stirred at 25° C. for 20 hours, followed by the addition of dichloromethane and 1N aqueous hydrochloric acid. The resulting organic layer is separated and dried over magnesium sulfate, and filtered to provide the title compound.

EXAMPLE 439

N-[3-(4-hydroxy-1-isopentyl-2-oxo-1,2-dihydro[1,8] naphthyridin-3-yl)-1,1-dioxido-4H-1,2,4-benzothiadiazin-7-yl]-N'-propylsulfamide A solution of the product of Example 438 in methanol is treated with 10% palladium on carbon and stirred at 25° C. for 5 hours under hydrogen atmosphere. The resulting solution is then filtered and the filtrate concentrated under reduced pressure to provide the title compound.

EXAMPLE 440 methyl 3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxylate 2,2-dioxide To a stirred solution of chlorosulfonyl isocyanate (4.9 µL, 0.0562 mmol) in dichloromethane (2 mL) was added dropwise methanol (2.3 µL, 0.0562 mmol) at 25° C. After 30 minutes, a solution of the product of Example 205 (20 mg, 0.0468 mmol) and triethylamine (26 µL, 0.187 mmol) in dichloromethane (2 mL) was added and stirred for 24 hours at 25° C. The reaction mixture was diluted with dichloromethane (10 mL) and 1N aqueous hydrochloric acid (10 mL). The resulting organic layer was separated and dried over magnesium sulfate, filtered, and concentrated under reduced pressure to provide the title compound (12 mg, 39%) as a triethylamine salt. $^1$H NMR (300 MHz, DMSO-$d_6$) δ 0.98 (d, J=6.3 Hz, 3H), 1.38 (m, 2H), 1.67 (m, 1H), 3.63 (s, 3H), 4.50 (m, 2H), 7.53 (m, 2H), 7.63 (d, J=2.2 Hz, 1H), 7.77 (d, J=8.8 Hz, 1H), 8.57 (dd, J=8.1, 1.8 Hz, 1H), 8.90 (dd, J=4.4, 1.8 Hz, 1H), 11.15 (s, 1H), 12.10 (s, 1H), 14.10 (s, 1H). MS (ESI$^-$) m/z 563 (M−H)$^-$.

EXAMPLE 441 benzyl 3-[3-(4-hydroxy-1-isopentyl-2-oxo-1,2-dihydro[1,8]naphthyridin-3-yl)-1,1-dioxido-4H-1,2,4-benzothiadiazin-7-yl]-1-methyldiazathiane-1-carboxylate 2,2-dioxide A solution of the product of Example 436 (0.032 g, 0.05 mmol) in 1:1 tetrahydrofuran/methanol (2 ml) at −10° C. was treated dropwise with trimethylsilyl diazomethane (2.0 M in hexanes, 50 µL, 0.1 mmol), then stirred at 25° C. for 16 hours and concentrated under reduced pressure. The residue was chromatographed on silica gel eluting with 3% methanol in dichloromethane to provide the title compound (5 mg, 15% yield). $^1$H NMR (300 MHz, DMSO-$d_6$) δ 0.99 (d, J=6.25 Hz, 6 H) 1.58 (m, 2 H) 1.69 (m, 1 H) 3.21 (s, 3 H) 4.49 (m, 2 H) 5.19 (s, 2 H) 7.32 (m, 5 H) 7.46 (m, 1 H) 7.51 (dd, J=7.91, 4.60 Hz, 1 H) 7.58 (d, J=2.21 Hz, 1 H) 7.68 (d, J=8.82 Hz, 1 H) 8.57 (dd, J=8.09, 1.84 Hz, 1 H) 8.90 (dd, J=4.78, 1.47 Hz, 1 H) 11.29 (s, 1 H) 14.09 (s, 1 H). MS (ESI$^-$) m/z 653 (M−H)$^-$.

EXAMPLE 442

N-[3-(4-hydroxy-1-isopentyl-2-oxo-1,2-dihydro[1,8] naphthyridin-3-yl)-1,1-dioxido-4H-1,2,4-benzothiadiazin-7-yl]-N'-methylsulfamide A solution of the product of Example 441 (14 mg, 0.0214 mmol) in methanol (3 mL) was reacted with 10% palladium on carbon (10 mg) under a hydrogen atmosphere at 25° C. with stirring for 2 hours. The solution was filtered and concentrated under reduced pressure to provide the title compound (8 mg, 73%). $^1$H NMR (300 MHz, DMSO-$d_6$) δ 0.94 (d, J=6.6 Hz, 6H), 1.57 (m, 2H), 1.69 (m, 1H), 2.49 (s, 3H), 4.45 (m, 2H), 7.50 (m, 2H), 7.62 (m, 2H), 8.57 (m, 1H), 8.84 (m, 1H), 10.18 (bs, 1H). MS (ESI$^-$) m/z 519 (M−H)$^-$.

EXAMPLE 443

2-aminoethyl 3-[3-(4-hydroxy-1-isopentyl-2-oxo-1, 2-dihydro[1,8]naphthyridin-3-yl)-1,1-dioxido-4H-1, 2,4-benzothiadiazin-7-yl]diazathiane-1-carboxylate 2,2-dioxide To a solution of chlorosulfonyl isocyanate (7.3 µL, 0.0843 mmol) in dichloromethane (2 mL) was added t-butyl N-(2-hydroxyethyl)carbamate (13.6 mg, 0.0843 mmol) at 25° C. After 30 minutes, the solution was treated with a solution of the product of Example 205 (30 mg, 0.0703 mmol) and triethylamine (39 µL, 0.281 mmol) in dichloromethane (2 mL) and stirred for 24 hours. The reaction mixture was diluted with dichloromethane (10 mL) and 1N aqueous hydrochloric acid (10 mL). The resulting organic layer was separated and dried over magnesium sulfate, filtered, and concentrated under reduced pressure. The residue was purified by reverse phase preparative HPLC on a Waters Symmetry C8 column (25 mm×100 mm, 7 µm particle size) using a gradient of 10% to 100% acetonitrile/10 mM ammonium acetate in water over 8 minutes (10 minutes run time) at a flow rate of 40 mL/min to provide 8 mg of a solid. This solid was treated with a solution of trifluoroacetic acid (1.6 mL) and dichloromethane (0.4 mL) at 25° C. for 3 hours. The solvent was removed under reduced pressure to provide the title compound (12 mg, 24%) as a trifluoroacetic acid salt. $^1$H NMR (300 MHz, DMSO-$d_6$) δ 0.98 (d, J=6.6 Hz, 6H), 1.57 (m, 2H), 1.68 (m, 1H), 3.06 (m, 2H), 4.21 (t, J=5.1 Hz, 2H), 4.46 (m, 2H), 7.49 (m, 2H), 7.63 (d, J=2.2 Hz, 1H), 7.71 (d, J=8.8 Hz, 1H), 7.83 (bs, 2H), 8.55 (dd, J=7.7, 1.8 Hz, 1H), 8.86 (m, 1H). MS (ESI$^-$) m/z 592 (M−H)$^-$.

EXAMPLE 444

N-cyclopentyl-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide To the product of Example 435B (0.029 g, 0.05 mmol) in acetonitrile (2 mL) was added 1-amino cyclopentane (0.0085 g, 0.0099 mL, 0.1 mmol). The reaction mixture was heated in a microwave reactor at 80° C. for 2 hours and cooled to about 25° C. The solvent was removed under a stream of warm nitrogen gas, and the residue was purified by reverse phase preparative HPLC on a Waters Symmetry C8 column (25 mm×100 mm, 7 µm particle size) using a gradient of 10% to 100% acetonitrile/10 mM ammonium acetate in water over 8 minutes (10 minutes run time) at a flow rate of 40 mL/min give the title compound (11 mg, 38%). $^1$H NMR (300 MHz, DMSO-$d_6$) δ 0.97 (d, J=6.62 Hz, 6 H) 1.51 (m, 11 H) 3.53 (m, 1 H) 4.48 (m, 2 H) 7.49 (m, 2 H) 7.60 (d, J=2.57 Hz, 1 H) 7.70 (d, J=9.19 Hz, 1 H) 7.83 (d, J=7.35 Hz, 1 H) 8.55 (d, J=8.09, 1.84 Hz, 1 H) 8.88 (dd, J=4.60, 1.65 Hz, 1 H) 10.19 (s, 1 H) 14.06 (s, 1 H). (ESI−) m/z 573 (M−H)$^-$.

EXAMPLE 445

N-cyclobutyl-N'-[3-(4-hydroxy-1-isopentyl-2-oxo-1, 2-dihydro[1,8]naphthyridin-3-yl)-1,1-dioxido-4H-1, 2,4-benzothiadiazin-7-yl]sulfamide To the product of Example 435B (0.029 g, 0.05 mmol) in acetonitrile (2 mL) was added 1-amino cyclobutane (0.0071 g, 0.0085 mL, 0.1 mmol). The reaction mixture was heated in a microwave reactor at 80° C. for 2 hours and cooled to about 25° C. The solvent was removed under a stream of warm nitrogen gas, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (8 mg, 28%). $^1$H NMR (300 MHz, DMSO-d$_6$) δ 0.98 (d, J=6.62 Hz, 6 H) 1.64 (m, 7 H) 2.05 (m, 2 H) 3.68 (m, 1 H) 4.49 (m, 2 H) 7.50 (m, 2 H) 7.59 (d, J=2.57 Hz, 1 H) 7.73 (d, J=8.82 Hz, 1 H) 8.16 (d, J=8.46 Hz, 1 H) 8.56 (dd, J=8.09, 1.84 Hz, 1 H) 8.90 (dd, J=4.60, 1.65 Hz, 1 H) 10.17 (s, 1 H) 14.02 (s, 1 H). MS (ESI−) m/z 559 (M−H)$^-$.

EXAMPLE 446A tert-butyl 4-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]-1-piperidinecarboxylate To the product of Example 435B (0.029 g, 0.05 mmol) in acetonitrile (2 mL) was added N-1-Boc-4-amino piperidine (0.020 g, 0.1 mmol). The reaction mixture was heated in a microwave reactor at 80° C. for 2 hours and cooled to about 25° C. The solvent was removed under a stream of warm nitrogen gas, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (12 mg, 35%).

EXAMPLE 446B

N-[3-(4-hydroxy-1-isopentyl-2-oxo-1,2-dihydro[1,8]naphthyridin-3-yl)-1,1-dioxido-4H-1,2,4-benzothiadiazin-7-yl]-N'-(4-piperidinyl)sulfamide The product of Example 446A (0.012 g, 0.017 mmol) was dissolved in the solution of hydrogen chloride in 1,4-dioxane (4 N, 3 mL). The mixture was stirred at 25° C. for 18 hours. The solvent was removed under reduced pressure to give the title compound as its hydrochloride salt (10 mg, 92%). $^1$H NMR (300 MHz, DMSO-d$_6$) δ 0.99 (d, J=6.25 Hz, 6 H) 1.70 (m, 7 H) 2.95 (m, 2 H) 3.16 (m, 3 H) 4.49 (m, 2 H) 7.50 (m, 2 H) 7.63 (d, J=2.21 Hz, 1 H) 7.73 (d, J=9.19 Hz, 1 H) 8.17 (d, J=7.35 Hz, 1 H) 8.52 (m, 1 H) 8.56 (dd, J=7.91, 1.65 Hz, 1 H) 8.75 (m, 1 H) 8.90 (dd, J=4.60, 1.65 Hz, 1 H) 10.34 (s, 1 H) 14.08 (s, 1 H). MS (ESI−) m/z 588 (M−H)$^-$.

EXAMPLE 447

N-(2-hydroxyethyl)-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide To the product of Example 435 B (0.006 g, 0.0104 mmol) in tetrahydrofuran (2 ml) was added water (0.1 ml) and sodium ethoxide in ethanol (20% w/w, 1 ml). The mixture was stirred for 24 hours at 25° C. The reaction was concentrated under a stream of warm nitrogen gas, and the residue was treated with 1N hydrochloric acid (2 ml) with stirring for 10 min. The resulting solid was filtered and dried to give the title compound (4 mg, 70%). $^1$H NMR (300 MHz, DMSO-d$_6$) δ 0.99 (d, J=6.62 Hz, 6 H) 1.58 (m, 2 H) 1.71 (m, 1 H) 2.92 (m, 2 H) 3.39 (m, 2 H) 4.50 (m, 2 H) 7.51 (m, 2 H) 7.61 (d, J=2.21 Hz, 1 H) 7.72 (d, J=8.82 Hz, 1 H) 7.80 (t, J=5.88 Hz, 1 H) 8.56 (dd, J=8.09, 1.84 Hz, 1 H) 8.89 (dd, J=4.41, 1.47, 1 H) 10.21 (s, 1 H) 14.08 (s, 1 H). MS (ESI−) m/z 549 (M−H)$^-$.

EXAMPLE 448

3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]propanamide To the product of Example 435B (0.029 g, 0.05 mmol) in acetonitrile (2 mL) was added glycinamide hydrochloride (0.0125 g, 0.1 mmol) and potassium carbonate (0.4 mmol). The reaction mixture was heated in a microwave reactor at 80° C. for 2 hours and cooled to about 25° C. The solvent was removed under a stream of warm nitrogen gas and, the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (3 mg, 10%). $^1$H NMR (300 MHz, DMSO-d$_6$) δ 0.99 (d, J=6.62 Hz, 6 H) 1.59 (m, 2 H) 1.70 (m, 1 H) 2.25 (t, J=7.54 Hz, 2 H) 3.07 (m, 2 H) 4.49 (m, 2 H) 6.80 (s, 1 H) 7.30 (s, 1 H) 7.50 (m, 2 H) 7.61 (d, J=2.21 Hz, 1 H) 7.70 (d, J=8.82 Hz, 1 H) 7.82 (t, J=5.70 Hz, 1 H) 8.56 (dd, J=7.72, 1.84 Hz, 1 H) 8.89 (dd, J=4.41 Hz, 1.47 Hz, 1 H) 10.23 (s, 1 H) 14.13 (s, 1 H). MS (ESI−) m/z 576 (M−H)$^-$.

EXAMPLE 449

N-[3-(4-hydroxy-1-isopentyl-2-oxo-1,2-dihydro[1,8]naphthyridin-3-yl)-1,1-dioxido-4H-1,2,4-benzothiadiazin-7-yl]-1-azetidinesulfonamide To the product of Example 435B (0.029 g, 0.05 mmol) in acetonitrile (2 mL) was added azetidine hydrochloride (0.0095 g, 0.1 mmol) and potassium carbonate (0.4 mmol). The reaction mixture was heated in a microwave reactor at 80° C. for 2 hours and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (2 mg, 7%). $^1$H NMR (300 MHz, DMSO-d$_6$) δ 0.99 (d, J=6.62 Hz, 6 H) 1.58 (m, 2 H) 1.71 (m, 1 H) 2.15 (m, 2 H) 3.83 (t, J=7.54 Hz, 4 H) 4.49 (m, 2 H) 7.53 (m, 2 H) 7.63 (d, J=2.21 Hz, 1 H) 7.72 (d, J=9.19 Hz, 1 H) 8.56 (dd, J=8.09, 1.84 Hz, 1 H) 8.90 (dd, J=4.41, 1.84 Hz, 1 H) 10.50 (s, 1 H) 14.11 (s, 1 H). MS (ESI−) m/z 545 (M−H)$^-$.

EXAMPLE 450

3-hydroxy-N-[3-(4-hydroxy-1-isopentyl-2-oxo-1,2-dihydro[1,8]naphthyridin-3-yl)-1,1-dioxido-4H-1,2,4-benzothiadiazin-7-yl]-1-azetidinesulfonamide To the product of Example 435B (0.029 g, 0.05 mmol) in acetonitrile (2 mL) was added 3-hydroxyazetidine hydrochloride (0.011 g, 0.1 mmol) and potassium carbonate (0.4 mmol). The reaction mixture was heated in a microwave reactor at 80° C. for 2 hours and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (3 mg, 13%). $^1$H NMR (300 MHz, DMSO-$d_6$) δ 0.99 (d, J=6.62 Hz, 6 H) 1.58 (m, 2 H) 1.71 (m, 1 H) 3.66 (m, 2 H) 3.92 (m, 2 H) 4.38 (m, 1 H) 4.50 (m, 2 H) 7.55 (m, 3 H) 7.73 (d, J=8.82 Hz, 1 H) 8.57 (dd, J=8.09 Hz, 1.08 Hz, 1 H) 8.90 (dd, J=4.41, 1.84 Hz, 1 H) 10.55 (s, 1 H) 14.08 (s, 1 H). MS (ESI−) m/z 561 (M−H)−.

EXAMPLE 451A tert-butyl 1-({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)-3-pyrrolidinylcarbamate To the product of Example 435B (0.029 g, 0.05 mmol) in acetonitrile (2 mL) was added N-Boc-3-amino pyrrolidine (0.0186 g, 0.1 mmol). The reaction mixture was heated in a microwave reactor at 80° C. for 2 hours and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (23 mg, 68%).

EXAMPLE 451B 3-amino-N-[3-(4-hydroxy-1-isopentyl-2-oxo-1,2-dihydro[1,8]naphthyridin-3-yl)-1,1-dioxido-4H-1,2,4-benzothiadiazin-7-yl]-1-pyrrolidinesulfonamide The product of Example 446A (0.012 g, 0.017 mmol) was dissolved in a solution of hydrogen chloride in 1,4-dioxane (4N, 3 mL). The mixture was stirred at 25° C. for about 18 hours. The solvent was removed under reduced pressure to give the title compound as its hydrochloride salt (16 mg, 88%). $^1$H NMR (300 MHz, DMSO-$d_6$) δ 0.98 (d, J=6.62 Hz, 6 H) 1.54 (m, 2 H) 1.67 (m, 1 H) 1.91 (m, 1 H) 2.18 (m, 1 H) 3.26 (m, 2 H) 3.50 (m, 2 H) 3.79 (m, 1 H) 4.43 (m, 2 H) 7.40 (dd, J=7.72, 4.78 Hz, 1 H) 7.58 (m, 3 H) 8.22 (s, 3 H) 8.50 (dd, J=7.71 Hz, 1.47 Hz, 1 H) 8.80 (d, J=3.31 Hz, 1 H) 10.52 (s, 1 H) 14.55 (s, 1 H). MS (ESI−) m/z 574 (M−H)−.

EXAMPLE 452A 1-piperidinesulfonyl chloride

A solution of sulfuryl chloride (1N in dichloromethane, 75 mL, 75 mmol) at −20° C. was treated dropwise with piperidine (12.6 g, 150 mmol), stirred at 0° C. for 2 hours, and partitioned between dichloromethane and water (50 mL). The organic layer was washed with aqueous 1N HCl, brine and dried over anhydrous magnesium sulfate, filtered, and concentrated under reduced pressure. The residue was distilled under reduced pressure (1 mm Hg) at 105° C. to give the title compound (5 grams).

EXAMPLE 452B

N-[3-(4-hydroxy-1-isopentyl-2-oxo-1,2-dihydro[1,8]naphthyridin-3-yl)-1,1-dioxido-4H-1,2,4-benzothiadiazin-7-yl]-1-piperidinesulfonamide A mixture of the product of Example 205 (2 mg, 0.1 ml), the product of Example 451A (17 mg, 0.1 mmol) and triethylamine (0.1 mL) in dichloromethane (2 mL) was stirred for 18 hours at 25° C., diluted with dichloromethane (25 mL) and washed with 1 N HCl and brine. The organic layer was dried over anhydrous sodium sulfate, filtered, and concentrated under reduced pressure. The product was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min to provide the title compound (10 mg). $^1$H NMR (300 MHz, DMSO-$d_6$) δ 0.98 (d, J=6.62 Hz, 6 H) 1.43 (s, 6 H) 1.57 (m, 2 H) 1.69 (m, 1 H) 3.14 (s, 4 H) 4.49 (m, 2 H) 7.51 (m, 1 H) 7.53 (s, 1 H) 7.60 (d, J=2.21 Hz, 1 H) 7.72 (d, J=8.82 Hz, 1 H) 8.56 (dd, J=8.09, 1.84 Hz, 1 H) 8.90 (dd, J=4.78, 1.84 Hz, 1 H) 10.47 (s, 1 H) 14.06 (s, 1 H) 15.05 (s, 1 H). MS (ESI−) m/z 573 (M−H)−.

EXAMPLE 453

N-benzyl-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide A mixture of the product of Example 435B (28 mg, 0.05 mmole), benzylamine (6 mg, 0.05 mmol) and triethylamine (0.5 mL) in acetonitrile (2 mL) was stirred at 70° C. for 18 hours. The reaction mixture was cooled to about 25° C., partitioned between ethyl acetate and 1 N HCl (10 mL). The organic layer was washed with brine and dried over anhydrous $Na_2SO_4$, filtered, and concentrated under reduced pressure. The residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min to give the title compound (12 mg). $^1$H NMR (300 MHz, DMSO-$d_6$) δ 0.99 (d, J=6.25 Hz, 6 H) 1.65 (m, 3 H) 4.08 (d, J=6.25 Hz, 2 H) 4.49 (m, 2 H) 7.22 (m, 5 H) 7.45 (m, 1 H) 7.51 (dd, J=8.09, 4.78 Hz, 1 H) 7.61 (d, J=2.57 Hz, 1 H) 7.69 (d, J=8.82 Hz, 1 H) 8.41 (t, J=6.25 Hz, 1 H) 8.57 (dd, J=8.09, 1.84 Hz, 1 H) 8.90 (dd, J=4.78, 1.84 Hz, 1 H) 10.33 (s, 1 H) 14.08 (s, 1 H) 15.15 (s, 1 H). MS (ESI−) m/z 595 (M−H)−.

EXAMPLE 454 ethyl 3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]benzoate A solution of 3-amino-benzoic acid ethyl ester (0.165 g, 1.0 mmol) in dichloromethane (6 mL) at about 0° C. was added dropwise with chlorosulfonic acid (0.128 g, 1.1 mmol). The reaction mixture was stirred at 25° C. for 1 h and then phosphorous pentachloride (0.229 g, 1.1 mmol) was added and the reaction mixture heated under reflux for 3.5 hours. The reaction mixture was then cooled to about 25° C. and the solvent evaporated under reduced pressure. A solution of the residue in dichloromethane (10 mL) was treated with the product of Example 205 (0.214 g, 0.5 mmol), followed by triethylamine (0.152 g, 1.5 mmol). The reaction mixture was stirred at 25° C. for 3 hours and then poured into 25 mL of 1N aqueous hydrochloric acid. The reaction mixture was then extracted with dichloromethane (3×25 mL). The combined organics were dried over anhydrous magnesium sulfate, filtered, and evaporated under reduced pressure. The residue was purified by chromatography on silica gel, eluting with 0-2% methanol/dichloromethane to provide the title compound (0.166 g, 48% yield). $^1$H NMR (300 MHz, DMSO-$d_6$) δ 0.98 (d, J=6.25 Hz, 6 H) 1.30 (t, J=7.17 Hz, 3 H) 1.56 (m, 2 H) 1.68 (m, 1 H) 4.29 (q, J=6.99 Hz, 2 H) 4.48 (m, 2 H) 7.44

(m, 4 H) 7.57 (d, J=2.21 Hz, 1 H) 7.62 (dt, J=7.36, 1.47 Hz, 1 H) 7.69 (d, J=8.82 Hz, 1 H) 7.74 (s, 1 H) 8.55 (dd, J=8.09, 1.84 Hz, 1 H) 8.88 (dd, J=4.41, 1.84 Hz, 1 H) 10.80 (s, 1 H) 10.88 (s, 1 H) 14.11 (s, 1 H). MS (ESI$^+$) m/z 655.1 (M+H)$^+$, 672.2 (M+NH$_4$)$^+$, 677.0 (M+Na)$^+$, (ESI$^-$) m/z 653.1 (M–H)$^-$.

EXAMPLE 455

3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]benzoic acid A solution of the product of Example 454 (25.5 mg, 0.389 mmol) in 1 mL of 1N aqueous sodium hydroxide and 1ML of methanol was stirred at 25° C. for 17 hours, and concentrated under a stream of warm nitrogen. The residue was treated with 2 mL of 1N aqueous hydrochloric acid. The resulting solid was isolated by vacuum filtration, washed with 10 mL of water, and dried to provide the title compound (21.4 mg, 88% yield). $^1$H NMR (300 MHz, DMSO-d$_6$) δ 0.98 (d, J=6.62 Hz, 6 H) 1.56 (m, 2 H) 1.68 (m, 1 H) 4.48 (m, 2 H) 7.32-7.53 (m, 4 H) 7.59 (m, 2 H) 7.69 (d, J=8.82 Hz, 1 H) 7.75 (s, 1 H) 8.55 (dd, J=8.09, 1.84 Hz, 1 H) 8.88 (dd, J=4.78, 1.47 Hz, 1 H) 10.79 (s, 1 H) 10.88 (s, 1 H) 13.01 (bs, 1 H) 14.12 (bs, 1 H). MS (ESI$^+$) m/z 627.1 (M+H)$^+$, 649.1 (M+Na)$^+$, (ESI$^-$) m/z 625.1 (M–H)$^-$.

EXAMPLE 456

3-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]benzamide A solution of the product of Example 454 (7.6 mg, 0.012 mmol) in 1 mL of ammonium hydroxide was stirred at 25° C. for 17 hours. The solvent was evaporated under a stream of warm nitrogen to provide the title compound (7.4 mg). $^1$H NMR (300 MHz, DMSO-d$_6$) δ 0.96 (d, J=6.62 Hz, 6 H) 1.47 (m, 2 H) 1.64 (m, 1 H) 4.30 (m, 2 H) 7.14 (m, 1H) 7.28 (m, 6 H) 7.43 (s, 1 H) 7.49 (d, J=7.72 Hz, 1 H) 7.66 (s, 1 H) 7.87 (s, 1 H) 8.36 (dd, J=7.54, 1.65 Hz, 1 H) 8.54 (s, 1 H) 10.45 (bs, 1 H) 10.51 (bs, 1 H) 15.89 (bs, 1 H).

EXAMPLE 457A 4-(benzyloxy)-1-isopentyl-2(1H)-pyridinone

A solution of 4-benzyloxy-1H-pyridin-2-one (1.0 g, 4.97 mmol) and 1,8-diazabicyclo[5.4.0]undec-7-ene (1.86 mL, 12.43 mmol) and 1-bromo-3-methyl butane (0.715 mL, 5.96 mmol) in N,N-dimethylacetamide (20 mL) was heated at 65° C. for 5 days. The solution was cooled to about 25° C. and partitioned between 10% aqueous ammonium chloride and dichloromethane, the organic layer separated and concentrated under reduced pressure. The residue was chromatographed on silica gel, eluting with 1% methanol in dichloromethane to provide the title compound (0.569 g, 42%).

EXAMPLE 457B 4-hydroxy-1-isopentyl-2(1H)-pyridinone

The product of Example 457A (0.452 g, 1.67 mmol) in tetrahydrofuran (20 mL) was treated with ammonium formate (0.30 g, 5.01 mmol) and a catalytic amount of 20% palladium hydroxide on carbon at 60° C. for 2 hours. The reaction was filtered through diatomaceous earth and the filtrate concentrated under reduced pressure to provide the title compound (0.30 g, 100%).

EXAMPLE 457C

3-[bis(methylsulfanyl)methylene]-1-isopentyl-2,4(1H,3H)-pyridinedione

The product of Example 457B (2.24 g, 12.37 mmol) in pyridine (8.0 mL, 98.96 mmol) and dioxane (50 mL) at 90° C. was treated with excess tris(methylthio)methyl methyl sulfate (prepared using the procedures in *Synthesis*, 22-25, 1988; M. Barbero, S. Cadamuro, I. Degani, R. Fochi, A. Gatti, V. Regondi), stirred at 90° C. for 1.5 hours and cooled to about 25° C. The reaction solution was decanted from the resulting solids and the solvent was removed under reduced pressure. The residue was dissolved in hexanes and loaded onto a pad of silica gel (300 mL) and eluted with hexane followed by dichloromethane then 25% ethyl acetate in dichloromethane to provide the title compound (2.42 g, 75%).

EXAMPLE 457D 3-(7-amino-1,1-dioxido-4H-1,2,4-benzothiadiazin-3-yl)-4-hydroxy-1-isopentyl-2(1H)-pyridinone The product of Example 457C (2.08 g, 7.29 mmol) was treated with the product of Example 414A (2.00 g, 6.96 mmol) in dioxane (20 mL) at 115° C. for 30 minutes, cooled to 25° C. and concentrated under reduced pressure. A solution of the residue in 4M hydrochloric acid in dioxane (20 mL) was stirred at 25° C. for 18 hours and concentrated under reduced pressure. The residue was triturated with dichloromethane and filtered to give the title compound. The filtrate containing the protected intermediate was concentrated and purified by chromatography on silica gel eluting with 1% methanol in dichloromethane. The protected product was re-subjected to the above deprotection conditions to provide the title compound as its hydrochloride salt (2.02 g, 96%). $^1$H NMR (300 MHz, DMSO-d$_6$) δ 0.92 (s, 3 H) 0.94 (s, 3 H) 1.58 (m, 3 H) 3.99 (m, 2 H) 6.31 (d, J=7.35 Hz, 1 H) 6.96 (m, 2 H) 7.34 (d, J=8.46 Hz, 1 H) 8.04 (d, J=7.35 Hz, 1 H) 14.04 (s, 1 H) 14.19 (s, 1 H). MS (ESI–) m/z 375 (M–H)$^-$.

EXAMPLE 457E benzyl 3-[3-(4-hydroxy-1-isopentyl-2-oxo-1,2-dihydro-3-pyridinyl)-1,1-dioxido-4H-1,2,4-benzothiadiazin-7-yl]diazathiane-1-carboxylate 2,2-dioxide A solution of chlorosulfonylisocynate (61.8 mg, 0.436 mmol) and benzyl alcohol (47.0 mg, 0.436 mmol) in dichloromethane (7.5 ml) was stirred at 25° C. for 1 hour followed by the addition of a solution of the product of Example 457D (150 mg, 0.363 mmol) and triethylamine (183.7 mg, 1.82 mmol) in dichloromethane (14 mL), stirred at 25° C. for 20 hours, and partitioned between dichloromethane (25 mL) and 1N aqueous hydrochloric acid (25 mL). The organic layer was separated and dried over magnesium sulfate, filtered and concentrated under reduced pressure to provide the title compound (200 mg, 93%). $^1$H NMR (300 MHz, DMSO-d$_6$) δ 0.93 (s, 3 H) 0.95 (s, 3 H) 1.58 (m, 3 H) 4.00 (m, 2 H) 5.11 (s, 2 H) 6.35 (d, J=7.72 Hz, 1 H) 7.32 (m, 5 H) 7.46 (dd, J=9.01, 2.39 Hz, 1 H) 7.61 (d, J=2.57 Hz, 1 H) 7.65 (d, J=9.19 Hz, 1 H) 8.09

(d, J=7.72 Hz, 1 H) 11.10 (s, 1 H) 12.14 (s, 1 H) 13.87 (s, 1 H) 14.25 (s, 1 H). MS (ESI−) m/z 588 (M−H)⁻.

EXAMPLE 458

N-[3-(4-hydroxy-1-isopentyl-2-oxo-1,2-dihydro-3-pyridinyl)-1,1-dioxido-4H-1,2,4-benzothiadiazin-7-yl]sulfamide A solution of the product of Example 457E (40 mg, 0.068 mmol) in methanol (5 mL) was stirred with 10% palladium on carbon (22 mg) under hydrogen atmosphere at 25° C. for 4 hours. The reaction was filtered and the filtrate concentrated under reduced pressure to provide the title compound (28 mg, 99%). $^1$H NMR (300 MHz, DMSO-$d_6$) δ 0.92 (s, 3 H) 0.94 (s, 3 H) 1.58 (m, 3 H) 3.98 (m, 2 H) 6.32 (d, J=4.41 Hz, 1 H) 7.36 (s, 2 H) 7.47 (m, 1 H) 7.60 (m, 2 H) 8.06 (s, 1 H) 10.00 (s, 1 H) 13.97 (s, 1 H) 14.23 (s, 1 H). MS (ESI−) m/z 454 (M−H)⁻.

EXAMPLE 459A tert-butyl 2-[({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)amino]ethyl-carbamate To the product of Example 435B (0.029 g, 0.05 mmol) in acetonitrile (2 mL) was added tert-butyl N-(2-aminoethyl) carbamate (0.016 g, 0.016 mL, 0.1 mmol). The reaction mixture was heated in a microwave reactor at 80° C. for 2 hours and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (6.3 mg, 20%). $^1$H NMR (300 MHz, DMSO-$d_6$) δ 0.99 (d, J=6.25 Hz, 6 H) 1.34 (s, 9 H) 1.58 (m, 2 H) 1.68 (m, 1 H) 2.88 (m, 2 H) 2.97 (m, 2 H) 4.50 (m, 2 H) 6.75 (s, 1 H) 7.50 (m, 2 H) 7.60 (d, J=2.21 Hz, 1 H) 7.72 (d, J=8.82 Hz, 1 H) 7.87 (t, J=5.70 Hz, 1 H) 8.57 (dd, J=8.09, 1.84 Hz, 1 H) 8.90 (dd, J=4.41, 1.84 Hz, 1 H) 10.26 (s, 1 H) 14.09 (s, 1 H). MS (ESI−) m/z 648 (M−H)⁻.

EXAMPLE 459B

N-(2-aminoethyl)-N'-[3-(4-hydroxy-1-isopentyl-2-oxo-1,2-dihydro[1,8]naphthyridin-3-yl)-1,1-dioxido-4H-1,2,4-benzothiadiazin-7-yl]sulfamide A solution of the product of Example 459A (0.0053 g, 0.0082 mmol) in a solution of hydrogen chloride in 1,4-dioxane (4 N, 3 mL) and stirred at 25° C. and stirred for 18 hours. The solvent was removed under reduced pressure to give the title compound as the hydrochloride salt (4 mg, 89%). $^1$H NMR (300 MHz, DMSO-$d_6$) δ 0.99 (d, J=6.62 Hz, 6 H) 1.56 (m, 2 H) 1.68 (m, 1 H) 2.89 (m, 2 H) 3.10 (m, 2 H) 4.49 (m, 2 H) 7.51 (m, 2 H) 7.62 (d, J=2.21 Hz, 1 H) 7.74 (d, J=8.82 Hz, 1 H) 7.79 (s, 2 H) 8.03 (t, J=5.70 Hz, 1 H) 8.56 (dd, J=7.72, 1.84 Hz, 1 H) 8.89 (dd, J=4.41, 1.84 Hz, 1 H) 10.37 (s, 1 H) 14.16 (s, 1 H). MS (ESI−) m/z 548 (M−H)⁻.

EXAMPLE 460 ethyl 1-({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)-3-piperidinecarboxylate To the product of Example 435B (0.029 g, 0.05 mmol) in acetonitrile (2 mL) was added ethyl nipecotate (0.016 g, 0.016 mL, 0.1 mmol). The reaction mixture was heated in a microwave reactor at 80° C. for 2 hours, and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (20.3 mg, 63%). $^1$H NMR (300 MHz, DMSO-$d_6$) δ 0.98 (d, J=6.62 Hz, 6 H) 1.15 (t, J=7.17 Hz, 3 H) 1.45 (m, 2 H) 1.56 (m, 2 H) 1.68 (m, 2 H) 1.82 (m, 1 H) 2.88 (m, 1 H) 3.04 (m, 1 H) 3.63 (m, 1 H) 4.02 (m, 2 H) 4.49 (m, 2 H) 7.51 (dd, J=9.01, 2.39 Hz, 2 H) 7.57 (d, J=2.21 Hz, 1 H) 7.70 (d, J=8.46 Hz, 1 H) 8.56 (dd, J=8.09, 1.84 Hz, 1 H) 8.88 (d, J=3.68 Hz, 1 H) 10.52 (s, 1 H) 14.13 (s, 1 H). MS (ESI−) m/z 645 (M−H)⁻.

EXAMPLE 461A methyl (2S)-1-(chlorosulfonyl)-2-pyrrolidinecarboxylate

A solution of L-proline methyl ester hydrochloride (0.33 g, 0.002 mole) in toluene (5 ml), dichloromethane (2 ml) and triethylamine (0.6 ml, 0.004 mole) was added dropwise over a period of 3 minutes to a cold (−20° C.) solution of sulfuryl chloride (0.32 ml, 0.0039 mole) in toluene. The mixture was stirred an additional 45 minutes at −20° C. The reaction was filtered and the solvent was removed under reduced pressure to give the title compound (0.40 g). $^1$H NMR (300 MHz, CDCl$_3$) δ 2.13 (m, 2 H) 2.32 (m, 2 H) 3.58 (m, 1 H) 3.75 (m, 1 H) 3.79 (s, 3 H) 4.40 (dd, J=8.82, 4.04 Hz, 1 H).

EXAMPLE 461B methyl (2S)-1-({[3-(4-hydroxy-1-isopentyl-2-oxo-1,2-dihydro[1,8]naphthyridin-3-yl)-1,1-dioxido-4H-1,2,4-benzothiadiazin-7-yl]amino}sulfonyl)-2-pyrrolidinecarboxylate The product of Example 205 (0.030 g, 0.0703 mmol) in acetonitrile (2 ml) was treated with the product of Example 461A (0.018 g, 0.077 mmol) and triethylamine (0.011 ml, 0.077 mmol), stirred at 60° C. for 20 hours and cooled to about 25° C. The solvent was evaporated under reduced pressure, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (7 mg, 16%). $^1$H NMR (300 MHz, DMSO-$d_6$) δ 0.99 (d, J=6.25 Hz, 6 H) 1.59 (m, 2 H) 1.67 (m, 2 H) 1.87 (m, 4 H) 2.09 (d, J=8.46 Hz, 1 H) 3.60 (s, 3 H) 4.26 (dd, J=8.64, 3.86 Hz, 1 H) 4.50 (m, 2 H) 7.55 (m, 4 H) 7.73 (d, J=8.82 Hz, 1 H) 8.57 (dd, J=8.09, 1.84 Hz, 1 H) 8.90 (dd, J=4.78, 1.84 Hz, 1 H) 10.53 (s, 1 H) 14.07 (s, 1 H). MS (ESI−) m/z 617 (M−H)⁻.

EXAMPLE 462

N-[3-(4-hydroxy-1-isopentyl-2-oxo-1,2-dihydro[1,8]naphthyridin-3-yl)-1,1-dioxido-4H-1,2,4-benzothiadiazin-7-yl]-1-pyrrolidinesulfonamide The product of Example 435B (0.029 g, 0.05 mmol) in acetonitrile (2 mL) was treated with pyrrolidine (0.0076 g, 0.009 mL, 0.1 mmol). The reaction mixture was heated in a microwave reactor at 80° C. for 2 hours and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (2.6 mg, 9%). $^1$H NMR (300 MHz, DMSO-$d_6$) δ 0.98 (d, J=6.25 Hz, 6 H) 1.23 (s, 1 H) 1.55 (s, 1 H) 1.75 (m, 1 H) 2.51 (m, 4 H) 3.21 (t, J=6.62 Hz, 4 H) 4.48 (s, 2 H) 7.60 (s, 6 H) 8.53 (s, 1 H) 8.87 (s, 1 H) 10.35 (s, 1 H). MS (ESI–) m/z 559 (M–H)$^-$.

EXAMPLE 463

3-hydroxy-N-[3-(4-hydroxy-1-isopentyl-2-oxo-1,2-dihydro[1,8]naphthyridin-3-yl)-1,1-dioxido-4H-1,2,4-benzothiadiazin-7-yl]-1-piperidinesulfonamide To the product of Example 435B (0.029 g, 0.05 mmol) in acetonitrile (2 mL) was treated with 3-hydroxypiperidine hydrochloride (0.0079 g, 0.1 mmol) and triethylamine (0.00796 ml, 0.057 mmol). The reaction mixture was heated in a microwave reactor at 80° C. for 2 hours and cooled to about 25° C. The solvent was removed under a stream of warm nitrogen, and the residue was purified by reverse phase preparative HPLC on a Waters Symmetry C8 column (25 mm×100 mm, 7 μm particle size) using a gradient of 10% to 100% acetonitrile/10 mM ammonium acetate in water over 8 minutes (10 minutes run time) at a flow rate of 40 mL/min give the title compound (4.8 mg, 18%). $^1$H NMR (300 MHz, DMSO-$d_6$) δ 0.99 (d, J=6.62 Hz, 6 H) 1.18 (s, 1 H) 1.35 (s, 1 H) 1.59 (m, 2 H) 1.67 (d, J=34.56 Hz, 2 H) 2.71 (s, 4 H) 3.51 (s, 4 H) 4.50 (m, 2 H) 7.51 (m, 2 H) 7.58 (m, 1 H) 7.72 (d, J=8.82 Hz, 1 H) 8.57 (dd, J=8.09, 1.84 Hz, 1 H) 8.90 (dd, J=4.60, 1.65 Hz, 1 H) 10.46 (s, 1 H) 14.08 (s, 1 H). MS (ESI–) m/z 589 (M–H)$^-$.

EXAMPLE 464A tert-butyl 3-[1-(cyclobutylamino)-4-hydroxy-2-oxo-1,2-dihydro-3-quinolinyl]-1,1-dioxido-4H-1,2,4-benzothiadiazin-7-ylcarbamate A mixture of the product of Example 432B (1.25 g, 3.74 mmol) and the product of Example 414A (1.06 g, 3.7 mmol) in anhydrous dioxane (50 mL) was heated at reflux for 3 hours, cooled to 25° C., and concentrated under reduced pressure. The residue was triturated in hot 3:1 hexane/ethyl acetate (30 mL), cooled, and the solid was collected by filtration and dried to provide the title compound (1.5 g, 76% yield).

EXAMPLE 464B 3-(7-amino-1,1-dioxido-4H-1,2,4-benzothiadiazin-3-yl)-1-(cyclobutylamino)-4-hydroxy-2(1H)-quinolinone A slurry of the product of Example 464A (1.5 g, 2.85 mmol) in dichloromethane (10 mL) at 0° C. was treated dropwise with 6 mL of trifluoroacetic acid, stirred at 25° C. for 2 hours and concentrated under reduced pressure. The residue was dissolved in ethyl acetate, washed with 10% aqueous sodium bicarbonate (3×50 mL), washed with brine, dried over sodium sulfate, filtered and concentrated under reduced pressure to provide the title compound (1.1 g, 91% yield).

EXAMPLE 464C

N-{1,3-[1-(cyclobutylamino)-4-hydroxy-2-oxo-1,2-dihydro-3-quinolinyl]-1,1-dioxido-4H-1,2,4-benzothiadiazin-7-yl}ethanesulfonamide A solution of the product of Example 464B (0.0425 g, 0.1 mmol) in pyridine (300 μL) was treated dropwise with ethane sulfonyl chloride (0.026 mg, 0.2 mmol), stirred for 1 hour at 25° C. and concentrated under reduced pressure. The residue was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 mL/minute to provide the title compound (0.020 g, 39% yield). $^1$H NMR (300 MHz, DMSO-$d_6$) δ 1.23 (t, J=7.17 Hz, 3 H) 1.56 (m, 1 H) 1.70 (m, 1 H) 2.05 (m, 4 H) 3.19 (q, J=7.35 Hz, 2 H) 3.77 (m, 1 H) 6.56 (s, 1 H) 7.44 (t, J=7.54 Hz, 1 H) 7.60 (dd, J=8.82, 2.21 Hz, 1 H) 7.67 (m, 2 H) 7.89 (m, 1 H) 8.06 (d, J=8.46 Hz, 1 H) 8.17 (d, J=8.09 Hz, 1 H) 10.33 (s, 1 H) 14.16 (s, 1 H) 15.03 (br. s., 1 H). MS (ESI$^-$) m/z 516 (M–H)$^-$.

EXAMPLE 465 benzyl 3-{3-[1-(cyclobutylamino)-4-hydroxy-2-oxo-1,2-dihydro-3-quinolinyl]-1,1-dioxido-4H-1,2,4-benzothiadiazin-7-yl}diazathiane-1-carboxylate 2,2-dioxide A solution of chlorosulfonyl isocyanate (0.051 g, 0.36 mmol) in dichloromethane (2 mL) was treated dropwise with benzyl alcohol (0.039 g, 0.36 mmol) at 0° C., stirred at 25° C. for 30 minutes and treated with a solution of the product of Example 464B (0.127 g, 0.03 mmol) and triethylamine (0.12 g, 1.2 mmol) in dichloromethane (4 mL). The reaction mixture was stirred for 2 hours at 25° C. and partitioned between dichloromethane (10 mL) and 1N aqueous hydrochloric acid (10 mL). The resulting organic layer was separated, dried over sodium sulfate, filtered, and concentrated under reduced pressure. The residue was chromatographed on silica gel eluting with 3% methanol in dichloromethane to provide the title compound (0.127 g, 66% yield). $^1$H NMR (300 MHz, DMSO-$d_6$) δ 1.57 (m, 1 H) 1.70 (m, 1 H) 2.04 (m, 4 H) 3.78 (m, 1 H) 5.12 (s, 2 H) 6.57 (s, 1 H) 7.30 (m, 5 H) 7.44 (t, J=7.54 Hz, 1 H) 7.50 (m, 1 H) 7.66 (m, 2 H) 7.89 (t, J=7.91 Hz, 1 H) 8.07 (d, J=8.09 Hz, 1 H) 8.17 (d, J=8.46 Hz, 1 H) 11.13 (s, 1 H) 12.16 (s, 1 H) 14.15 (s, 1 H) 15.06 (s, 1 H). MS (ESI$^-$) m/z 637 (M–H)$^-$.

EXAMPLE 466A benzyl 3-{3-[1-(cyclobutylamino)-4-hydroxy-2-oxo-1,2-dihydro-3-quinolinyl]-1,1-dioxido-4H-1,2,4-benzothiadiazin-7-yl}-1-methyldiazathiane-1-carboxylate 2,2-dioxide A solution of the product of Example 465 (0.045 g, 0.07 mmol) in 1:1 tetrahydrofuran/methanol (2 ml) at –10° C. was treated dropwise with trimethylsilyl diazomethane (2.0 M in hexanes, 70 μL, 0.14 mmol), stirred at 25° C. for 16 hours and concentrated under reduced pressure to provide the title compound (0.045 g, 98% yield).

EXAMPLE 466B

N-{3-[1-(cyclobutylamino)-4-hydroxy-2-oxo-1,2-dihydro-3-quinolinyl]-1,1-dioxido-4H-1,2,4-benzothiadiazin-7-yl}-N'-methylsulfamide A solution of the product of Example 466A (0.045 g, 0.069 mmol) in tetrahydrofuran (8 mL) and methanol (2 mL) was treated with 10% palladium on carbon (20 mg) and stirred for 24 hours at 25° C. under a hydrogen atmosphere. The resulting solution was filtered through Celite® (diatomaceous earth) and the filtrate concentrated under reduced pressure. The residue was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 mL/minute to provide the title compound (0.006 g, 17% yield). $^1$H NMR (300 MHz, DMSO-$d_6$) δ 1.55 (m, 1 H) 1.69 (m, 1 H) 2.03 (m, 4 H) 3.78 (m, 1 H) 6.55 (s, 1 H) 7.40 (d, J=5.52 Hz, 1 H) 7.45 (m, 1 H) 7.52 (dd, J=8.82, 2.57 Hz, 1 H) 7.65 (m, 2 H) 7.88 (t, J=7.91 Hz, 1 H) 8.07 (d, J=8.46 Hz, 1 H) 8.16 (d, J=6.99 Hz, 1 H) 10.24 (s, 1 H) 14.11 (s, 1 H) 15.11 (s, 1 H). MS (ESI$^-$) m/z 517 (M–H)$^-$.

EXAMPLE 467

N-{3-[1-(cyclobutylamino)-4-hydroxy-2-oxo-1,2-dihydro-3-quinolinyl]-1,1-dioxido-4H-1,2,4-benzothiadiazin-7-yl}sulfamide A solution of the product of Example 465 (0.790 g, 1.2 mmol) in tetrahydrofuran (80 mL) and methanol (20 mL) was treated with 10% palladium on carbon (200 mg) and stirred for 24 hours at 25° C. under a hydrogen atmosphere. The reaction was filtered through Celite® (diatomaceous earth) and the filtrate concentrated under reduced pressure to provide the title compound (0.500 g, 83% yield). $^1$H NMR (300 MHz, DMSO-$d_6$) δ 1.58 (m, 1 H) 1.67 (m, 1 H) 2.03 (m, 4 H) 3.78 (m, 1 H) 6.56 (s, 1 H) 7.39 (s, 2 H) 7.44 (t, J=7.54 Hz, 1 H) 7.52 (m, 1 H) 7.64 (m, 2 H) 7.89 (t, J=7.91 Hz, 1 H) 8.07 (d, J=8.82 Hz, 1 H) 8.17 (d, J=8.46 Hz, 1 H) 10.06 (s, 1 H) 14.09 (s, 1 H) 15.14 (s, 1 H). MS (ESI$^-$) m/z 503 (M–H)$^-$.

EXAMPLE 468A 4-(benzyloxy)-1-(cyclobutylmethyl)-2(1H)-pyridinone

A solution of 4-benzyloxy-1H-pyridin-2-one (0.60 g, 2.98 mmol) in N,N-dimethylacetamide (10 mL) at 0° C. was treated with sodium hydride (0.086 g, 3.58 mmol) for 30 min, then bromomethyl cyclobutane (0.40 mL, 3.58 mmol) was added and the mixture was stirred at 25° C. for 48 hours. The solution was partitioned between 10% aqueous ammonium chloride solution and dichloromethane, the organic layer was separated, concentrated under reduced pressure and the residue was chromatographed on silica gel, eluting with 1% methanol in dichloromethane to provide the title compound (0.426 g, 53%).

EXAMPLE 468B 1-(cyclobutylmethyl)-4-hydroxy-2(1H)-pyridinone

A solution of the product of Example 468A (0.426 g, 1.58 mmol) in tetrahydrofuran (20 mL) was treated with ammonium formate (0.38 g, 6.03 mmol) and a catalytic amount of 20% palladium hydroxide on carbon at 70° C. for 2 hours. The reaction mixture was cooled to about 25° C., filtered through diatomaceous earth and the filtrate concentrated under reduced pressure to provide the title compound (0.244 g, 86%).

EXAMPLE 468C

3-[bis(methylsulfanyl)methylene]-1-(cyclobutylmethyl)-2,4(1H,3H)-pyridinedione

A solution of the product of Example 468B (0.244 g, 1.36 mmol) and pyridine (0.88 mL, 10.89 mmol) in dioxane (6 mL) was treated with excess tris(methylthio)methyl methyl sulfate (prepared using the procedures in *Synthesis*, 22-25, 1988; M. Barbero, S. Cadamuro, I. Degani, R. Fochi, A. Gatti, V. Regondi), stirred at 90° C. for 1.5 hours, and cooled to about 25° C. The reaction solution was decanted from the resulting solids and the solvent was removed under a stream of warm nitrogen. The residue was dissolved in hexanes and loaded onto a 2 g Alltech Seppack and eluted with hexanes followed by dichloromethane followed by 25% ethyl acetate in dichloromethane to provide the title compound (0.192 g, 50%).

EXAMPLE 468D

N-{3-[1-(cyclobutylmethyl)-4-hydroxy-2-oxo-1,2-dihydro-3-pyridinyl]-1,1-dioxido-4H-1,2,4-benzothiadiazin-7-yl}methanesulfonamide A solution of the product of Example 468C (0.050 g, 0.176 mmol) in dioxane (5 mL) was treated with the product of Example 425D (0.030 g, 0.113 mmol), stirred at 110° C. for 1 hour, and cooled to 25° C. The solid precipitate was collected by filtration and dried to provide the title compound (0.018 g, 35%). $^1$H NMR (300 MHz, DMSO-$d_6$) δ 1.88 (m, 6 H) 2.74 (dt, J=15.17, 7.68 Hz, 1 H) 3.08 (s, 3 H) 4.03 (d, J=7.35 Hz, 2 H) 6.32 (d, J=7.72 Hz, 1H) 7.56 (dd, J=8.82, 2.57 Hz, 1 H) 7.62 (d, J=2.21 Hz, 1 H) 7.66 (m, 1 H) 8.06 (d, J=7.35 Hz, 1 H) 10.24 (s, 1 H) 13.83 (s, 1 H) 14.28 (s, 1 H). MS (ESI–) m/z 451 (M–H)$^-$.

EXAMPLE 469

N-{3-[5-bromo-1-(cyclobutylmethyl)-4-hydroxy-2-oxo-1,2-dihydro-3-pyridinyl]-1,1-dioxido-4H-1,2,4-benzothiadiazin-7-yl}methanesulfonamide A solution of the product of Example 468D (0.030 g, 0.066 mmol) in tetrahydrofuran (2 mL) was treated with 1,3-dibromo-5,5-dimethyl-hydantoin (0.015 g, 0.052 mmol) at 25° C. for 18 hours. The reaction was concentrated under a warm stream of nitrogen and the residue was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 mL/min to provide the title compound (0.008 g, 23%). $^1$H NMR (300 MHz, DMSO-$d_6$) δ 1.83 (m, 4 H) 1.95 (m, 2 H) 2.75 (m, 1 H) 3.08 (s, 3H) 4.03 (d, J=6.99 Hz, 2 H) 7.56 (dd, J=9.01, 2.39 Hz, 1 H) 7.62 (d, J=2.21 Hz, 1 H) 7.67 (d, J=8.82 Hz, 1 H) 8.55 (s, 1 H) 10.24 (s, 1 H) 14.35 (s, 1 H). MS (ESI–) m/z 530 (M–H)$^-$.

EXAMPLE 470A

N-[3-(4-hydroxy-1-isopentyl-2-oxo-1,2-dihydro-3-pyridinyl)-1,1-dioxido-4H-1,2,4-benzothiadiazin-7-yl]methanesulfonamide A solution of the product of Example 457C (0.195 g, 0.68 mmol) in dioxane (10 mL) was reacted with the product of Example 425D (0.17 g, 0.64 mmol) at 115° C. for 1 hour.

After cooling to about 25° C., the solid precipitate was collected by filtration and dried to provide the title compound (0.258 g, 89%). $^1$H NMR (300 MHz, DMSO-d$_6$) δ 0.93 (d, J=6.25 Hz, 6 H) 1.58 (m, 3 H) 3.08 (s, 3 H) 3.99 (m, 2 H) 6.33 (d, J=6.62 Hz, 1 H) 7.57 (m, 2 H) 7.67 (d, J=8.82 Hz, 1 H) 8.07 (d, J=6.62 Hz, 1 H) 10.25 (s, 1 H) 13.84 (s, 1 H) 14.28 (s, 1 H). MS (ESI−) m/z 453 (M−H)$^−$.

EXAMPLE 470B

N-[3-(5-bromo-4-hydroxy-1-isopentyl-2-oxo-1,2-dihydro-3-pyridinyl)-1,1-dioxido-4H-1,2,4-benzothiadiazin-7-yl]methanesulfonamide A solution of the product of Example 470A (0.258 g, 0.57 mmol) in tetrahydrofuran (10 mL) was treated with 1,3-dibromo-5,5-dimethyl hydantoin (0.24 g, 0.84 mmol) at 25° C. for 18 hours. The solvent was under a warm stream of nitrogen and the residue was chromatographed on silica gel eluting with dichloromethane to provide the title compound (0.13 g, 43%). $^1$H NMR (300 MHz, DMSO-d$_6$) δ 0.94 (d, J=6.25 Hz, 6 H) 1.61 (m, 3 H) 3.08 (s, 3 H) 4.00 (m, 2 H) 7.56 (dd, J=8.82, 2.21 Hz, 1 H) 7.63 (d, J=2.21 Hz, 1 H) 7.70 (m, 1 H) 8.59 (s, 1 H) 10.26 (s, 1 H) 14.29 (s, 1 H). MS (ESI−) m/z 532 (M−H)$^−$.

EXAMPLE 470C

N-[3-(4-hydroxy-1-isopentyl-2-oxo-5-vinyl-1,2-dihydro-3-pyridinyl)-1,1-dioxido-4H-1,2,4-benzothiadiazin-7-yl]methanesulfonamide The product of Example 470B (0.027 g, 0.051 mmol) and tributyl(vinyl)tin (0.015 mL, 0.051 mmol) in tetrahydrofuran and a catalytic amount of dichlorobis(triphenyl phospine) palladium(II) were reacted at 75° C. for 20 hours. The solution was cooled to about 25° C. and concentrated. The residue was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 mL/min to provide the title compound (0.005 g, 21%). $^1$H NMR (300 MHz, DMSO-d$_6$) δ 0.95 (d, J=5.88 Hz, 6 H) 1.61 (m, 3 H) 3.08 (s, 3 H) 4.05 (m, 2 H) 5.32 (d, J=11.03 Hz, 1 H) 5.87 (d, J=18.02 Hz, 1 H) 6.64 (m, 1 H) 7.64 (m, 3 H) 8.42 (s, 1 H) 10.26 (s, 1 H) 14.42 (s, 1 H) 14.67 (s, 1 H). (ESI−) m/z 479 (M−H)$^−$.

EXAMPLE 471

N-(2-furylmethyl)-3-[3-(4-hydroxy-1-isopentyl-2-oxo-1,2-dihydro[1,8]naphthyridin-3-yl)-1,1-dioxido-4H-1,2,4-benzothiadiazin-7-yl]diazathiane-1-carboxamide 2,2-dioxide A solution of chlorosulfonyl isocyanate (4.9 µL, 0.0562 mmol) in dichloromethane (2 mL) was treated dropwise with furfurylamine (5 µL, 0.0562 mmol) at 25° C., stirred at 25° C. for 30 min, treated with a solution of product of Example 205 (20 mg, 0.0468 mmol) and triethylamine (26 µL, 0.187 mmol) in dichloromethane (2 mL) and stirred for 24 hours at 25° C. The reaction mixture was partitioned between dichloromethane (10 mL) and 1N aqueous hydrochloric acid (10 mL). The resulting organic layer was separated, dried over magnesium sulfate, filtered, and concentrated under reduced pressure to provide the title compound (15%). MS m/z 630 (M+H)$^+$.

The following additional compounds of the present invention, can be prepared by one skilled in the art using known synthetic methodology or by using synthetic methodology described in the Schemes and Examples contained herein. The additional compounds encompassed by the following tables can be described by taking one core from Table 1, one R$^1$ substituent from Table 2 (wherein X$_1$ represents the Core Ring Structure), one or two Y$^3$ substituent from Table 4, and when needed Y$_1$ and/or Y$_2$ substituent from Table 3.

TABLE 1

Examples of Core Ring Structures

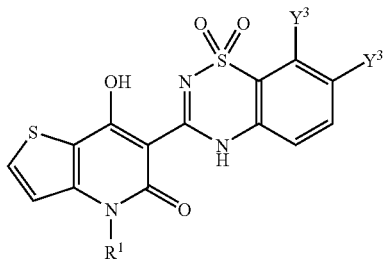

1

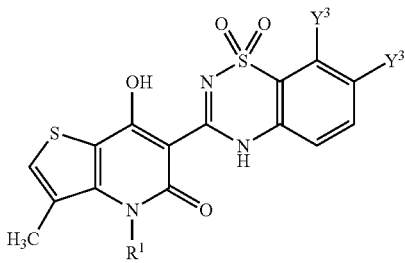

2

TABLE 1-continued
Examples of Core Ring Structures
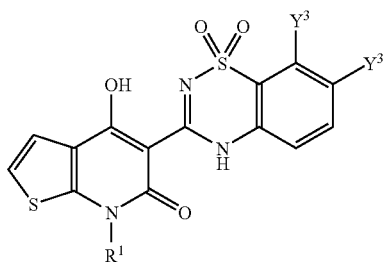
3
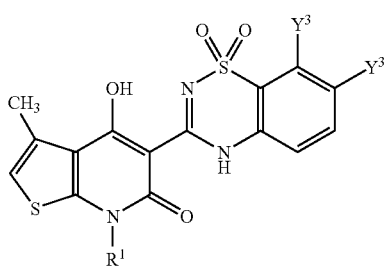
4
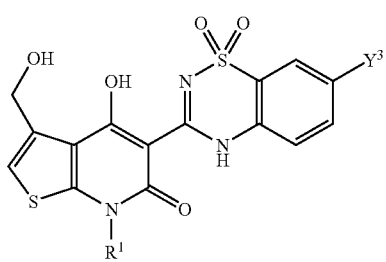
5
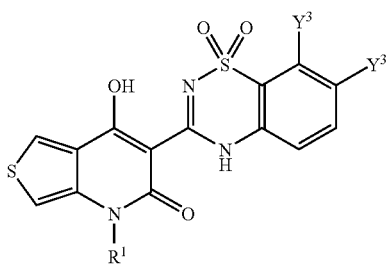
6
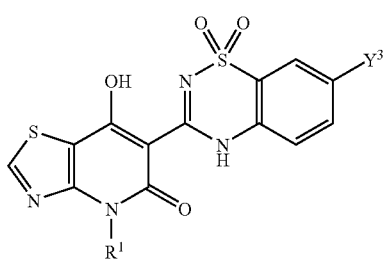
7

TABLE 1-continued
Examples of Core Ring Structures
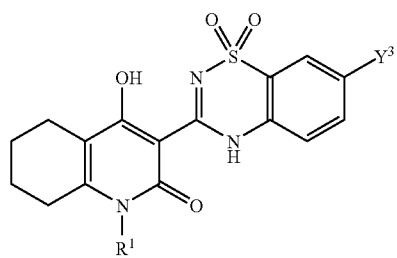
8
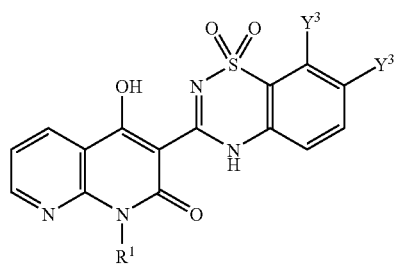
9
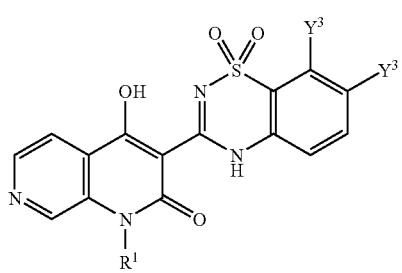
10
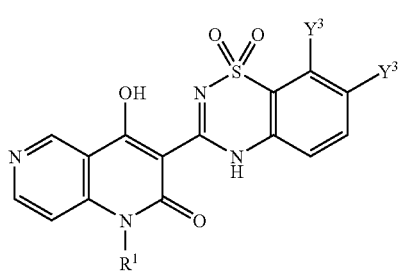
11
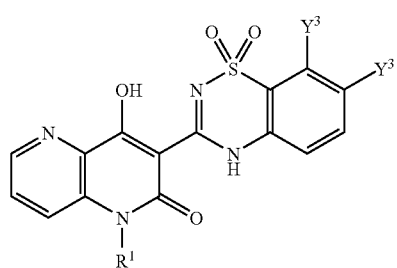
12

TABLE 1-continued
Examples of Core Ring Structures
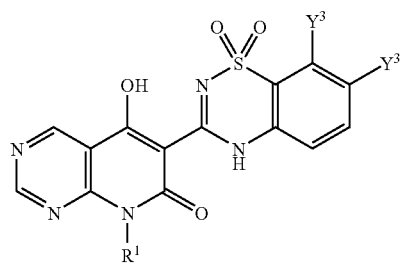
13
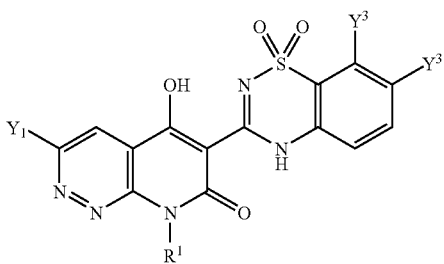
14
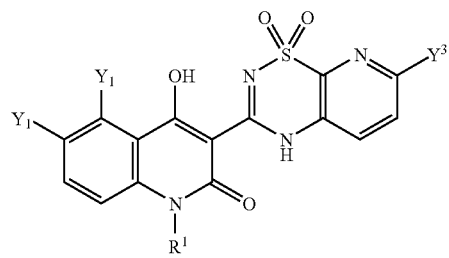
15
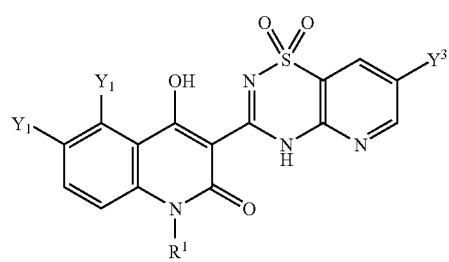
16
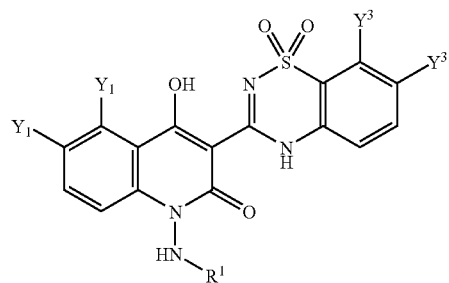
17

TABLE 1-continued
Examples of Core Ring Structures
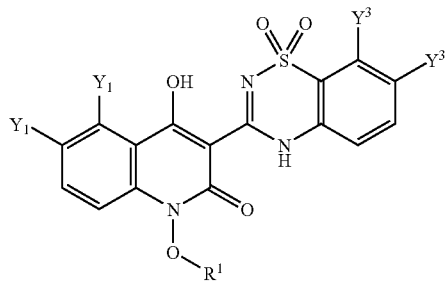
18
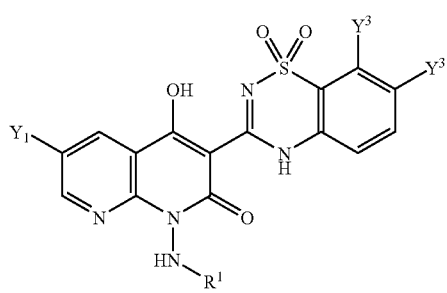
19
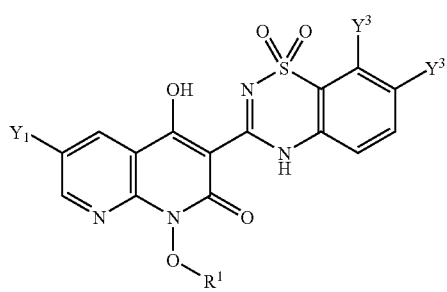
20
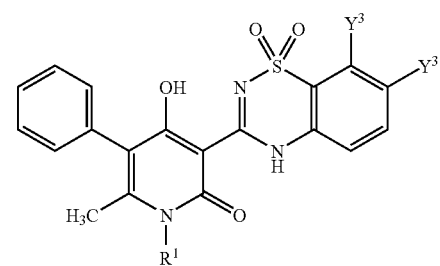
21
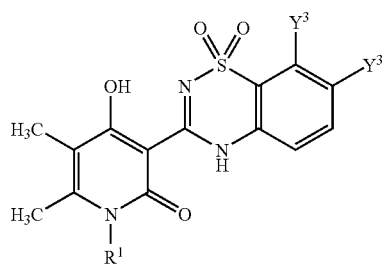
22

TABLE 1-continued
Examples of Core Ring Structures
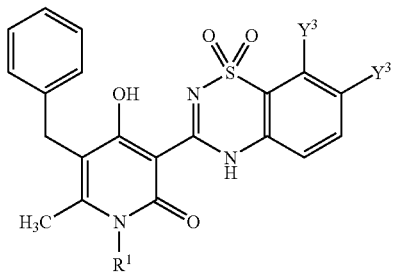
23
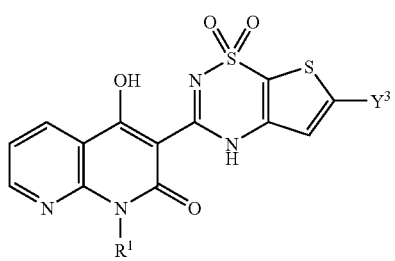
24
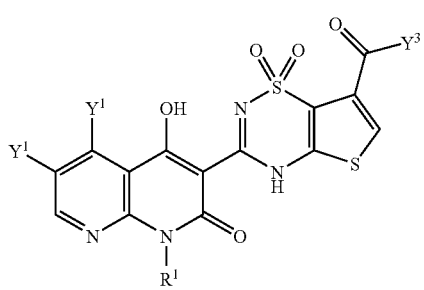
25
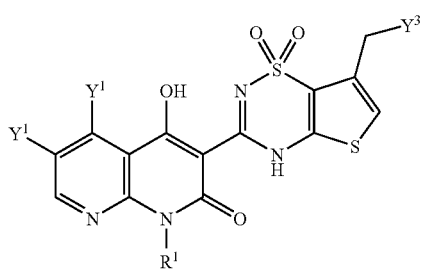
26
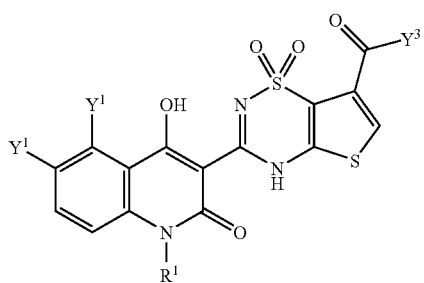
27

TABLE 1-continued
Examples of Core Ring Structures
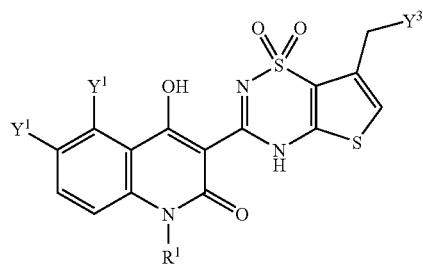
28
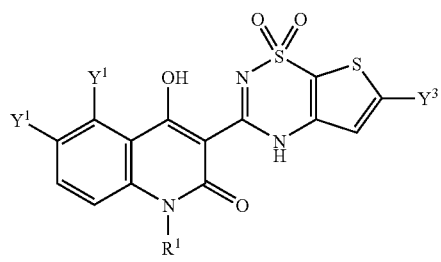
29
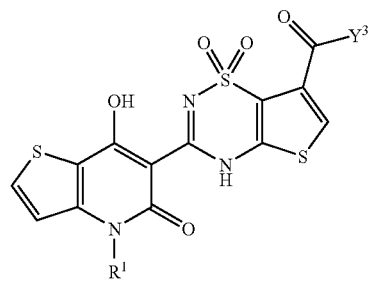
30
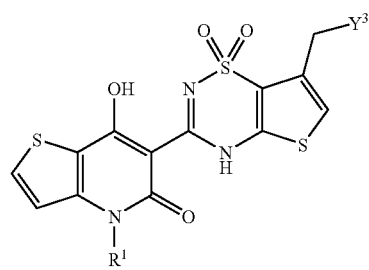
31
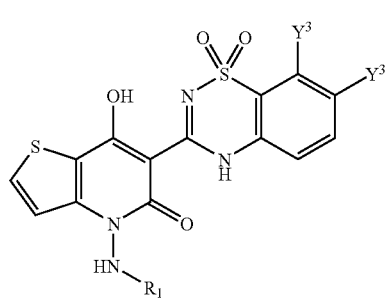
32

TABLE 1-continued
Examples of Core Ring Structures
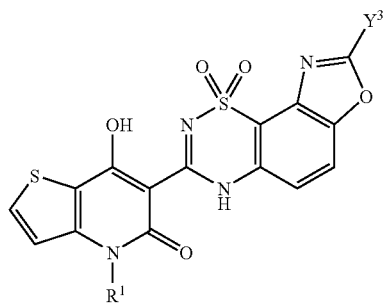
33
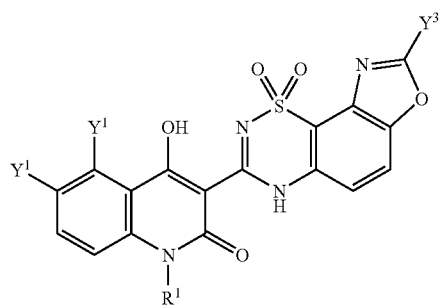
34
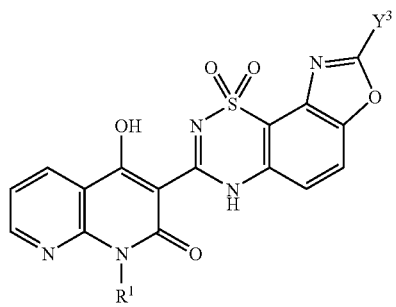
35
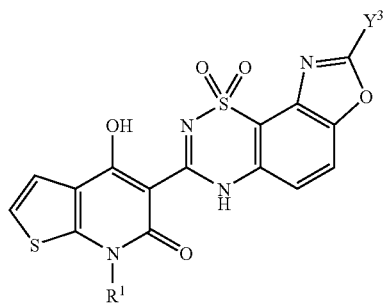
36

TABLE 1-continued
Examples of Core Ring Structures
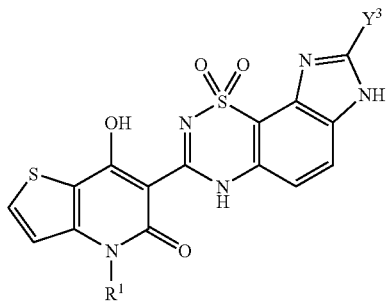
37
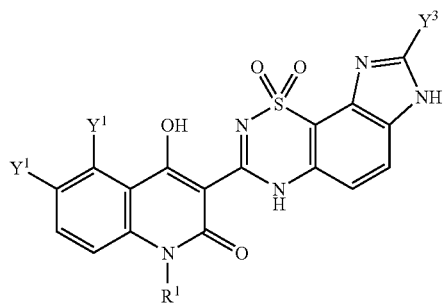
38
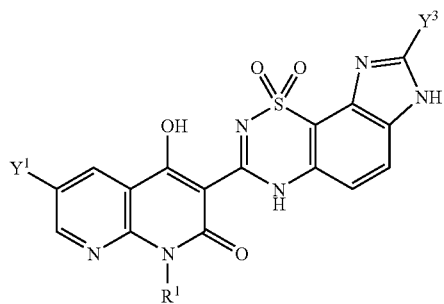
39
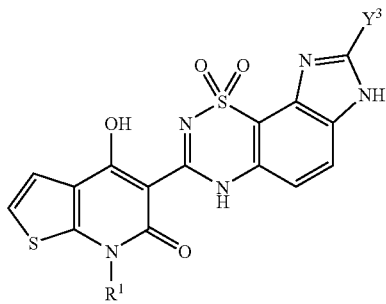
40

TABLE 1-continued
Examples of Core Ring Structures
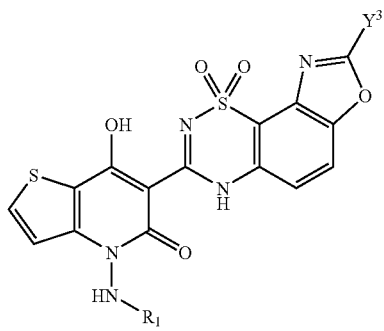
41
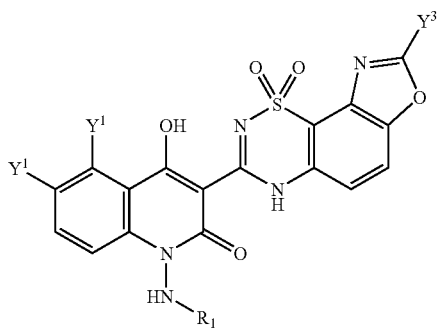
42
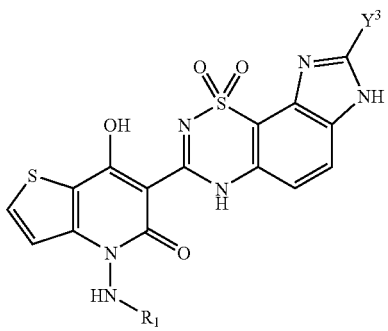
43
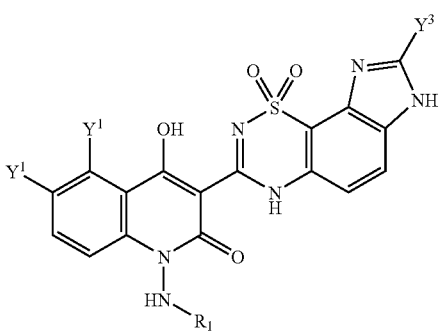
44

TABLE 1-continued
Examples of Core Ring Structures
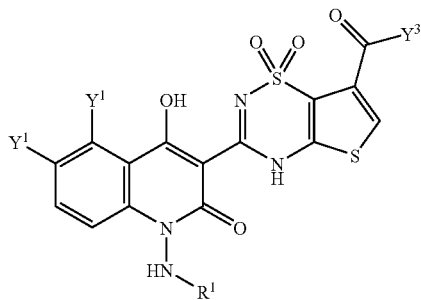
45
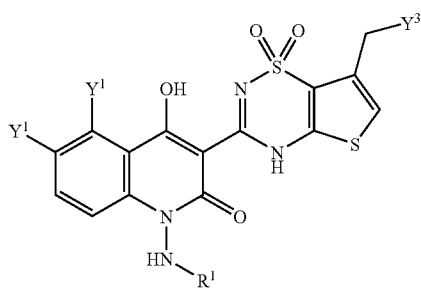
46
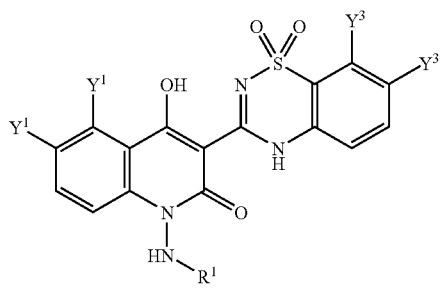
47
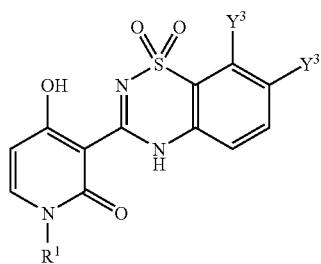
48

TABLE 1-continued
Examples of Core Ring Structures
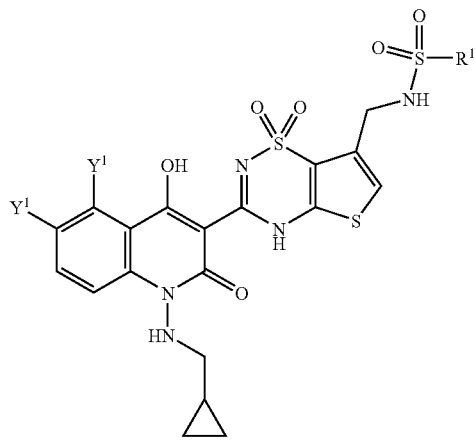
49
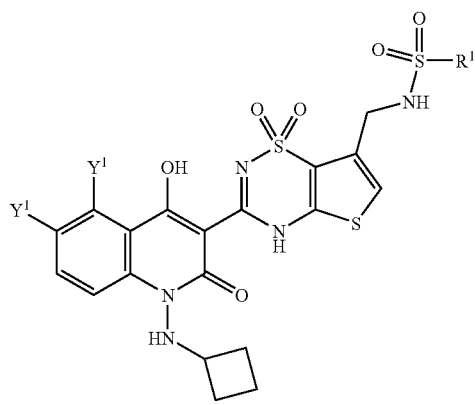
50
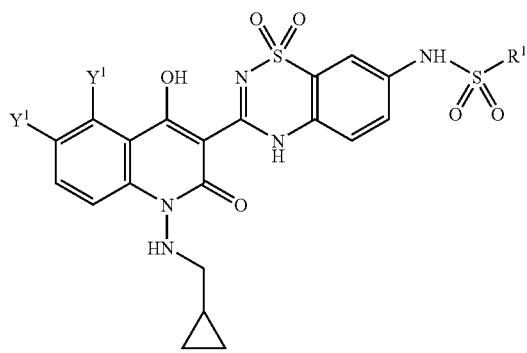
51

TABLE 1-continued
Examples of Core Ring Structures
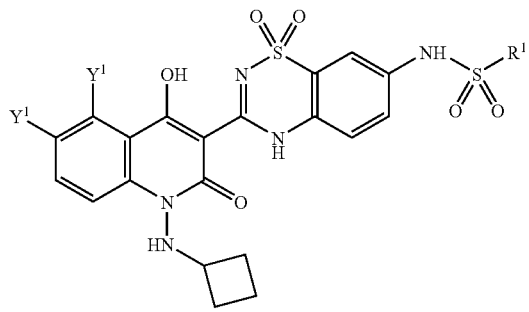
52
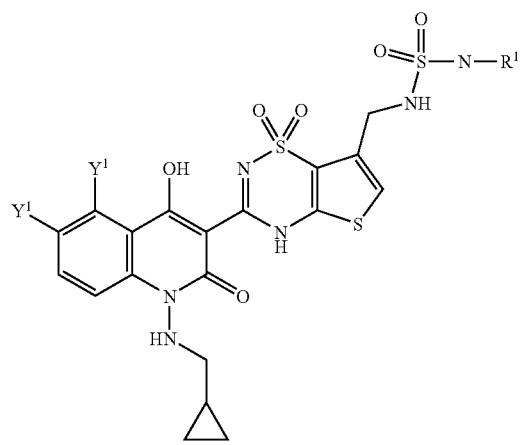
53
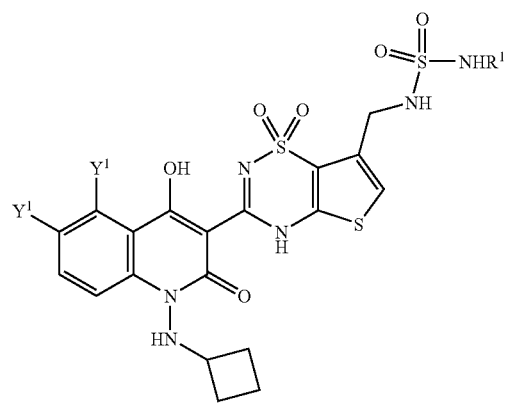
54

TABLE 1-continued
Examples of Core Ring Structures
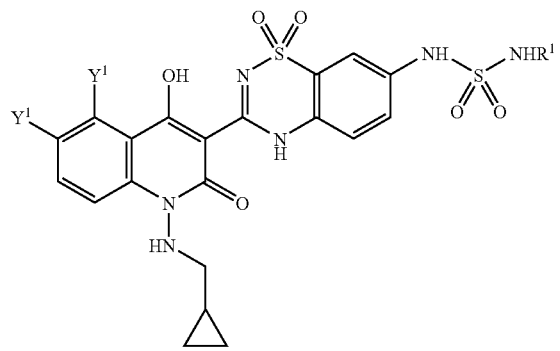
55
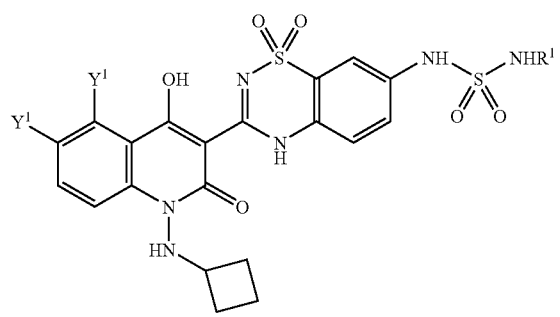
56
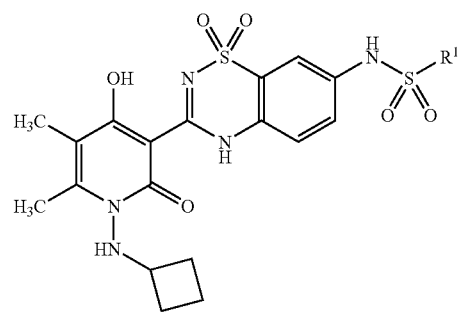
57
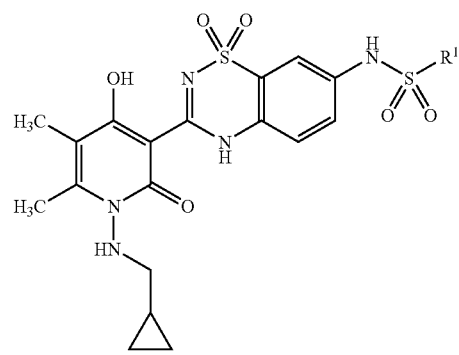
58

TABLE 1-continued
Examples of Core Ring Structures
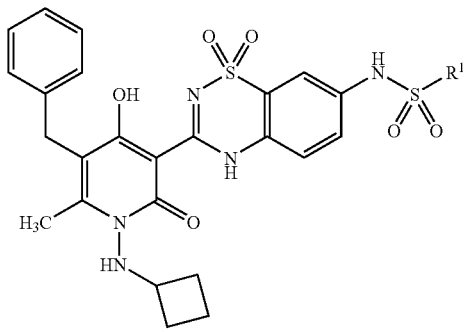
59
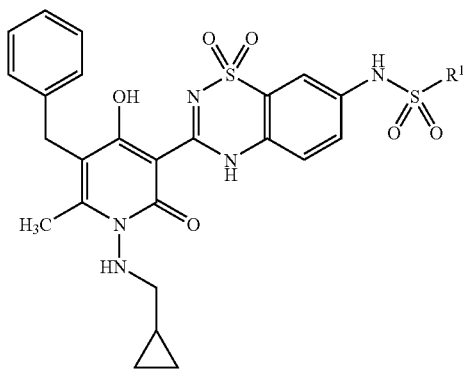
60
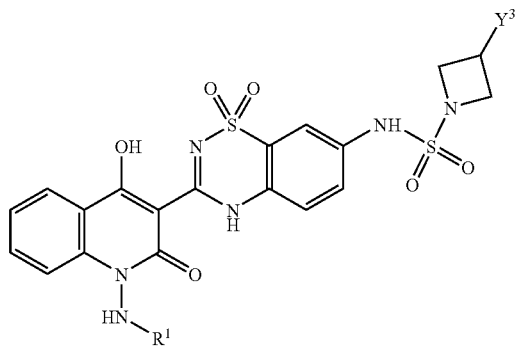
61
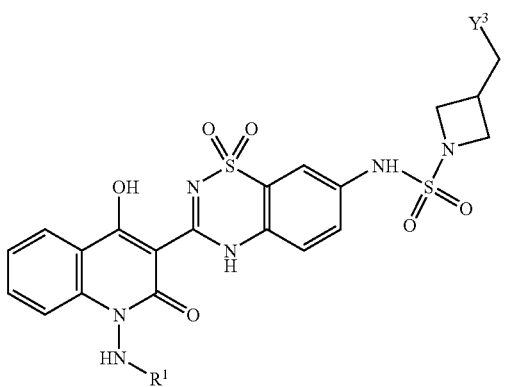
62

TABLE 1-continued
Examples of Core Ring Structures
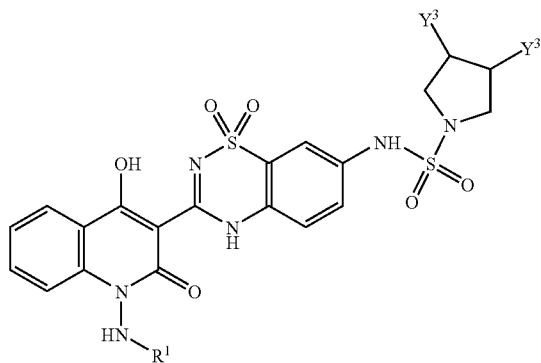
63
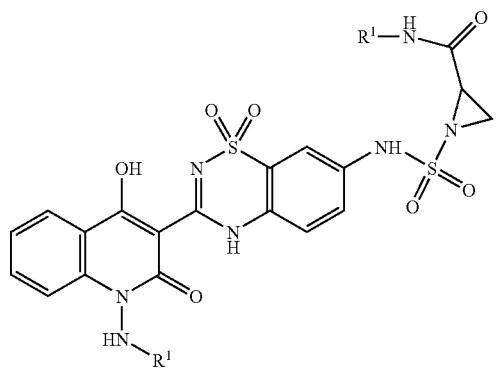
64
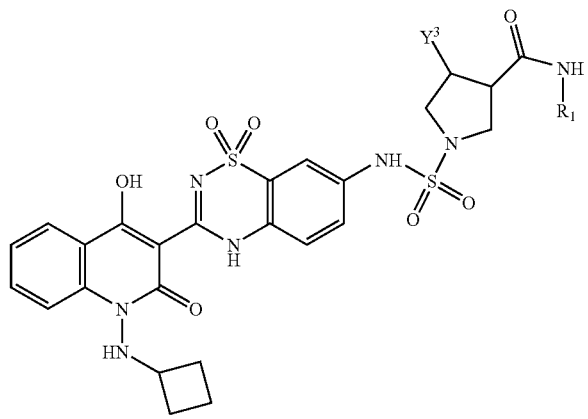
65

TABLE 1-continued
Examples of Core Ring Structures
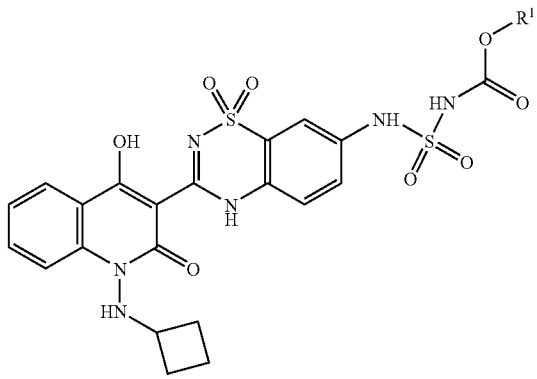
66
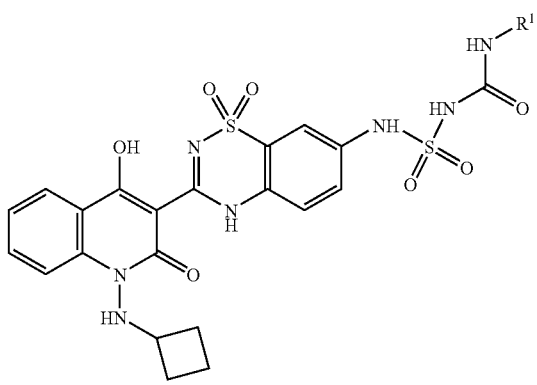
67
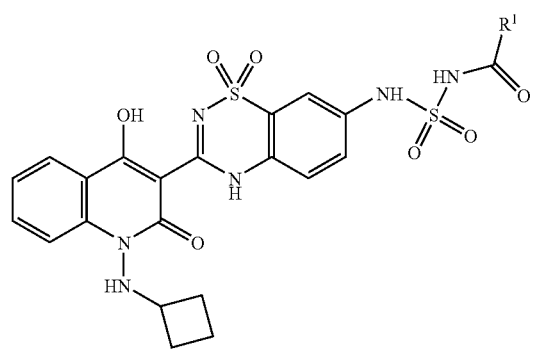
68

TABLE 1-continued
Examples of Core Ring Structures
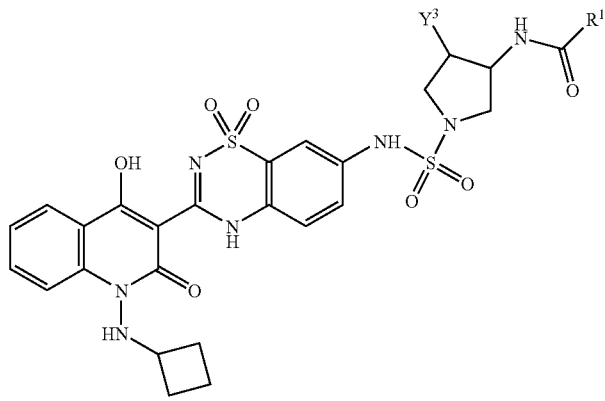
69
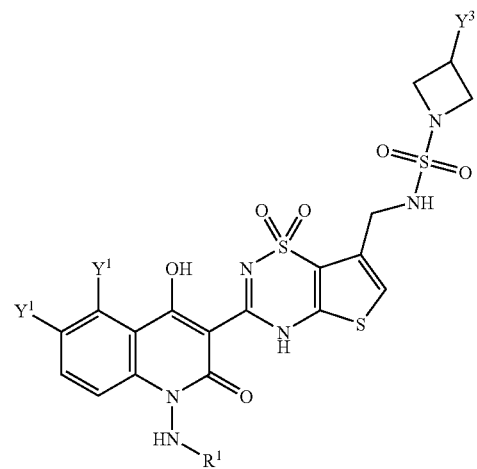
70
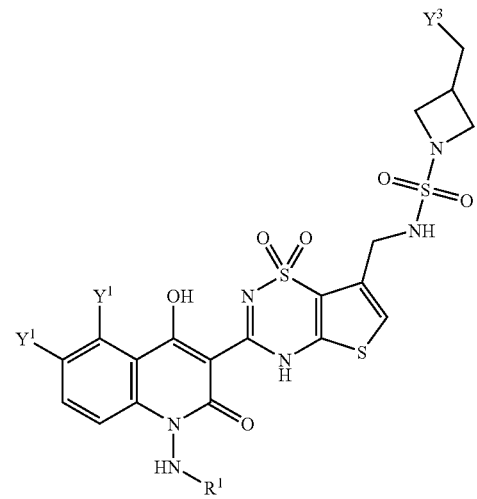
71

TABLE 1-continued
Examples of Core Ring Structures
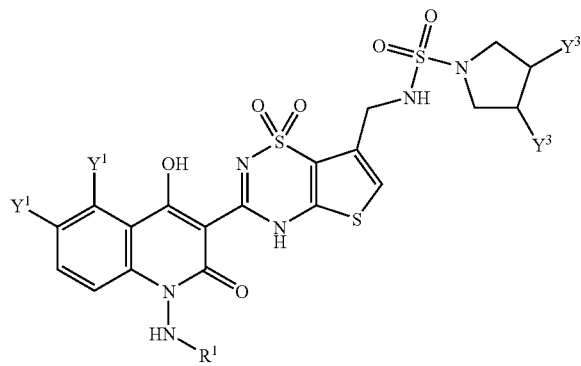
72
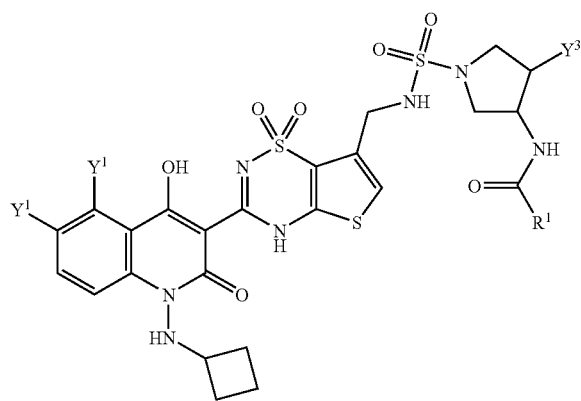
73
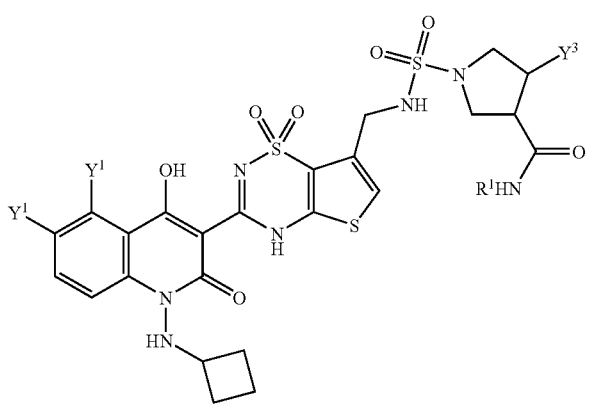
74

TABLE 1-continued
Examples of Core Ring Structures
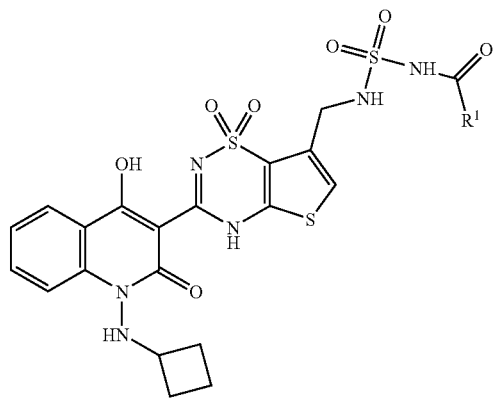
75
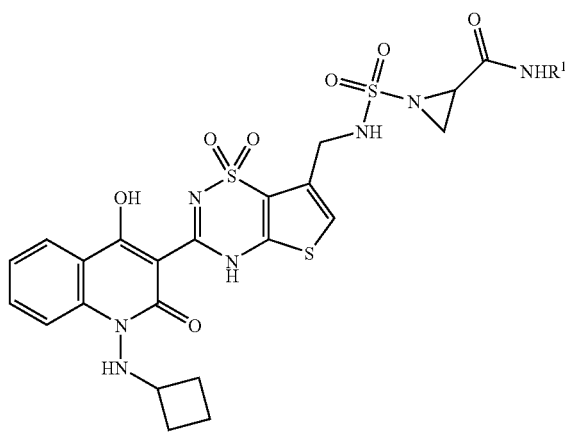
76
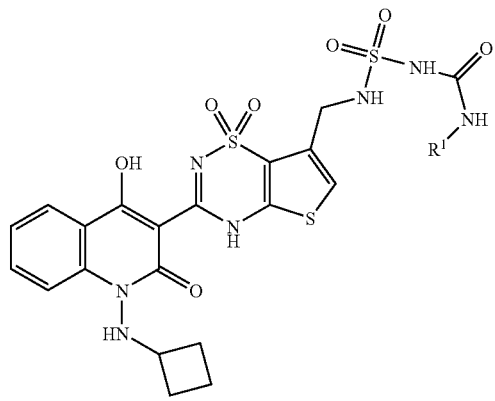
77

TABLE 1-continued
Examples of Core Ring Structures
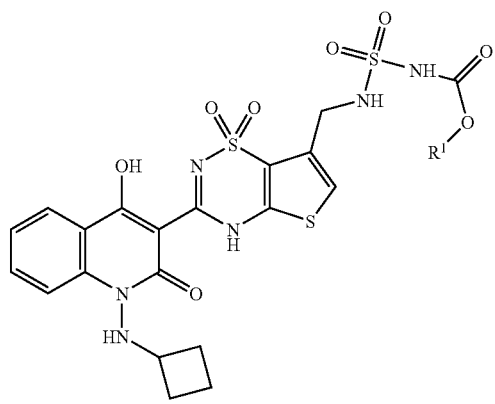
78
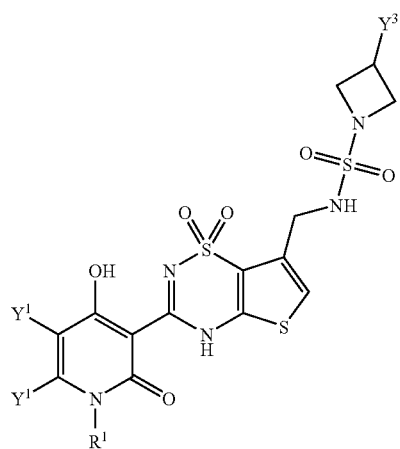
79
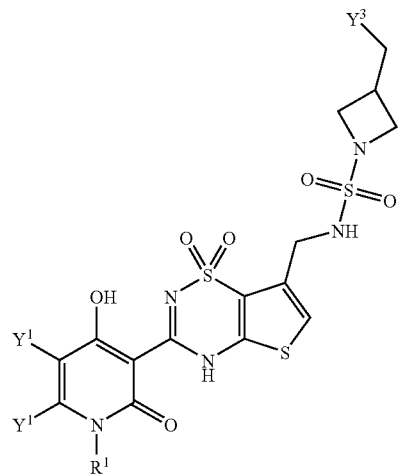
80

TABLE 1-continued
Examples of Core Ring Structures
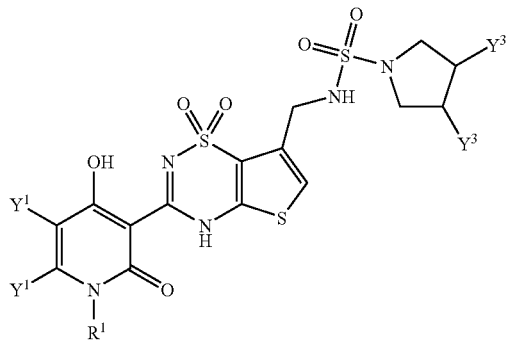
81
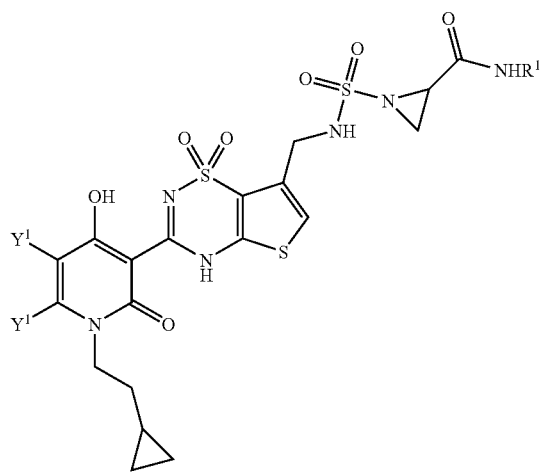
82
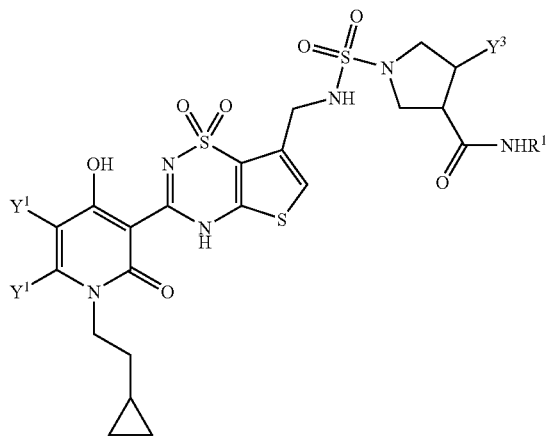
83

TABLE 1-continued
Examples of Core Ring Structures
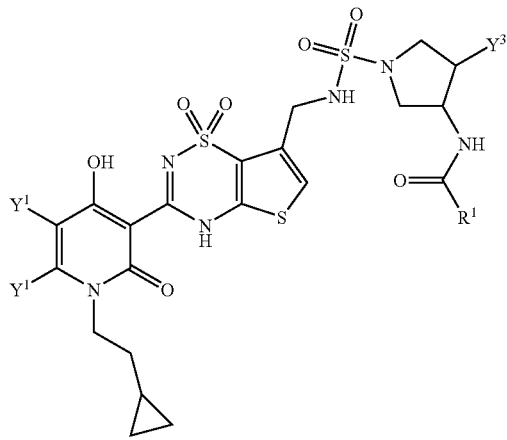
84
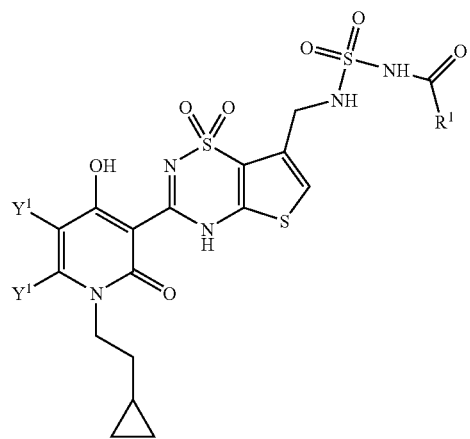
85
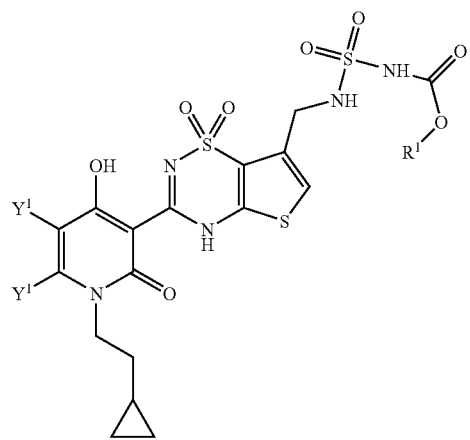
86

413 414
TABLE 1-continued
Examples of Core Ring Structures
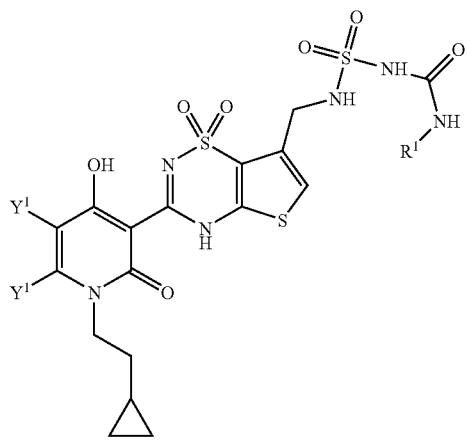
87
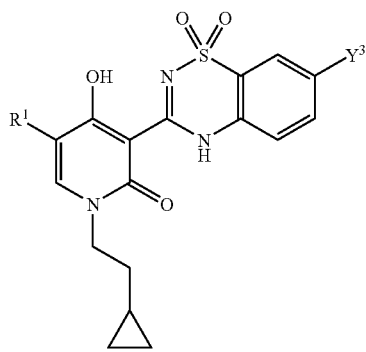
88
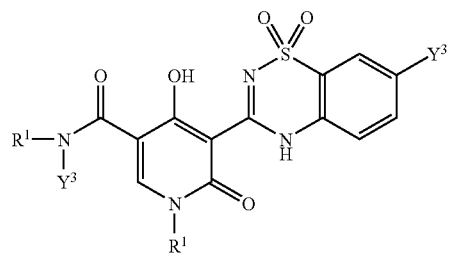
89
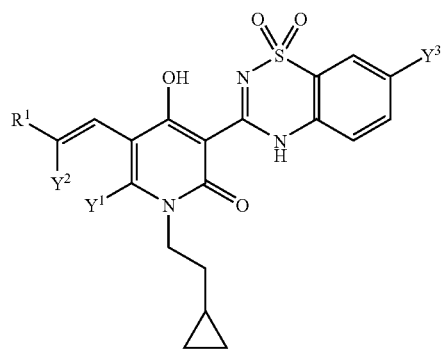
90

TABLE 1-continued
Examples of Core Ring Structures
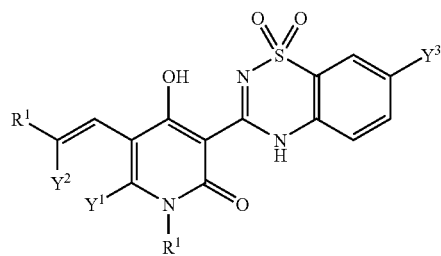
91
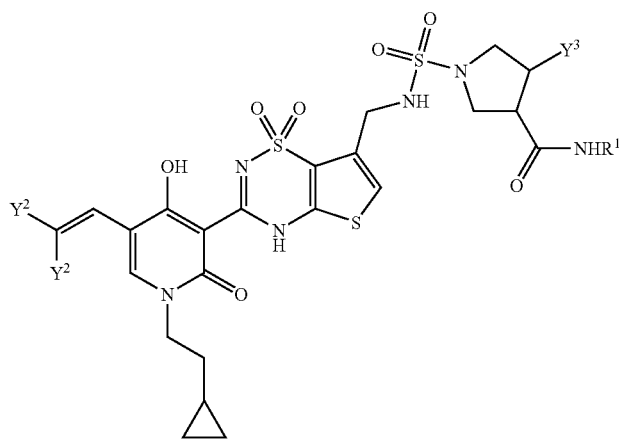
92
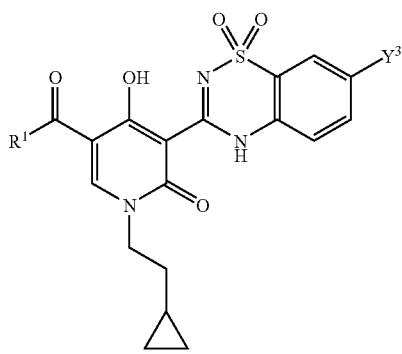
93
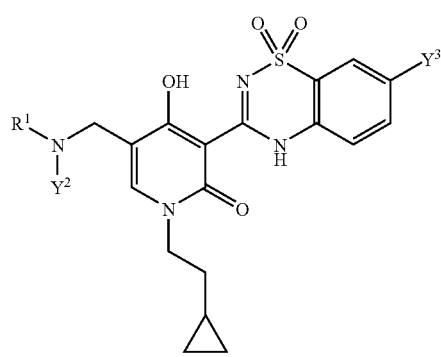
94

TABLE 1-continued
Examples of Core Ring Structures
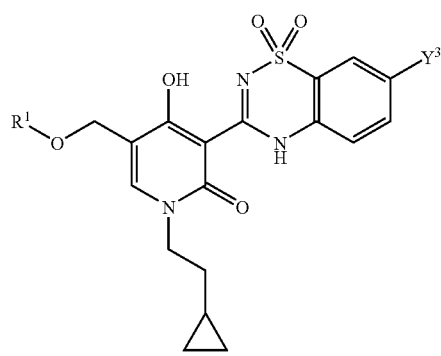
95
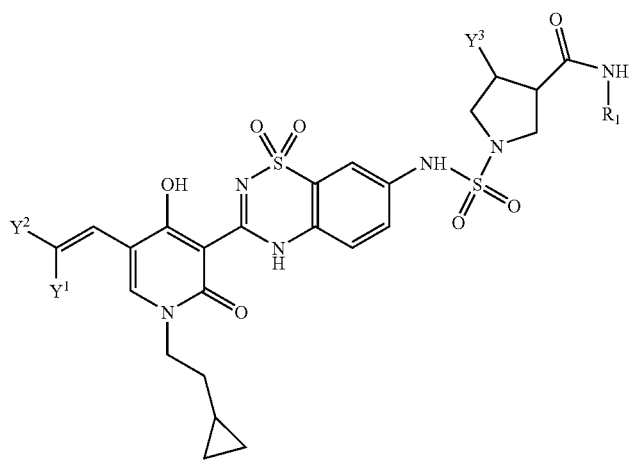
96
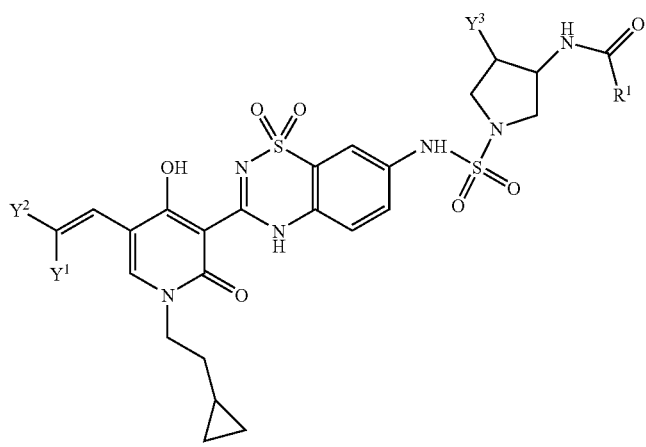
97
98
99
100

TABLE 2
Examples of R$^1$ Substituents
X$_1$-H
1
X$_1$-CH$_3$
2
3
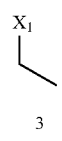
4
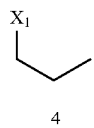
5
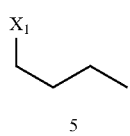
6
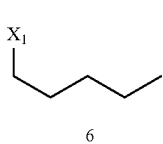
7
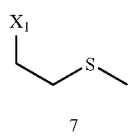
8
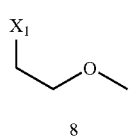
9
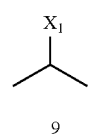
10
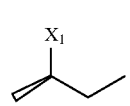
11
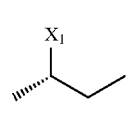
12
TABLE 2-continued
Examples of R$^1$ Substituents
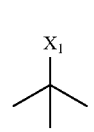
13
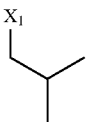
14
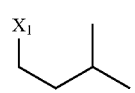
15
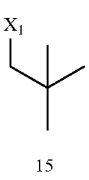
16
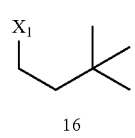
17
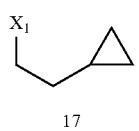
18
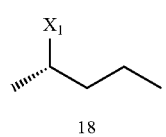
19
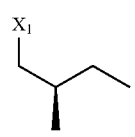
20
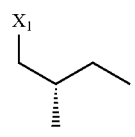
21

TABLE 2-continued
Examples of R¹ Substituents
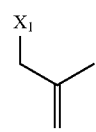
22
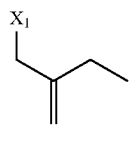
23
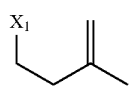
24
25
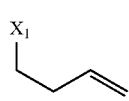
26
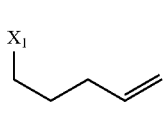
27
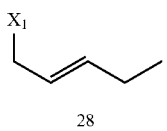
28
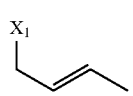
29
30
TABLE 2-continued
Examples of R¹ Substituents
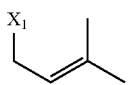
31
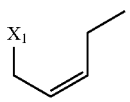
32
33
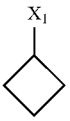
34
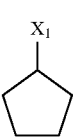
35
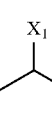
36
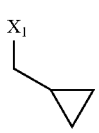
37
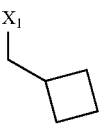
38
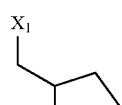
39

TABLE 2-continued
Examples of R¹ Substituents
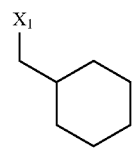
40
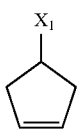
41
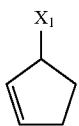
42
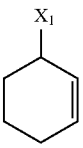
43
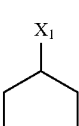
44
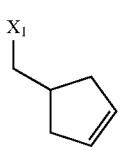
45
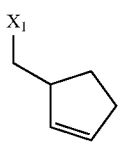
46
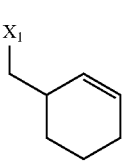
47
TABLE 2-continued
Examples of R¹ Substituents
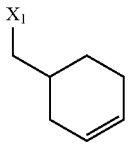
48
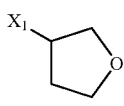
49
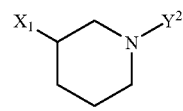
50
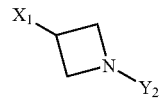
51
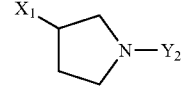
52
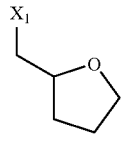
53
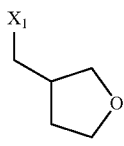
54
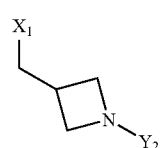
55
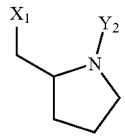
56

TABLE 2-continued
Examples of R¹ Substituents
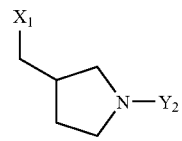
57
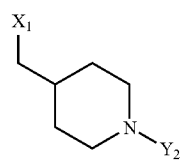
58
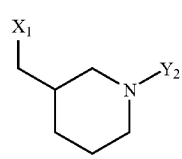
59
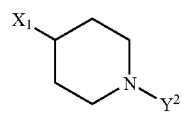
60
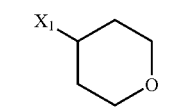
61
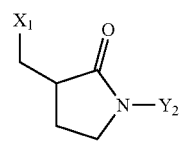
62
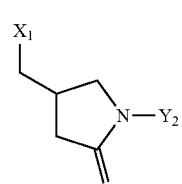
63
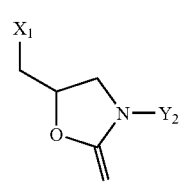
64
TABLE 2-continued
Examples of R¹ Substituents
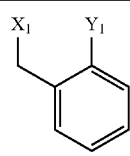
65
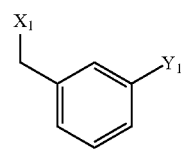
66
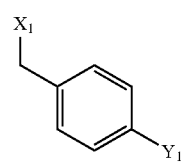
67
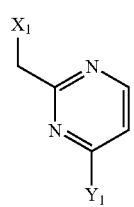
68
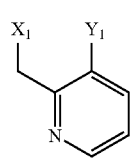
69
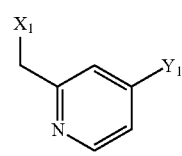
70
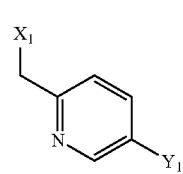
71

TABLE 2-continued

Examples of R¹ Substituents

| # | Structure |
|---|---|
| 72 | pyridine with X₁-CH₂ at 2-position, Y₁ at 6-position |
| 73 | pyridine with X₁-CH₂ at 3-position, Y₁ at 4-position |
| 74 | pyridine with X₁-CH₂ at 3-position, Y₁ at 5-position |
| 75 | pyridine with X₁-CH₂ at 5-position, Y₁ at 2-position |
| 76 | pyridine with X₁-CH₂ at 3-position, Y₁ at 2-position |
| 77 | pyridine with X₁-CH₂ at 4-position, Y₁ at 3-position |
| 78 | pyridine with X₁-CH₂ at 4-position, Y₁ at 2-position |
| 79 | pyridazine with X₁-CH₂ and Y₁ |
| 80 | pyridazine with X₁-CH₂, Y₁, Y₁ |
| 81 | pyrimidine with X₁-CH₂ and Y₁ |
| 82 | pyrimidine with X₁-CH₂ at 5-position, Y₁ at 2-position |
| 83 | pyrimidine with X₁-CH₂, Y₂, Y₁ |
| 84 | pyrimidine with X₁-CH₂, Y₁, Y₂ |
| 85 | thiophene with X₁-CH₂ and Y₁ |

TABLE 2-continued
Examples of R¹ Substituents
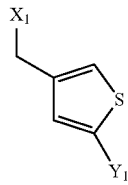
86
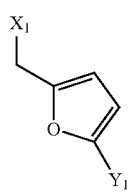
87
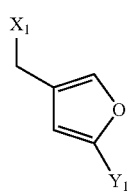
88
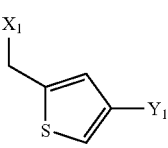
89
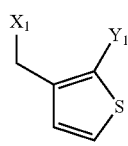
90
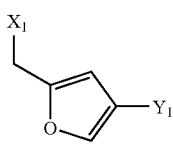
91
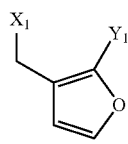
92
TABLE 2-continued
Examples of R¹ Substituents
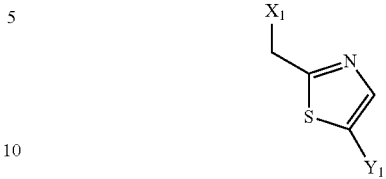
93
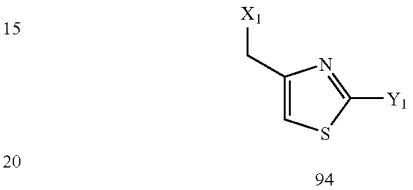
94
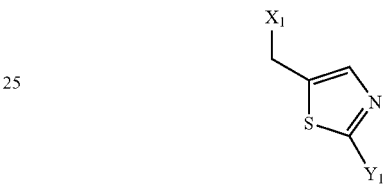
95
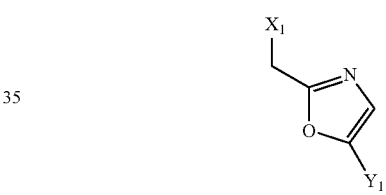
96
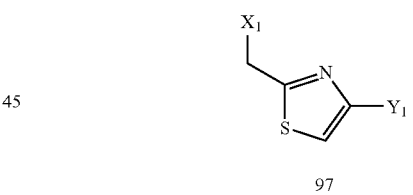
97
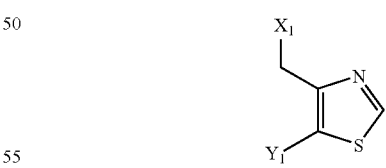
98
99

TABLE 2-continued
Examples of R¹ Substituents
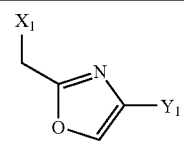
100
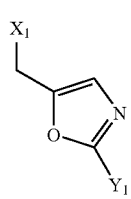
101
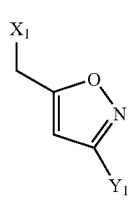
102
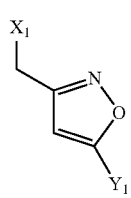
103
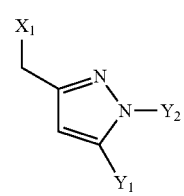
104
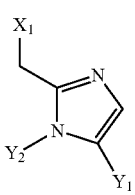
105
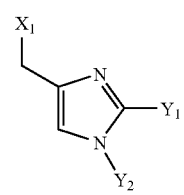
106
TABLE 2-continued
Examples of R¹ Substituents
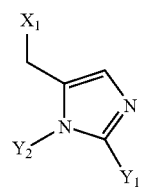
107
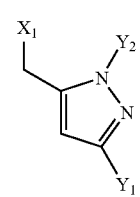
108
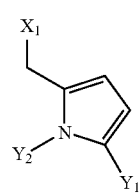
109
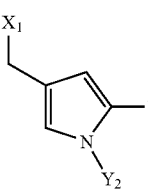
110
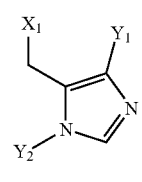
111
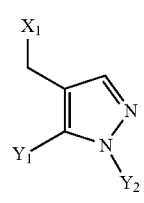
112

TABLE 2-continued
Examples of R¹ Substituents
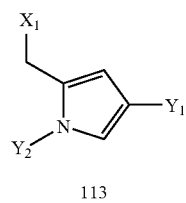
113
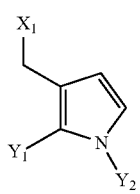
114
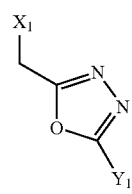
115
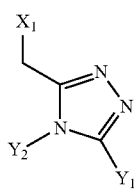
116
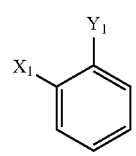
117
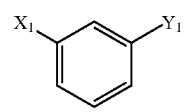
118
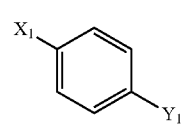
119
TABLE 2-continued
Examples of R¹ Substituents
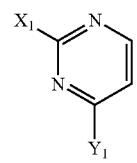
120
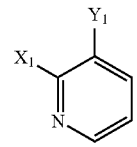
121
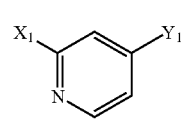
122
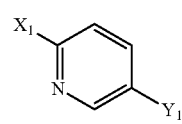
123
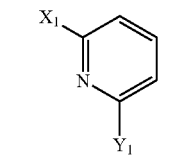
124
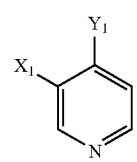
125
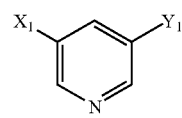
126
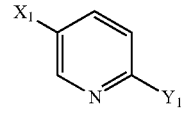
127

TABLE 2-continued
Examples of R¹ Substituents
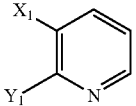
128
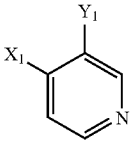
129
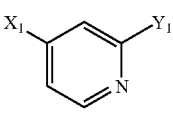
130
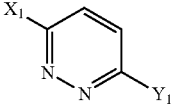
131
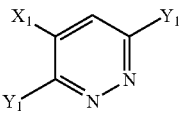
132
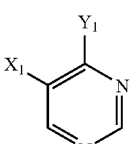
133
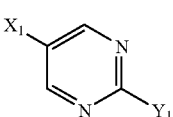
134
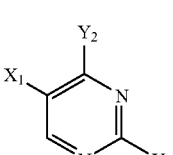
135
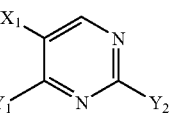
136
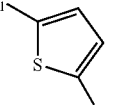
137
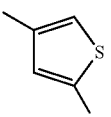
138
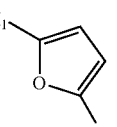
139
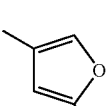
140
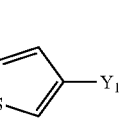
141
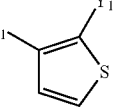
142
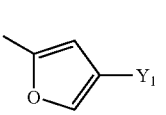
143
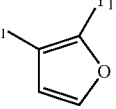
144

TABLE 2-continued
Examples of R¹ Substituents
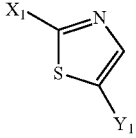
145
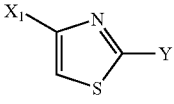
146
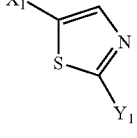
147
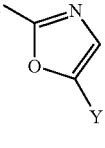
148
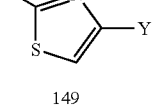
149
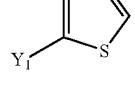
150
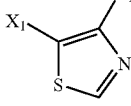
151
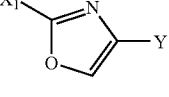
152
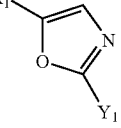
153
TABLE 2-continued
Examples of R¹ Substituents
154
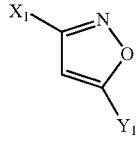
155
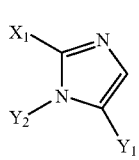
156
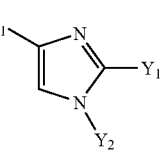
157
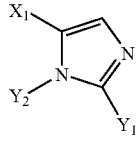
158
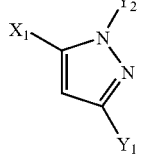
159
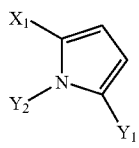
160
161

TABLE 2-continued

Examples of R[1] Substituents

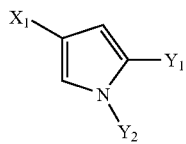

162

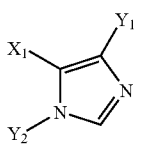

163

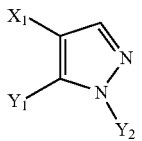

164

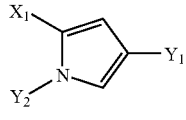

165

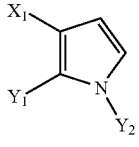

166

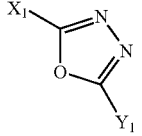

167

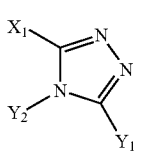

168

TABLE 3

Substituents of $Y_1$ and $Y_2$

| H | $CH_3$ | $-CH_2CH_3$ | $-CH(CH_3)_2$ |
|---|---|---|---|
| —F | —Cl | —Br | $NO_2$ |
| —CN | $-OCH_3$ | $-NHCH_3$ | $-N(CH_3)_2$ |

TABLE 3-continued

| $-NH_2$ | —OH | $-C(O)NH_2$ | $-NC(O)NH_2$ |
|---|---|---|---|

$Y_2$

| H | $CH_3$ | $-CH_2CH_3$ | $-CH(CH_3)_2$ |
|---|---|---|---|
| $-COCH_3$ | $-CO_2CH_3$ | $CO_2CH_3$ | $-NC(O)NH_2$ |
| $-NH_2$ | —OH | $-C(O)NH_2$ | |

TABLE 4

Examples of $Y_3$ $X_1$-H
1
$X_1$-$CH_3$
2
$X_1$-OH
3
$X_1$-$NH_2$ $X_1$—NH—CH₂—C(=O)—NH₂

5

$X_1$—O—CH₂—C(=O)—NH₂

6

$X_1$—NH—CH₂—C(=O)—NH—CH₃

7

$X_1$—O—CH₂—C(=O)—NH—CH₃

8

$X_1$—NH—CH₂—CN

9

$X_1$—O—CH₂—CN

10

TABLE 4-continued

Examples of Y₃

11. X₁—NH—CH₂—C(=O)OH

12. X₁—O—CH₂—C(=O)OH

13. X₁-Cl
14. X₁F
15. X₁-NHCH₃
16. X₁-OCH₃

17. X₁-NH-CH₂-CH₂-NH₂

18. HN(X₁)-CH₂-CH₂-OH

19. X₁-NH-CH₂-CH=CH₂

20. X₁-NH-CH₂-CH(CH₃)₂

21. X₁-O-CH₂-CH₂-NH₂

22. X₁-O-CH₂-CH₂-OH

TABLE 4-continued

Examples of Y₃

23. X₁-O-CH₂-CH=CH₂

24. X₁-O-CH₂-CH(CH₃)₂

25. X₁-NH-CH₂-C(=O)-N(pyrrolidine)

26. X₁-NH-CH₂-C(=O)-N(piperidine)

27. X₁-NH-CH₂-C(=O)-N(piperazine)

28. X₁-NH-CH₂-C(=O)-N(4-aminopiperidine)

29. X₁-NH-CH₂-C(=O)-N((3S)-3-aminopyrrolidine)

30. X₁-NH-CH₂-C(=O)-N((3R)-3-aminopyrrolidine)

TABLE 4-continued
Examples of Y₃
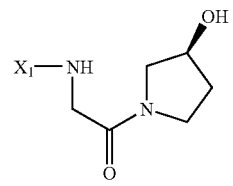
31
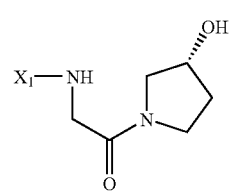
32
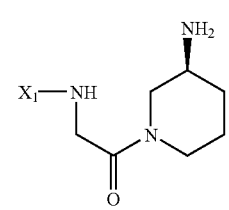
33
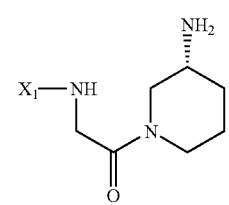
34
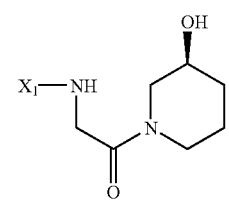
35
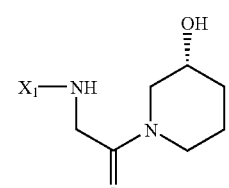
36
TABLE 4-continued
Examples of Y₃
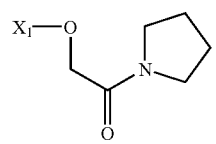
37
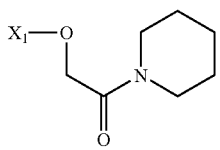
38
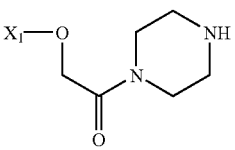
39
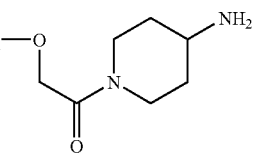
40
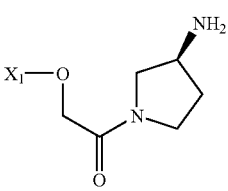
41
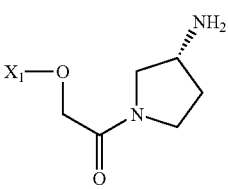
42
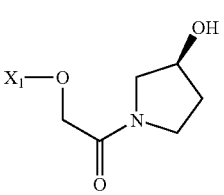
43

TABLE 4-continued
Examples of Y₃ | Examples of Y₃
--- | ---
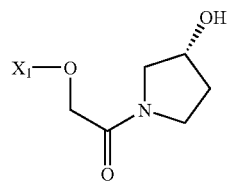<br>44 | 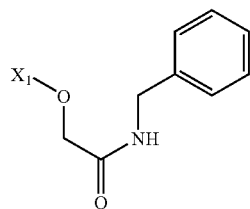<br>50
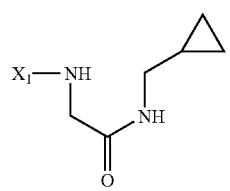<br>45 | 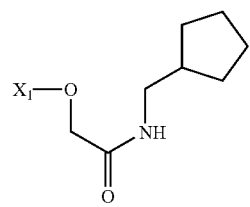<br>51
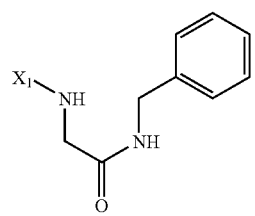<br>46 | 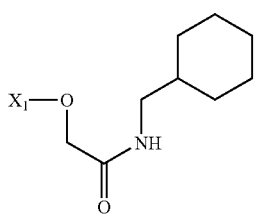<br>52
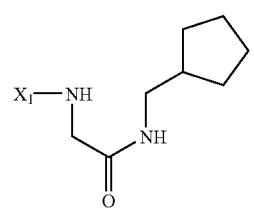<br>47 | 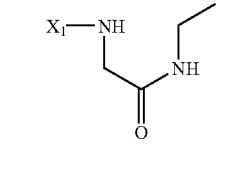<br>53
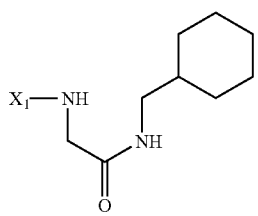<br>48 | 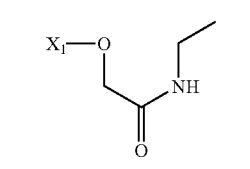<br>54
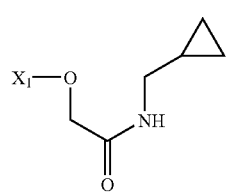<br>49 | 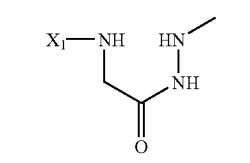<br>55
 | 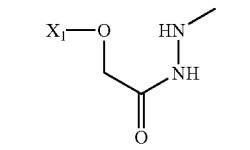<br>56

TABLE 4-continued
| Examples of $Y_3$ | | Examples of $Y_3$ | |
|---|---|---|---|
| 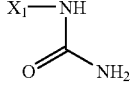<br>57 | | 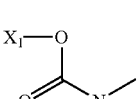<br>66 | |
| 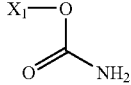<br>58 | | 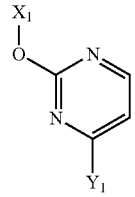<br>67 | |
| 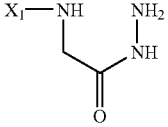<br>59 | | 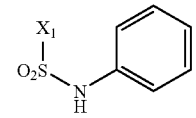<br>68 | |
| 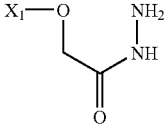<br>60 | | 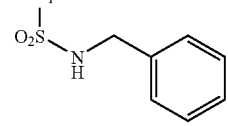<br>69 | |
| 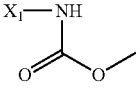<br>61 | | 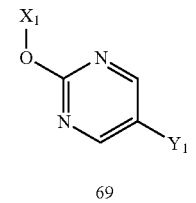<br>70 | |
| 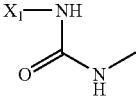<br>62 | | 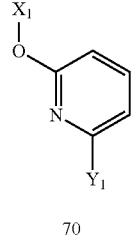<br>71 | |
| 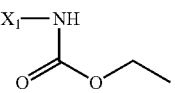<br>63 | | 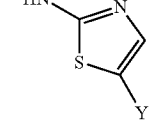<br>72 | |
| 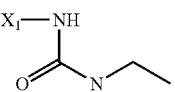<br>64 | | | |

TABLE 4-continued
Examples of Y₃
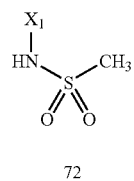
72
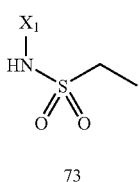
73
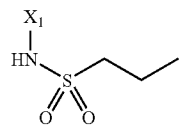
74
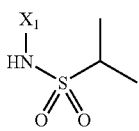
75
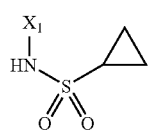
76
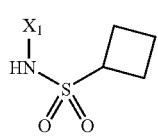
77
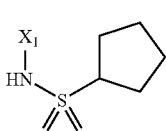
78
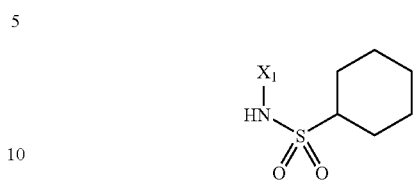
79
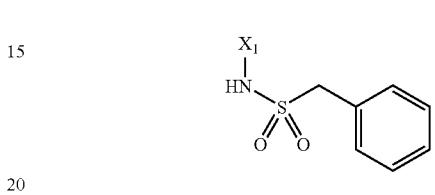
80
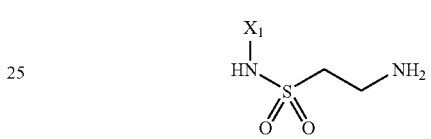
81
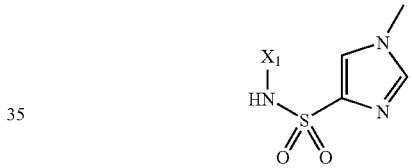
82
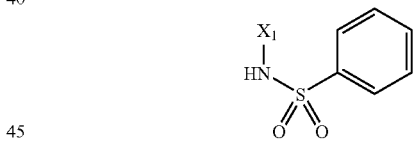
83
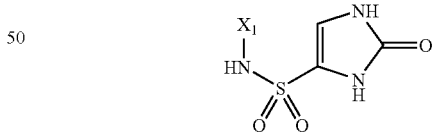
84
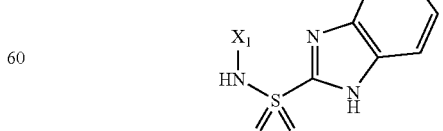
85

TABLE 4-continued
Examples of Y₃
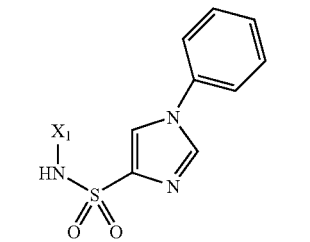
86
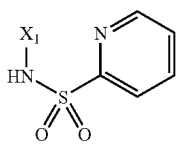
87
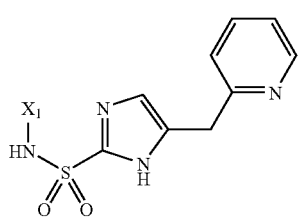
88
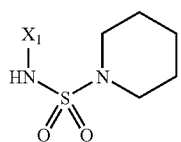
89
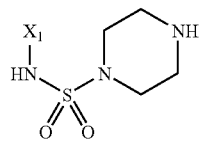
90
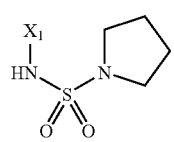
91
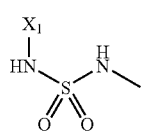
92
TABLE 4-continued
Examples of Y₃
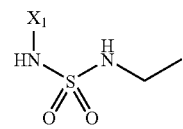
93
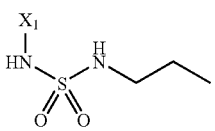
94
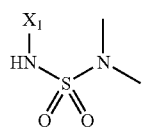
95
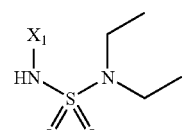
96
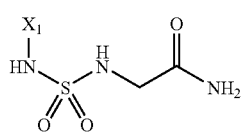
97
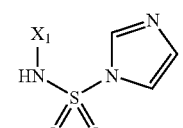
98
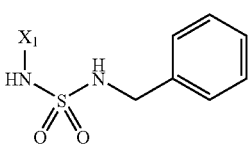
100

TABLE 4-continued

Examples of Y₃

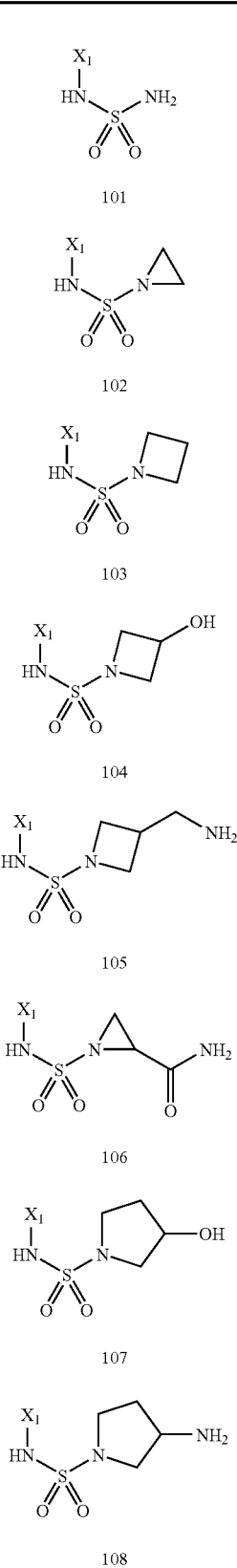

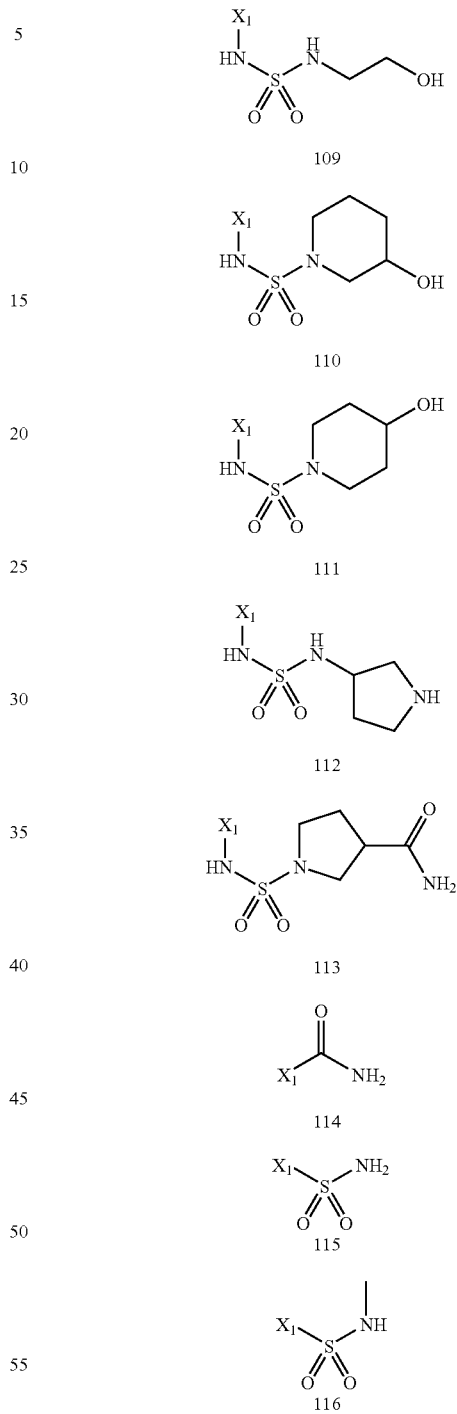

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound or a pharmaceutically acceptable salt form, stereoisomer or tautomer thereof, wherein:
the compound corresponds in structure to formula (VIII):

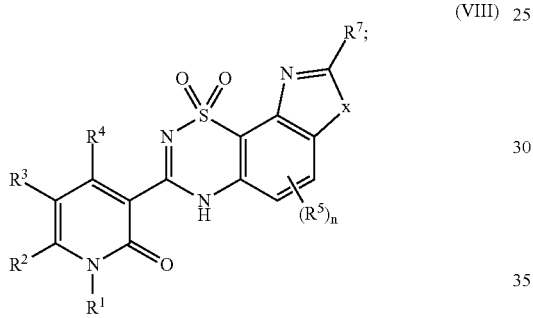

(VIII)

X is NH, N(alkyl), O or S;

$R^1$ is selected from the group consisting of hydrogen, alkenyl, alkoxyalkyl, alkoxycarbonylalkyl, alkyl, alkylcarbonylalkyl, alkylsulfanylalkyl, alkylsulfinylalkyl, alkylsulfonylalkyl, alkynyl, aryl, arylalkenyl, arylalkyl, arylsulfanylalkyl, arylsulfonylalkyl, carboxyalkyl, cyanoalkyl, cycloalkenyl, cycloalkenylalkyl, cycloalkyl, (cycloalkyl)alkenyl, (cycloalkyl)alkyl, formylalkyl, haloalkoxyalkyl, haloalkyl, heteroaryl, heteroarylalkenyl, heteroarylalkyl, heteroarylsulfonylalkyl, heterocycle, heterocyclealkenyl, heterocyclealkyl, hydroxyalkyl, nitroalkyl, $R_aR_bN$—, $R_aR_b$Nalkyl-, $R_aR_b$NC(O)alkyl-, $R_aR_b$NC(O)Oalkyl-, $R_aR_b$NC(O)$NR_c$alkyl-, $R_fR_g$C═N—, and $R_k$O—, wherein $R^1$ is substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_e$), —$SR_c$, —S(O)$R_c$, —S(O)$_2R_c$, —$OR_c$, —N($R_c$)($R_e$), —C(O)$R_c$, —C(O)$OR_c$ and —C(O)$NR_cR_e$;

$R^2$ and $R^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N($R_a$)($R_b$), $R_aR_b$NC(O)—, —$SR_a$, —S(O)$R_a$, —S(O)$_2R_a$, and $R_a$C(O)—, wherein $R^2$ and $R^3$ are independently substituted with 0, 1, 2 or 3 substituents independently selected from the group consisting of $R_a$, alkyl, alkenyl, alkynyl, oxo, halo, cyano, nitro, haloalkyl, -(alkyl)($OR_k$), -(alkyl)($NR_aR_b$), —$SR_a$, —S(O)$R_a$, —S(O)$_2R_a$, —$OR_k$, —N($R_a$)($R_b$), —C(O)$R_a$, —C(O)$OR_a$, and —C(O)$NR_aR_b$;

alternatively, $R^2$ and $R^3$, together with the carbon atoms to which they are attached, form a five- or six-membered ring selected from the group consisting of aryl, cycloalkyl, heteroaryl and heterocycle, wherein said aryl, cycloalkyl, heteroaryl and heterocycle is optionally substituted with $(R^6)_m$;

$R^4$ is selected from the group consisting of alkoxy, arylalkoxy, aryloxy, halo, hydroxy, $R_aR_bN$—, $N_3$—, $R_e$S—, wherein $R^4$ is independently substituted with 0, 1 or 2 substituents independently selected from the group consisting of halo, nitro, cyano, —OH, —$NH_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_a$C(O)—, $R_a$S—, $R_a$(O)S—, $R_a$(O)$_2$S—, $R_aR_b$Nalkyl-, $R_a$(O)SN($R_f$)—, $R_aSO_2N(R_f)$—, $R_a$(O)SN($R_f$)alkyl-, $R_aSO_2N(R_f)$alkyl-, $R_aR_bNSO_2N(R_f)$—, $R_aR_bNSO_2N(R_f)$alkyl-, $R_aR_b$NC(O)—, $R_k$OC(O)—, $R_k$OC(O)alkyl-, $R_k$Oalkyl-, $R_aR_bNSO_2$—, $R_aR_bNSO_2$alkyl-, ($R_b$O)($R_a$)P(O)O—, and —$OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —S(O)$R_c$, —S(O)$_2R_c$, —$OR_c$, —N($R_c$)($R_d$), —C(O)$R_c$, —C(O)$OR_c$ and —C(O)$NR_cR_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)($OR_k$), -(alkyl)($NR_aR_b$), —$SR_a$, —S(O)$R_a$, —S(O)$_2R_a$, —$OR_k$, —N($R_a$)($R_b$), —C(O)$R_a$, —C(O)$OR_a$, and —C(O)$NR_aR_b$, wherein each $R^6$ is independently substituted with 0, 1, 2 or 3 substituents independently selected from the group consisting of alkyl, alkenyl, alkynyl, oxo, halo, haloalkyl, cyano, nitro, —$OR_a$, —$NR_aR_b$, —$SR_a$, $SOR_a$, —$SO_2R_a$, —C(O)$OR_a$, —C(O)$NR_aR_b$, and —NC(O)$R_a$;

$R^7$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN—$, $R_aC(O)—$, $R_aS—$, $R_a(O)S—$, $R_a(O)_2S—$, $R_aR_bNalkyl-$, $R_a(O)SN(R_f)—$, $R_aSO_2N(R_f)—$, $R_a(O)SN(R_f)alkyl-$, $R_aSO_2N(R_f)alkyl-$, $R_aR_bNSO_2N(R_f)—$, $R_aR_bNSO_2N(R_f)alkyl-$, $R_aR_bNC(O)—$, $R_kOC(O)—$, $R_kOC(O)alkyl-$, $R_kOalkyl-$, $R_aR_bNSO_2—$, $R_aR_bNSO_2alkyl-$, $(R_kO)(R_a)P(O)O—$, and $—OR_k$, wherein each $R^7$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $—SR_c$, $—S(O)R_c$, $—S(O)_2R_c$, $—OR_c$, $—N(R_c)(R_d)$, $—C(O)R_c$, $—C(O)OR_c$, and $—C(O)NR_cR_d$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN—$, $R_cR_dNalkyl-$, $R_cR_dNC(O)alkyl-$, $R_cSO_2—$, $R_cSO_2alkyl-$, $R_cC(O)—$, $R_cC(O)alkyl-$, $R_cOC(O)—$, $R_cOC(O)alkyl-$, $R_cR_dNalkylC(O)—$, $R_cR_dNC(O)—$, $R_cR_dNC(O)Oalkyl-$, and $R_cR_dNC(O)N(R_e)alkyl-$, wherein $R_a$ and $R_b$ are substituted with 0, 1 or 2 substituents selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $—SR_c$, $—S(O)R_c$, $—S(O)_2R_c$, $—OR_c$, $—N(R_c)(R_d)$, $—C(O)R_c$, $—C(O)OR_c$, and $—C(O)NR_cR_d$;

alternatively, $R_a$ and $R_b$, together with the nitrogen atom to which they are attached, form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -alkylSO$_2$NR$_c$R$_d$, -alkylC(O)NR$_c$R$_d$, $—SR_c$, $—S(O)R_c$, $—S(O)_2R_c$, $—OR_c$, $—N(R_c)(R_d)$, $—C(O)R_c$, $—C(O)OR_c$, and $—C(O)NR_cR_d$;

$R_c$ and $R_d$, at each occurrence, are independently selected from the group consisting of hydrogen, $—NR_fR_h$, $—OR_f$, $—CO(R_f)$, $—SR_f$, $—SOR_f$, $—SO_2R_f$, $—C(O)NR_fR_h$, $—SO_2NR_fR_h$, $—C(O)OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkyl, -(alkyl)($OR_f$), -(alkyl)($NR_fR_h$), $—SR_f$, $—S(O)R_f$, $—S(O)_2R_f$, $—OR_f$, $—N(R_f)(R_h)$, $—C(O)OR_f$, $—C(O)NR_fR_h$, $—C(O)N(H)NR_fR_h$, $—N(R_e)C(O)OR_f$, $—N(R_e)SO_2NR_fR_h$, $—N(R_e)C(O)NR_fR_h$, -alkylN(R$_e$)C(O)OR$_f$, -alkylN(R$_e$)SO$_2$NR$_f$R$_h$, and -alkylN(R$_e$)C(O)NR$_f$R$_h$;

alternatively, $R_c$ and $R_d$, together with the nitrogen atom to which they are attached form a three- to six-membered ring selected from the group consisting of heteroaryl and heterocycle, wherein the heteroaryl and heterocycle are independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), $—SR_f$, $—S(O)R_f$, $—S(O)_2R_f$, $—OR_f$, $—N(R_f)(R_h)$, $—C(O)R_f$, $—C(O)OR_f$, and $—C(O)NR_fR_h$;

$R_e$ is selected from the group consisting of hydrogen, alkenyl, alkyl and cycloalkyl;

$R_f$, $R_g$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$, $R_g$, and $R_h$ is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, $—OH$, $—O(alkyl)$, $—NH_2$, $—N(H)(alkyl)$, $—N(alkyl)_2$, $—S(alkyl)$, $—S(O)(alkyl)$, $—SO_2alkyl$, -alkyl-OH, -alkyl-O-alkyl, -alkylNH$_2$, -alkylN(H)(alkyl), -alkylN(alkyl)$_2$, -alkylS(alkyl), -alkylS(O)(alkyl), -alkylSO$_2$alkyl, $—N(H)C(O)NH_2$, $—C(O)OH$, $—C(O)O(alkyl)$, $—C(O)alkyl$, $—C(O)NH_2$, $—C(O)NH_2$, $—C(O)N(H)(alkyl)$, and $—C(O)N(alkyl)_2$;

alternatively, $R_f$ and $R_g$, together with the carbon atom to which they are attached form a three- to seven-membered ring selected from the group consisting of cycloalkyl, cycloalkenyl and heterocycle;

alternatively, $R_f$ and $R_h$, together with the nitrogen atom to which they are attached, form a three- to seven-membered ring selected from the group consisting of heterocycle and heteroaryl; wherein each of the heterocycle and heteroaryl is independently substituted with 0, 1, 2 or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, $—OH$, $—O(alkyl)$, $—NH_2$, $—N(H)(alkyl)$, $—N(alkyl)_2$, $—S(alkyl)$, $—S(alkyl)$, $—S(O)(alkyl)$, -alkyl-OH, -alkyl-O-alkyl, -alkylNH$_2$, -(alkyl)N(H)(alkyl), -alkylS(alkyl), -(alkyl)S(O)(alkyl), -alkylSO$_2$alkyl, -alkylN(alkyl)$_2$, $—N(H)C(O)NH_2$, $—C(O)OH$, $—C(O)O(alkyl)$, $—C(O)alkyl$, $—C(O)NH_2$, $—C(O)NH_2$, $—C(O)N(H)(alkyl)$, and $—C(O)N(alkyl)_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_bNalkyl-$, $R_aOalkyl-$, $R_aR_bNC(O)—$, $R_aR_bNC(O)alkyl-$, $R_aS—$, $R_aS(O)—$, $R_aSO_2—$, $R_aSalkyl-$, $R_a(O)Salkyl-$, $R_aSO_2alkyl-$, $R_aOC(O)—$, $R_aOC(O)alkyl-$, $R_aC(O)—$, $R_aC(O)alkyl-$, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(N$_c$R$_d$), —SR$_c$, —S(O)R$_c$, —S(O)$_2$R$_c$, —OR$_c$, —N(R$_c$)(R$_d$), —C(O)R$_c$, —C(O)O$_c$, and —C(O)NR$_c$R$_d$;

m is 0, 1, 2, 3, or 4; and n is 0, 1 or 2.

2. The compound, salt, stereoisomer, or tautomer of claim 1, wherein R$^2$ and R$^3$, together with the carbon atoms to which they are attached, form a five- or six-membered ring selected from the group consisting of aryl, cycloalkyl, heteroaryl and heterocycle, wherein said aryl, cycloalkyl, heteroaryl and heterocycle is optionally substituted with (R$^6$)$_m$.

3. The compound, salt, stereoisomer, or tautomer of claim 2, wherein R$^2$ and R$^3$, together with the carbon atoms to which they are attached, form a five- or six-membered ring selected from the group consisting of phenyl, pyridyl, pyridazinyl, pyrimidinyl, pyrazolyl, cyclopentyl, cyclohexyl and thienyl.

4. The compound, salt, stereoisomer, or tautomer of claim 3, wherein R$^4$ is hydroxy.

5. The compound salt, stereoisomer, or tautomer of claim 4, wherein the compound is selected from the group consisting of:

3-[8-(chloromethyl)-1,1-dioxido-4H-[1,3]oxazolo[5,4-h][1,2,4]benzothiadiazin-3-yl]-4-hydroxy-1-(isobutylamino)quinolin-2(1H)-one;

3-{3-[4-hydroxy-1-(isobutylamino)-2-oxo-1,2-dihydroquinolin-3-yl]-1,1-dioxido-4H-[1,3]oxazolo[5,4-h][1,2,4]benzothiadiazin-8-yl}propanoic acid;

3-(8-{[(2-aminoethyl)amino]methyl}-1,1-dioxido-4H-[1,3]oxazolo[5,4-h][1,2,4]benzothiadiazin-3-yl)-4-hydroxy-1-(isobutylamino)quinolin-2(1H)-one;

methyl {3-[4-hydroxy-1-(isobutylamino)-2-oxo-1,2-dihydroquinolin-3-yl]-1,1-dioxido-4H-[1,3]oxazolo[5,4-h][1,2,4]benzothiadiazin-8-yl}acetate;

4-hydroxy-3-(8-{[(3R)-3-hydroxypyrrolidin-1-yl]methyl}-1,1-dioxido-4H-[1,3]oxazolo[5,4-h][1,2,4]benzothiadiazin-3-yl)-1-(isobutylamino)quinolin-2(1H)-one;

3-[1,1-dioxido-8-(pyridinium-1-ylmethyl)-4H-[1,3]oxazolo[5,4-h][1,2,4]benzothiadiazin-3-yl]-1-(isobutylamino)-2-oxo-1,2-dihydroquinolin-4-olate;

3-[1,1-dioxido-8-(pyrrolidin-1-ylmethyl)-4H-[1,3]oxazolo[5,4-h][1,2,4]benzothiadiazin-3-yl]-4-hydroxy-1-(isobutylamino)quinolin-2(1H)-one;

3-[8-(3-aminophenyl)-1,1-dioxido-4H-[1,3]oxazolo[5,4-h][1,2,4]benzothiadiazin-3-yl]-4-hydroxy-1-(isobutylamino)quinolin-2(1H)-one;

3-[8-(aminomethyl)-1,1-dioxido-4H-[1,3]oxazolo[5,4-h][1,2,4]benzothiadiazin-3-yl]-4-hydroxy-1-(isobutylamino)quinolin-2(1H)-one;

4-hydroxy-3-[8-(hydroxymethyl)-1,1-dioxido-4H-[1,3]oxazolo[5,4-h][1,2,4]benzothiadiazin-3-yl]-1-(isobutylamino)quinolin-2(1H)-one;

3-{8-[(butylamino)methyl]-1,1-dioxido-4H-[1,3]oxazolo[5,4-h][1,2,4]benzothiadiazin-3-yl}-4-hydroxy-1-(isobutylamino)quinolin-2(1H)-one;

4-hydroxy-1-(3-methylbutyl)-3-(8-methyl-1,1-dioxido-4H-[1,3]oxazolo[5,4-h][1,2,4]benzothiadiazin-3-yl)-1,8-naphthyridin-2(1H)-one;

3-[1,1-dioxido-8-(trifluoromethyl)-4,7-dihydroimidazo[4,5-h][1,2,4]benzothiadiazin-3-yl]-4-hydroxy-1-(3-methylbutyl)-1,8-naphthyridin-2(1H)-one;

4-hydroxy-3-(8-hydroxy-1,1-dioxido-4,7-dihydroimidazo[4,5-h][1,2,4]benzothiadiazin-3-yl)-1-(3-methylbutyl)-1,8-naphthyridin-2(1H)-one;

4-hydroxy-1-(3-methylbutyl)-3-(8-methyl-1,1-dioxido-4,7-dihydroimidazo[4,5-h][1,2,4]benzothiadiazin-3-yl)-1,8-naphthyridin-2(1H)-one;

3-[1,1-dioxido-8-(pentafluoroethyl)-4,7-dihydroimidazo[4,5-h][1,2,4]benzothiadiazin-3-yl]-4-hydroxy-1-(3-methylbutyl)-1,8-naphthyridin-2(1H)-one;

3-[8-(chloromethyl)-1,1-dioxido-4,7-dihydroimidazo[4,5-h][1,2,4]benzothiadiazin-3-yl]-4-hydroxy-1-(3-methylbutyl)-1,8-naphthyridin-2(1H)-one;

{3-[4-hydroxy-1-(3-methylbutyl)-2-oxo-1,2-dihydro-1,8-naphthyridin-3-yl]-1,1-dioxido-4,7-dihydroimidazo[4,5-h][1,2,4]benzothiadiazin-8-yl}acetonitrile;

methyl {3-[4-hydroxy-1-(3-methylbutyl)-2-oxo-1,2-dihydro-1,8-naphthyridin-3-yl]-1,1-dioxido-4,7-dihydroimidazo[4,5-h][1,2,4]benzothiadiazin-8-yl}acetate;

3-(8-amino-1,1-dioxido-4,7-dihydroimidazo[4,5-h][1,2,4]benzothiadiazin-3-yl)-4-hydroxy-1-(3-methylbutyl)-1,8-naphthyridin-2(1H)-one; and 4-hydroxy-3-[8-(hydroxymethyl)-1,1-dioxido-4,9-dihydroimidazo[4,5-h][1,2,4]benzothiadiazin-3-yl]-1-(3-methylbutyl)-1,8-naphthyridin-2(1H)-one.

6. The compound, salt, stereoisomer, or tautomer of claim 1, wherein:

R$^5$ is R$_a$SO$_2$N(R$_f$)alkyl-, and

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, and nitroalkyl.

7. The compound, salt, stereoisomer, or tautomer of claim 1, wherein:

R$^1$ is R$_a$R$_b$N—, and

R$_a$ and R$_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, and nitroalkyl.

8. A method of treating an infection caused by a hepatitis C virus, wherein the method comprises administering to a patient in need of such treatment a therapeutically effective amount of one or more compounds, salts, stereoisomers, or tautomers recited in claim 1.

9. A compound or a pharmaceutically acceptable salt form, stereoisomer, or tautomer thereof, wherein the compound is selected from the group consisting of:

N-{3-[1-(cyclobutylamino)-4-hydroxy-2-oxo-1,2-dihydroquinolin-3-yl]-1,1-dioxido-4H-1,2,4-benzothiadiazin-7-yl}methanesulfonamide;

N-[(3-{1-[(cyclopropylmethyl)amino]-4-hydroxy-2-oxo-1,2-dihydroquinolin-3-yl}-1,1-dioxido-4H-thieno[2,3-e][1,2,4-]thiadiazin-7-yl)methyl]methanesulfonamide;

N-(3-{1-[(cyclopropylmethyl)amino]-4-hydroxy-2-oxo-1,2-dihydro-3-quinolinyl}-1,1-dioxido-4H-1,2,4-benzothiadiazin-7-yl)methanesulfonamide;

N-{3-[1-(cyclobutylamino)-4-hydroxy-2-oxo-1,2-dihydro-3-quinolinyl]-1,1-dioxido-4H-1,2,4-benzothiadiazin-7-yl}sulfamide; and N-{3-[1-(cyclobutylamino)-4-hydroxy-2-oxo-1,2-dihydro-3-quinolinyl]-1,1-dioxido-4H-1,2,4-benzothiadiazin-7-yl}-N'-methylsulfamide.

10. A pharmaceutical composition comprising a therapeutically effective amount of one or more compounds, salts, stereoisomers, or tautomers recited in claim 9 and a pharmaceutically acceptable carrier.

11. The pharmaceutical composition of claim 10, wherein each of the composition further comprises one or more agents selected from the group consisting of a host immune modulator and a second antiviral agent.

12. The pharmaceutical composition of claim 11, wherein each of the one or more the host immune modulator is selected from the group consisting of interferon-alpha, pegylated-interferon-alpha, interferon-beta, interferon-gamma, a cytokine, a vaccine and a vaccine comprising an antigen and an adjuvant.

13. The pharmaceutical composition of claim 11, wherein the second antiviral agent inhibits replication of HCV by inhibiting host cellular functions associated with viral replication.

14. The pharmaceutical composition of claim 11, wherein the second antiviral agent inhibits the replication of HCV by targeting proteins of the viral genome.

15. The pharmaceutical composition of claim 10, wherein the composition further comprises an agent or combination of agents that treat or alleviate symptoms of HCV infection.

16. The pharmaceutical composition of claim 10, wherein the composition further comprises one or more agents that treat patients for disease caused by hepatitis B (HBV) infection.

17. The pharmaceutical composition of claim 16, wherein each of the one or more agents that treat patients for disease caused by hepatitis B (HBV) infection is selected from the group consisting of L-deoxythymidine, adefovir, lamivudine and tenofovir.

18. The pharmaceutical composition of claim 10, wherein the composition further comprising one or more agents that treat patients for disease caused by human immunodeficiency virus (HIV) infection.

19. The pharmaceutical composition of claim 18, wherein each of the one or more agents that treat patients for disease caused by human immunodeficiency virus (HIV) infection is selected from the group consisting of ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) and T-1249.

20. A method of treating an infection caused by a hepatitis C virus, wherein the method comprises administering to a patient in need of such treatment a therapeutically effective amount of one or more compounds, salts, stereoisomers, or tautomers recited in claim 9.

21. A compound, or a pharmaceutically acceptable salt, stereoisomer, or tautomer thereof, wherein:
the compound corresponds in structure to formula (I):

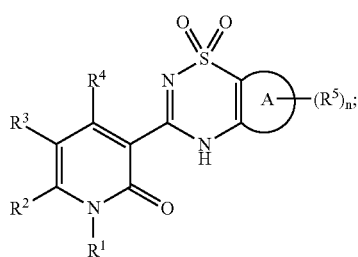

A is a monocyclic or bicyclic ring selected from the group consisting of aryl, cycloalkyl, cycloalkenyl, heteroaryl, and heterocycle;

$R^1$ is $R_aR_bN$—;

$R^2$ and $R^3$, together with the carbon atoms to which they are attached, form a five- or six-membered ring selected from the group consisting of aryl, cycloalkyl, heteroaryl, and heterocycle;

$R^4$ is selected from the group consisting of alkoxy, arylalkoxy, aryloxy, halo, hydroxy, $R_aR_bN$—, $N_3$—, and $R_eS$—, wherein $R^4$ is substituted with 0, 1, or 2 substituents independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, $R_aR_bN$—, $R_aC(O)$—, $R_aS$—, $R_a(O)S$—, $R_a(O)_2S$—, $R_aR_b$Nalkyl-, $R_a(O)SN(R_f)$—, $R_aSO_2N(R_f)$—, $R_a(O)SN(R_f)$alkyl-, $R_aSO_2N(R_f)$alkyl-, $R_aR_bNSO_2N(R_f)$—, $R_aR_bNSO_2N(R_f)$alkyl-, $R_aR_bNC(O)$—, $R_kOC(O)$—, $R_kOC(O)$alkyl-, $R_kOalkyl$-, $R_aR_bNSO_2$—, $R_aR_bNSO_2$alkyl-, $(R_bO)(R_a)P(O)O$— and —$OR_k$, wherein each $R^5$ is independently substituted with 0, 1, 2 or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R_a$ and $R_b$, at each occurrence, are independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, and nitroalkyl;

$R_c$ and $R_d$, at each occurrence, are independently selected from the group consisting of hydrogen, —NR$_f$R$_h$, —OR$_f$, —CO(R$_f$), —SR$_f$, —SOR$_f$, —SO$_2$R$_f$, —S(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle, and heterocycloalkyl, wherein each R$_c$ and R$_d$ is independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —S(O)R$_f$, —C(O)OR$_f$, —C(O)NR$_f$R$_h$, —C(O)N(H)NR$_f$R$_h$, —N(R$_e$)C(O)OR$_f$, —N(R$_e$)SO$_2$NR$_f$R$_h$, —N(R$_e$)C(O)NR$_f$R$_h$, -alkylN(R$_e$)C(O)OR$_f$, -alkylN(R$_e$)SO$_2$NR$_f$R$_h$, and -alkylN(R$_e$)C(O)NR$_f$R$_h$;

alternatively, R$_c$ and R$_d$, together with the nitrogen atom to which they are attached, form a three- to six-membered ring selected from the group consisting of heteroaryl and heterocycle, wherein the heteroaryl and heterocycle are independently substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)

$(OR_f)$, -(alkyl)$(NR_fR_h)$, —$SR_f$, —$S(O)R_f$, —$S(O)_2R_f$, —$OR_f$, —$N(R_f)(R_h)$, —$C(O)R_f$, —$C(O)OR_f$, and —$C(O)NR_fR_h$;

$R_e$ is selected from the group consisting of hydrogen, alkenyl, alkyl, and cycloalkyl;

$R_f$ and $R_h$, at each occurrence, are independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl, and heteroarylalkyl, wherein each $R_f$ and $R_h$ is independently substituted with 0, 1, 2, or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(O)(alkyl), -$SO_2$alkyl, -alkyl-OH, -alkyl-O-alkyl, -alkyl$NH_2$, -alkylN(H)(alkyl), -alkylN(alkyl)$_2$, -alkylS(alkyl), -alkylS(O)(alkyl), -alkyl$SO_2$alkyl, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

alternatively, $R_f$ and $R_h$, together with the nitrogen atom to which they are attached, form a three- to seven-membered ring selected from the group consisting of heterocycle and heteroaryl, wherein each of the heterocycle and heteroaryl is independently substituted with 0, 1, 2, or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(alkyl), —S(O)(alkyl), -alkyl-OH, —alkyl-O-alkyl, -alkyl$NH_2$, -alkylN(H)(alkyl), -alkylS(alkyl), -alkylS(O)(alkyl), -alkyl$SO_2$alkyl, -alkylN(alkyl)$_2$, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

$R_k$ is selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_a$S—, $R_a$S(O)—, $R_aSO_2$—, $R_a$Salkyl-, $R_a$(O)Salkyl-, $R_aSO_2$alkyl-, $R_a$OC(O)—, $R_a$OC(O)alkyl-, $R_a$C(O)—, and $R_a$C(O)alkyl-, wherein each $R_k$ is substituted with 0, 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)$(OR_c)$, -(alkyl)$(NR_cR_d)$, —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$; and n is 0, 1, 2, 3, or 4.

22. The compound, salt, stereoisomer or tautomer of claim 21, wherein the compound is selected from the group consisting of:

N-{[3-(1-benzyl-4-hydroxy-2-oxo-1,2-dihydroquinolin-3-yl)-1,1-dioxido-4H-thieno[2,3-e][1,2,4]thiadiazin-7-yl]methyl}methanesulfonamide;

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]methanesulfonamide;

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]ethanesulfonamide;

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]propane-1-sulfonamide;

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]propane-2-sulfonamide;

N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]benzenesulfonamide; and N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]-1-phenylmethanesulfonamide.

23. A method of treating an infection caused by a hepatitis C virus, wherein the method comprises administering to a patient in need of such treatment a therapeutically effective amount of one or more compounds, salts, stereoisomers, or tautomers recited in claim 21.

* * * * *